US009780310B2

(12) United States Patent
Oka et al.

(10) Patent No.: US 9,780,310 B2
(45) Date of Patent: Oct. 3, 2017

(54) HETEROCYCLIC COMPOUND FOR ORGANIC ELECTROLUMINESCENT DEVICE AND ITS APPLICATION

(71) Applicant: TOSOH CORPORATION, Yamaguchi (JP)

(72) Inventors: Yuji Oka, Ayase (JP); Nobumichi Arai, Ayase (JP); Yuuichi Miyashita, Kanagawa (JP); Tadahiro Yotsuya, Kanagawa (JP); Kana Fujita, Kanagawa (JP); Naoki Uchida, Kanagawa (JP); Keisuke Nomura, Kanagawa (JP); Tsuyoshi Tanaka, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 0 days.

(21) Appl. No.: 14/783,110

(22) PCT Filed: Apr. 18, 2014

(86) PCT No.: PCT/JP2014/061069
§ 371 (c)(1),
(2) Date: Oct. 8, 2015

(87) PCT Pub. No.: WO2014/171541
PCT Pub. Date: Oct. 23, 2014

(65) Prior Publication Data
US 2016/0056388 A1 Feb. 25, 2016

(30) Foreign Application Priority Data

Apr. 18, 2013 (JP) ................................ 2013-087142
Jun. 26, 2013 (JP) ................................ 2013-133811

(51) Int. Cl.
| C07D 251/24 | (2006.01) |
| C07D 401/10 | (2006.01) |
| C07D 401/14 | (2006.01) |
| C07D 403/10 | (2006.01) |
| C07D 403/14 | (2006.01) |
| H01L 51/50 | (2006.01) |
| H01L 51/00 | (2006.01) |
| C07D 239/26 | (2006.01) |
| C07D 213/22 | (2006.01) |

(52) U.S. Cl.
CPC ........ *H01L 51/0067* (2013.01); *C07D 213/22* (2013.01); *C07D 239/26* (2013.01); *C07D 251/24* (2013.01); *C07D 401/10* (2013.01); *C07D 401/14* (2013.01); *C07D 403/10* (2013.01); *C07D 403/14* (2013.01); *H01L 51/0052* (2013.01); *H01L 51/0054* (2013.01); *H01L 51/0058* (2013.01); *H01L 51/0072* (2013.01); *H01L 51/5072* (2013.01); *H01L 51/5092* (2013.01)

(58) Field of Classification Search
CPC .. C07D 251/24; C07D 401/04; C07D 401/10; C07D 401/14; C09K 11/06
USPC ................................ 544/180; 345/82, 72, 76
See application file for complete search history.

(56) References Cited

U.S. PATENT DOCUMENTS

| 7,994,316 | B2 * | 8/2011 | Yamakawa | .......... C07D 401/10 313/504 |
| 8,268,997 | B2 * | 9/2012 | Yamakawa | .......... C07D 251/24 313/504 |
| 8,569,485 | B2 * | 10/2013 | Yamakawa | .......... C07D 251/24 544/180 |
| 8,674,091 | B2 * | 3/2014 | Aihara | ................. C07D 401/14 345/76 |
| 8,735,577 | B2 * | 5/2014 | Aihara | ................. C07D 401/14 345/72 |
| 9,120,775 | B2 * | 9/2015 | Jeynes | ................. A61K 31/427 |
| 9,252,368 | B2 * | 2/2016 | Aihara | ................. C07D 401/14 |
| 2009/0281311 | A1 | 11/2009 | Yamakawa et al. | |
| 2010/0249406 | A1 | 9/2010 | Yamakawa et al. | |
| 2011/0190494 | A1 | 8/2011 | Aihara et al. | |
| 2011/0288295 | A1 | 11/2011 | Aihara et al. | |
| 2012/0214993 | A1 | 8/2012 | Aihara et al. | |
| 2012/0313090 | A1 | 12/2012 | Yamakawa et al. | |

FOREIGN PATENT DOCUMENTS

| CN | 101675038 | 3/2010 |
| JP | 2004-22334 | 1/2004 |
| JP | 2007-314503 | 12/2007 |
| JP | 2008-280330 | 11/2008 |
| JP | 2009-224512 | 10/2009 |
| JP | 2010-155826 | 7/2010 |
| JP | 2011-63584 | 3/2011 |
| JP | 2012-254976 | 12/2012 |
| WO | 2008/129912 | 10/2008 |
| WO | 2010/038854 | 4/2010 |
| WO | 2012/087960 | 6/2012 |
| WO | 2012/091026 | 7/2012 |
| WO | 2013/191177 | 12/2013 |

OTHER PUBLICATIONS

International Search Report issued in PCT/JP2014/061069, dated Jun. 24, 2014.
International Preliminary Examination Report in PCT/ JP2014/061069 issued Oct. 20, 2015.
Chinese Office Action issued in Counterpart Patent Appl. No. 201480021129.9, dated Apr. 24, 2017, along with an english translation thereof.

* cited by examiner

*Primary Examiner* — Venkataraman Balasubramanian
(74) *Attorney, Agent, or Firm* — Greenblum & Bernstein, P.L.C.

(57) ABSTRACT

A novel heterocyclic compound for an organic electroluminescent device excellent in long service life and light-emitting characteristics is provided. A cyclic azine compound has at least one substituent (substituent B) selected from a specific group.

5 Claims, 1 Drawing Sheet

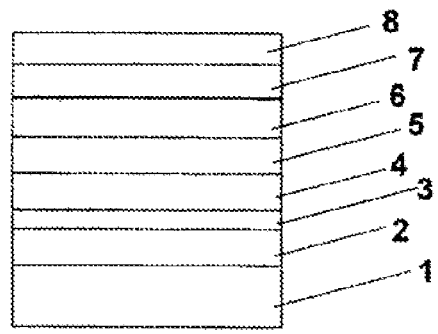

HETEROCYCLIC COMPOUND FOR ORGANIC ELECTROLUMINESCENT DEVICE AND ITS APPLICATION

TECHNICAL FIELD

The present invention relates to a novel heterocyclic compound for an organic electroluminescent device excellent in long service life, and its application.

BACKGROUND ART

An organic electroluminescent device is a device which has a basic structure such that a light emitting layer containing a light emitting material is sandwiched between a hole transport layer and an electron transport layer, and further an anode and a cathode are attached outside thereof, and which utilizes emission of light (fluorescence or phosphorescence) associated with excitation deactivation which occurs by recombination of holes and electrons injected to the light emitting layer, and it is applied to a display, etc. Incidentally, there may be a case where the hole transport layer is divided into a hole transport layer and a hole injection layer, where the light emitting layer is divided into an electron blocking layer, a light emitting layer and a hole blocking layer, or where the electron transport layer is divided into an electron transport layer and an electron injection layer.

Although recent organic electroluminescent devices have been gradually improved, it is still desired to improve luminous efficiency characteristics, drive voltage characteristics and long service life characteristics.

Organic electroluminescent devices have been known wherein as electron-transporting materials, various triazine compounds and pyrimidine compounds are used (for example, see Patent Documents 1, 2, 3 and 4), but also for such devices, further improvement of long service life has been desired.

PRIOR ART DOCUMENTS

Patent Documents

Patent Document 1: JP-A-2007-314503
Patent Document 2: JP-A-2008-280330
Patent Document 3: JP-A-2010-155826
Patent Document 4: JP-A-2011-063584

DISCLOSURE OF INVENTION

Technical Problem

The present invention has been made in view of the above background art, and its object is to provide a novel heterocyclic compound for an organic electroluminescent device excellent particularly in long service life, and an organic electroluminescent device using such a heterocyclic compound.

Solution to Problem

As a result of an extensive study to solve the above problem, the present inventors have considered that in a nitrogen-containing hetero-aromatic group in a conventional electron transport material for an organic electroluminescent device, carbon atoms adjacent to a nitrogen atom tend to be deficient in electrons due to a difference in electronegativity, and electrons tend to be localized, and that decomposition of the material starting from such an electron-localized portion is one of factors influential to the service life. Therefore, a further study has been made based on an idea that by delocalizing the localized orbit, it may be possible to prolong the service life of the compound and eventually to prolong the service life of the organic electroluminescent device.

As a result, the present inventors have found that an organic electroluminescent device using, in an electron transport layer or an electron injection layer, compound A having at least one substituent (substituent B) selected from the group consisting of an azabenzene group, a diazabenzene group, a triazine group, an azanaphthalene group, a diazanaphthalene group, a triazanaphthalene group, a tetraazanaphthalene group, a pentaazanaphthalene group, an azaanthracene group, a diazaanthracene group, a triazaanthracene group, a tetraazaanthracene group, a pentaazaanthracene group, a hexaazaanthracene group, a heptaazaanthracene group, an azaphenanthrene group, a diazaphenanthrene group, a triazaphenanthrene group, a tetraazaphenanthrene group, a pentaazaphenanthrene group, a hexaazaphenanthrene group, a heptaazaphenanthrene group, an azapentadiene group, a diazapentadiene group, an oxaazapentadiene group, a thiaazapentadiene group, an oxadiazapentadiene group, a thiodiazapentadiene group, an azaindene group, an oxaazaindene group, a thioazaindene group, a diazaindene group and a carboline group, having a substituent selected from the group consisting of an alkyl group, an alkoxy group, a halogen group, an amino group, a phosphyl group, a silyl group, a thiol group and an acyl group, on at least one carbon atom among carbon atoms adjacent to a nitrogen atom, is distinctly superior in long service life, as compared with a device using a conventional electron transport material.

More specifically, the present inventors have found that an organic electroluminescent device using, in an electron transport layer or an electron injection layer, a novel cyclic azine compound represented by the following general formula (1), general formula (2) or general formula (2'), is distinctly superior in long service life, as compared with a device using a conventional electron transport material, and thus have accomplished the present invention.

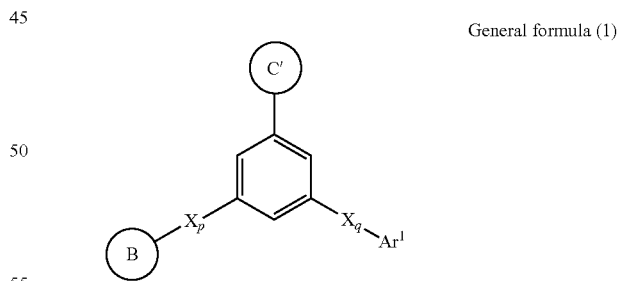

General formula (1)

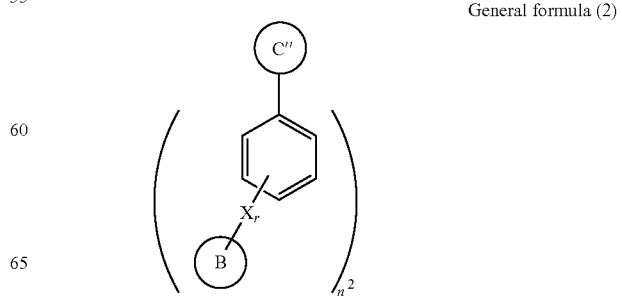

General formula (2)

General formula (2')

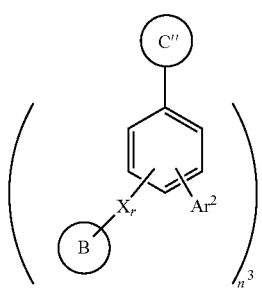

In the above formulae, each substituent B independently represents an azabenzene group, a diazabenzene group or an azanaphthalene group, which has a $C_{1-12}$ alkyl group on at least one carbon atom among carbon atoms adjacent to a nitrogen atom.

Substituent C' represents a diaryl pyrimidine group or a diaryl triazine group (each aryl group in the diaryl pyrimidine group and in the diaryl triazine group independently is a $C_{6-12}$ aromatic hydrocarbon group which may be substituted by a $C_{1-4}$ alkyl group).

Ar1 represents a C6-20 aromatic hydrocarbon group which may be substituted by a C1-4 alkyl group, or a C4-14 nitrogen-containing heteroaromatic group which may be substituted by a C1-4 alkyl group.

Each X independently represents a phenylene group or an azabenzenediyl group, which may be substituted by a $C_{1-4}$ alkyl group. Each of p and q independently represents 0, 1 or 2.

$Ar^2$ represents a $C_{6-12}$ aromatic hydrocarbon group which may be substituted. Each r independently represents 0, 1 or 2. $n^2$ represents 1, 2 or 3. $n^3$ represents 2 or 3.

Each substituent C" independently represents the following formula (C"-56), (C"-57), (C"-66), (C"-68) or (C"-81):

C"-56

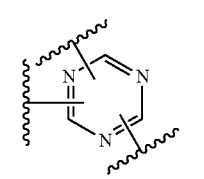

C"-57

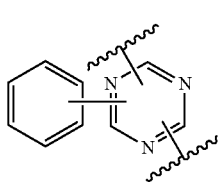

C"-66

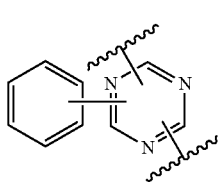

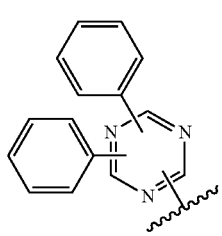

C"-68

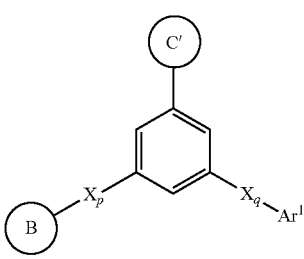

C"-81

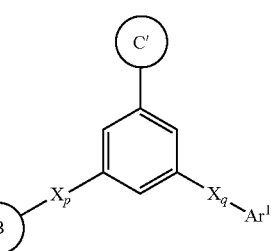

(Each $R^2$ independently represents a $C_{1-4}$ alkyl group.)

Advantageous Effects of Invention

According to the present invention, it is possible to provide an organic electroluminescent device excellent in long service life as compared with a conventional device. Further, it is possible to provide an organic electroluminescent device which is excellent in luminous efficiency characteristics and drive voltage characteristics in addition to long service life, and a novel cyclic azine compound to be contained in an electron transport layer and an electron injection layer of such an organic electroluminescent device.

BRIEF DESCRIPTION OF DRAWING

FIG. 1 is a schematic view illustrating a construction of a device to be prepared in Device Examples of the present invention.

DESCRIPTION OF EMBODIMENTS

The material for the organic electroluminescent device of the present invention contains a cyclic azine compound represented by the following general formula (1), general formula (2) or general formula (2'):

General formula (1)

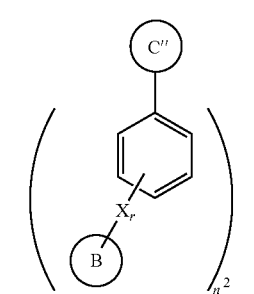

General formula (2)

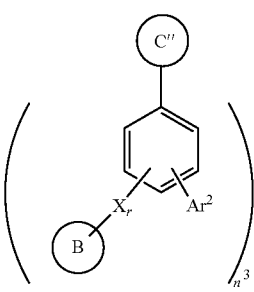

General formula (2')

(Substituent B, substituent C', $Ar^1$, X, p, q, substituent C", $Ar^2$, r, $n^2$ and $n^3$ are as defined above.)

The azabenzene group represented by substituent B, is not particularly limited, and may, for example, be a 2-pyridyl group, a 3-pyridyl group or a 4-pyridyl group, and from the viewpoint of long service life of the organic electroluminescent device, a 2-pyridyl group or a 3-pyridyl group is preferred.

The diazabenzene group represented by substituent B, is not particularly limited, and may, for example, be a 2-pyrimidyl group, a 4-pyrimidyl group, a 5-pyrimidyl group, a 2-pyrazyl group, a 3-pyridazine group or a 4-pyridazine group, and from the viewpoint of long service life of the organic electroluminescent device, a 2-pyrimidyl group is preferred.

The azanaphthalene group represented by substituent B, is not particularly limited, and may, for example, be a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group or a 8-isoquinolyl group.

The diazanaphthalene group represented by substituent B, is not particularly limited, and may, for example, be a 1,5-naphthyridin-2-yl group, a 1,5-naphthyridin-3-yl group, a 1,5-naphthyridin-4-yl group, a 1,6-naphthyridin-2-yl group, a 1,6-naphthyridine-3-yl group, a 1,6-naphthyridin-2-yl group, a 1,6-naphthyridin-3-yl group, a 1,6-naphthyridin-4-yl group, a 1,6-naphthyridin-5-yl group, a 1,6-naphthyridin-7-yl group, a 1,6-naphthyridin-8-yl, a 1,7-naphthyridin-2-yl group, a 1,7-naphthyridin-3-yl group, a 1,7-naphthyridin-4-yl group, a 1,7-naphthyridin-5-yl group, a 1,7-naphthyridin-6-yl group, a 1,7-naphthyridin-8-yl, a 1,8-naphthyridin-2-yl group, a 1,8-naphthyridin-3-yl group, a 1,8-naphthyridin-4-yl group, a 2,6-naphthyridin-1-yl group, a 2,6-naphthyridin-3-yl group, a 2,6-naphthyridin-4-yl group, a 2,7-naphthyridin-1-yl group, a 2,7-naphthyridin-3-yl group, a 2,7-naphthyridin-4-yl group, a 1-phthalazyl group, a 5-phthalazyl group, a 6-phthalazyl group, a 2-quinoxal group, a 5-quinoxal group, a 6-quinoxal group, a 2-quinazolyl group, a 4-quinazolyl group, a 5-quinazolyl group, a 6-quinazolyl group, a 7-quinazolyl group, a 8-quinazolyl group, a 3-cinnolyl group, a 4-cinnolyl group, a 5-cinnolyl group, a 6-cinnolyl group, a 7-cinnolyl group or a 8-cinnolyl group.

The azaanthracene group represented by substituent B, is not particularly limited, and may, for example, be a 2-benzo[g]quinolyl group, a 3-benzo[g]quinolyl group, a 4-benzo[g]quinolyl group, a 5-benzo[g]quinolyl group, a 6-benzo[g]quinolyl group, a 7-benzo[g]quinolyl, a 8-benzo[g]quinolyl group, a 9-benzo[g]quinolyl group, a 10-benzo[g]quinolyl group, a 1-benzo[g]isoquinolyl group, a 3-benzo[g]isoquinolyl group, a 4-benzo[g]isoquinolyl group, a 5-benzo[g]isoquinolyl group, 6-benzo[g]isoquinolyl group, a 7-benzo[g]isoquinolyl group, a 8-benzo[g]isoquinolyl group, a 9-benzo[g]isoquinolyl group or a 10-benzo[g]isoquinolyl group.

The diazaanthracene group represented by substituent B, is not particularly limited, and may, for example, be a 3-benzo[g]cinnolyl group, a 4-benzo[g]cinnolyl group, a 5-benzo[g]cinnolyl group, a 6-benzo[g]cinnolyl group, a 7-benzo[g]cinnolyl group, a 8-benzo[g]cinnolyl group, a 9-benzo[g]cinnolyl group, a 10-benzo[g]cinnolyl group, a 2-benzo[g]quinazolyl group, a 4-benzo[g]quinazolyl group, a 5-benzo[g]quinazolyl group, a 6-benzo[g]quinazolyl group, a 7-benzo[g]quinazolyl group, a 8-benzo[g]quinazolyl group, a 9-benzo[g]quinazolyl group, a 10-benzo[g]quinazolyl group, a 2-benzo[g]quinoxalyl group, a 3-benzo[g]quinoxalyl group, a 5-benzo[g]quinoxalyl group, a 6-benzo[g]quinoxalyl group, a 7-benzo[g]quinoxalyl group, a 8-benzo[g]quinoxalyl group, a 9-benzo[g]quinoxalyl group, a 10-benzo[g]quinoxalyl group, a 1-benzo[g]phthalazyl group, a 4-benzo[g]phthalazyl group, a 5-benzo[g]phthalazyl group, a 6-benzo[g]phthalazyl group, a 7-benzo[g]phthalazyl group, a 8-benzo[g]phthalazyl group, a 9-benzo[g]phthalazyl group, a 10-benzo[g]phthalazyl group, a 1,5-benzo[g]naphthyridin-2-yl group, a 1,5-benzo[g]naphthyridin-3-yl group, a 1,5-benzo[g]naphthyridin-4-yl group, a 1,5-benzo[g]naphthyridin-6-yl group, a 1,5-benzo[g]naphthyridin-7-yl group, a 1,5-benzo[g]naphthyridin-8-yl group, a 1,5-benzo[g]naphthyridine-9-yl group, a 1,5-benzo[g]naphthyridine-10-yl group, a 1,2-benzo[g]naphthyridin-3-yl group, a 1,2-benzo[g]naphthyridin-4-yl group, a 1,2-benzo[g]naphthyridin-5-yl group, a 1,2-benzo[g]naphthyridin-6-yl group, a 1,2-benzo[g]naphthyridin-7-yl group, a 1,2-benzo[g]naphthyridin-8-yl group, a 1,2-benzo[g]naphthyridin-9-yl group, a 2,5-benzo[g]naphthyridin-1-yl group, a 2,5-benzo[g]naphthyridin-3-yl group, a 2,5-benzo[g]naphthyridin-4-yl group, a 2,5-benzo[g]naphthyridin-6-yl group, a 2,5-benzo[g]naphthyridin-7-yl group, a 2,5-benzo[g]naphthyridin-8-yl group, a 2,5-benzo[g]naphthyridin-9-yl group, a 2,5-benzo[g]naphthyridin-10-yl group, a 2,10-benzo[g]naphthyridin-1-yl group, a 2,10-benzo[g]naphthyridin-3-yl group, a 2,10-benzo[g]naphthyridin-4-yl group, a 2,10-benzo[g]naphthyridin-5-yl group, a 2,10-benzo[g]naphthyridin-6-yl group, a 2,10-benzo[g]naphthyridin-7-yl group, a 2,10-benzo[g]naphthyridin-8-yl group, a 2,10-benzo[g]naphthyridin-9-yl group, a 9-pyridino[7,8,g]quinolin-2-yl group, a 9-pyridino[7,8,g]quinolin-3-yl group, a 9-pyridino[7,8,g]quinolin-4-yl group, a 9-pyridino[7,8,g]quinolin-5-yl group, a 9-pyridino[7,8,g]quinolin-10-yl group, a 6-pyridino[7,8,g]quinolin-2-yl group, a 6-pyridino[7,8,g]quinolin-3-yl group, a 6-pyridino[7,8,g]quinolin-4-yl group, a 6-pyridino[7,8,g]quinolin-5-yl group, a 7-pyridino[7,8,g]quinolin-2-yl group, a 7-pyridino[7,8,g]quinolin-3-yl group, a 7-pyridino[7,8,g]quinolin-4-yl group, a 7-pyridino[7,8,g]quinolin-5-yl group, a 7-pyridino[7,8,g]

quinolin-6-yl group, a 7-pyridino[7,8,g]quinolin-8-yl group, a 7-pyridino[7,8,g]quinolin-9-yl group, a 7-pyridino[7,8,g]quinolin-10-yl group, a 8-pyridino[7,8,g]quinolin-2-yl group, a 7-pyridino[7,8,g]quinolin-3-yl group, a 7-pyridino[7,8,g]quinolin-4-yl group, a 7-pyridino[7,8,g]quinolin-5-yl group, a 7-pyridino[7,8,g]quinolin-6-yl group, a 7-pyridino[7,8,g]quinolin-8-yl group, a 7-pyridino[7,8,g]quinolin-9-yl group, a 7-pyridino[7,8,g]quinolin-10-yl group, a 8-pyridino[7,8,g]quinolin-2-yl group, a 8-pyridino[7,8,g]quinolin-3-yl group, a 8-pyridino[7,8,g]quinolin-4-yl group, a 8-pyridino[7,8,g]quinolin-5-yl group, a 8-pyridino [7,8,h]quinolin-6-yl group, a 8-pyridino[7,8,g]quinolin-7-yl group, a 8-pyridino[7,8,g]quinolin-9-yl group, a 8-pyridino[7,8,g]quinolin-10-yl group, a 8-pyridino[7,8,g]isoquinolin-1-yl group, a 8-pyridino[7,8,g]isoquinolin-3-yl group, a 8-pyridino[7,8,g]isoquinolin-4-yl group, a 8-pyridino[7,8,f]isoquinoline-5-yl group, a 8-pyridino[7,8,g]isoquinoline-10-yl group, a 7-pyridino[7,8,g]isoquinolin-1-yl group, a 7-pyridino[7,8,g]isoquinolin-3-yl group, a 7-pyridino[7,8,g]isoquinolin-4-yl group or a 7-pyridino[7,8,g]isoquinolin-5-yl group.

The azaphenanthrene group represented by substituent B, is not particularly limited, and may, for example, be a 3-benzo[h]quinolyl group, a 4-benzo[h]quinolyl group, a 5-benzo[h]quinolyl group, a 6-benzo[h]quinolyl group, a 7-benzo[h]quinolyl, a 8-benzo[h]quinolyl group, a 9-benzo[h]quinolyl group, a 10-benzo[h]quinolyl group, a 1-benzo[h]isoquinolyl group, a 3-benzo[h]isoquinolyl group, a 4-benzo[h]isoquinolyl group, a 5-benzo[h]isoquinolyl group, a 6-benzo[h]isoquinolyl group, a 7-benzo[h]isoquinolyl group, a 8-benzo[h]isoquinolyl group, a 9-benzo[h]isoquinolyl group, a 10-benzo[h]isoquinolyl group, a 1-benzo[f]isoquinolyl group, a 2-benzo[f]isoquinolyl group, a 4-benzo[f]isoquinolyl group, a 5-benzo[f]isoquinolyl group, a 6-benzo[f]isoquinolyl group, a 7-benzo[f]isoquinolyl group, a 8-benzo[f]isoquinolyl group, a 9-benzo[f]isoquinolyl group, a 10-benzo[f]isoquinolyl group, a 1-benzo[f]quinolyl group, a 2-benzo[f]quinolyl group, a 3-benzo[f]quinolyl group, a 5-benzo[f]quinolyl group, a 6-benzo[f]quinolyl group, a 7-benzo[f]quinolyl, a 8-benzo[f]quinolyl group, a 9-benzo[f]quinolyl group, a 10-benzo[f]quinolyl group, a 1-phenanthridyl group, a 2-phenanthridyl group, a 3-phenanthridyl group, a 4-phenanthridyl group, a 6-phenanthridyl group, 7-phenanthridyl group, 8-phenanthridyl group, 9-phenanthridyl group or a 10-phenanthridyl group.

The diazaphenanthrene group represented by substituent B, is not particularly limited, and may, for example, be a 1,10-phenanthrolin-2-yl group, a 1,10-phenanthrolin-3-yl group, a 1,10-phenanthrolin-4-yl group, a 1,10-phenanthrolin-5-yl group, a 1,10-phenanthrolin-6-yl group, a 1,10-phenanthrolin-7-yl group, a 1,10-phenanthrolin-8-yl group, a 1,10-phenanthrolin-9-yl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-7-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,6-phenanthrolin-2-yl group, a 1,6-phenanthrolin-3-yl group, a 1,6-phenanthrolin-4-yl group, a 1,6-phenanthrolin-5-yl group, a 1,6-phenanthrolin-7-yl group, a 1,6-phenanthrolin-8-yl group, a 1,6-phenanthrolin-9-yl group, a 1,6-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,9-phenanthrolin-1-yl group, a 2,9-phenanthrolin-3-yl group, a 2,9-phenanthrolin-4-yl group, a 2,9 phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 3,7-phenanthrolin-1-yl group, a 3,7-phenanthrolin-2-yl group, a 3,7-phenanthrolin-4-yl group, a 3,7-phenanthrolin-5-yl group, a 3,7-phenanthrolin 6-yl group, a 3,7-phenanthrolin-8-yl group, a 3,7-phenanthrolin-9-yl group, a 3,7-phenanthrolin-10-yl group, a 3,8-phenanthrolin-1-yl group, a 3,8-phenanthrolin-2-yl group, a 3,8-phenanthrolin-4-yl group, a 3,8-phenanthrolin-5-yl group, a 3,8-phenanthroline-6-yl group, a 3,8-phenanthrolin-7-yl group, a 3,8-phenanthrolin-9-yl group, a 3,8-phenanthrolin-10-yl group, a 4,7-phenanthrolin-1-yl group, a 4,7-phenanthrolin-2-yl group, a 4,7-phenanthrolin-3-yl group, a 4,7-phenanthrolin-5-yl group, a 4,7-phenanthrolin-6-yl group, a 4,7-phenanthrolin-8-yl group, a 4,7-phenanthrolin-9-yl group, a 4,7-phenanthrolin-10-yl group, a 3-benzo[h]cinnolyl group, a 4-benzo[h]cinnolyl group, a 5-benzo[h]cinnolyl group, a 6-benzo[h]cinnolyl group, a 7-benzo[h]cinnolyl group, a 8-benzo[h]cinnolyl group, a 9-benzo[h]cinnolyl group, a 10-benzo[h]cinnolyl group, a 2-benzo[h]quinazolyl group, a 4-benzo[h]quinazolyl group, a 5-benzo[h]quinazolyl group, a 6-benzo[h]quinazolyl group, a 7-benzo[h]quinazolyl group, a 8-benzo[h]quinazolyl group, a 9-benzo[h]quinazolyl group, a 10-benzo[h]quinazolyl group, a 2-benzo[h]quinoxalyl group, a 3-benzo[h]quinoxalyl group, a 5-benzo[h]quinoxalyl group, a 6-benzo[h]quinoxalyl group, a 7-benzo[h]quinoxalyl group, a 8-benzo[h]quinoxalyl group, a 9-benzo[h]quinoxalyl group, a 10-benzo[h]quinoxalyl group, a 1-benzo[g]cinnolyl group, a 4-benzo[g]cinnolyl group, a 5-benzo[g]cinnolyl group, a 6-benzo[g]cinnolyl group, a 7-benzo[g]cinnolyl group, a 8-benzo[g]cinnolyl group, a 9-benzo[g]cinnolyl group, a 10-benzo[g]cinnolyl group, a 1-benzo[g]quinazolyl group, a 3-benzo[g]quinazolyl group, a 5-benzo[g]quinazolyl group, a 6-benzo[g]quinazolyl group, a 7-benzo[g]quinazolyl group, a 8-benzo[g]quinazolyl group, a 9-benzo[g]quinazolyl group, a 10-benzo[g]quinazolyl group, a 1-benzo[f]cinnolyl group, a 2-benzo[f]cinnolyl group, a 5-benzo[f]cinnolyl group, a 6-benzo[f]cinnolyl group, a 7-benzo[f]cinnolyl group, a 8-benzo[f]cinnolyl group, a 9-benzo[t]cinnolyl group, a 10-benzo[t]cinnolyl group, a 1,5-benzo[h]naphthyridin-2-yl group, a 1,5-benzo[h]naphthyridin-3-yl group, a 1,5-benzo[h]naphthyridin-4-yl group, a 1,5-benzo[h]naphthyridin-6-yl group, a 1,5-benzo[h]naphthyridin-7-yl group, a 1,5-benzo[h]naphthyridin-8-yl group, a 1,5-benzo[h]naphthyridin-9-yl group, a 1,5-benzo[h]naphthyridin-10-yl group, a 1,6-benzo[h]naphthyridin-2-yl group, a 1,6-benzo[h]naphthyridin-3-yl group, a 1,6-benzo[h]naphthyridin-4-yl group, a 1,6-benzo[h]naphthyridin-5-yl group, a 1,6-benzo[h]naphthyridin-7-yl group, a 1,6-benzo[h]naphthyridin-8-yl group, a 1,6-benzo[h]naphthyridin-9-yl group, a 1,6-benzo[h]naphthyridin-10-yl group, a 2,5-benzo[h]naphthyridin-1-yl group, a 2,5-benzo[h]naphthyridin-3-yl group, a 2,5-benzo[h]naphthyridin-4-yl group, a 2,5-benzo[h]naphthyridin-6-yl group, a 2,5-benzo[h]naphthyridin-7-yl group, a 2,5-benzo[h]naphthyridin-8-yl group, a 2,5-benzo[h]naphthyridin-9-yl group, a 2,5-benzo[h]naphthyridin-10-yl group, a 2,6-benzo[h]naphthyridin-1-yl group, a 2,6-benzo[h]naphthyridin-3-yl group, a 2,6-benzo[h]naphthyridin-4-yl group, a 2,6-benzo[h]naphthyridin-5-yl group, a 2,6-benzo[h]naphthyridin-7-yl group, a 2,6-benzo[h]naphthyridin-8-yl group, a 2,6-benzo[h]naphthyridin-9-yl group, a 2,6-benzo[h]naphthyridin-10-yl group, a 3,5-benzo[h]naphthyridin-1-yl group, a 3,5-benzo[h]naphthyridin-2-yl group, a 3,5-benzo[h]naphthyridin-4-yl group, a 3,5-benzo[h]naphthyridin-6-yl group, a 3,5-benzo[h]naphthyridin-7-yl group, a 3,5-benzo[h]naphthyridin-8-yl group, a 3,5-benzo[h]naphthyridin-9-yl group, a 3,5-benzo[h]naphthyridin-10-yl group, a 3,6-benzo[h]naphthyridin-1-yl group, a 3,6-benzo[h]naphthyridin-2-yl group, a 3,6-benzo[h]naphthyridin-4-yl group, a 3,6-benzo[h]naphthyridin-5-yl group, a 3,6-benzo[h]naphthyridin-7-yl group, a 3,6-benzo[h]naphthyridin-8-yl group, a 3,6-benzo[h]naphthyridin-9-yl group, a 3,6-benzo[h]naphthyridin-10-yl group, a 4,5-benzo[h]naphthyridin-1-yl group, a 4,5-benzo[h]naphthyridin-2-yl group, a 4,5-benzo[h]naphthyridin-3-yl group, a 4,5-benzo[h]naphthyridin-6-yl group, a 4,5-benzo[h]naphthyridin-7-yl group, a 4,5-benzo[h]naphthyridin-8-yl group, a 4,5-benzo[h]naphthyridin-9-yl group, a 4,5-benzo[h]naphthyridin-10-yl group, a 4,6-benzo[h]naphthyridin-1-yl group, a 4,6-benzo[h]naphthyridin-2-yl group, a 1,6-benzo[h]naphthyridin-3-yl group, a 4,6-benzo[h]naphthyridin-5-yl group, a 4,6-benzo[h]naphthyridin-7-yl group, a 4,6-benzo[h]naphthyridin-8-yl group, a 4,6-benzo[h]naphthyridin-9-yl group or a 4,6-benzo[h]naphthyridin-10-yl group.

The azapentadiene group represented by substituent B, is not particularly limited, and may, for example, be a 1-pyrrole group, a 2-pyrrole group or a 3-pyrrole group.

The oxaazapentadiene group represented by substituent B, is not particularly limited, and may, for example, be a 2-oxazole group, a 4-oxazole, a 5-oxazole, a 4-isoxazole group or a 5-isoxazole group.

The thiaazapentadiene group represented by substituent B, is not particularly limited, and may, for example, be a 2-thiazole group, a 4-thiazole group, a 5-thiazole group, a 4-isothiazole group or a 5-isothiazole group.

The diazapentadiene group represented by substituent B, is not particularly limited, and may, for example, be a 2-imidazole group, a 3-imidazole group, a 4-imidazole group, a 5-imidazole group, a 2-pyrazole group, a 3-pyrazole group, a 4-pyrazole group or a 5-pyrazole group.

The oxadiazapentadiene group represented by substituent B, is not particularly limited, and may, for example, be a 4-aoxadiazole group.

The thiodiazapentadiene group represented by substituent B, is not particularly limited, and may, for example, be a 4-thiadiazole group.

The azaindene group represented by substituent B, is not particularly limited, and may, for example, be a 1-indole group, a 3-indole group, a 4-indole group, a 5-indole group, a 6-indole group or a 7-indole group.

The oxaazaindene group represented by substituent B, is not particularly limited, and may, for example, be a 4-benzoxazole group, a 5-benzoxazole group, a 6-benzoxazole group, a 7-benzoxazole group, a 4-benzisoxazole group, a 5-benzisoxazole group, a 6-benzisoxazole group or a 7-benzisoxazole group.

The thioazaindene group represented by substituent B, is not particularly limited, and may, for example, be a 4-benzothiazole group, a 5-benzothiazole group, a 6-benzothiazole group, a 7-benzothiazole group, a 4-benzoisothiazole group, a 5-benzoisothiazole group, a 6-benzoisothiazole group or a 7-benzoisothiazole group.

The diazaindene group represented by substituent B, may, for example, be a 3-benzimidazole group, a 4-benzimidazole group, a 5-benzimidazole group, a 6-benzimidazole group or a 7-benzimidazole group.

In substituent B, the substituent present on at least one carbon atom among the carbon atoms adjacent to a nitrogen atom, is not particularly limited, and may, for example, be an alkyl group (e.g. a $C_{1-12}$ alkyl group), an alkoxyl group (e.g. a methoxy group, an ethoxy group, a tert-butoxy group, etc.), a halogen group (e.g. fluorine, chlorine, bromine or iodine), an amino group (e.g. an amino group, a dimethylamino group, a diphenylamino group, a ditolylamino group, a bis-biphenyl-amino group, etc.), phosphyl group (e.g. a methyl phosphyl group, a dimethylphosphyl group, a trimethyl phosphyl group, a triphenylphosphyl group, etc.), a silyl group, a thiol group or an acyl group (e.g. a methanoyl group, an ethanoyl group, a apropanoyl group, a cyclohexanoyl group, a benzoyl group, a pyridinoyl group, etc.), and from the viewpoint of long service life of the organic electroluminescent device, an alkyl group is particularly preferred.

The alkyl group is preferably a $C_{1-12}$ alkyl group, and although not particularly limited, it may, for example, be a methyl group, an ethyl group, a n-propyl group, an isopropyl group, a n-butyl group, a sec-butyl group, a tert-butyl group, a n-pentyl group, a 1-methyl-1-butyl group, a 2-methylbutyl group, a 3-methylbutyl group, a 1,1-dimethylpropyl group, a 1,2-dimethylpropyl group, a 2,2-dimethylpropyl group, a n-hexyl group, a 1-methylpentyl group, a 1,2-dimethylbutyl group, a 1,3-dimethylbutyl group, a 1,2,2-trimethylpropyl group, a 1,1-dimethylbutyl group, a 1,1,2-trimethylpropyl group, a 2-methylpentyl group, a 2,3-dimethylbutyl group, a 2,2-dimethylbutyl group, a 3-methylpentyl group, a 3,3-dimethylbutyl group, a 1-ethylbutyl group, a 1-ethyl-2-methylpropyl group, a 1-ethyl-1-methylpropyl group, a n-heptyl, a n-octyl group, a n-nonyl group, a n-decyl group, a n-undecyl group, a n-dodecyl group, a cyclopentyl group, a cyclohexyl group, a cycloheptyl group, a cyclooctyl group, a cyclononyl group, a cyclodecyl group, a cycloundecyl group or a cyclododecyl group. Particularly from the viewpoint of good performance of the organic electroluminescent device, a methyl group, an ethyl group, a n-propyl group, an isopropyl group, a n-butyl group, a sec-butyl group, or a tert-butyl group is preferred, and from the viewpoint of easy synthesis, a methyl group is more preferred.

That is, from the viewpoint of long service life of the organic electroluminescent device, each substituent B is preferably independently a substituent selected from the group consisting of an azabenzene group, a diazabenzene group, an azanaphthalene group, a diazanaphthalene group, an azaanthracene group, a diazaanthracene group, an azaphenanthrene group, a diazaphenanthrene group, an azapentadiene group, a diazapentadiene group, an oxaazapentadiene group, a thiaazapentadiene group, an oxadiazapentadiene group, a thiodiazapentadiene group, an azaindene group, an oxaazaindene group, a thioazaindene group and a diazaindene group, having a methyl group on at least one carbon atom among carbon atoms adjacent to a nitrogen atom.

Further, from the viewpoint of long service life of the organic electroluminescent device, each substituent B is more preferably independently a pyridyl group, a pyrimidyl group, a pyridazyl group, a pyrazyl group, a quinolyl group, an isoquinolyl group, a quinazolyl group, a quinoxalyl group, a naphthyridyl group, a benzoquinolyl group, a benzoisoquinolyl group, a phenanthridyl group, a phenanthrolyl group, a benzocinnolyl group, a benzoquinazolyl group, a benzonaphthyridyl group, a pyrrole group, an oxazole groups, an isoxazole group, a thiazole group, an isothiazole group, an imidazole group, a pyrazole group, an oxadiazole group, a thiadiazole group, an indole group, a benzoxazole group, a benzothiazole group or a benzimidazole group, having a methyl group on at least one carbon atom among carbon atoms adjacent to a nitrogen atom.

Furthermore, from the viewpoint of long service life of the organic electroluminescent device, each substituent B is further preferably independently a pyridyl group, a pyrimidyl group, a pyrazyl group, a quinolyl group, an isoquinolyl group, a quinazolyl group, a quinoxalyl group, a phenanthridyl group, a phenanthrolyl group, a pyrrole group, an oxazole group, a thiazole group, an imidazole group, a pyrazole group, a thiadiazole group, an indole group or a benzimidazole group, having a methyl group on at least one carbon atom among carbon atoms adjacent to a nitrogen atom.

Further, from the viewpoint of long service life of the organic electroluminescent device, each substituent B is still more preferably independently an azabenzene group, a diazabenzene group or an azanaphthalene group, having a methyl group on at least one carbon atom among carbon atoms adjacent to a nitrogen atom.

Further, from the viewpoint of long service life of the organic electroluminescent device, each substituent B is still further preferably independently a 6-methylpyridin-2-yl group, a 6-methyl-pyridin-3-yl group, a 2-methyl-pyridin-3-yl group, a 4,6-dimethyl-pyrimidin-2-yl group, a 2-methyl-quinolin-8-yl group, a 3-methyl-isoquinolin-1-yl group or a 2,3-dimethyl-quinoxalin-6-yl group.

Further, as substituent B, more specifically, the following heteroaryl groups may, for example, be mentioned, although it is not particularly limited thereto.

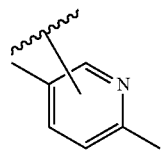
B-1

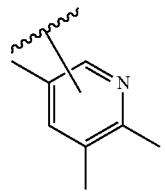
B-2

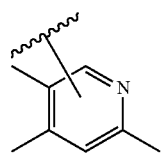
B-3

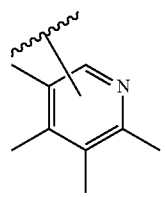
B-4

-continued

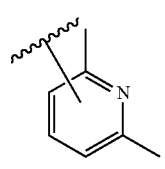
B-5

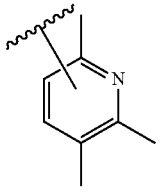
B-6

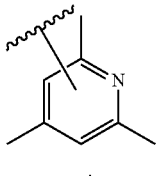
B-7

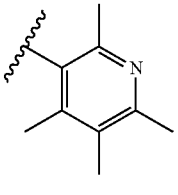
B-8

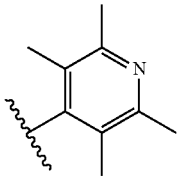
B-9

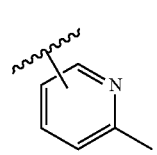
B-10

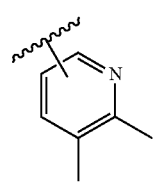
B-11

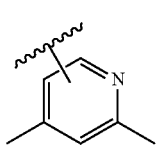
B-12

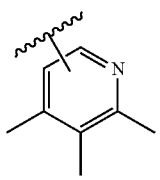
B-13

-continued
B-14 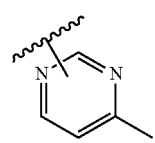
B-15 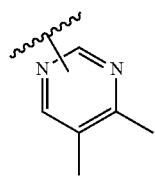
B-16 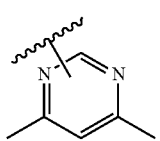
B-17 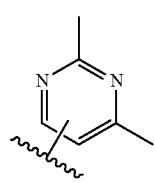
B-18 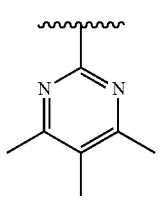
B-19 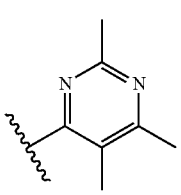
B-20 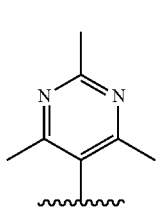
B-21 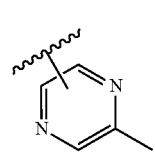
B-22 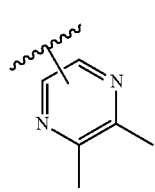
-continued
B-23 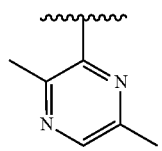
B-24 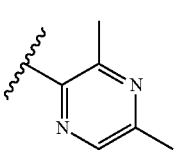
B-25 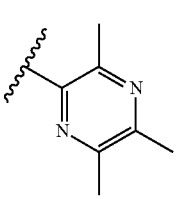
B-26 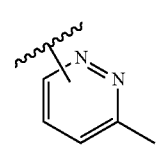
B-27 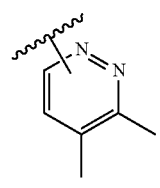
B-28 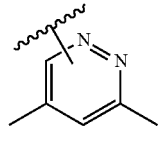
B-29 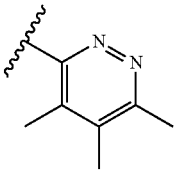
B-30 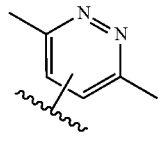
B-31 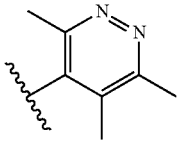

-continued
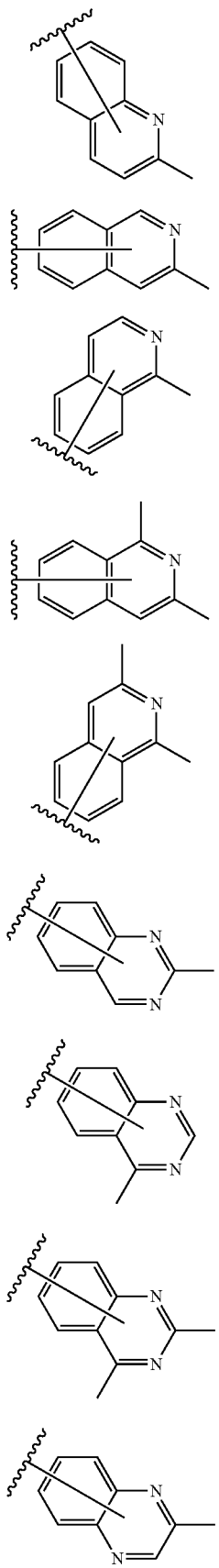
B-32
B-33
B-34
B-35
B-36
B-37
B-38
B-39
B-40
-continued
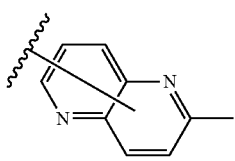
B-41
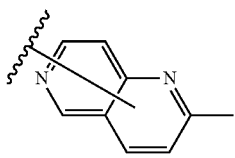
B-42
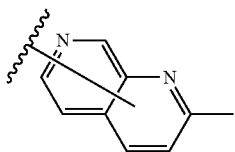
B-43
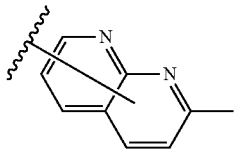
B-44
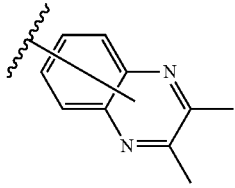
B-45
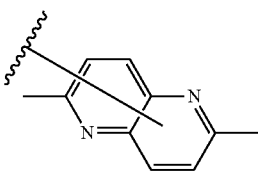
B-46
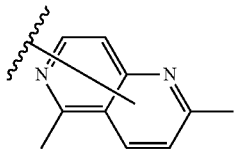
B-47
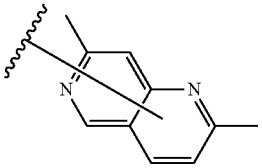
B-48
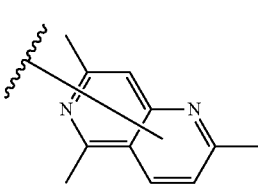
B-49

| | |
|---|---|
| 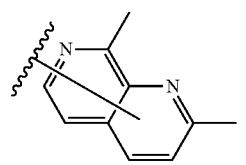 | B-50 |
| 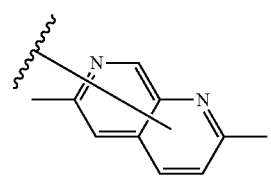 | B-51 |
| 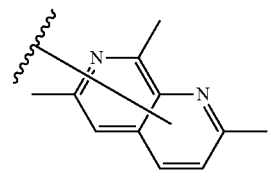 | B-52 |
| 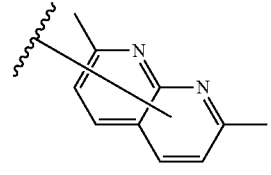 | B-53 |
| 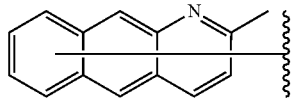 | B-54 |
| 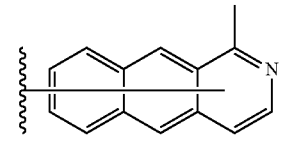 | B-55 |
| 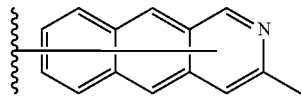 | B-56 |
| 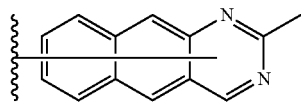 | B-57 |
| 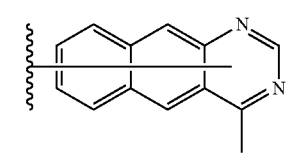 | B-58 |
| 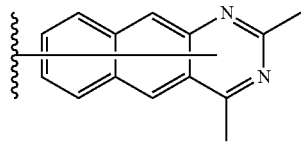 | B-59 |
| 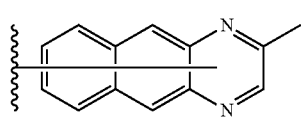 | B-60 |
| | |
|---|---|
| 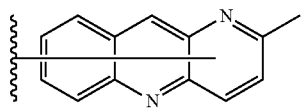 | B-61 |
| 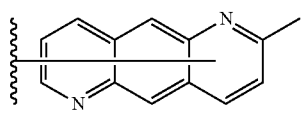 | B-62 |
| 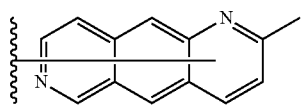 | B-63 |
| 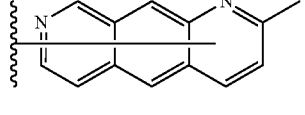 | B-64 |
| | B-65 |
| 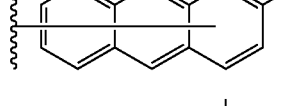 | B-66 |
| 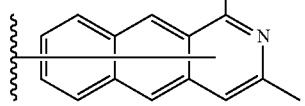 | B-67 |
| 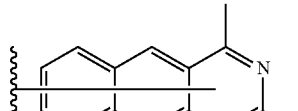 | B-68 |
| 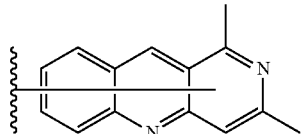 | B-69 |
| 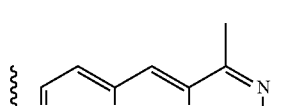 | B-70 |
| 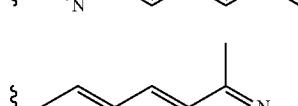 | B-71 |
| 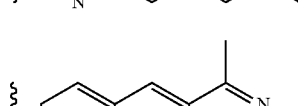 | B-72 |

B-73 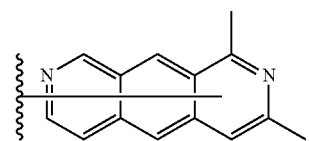
B-74 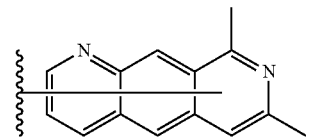
B-75 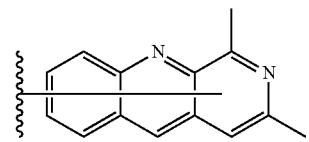
B-76 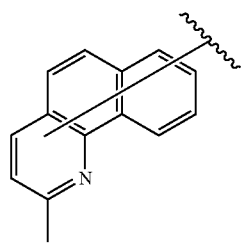
B-77 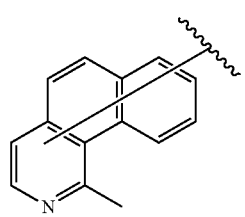
B-78 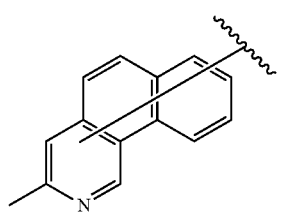
B-79 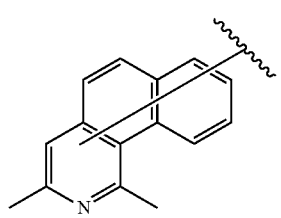
B-80 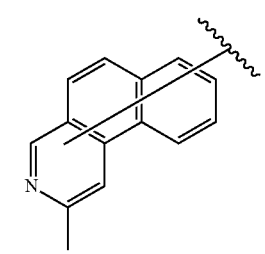
B-81 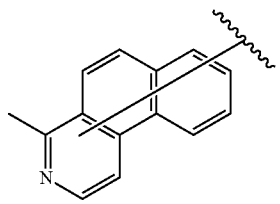
B-82 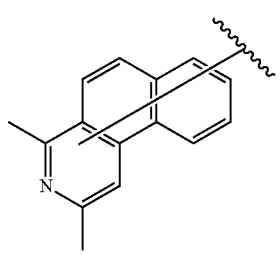
B-83 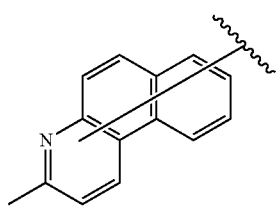
B-84 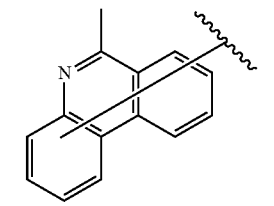
B-85 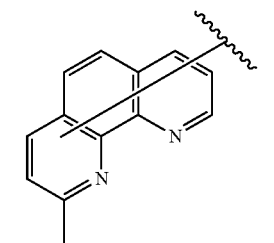
B-86 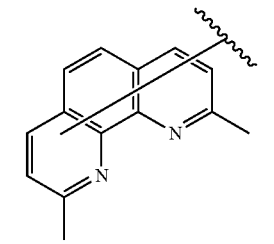
B-87 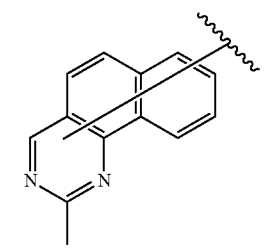

B-88 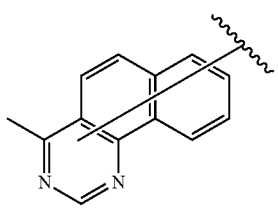
B-89 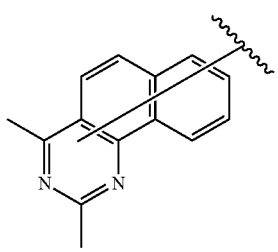
B-90 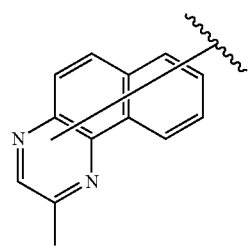
B-91 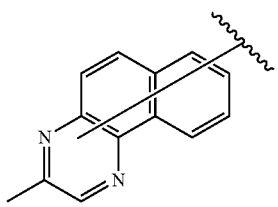
B-92 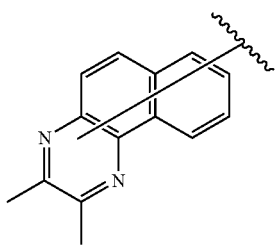
B-93 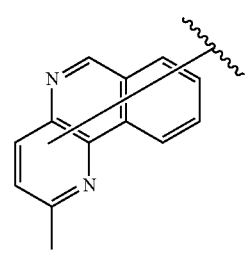
B-94 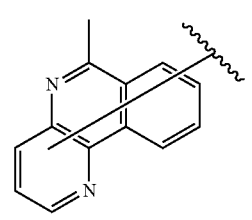
B-95 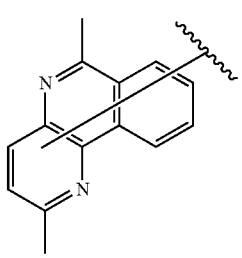
B-96 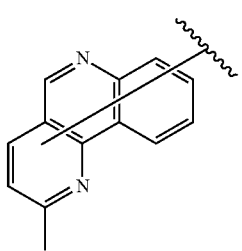
B-97 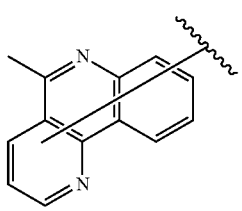
B-98
B-99 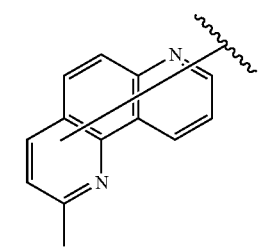
B-100 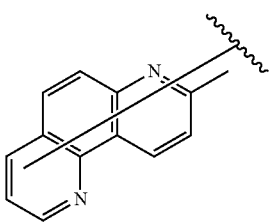

B-101
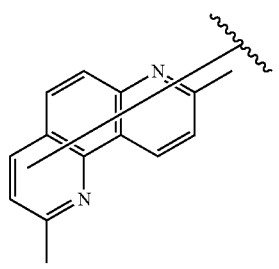
B-102
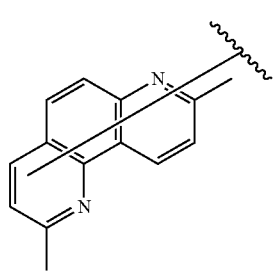
B-103
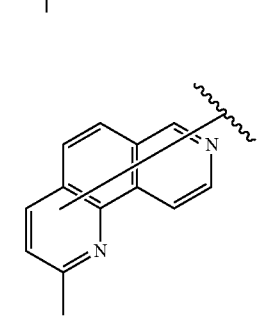
B-104
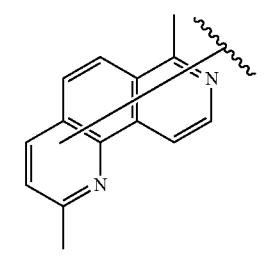
B-105
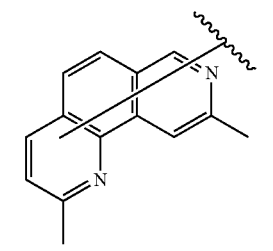
B-106
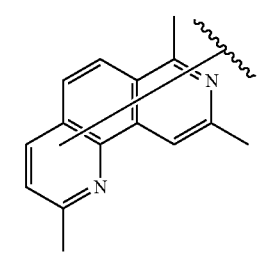
B-107
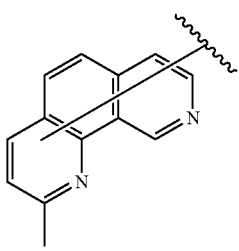
B-108
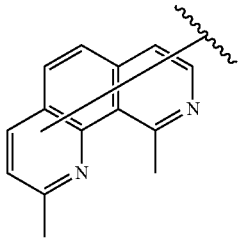
B-109
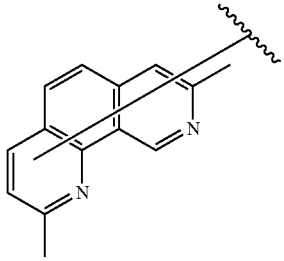
B-110
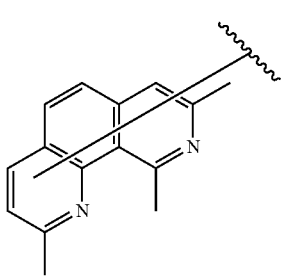
B-111
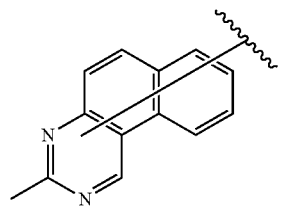
B-112
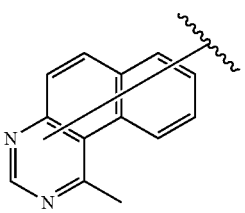

B-113 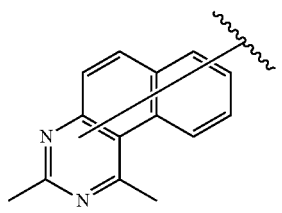
B-114 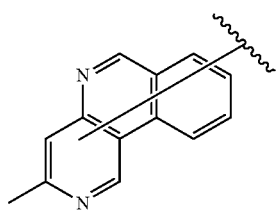
B-115 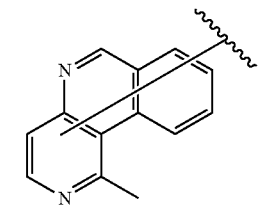
B-116 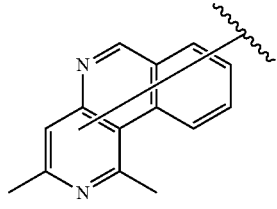
B-117 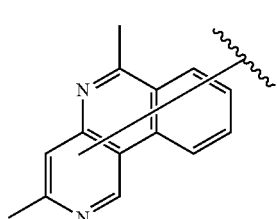
B-118 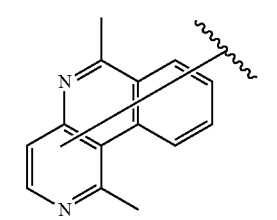
B-119
B-120 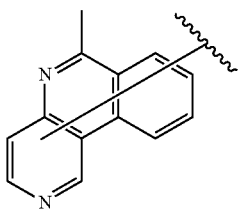
B-121 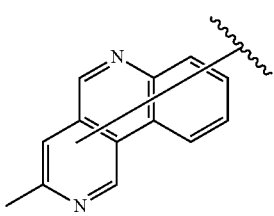
B-122 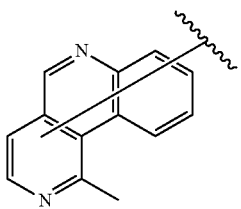
B-123 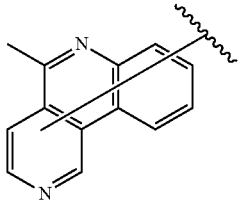
B-124 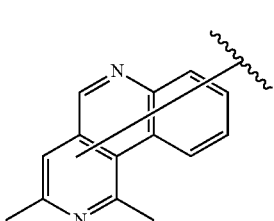
B-125 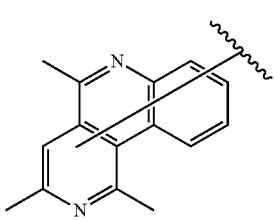
B-126 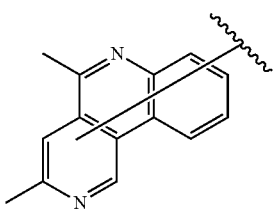

B-127
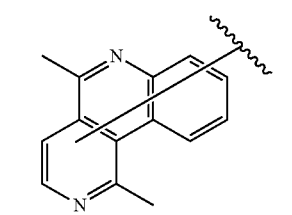
B-128
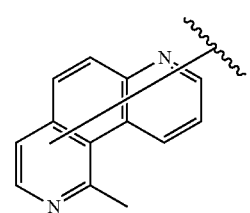
B-129
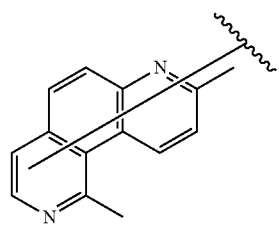
B-130
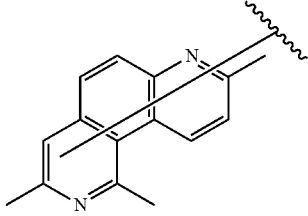
B-131
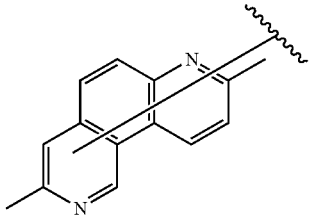
B-132
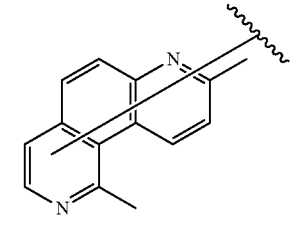
B-133
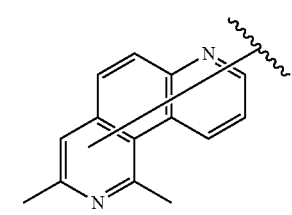
B-134
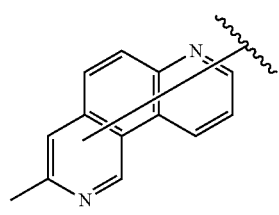
B-135
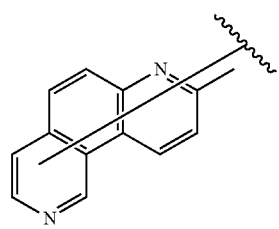
B-136
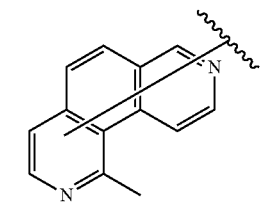
B-136
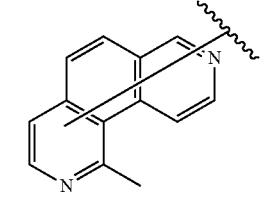
B-137
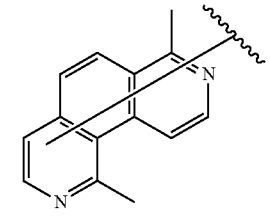
B-138
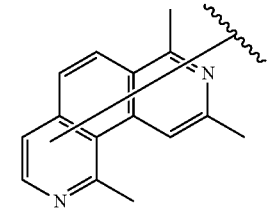
B-136
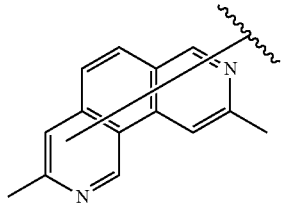

B-137 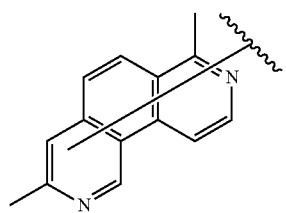
B-138 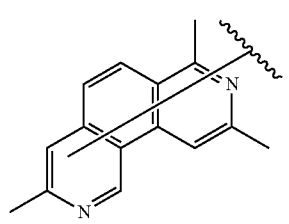
B-139 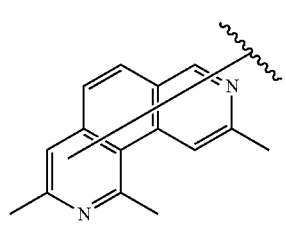
B-140 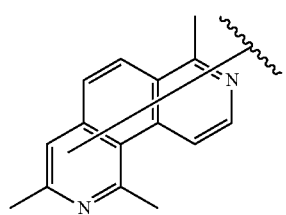
B-141 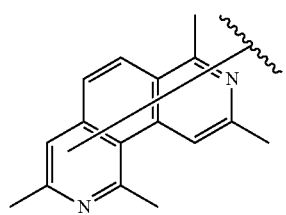
B-142
B-143 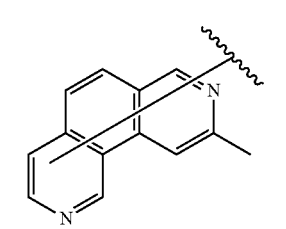
B-144 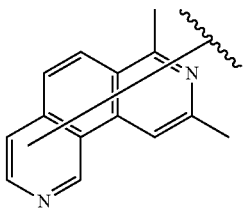
B-145 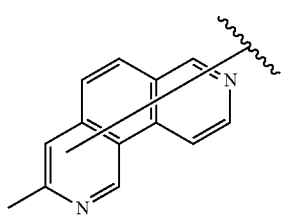
B-146 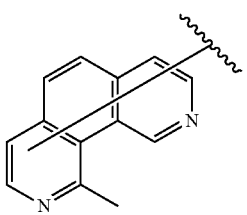
B-147 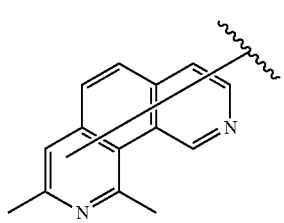
B-148 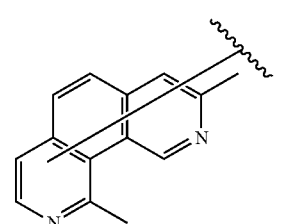
B-149 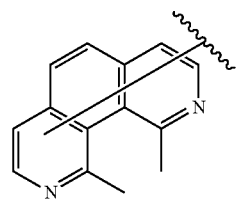
B-150 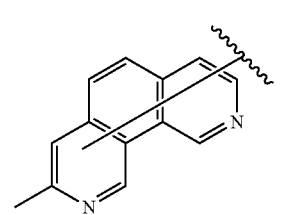

| | |
|---|---|
| B-151 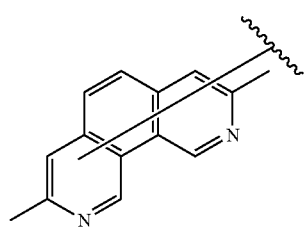 | B-159 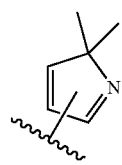 |
| B-152 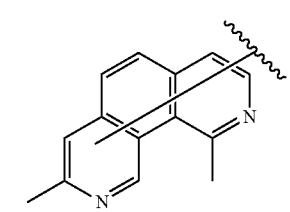 | B-160 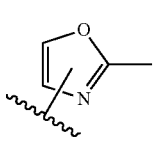 |
| B-153 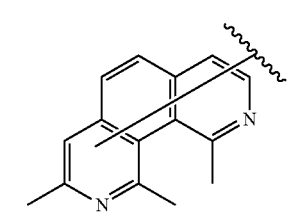 | B-161 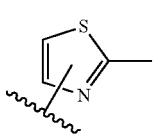 |
| B-154 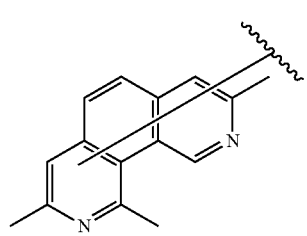 | B-162 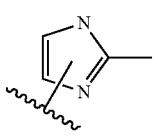 |
| B-155 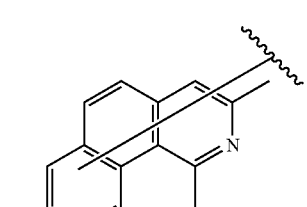 | B-163 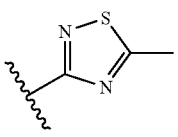 |
| B-156 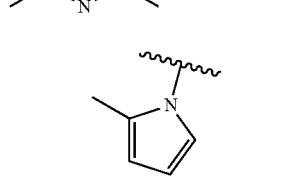 | B-164 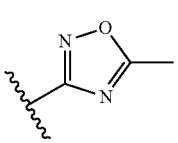 |
| B-157 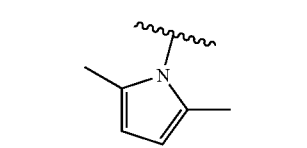 | B-165 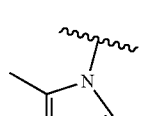 |
| B-158 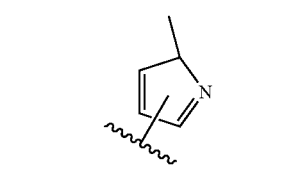 | B-166 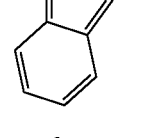 |
| | B-167 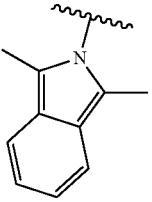 |
| | B-168 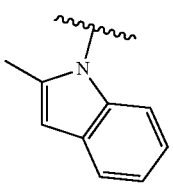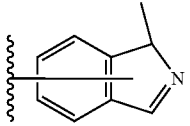 |

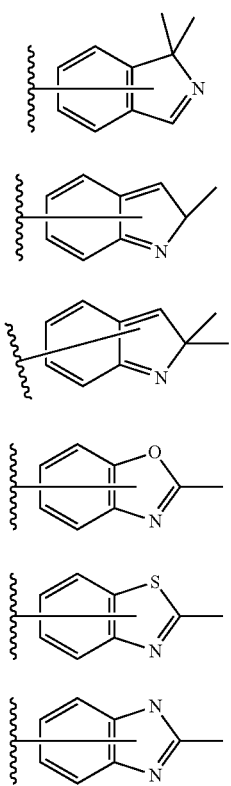
B-169
B-170
B-171
B-172
B-173
B-174
Among these, the following heteroaryl groups are preferred as substituent B from the viewpoint of long service life of the organic electroluminescent device.
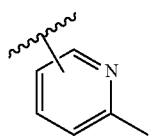 B-1
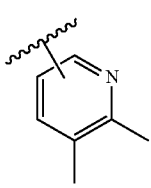 B-2
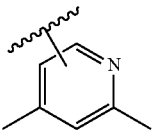 B-3
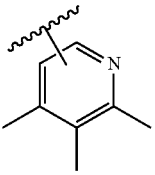 B-4
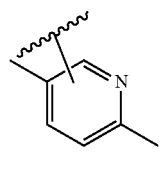 B-5
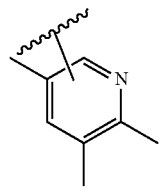 B-6
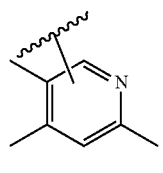 B-7
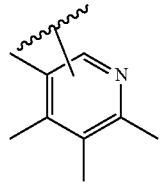 B-8
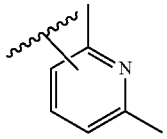 B-9
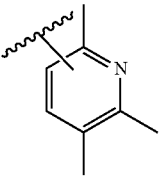 B-10
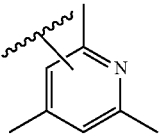 B-11
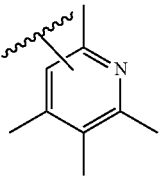 B-12
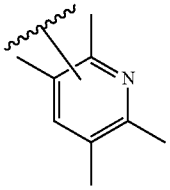 B-13

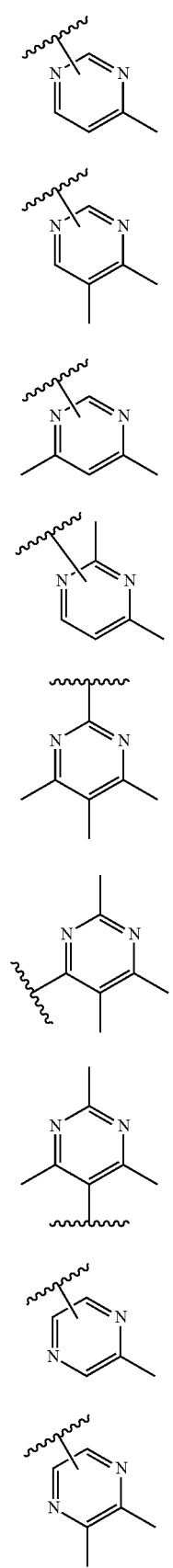
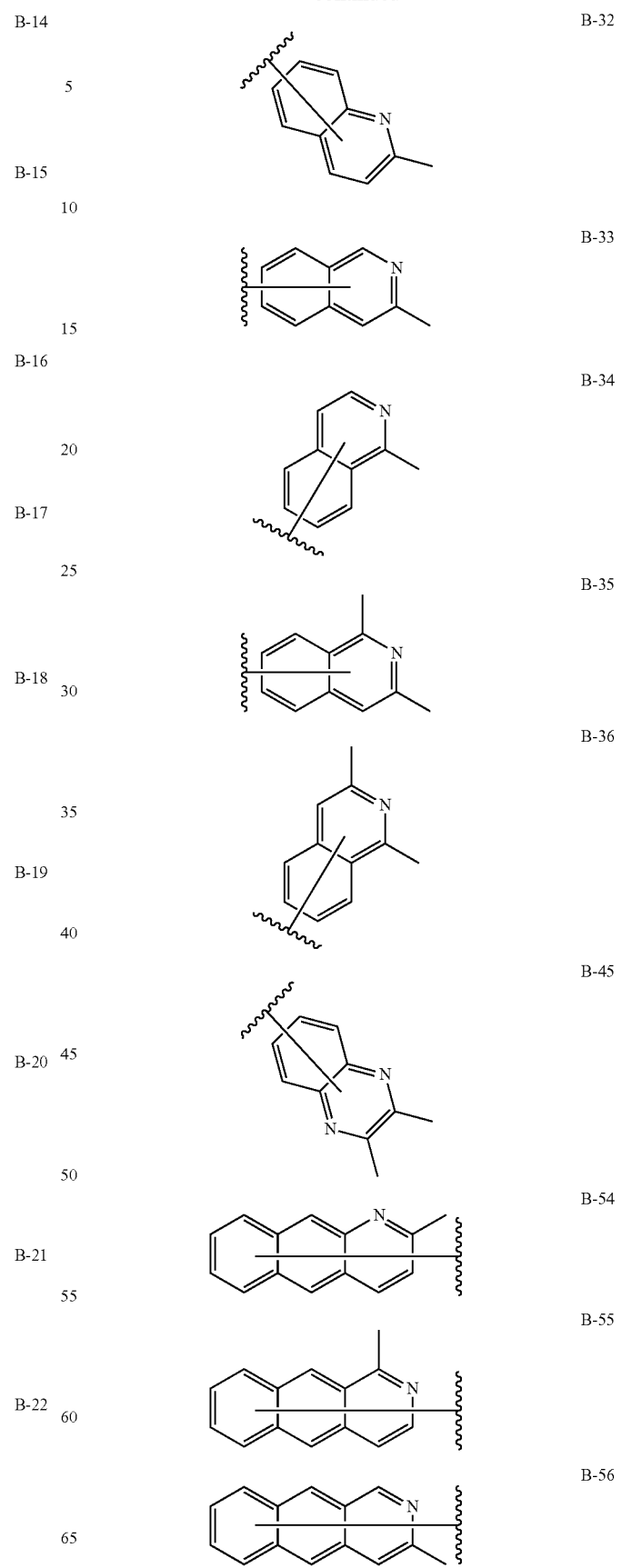

B-76 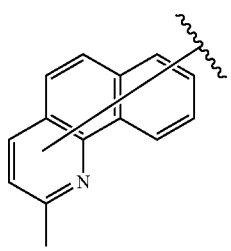
B-85 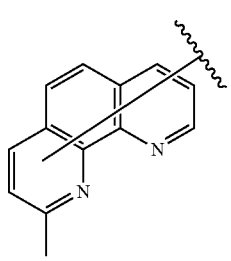
B-86 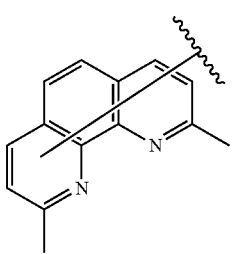
B-156 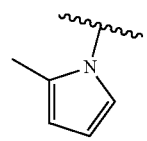
B-157 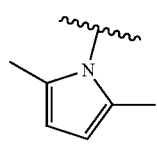
B-160 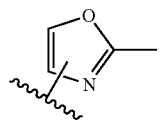
B-161 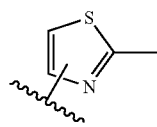
B-162 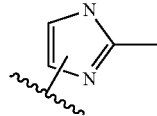
B-165 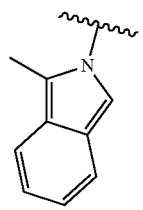
B-166 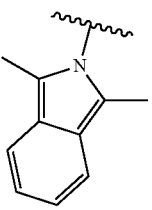
B-167 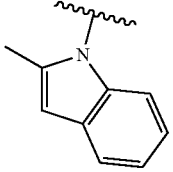
B-172 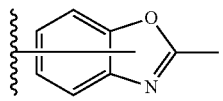
B-173 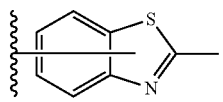
B-174 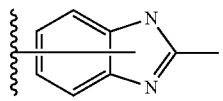
Further, from the viewpoint of easy synthesis, the following heteroaryl groups are preferred as substituent B.
B-1 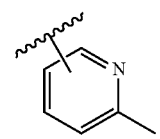
B-3 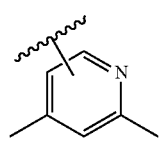
B-9 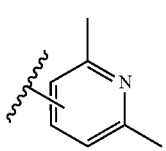

B-16

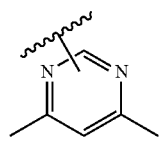

B-32

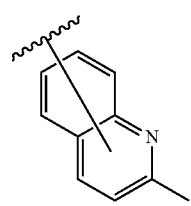

B-33

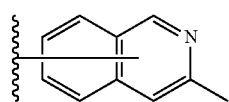

B-34

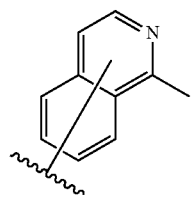

From the viewpoint of long service life of the organic electroluminescent device, compound A is preferably a compound which has, in addition to at least one substituent B, at least one substituent (hereinafter referred to as "substituent C") selected from the group consisting of a triaryl pyrimidine group and a triaryl triazine group (each aryl group in the triaryl pyrimidine group and in the triaryl triazine group is independently a $C_{6-12}$ aromatic hydrocarbon group which may be substituted by a $C_{1-4}$ alkyl group).

As the triaryl pyrimidine group represented by substituent C, the following substituents may, for example, be mentioned, although it is not particularly limited thereto.

C-1

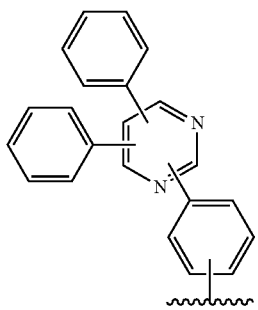

C-2

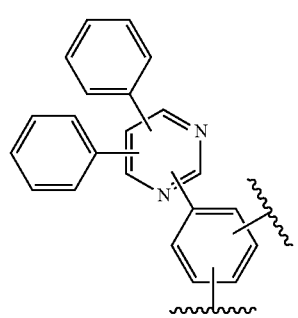

C-3

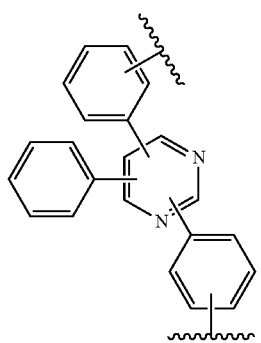

C-4

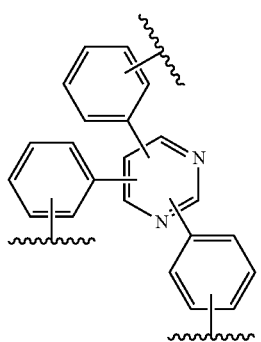

C-5

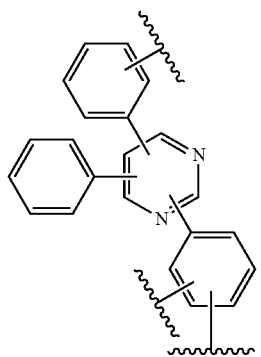

C-6 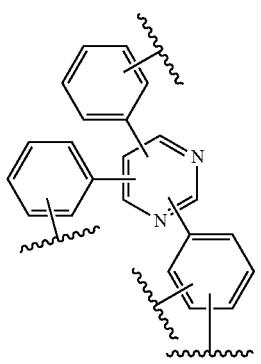
C-7 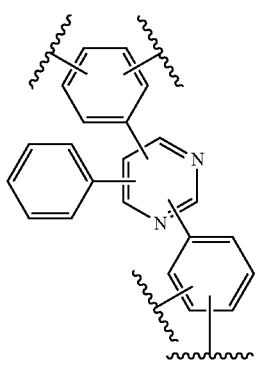
C-8 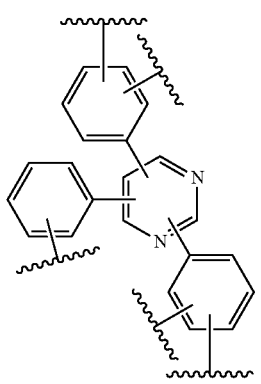
C-9 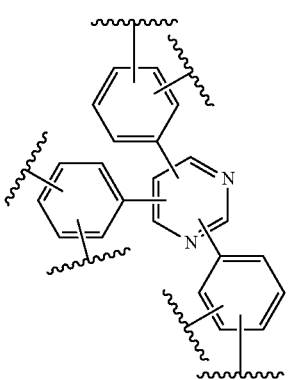
C-10 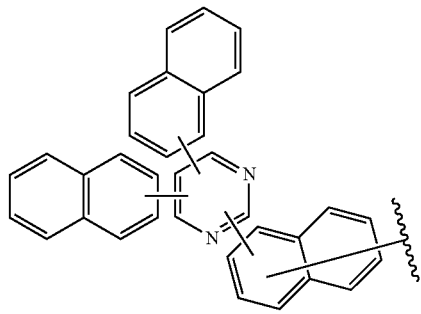
C-11 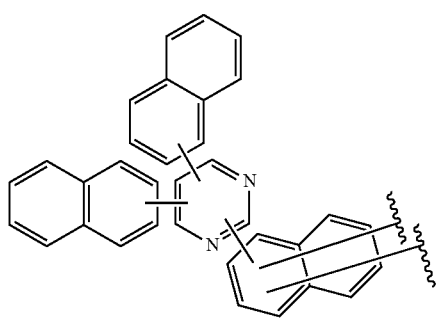
C-12 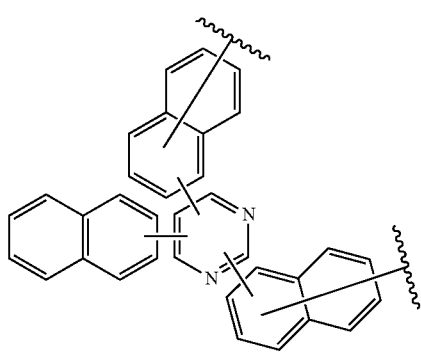
C-13 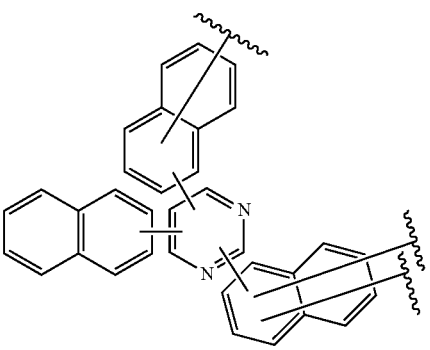

-continued
C-14
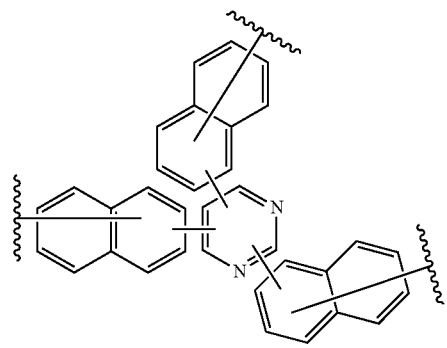
C-15
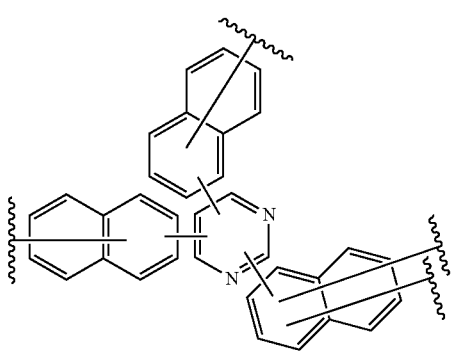
C-16
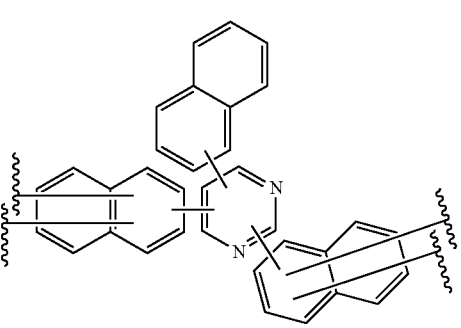
C-17
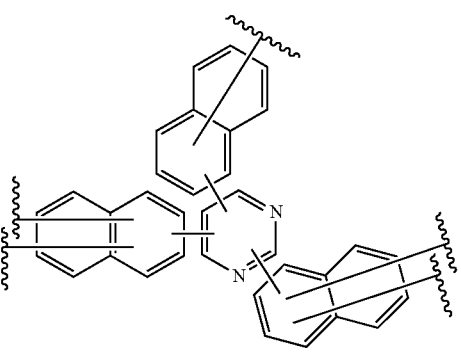
C-18
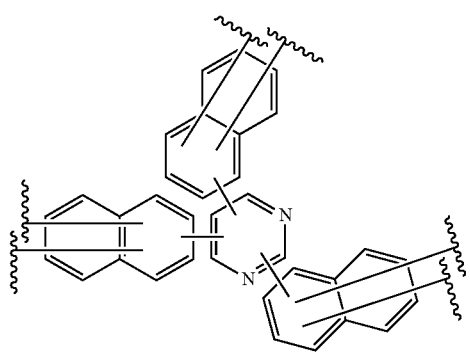
C-19
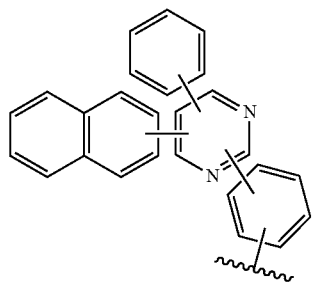
C-20
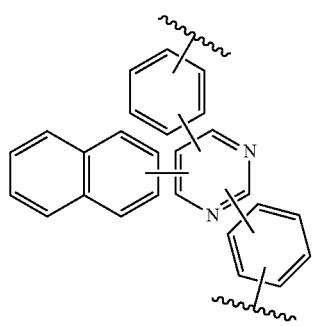
C-21
C-22
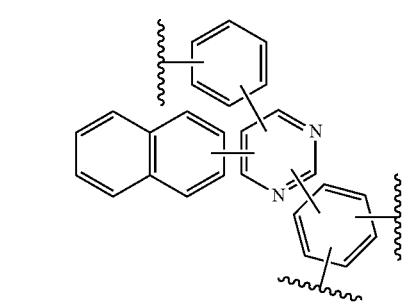

C-23
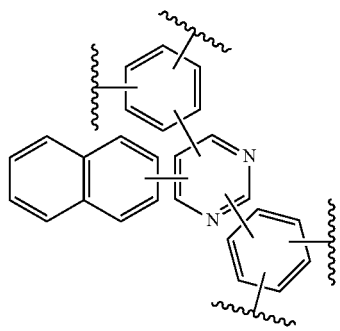
C-24
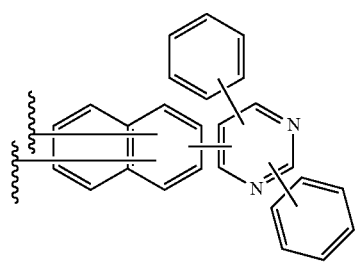
C-25
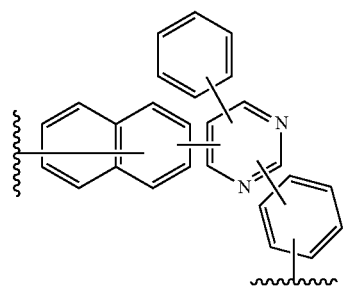
C-26
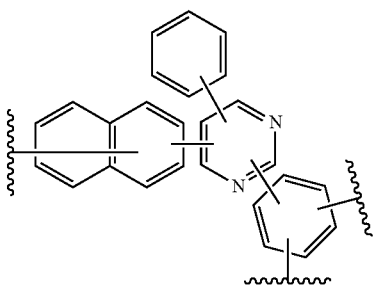
C-27
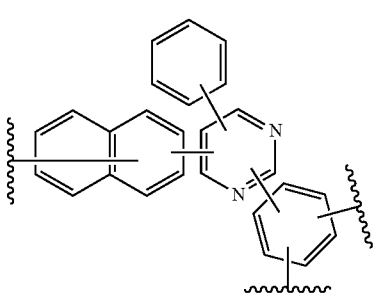
C-28
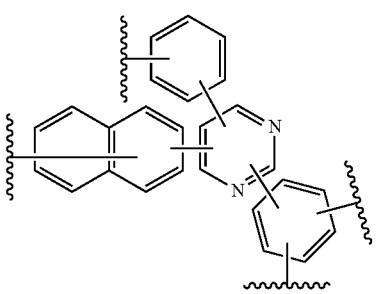
C-29
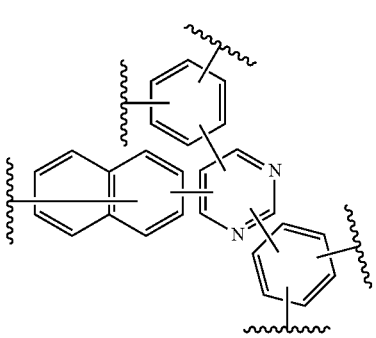
C-30
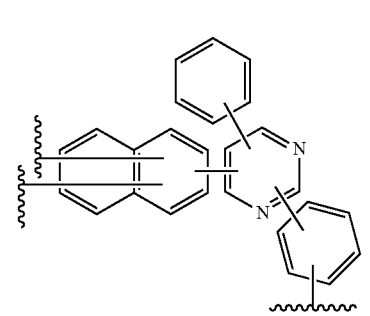
C-31
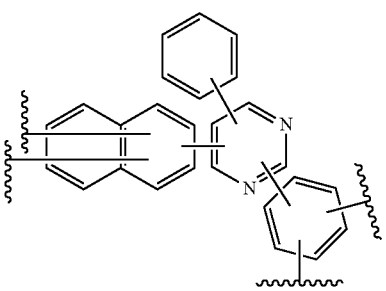
C-32
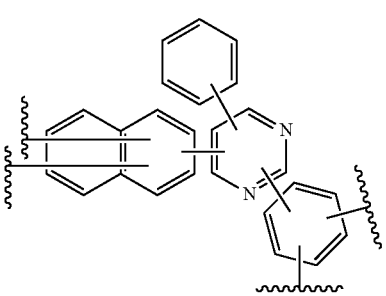

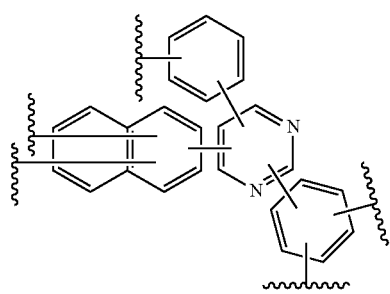
C-33
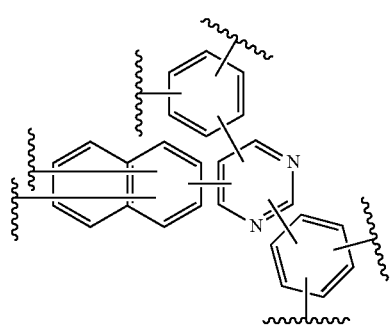
C-34
Among these, the following triaryl pyrimidine groups are preferred from the viewpoint of long service life of the organic electroluminescent device.
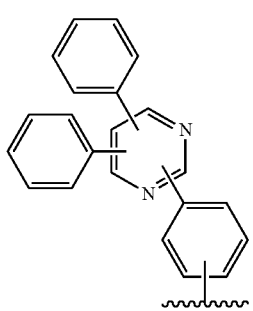
C-1
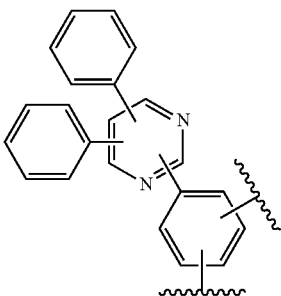
C-2
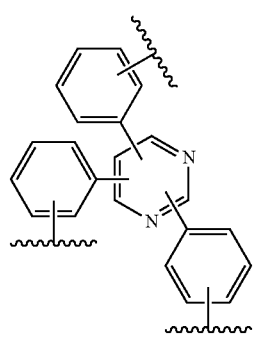
C-3
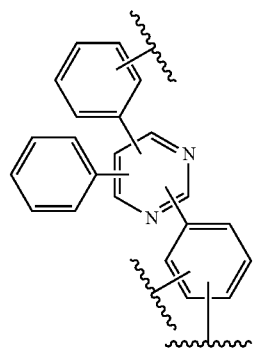
C-4
C-5
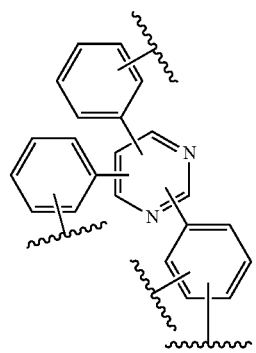
C-6

C-7
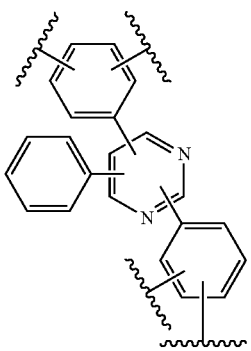
C-36
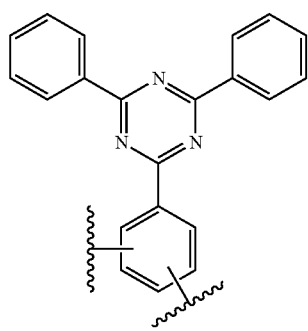
C-8
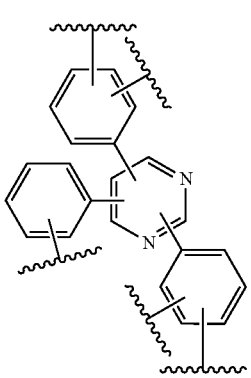
C-37
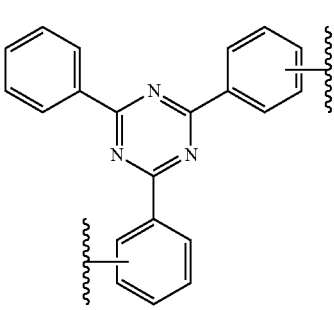
C-9
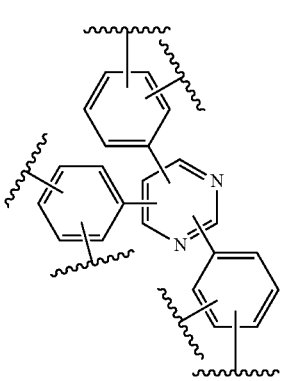
C-38
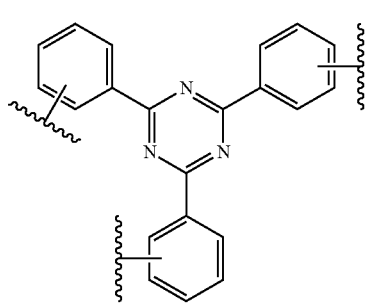
C-39
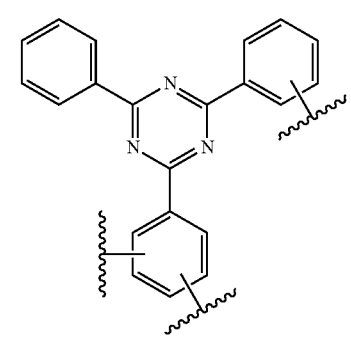
As the triaryl triazine group represented by substituent C, the following substituents may, for example, be mentioned, although it is not particularly limited thereto.
C-35
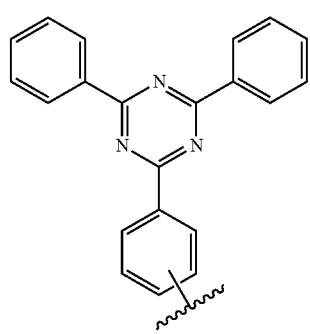
C-40
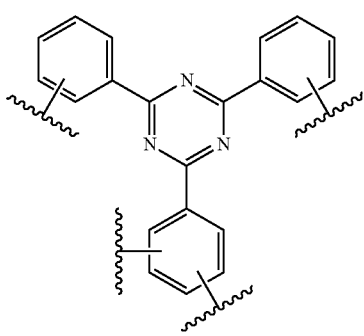

C-41
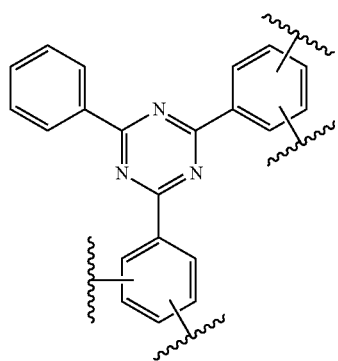
C-42
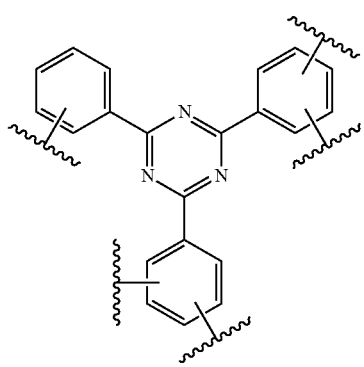
C-43
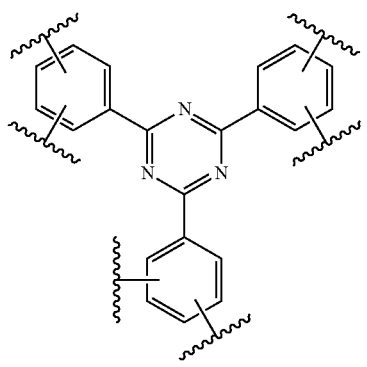
C-44
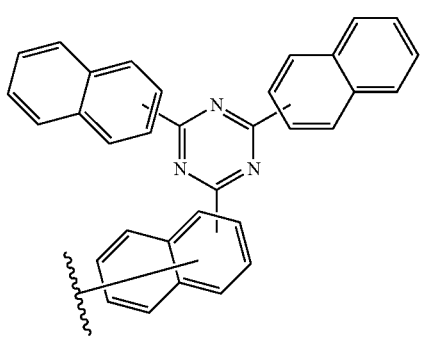
C-45
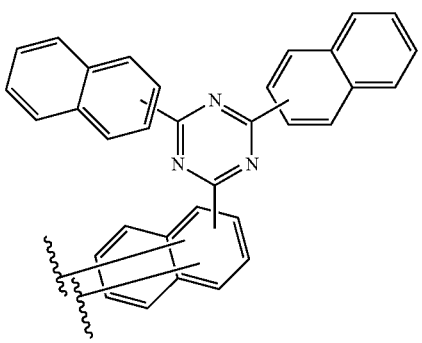
C-46
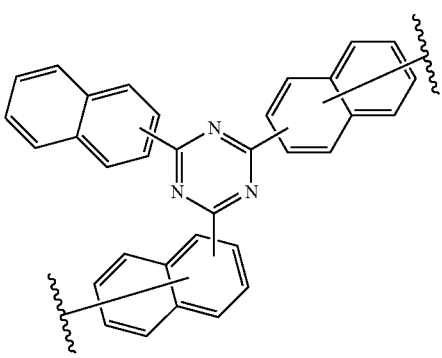
C-47
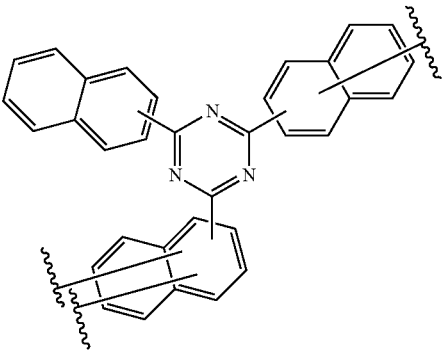
C-48
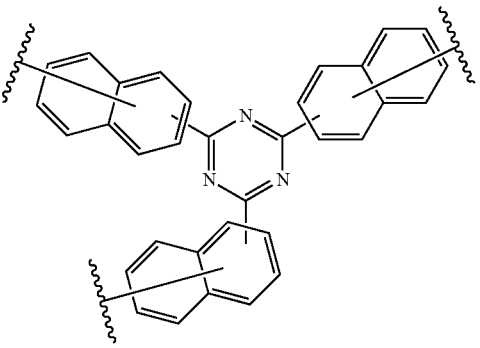

-continued
C-49
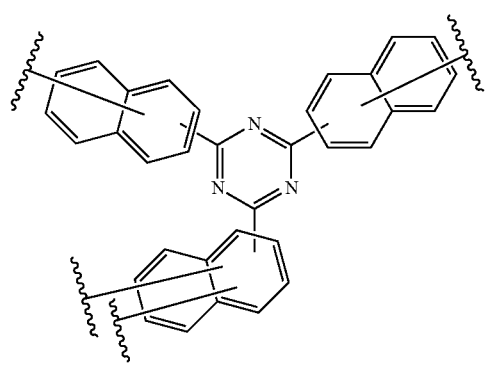
C-50
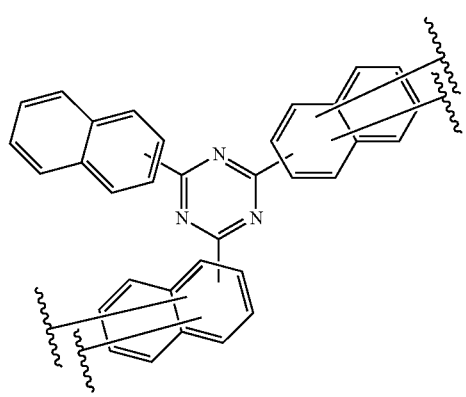
C-51
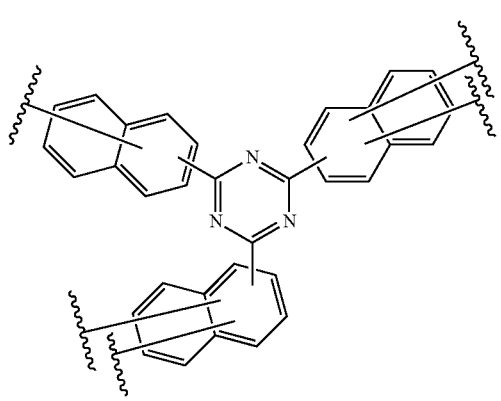
C-52
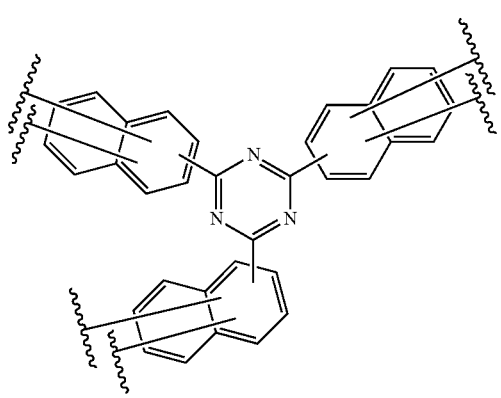
-continued
C-53
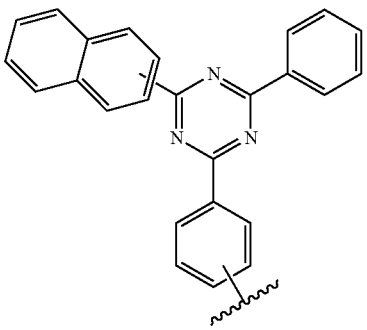
C-54
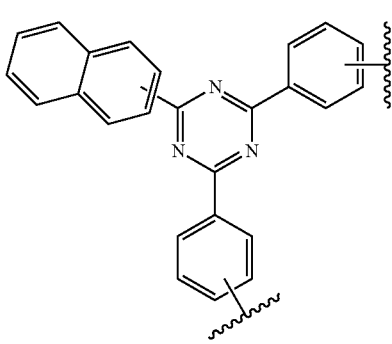
C-55
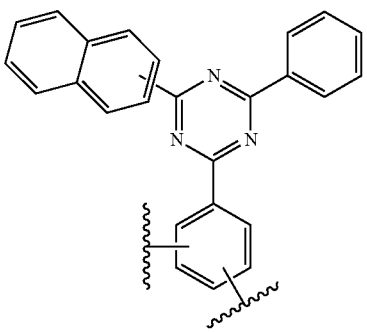
C-56
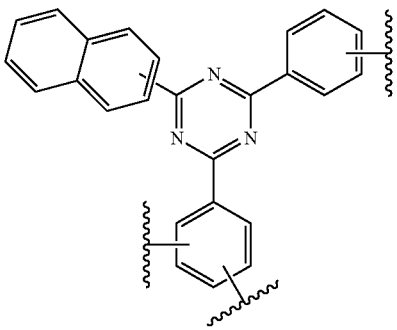

-continued
C-57
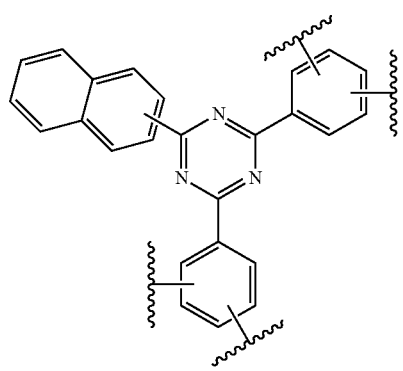
C-58
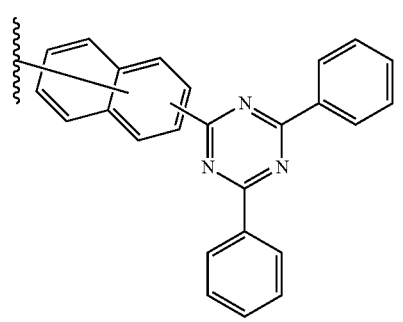
C-59
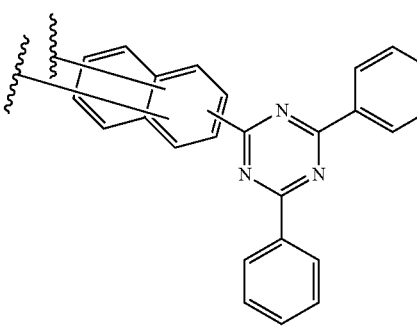
C-60
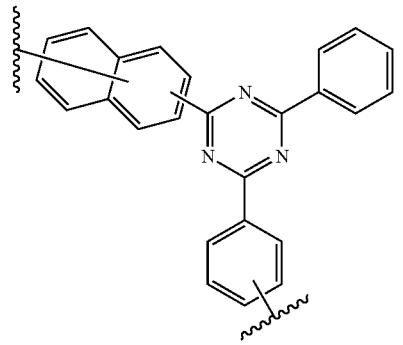
-continued
C-61
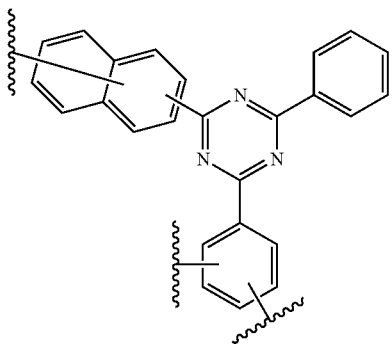
C-62
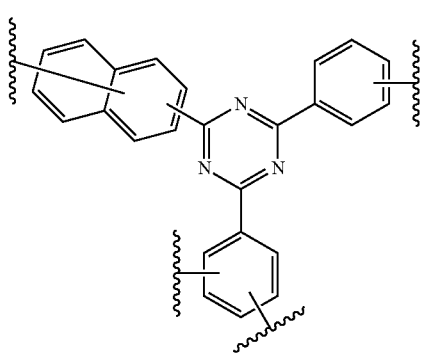
C-63
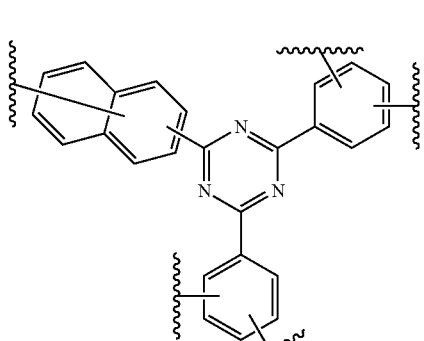
C-64
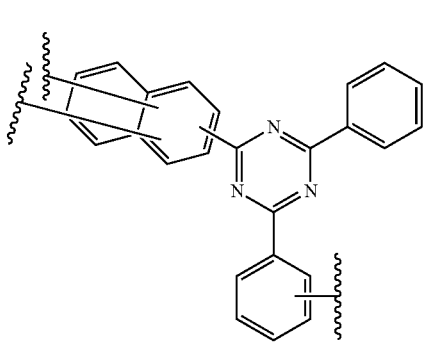

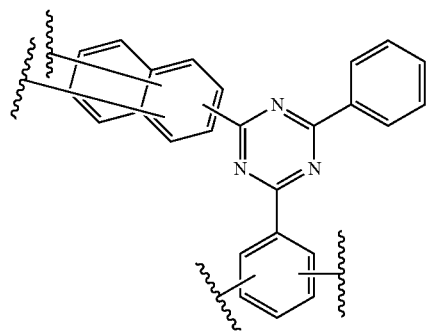
C-65
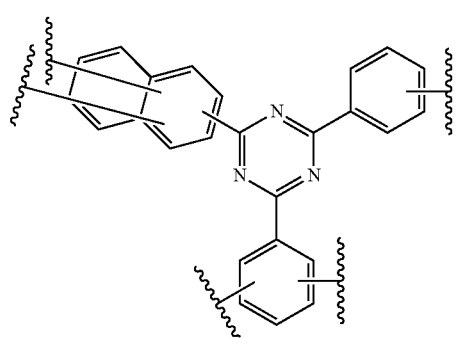
C-66

C-67
Among these, the following triaryl triazine groups are preferred from the viewpoint of good performance of the organic electroluminescent device.
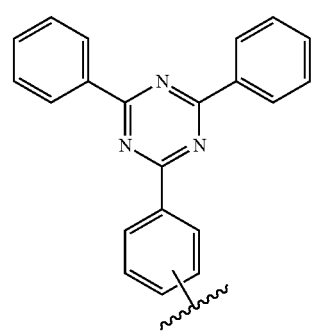
C-35
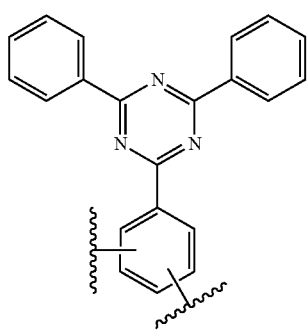
C-36
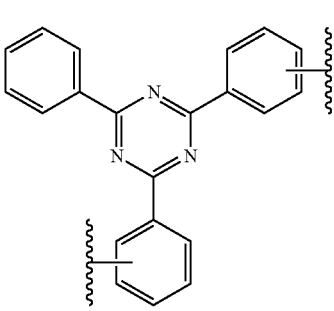
C-37
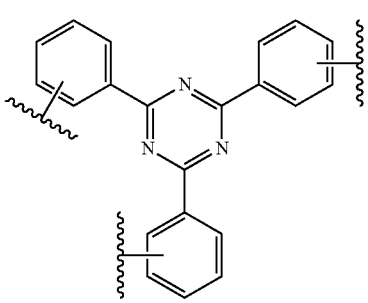
C-38
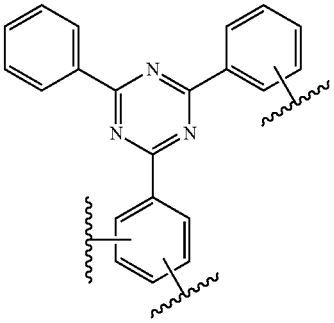
C-39
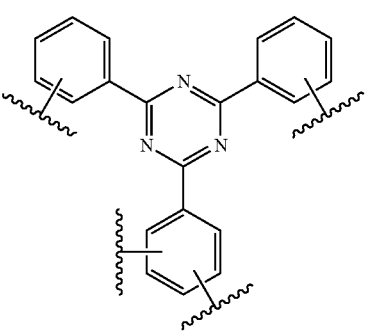
C-40

C-41

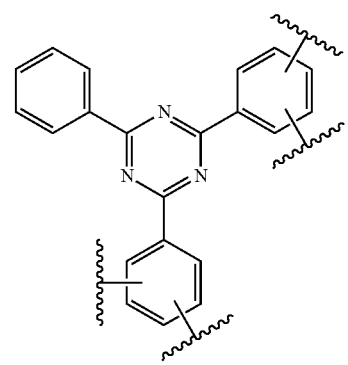

C-42

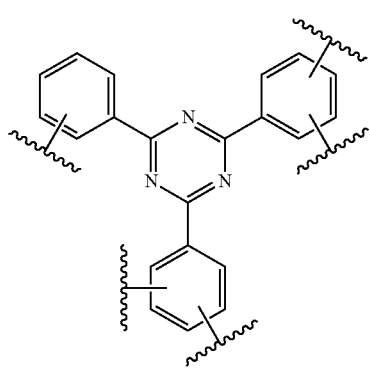

C-43

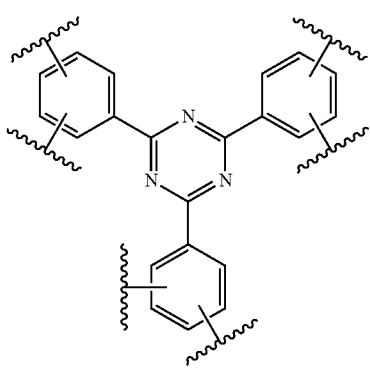

That is, from the viewpoint of excellent service life of the organic electroluminescent device, the material for the organic electroluminescent device of the present invention is preferably one represented by the following general formula (1), (2), (2'), (3) or (3').

General formula (1)

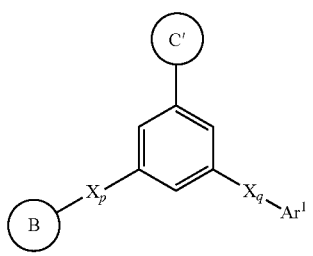

General formula (2)

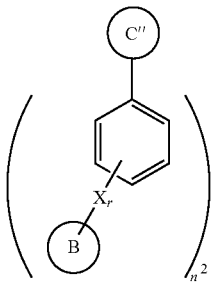

General formula (2')

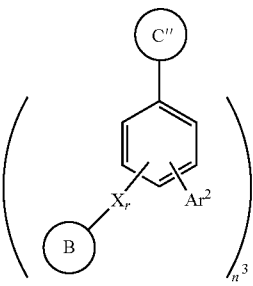

General formula (3)

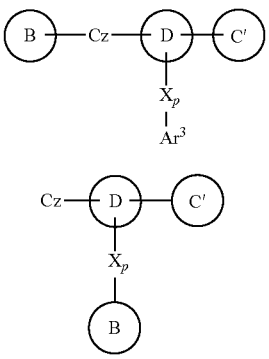

General formula (3')

Cz—(D)—C'
     |
     $X_p$
     |
     B

Each substituent B independently represents an azabenzene group, a diazabenzene group, an azanaphthalene group, a diazanaphthalene group, an azaanthracene group, a diazaanthracene group, an azaphenanthrene group, a diazaphenanthrene group, an azapentadiene group, a diazapentadiene group, an oxaazapentadiene group, a thiaazapentadiene group, an oxadiazapentadiene group, a thiodiazapentadiene group, an azaindene group, an oxaazaindene group, a thioazaindene group or a diazaindene group, having a methyl group on at least one carbon atom among carbon atoms adjacent to a nitrogen atom.

Substituent C' represents a diaryl pyrimidine group or a diaryl triazine group (each aryl group in the diaryl pyrimidine group and in the diaryl triazine group independently is a $C_{6-12}$ aromatic hydrocarbon group which may be substituted by a $C_{1-4}$ alkyl group).

Ar1 represents a C6-20 aromatic hydrocarbon group which may be substituted by a C1-4 alkyl group, or a C4-14 nitrogen-containing heteroaromatic group which may be substituted by a C1-4 alkyl group.

Each X independently represents a phenylene group, an azabenzenediyl group or a diazabenzenediyl group, which may be substituted by a $C_{1-4}$ alkyl group.

Each of p and q independently represents 0, 1 or 2.

Substituent C" represents a trivalent pyrimidine group or triazine group.

Each Ar² independently represents a $C_{6-12}$ aromatic hydrocarbon group which may be substituted.

Each r independently represents 0, 1 or 2. $n^2$ represents 1, 2 or 3.

$n^3$ represents 2 or 3.

Substituent D represents a trivalent $C_{6-12}$ aromatic hydrocarbon group.

Ar3 represents a C3-14 nitrogen-containing heteroaromatic group which may be substituted by a C1-4 alkyl group.

Cz represents a carbazolyl group which may be substituted by a pyridyl group.

Further, from the viewpoint of excellent service life of the organic electroluminescent device, the material for the organic electroluminescent device of the present invention is more preferably one represented by the following general formula (1), general formula (2) or general formula (2').

General formula (1)

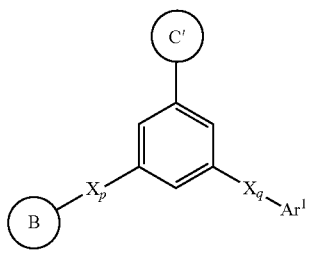

General formula (2)

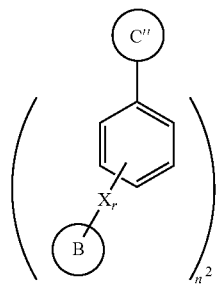

General formula (2')

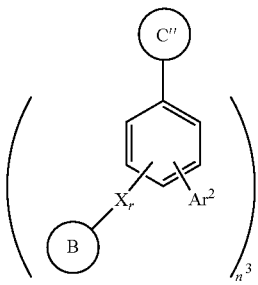

Substituent B, substituent C', $Ar^1$, X, p, q, substituent C", $Ar^2$, r, $n^2$ and $n^3$ are as defined above.

As the diaryl pyrimidine group represented by substituent C', the following diaryl pyrimidine groups may, for example, be mentioned, although it is not particularly limited thereto.

C'-1

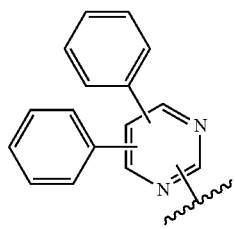

C'-2

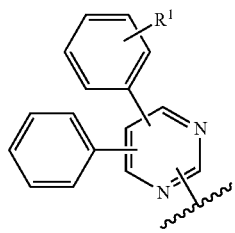

C'-3

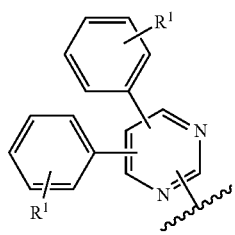

C'-4

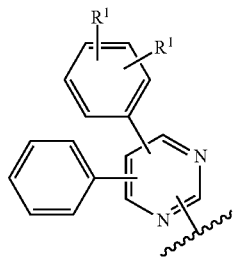

C'-5

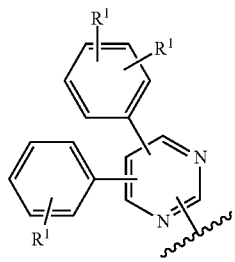

C'-6

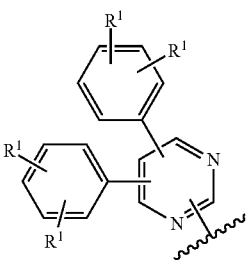

-continued
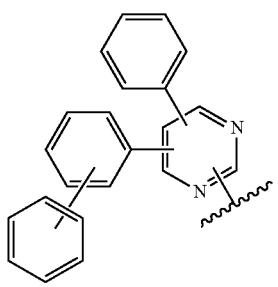
C'-7
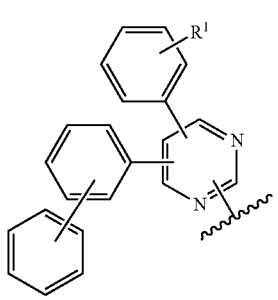
C'-8
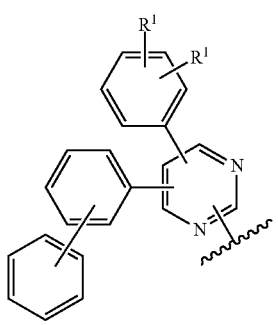
C'-9
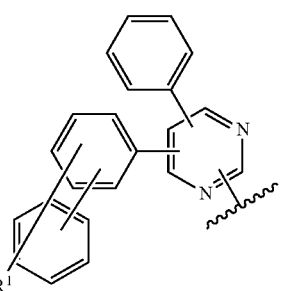
C'-10
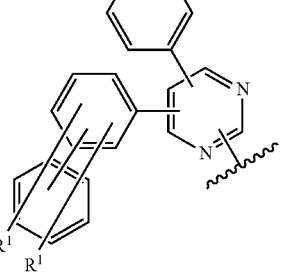
C'-11
-continued
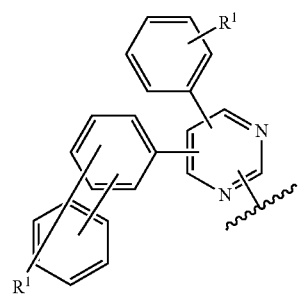
C'-12
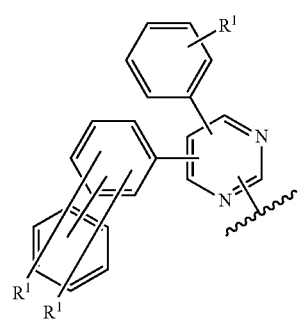
C'-13
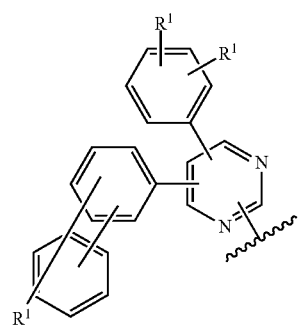
C'-14
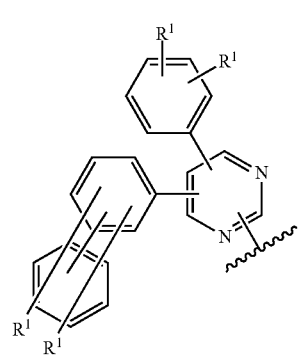
C'-15
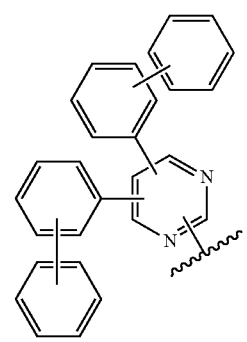
C'-16

C'-17
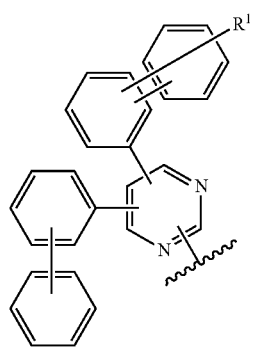
C'-18
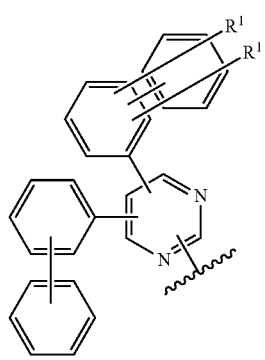
C'-19
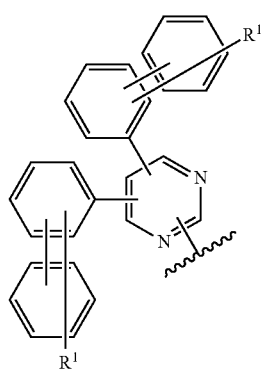
C'-20
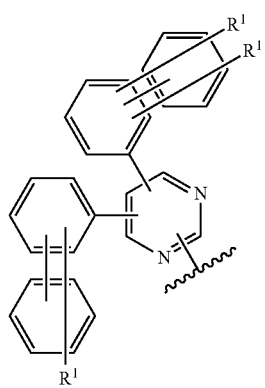
C'-21
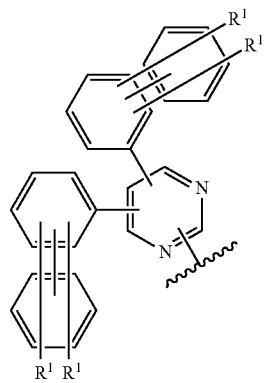
C'-22
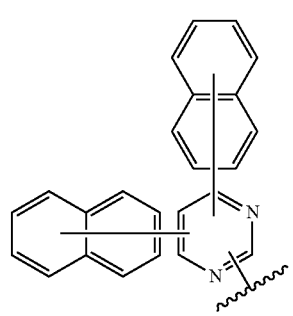
C'-23
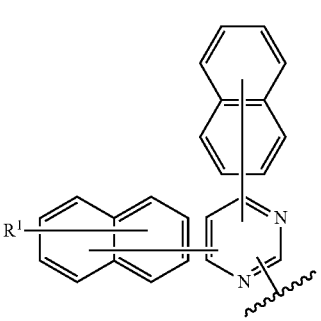
C'-24
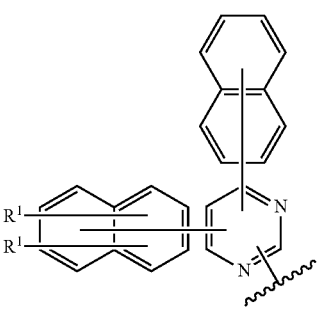
C'-25
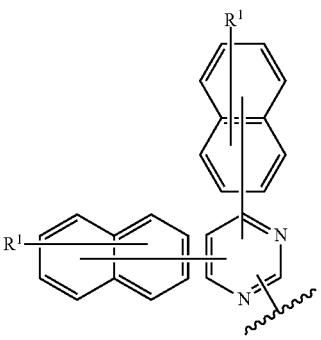

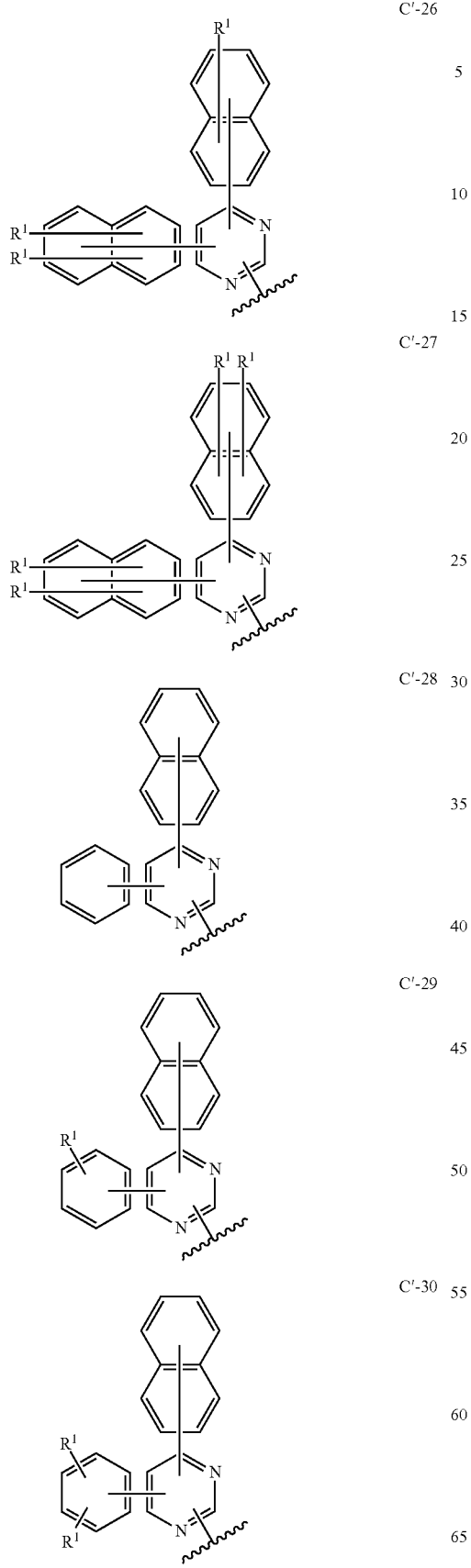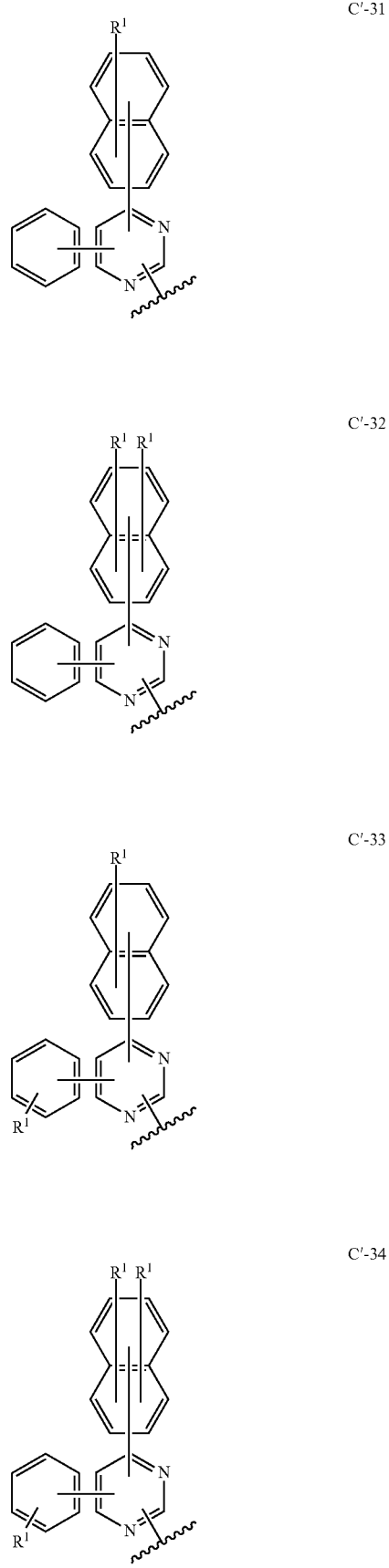

-continued
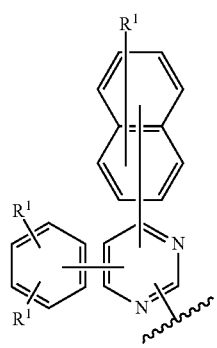
C'-35
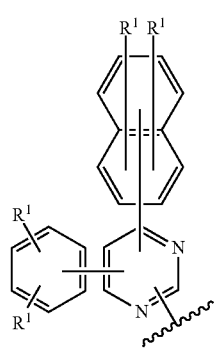
C'-36
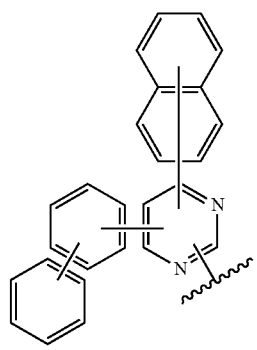
C'-37
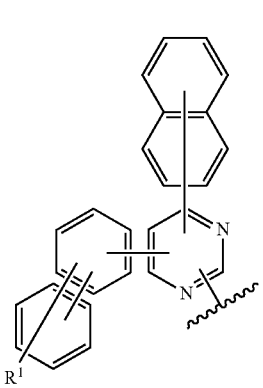
C'-38
-continued
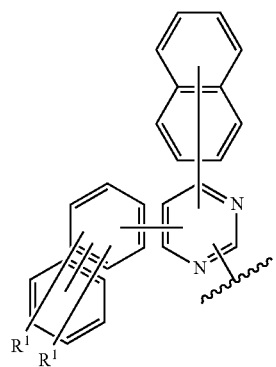
C'-39
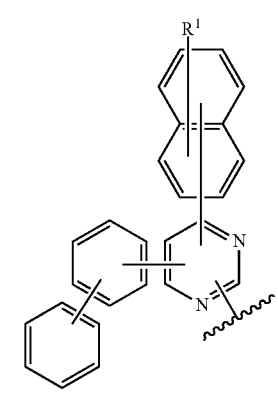
C'-40
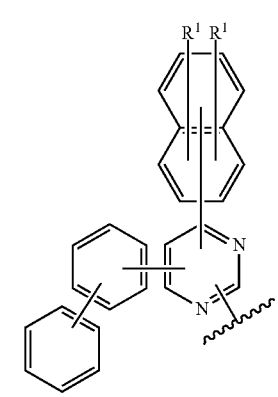
C'-41
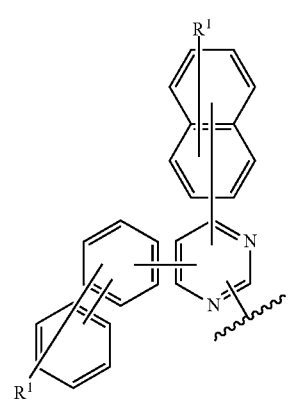
C'-42

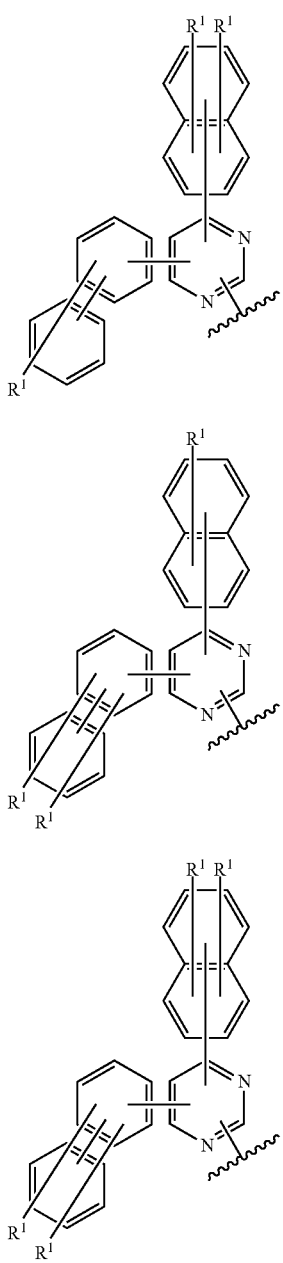

(Each R¹ independently represents a $C_{1-4}$ alkyl group.)

Among these, the following diaryl pyrimidine groups are preferred from the viewpoint of excellent performance of the organic electroluminescent device.

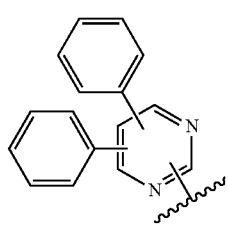

C'-1

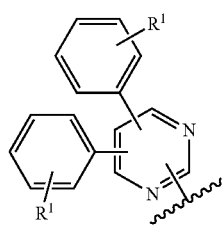

C'-3

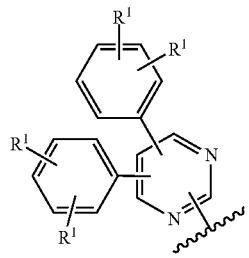

C'-6

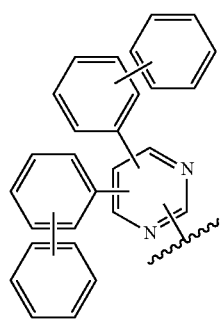

C'-16

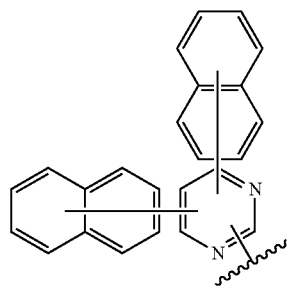

C'-22

(Each R¹ independently represents a $C_{1-4}$ alkyl group.)

Further, from the viewpoint of easy synthesis, the following diaryl pyrimidine group is more preferred.

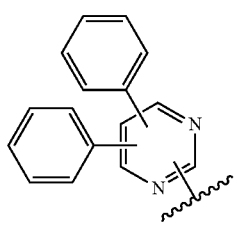

C'-1

As the diaryl triazine group represented by substituent C', the following diaryl triazine groups may, for example, be mentioned, although it is not particularly limited thereto.

C'-46
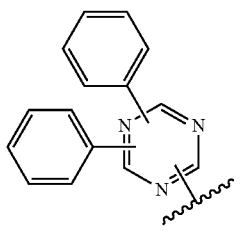
C'-47
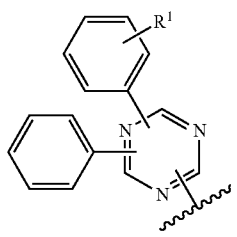
C'-48
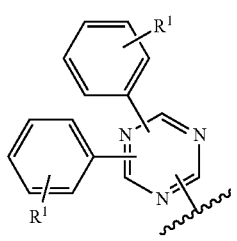
C'-49
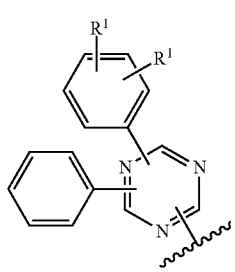
C'-50
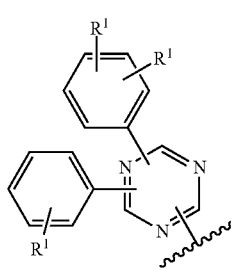
C'-51
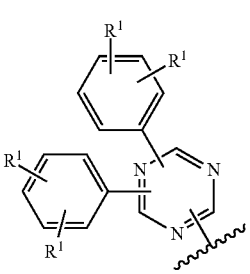
C'-52
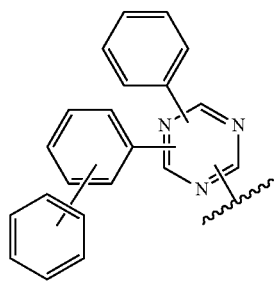
C'-53
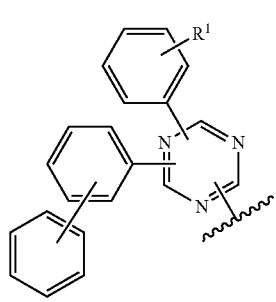
C'-54
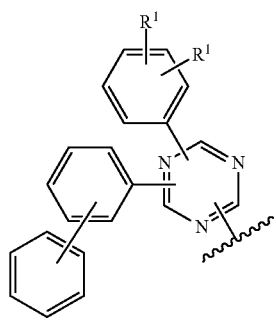
C'-55
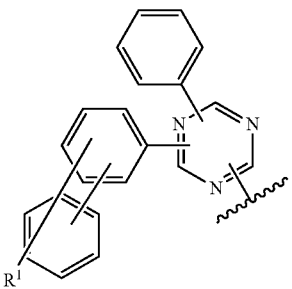
C'-56
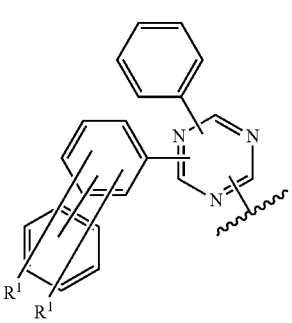

C'-57
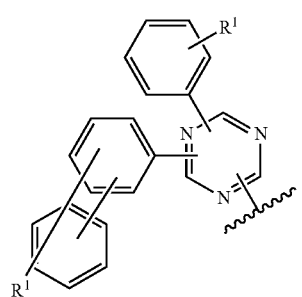
C'-58
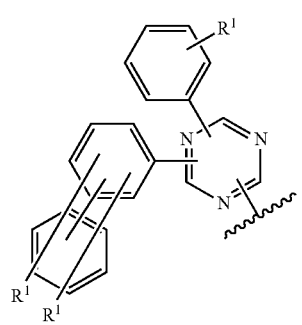
C'-59
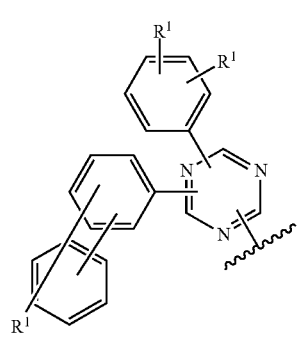
C'-60
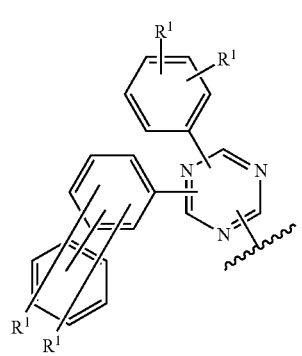
C'-61
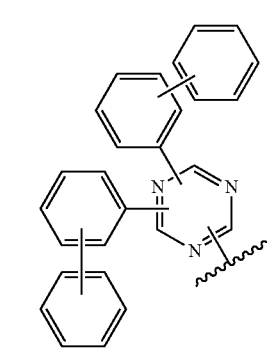
C'-62
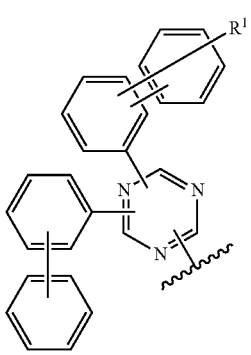
C'-63
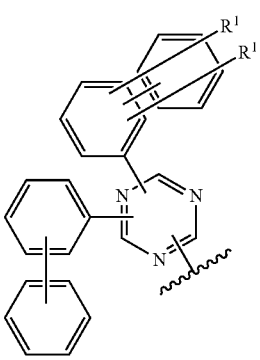
C'-64
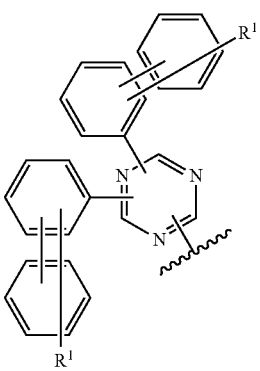
C'-65
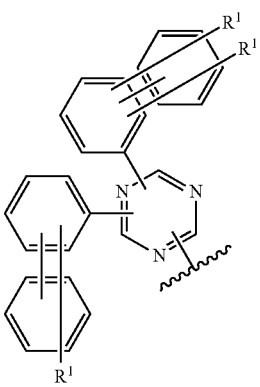

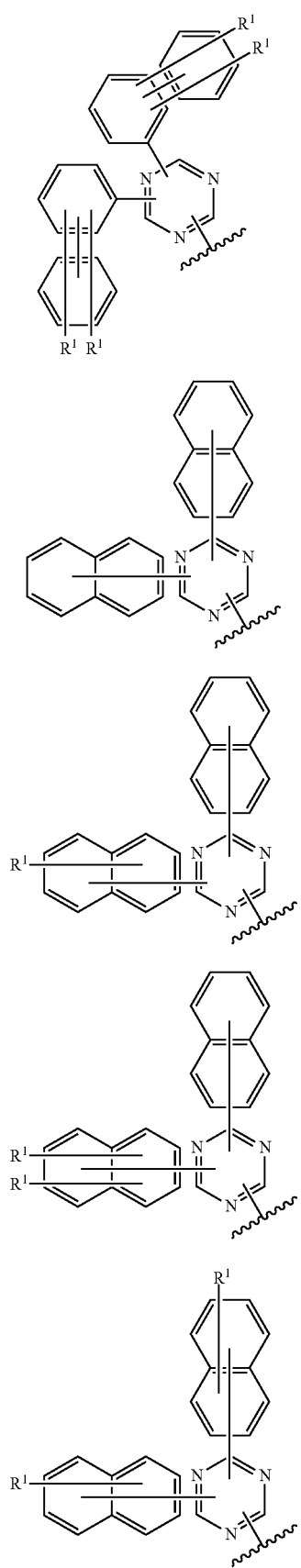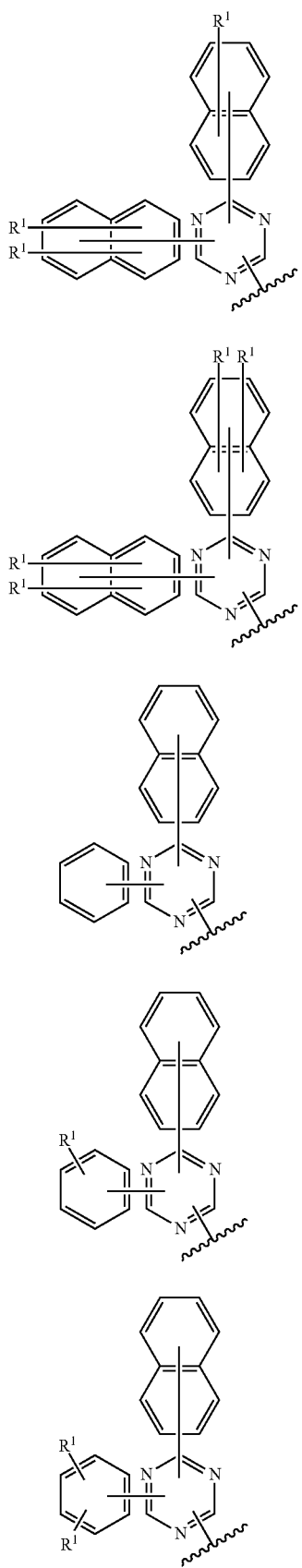

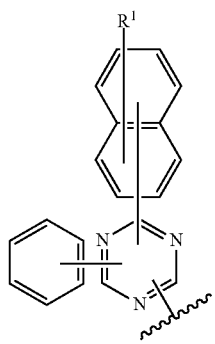 C'-76
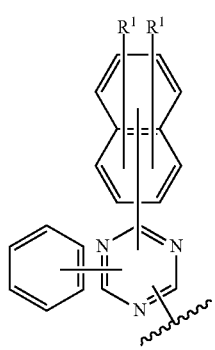 C'-77
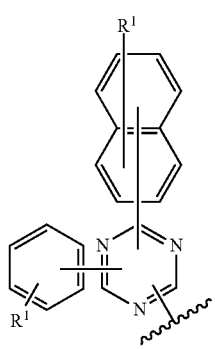 C'-78
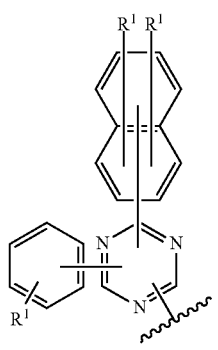 C'-79
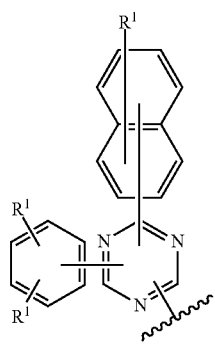 C'-80
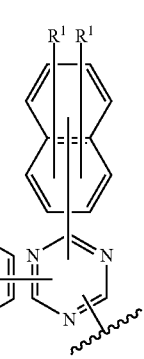 C'-81
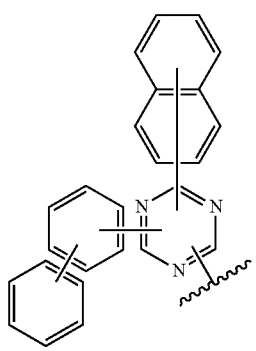 C'-82
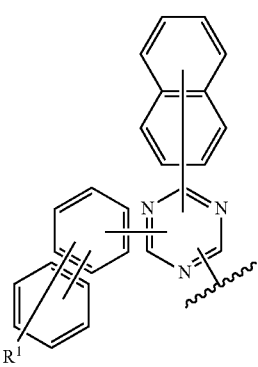 C'-83

C'-84 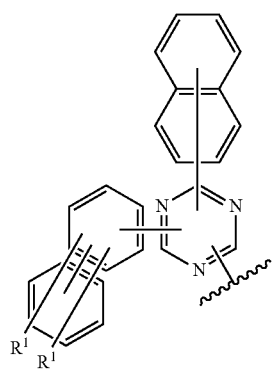
C'-85 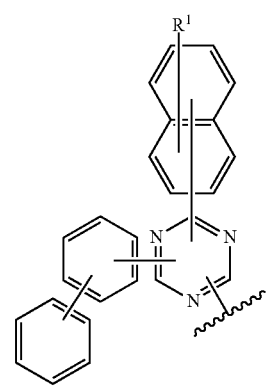
C'-86 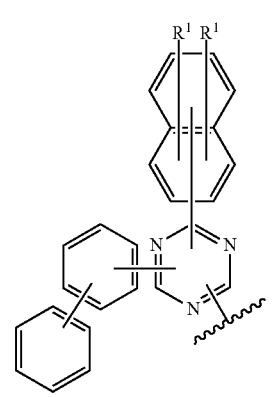
C'-87 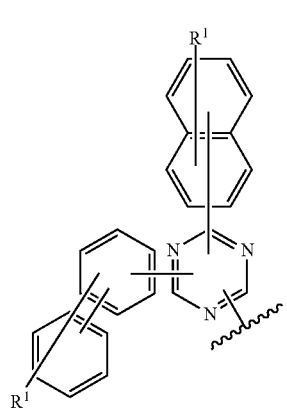
C'-88 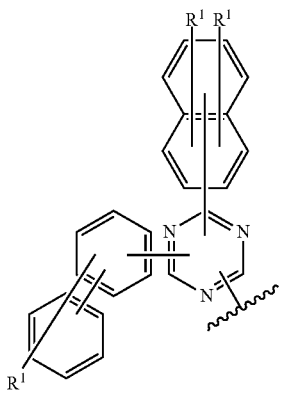
C'-89 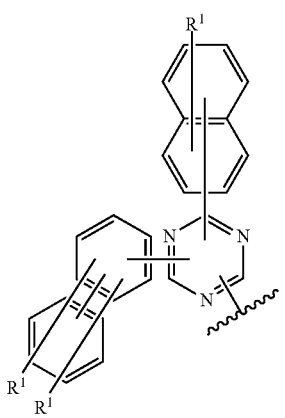
C'-90 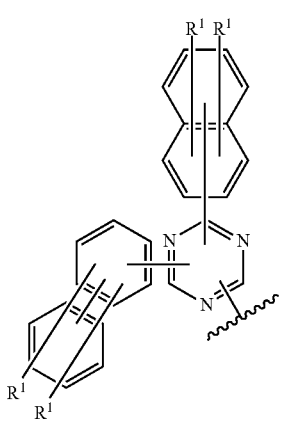
(Each $R^1$ independently represents a $C_{1-4}$ alkyl group.)
Among these, the following diaryl pyrimidine groups are preferred from the viewpoint of excellent performance of the organic electroluminescent device.
C'-46 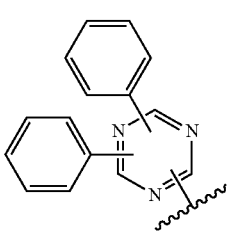

C'-48
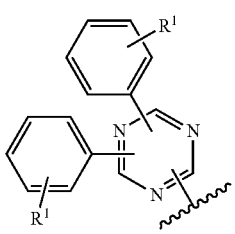
C'-51
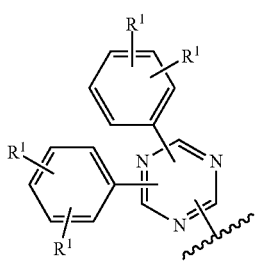
C'-61
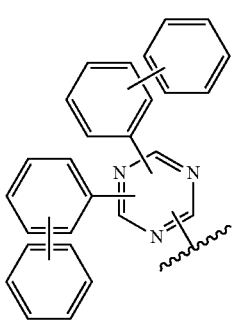
C'-64
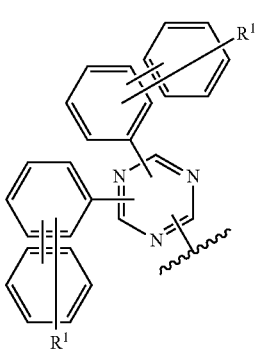
C'-66
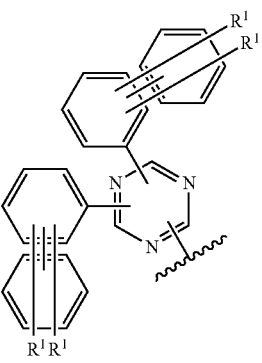
C'-67
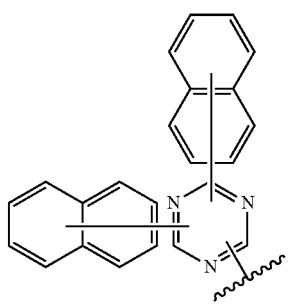
C'-70
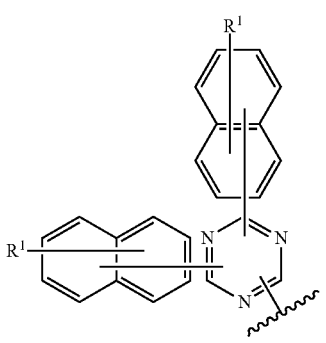
C'-72
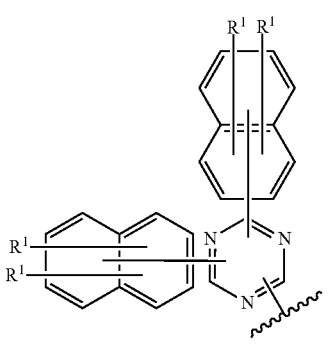
(Each R¹ independently represents a $C_{1-4}$ alkyl group.)
Further, from the viewpoint of easy synthesis, the following diaryl pyrimidine groups are more preferred.
C'-46
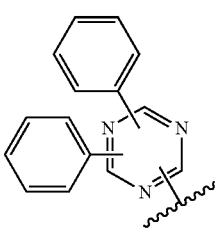
C'-48
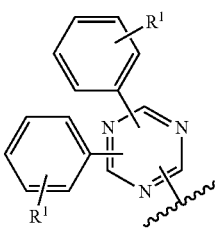

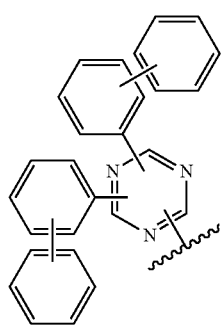
C'-61

That is, substituent C' is preferably the following (C'-1), (C'-3), (C'-6), (C'-16), (C'-46), (C'-48) or (C'-61).

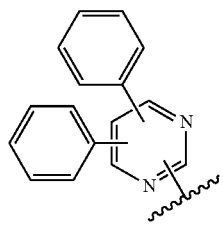
C'-1

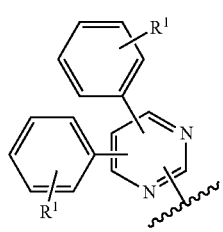
C'-3

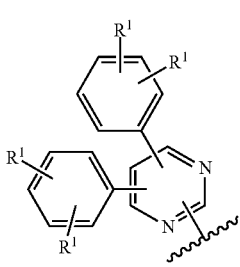
C'-6

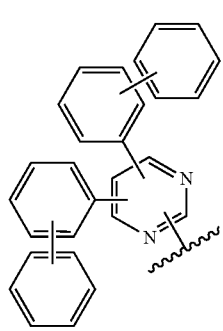
C'-16

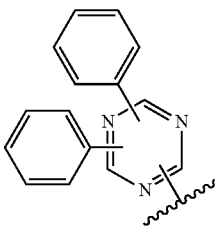
C'-46

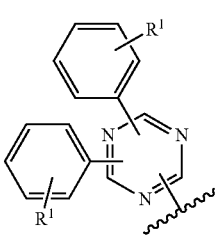
C'-48

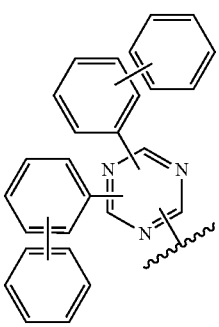
C'-61

($R^1$ represents a methyl group.)

Substituent C" represents a trivalent pyrimidine group or triazine group.

As the trivalent pyrimidine group represented by substituent C", the following substituents may, for example, be mentioned, although it is not particularly limited thereto.

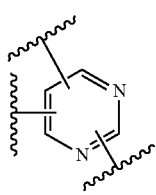
C"-1

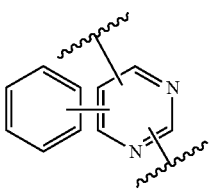
C"-2

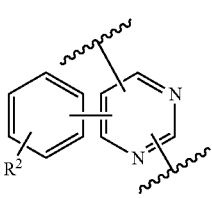
C"-3

-continued
C″-4
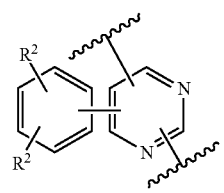
C″-5
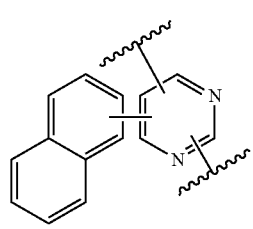
C″-6
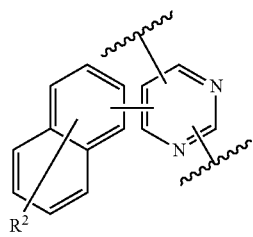
C″-7
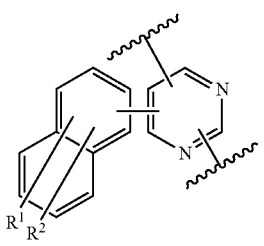
C″-8
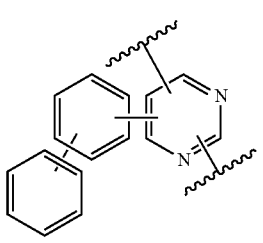
C″-9
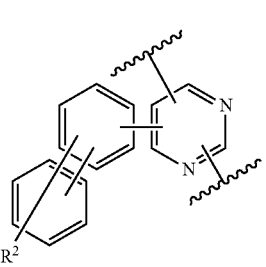
-continued
C″-10
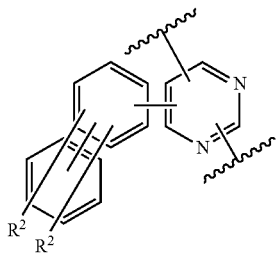
C″-11
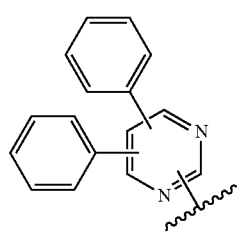
C″-12
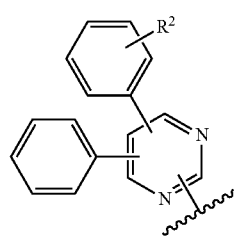
C″-13
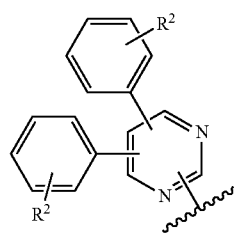
C″-14
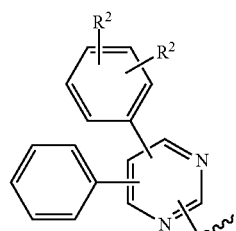
C″-15
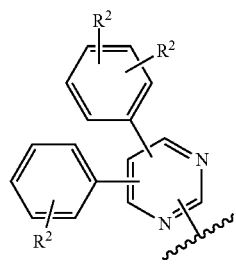

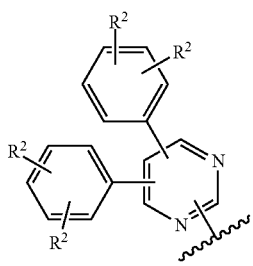 C″-16
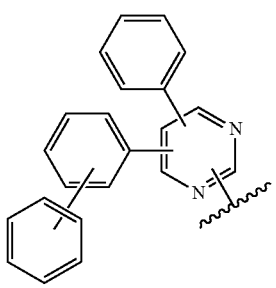 C″-17
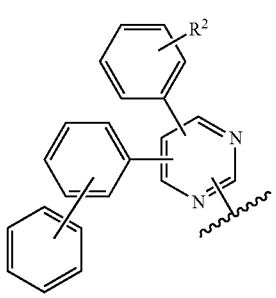 C″-18
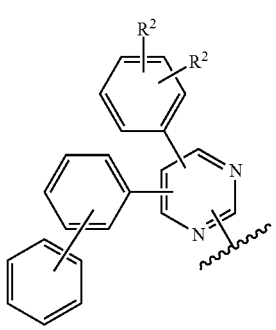 C″-19
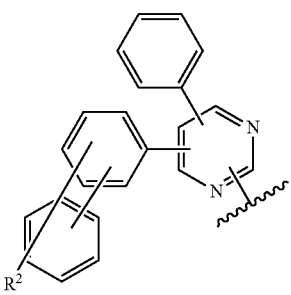 C″-20
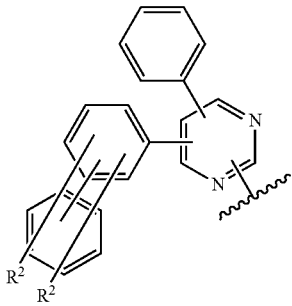 C″-21
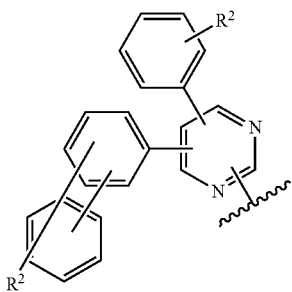 C″-22
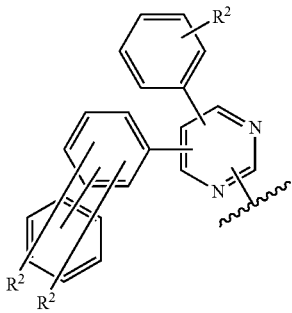 C″-23
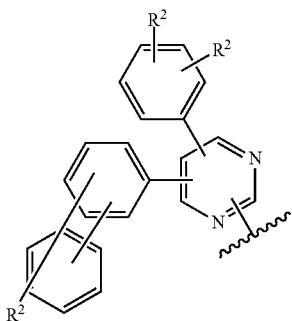 C″-24
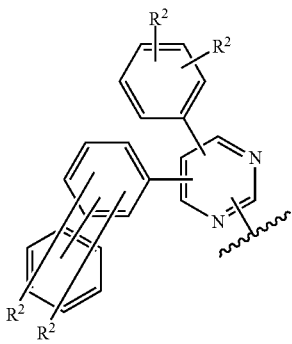 C″-25

C''-26
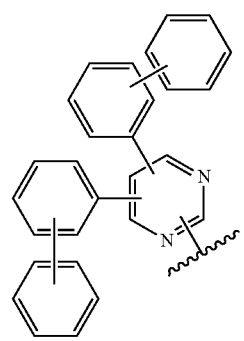
C''-27
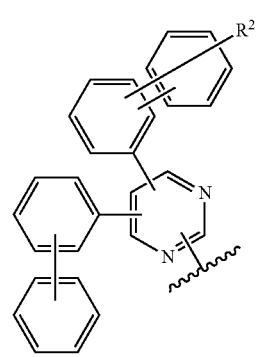
C''-28
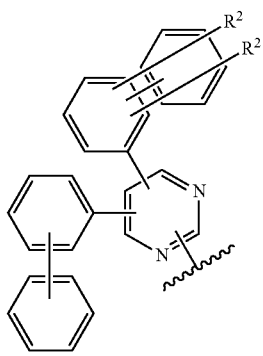
C''-29
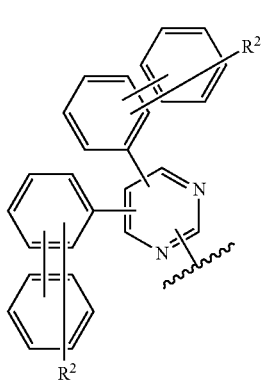
C''-30
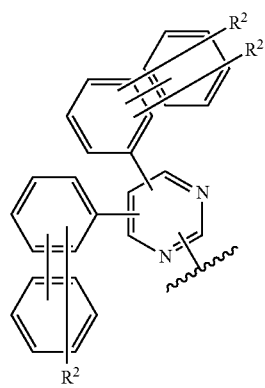
C''-31
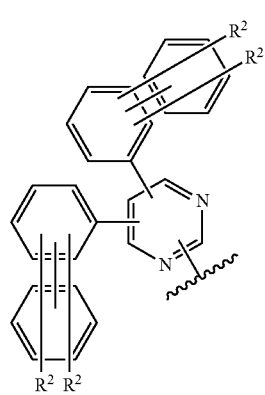
C''-32
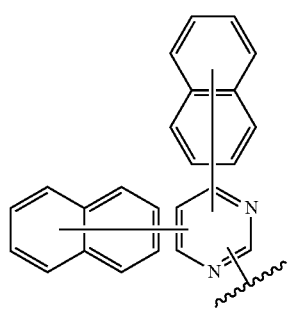
C''-33
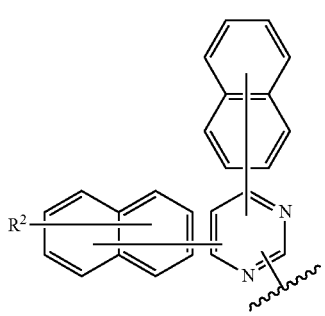

-continued
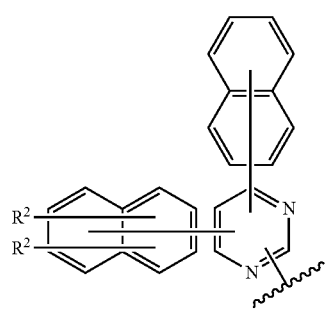
C''-34
C''-35
C''-36
C''-37
C''-38
-continued
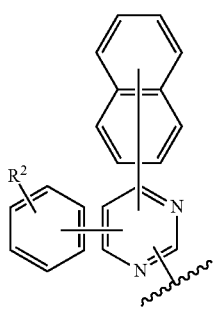
C''-39
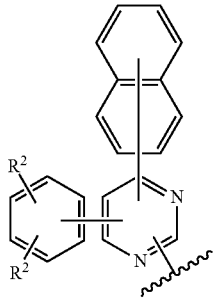
C''-40
C''-41
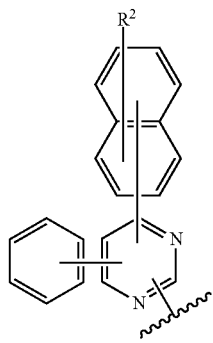
C''-42
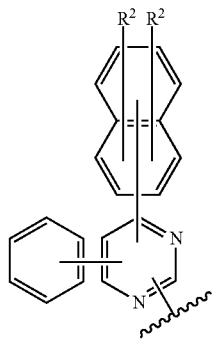
C''-43
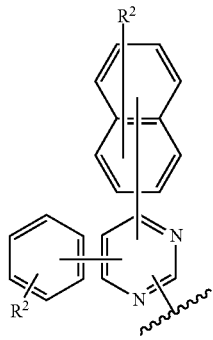

C''-44
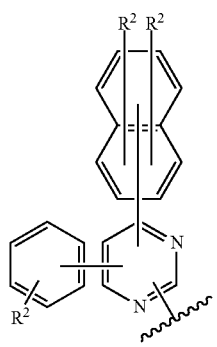
C''-45
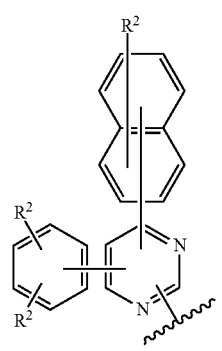
C''-46
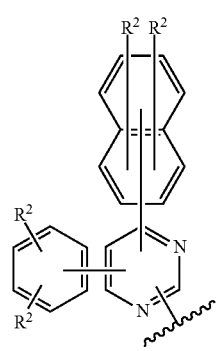
C''-47
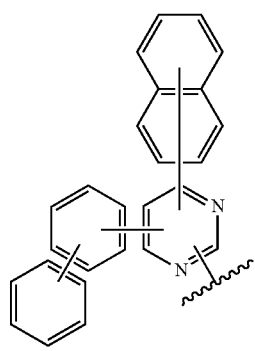
C''-48
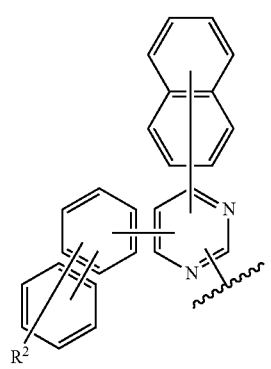
C''-49
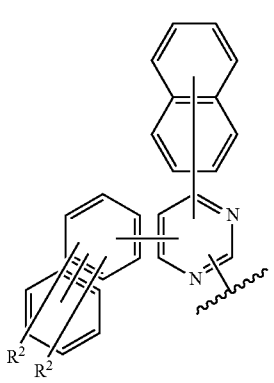
C''-50
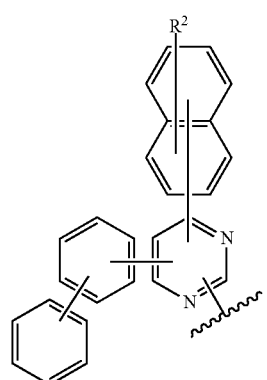
C''-51
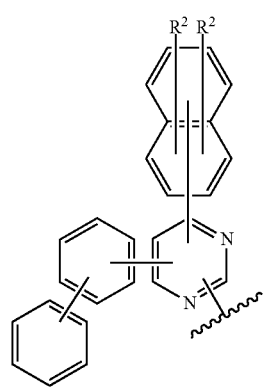

-continued
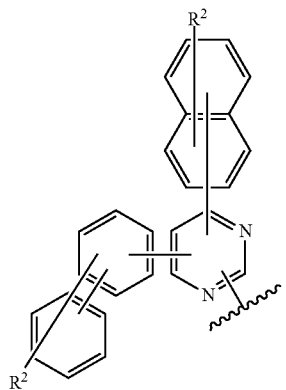
C″-52
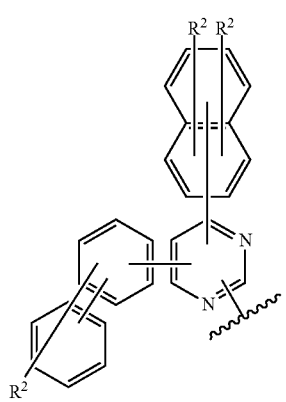
C″-53
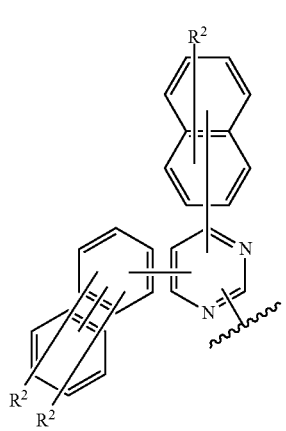
C″-54
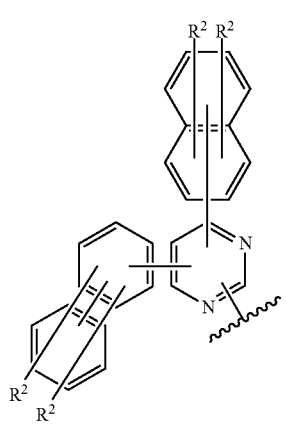
C″-55
(Each R² independently represents a C₁₋₄ alkyl group.)
Among these, the following trivalent pyrimidine groups are preferred from the viewpoint of excellent performance of the organic electroluminescent device.
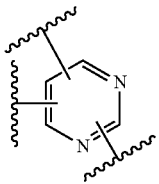
C″-1
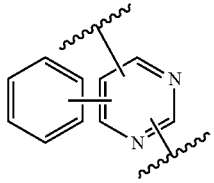
C″-2
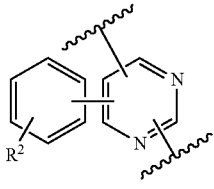
C″-3
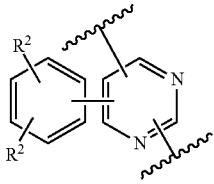
C″-4
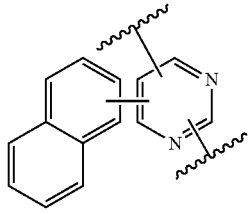
C″-5
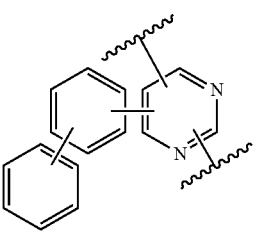
C″-8
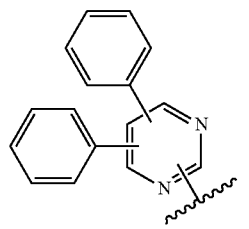
C″-11

C″-13
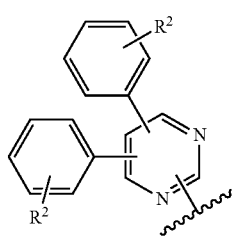
C″-16
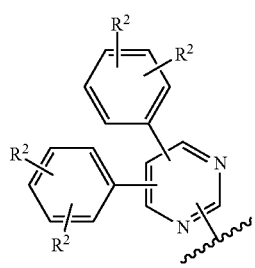
C″-26
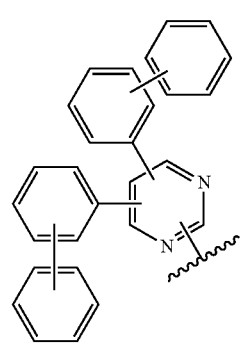
C″-32
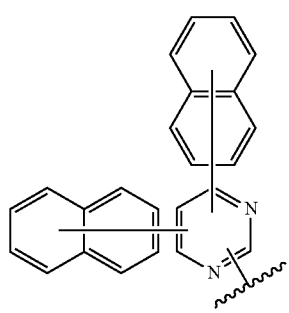
(Each R² independently represents a C₁₋₄ alkyl group.)
As the trivalent triazine group represented by substituent C″, the following substituents may, for example, be mentioned, although it is not particularly limited thereto.
C″-56
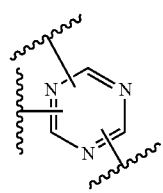
C″-57
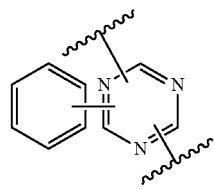
C″-58
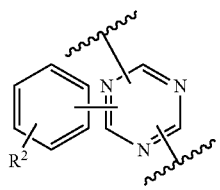
C″-59
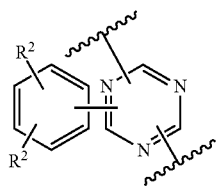
C″-60
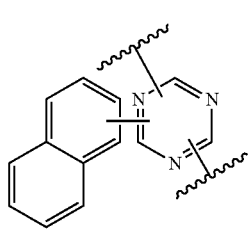
C″-61
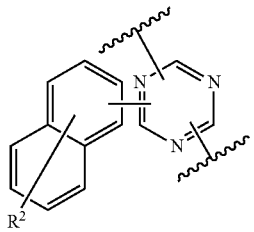
C″-62
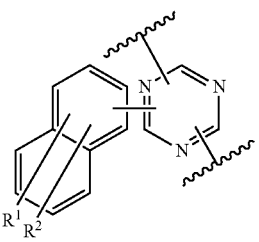
C″-63
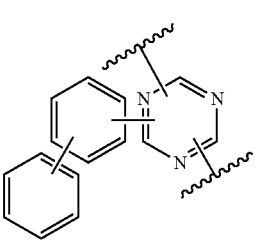

C″-64 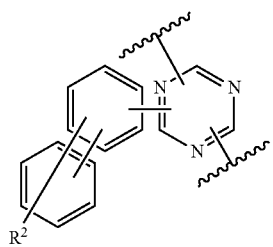
C″-65 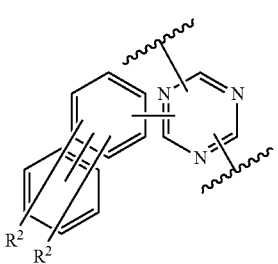
C″-66 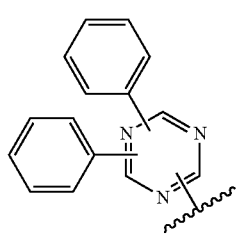
C″-67 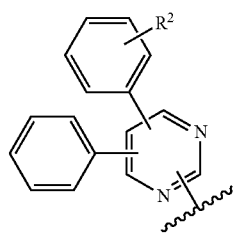
C″-68 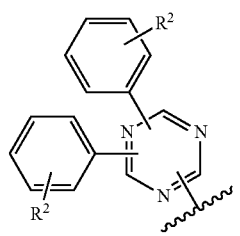
C″-69 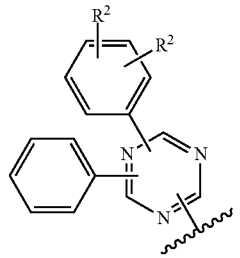
C″-70 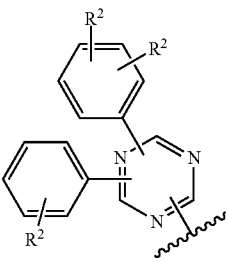
C″-71 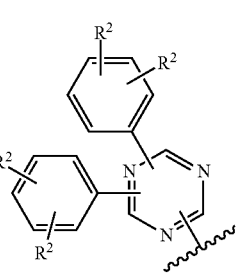
C″-72 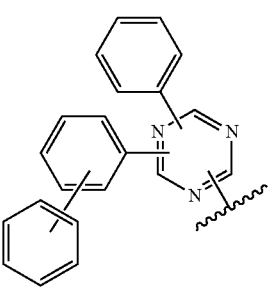
C″-73 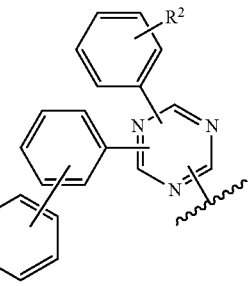
C″-74 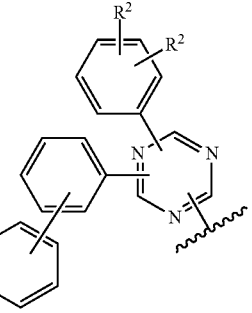

C″-75
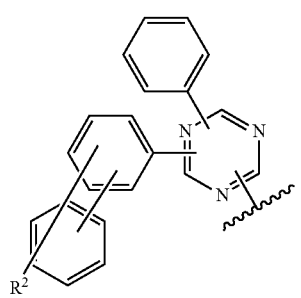
C″-76
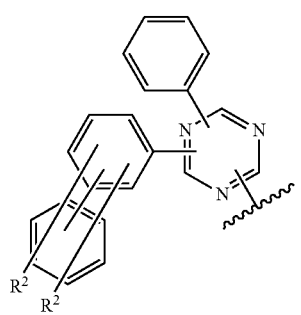
C″-77
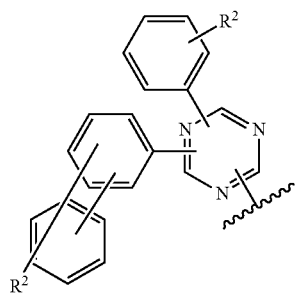
C″-78
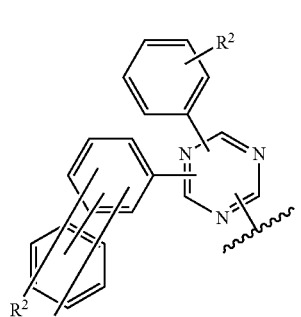
C″-79
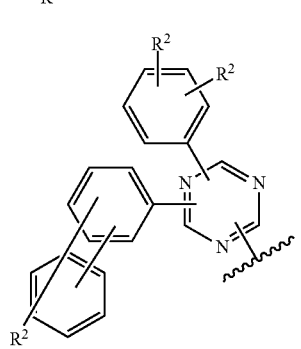
C″-80
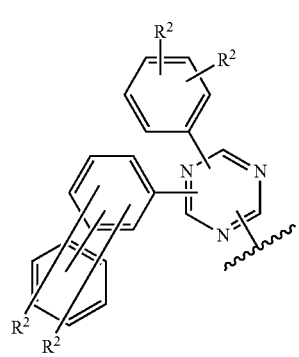
C″-81
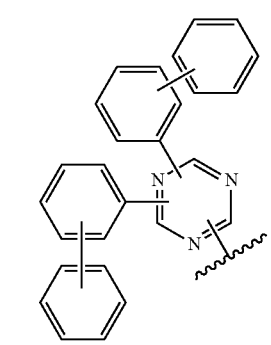
C″-82
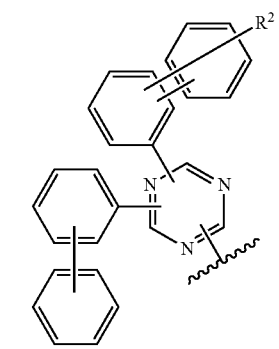
C″-83
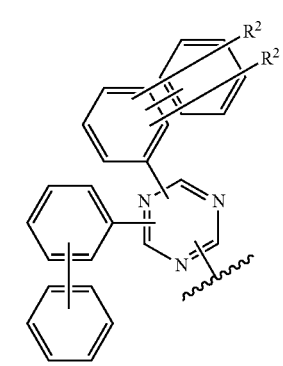

-continued
C″-84
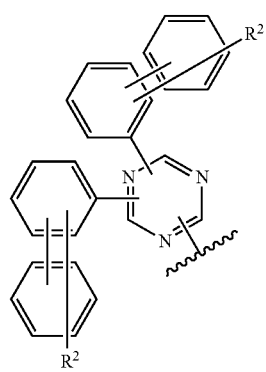
C″-85
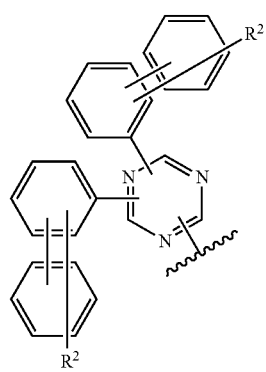
C″-86
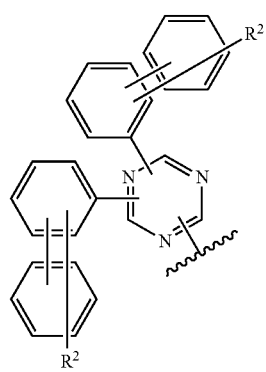
C″-87
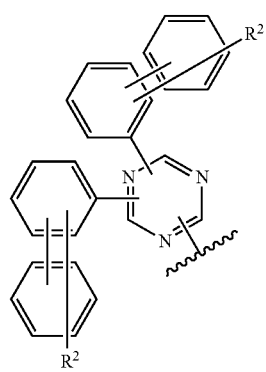
-continued
C″-88
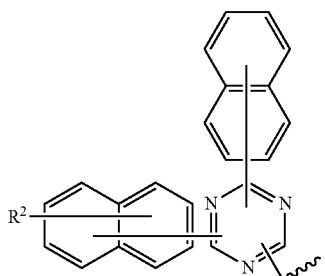
C″-89
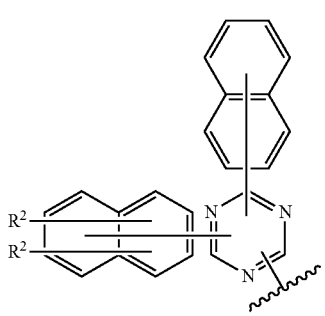
C″-90
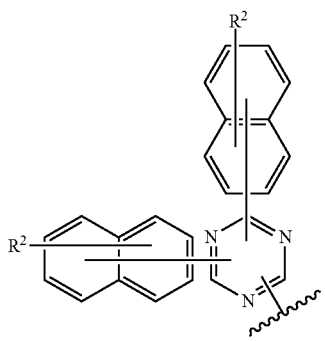
C″-91
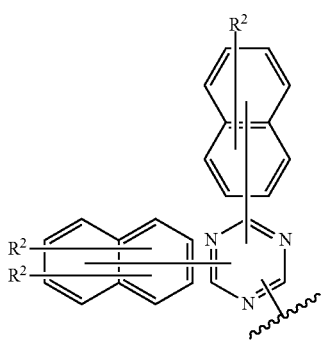
C″-92
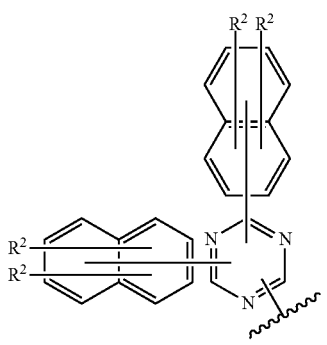

C''-93 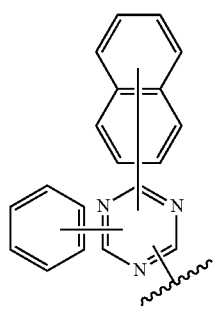
C''-94 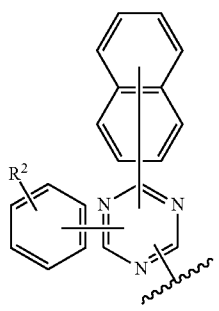
C''-95 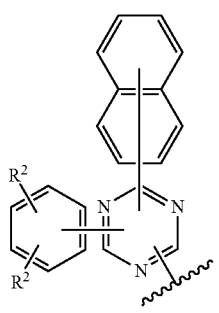
C''-96 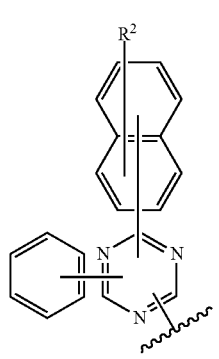
C''-97 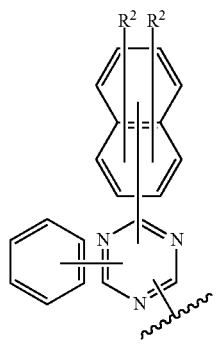
C''-98 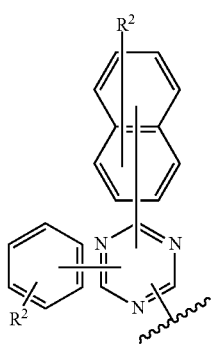
C''-99 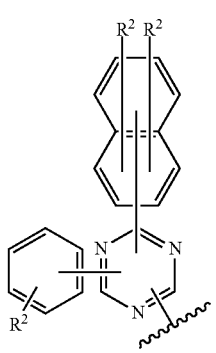
C''-100 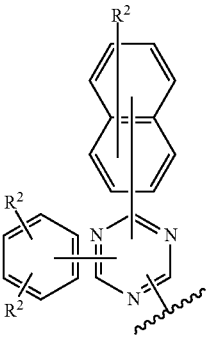
C''-101 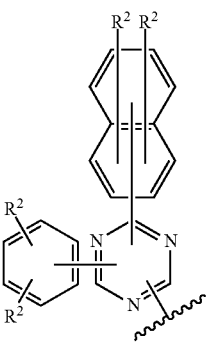

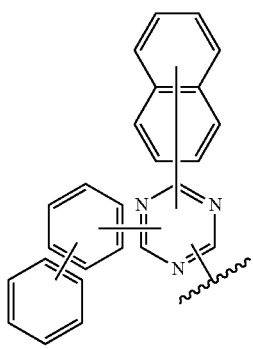
C″-102
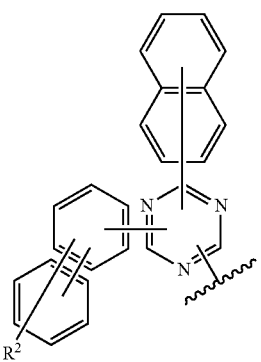
C″-103
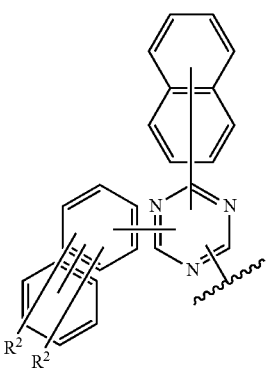
C″-104
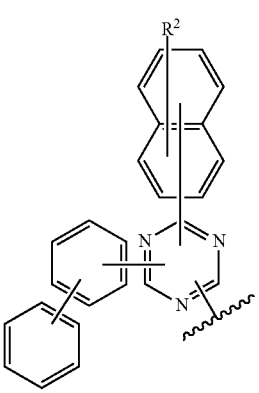
C″-105
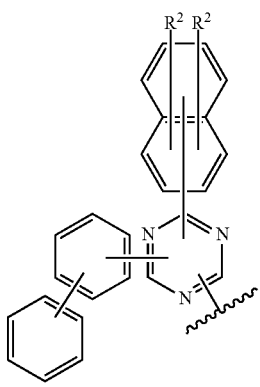
C″-106
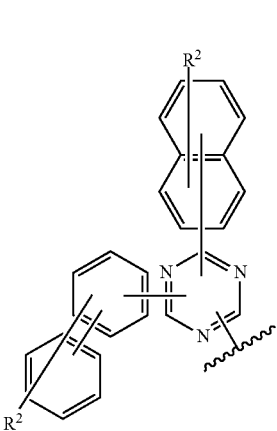
C″-107
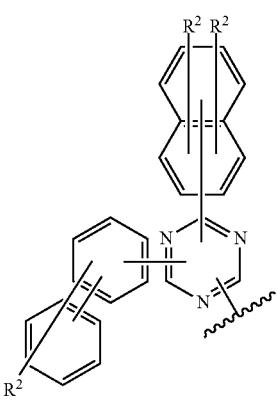
C″-108
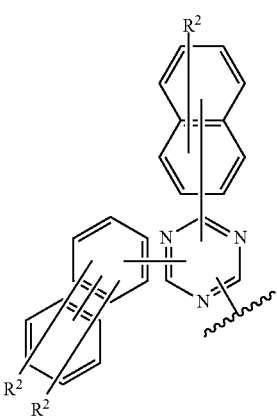
C″-109

C″-110
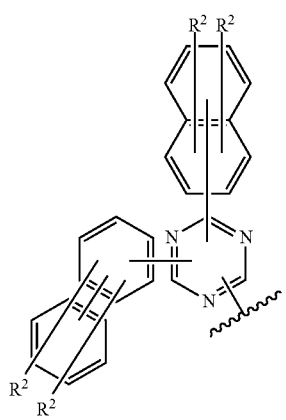
(Each R² independently represents a C₁₋₄ alkyl group.)
Among these, the following trivalent triazine groups are preferred from the viewpoint of excellent performance of the organic electroluminescent device.
C″-56
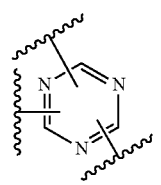
C″-57
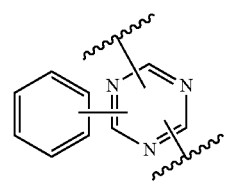
C″-58
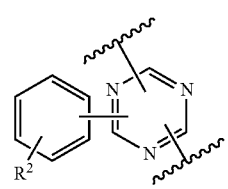
C″-59
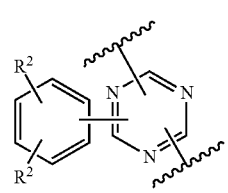
C″-60
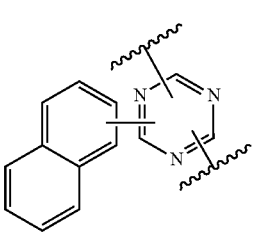
C″-63
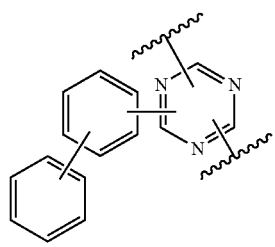
C″-66
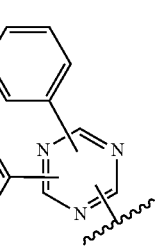
C″-68
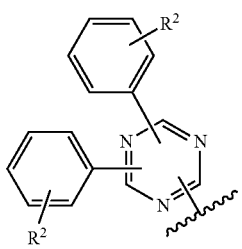
C″-71
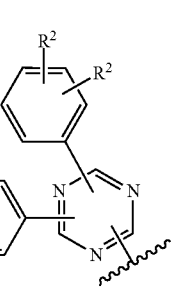
C″-81
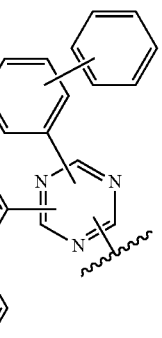

C″-84
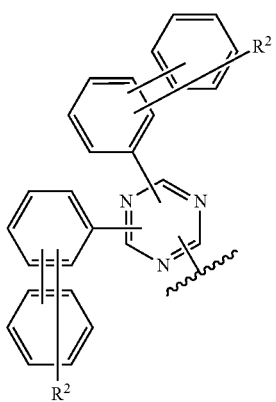
C″-86
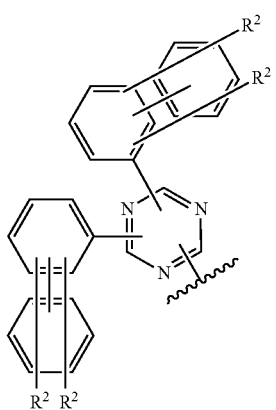
C″-87
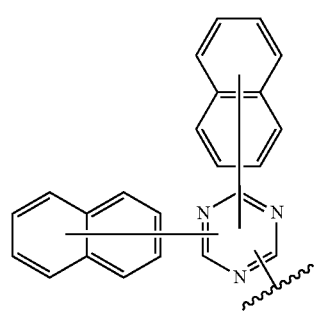
C″-90
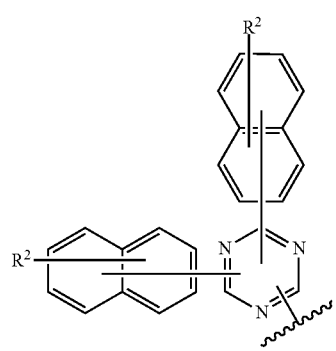
C″-92
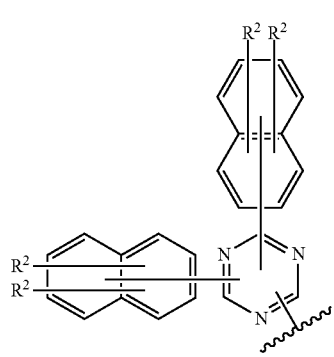
(Each $R^2$ independently represents a $C_{1-4}$ alkyl group.)
Further, from the viewpoint of easy synthesis, the following triazine groups are particularly preferred.
C″-56
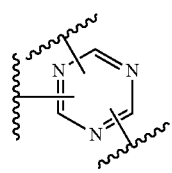
C″-57
C″-66
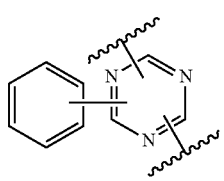
C″-68
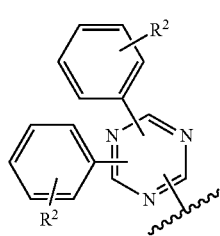

C″-81
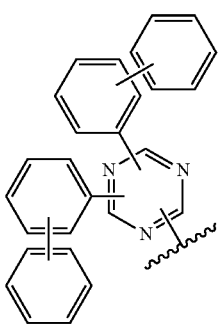
(Each R² independently represents a $C_{1-4}$ alkyl group.)
Further, R² is preferably a methyl group.
As the $C_{6-20}$ aromatic hydrocarbon group which may be substituted by a $C_{1-4}$ alkyl group, represented by $Ar^1$, the following substituents may, for example, be mentioned, although it is not particularly limited thereto.
1
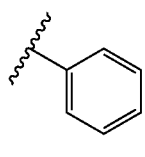
2
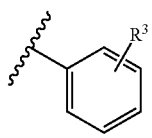
3
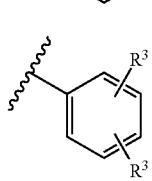
4
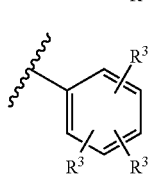
5
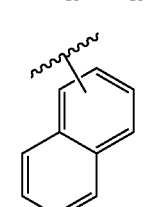
6
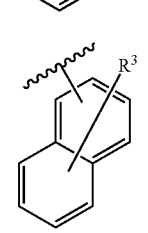
7
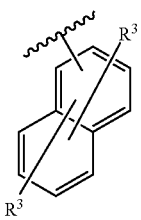
8
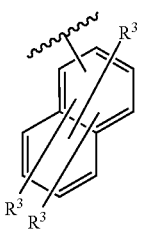
9
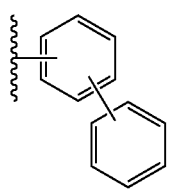
10
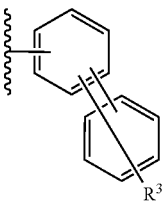
11
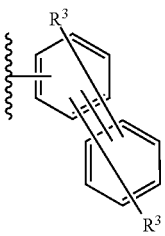
12
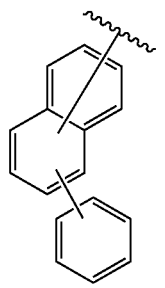

13
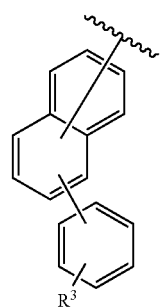
14
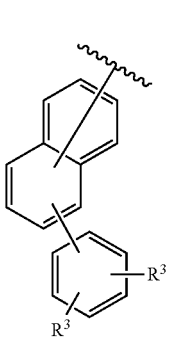
15
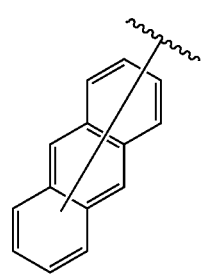
16
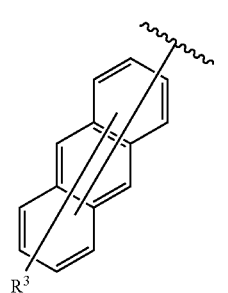
17
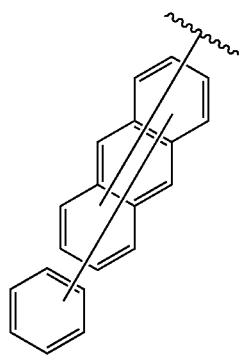
18
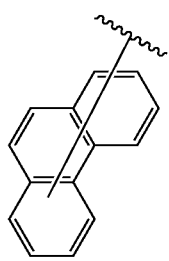
19
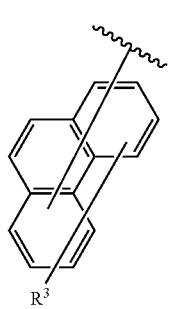
20
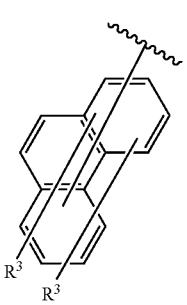
21
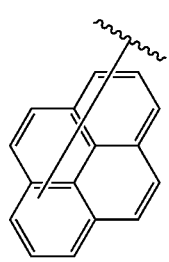
22

23
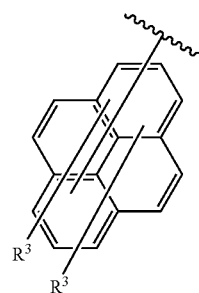
24
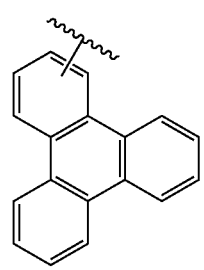
25
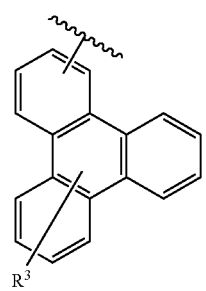
26
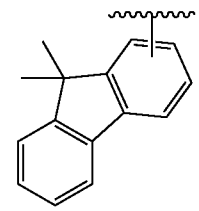
27
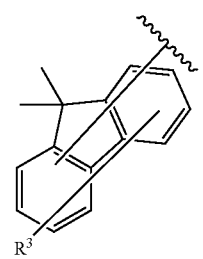
28
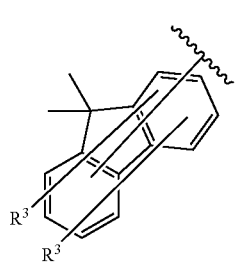
29
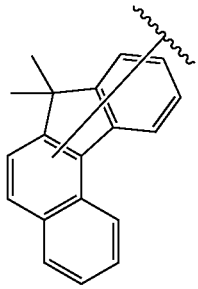
30
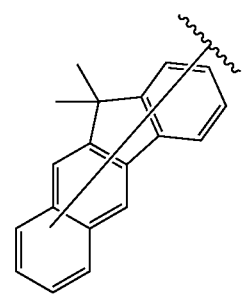
(Each $R^3$ independently represents a $C_{1-4}$ alkyl group.)
Among these, the following substituents are preferred from the viewpoint of good performance of the organic electroluminescent device.
1
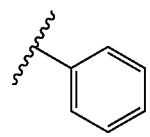
2
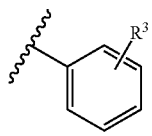
3
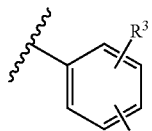
5
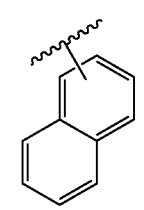
6
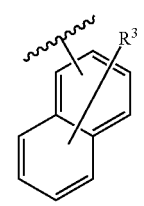

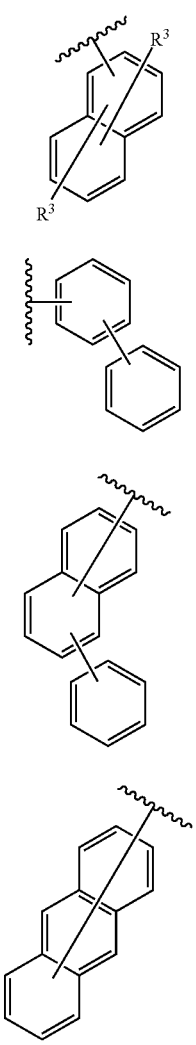
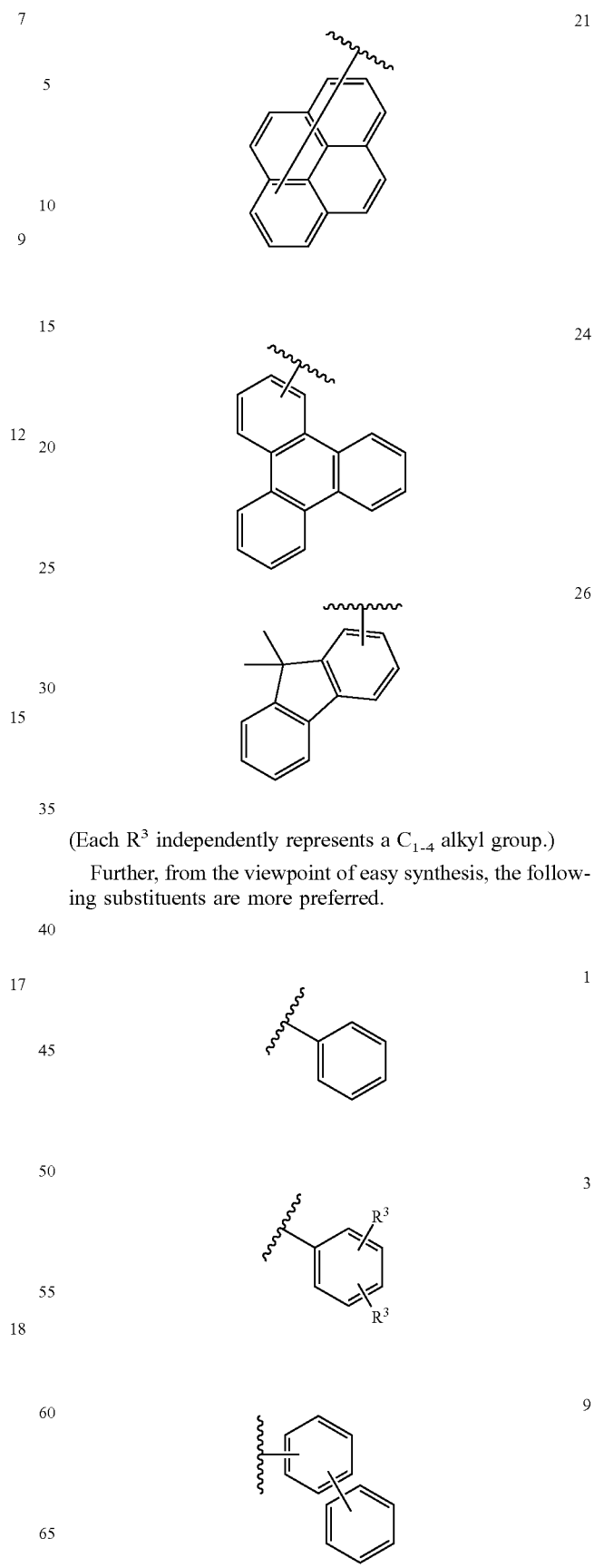
(Each R³ independently represents a C₁₋₄ alkyl group.)
Further, from the viewpoint of easy synthesis, the following substituents are more preferred.

-continued
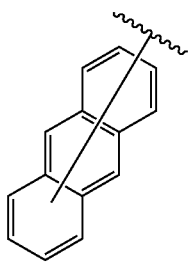
15
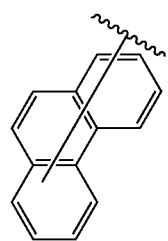
18
(Each R³ independently represents a C₁₋₄ alkyl group.)
As the C₄₋₁₄ nitrogen-containing heteroaromatic group which may be substituted by a C₁₋₄ alkyl group, represented by Ar¹, the following nitrogen-containing heteroaromatic groups may, for example, be mentioned, although it is not particularly limited thereto.
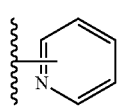
31
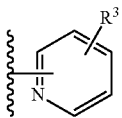
32
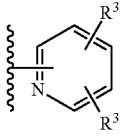
33
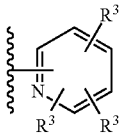
34
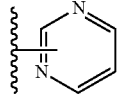
35
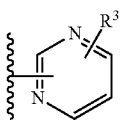
36
-continued
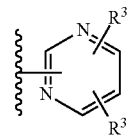
37
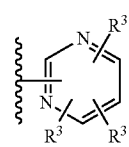
38
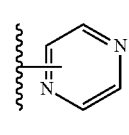
39
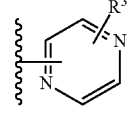
40
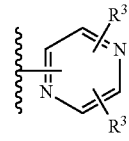
41
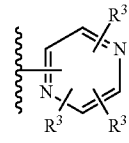
42
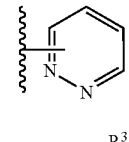
43
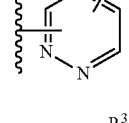
44
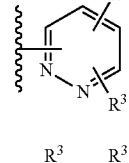
45
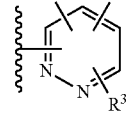
46
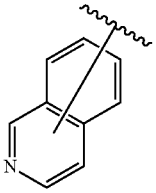
47

125
-continued
48
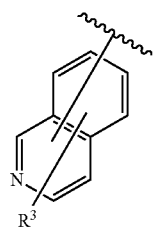
49
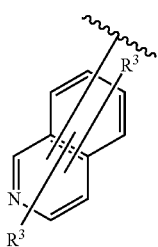
50
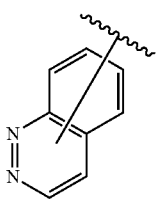
51
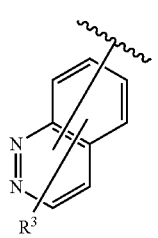
52
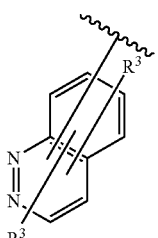
53
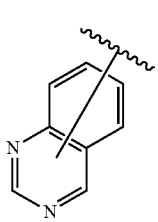
54
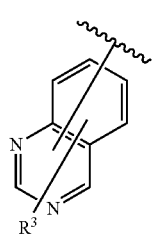
126
-continued
55
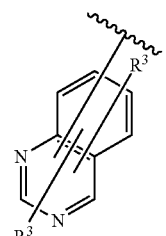
56
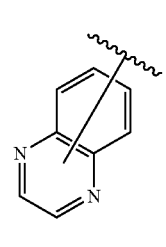
57
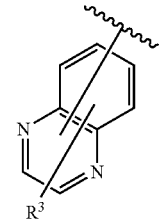
58
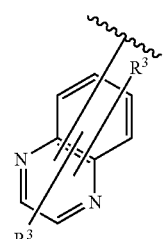
59
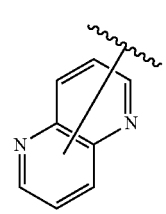
60
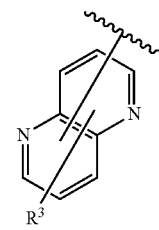
61
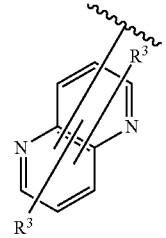

| | |
|---|---|
| 62 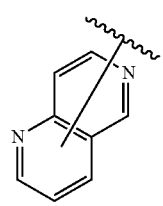 | 69 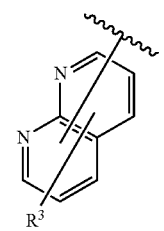 |
| 63 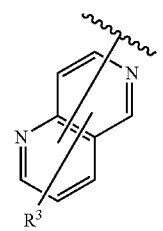 | 70 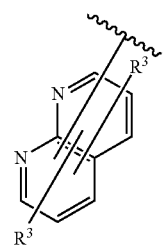 |
| 64 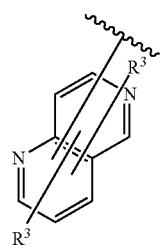 | 71 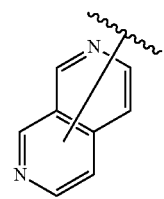 |
| 65 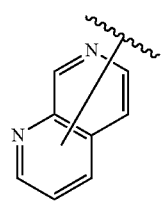 | 72 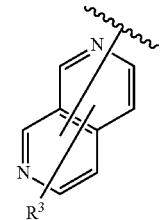 |
| 66 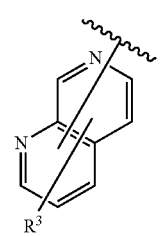 | 73 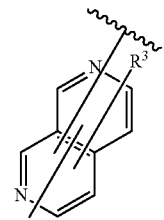 |
| 67 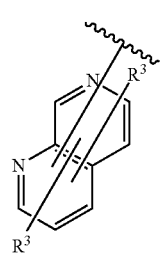 | 74 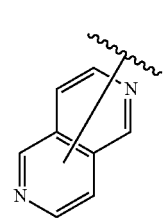 |
| 68 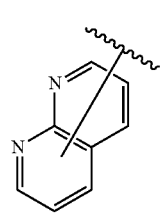 | 75 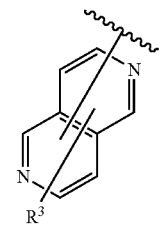 |

129
-continued
76
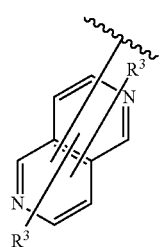
77
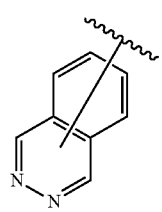
78
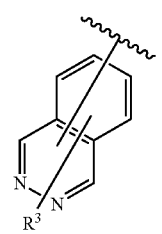
79
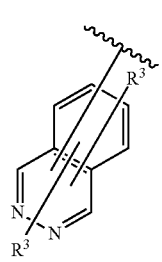
80
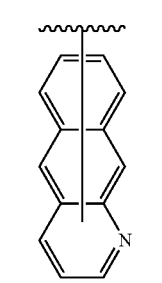
81
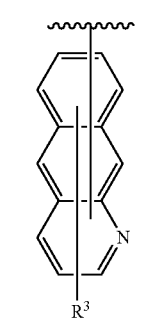
130
-continued
82
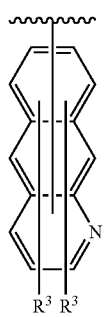
83
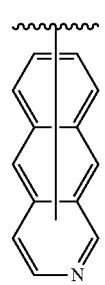
84
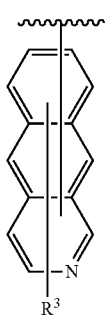
85
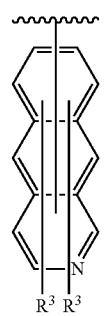
86

131
-continued
87 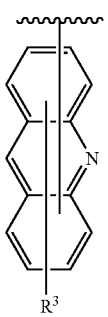
88 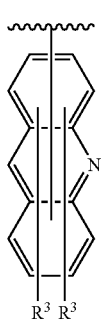
89 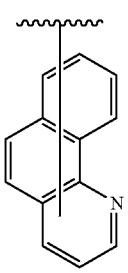
90 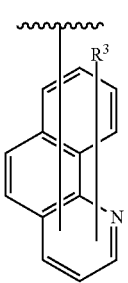
91 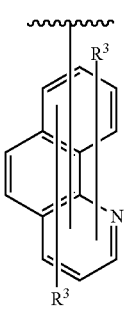
132
-continued
92 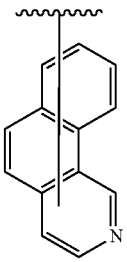
93 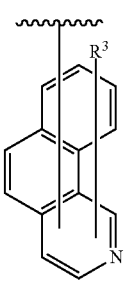
94 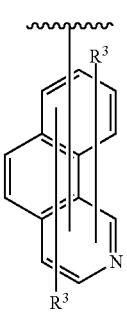
95 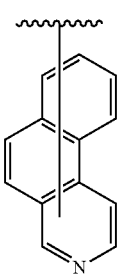
96 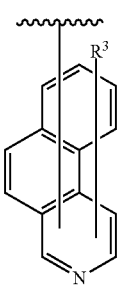

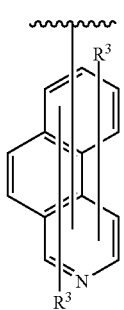 97
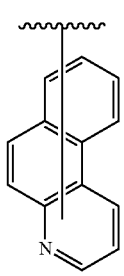 98
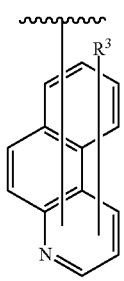 99
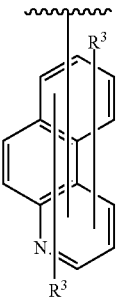 100
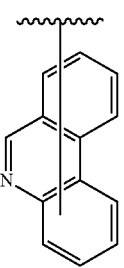 101
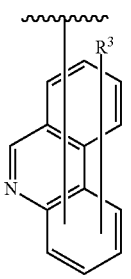 102
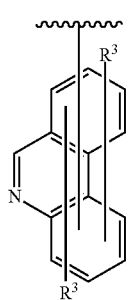 103
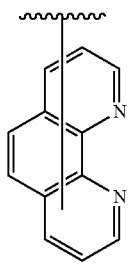 104
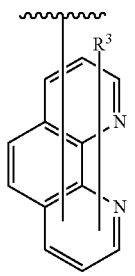 105
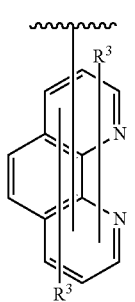 106

107
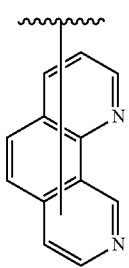
108
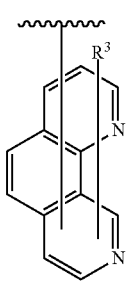
109
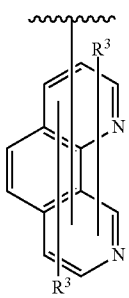
110
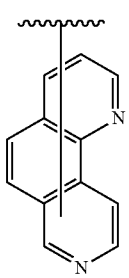
111
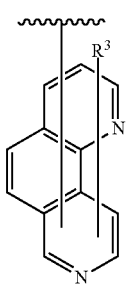
112
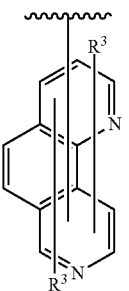
113
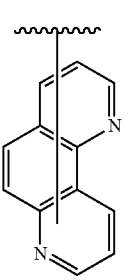
114
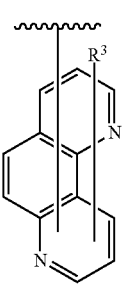
115
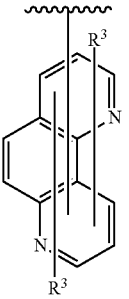
116
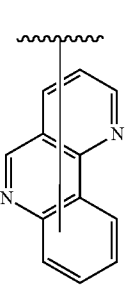

117
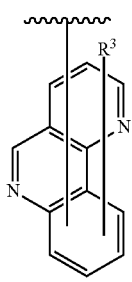
118
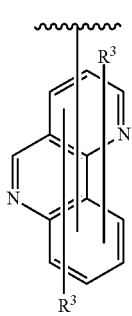
119
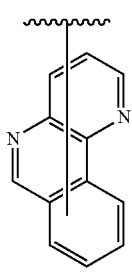
120
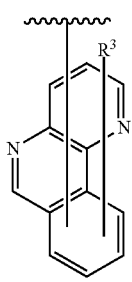
121
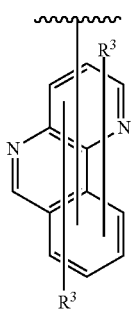
122
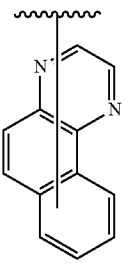
123
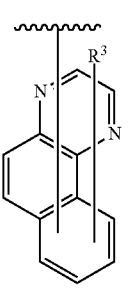
124
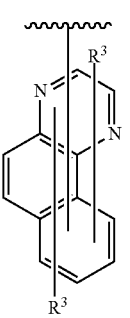
125
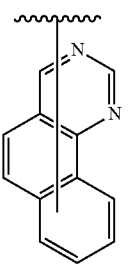
126
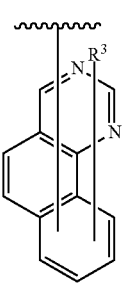

| | |
|---|---|
| 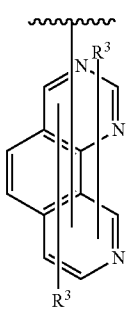 127 | 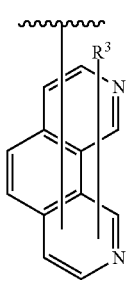 132 |
| 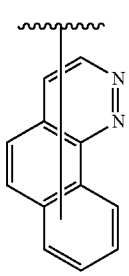 128 | 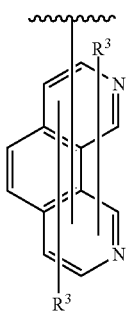 133 |
| 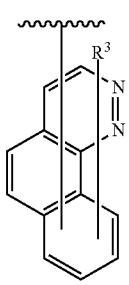 129 | 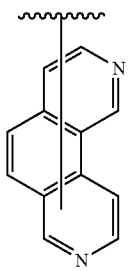 134 |
| 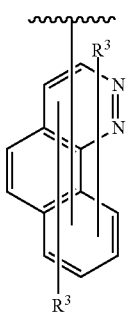 130 | 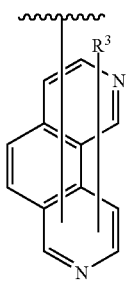 135 |
| 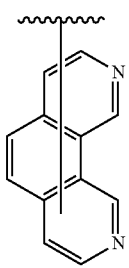 131 | 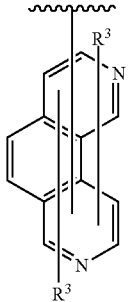 136 |

-continued
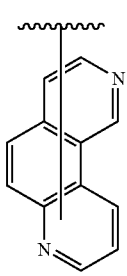
137
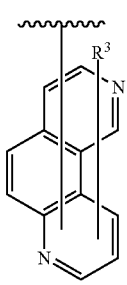
138
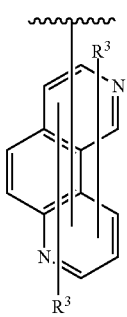
139
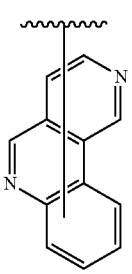
140
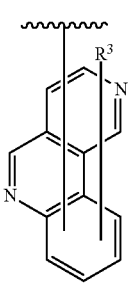
141
-continued
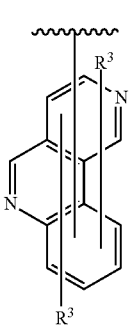
142
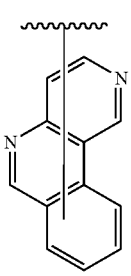
143
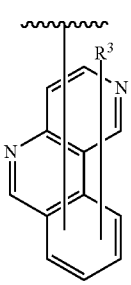
144
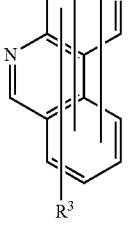
145
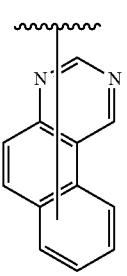
146

147 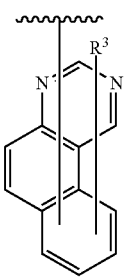
148 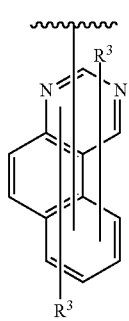
149 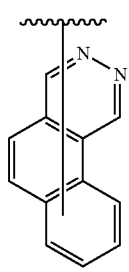
150 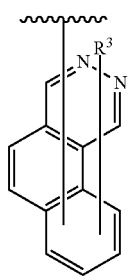
151 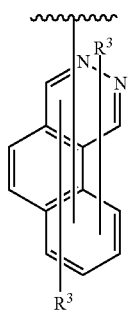
152 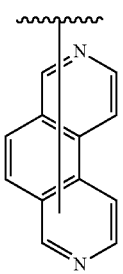
153 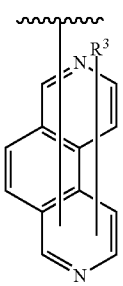
154 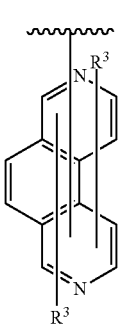
155 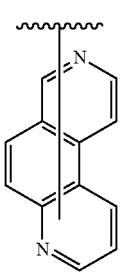
156 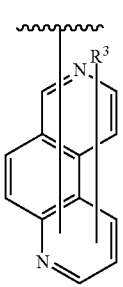

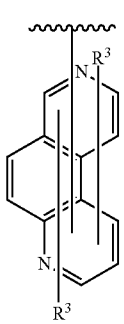 157
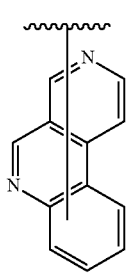 158
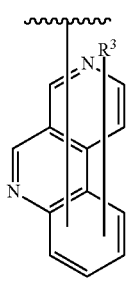 159
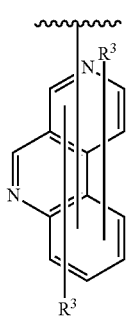 160
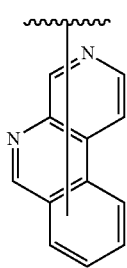 161
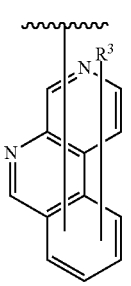 162
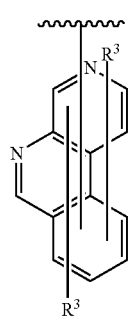 163
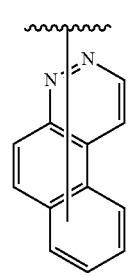 164
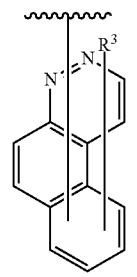 165
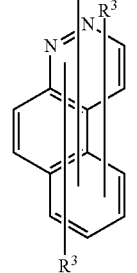 166

147
-continued
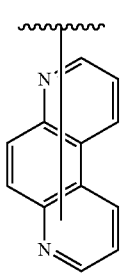
167
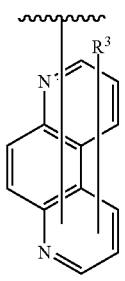
168
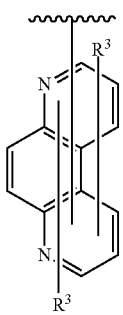
169
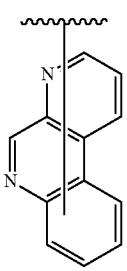
170
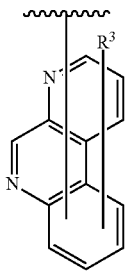
171
148
-continued
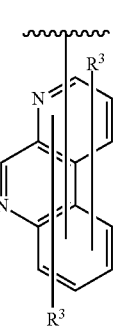
172
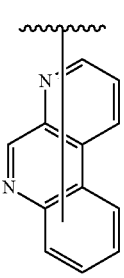
173
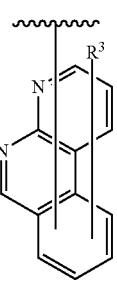
174
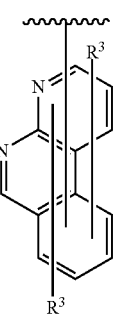
175
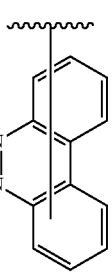
176

| | | |
|---|---|---|
| 177 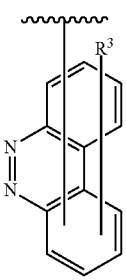 | 184 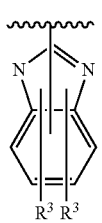 |
| 178 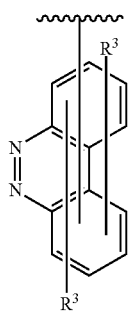 | 185 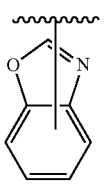 |
| 179 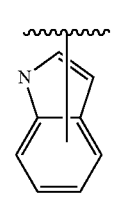 | 186 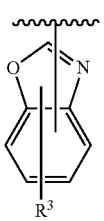 |
| 180 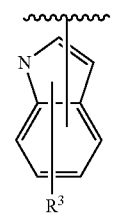 | 187 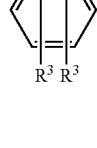 |
| 181 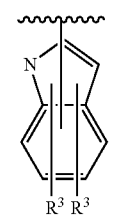 | 188 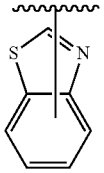 |
| 182 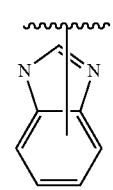 | 189  |
| 183 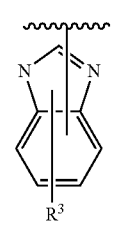 | 190 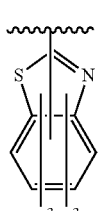 |

191
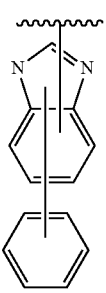
(Each R³ independently represents a C₁₋₄ alkyl group.)
Among these, the following nitrogen-containing heteroaromatic groups are preferred from the viewpoint of good performance of the organic electroluminescent device.
31
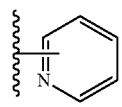
32
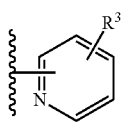
33
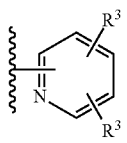
35
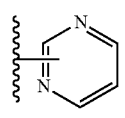
36
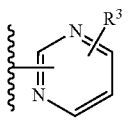
37
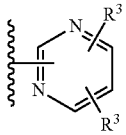
47
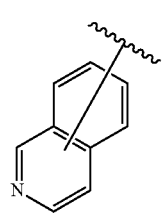
48
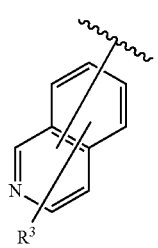
49
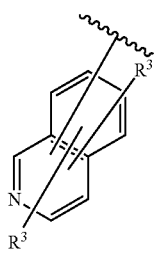
104
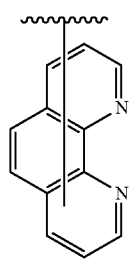
105
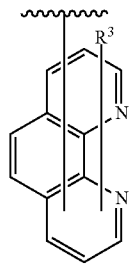
106
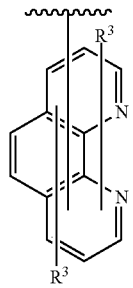
182
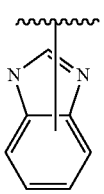

-continued

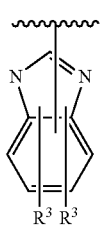
183

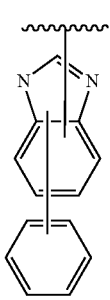
184

191

(Each R³ independently represents a $C_{1-4}$ alkyl group.)

Further, from the viewpoint of easy synthesis, the following nitrogen-containing heteroaromatic groups are more preferred.

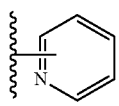
31

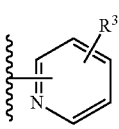
32

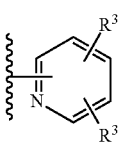
33

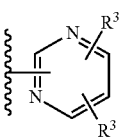
37

(Each R³ independently represents a $C_{1-4}$ alkyl group.)

As the phenylene group which may be substituted by a $C_{1-4}$ alkyl group, represented by X, the following phenylene groups may, for example, be mentioned, although it is not particularly limited thereto.

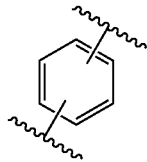
X-1

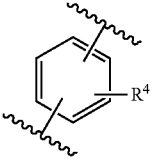
X-2

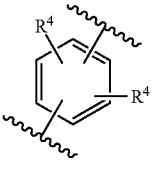
X-3

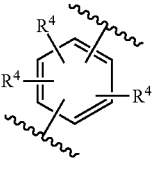
X-4

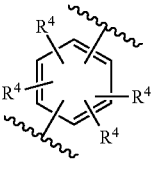
X-5

(Each R⁴ independently represents a $C_{1-4}$ alkyl group.)

Among these, the following aromatic hydrocarbon groups are preferred from the viewpoint of good performance of the organic electroluminescent device.

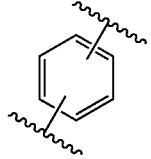
X-1

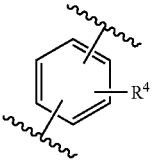
X-2

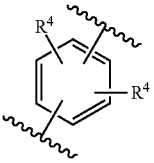
X-3

(Each R⁴ independently represents a $C_{1-4}$ alkyl group.)

Further, from the viewpoint of easy synthesis, the following aromatic hydrocarbon group is more preferred.

X-1

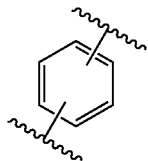

As the azabenzene group which may be substituted by a $C_{1-4}$ alkyl group, represented by X, the following azabenzene groups may, for example, be mentioned, although it is not particularly limited thereto.

X-6

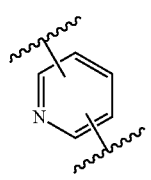

X-7

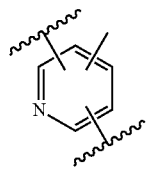

X-8

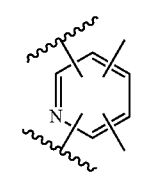

X-9

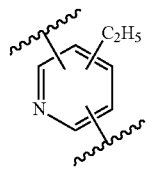

X-10

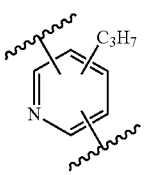

X-11

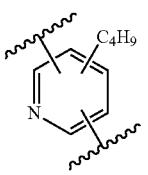

X-12

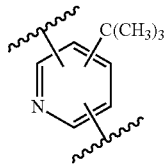

X-13

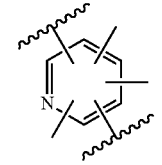

X-14

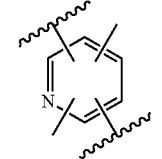

X-15

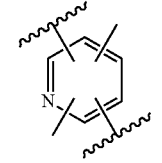

X-16

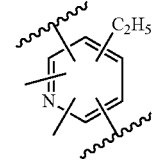

X-17

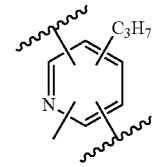

As the diazabenzene group which may be substituted by a $C_{1-4}$ alkyl group, represented by X, the following diazabenzene groups may, for example, be mentioned, although it is not particularly limited thereto.

X-18

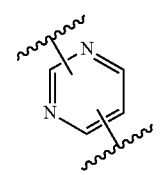

X-19

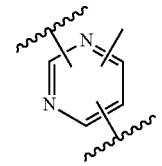

| | | |
|---|---|---|
| X-20 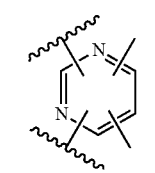 | X-29 | 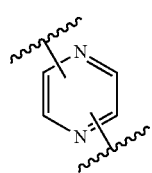 |
| X-21 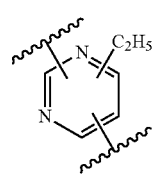 | X-30 | 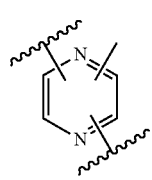 |
| X-22 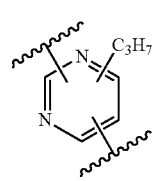 | X-31 | 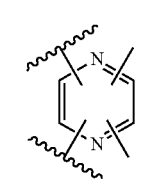 |
| X-23 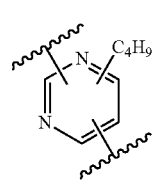 | X-32 | 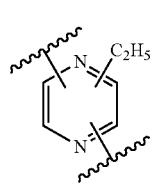 |
| X-24 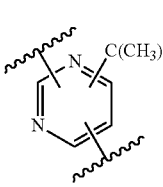 | X-33 | 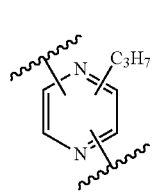 |
| X-25 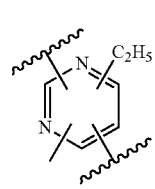 | X-34 | 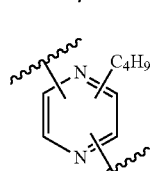 |
| X-26 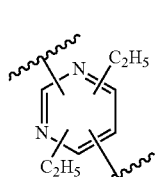 | X-35 | 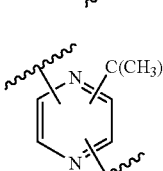 |
| X-27 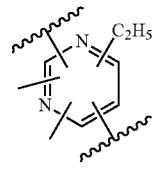 | X-36 | 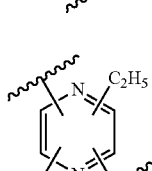 |
| X-28 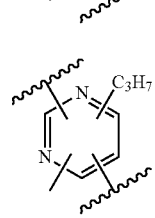 | X-37 | 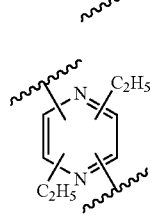 |

X-38
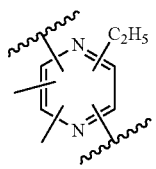

X-39
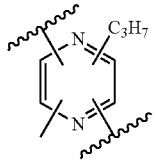

X-40
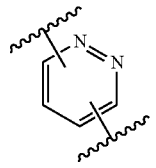

X-41
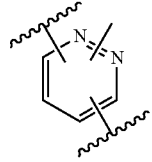

X-42
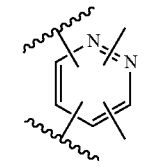

X-43
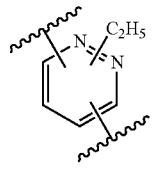

That is, each X independently is preferably a phenylene group or a pyridylene group from the viewpoint of good performance of the organic electroluminescent device.

Each of p and q representing the number of X is independently an integer of 0, 1 or 2. Here, p and q respectively represent that p number and q number of substituents X are linked.

Each of p and q independently is preferably 0 or 1 from the viewpoint of good performance of the organic electroluminescent device.

As the $C_{6-12}$ hydrocarbon group represented by $Ar^2$, the following hydrocarbon groups may, for example, be mentioned, although it is not particularly limited thereto.

1
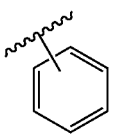

5
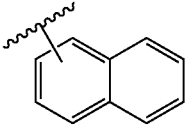

9
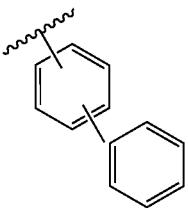

Among these, the following hydrocarbon group is preferred from the viewpoint of good performance of the organic electroluminescent device.

1
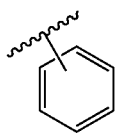

r representing the number of X is an integer of 0, 1 or 2.

As the $C_{6-12}$ aromatic hydrocarbon group represented by substituent (D), the following aromatic hydrocarbon groups may, for example, be mentioned, although it is not particularly limited thereto.

D-1
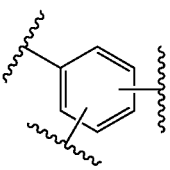

D-2
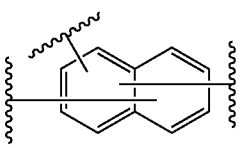

D-3
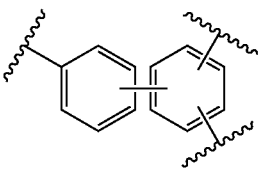

Among these, the following aromatic hydrocarbon group is preferred from the viewpoint of good performance of the organic electroluminescent device.

D-1
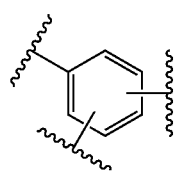
As the C$_{3-4}$ nitrogen-containing heteroaromatic group which may be substituted by a C$_{1-4}$ alkyl group, represented by Ar$^3$, the following nitrogen-containing heteroaromatic groups may, for example, be mentioned, although it is not particularly limited thereto.
31
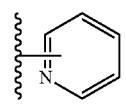
32
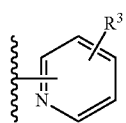
33
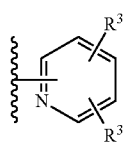
34
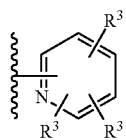
35
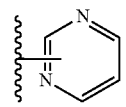
36
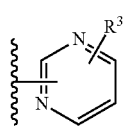
37
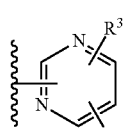
38
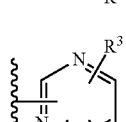
39
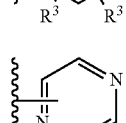
-continued
40
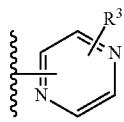
41
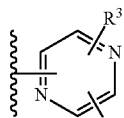
42
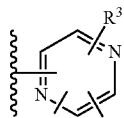
43
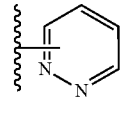
44
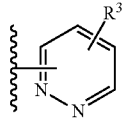
45
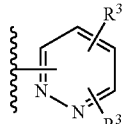
46
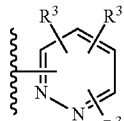
47
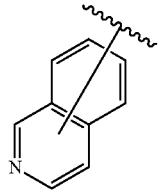
48
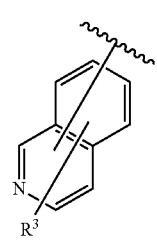

| 163 -continued | | 164 -continued | |
|---|---|---|---|
| 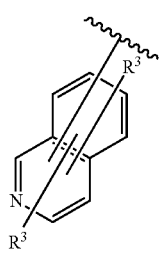 | 49 | 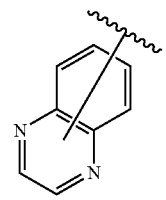 | 56 |
| 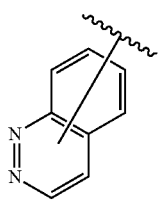 | 50 | 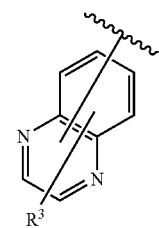 | 57 |
| 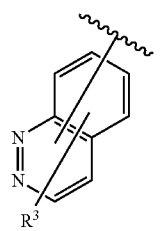 | 51 | 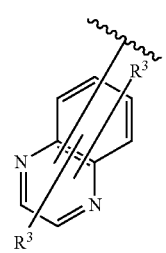 | 58 |
| 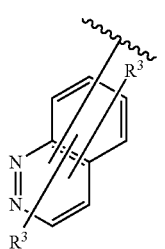 | 52 | 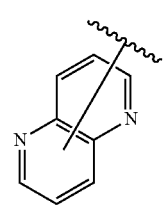 | 59 |
| 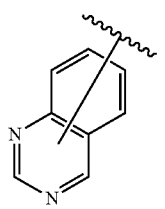 | 53 | 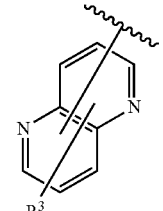 | 60 |
| 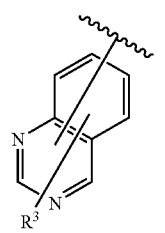 | 54 | 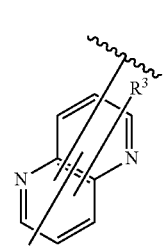 | 61 |
| 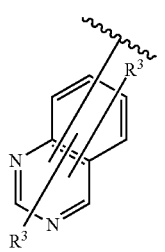 | 55 | 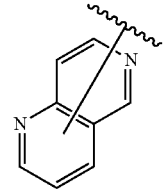 | 62 |

| 63 | 70 |
|---|---|
| 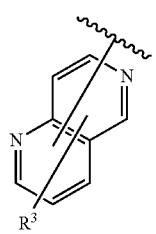 | 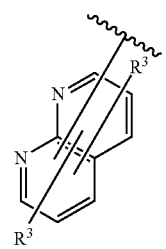 |
| 64 | 71 |
| 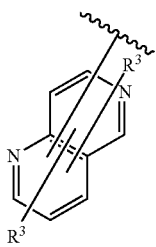 | 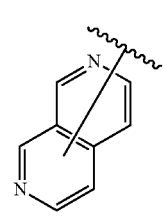 |
| 65 | 72 |
| 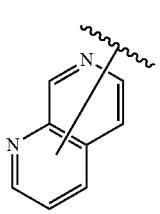 | 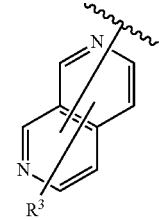 |
| 66 | 73 |
| 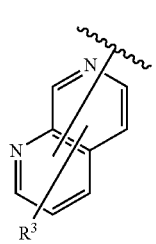 | 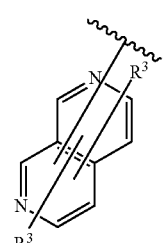 |
| 67 | 74 |
| 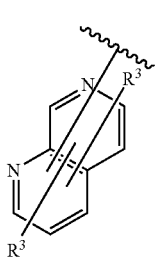 | 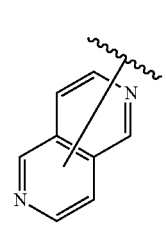 |
| 68 | 75 |
| 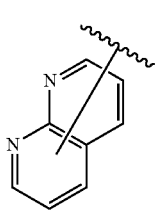 | 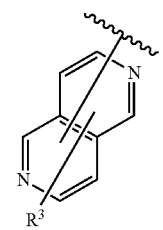 |
| 69 | 76 |
| 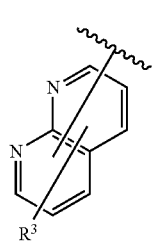 | 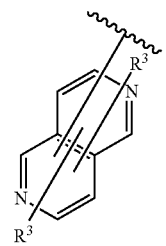 |

167
-continued
77 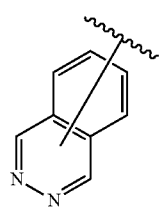
78 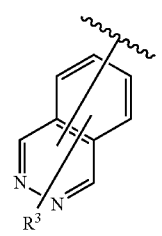
79 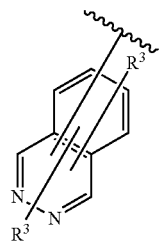
80 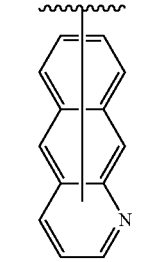
81 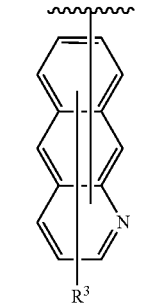
82 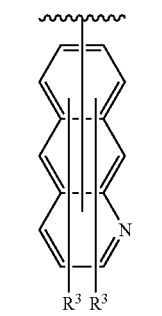
168
-continued
83 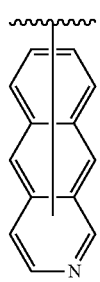
84 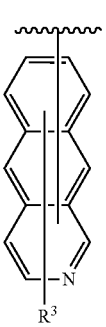
85 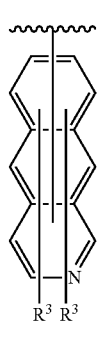
86 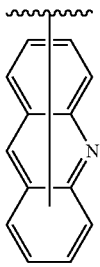
87 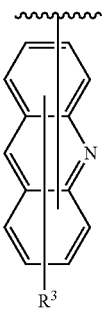

| 169 | | 170 | |
|---|---|---|---|
| -continued | | -continued | |
| 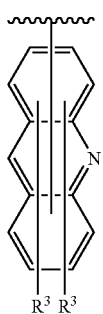 | 88 | 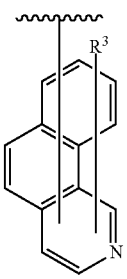 | 93 |
| 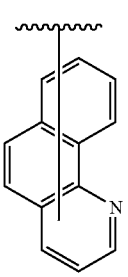 | 89 | 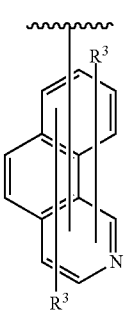 | 94 |
| 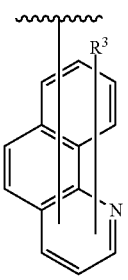 | 90 | 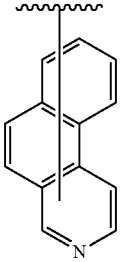 | 95 |
| 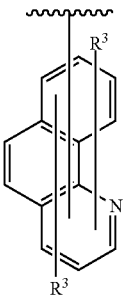 | 91 | 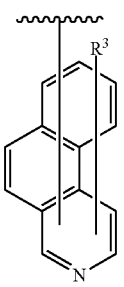 | 96 |
| 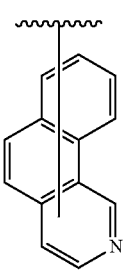 | 92 | 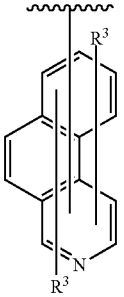 | 97 |

-continued
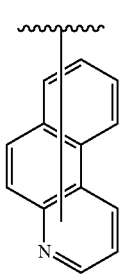 98
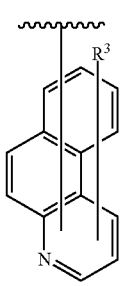 99
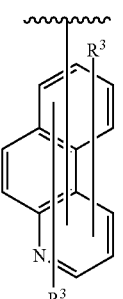 100
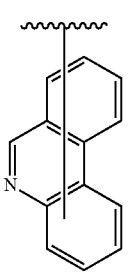 101
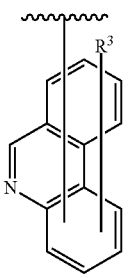 102
-continued
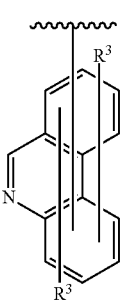 103
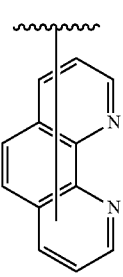 104
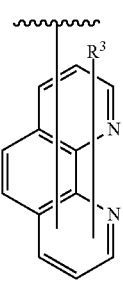 105
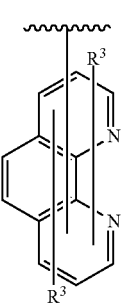 106
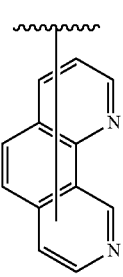 107

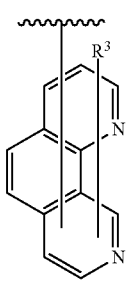 108
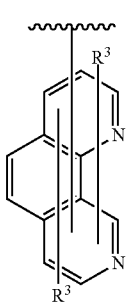 109
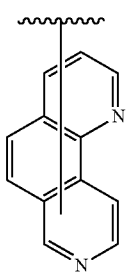 110
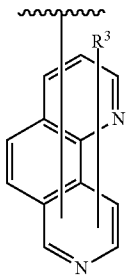 111
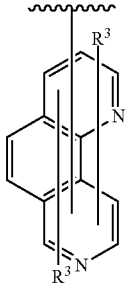 112
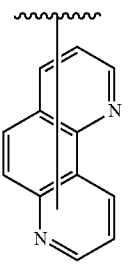 113
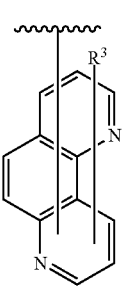 114
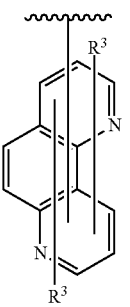 115
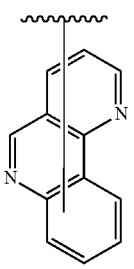 116
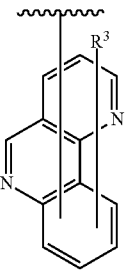 117

| | |
|---|---|
| 118 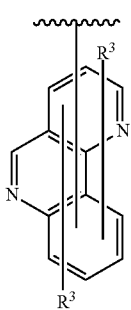 | 123 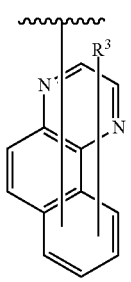 |
| 119 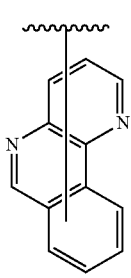 | 124 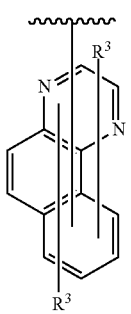 |
| 120 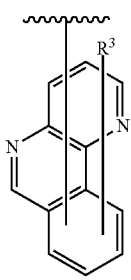 | 125 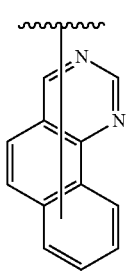 |
| 121 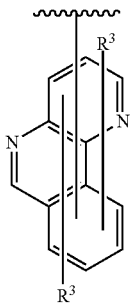 | 126 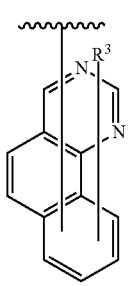 |
| 122 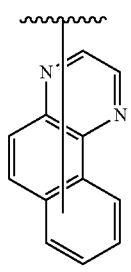 | 127 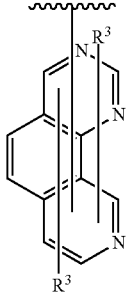 |

| | | |
|---|---|---|
| 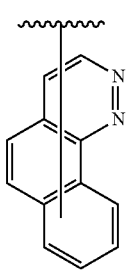 128 | 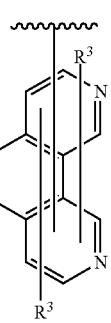 133 | |
| 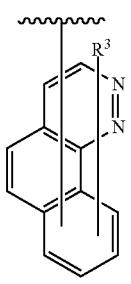 129 | 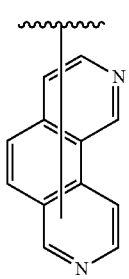 134 | |
| 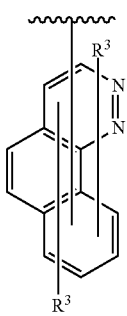 130 | 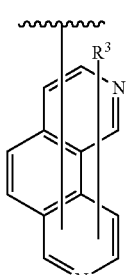 135 | |
| 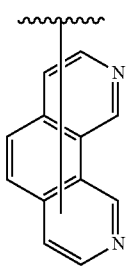 131 | 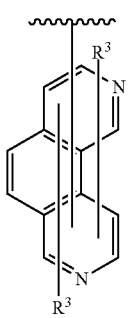 136 | |
| 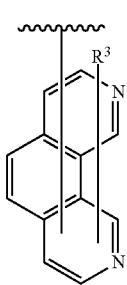 132 | 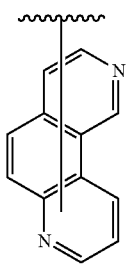 137 | |

| | |
|---|---|
| 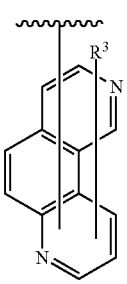 138 | 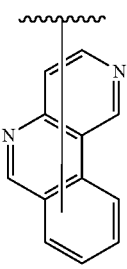 143 |
| 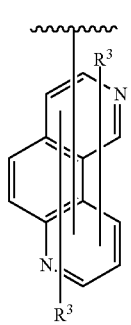 139 | 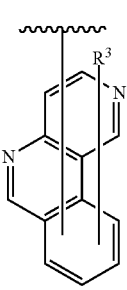 144 |
| 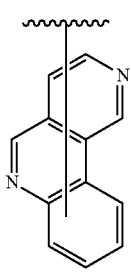 140 | 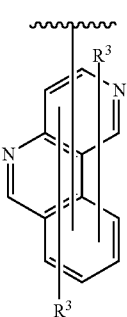 145 |
| 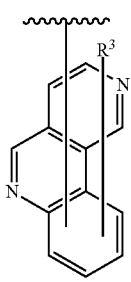 141 | 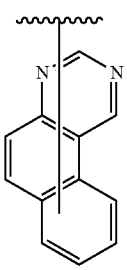 146 |
| 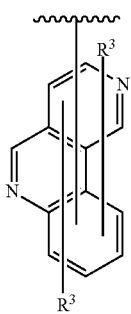 142 | 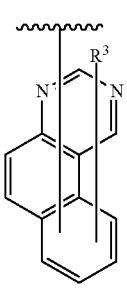 147 |

| | |
|---|---|
| 148 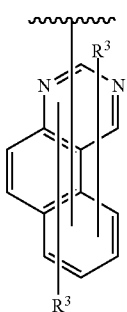 | 153 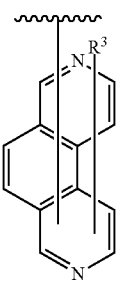 |
| 149 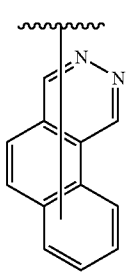 | 154 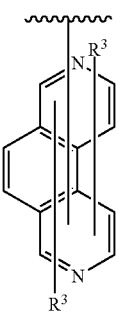 |
| 150 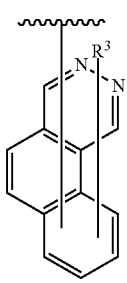 | 155 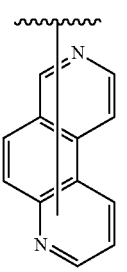 |
| 151 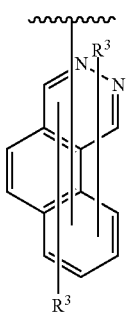 | 156 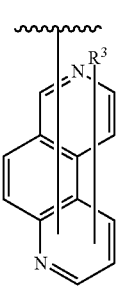 |
| 152 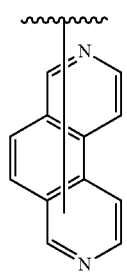 | 157 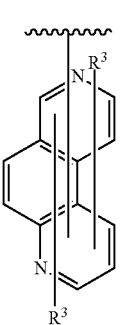 |

158 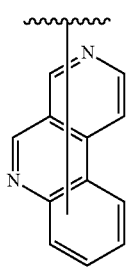
159
160
161
162 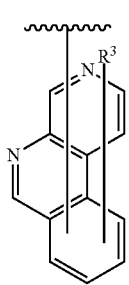
163 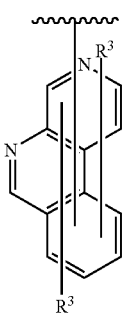
164
165 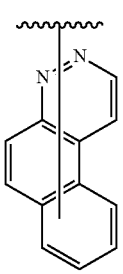
166 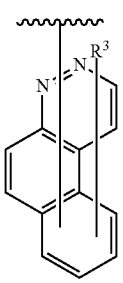
167 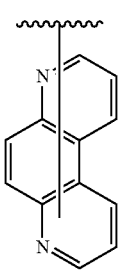

| | | |
|---|---|---|
| 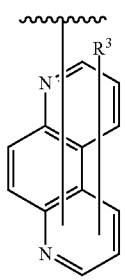 | 168 | 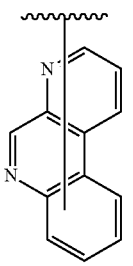 173 |
| 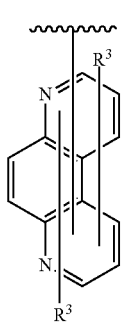 | 169 | 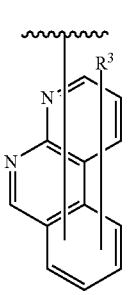 174 |
| 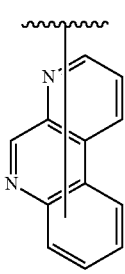 | 170 | 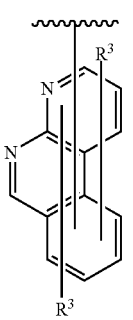 175 |
| 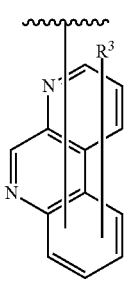 | 171 | 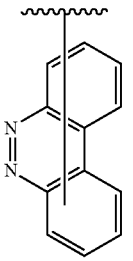 176 |
| 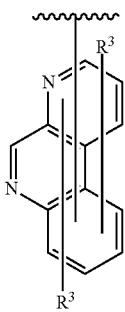 | 172 | 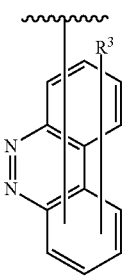 177 |

178 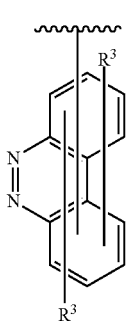
179 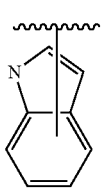
180 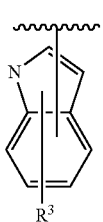
181 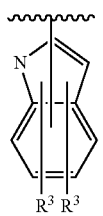
182 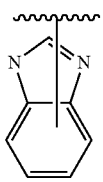
183 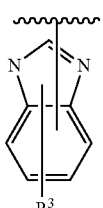
184 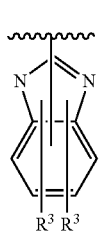
185 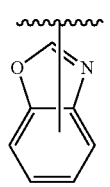
186 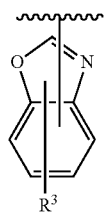
187 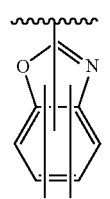
188 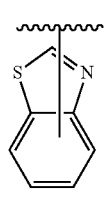
189 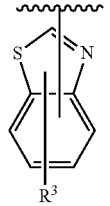
190 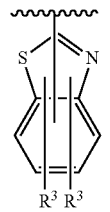
191 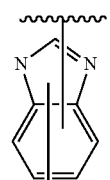
(Each $R^3$ independently represents a $C_{1-4}$ alkyl group.)
Among these, the following nitrogen-containing heteroaromatic groups are preferred from the viewpoint of good performance of the organic electroluminescent device.

| 189 | | 190 |
|---|---|---|
| 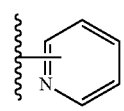 | 31 | 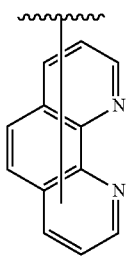 104 |
| 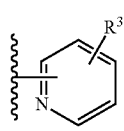 | 32 | |
| 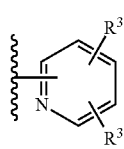 | 33 | 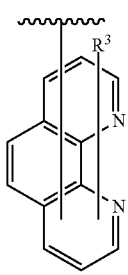 105 |
| 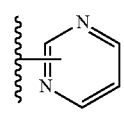 | 35 | |
| 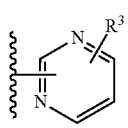 | 36 | 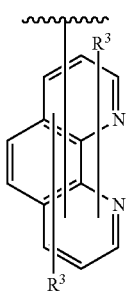 106 |
| 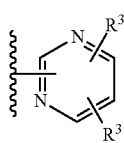 | 37 | |
| 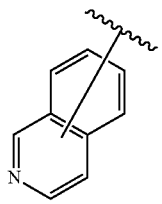 | 47 | 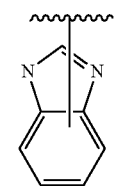 182 |
| 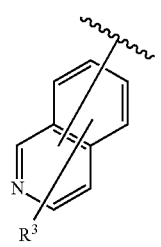 | 48 | 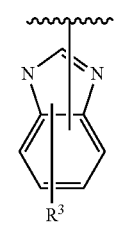 183 |
| 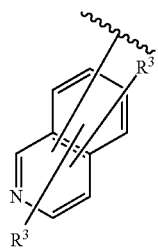 | 49 | 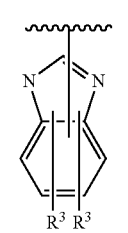 184 |

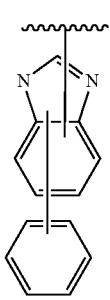

191

(Each R³ independently represents a C₁₋₄ alkyl group.)

Further, from the viewpoint of easy synthesis, the following nitrogen-containing heteroaromatic groups are more preferred.

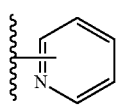

31

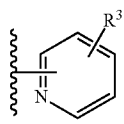

32

(Each R³ independently represents a C₁₋₄ alkyl group.)

Cz represents a carbazolyl group which may be substituted by a pyridyl group.

As the compound of the present invention, and as the compound exhibiting effects equivalent to the present invention, compounds (E-1) to (E-548) represented by the following formulae may, for example, be mentioned, although not particularly limited thereto.

In the compounds exemplified below, "—" bonded to a nitrogen-containing heteroaromatic group or a carbon ring represents that a methyl group is bonded.

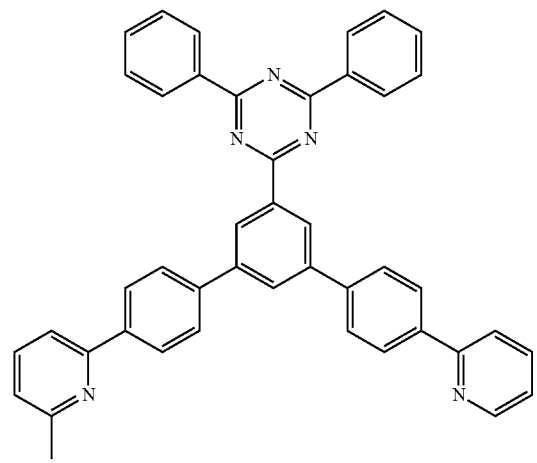

E-1

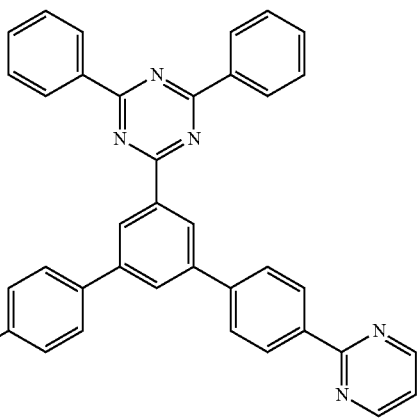

E-2

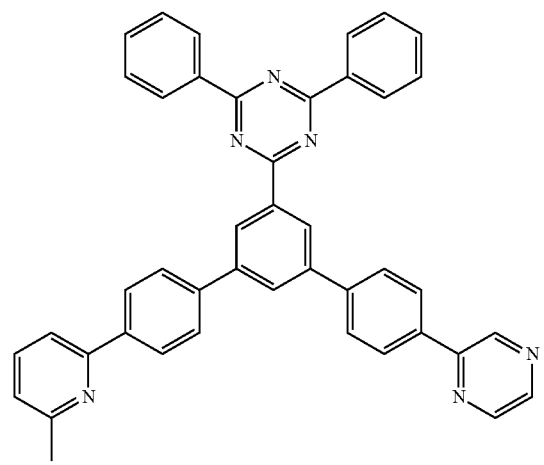

E-3

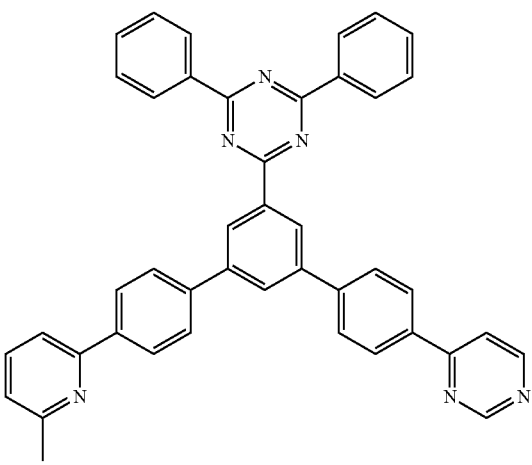

E-4

-continued
E-5
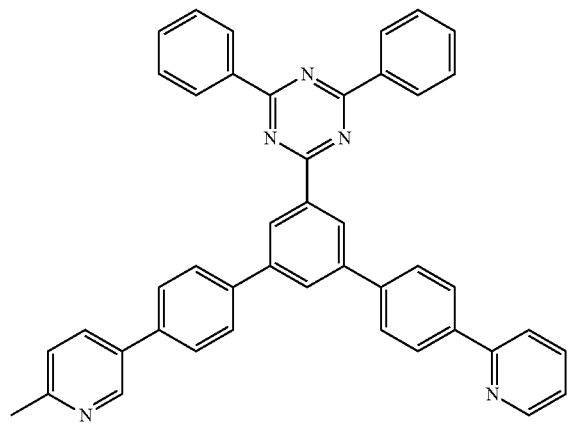
E-6
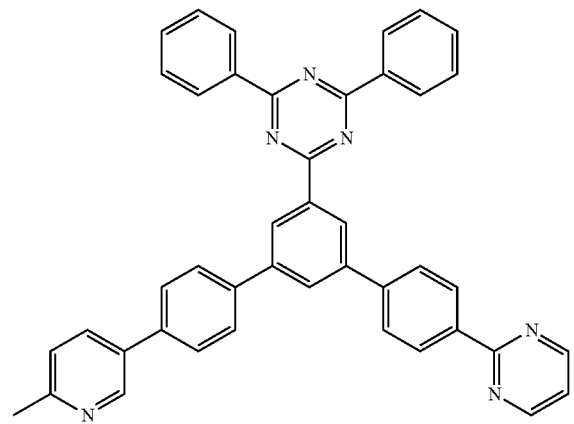
E-7
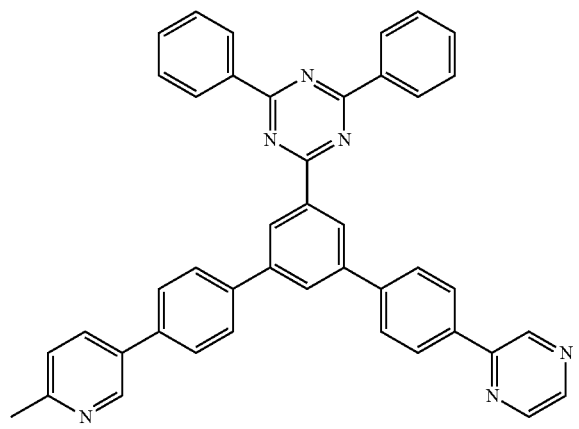
E-8
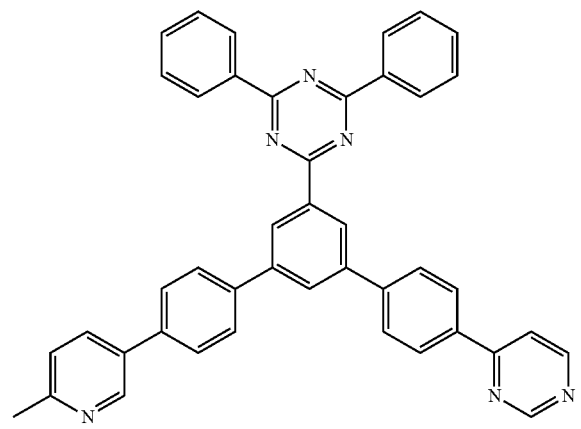
E-9
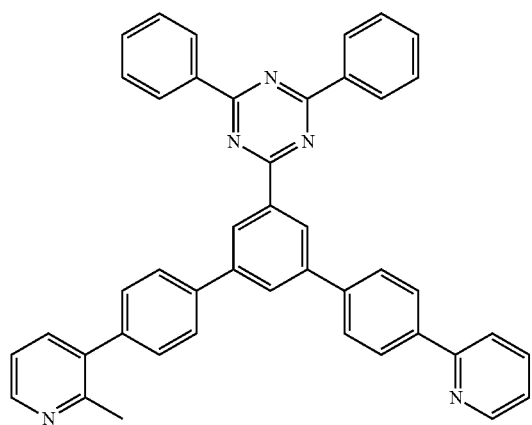
E-10
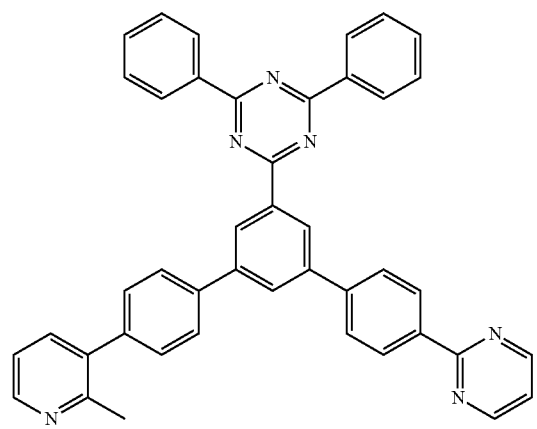

-continued
E-11
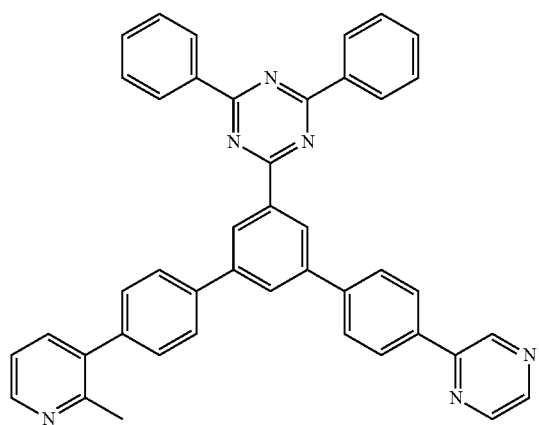
E-12
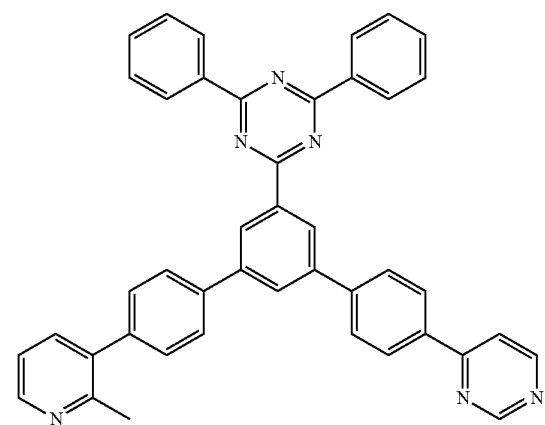
E-13
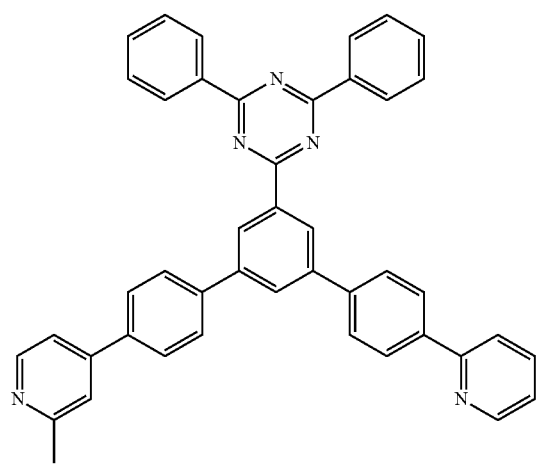
E-14
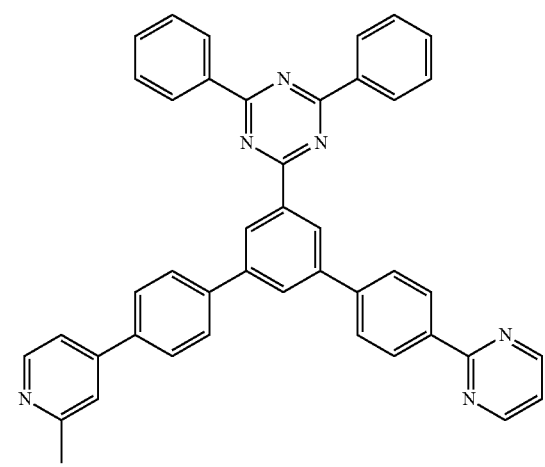
E-15
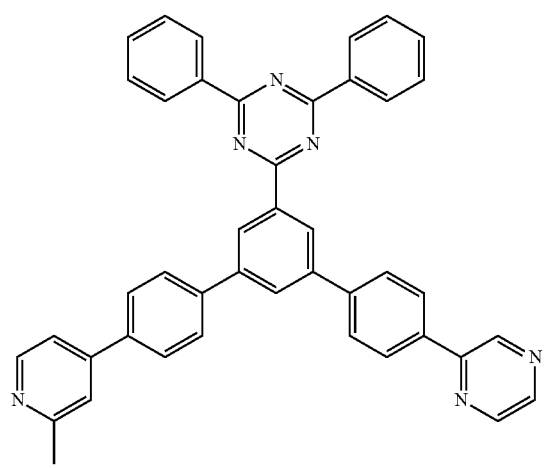
E-16
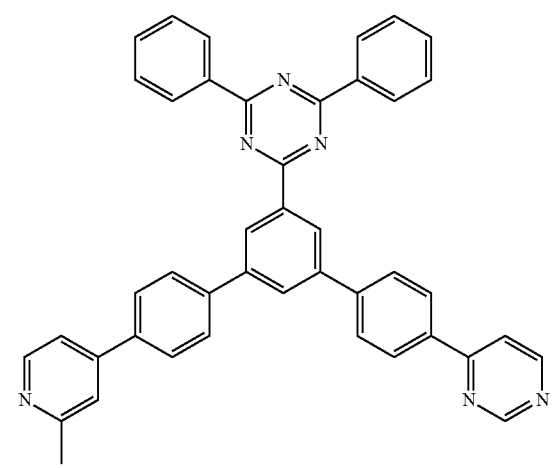

-continued
E-17
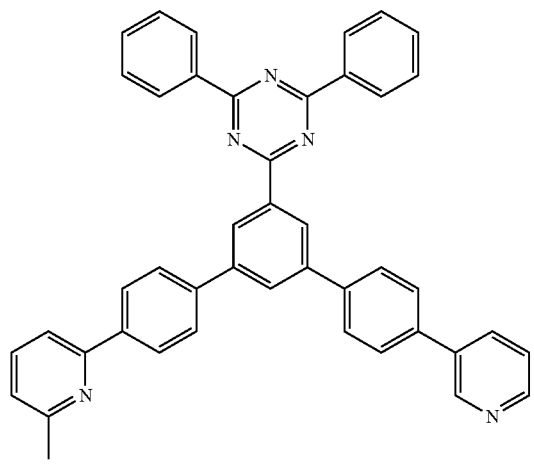
E-18
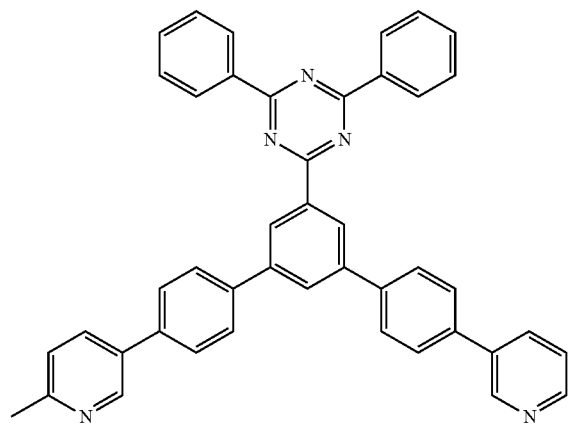
E-19
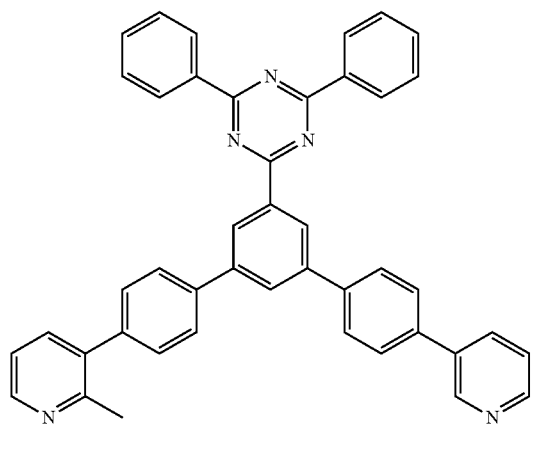
E-20
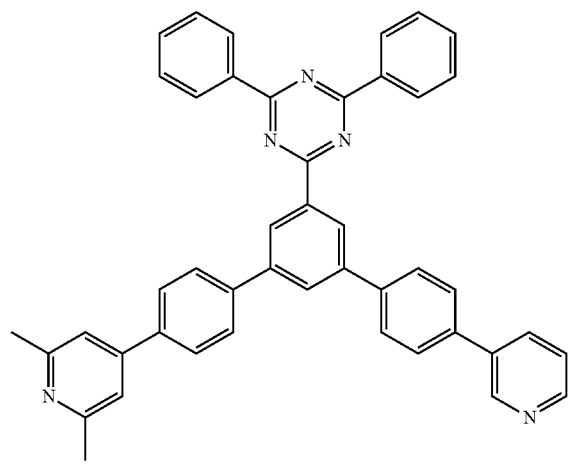
E-21
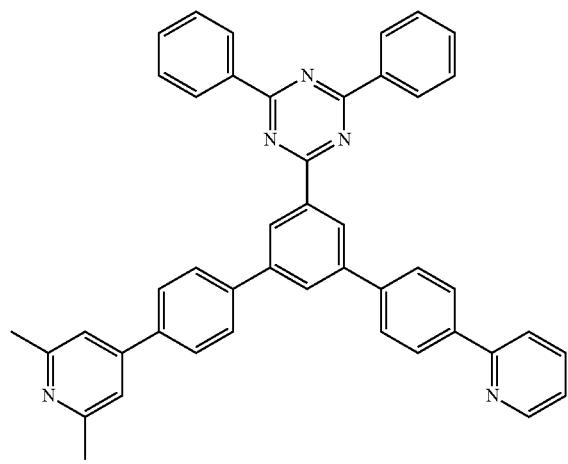
E-22
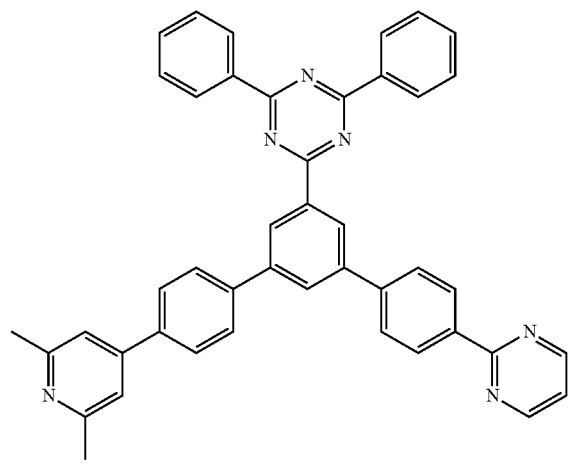

-continued
E-23
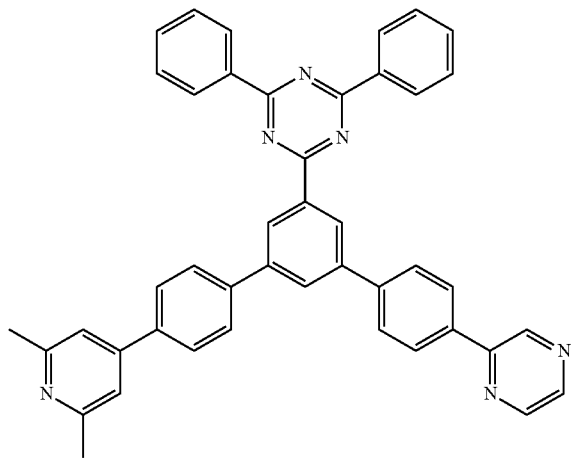
E-24
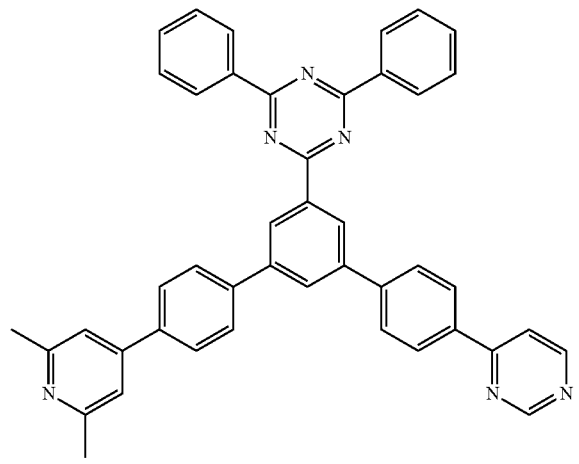
E-25
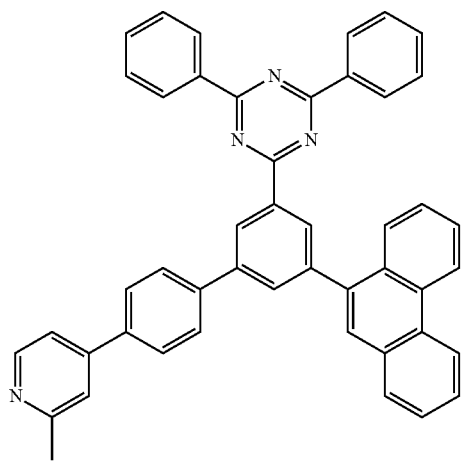
E-26
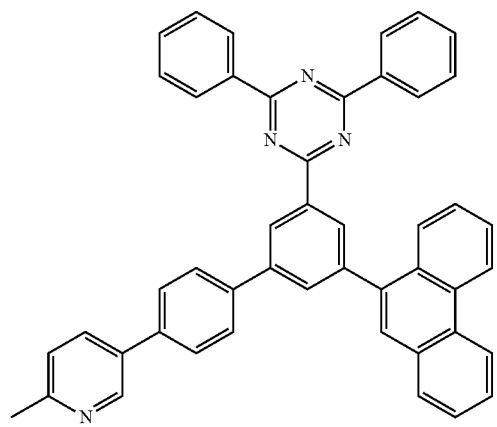
E-27
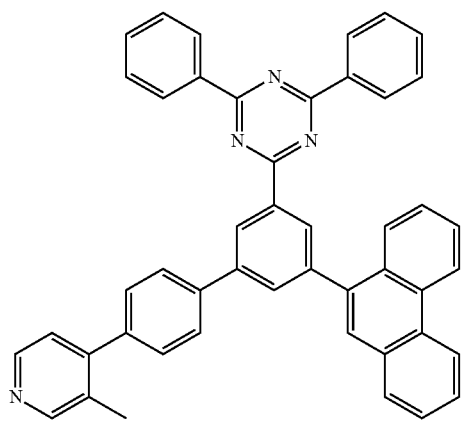
E-28
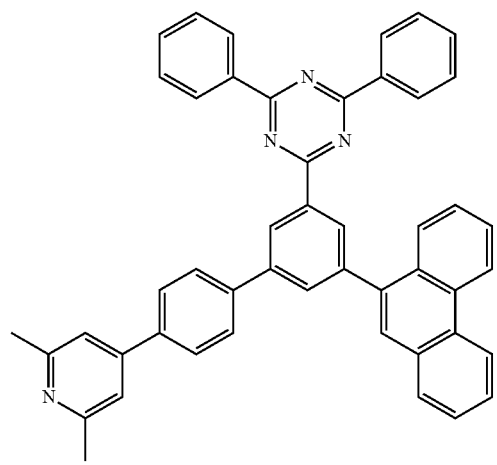

E-29
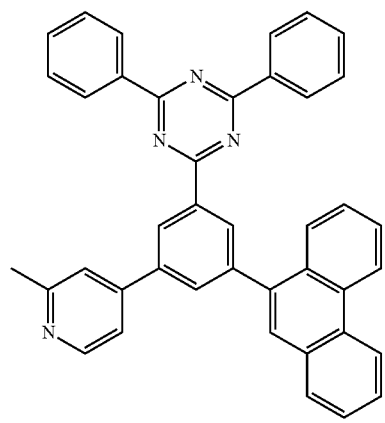
E-30
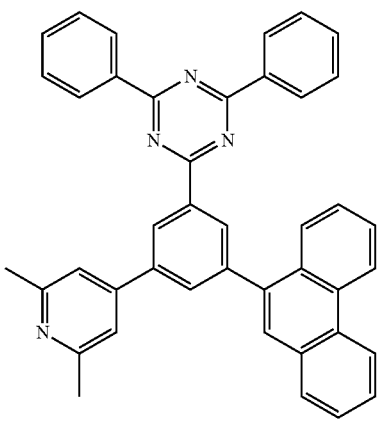
E-31
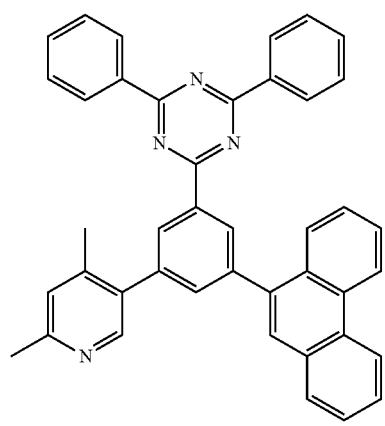
E-32
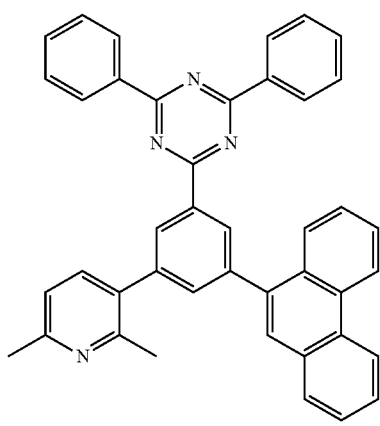
E-33
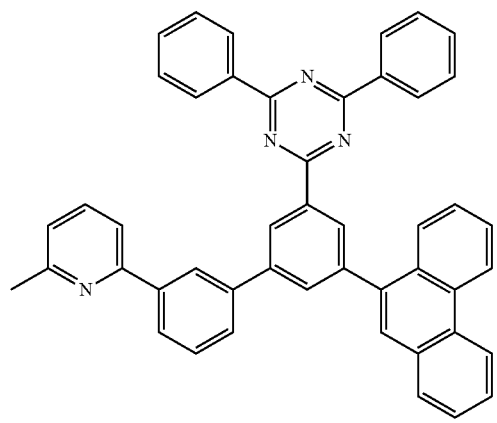
E-34
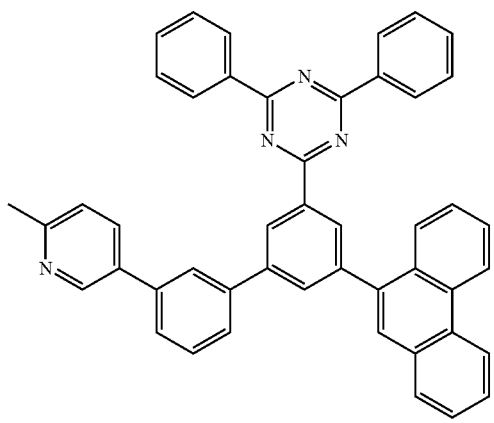

-continued
E-35
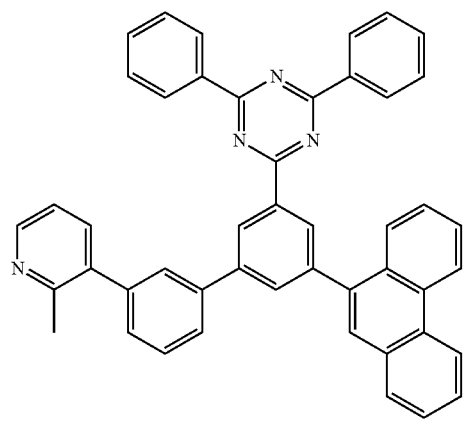
E-36
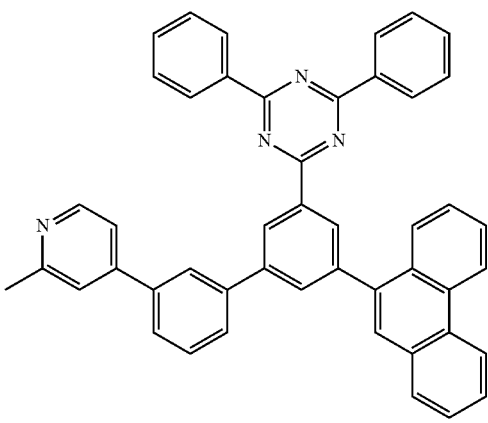
E-37
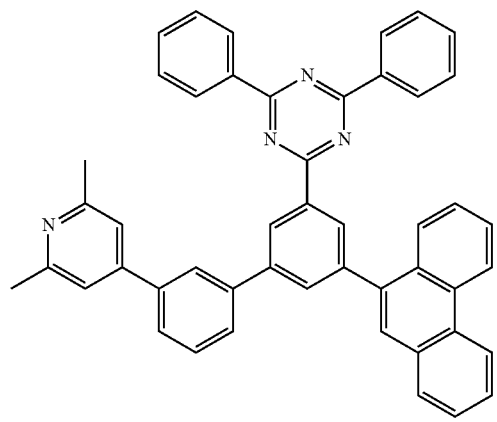
E-38
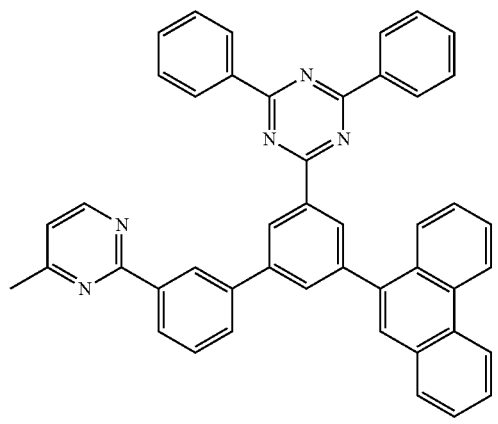
E-39
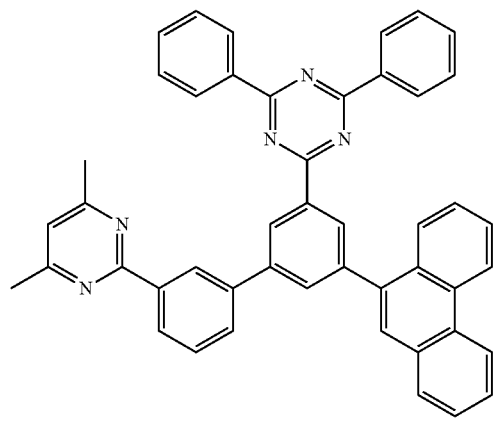
E-40
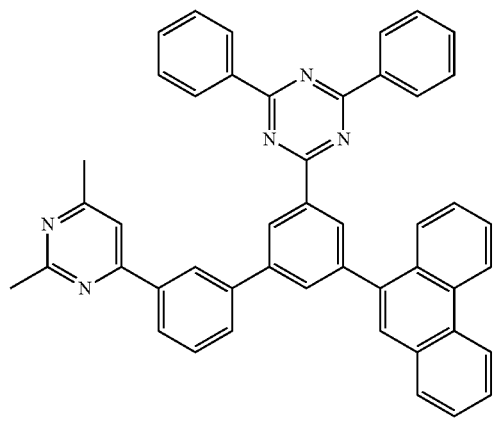

-continued
E-41
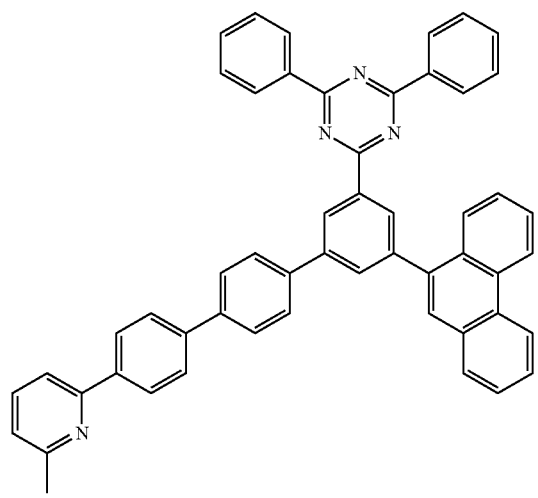
E-42
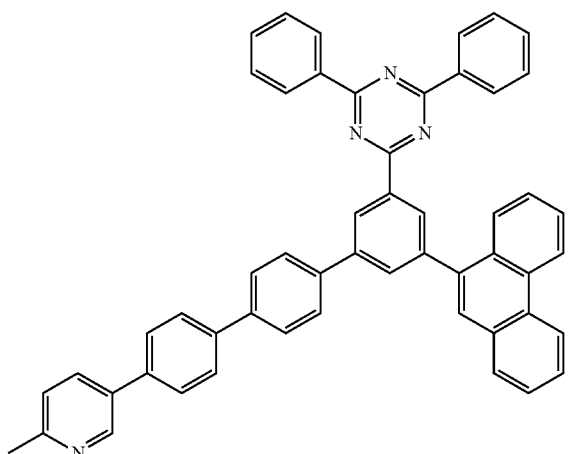
E-43
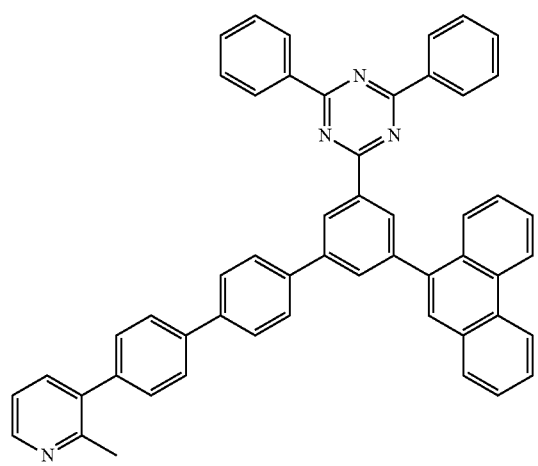
E-44
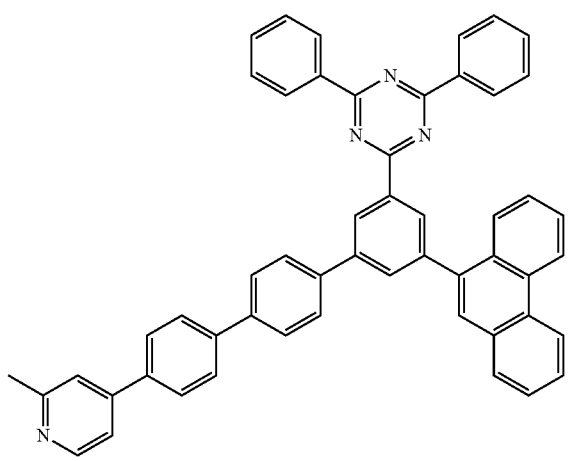
E-45
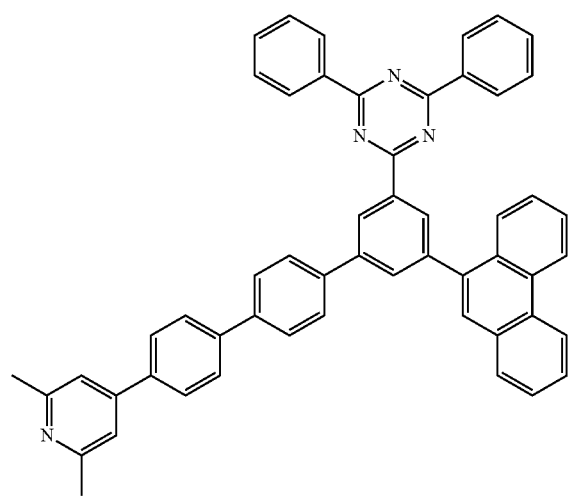
E-46
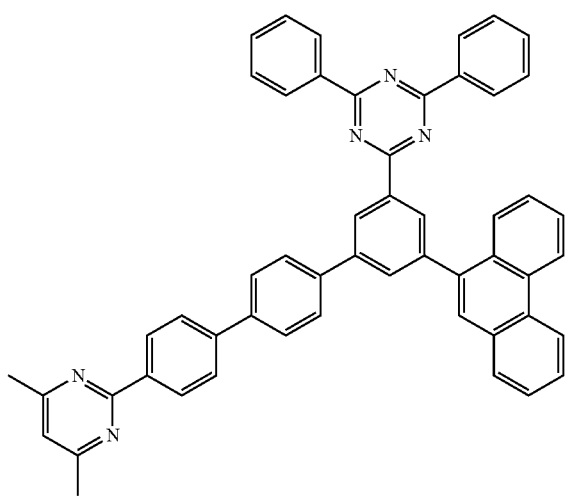

-continued
E-47
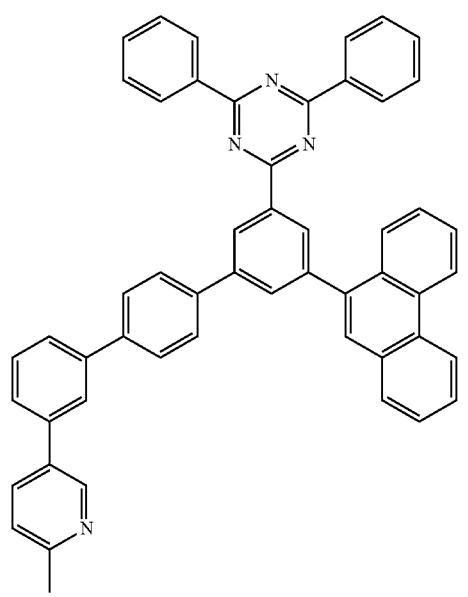
E-48
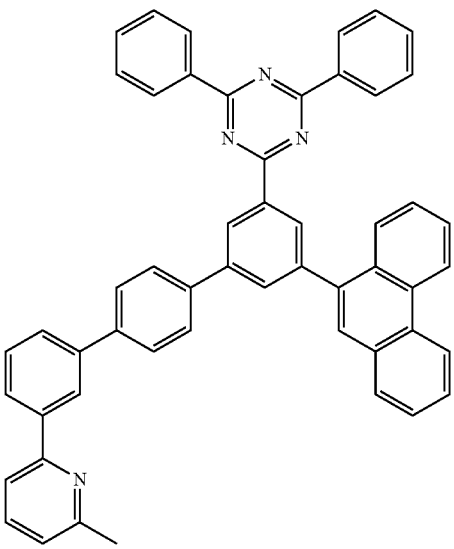
E-49
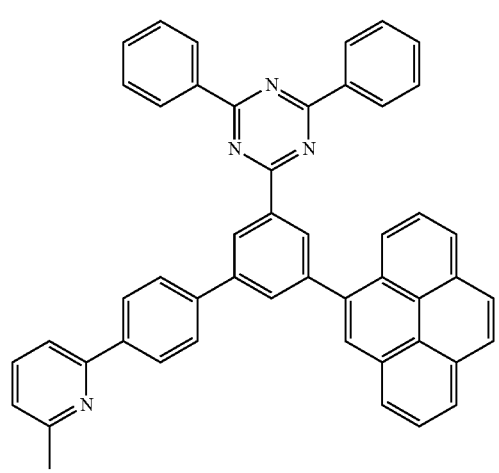
E-50
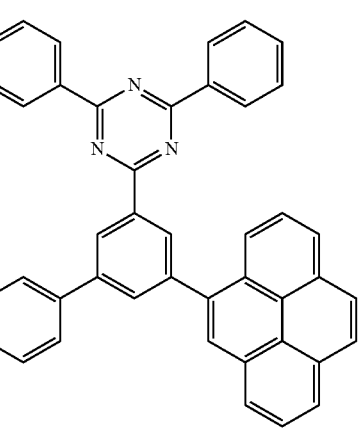
E-51
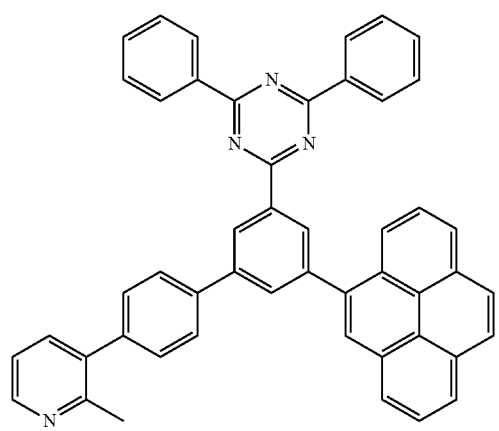
E-52
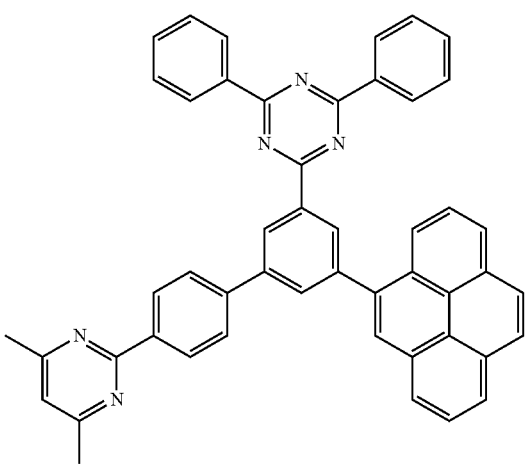

-continued
E-53
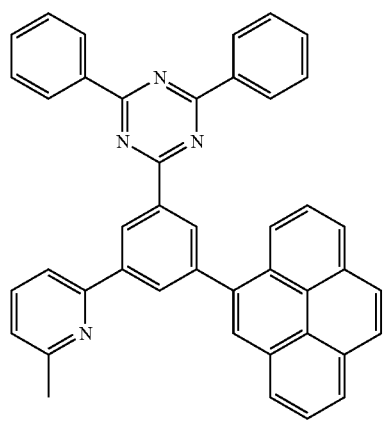
E-54
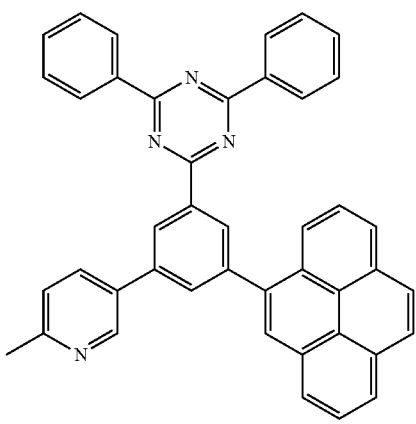
E-55
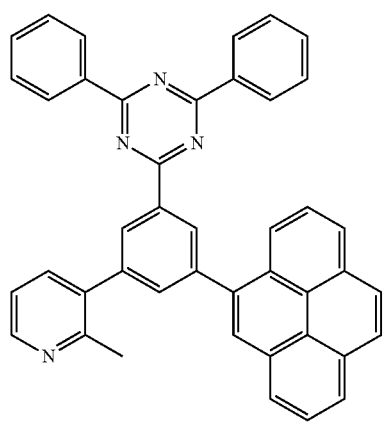
E-56
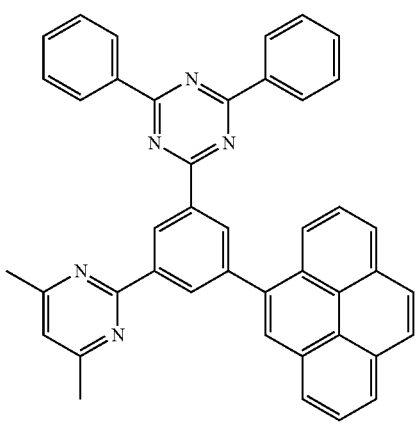
E-57
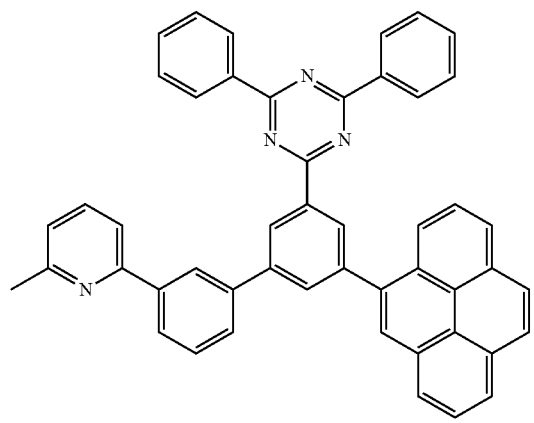
E-58
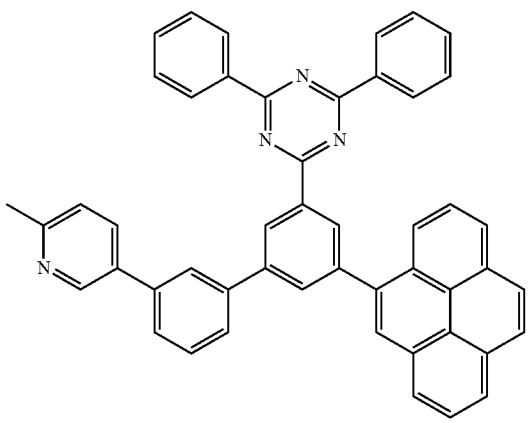

-continued
E-59
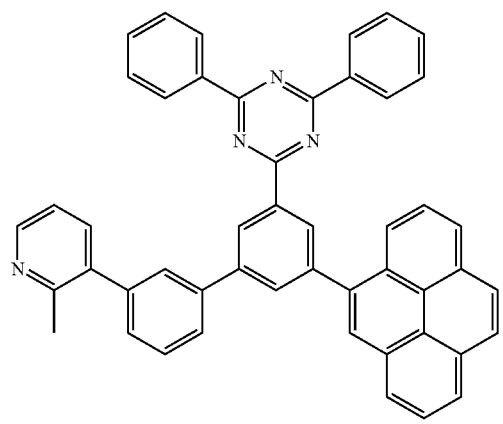
E-60
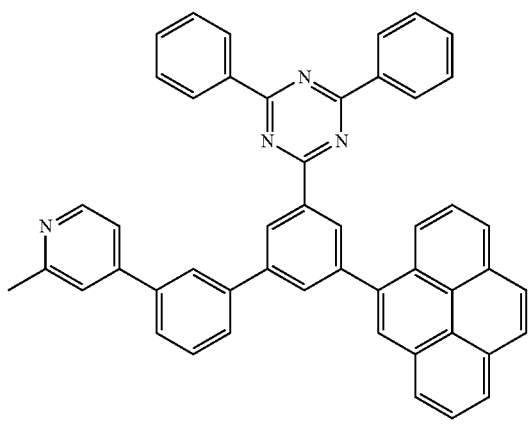
E-61
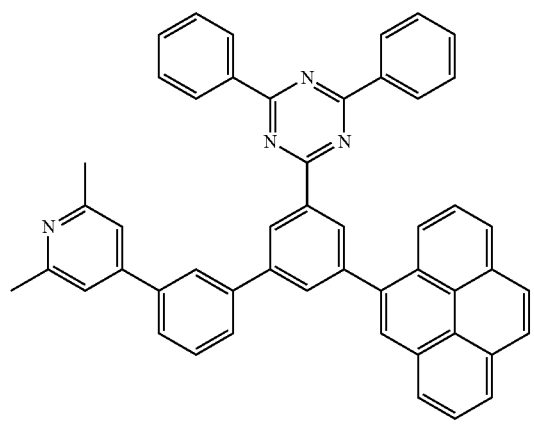
E-62
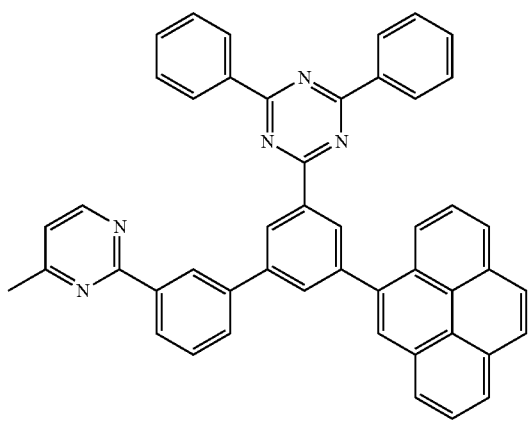
E-63
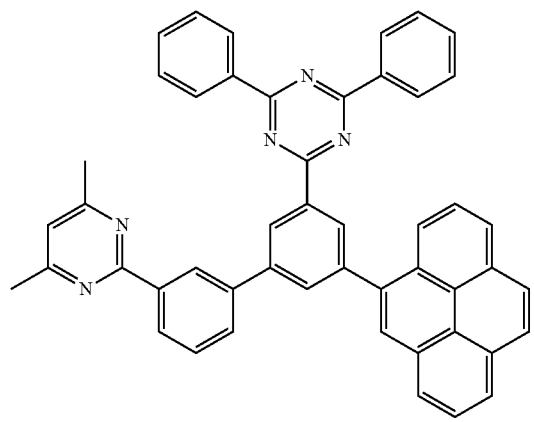
E-64
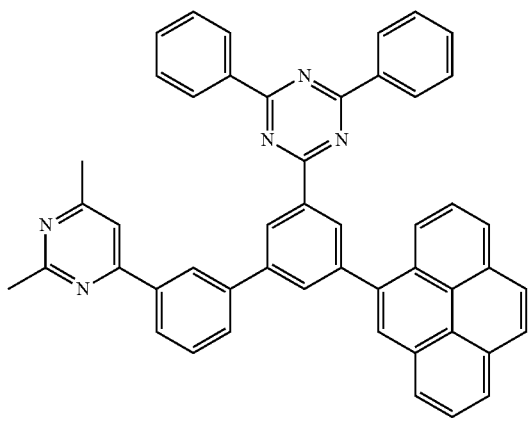

-continued
E-65
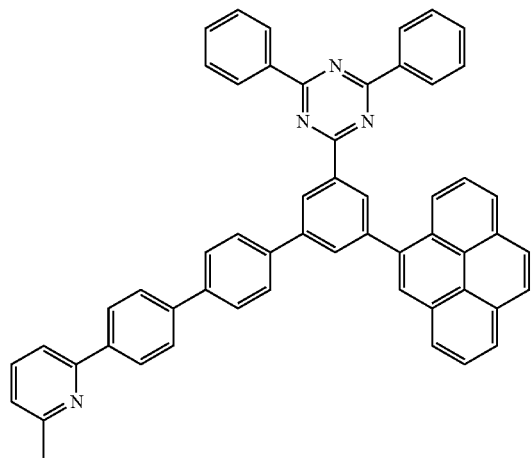
E-66
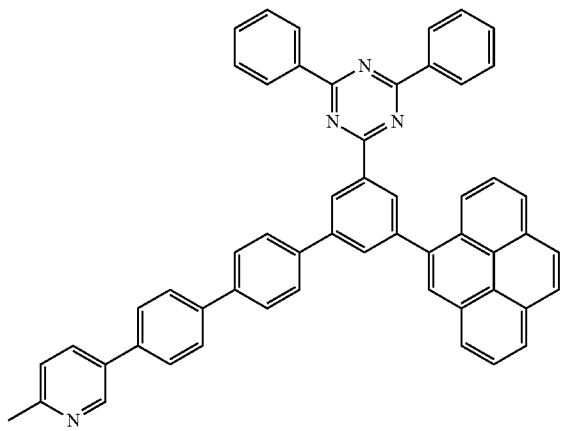
E-67
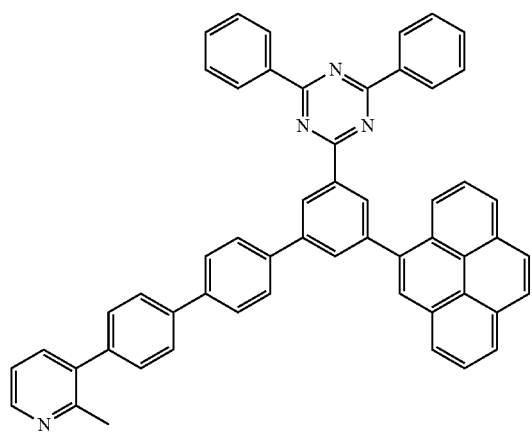
E-68
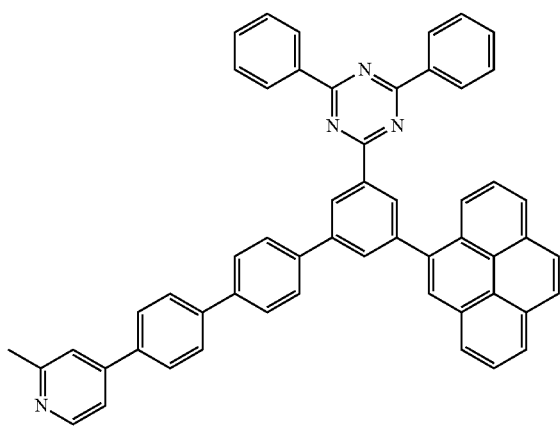
E-69
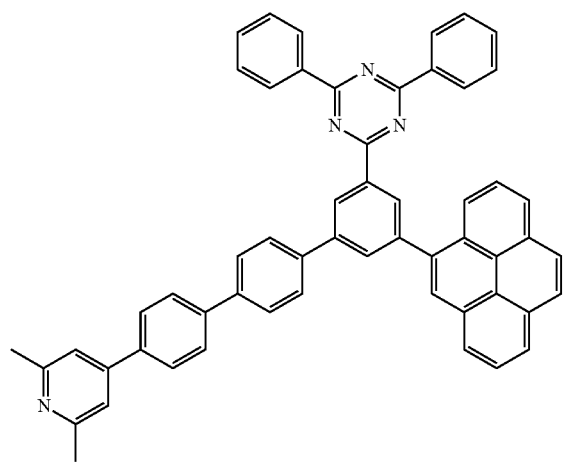
E-70
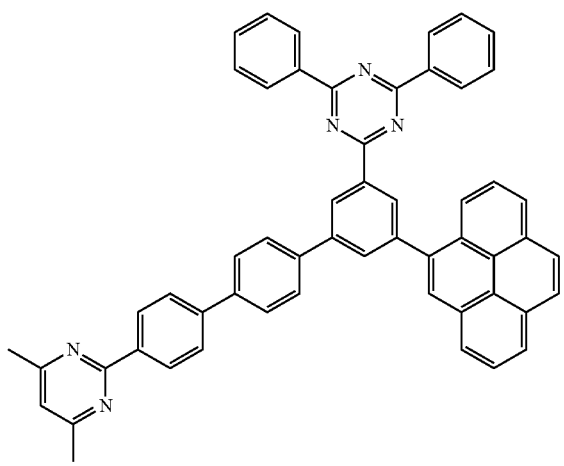

-continued
E-71
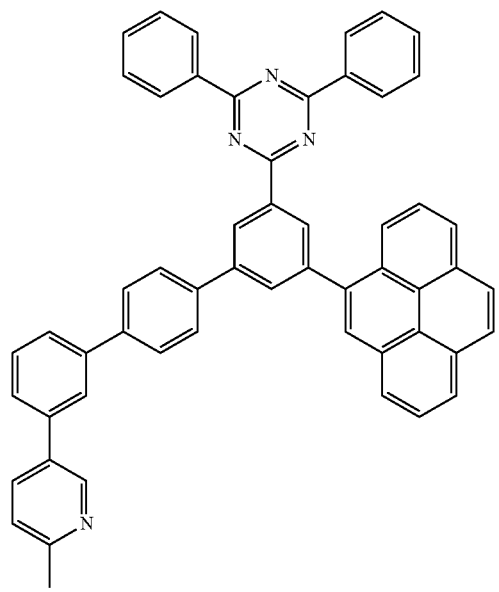
E-72
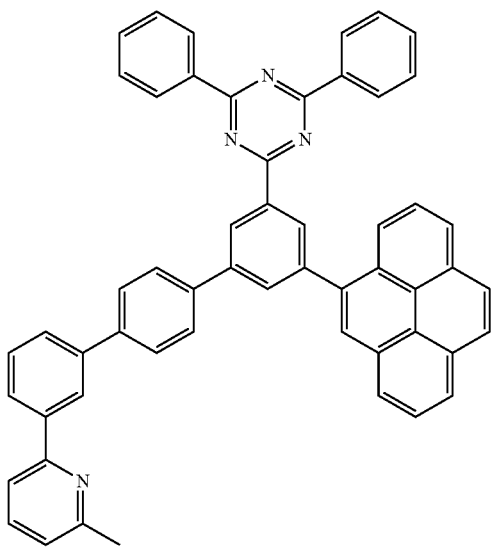
E-73
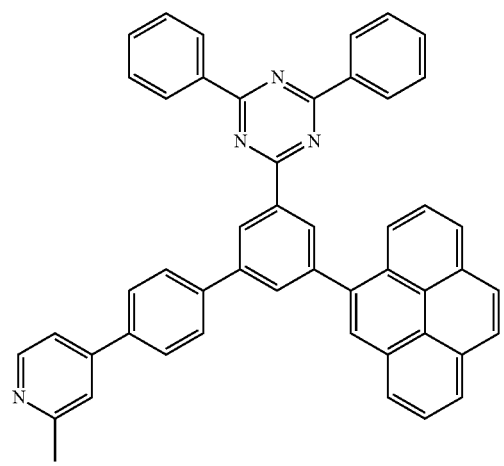
E-74
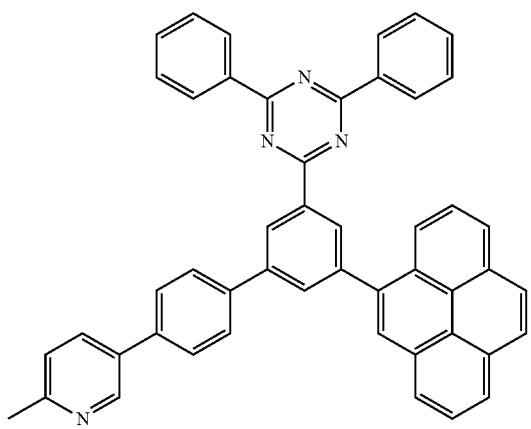
E-75
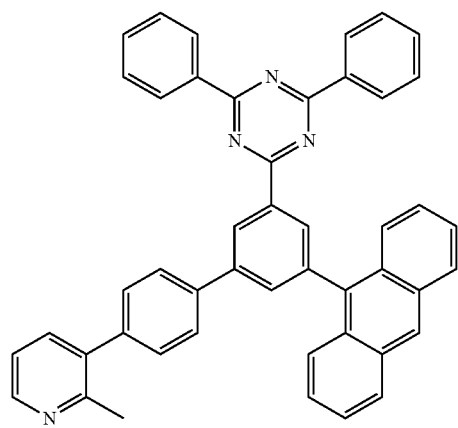
E-76
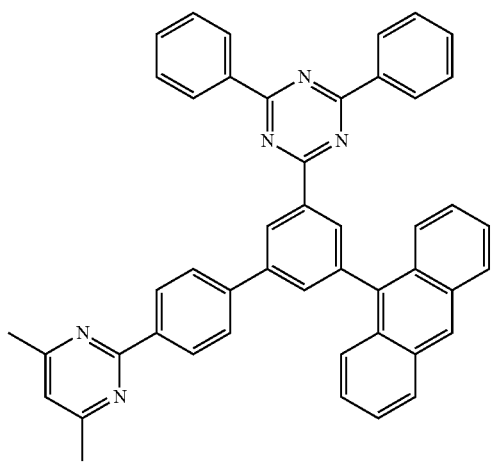

-continued
E-77
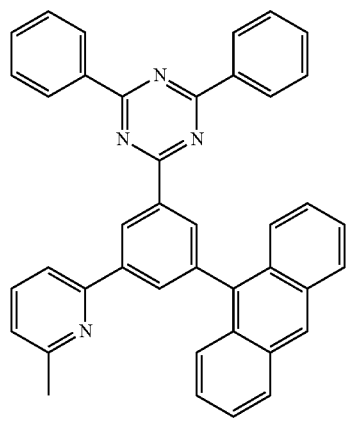
E-78
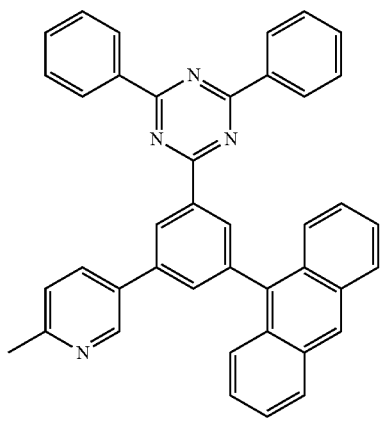
E-79
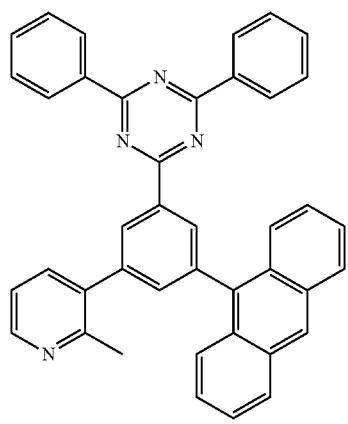
E-80
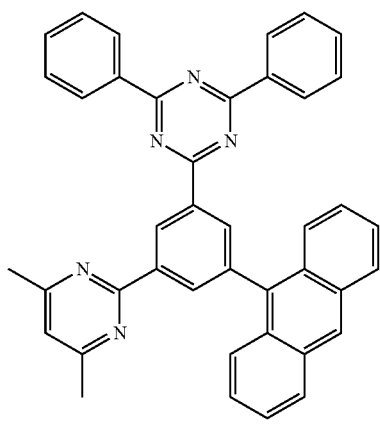
E-81
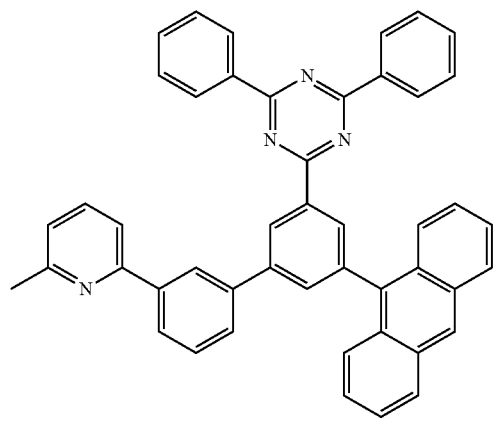
E-82
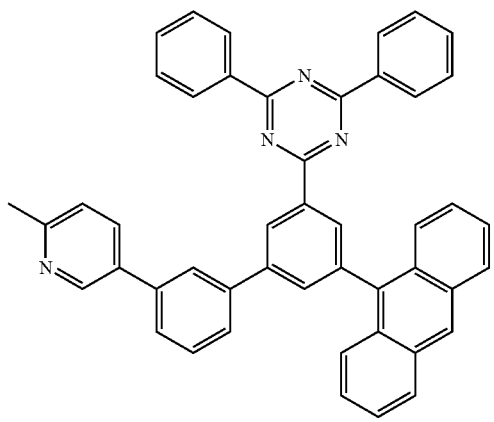

-continued
E-83
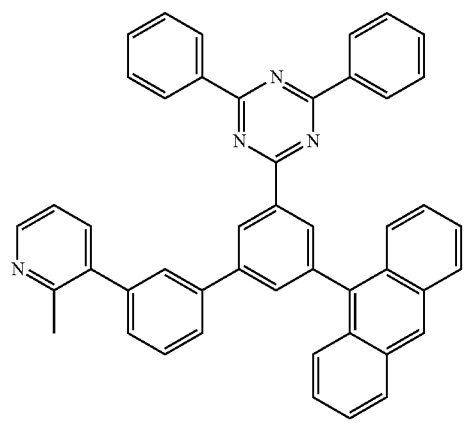
E-84
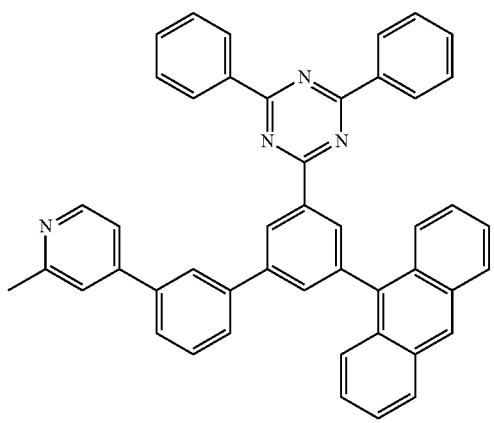
E-85
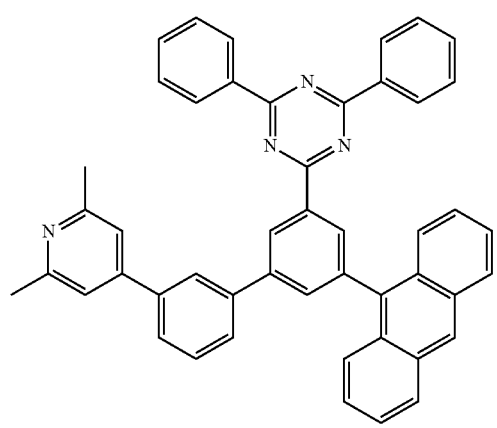
E-86
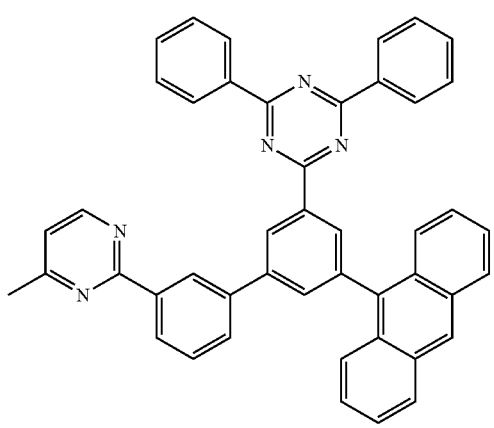
E-87
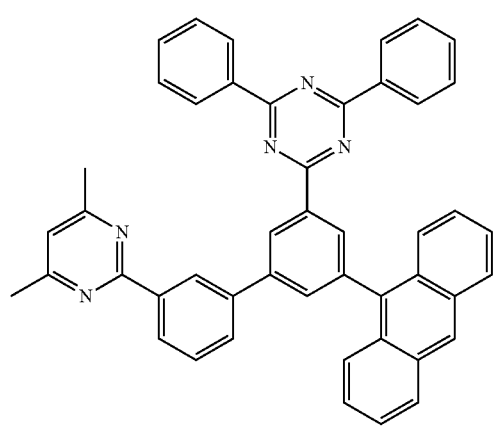
E-88
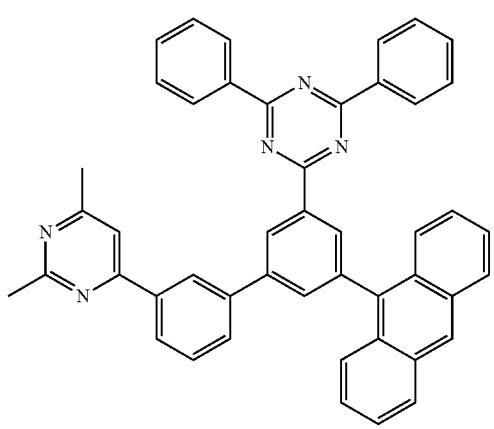

-continued
E-89
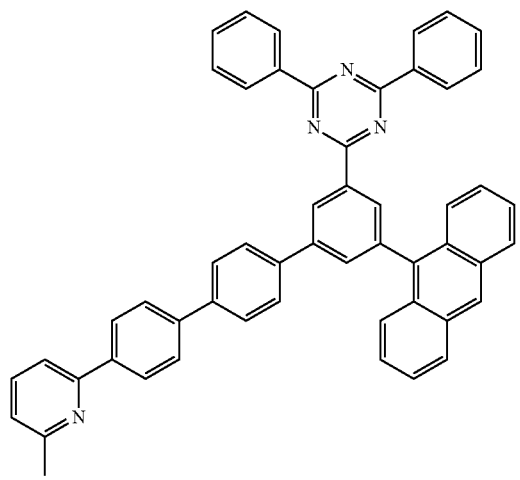
E-90
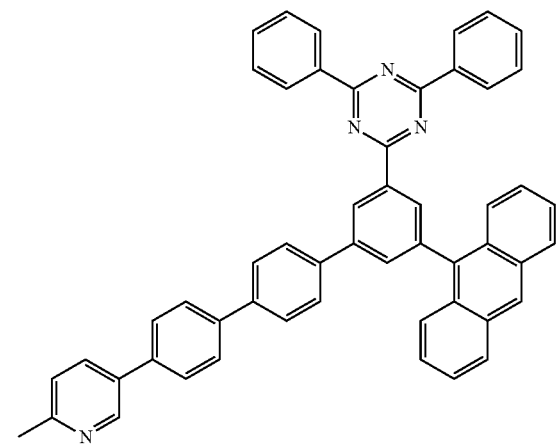
E-91
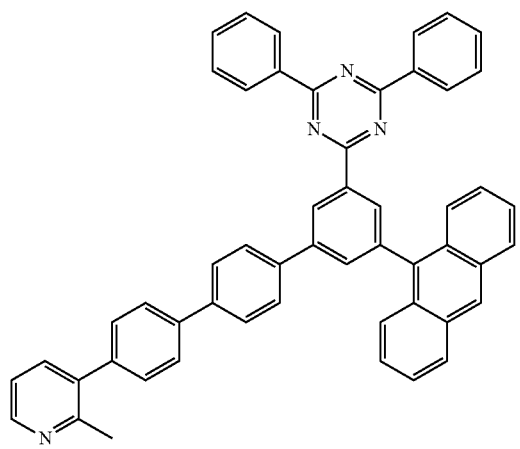
E-92
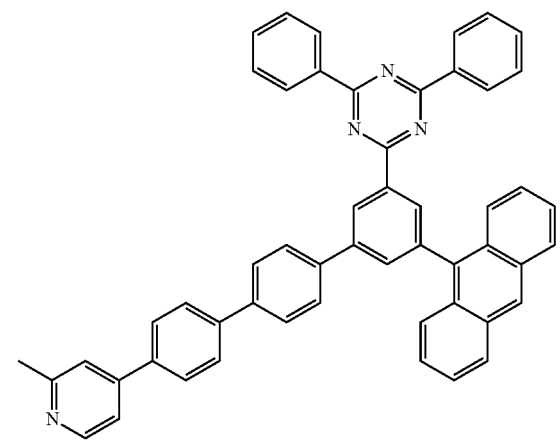
E-93
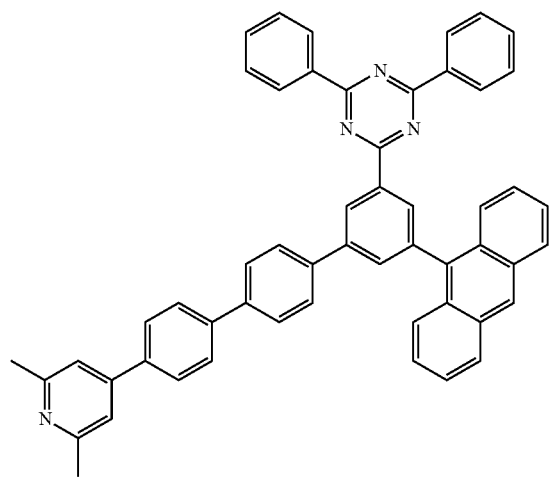
E-94
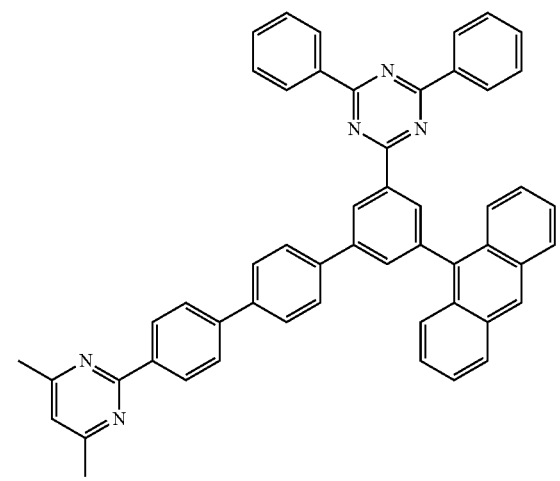

-continued
E-95
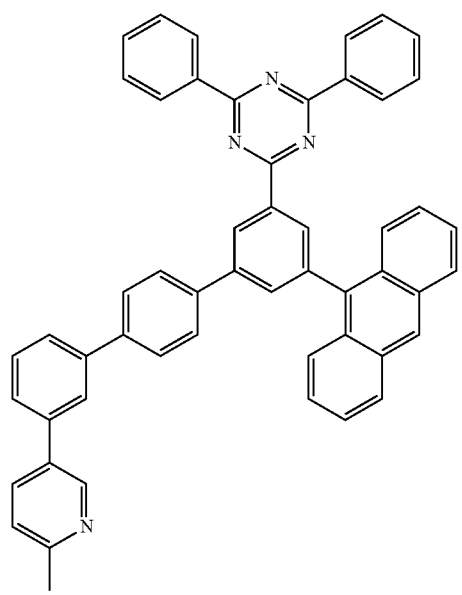
E-96
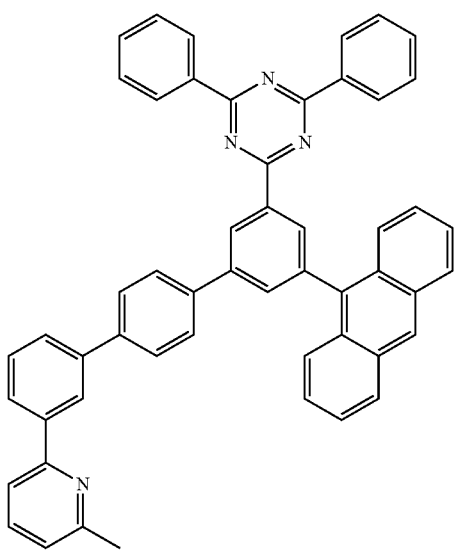
E-97
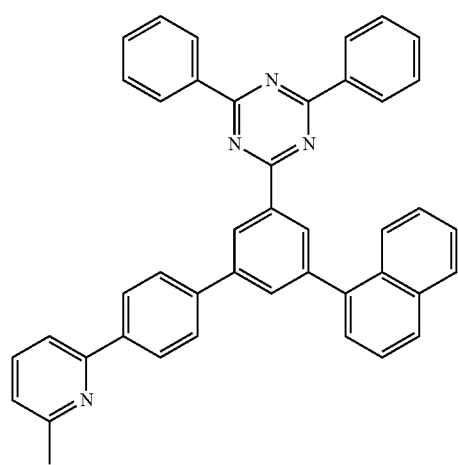
E-98
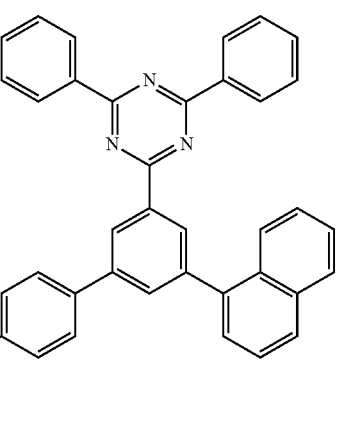
E-99
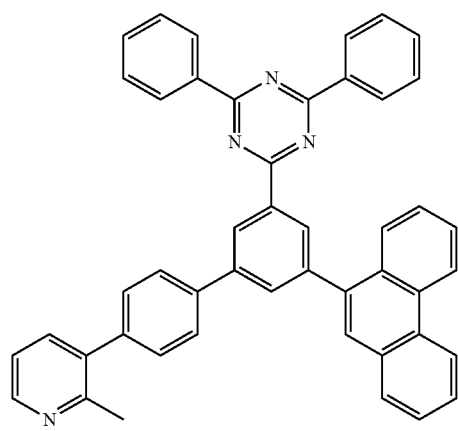
E-100
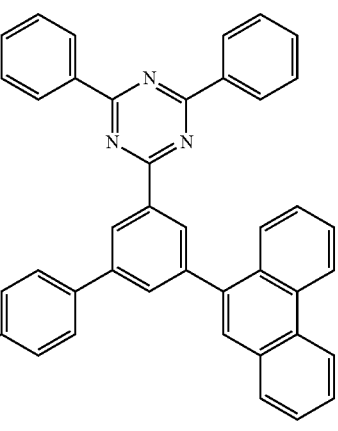

-continued
E-101
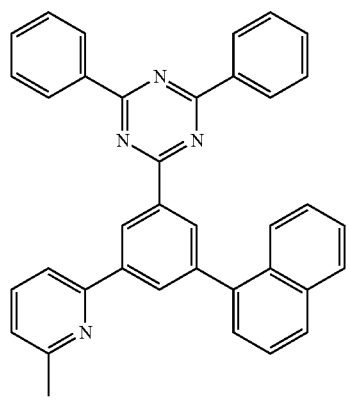
E-102
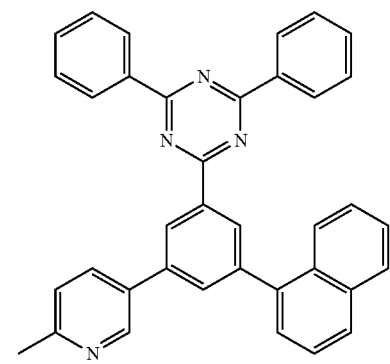
E-103
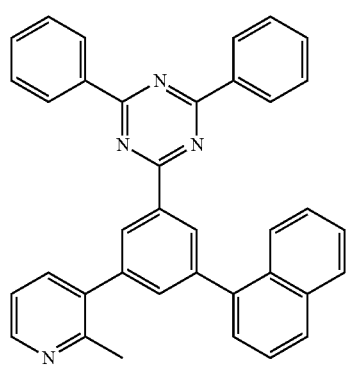
E-104
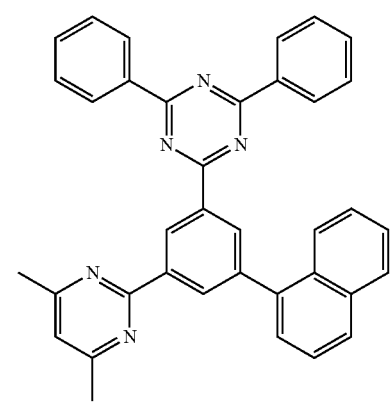
E-105
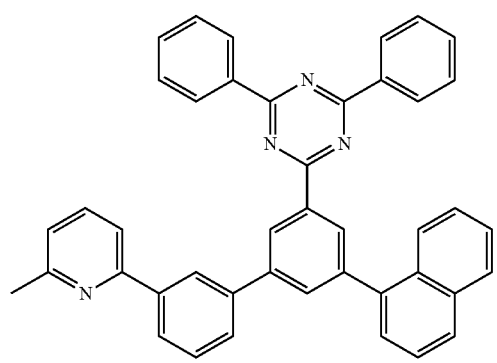
E-106
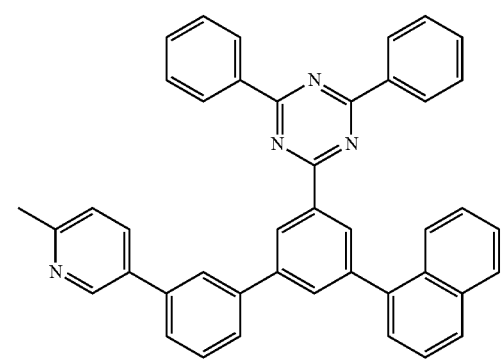
E-107
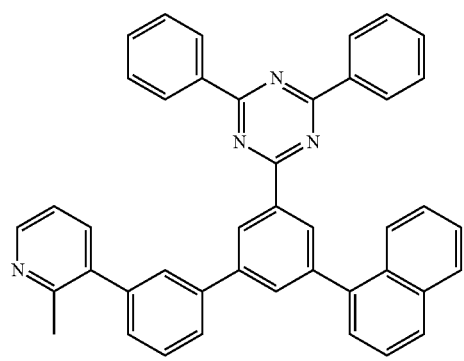
E-108
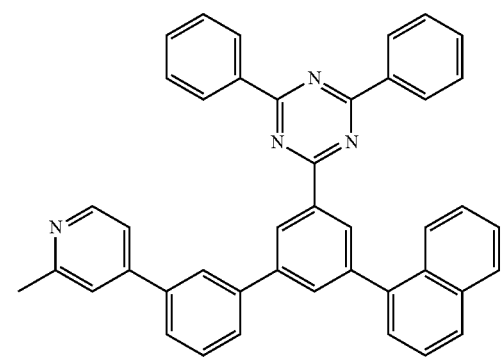

-continued
E-109
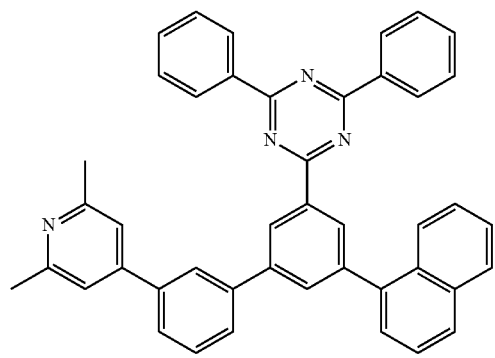
E-110
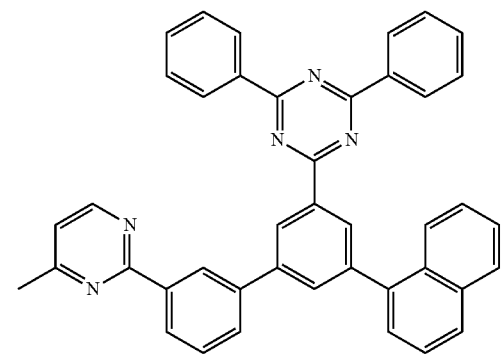
E-111
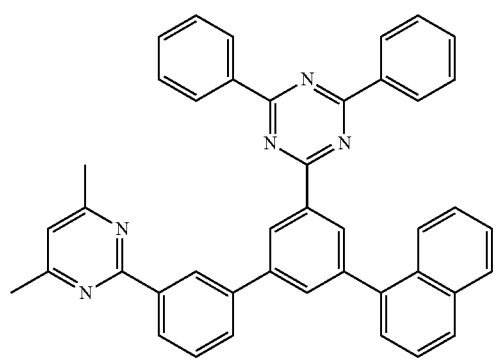
E-112
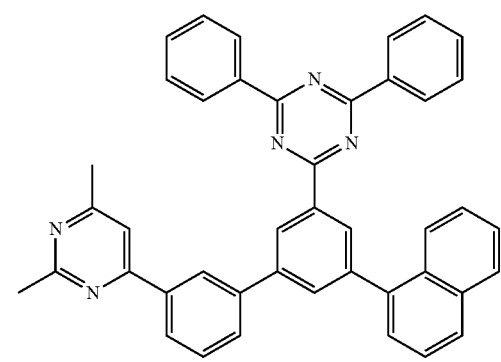
E-113
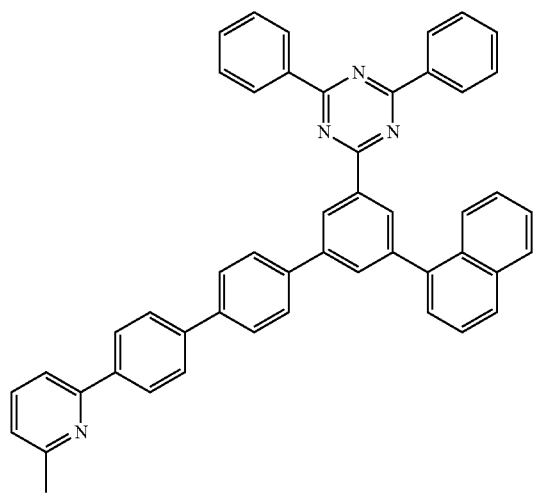
E-114
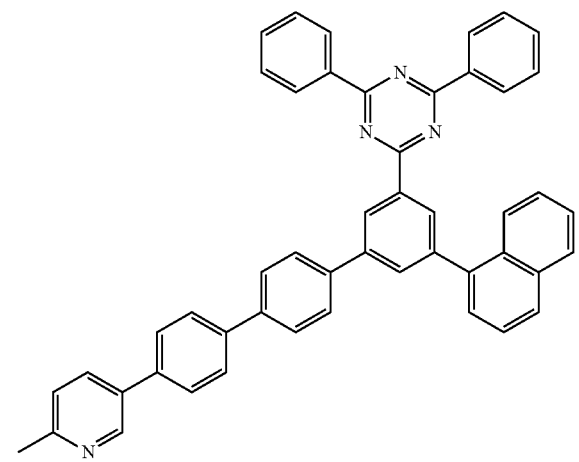

-continued
E-115
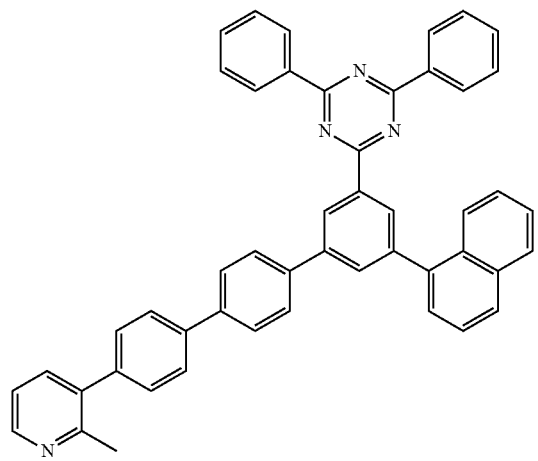
E-116
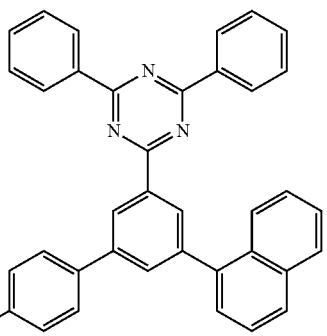
E-117
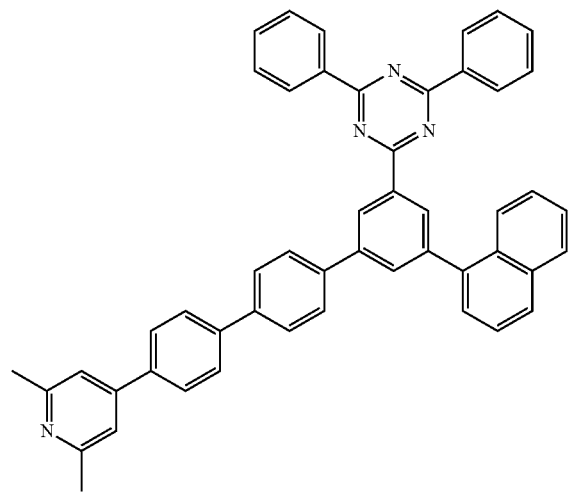
E-118
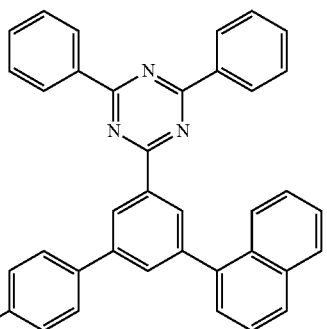
E-119
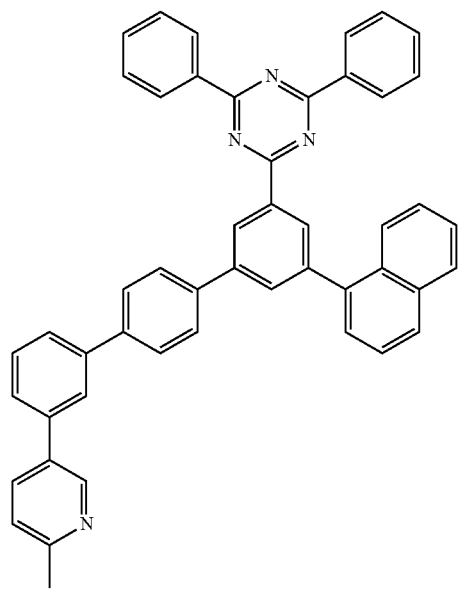
E-120
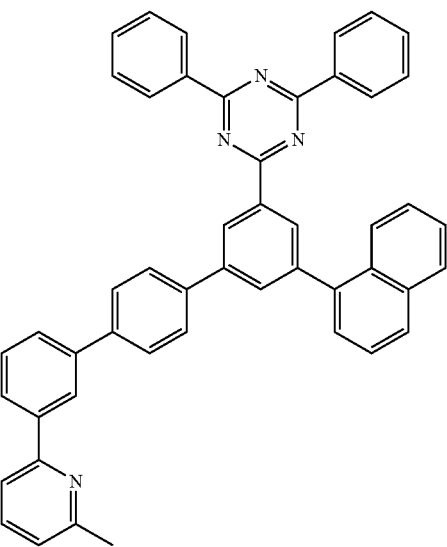

-continued
E-121
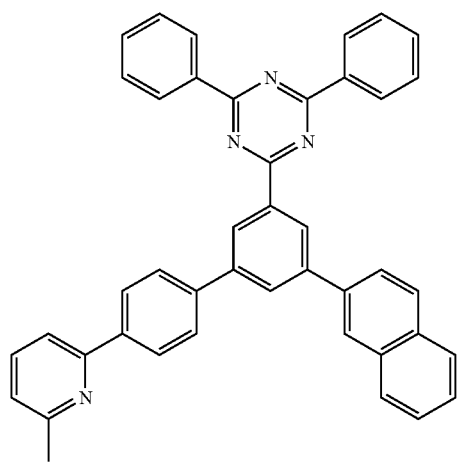
E-122
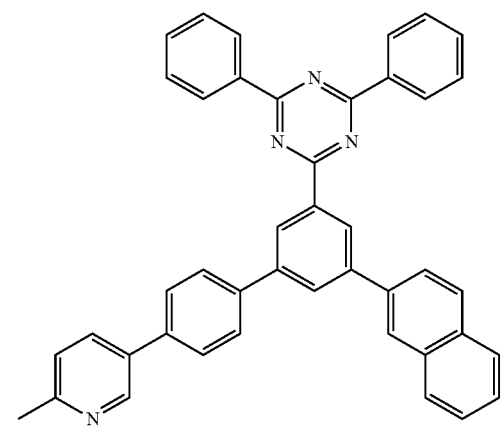
E-123
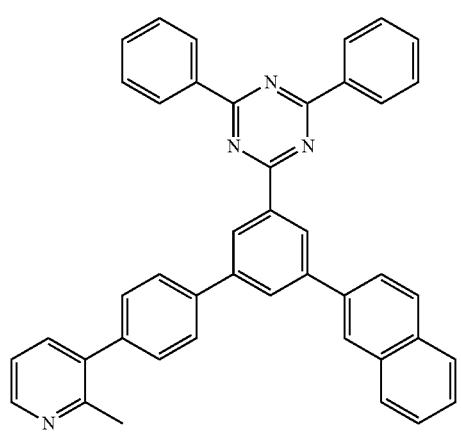
E-124
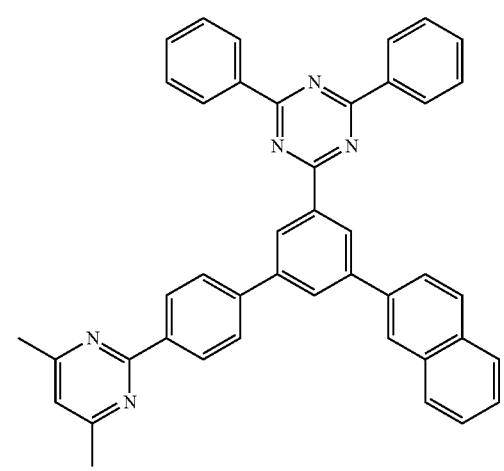
E-125
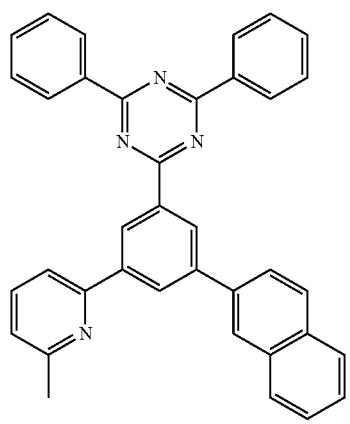
E-126
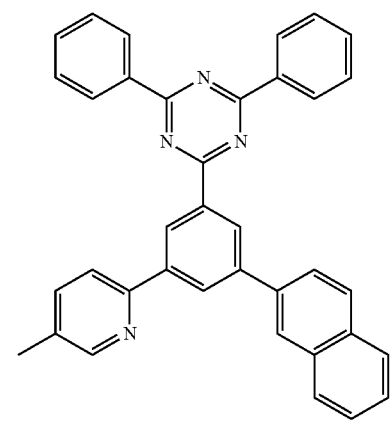

-continued
E-127
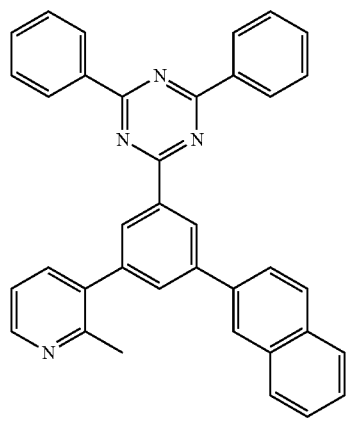
E-128
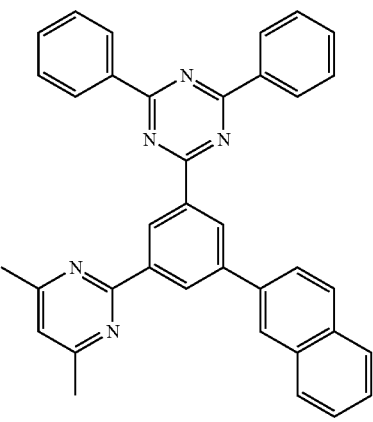
E-129
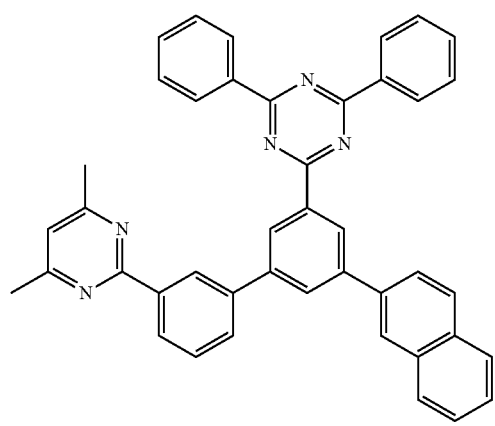
E-130
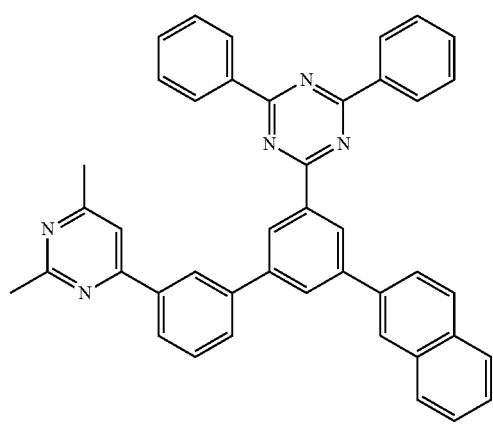
E-131
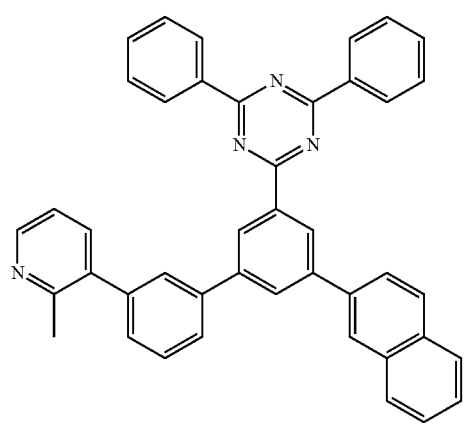
E-132
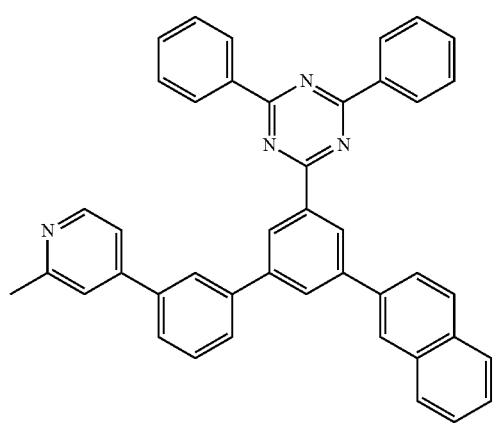

-continued
E-133
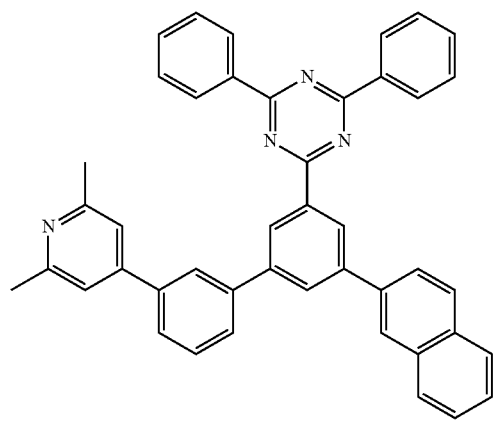
E-134
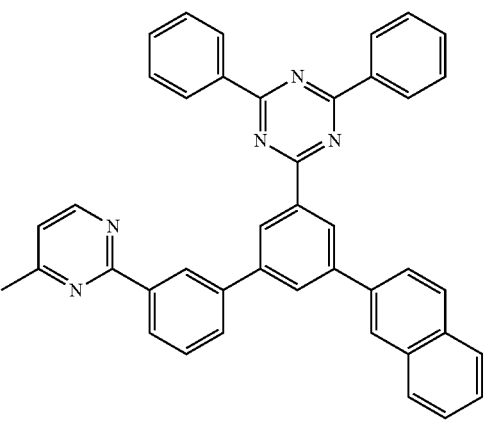
E-135
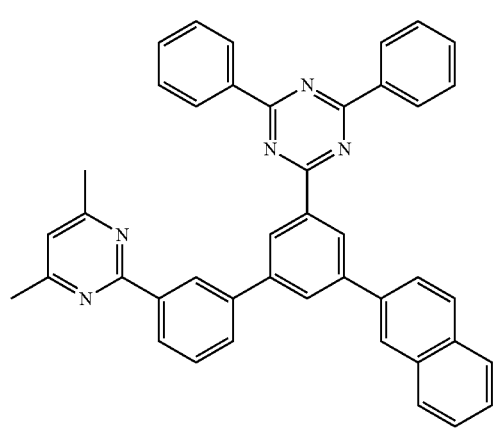
E-136
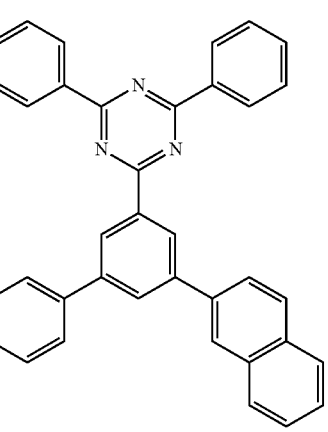
E-137
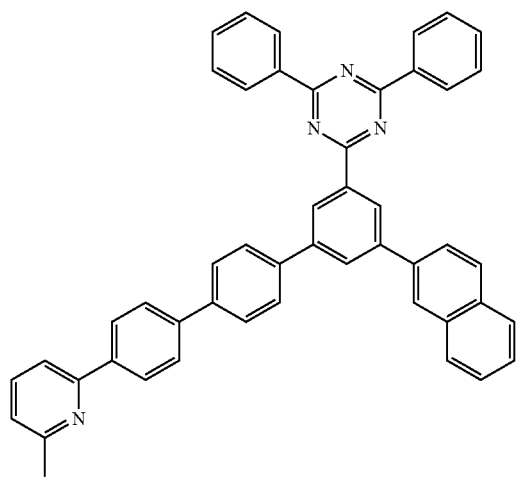
E-138
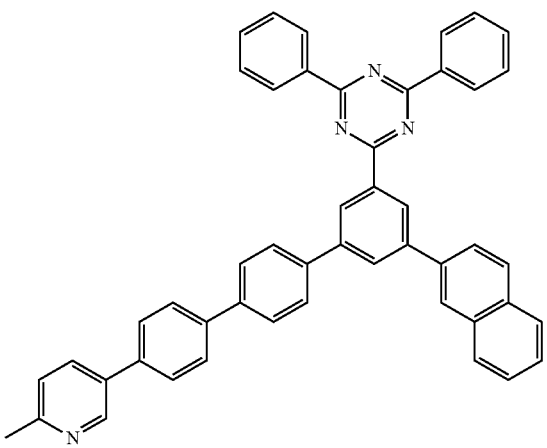

-continued
E-139
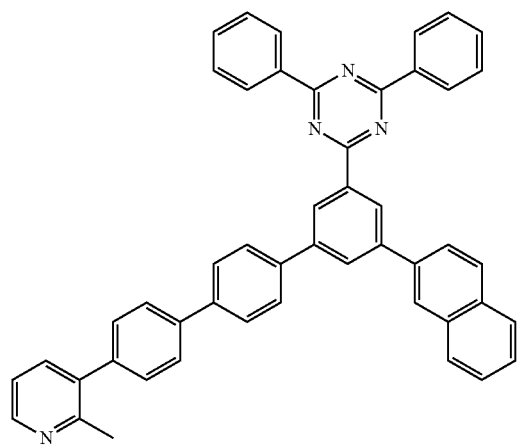
E-140
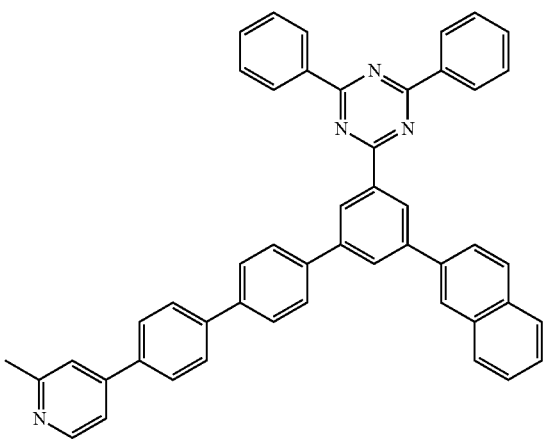
E-141
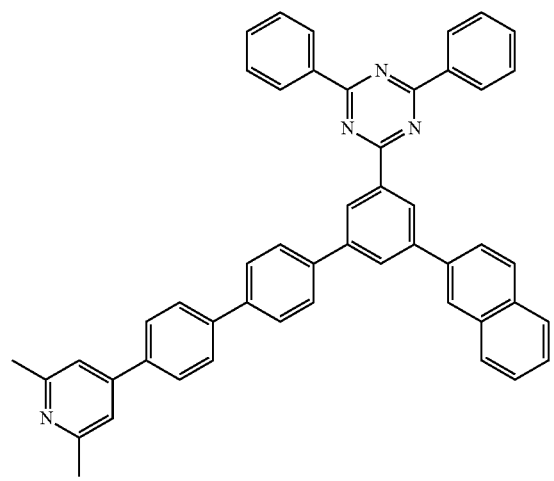
E-142
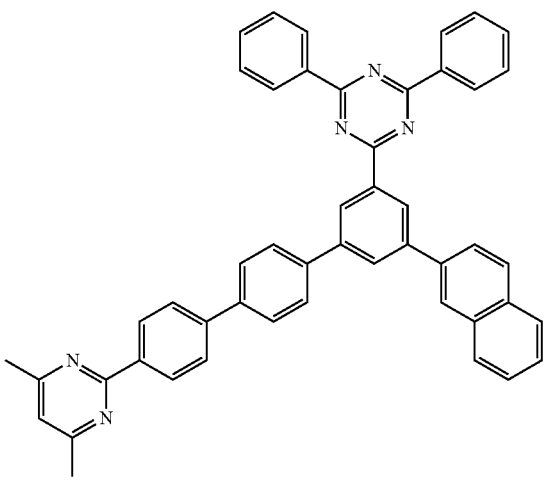
E-143
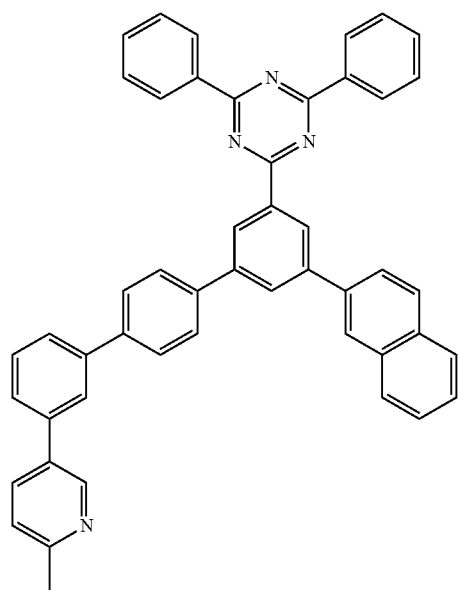
E-144
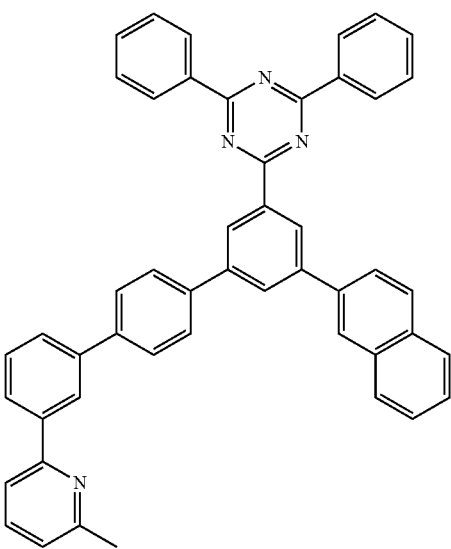

-continued
E-145
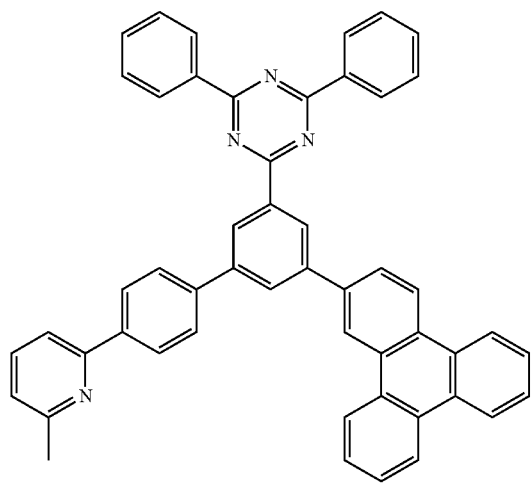
E-146
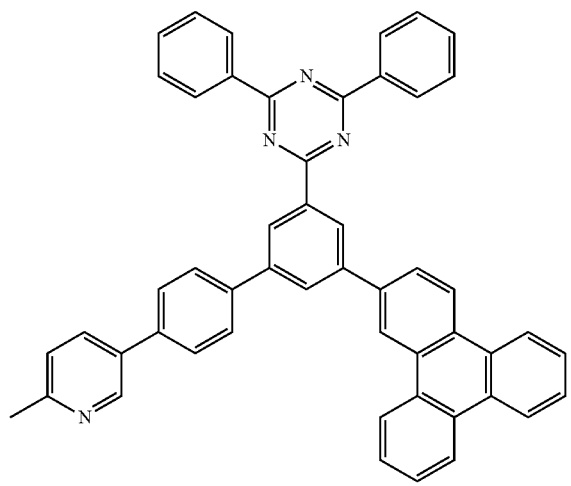
E-147
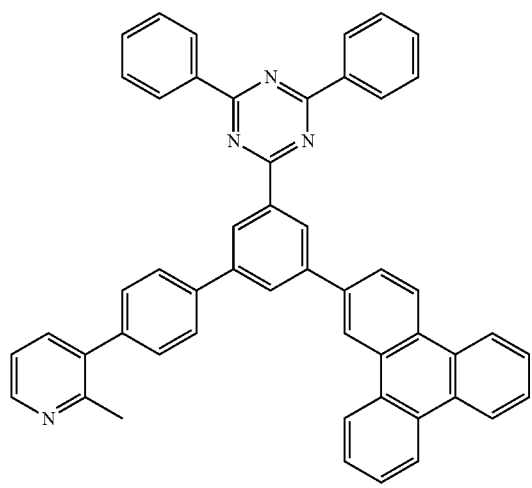
E-148
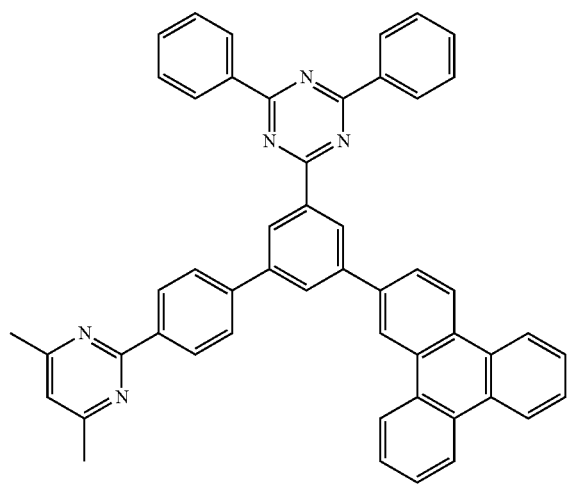
E-149
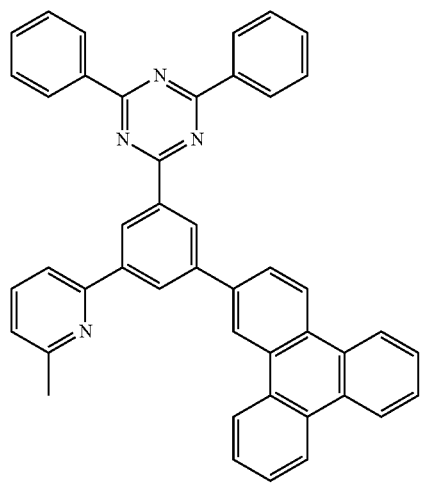
E-150
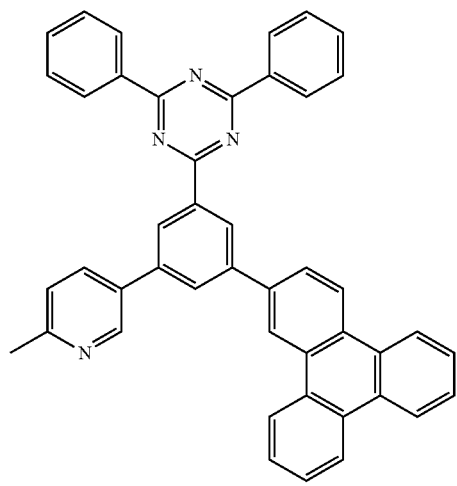

-continued
E-151
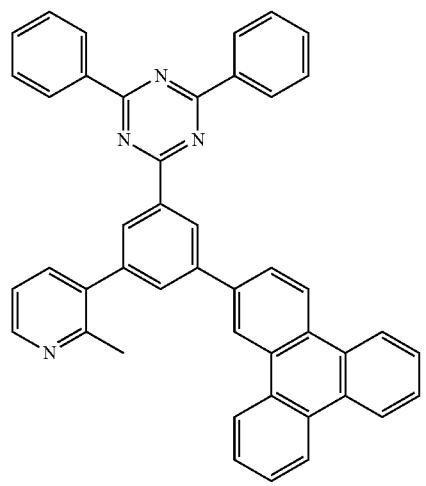
E-152
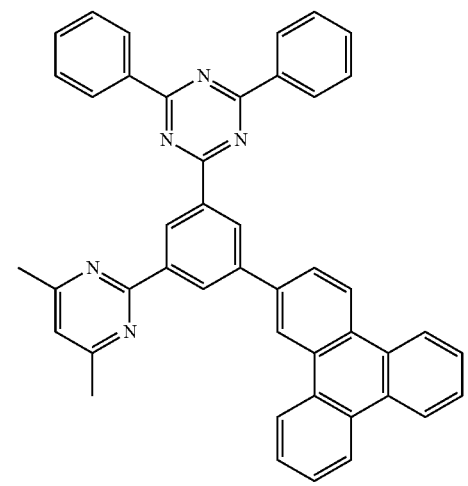
E-153
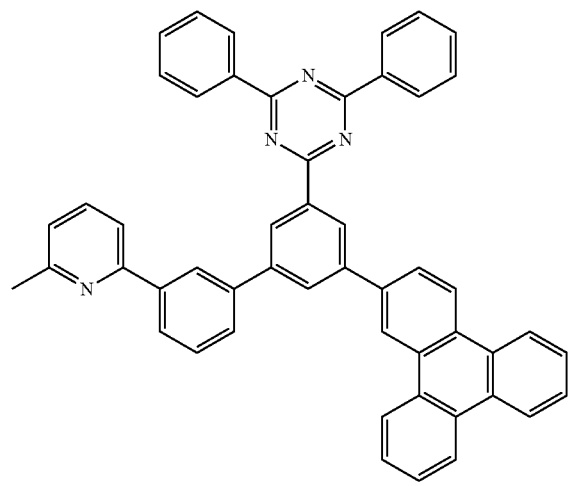
E-154
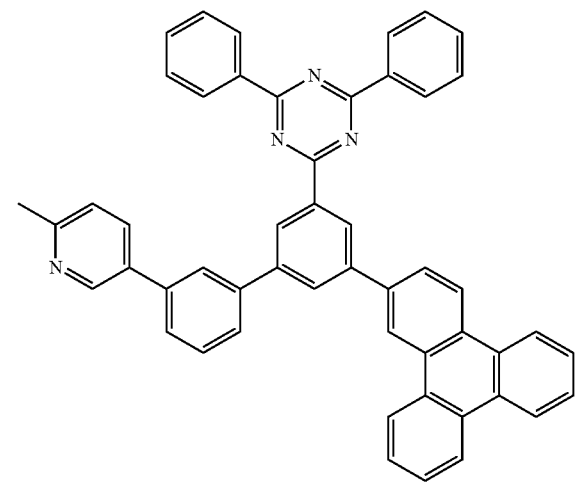
E-155
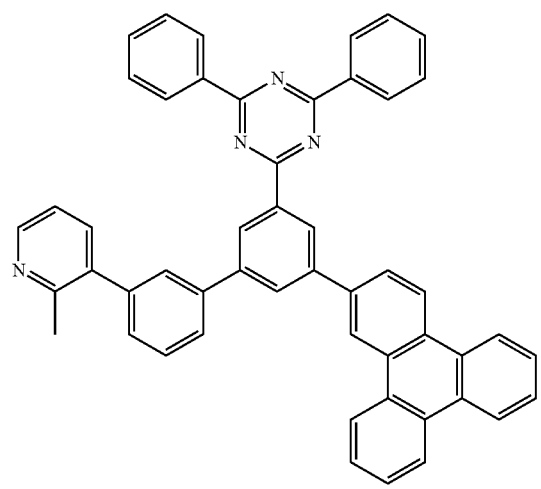
E-156
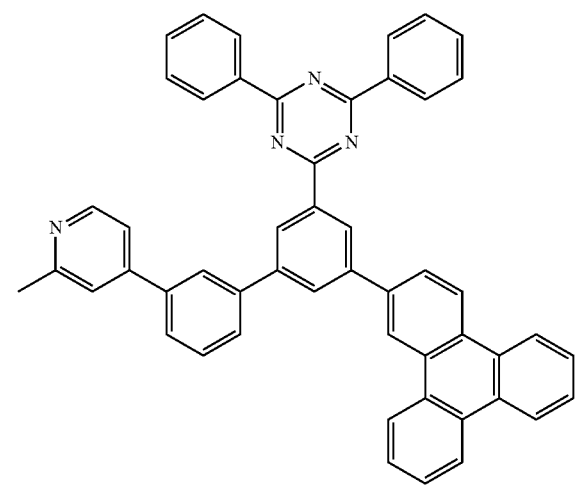

-continued
E-157
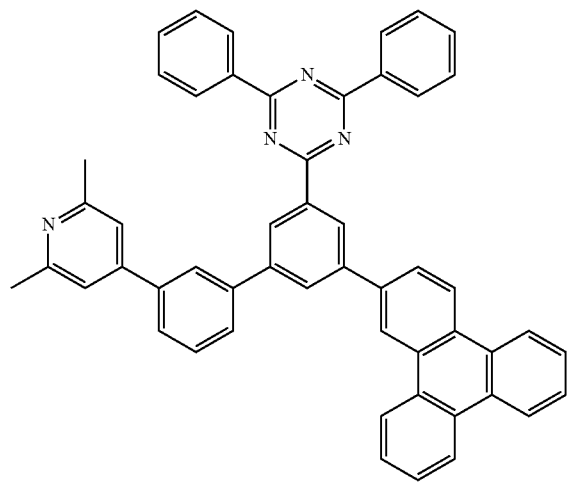
E-158
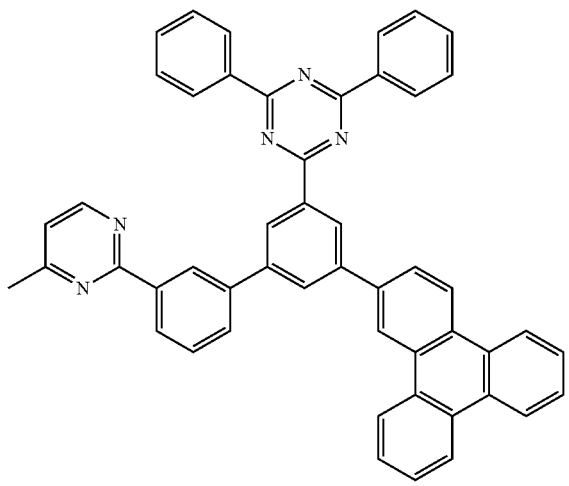
E-159
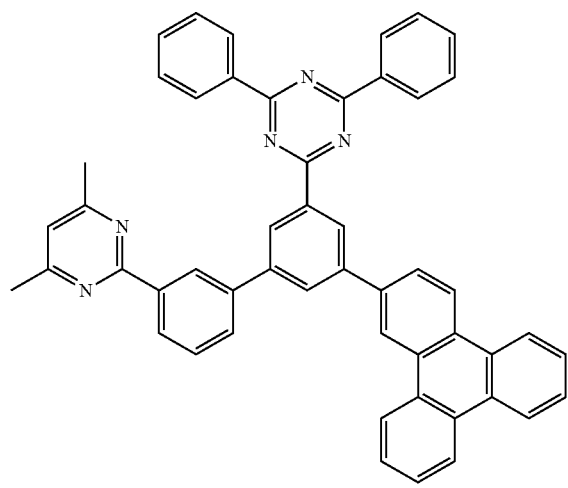
E-160
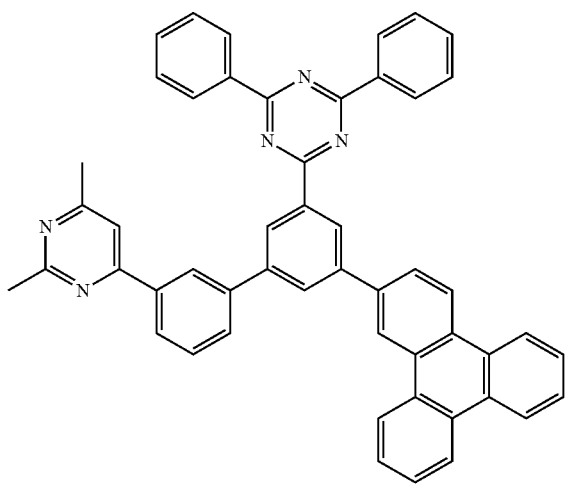
E-161
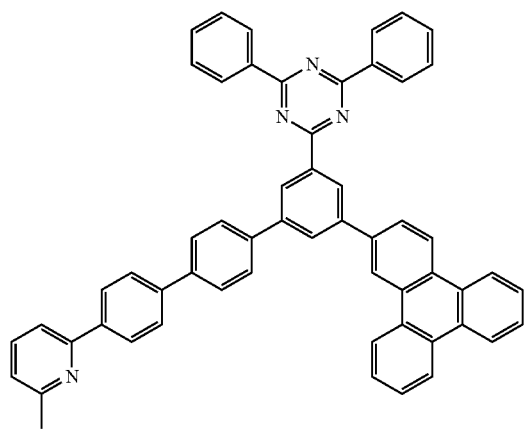
E-162
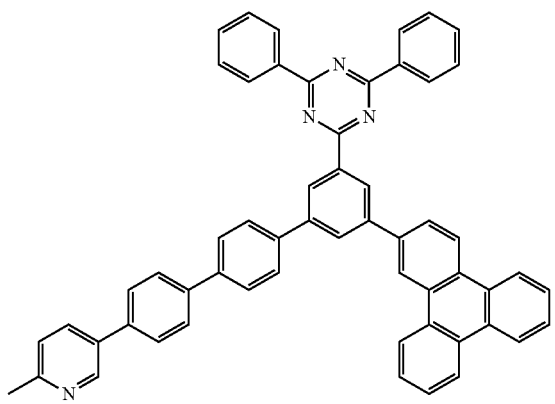

-continued
E-163
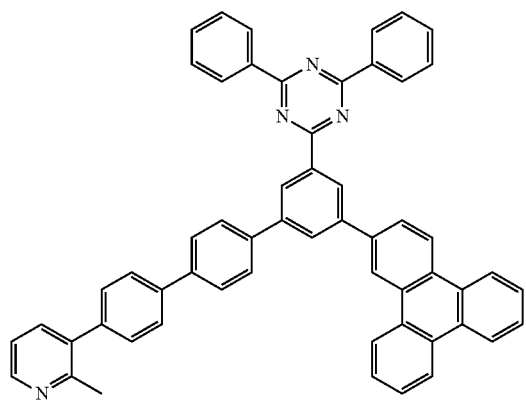
E-164
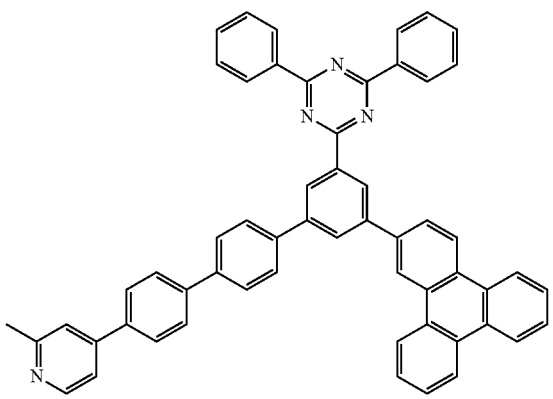
E-165
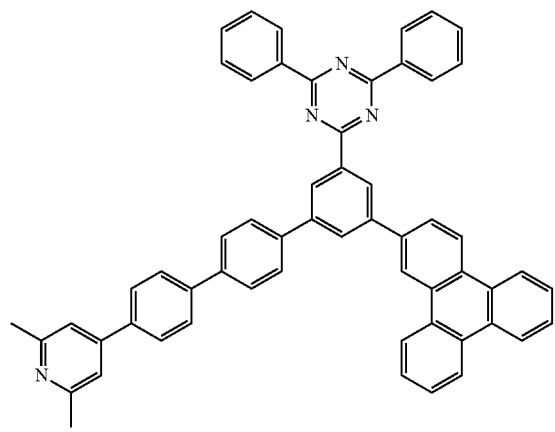
E-166
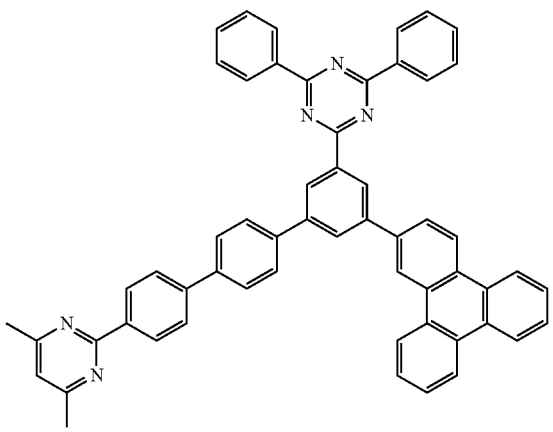
E-167
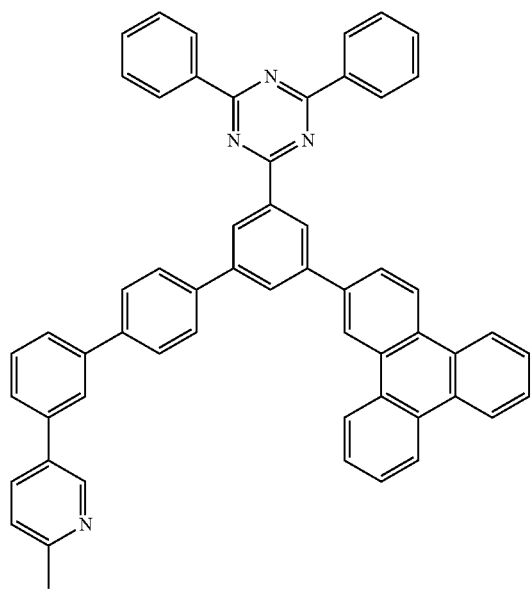
E-168
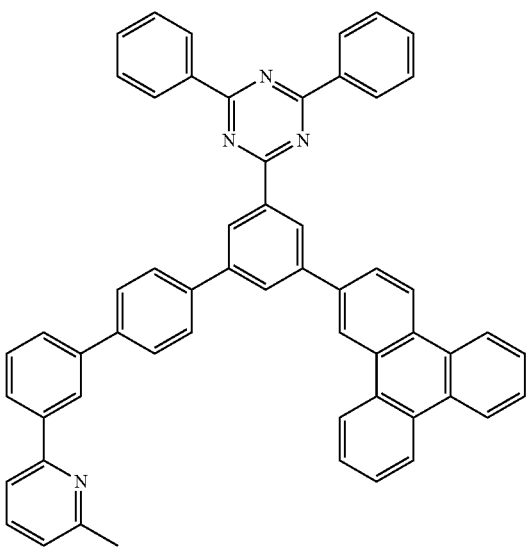

-continued
E-169
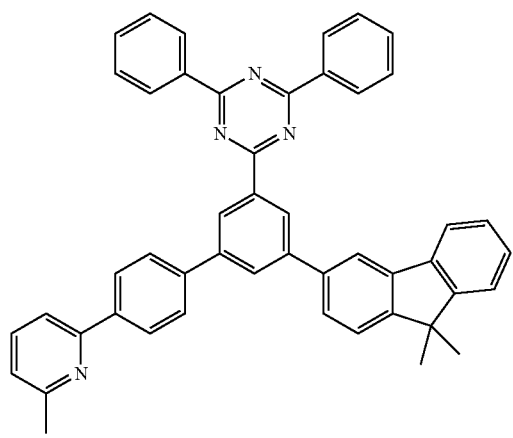
E-170
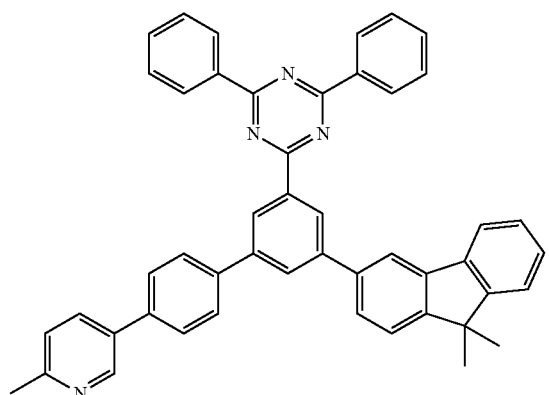
E-171
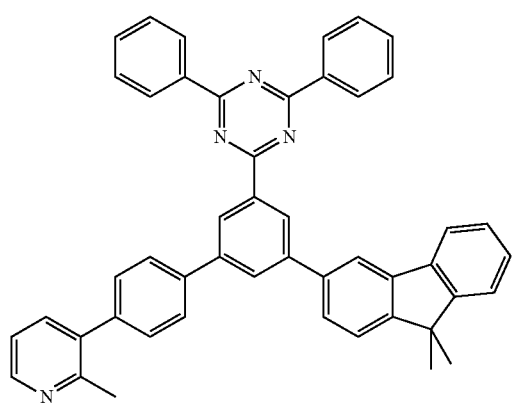
E-172
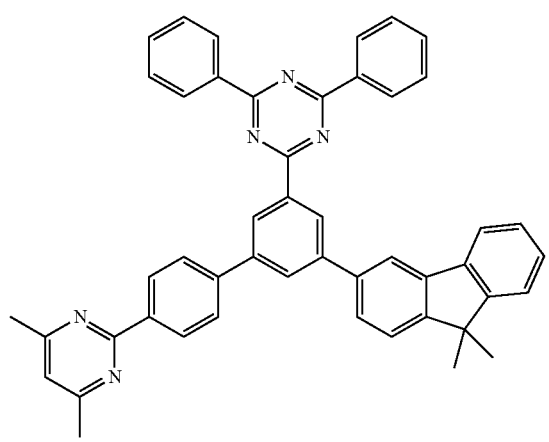
E-173
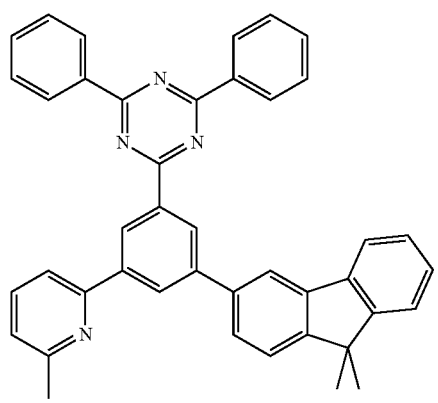
E-174
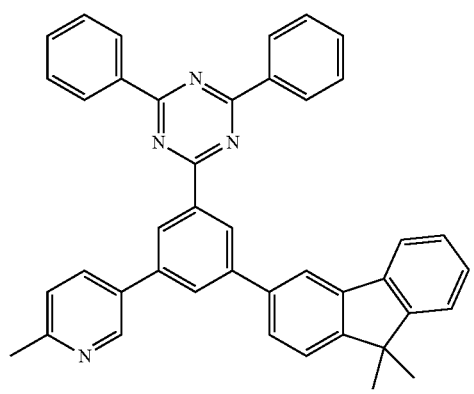

-continued
E-175
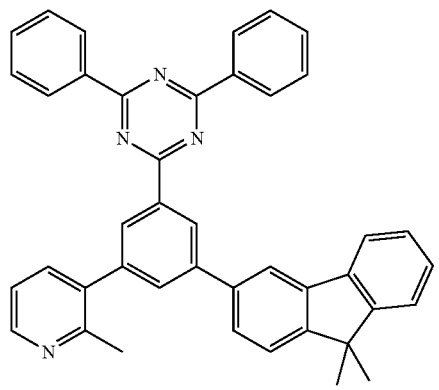
E-176
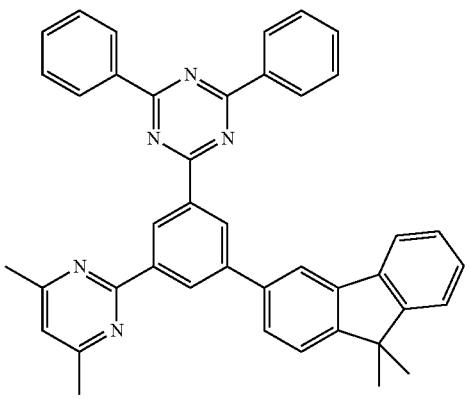
E-177
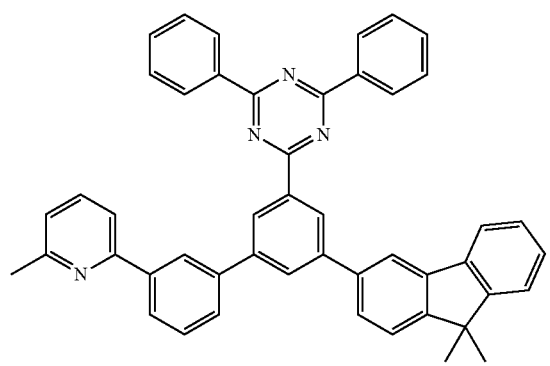
E-178
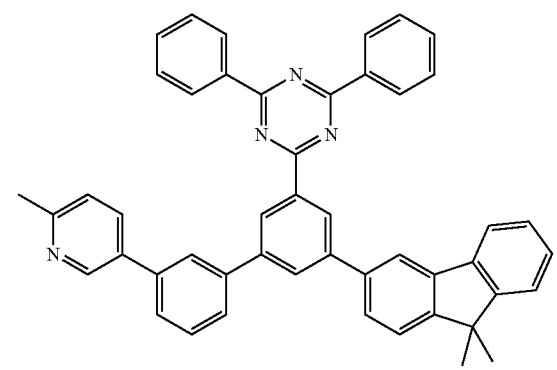
E-179
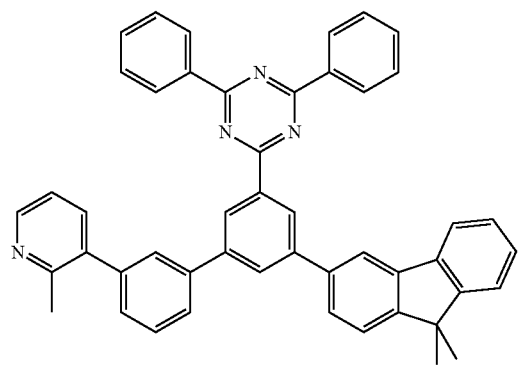
E-180
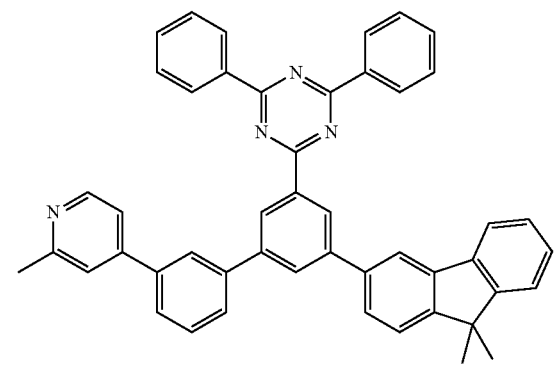
E-181
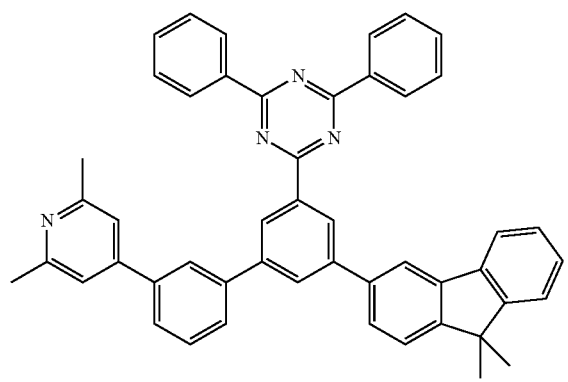
E-182
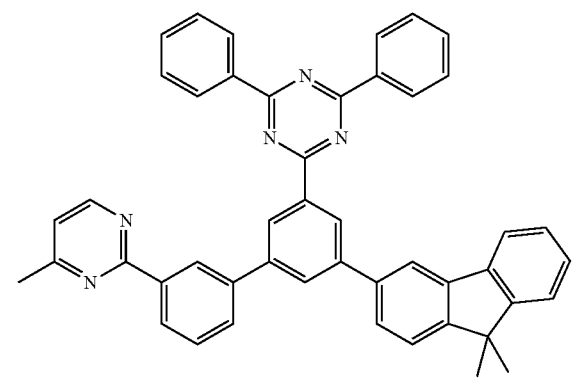

-continued
E-183
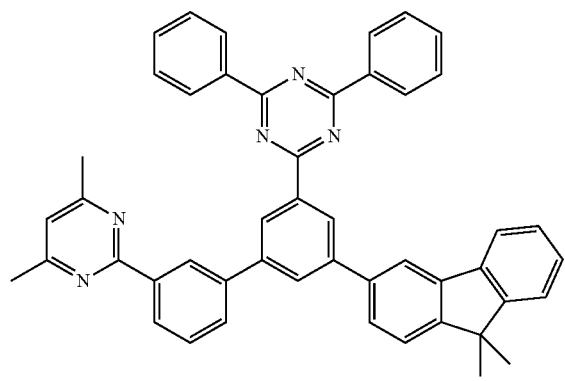
E-184
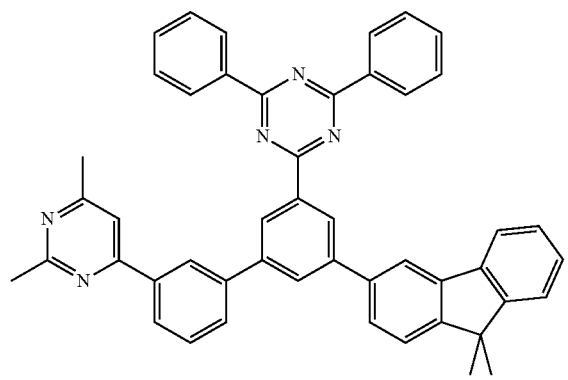
E-185
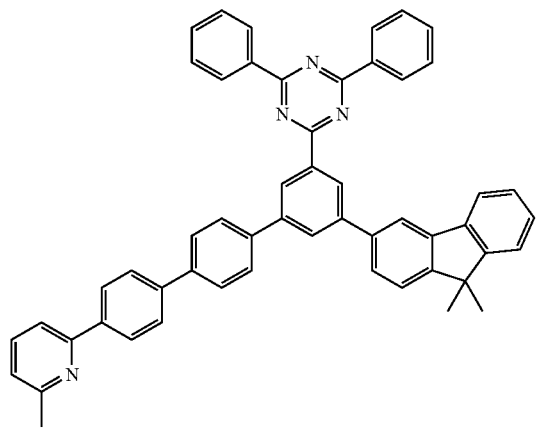
E-186
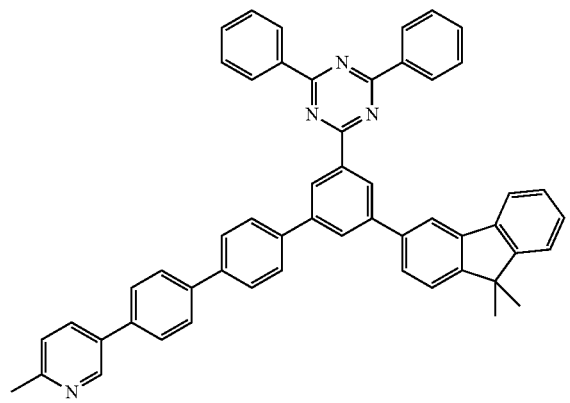
E-187
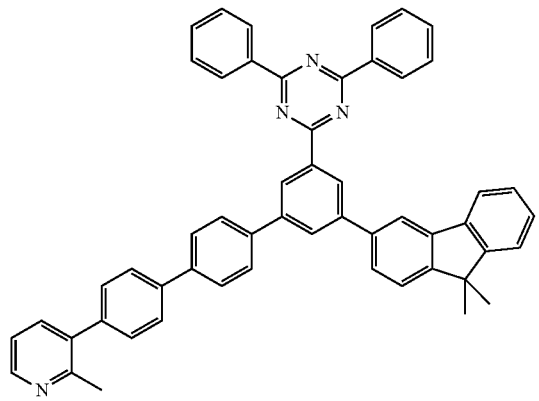
E-188
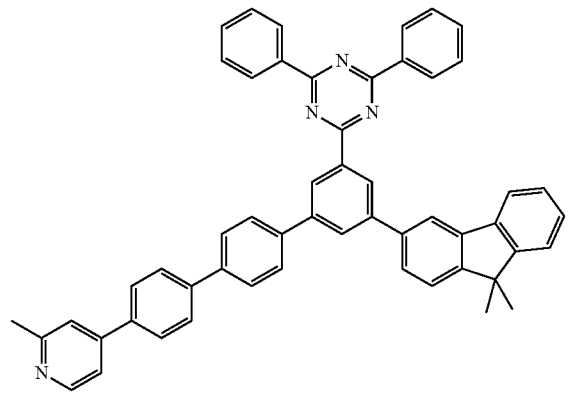

-continued
E-189
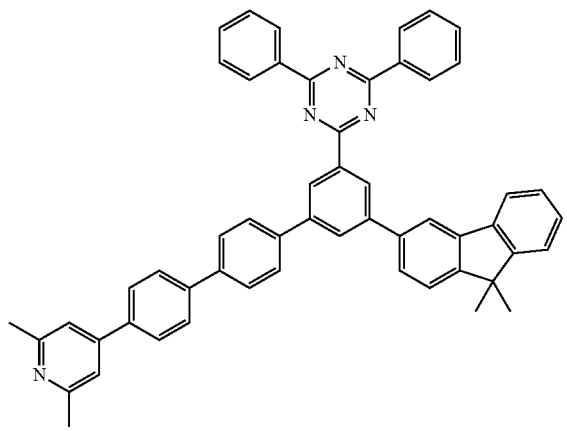
E-190
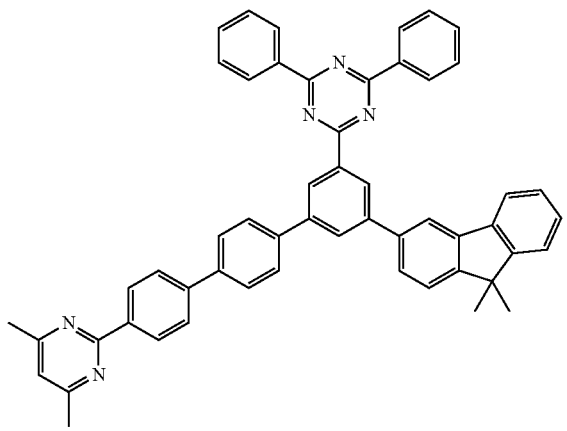
E-191
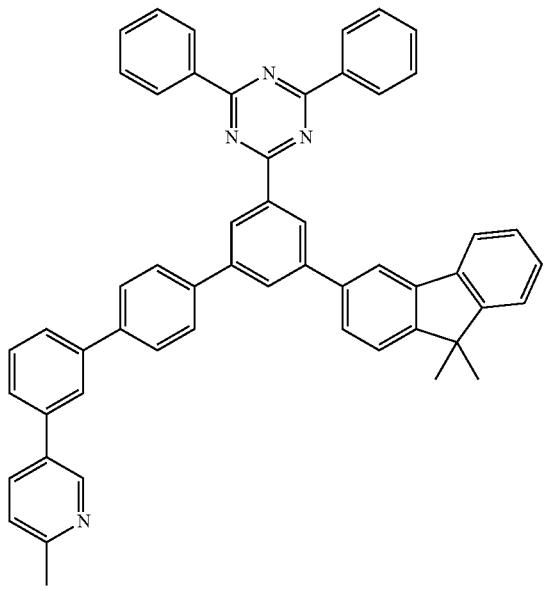
E-192
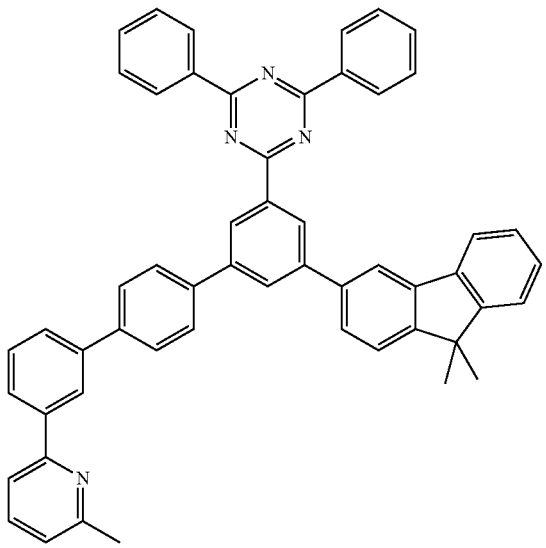
E-193
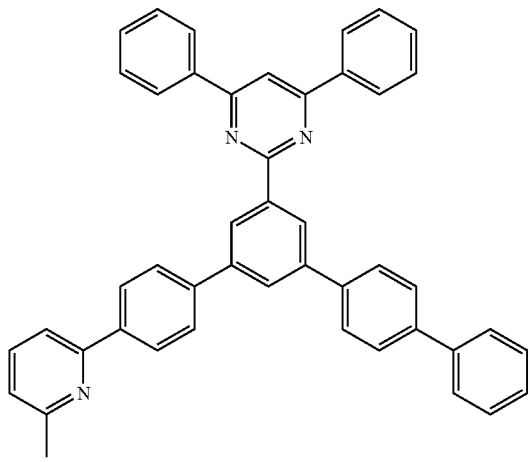
E-194
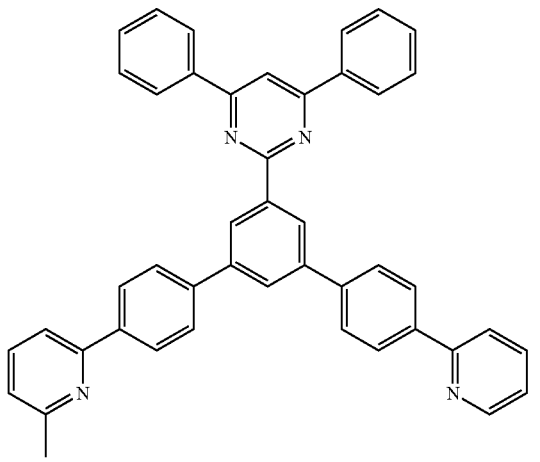

-continued
E-195
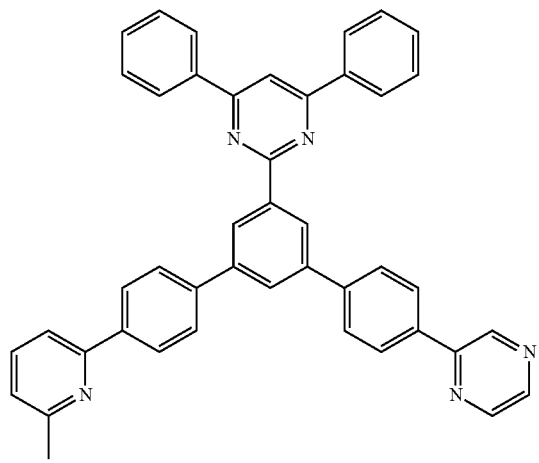
E-196
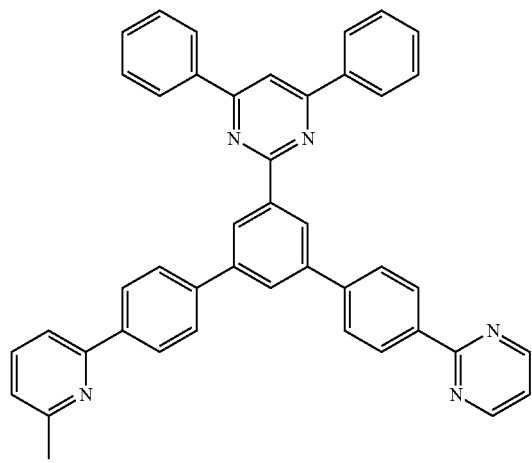
E-197
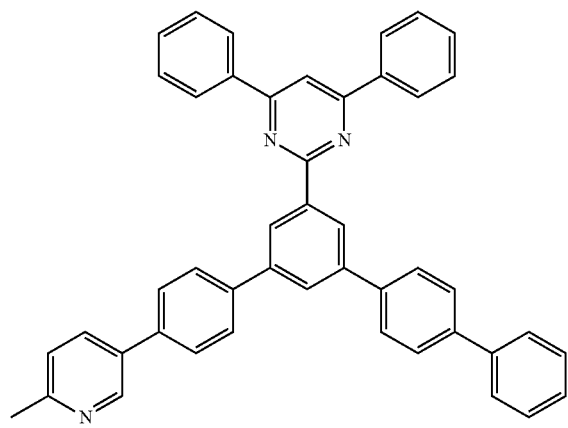
E-198
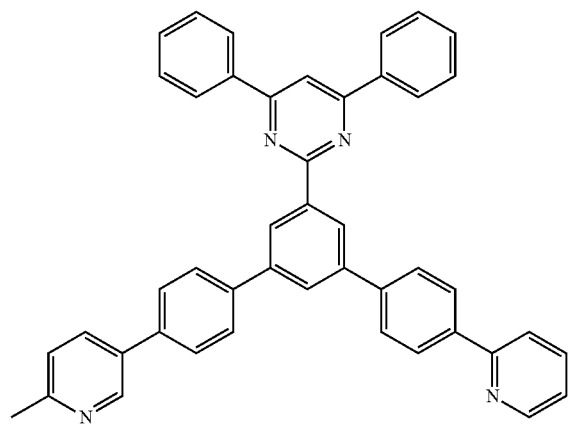
E-199
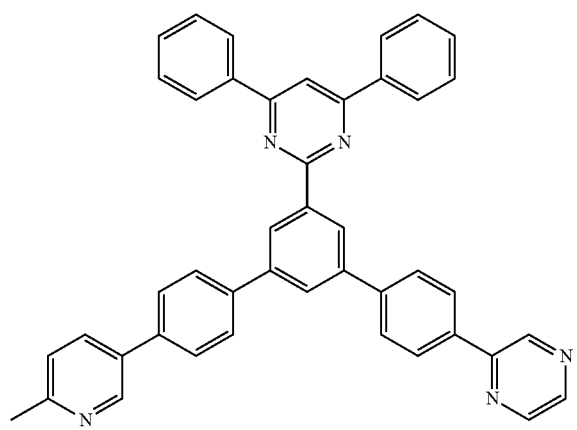
E-200
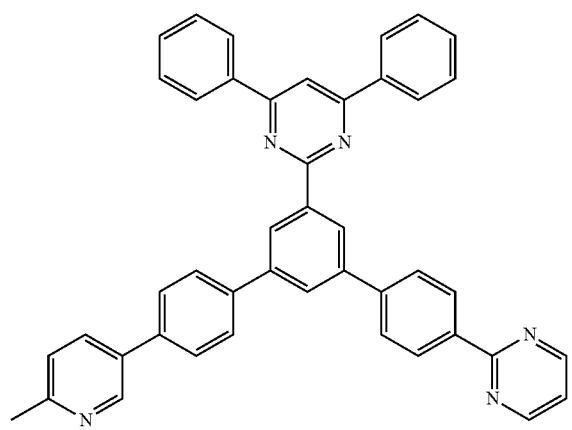

-continued
E-201
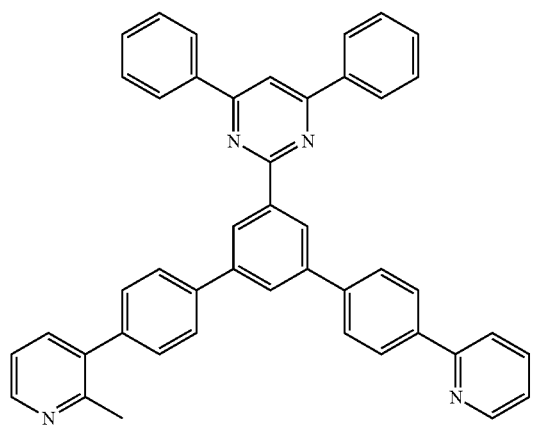
E-202
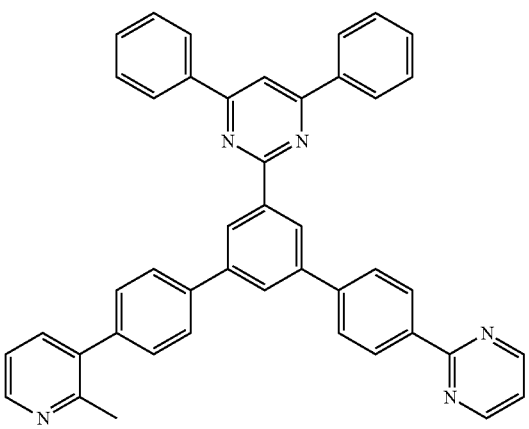
E-203
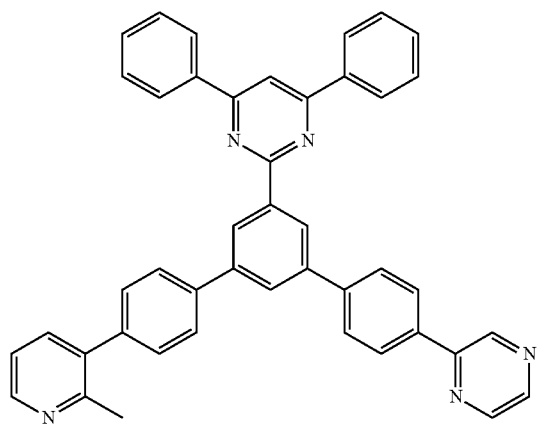
E-204
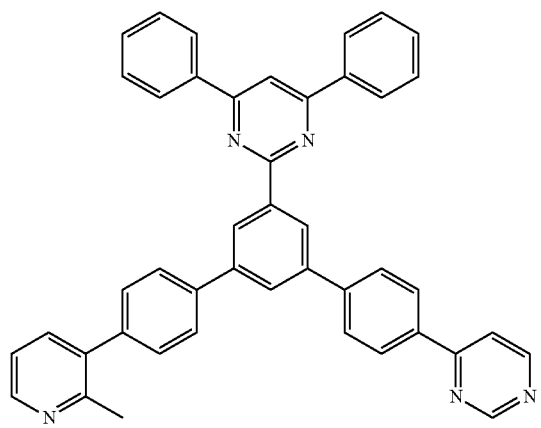
E-205
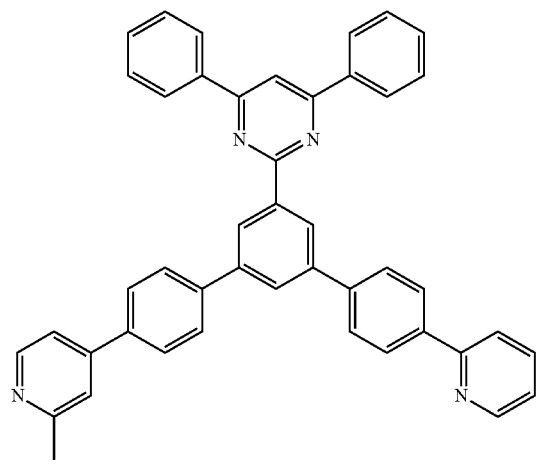
E-206
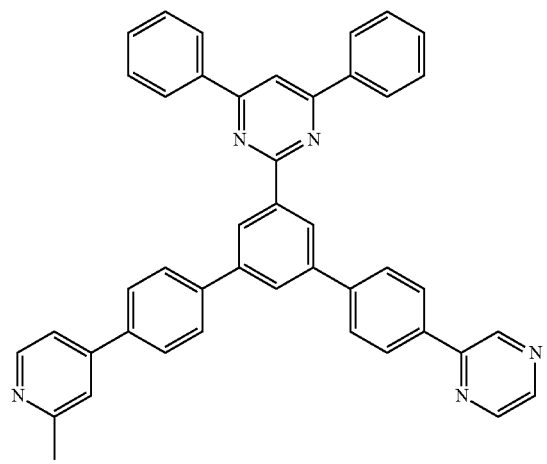

-continued
E-207
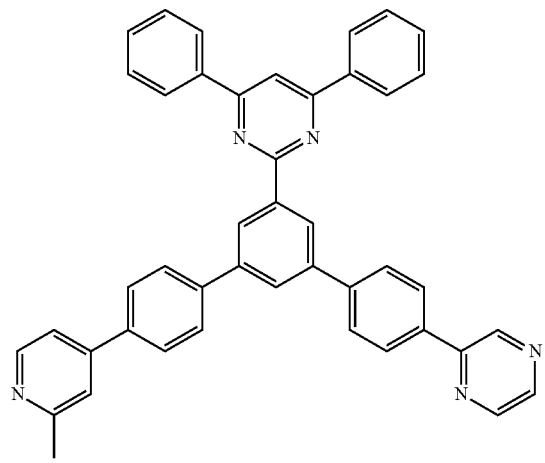
E-208
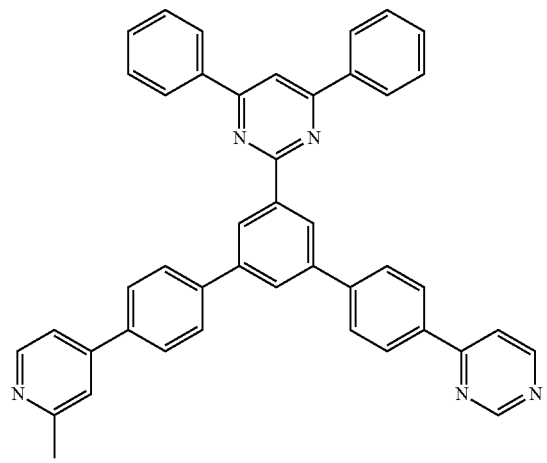
E-209
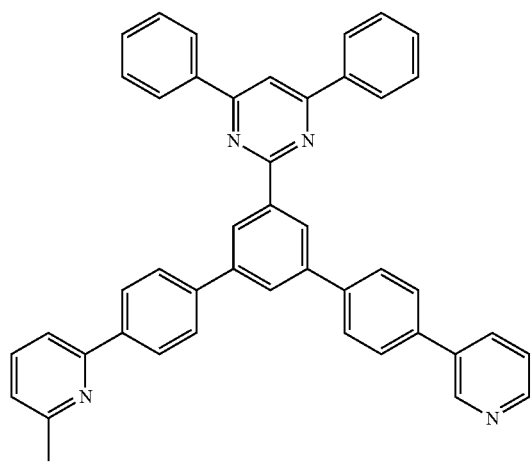
E-210
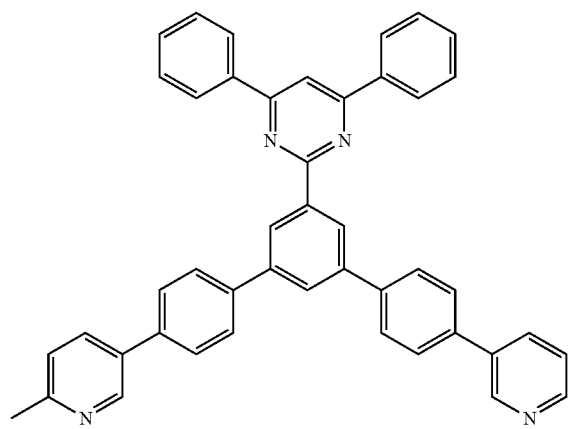
E-211
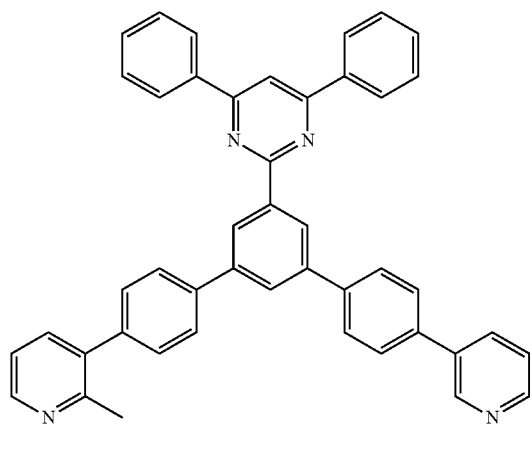
E-212
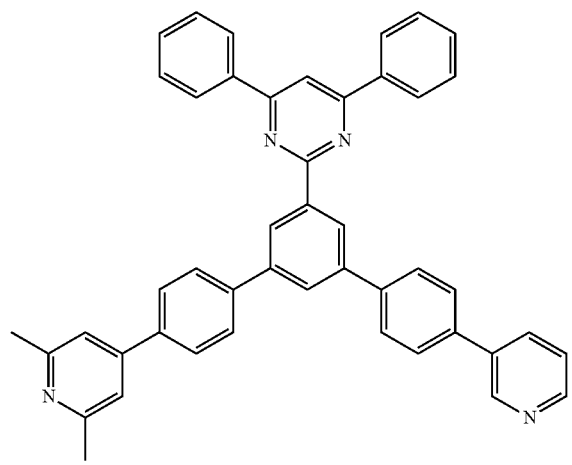

-continued
E-213
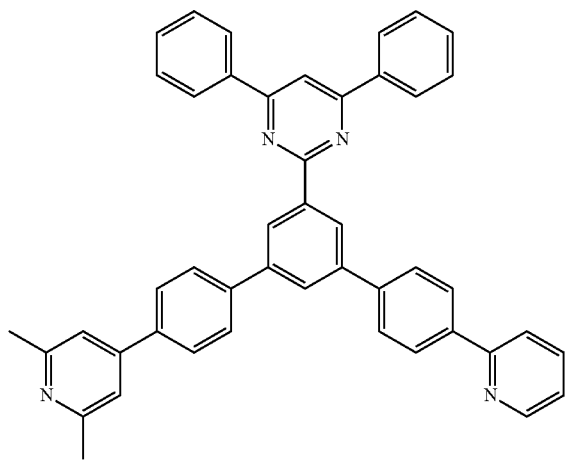
E-214
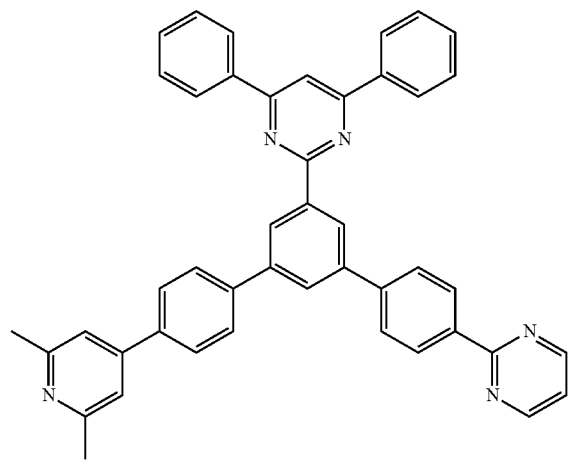
E-215
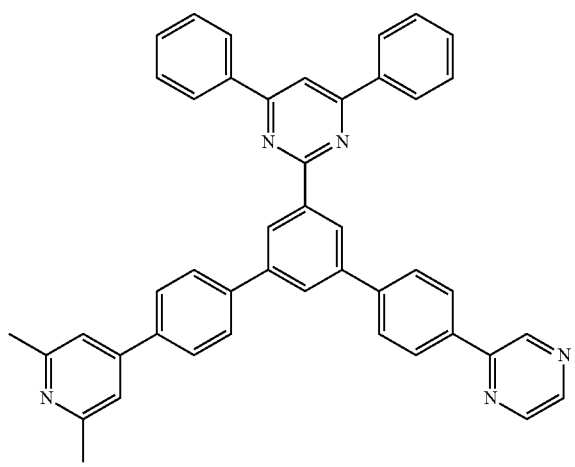
E-216
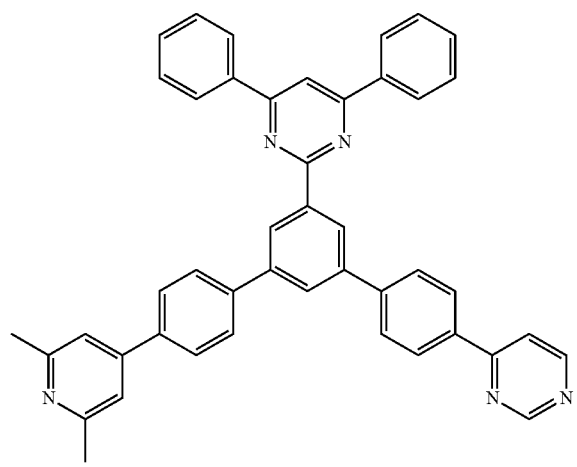
E-217
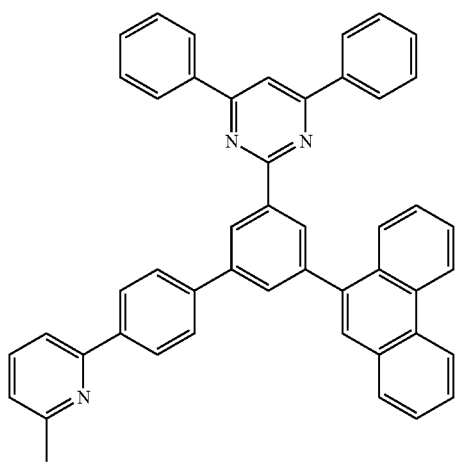
E-218
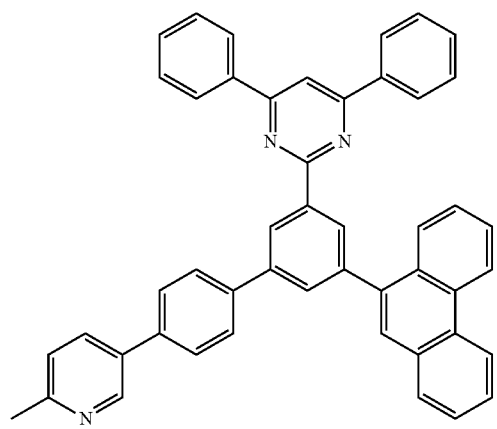

-continued
E-219
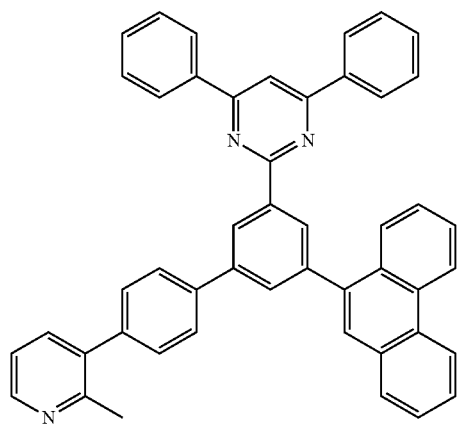
E-220
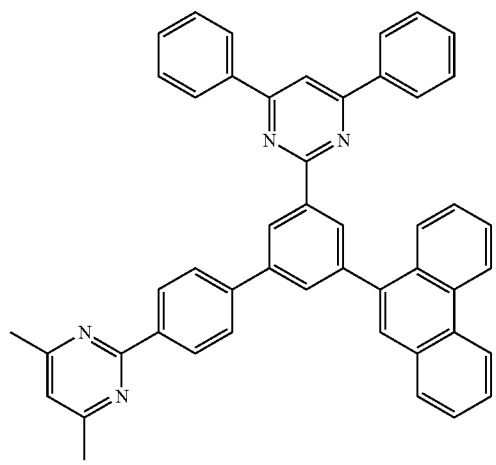
E-221
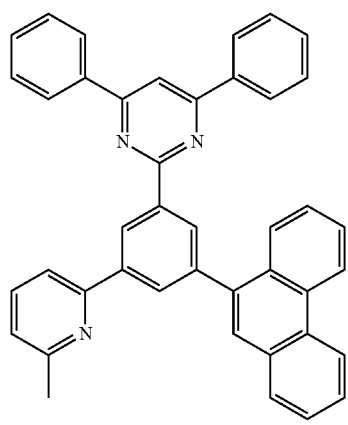
E-222
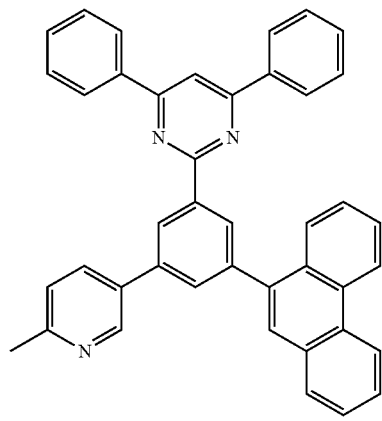
E-223
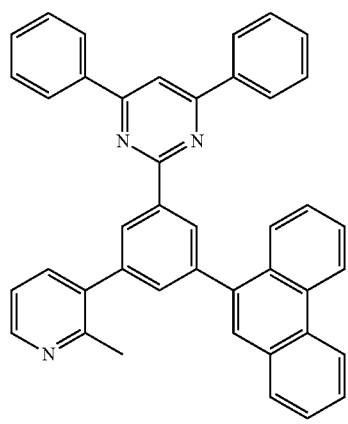
E-224
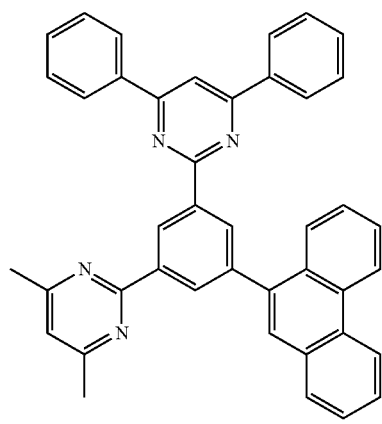

E-225
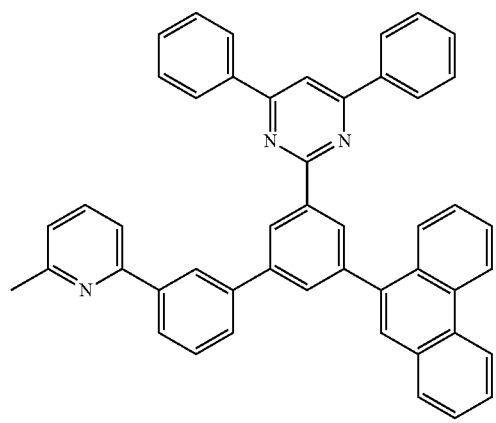
E-226
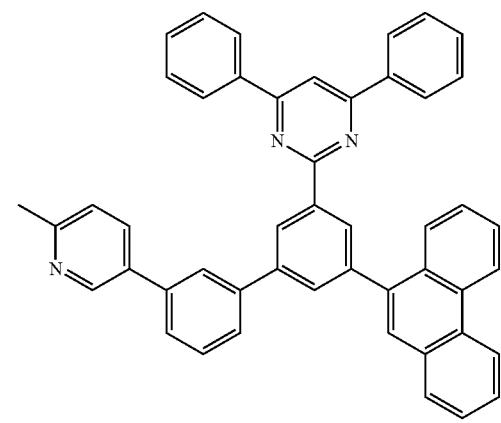
E-227
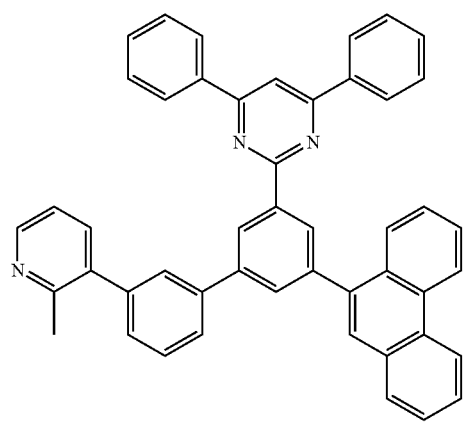
E-228
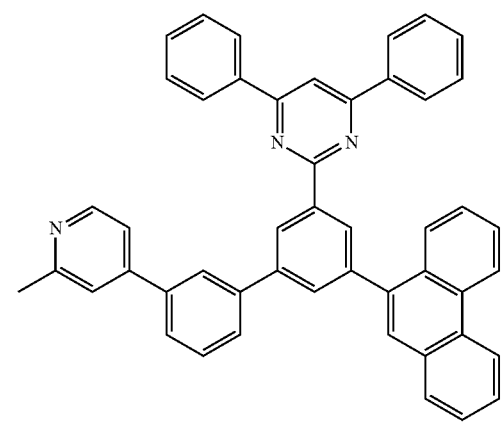
E-229
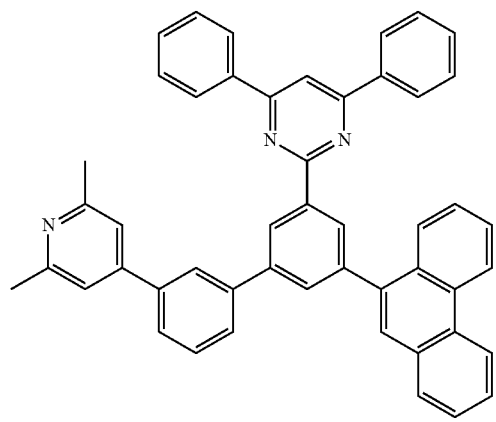
E-230
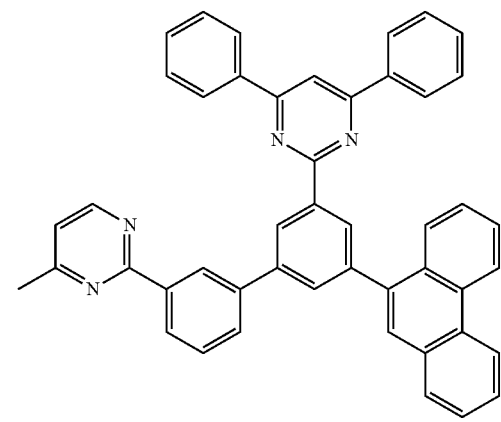

-continued
E-231
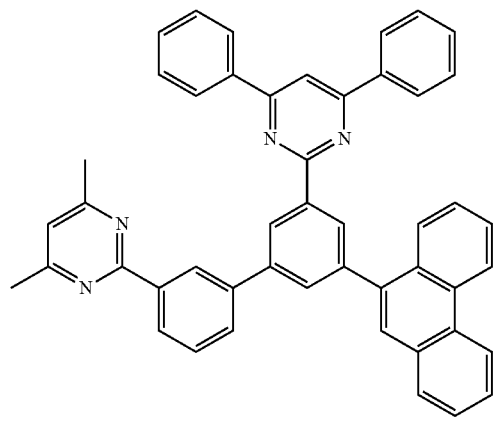
E-232
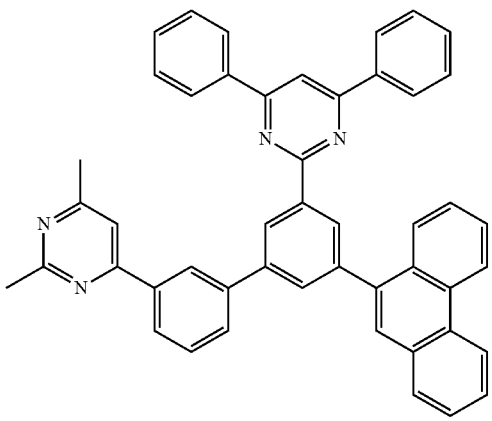
E-233
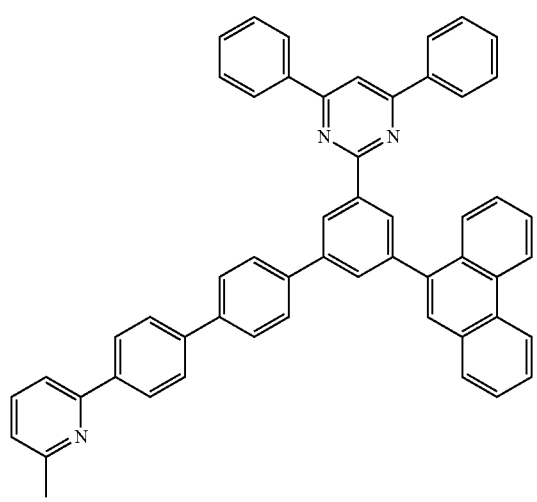
E-234
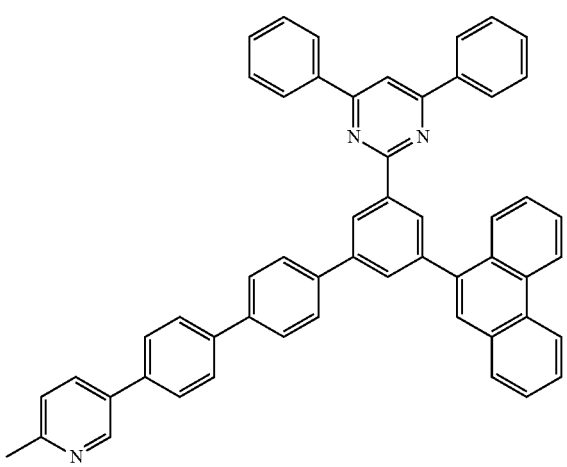
E-235
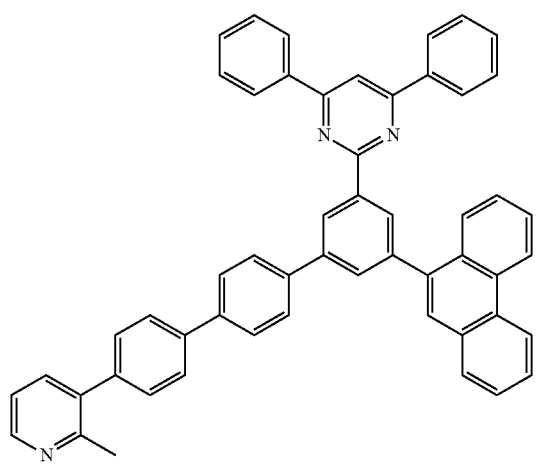
E-236
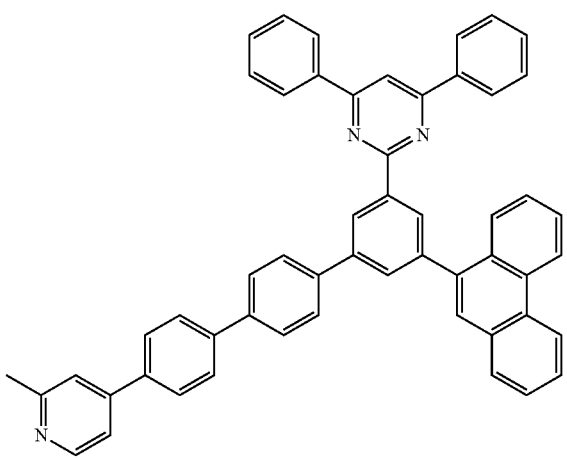

-continued
E-237
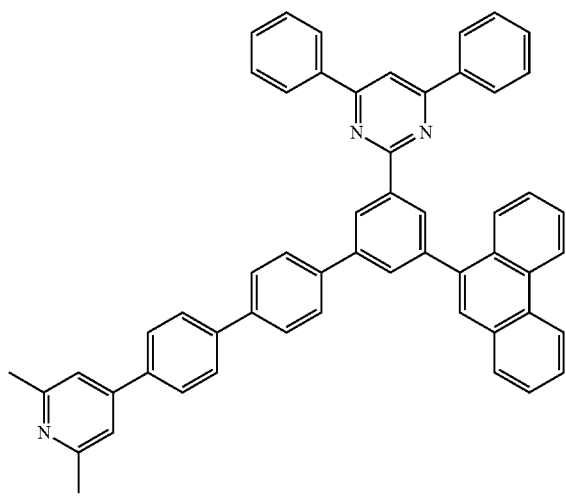
E-238
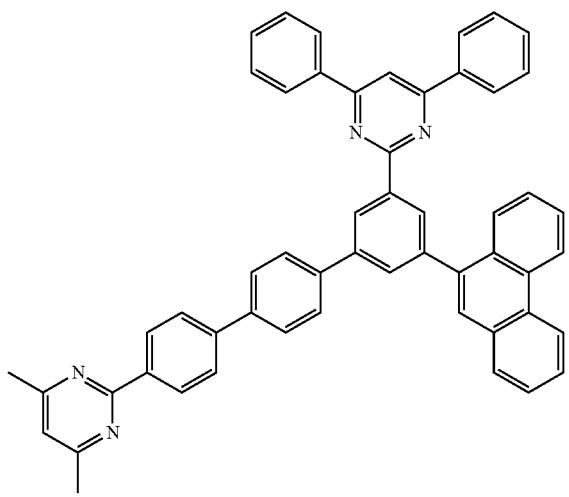
E-239
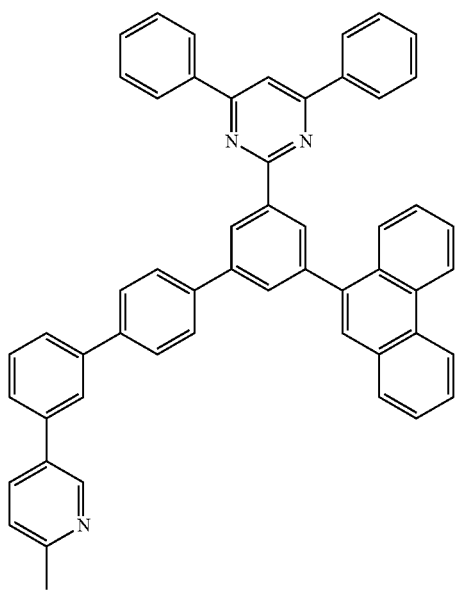
E-240
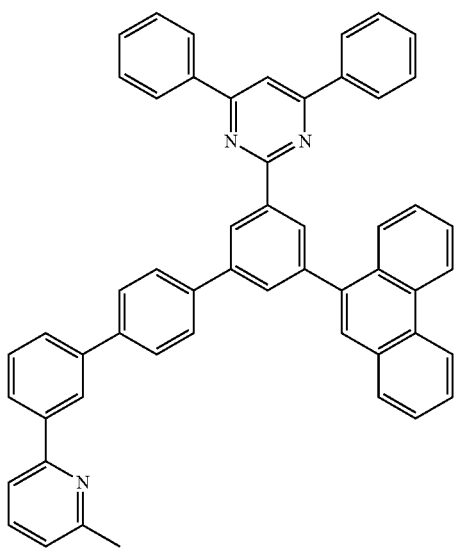
E-241
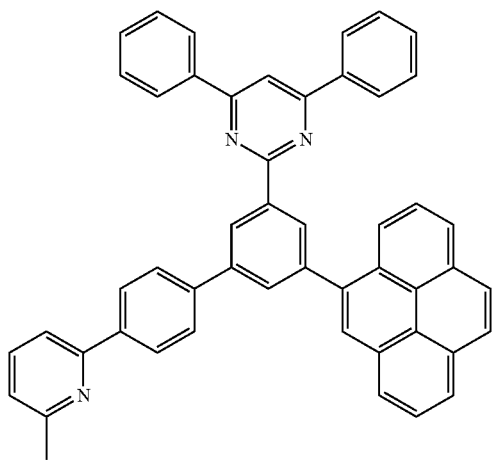
E-242
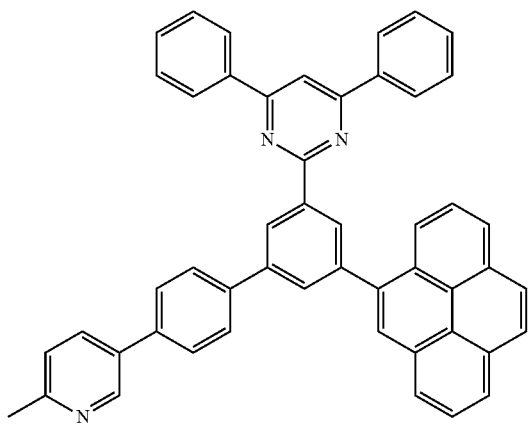

-continued
E-243
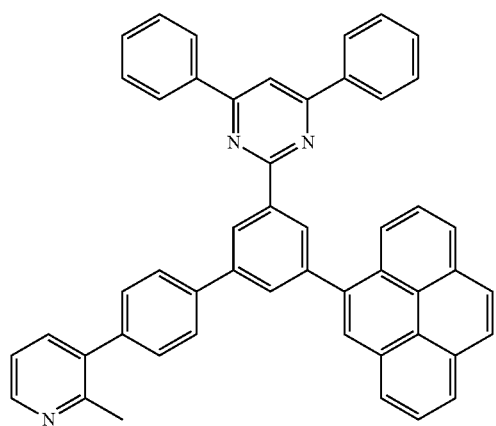
E-244
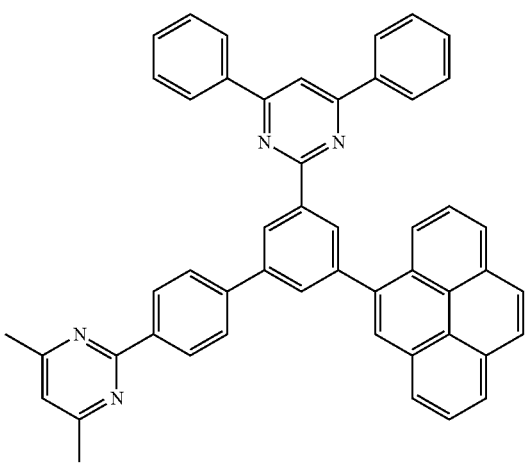
E-245
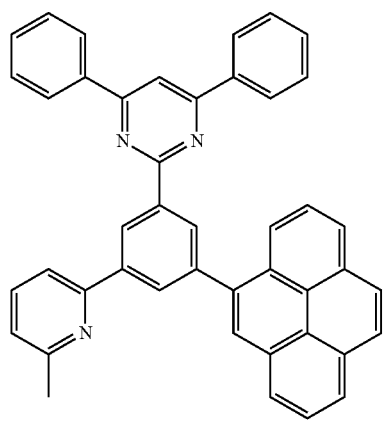
E-246
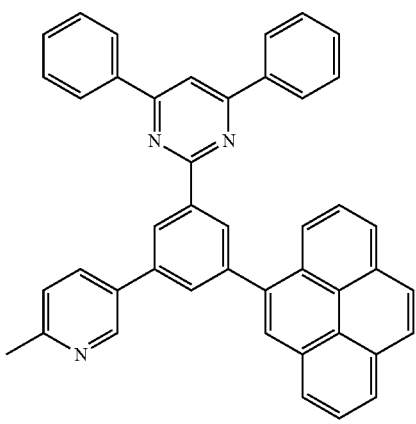
E-247
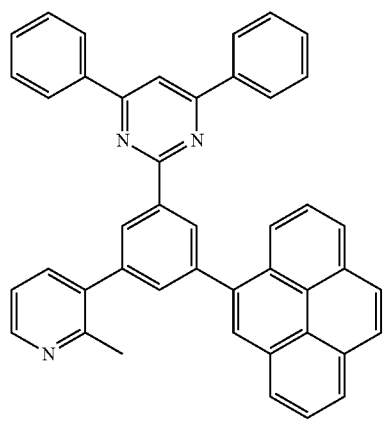
E-248
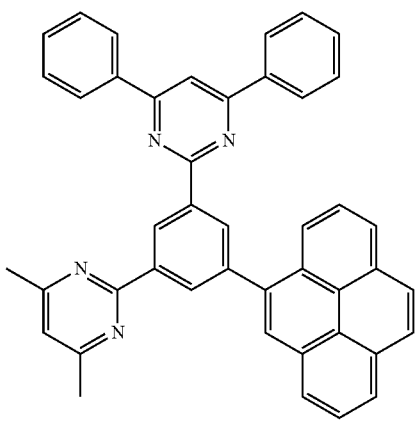

-continued
E-249
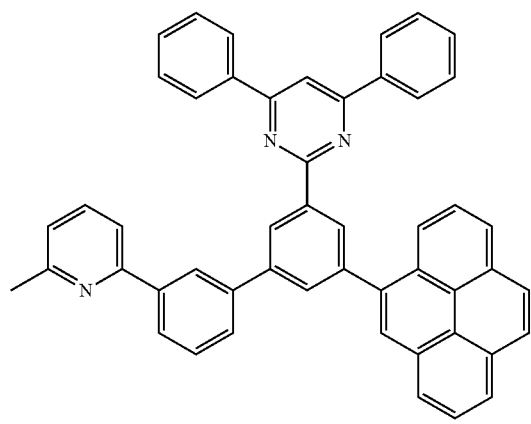
E-250
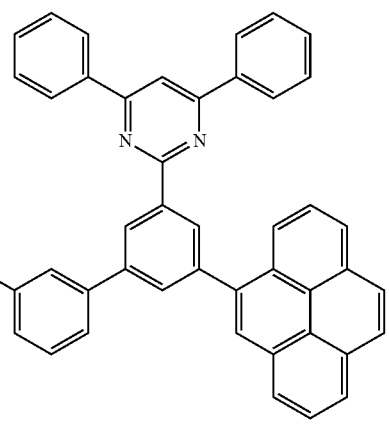
E-251
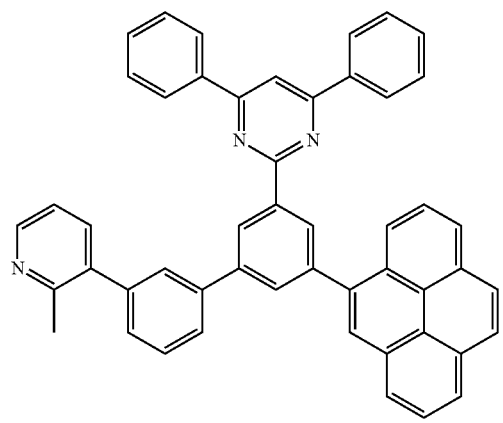
E-252
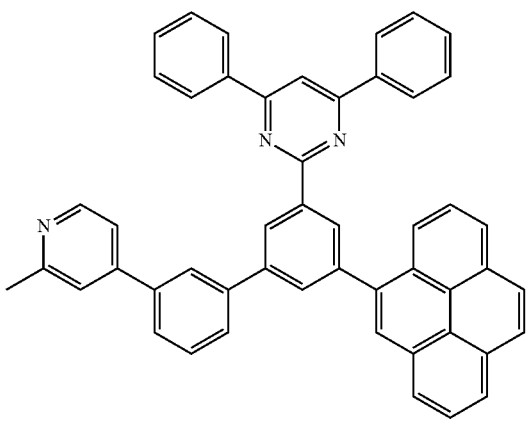
E-253
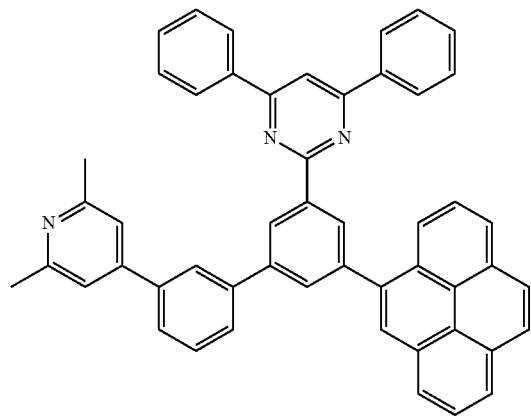
E-254
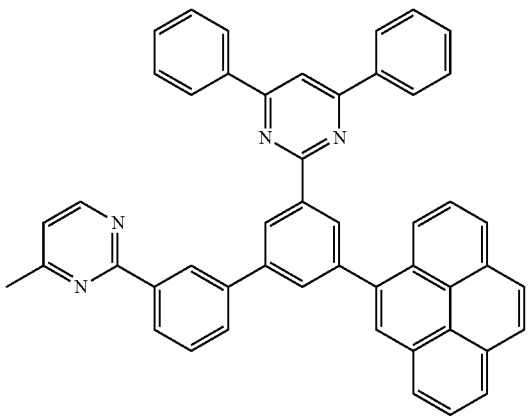

-continued
E-255
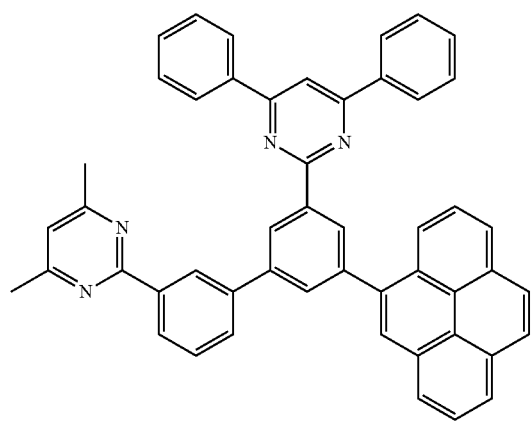
E-256
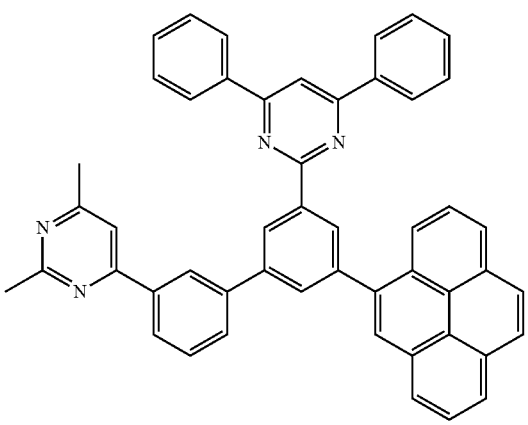
E-257
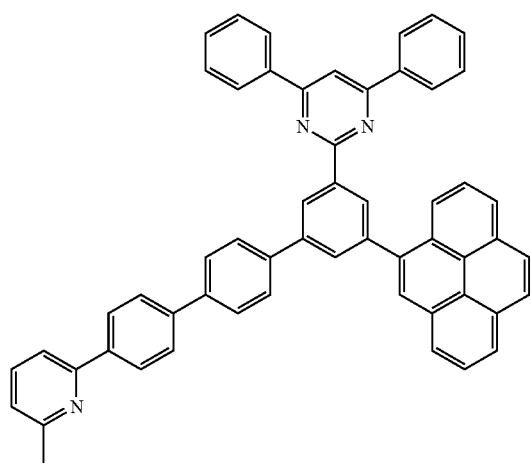
E-258
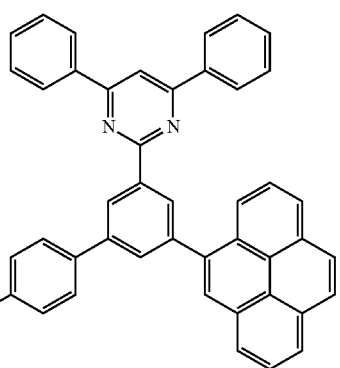
E-259
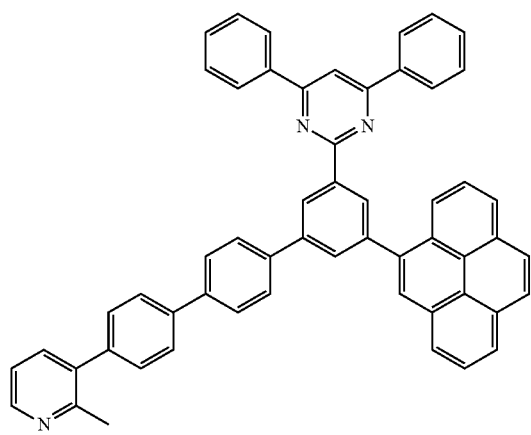
E-260
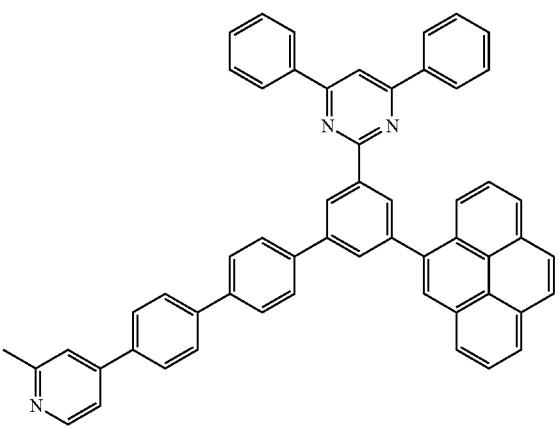

-continued
E-261
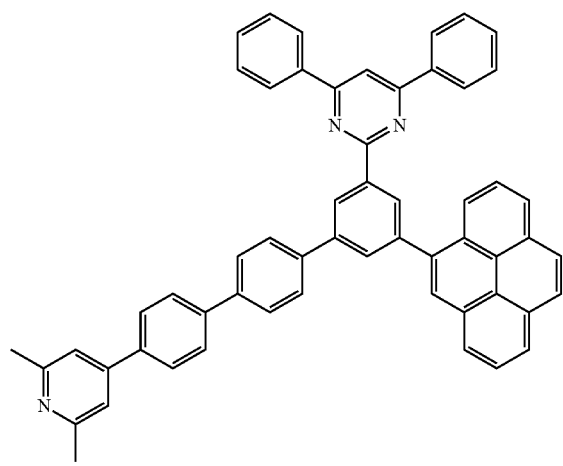
E-262
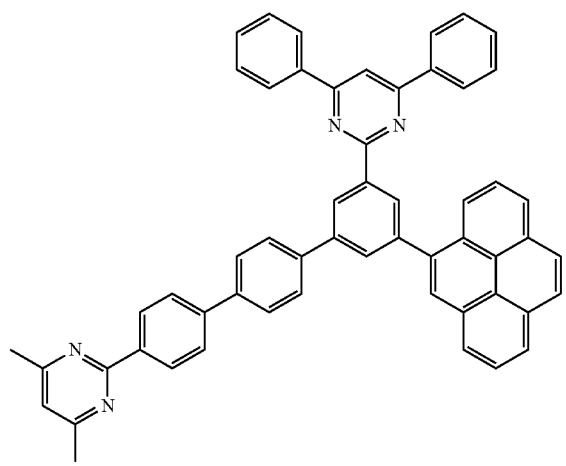
E-263
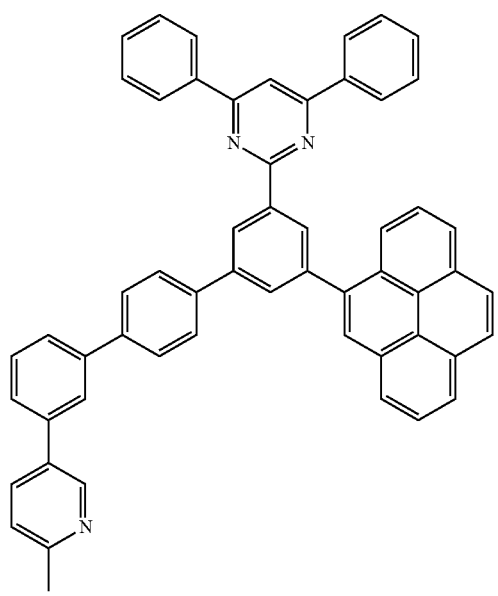
E-264
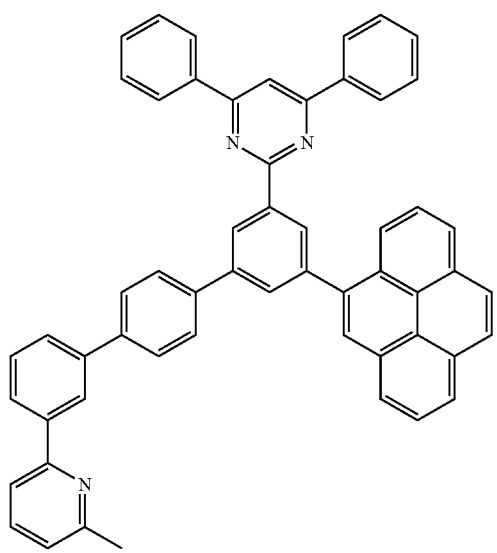
E-265
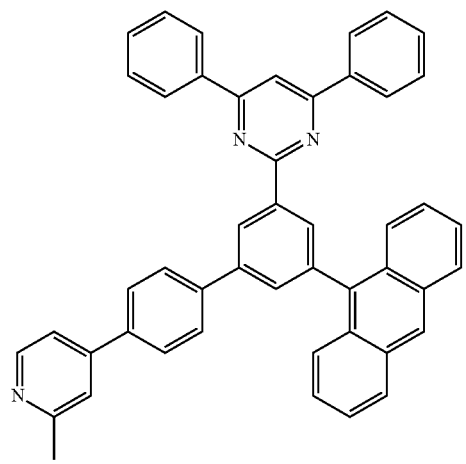
E-266
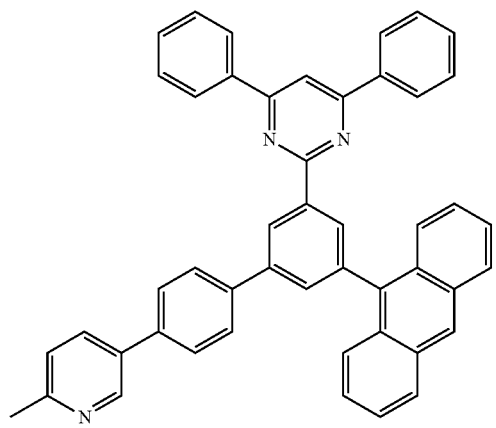

-continued
E-267
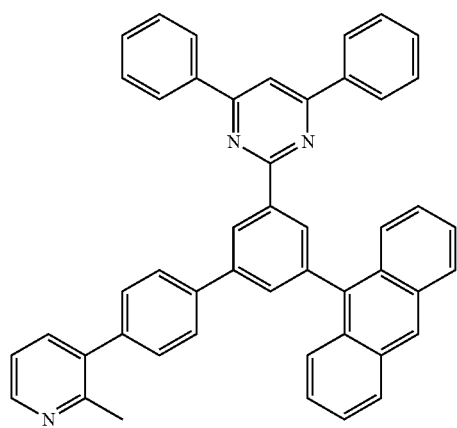
E-268
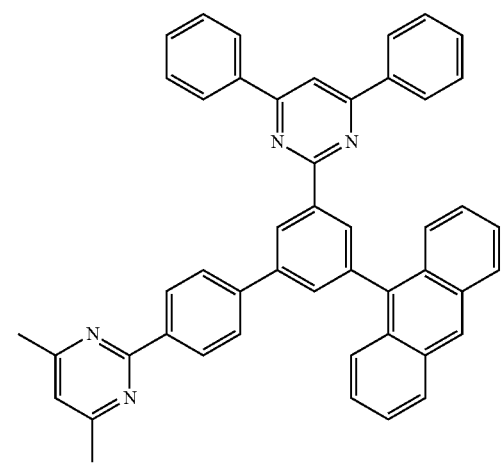
E-269
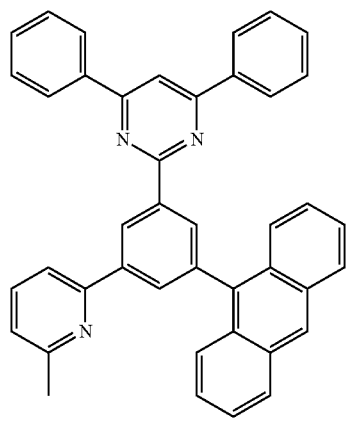
E-270
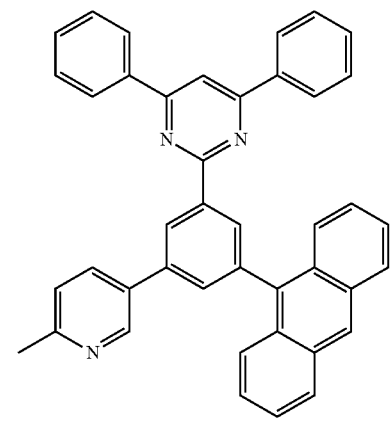
E-271
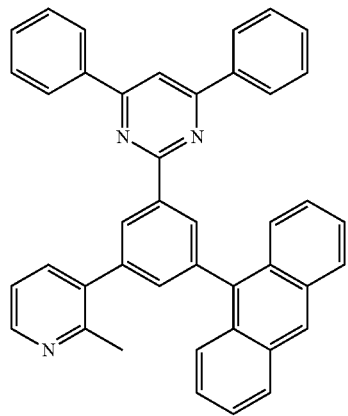
E-272
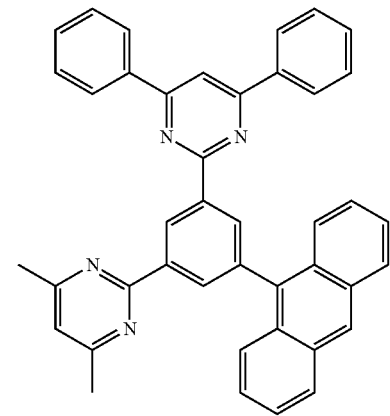

-continued
E-273
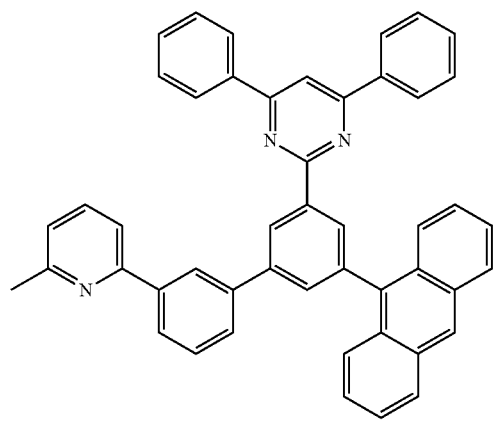
E-274
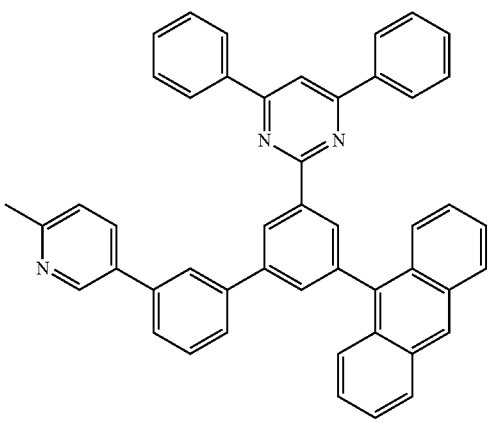
E-275
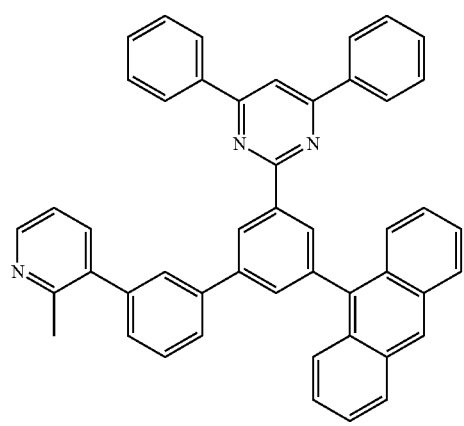
E-276
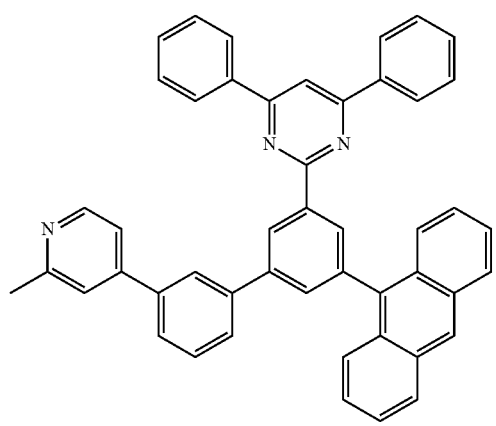
E-277
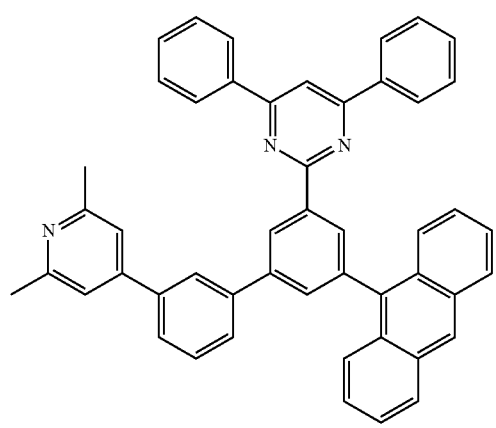
E-278
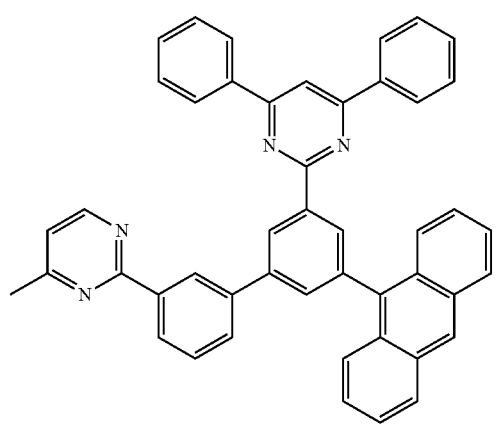

-continued
E-279
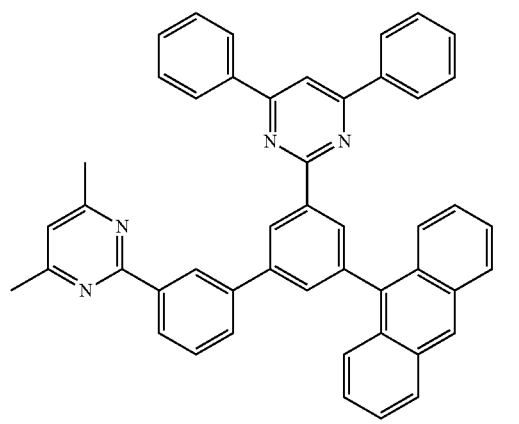
E-280
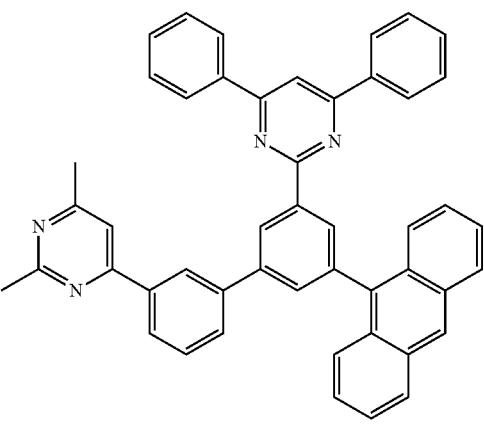
E-281
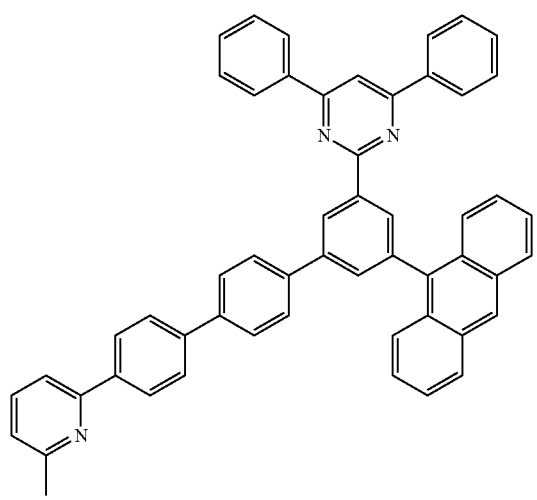
E-282
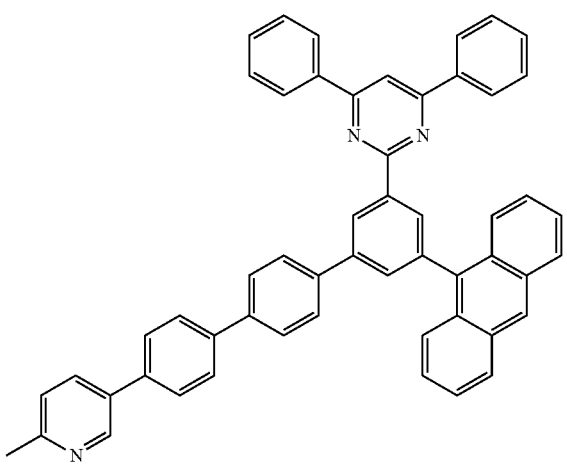
E-283
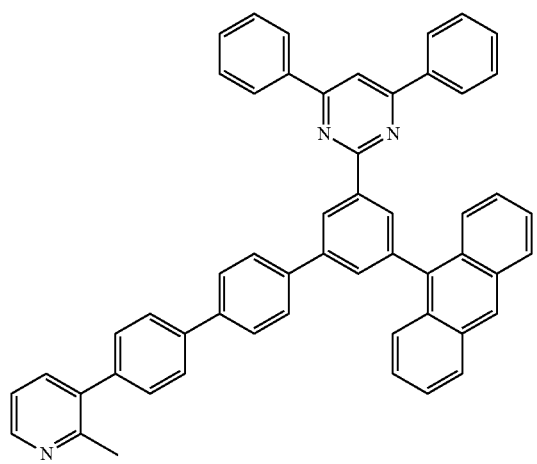
E-284
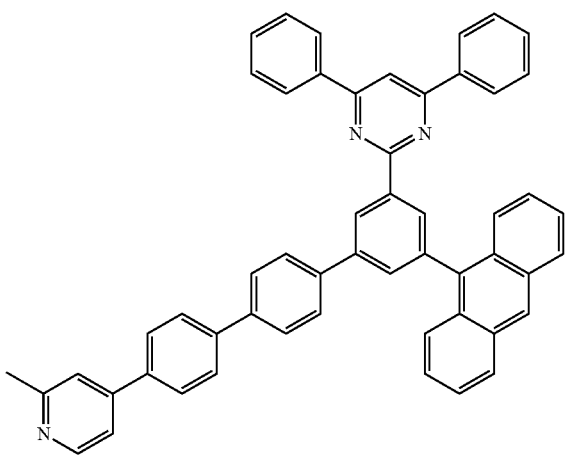

-continued
E-283
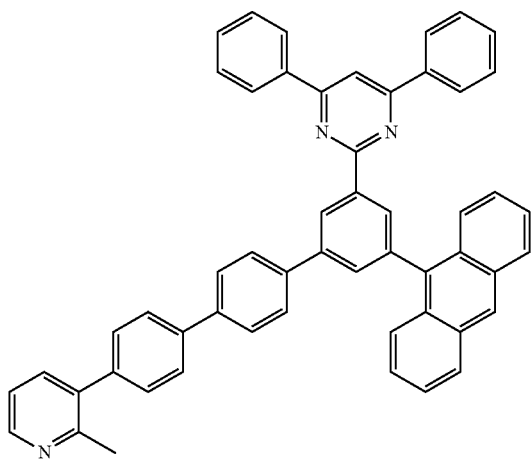
E-284
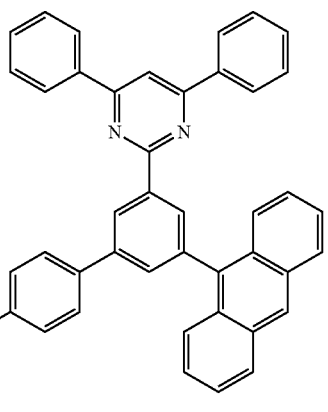
E-285
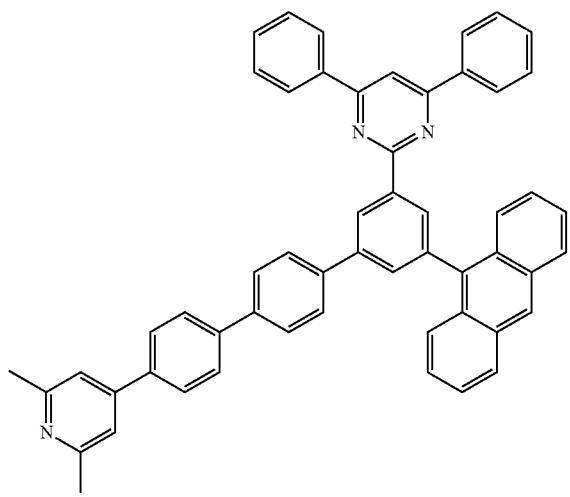
E-286
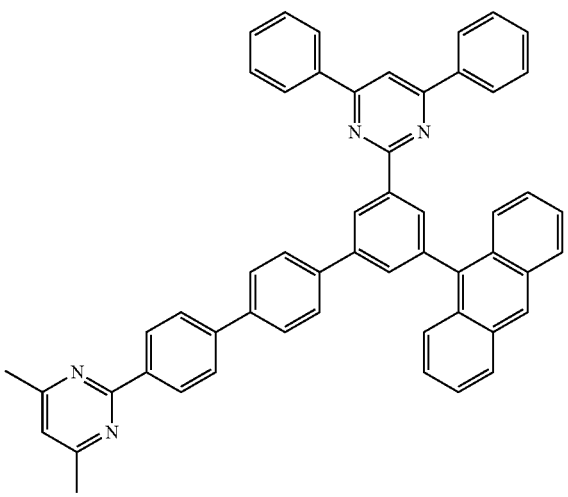
E-287
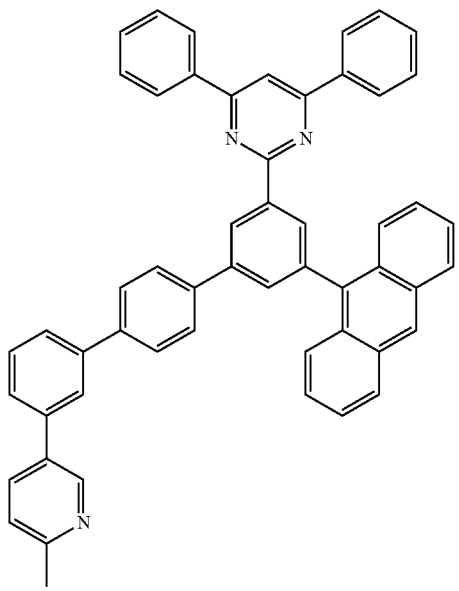
E-288
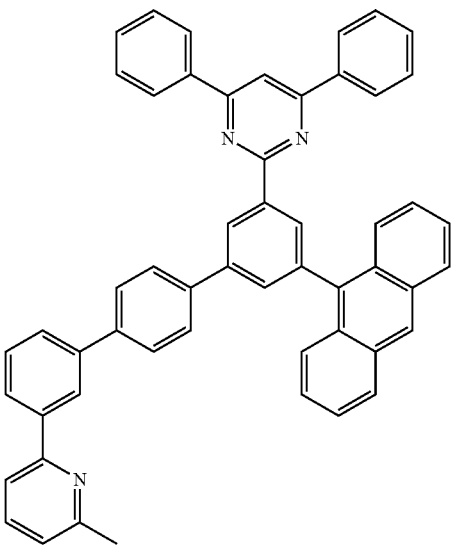

-continued
E-289
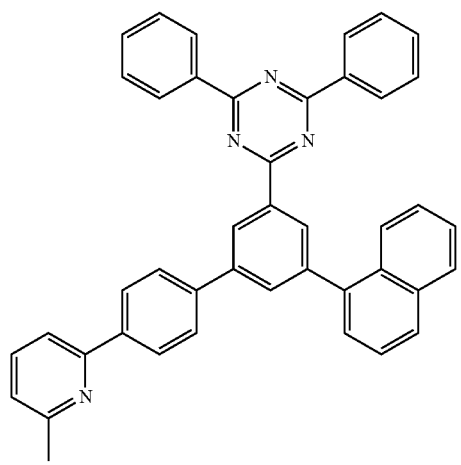
E-290
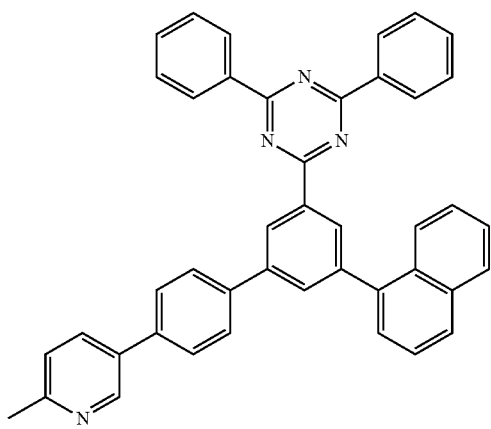
E-291
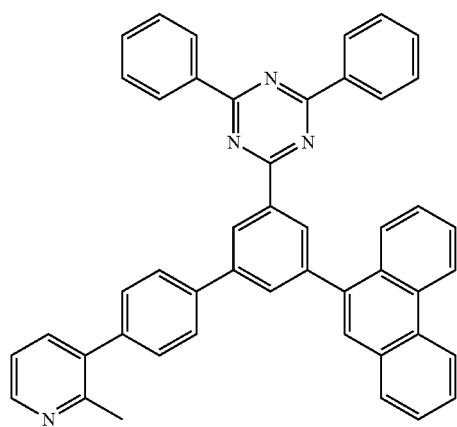
E-292
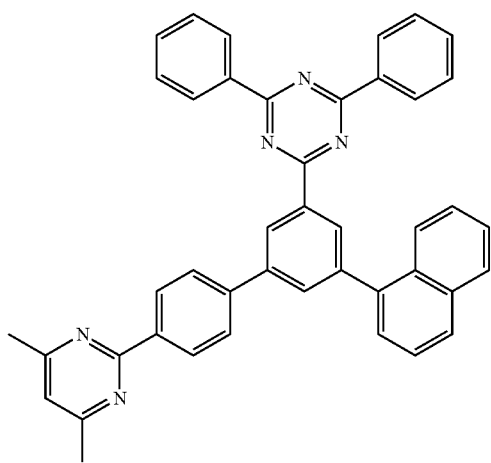
E-293
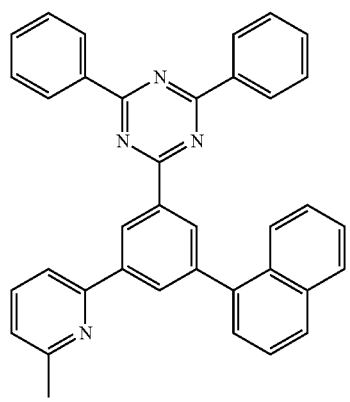
E-294
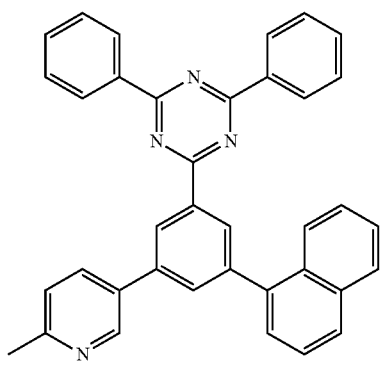

-continued
E-295
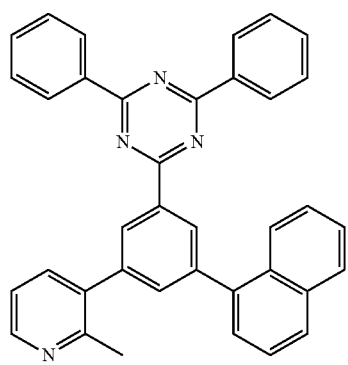
E-296
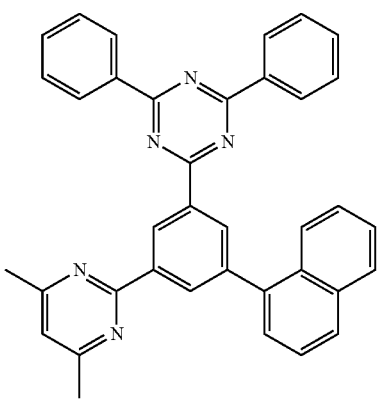
E-297
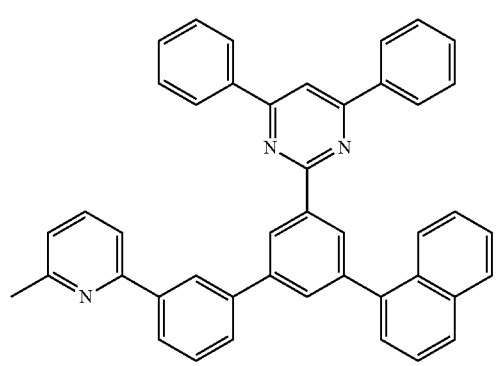
E-298
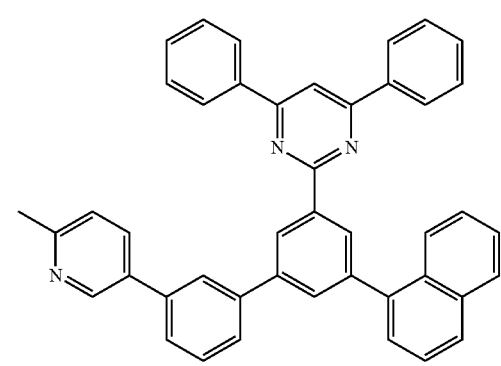
E-299
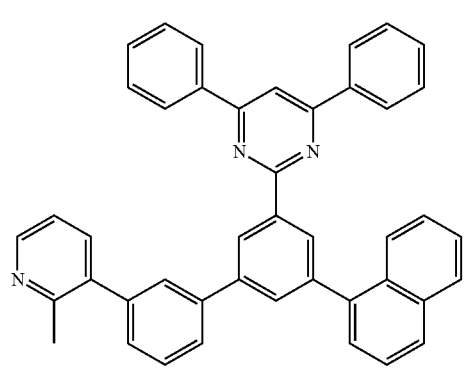
E-300
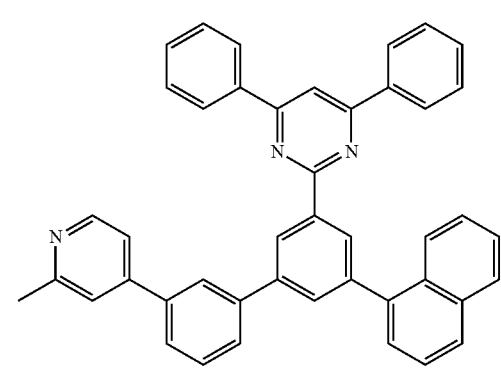
E-301
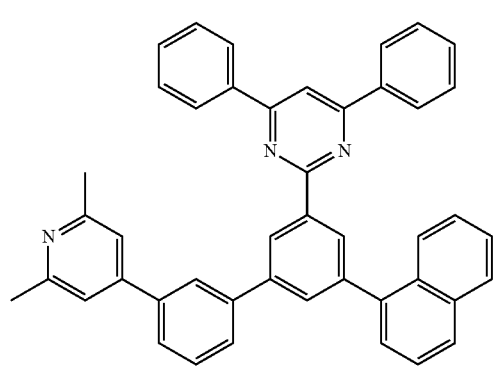
E-302
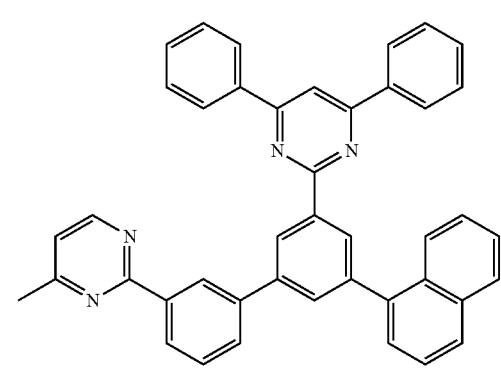

-continued
E-303
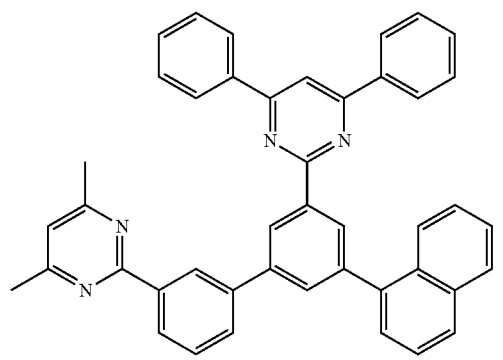
E-304
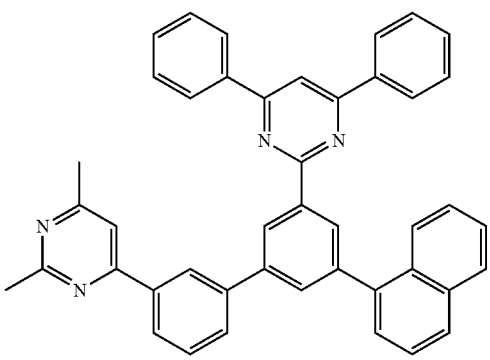
E-305
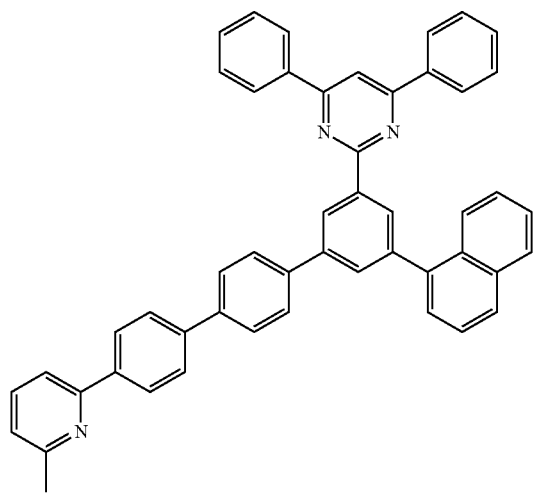
E-306
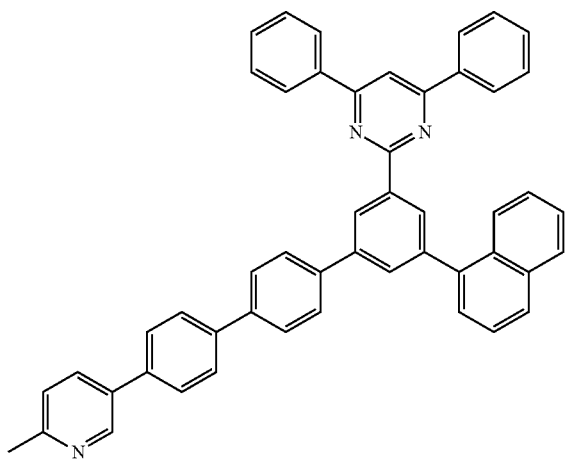
E-307
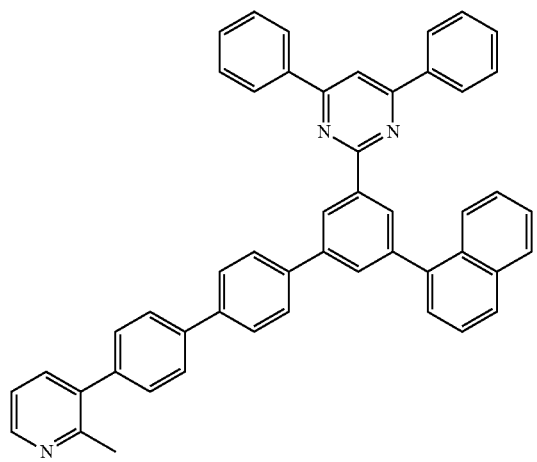
E-308
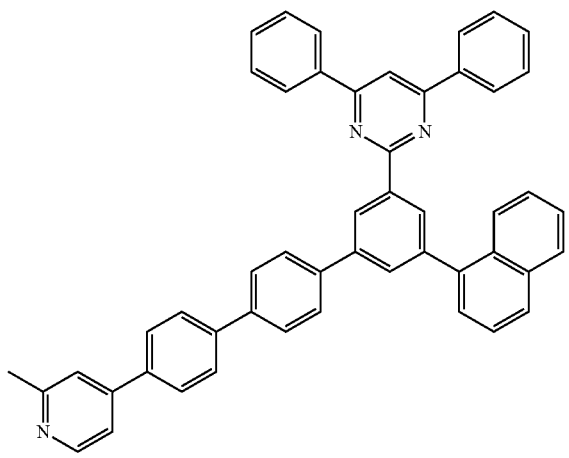

-continued
E-309
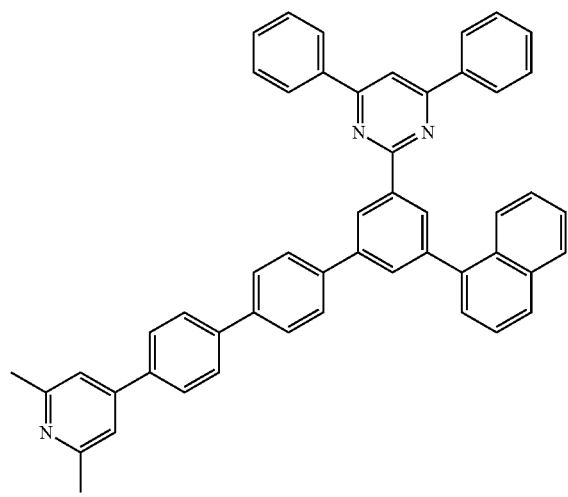
E-310
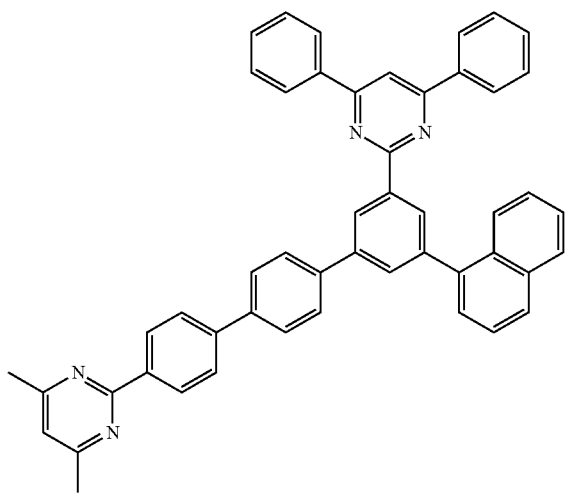
E-311
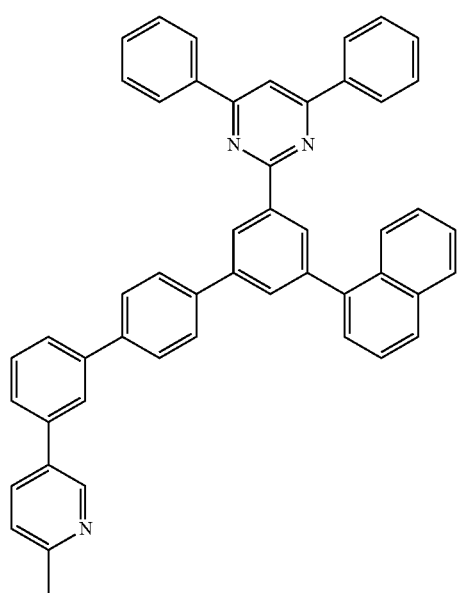
E-312
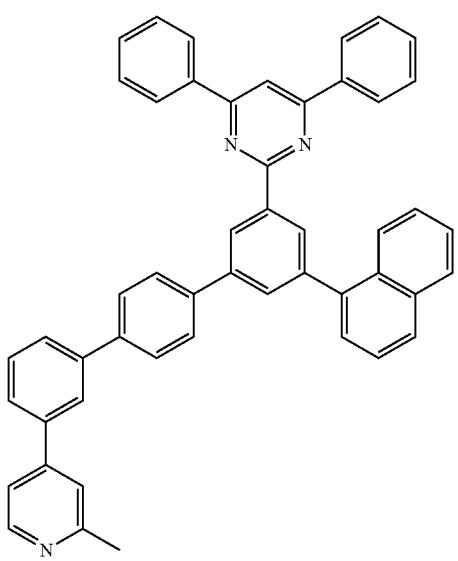
E-313
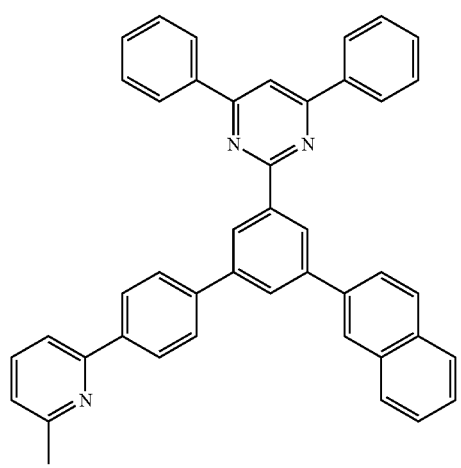
E-314
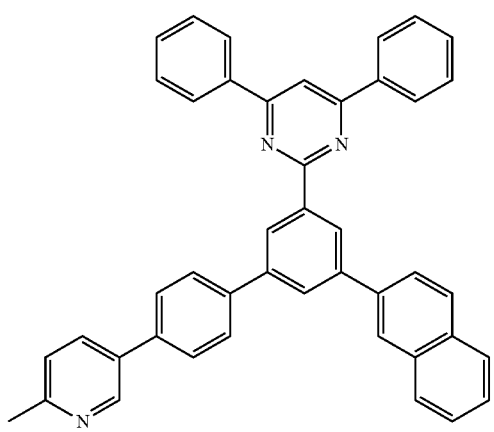

-continued
E-315
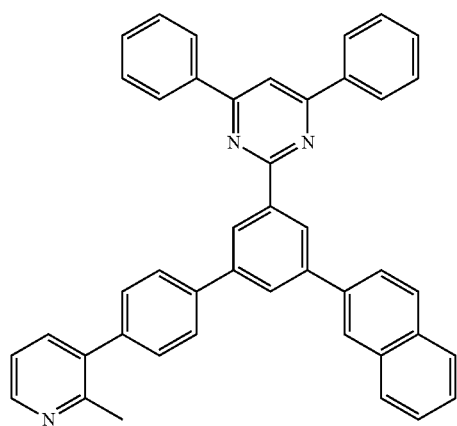
E-316
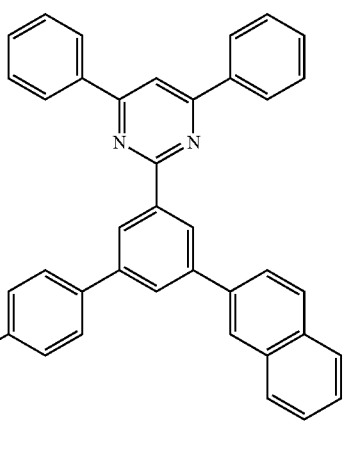
E-317
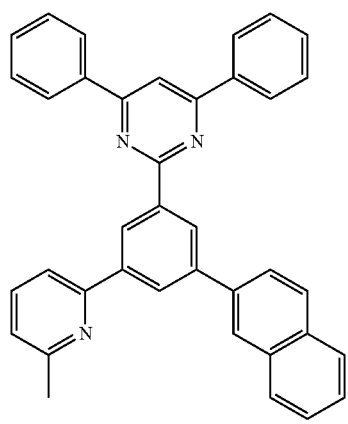
E-318
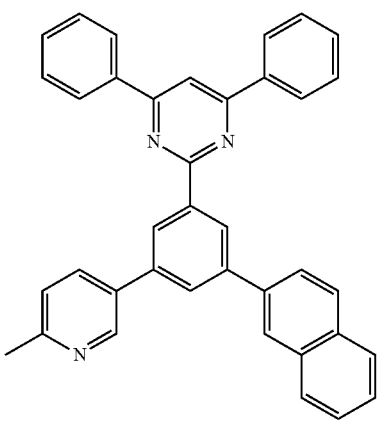
E-319
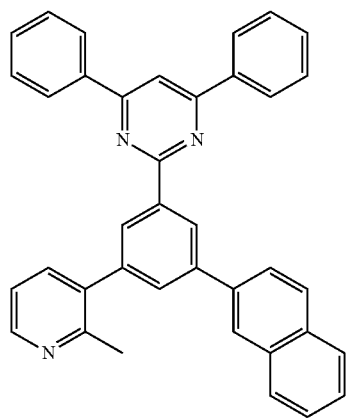
E-320
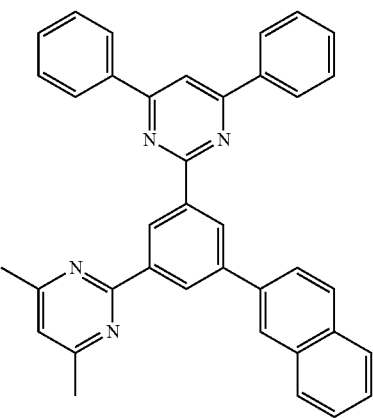

-continued
E-321
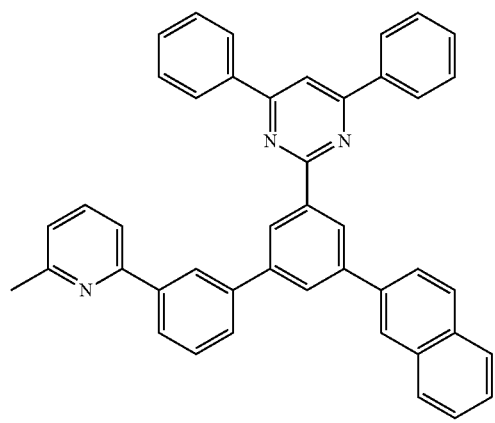
E-322
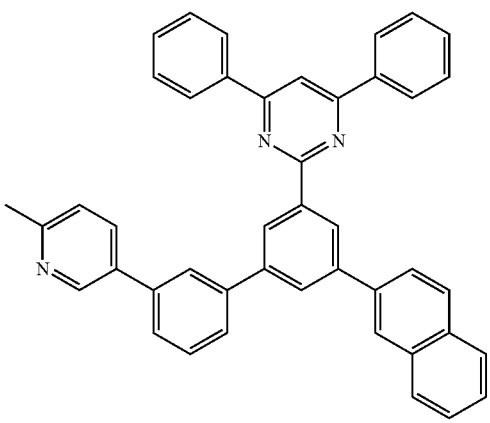
E-323
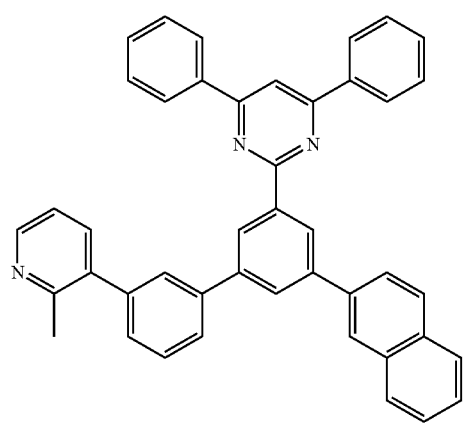
E-324
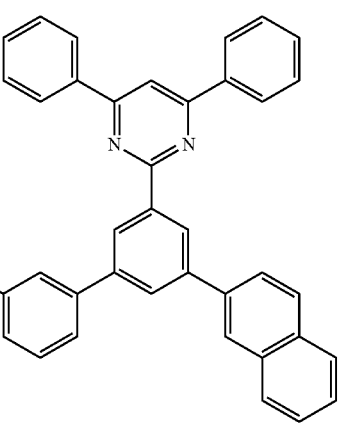
E-325
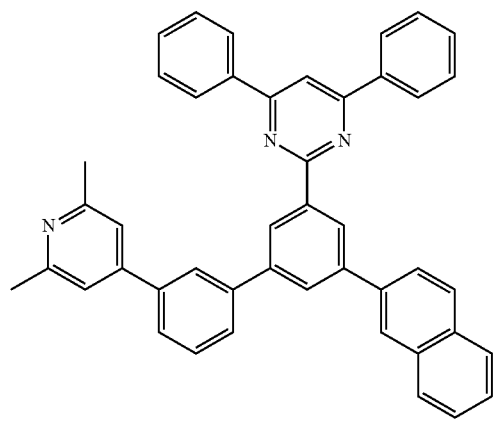
E-326
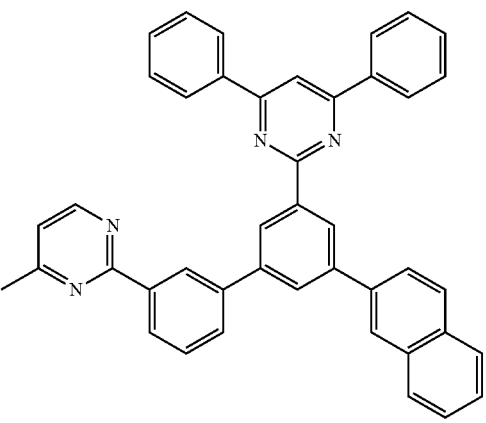

-continued
E-327
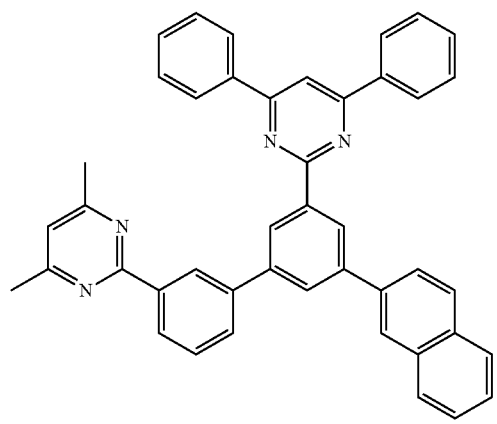
E-328
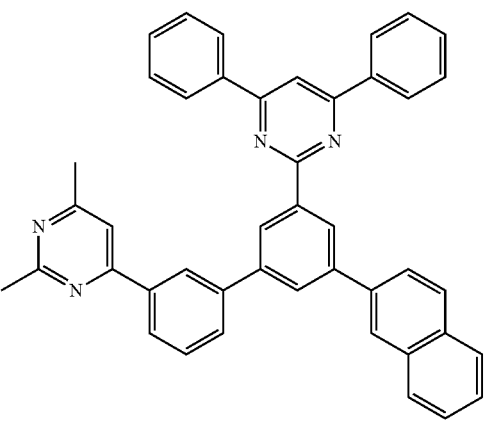
E-329
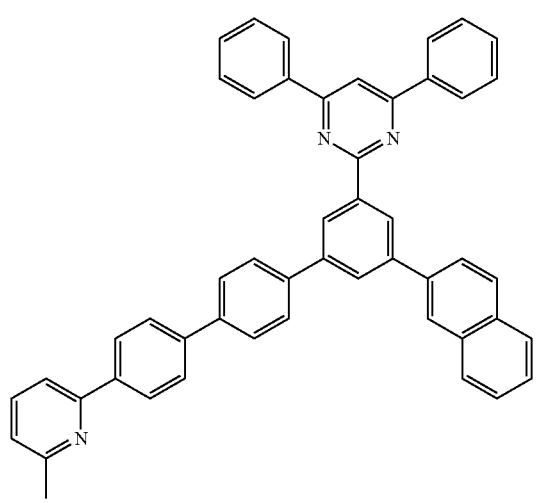
E-330
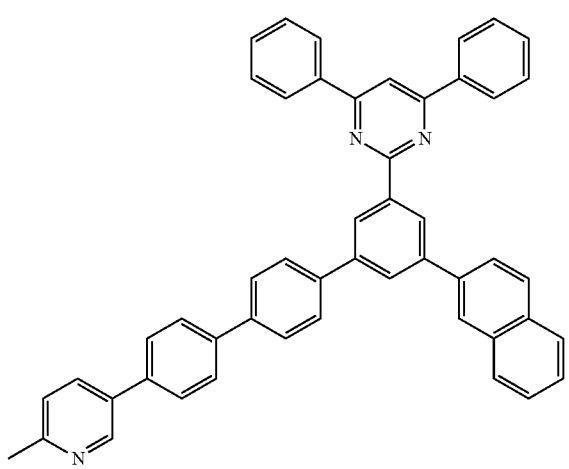
E-331
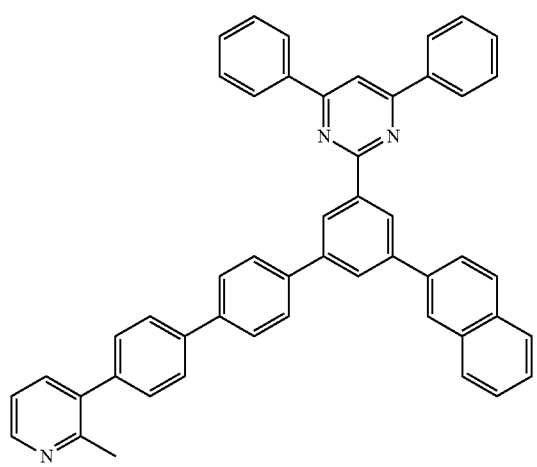
E-332
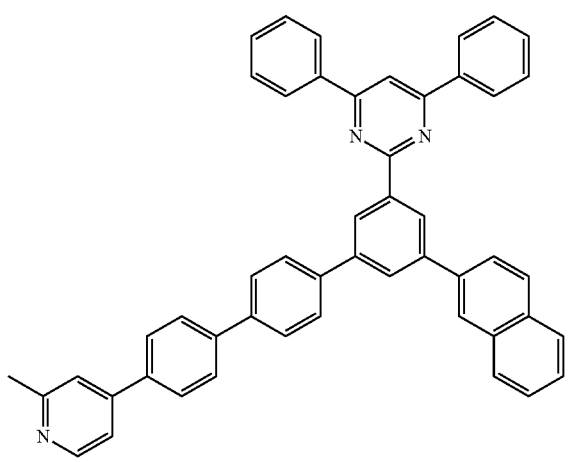

-continued
E-333
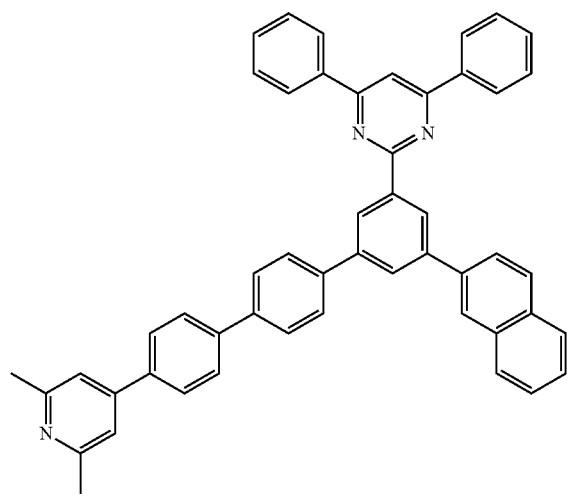
E-334
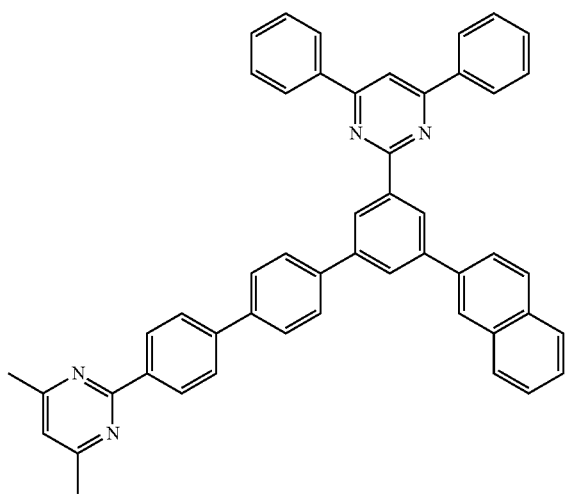
E-335
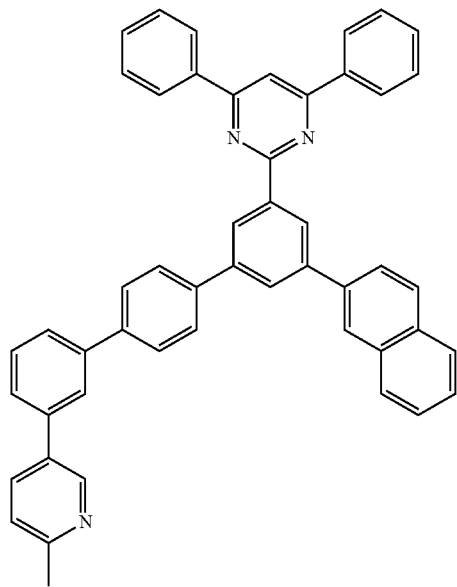
E-336
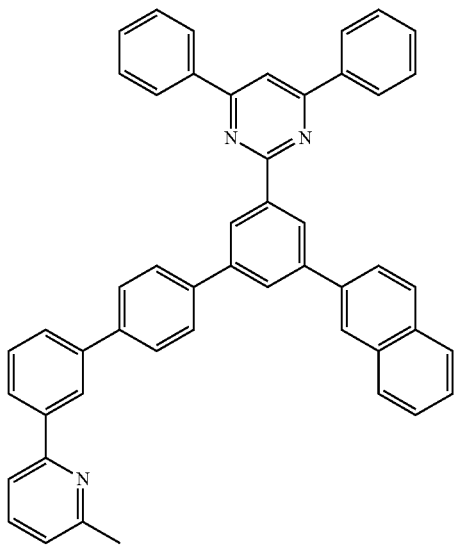
E-337
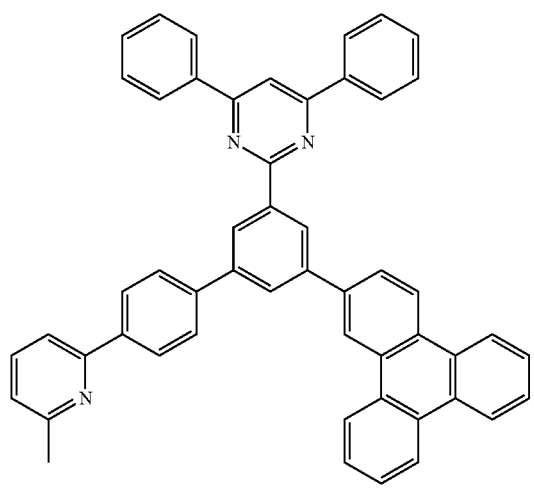
E-338
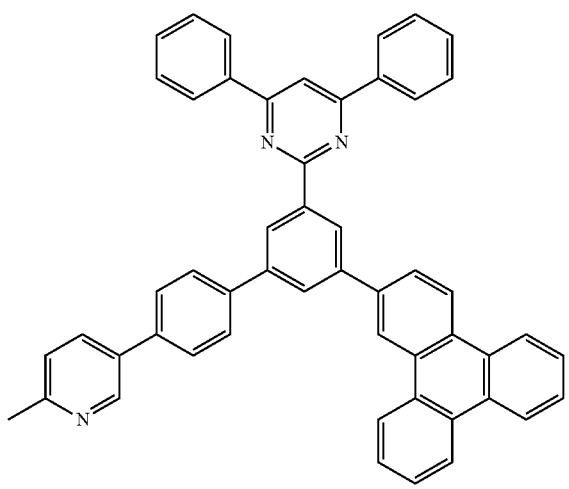

-continued
E-339
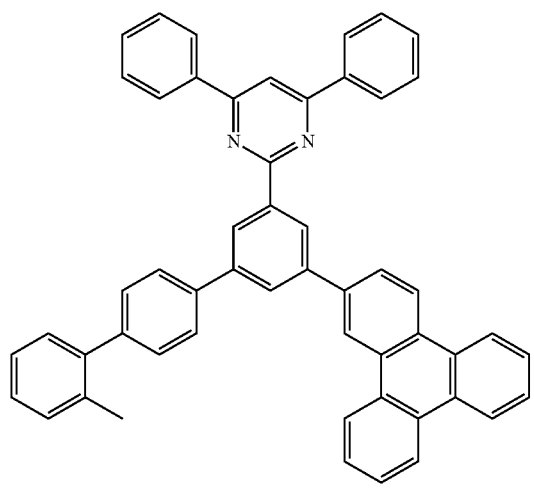
E-340
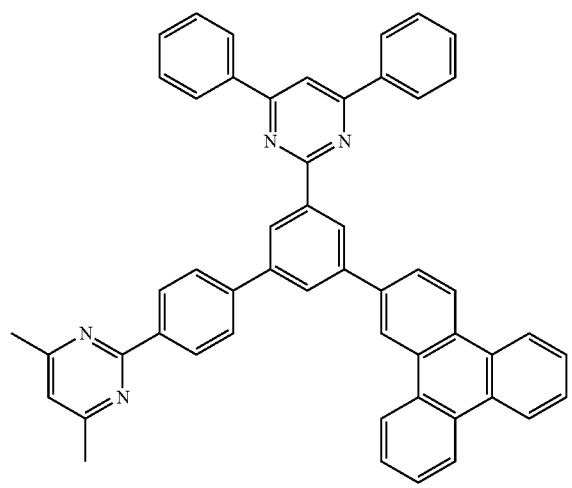
E-341
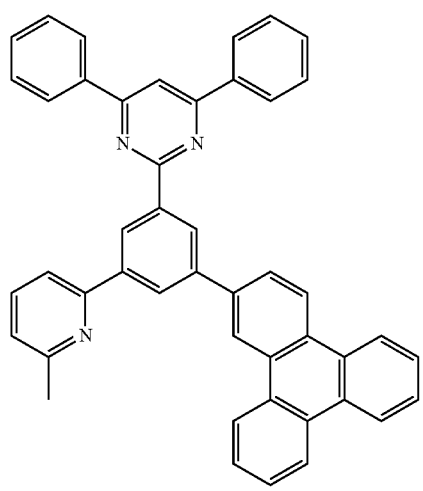
E-342
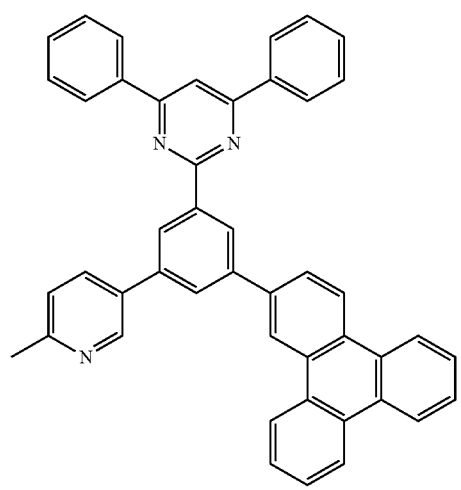
E-343
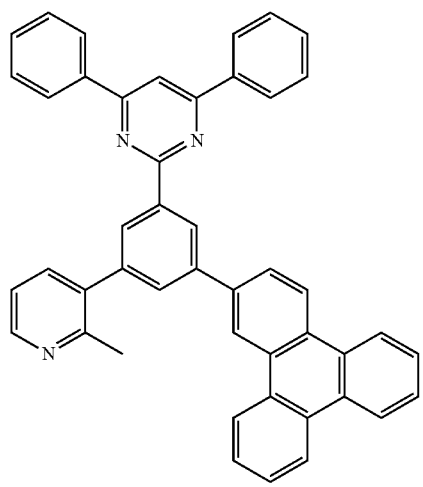
E-344
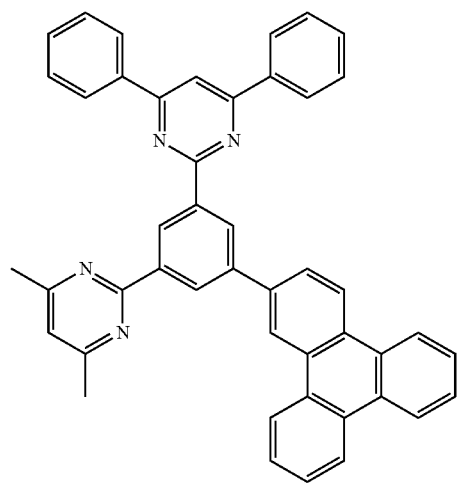

-continued
E-345
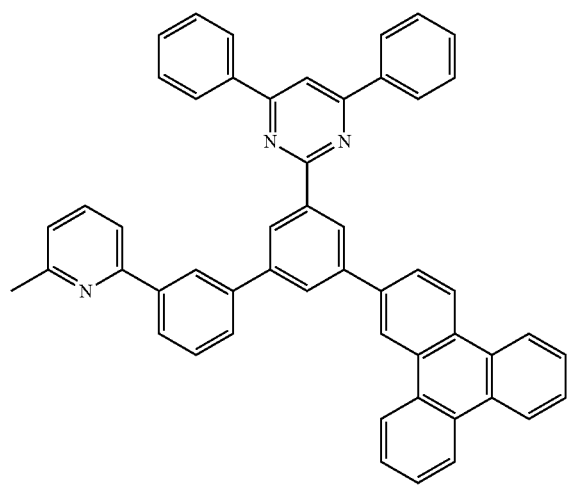
E-346
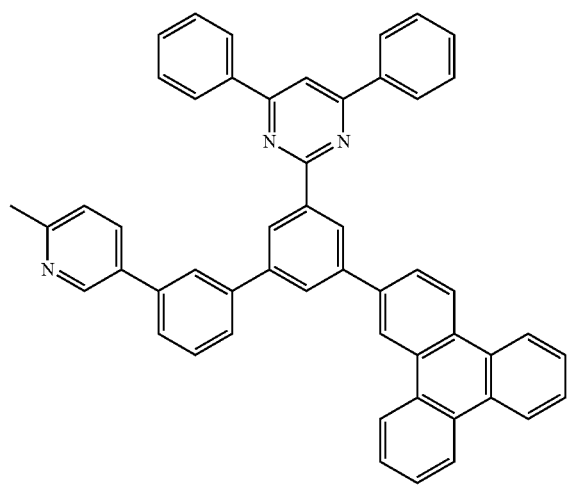
E-347
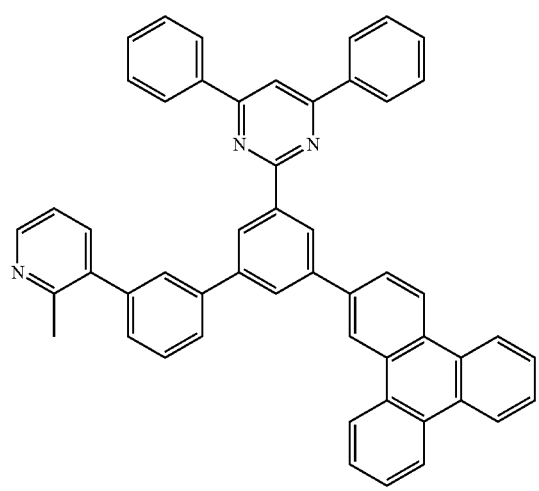
E-348
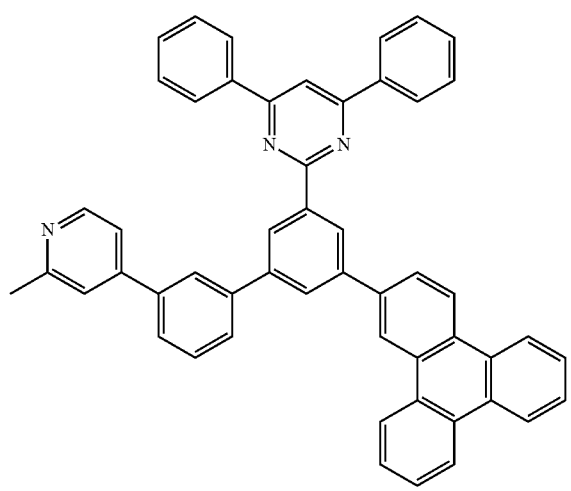
E-349
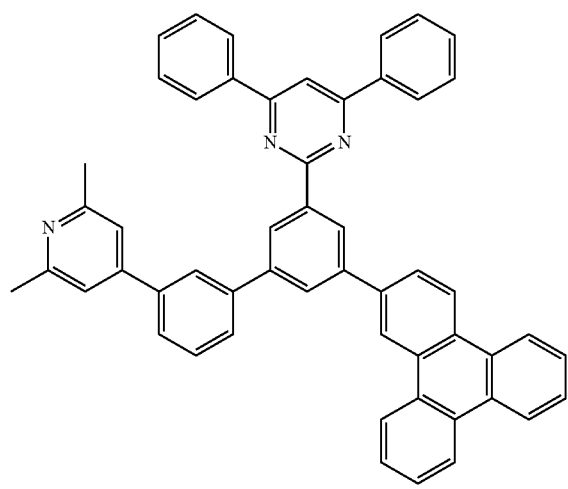
E-350
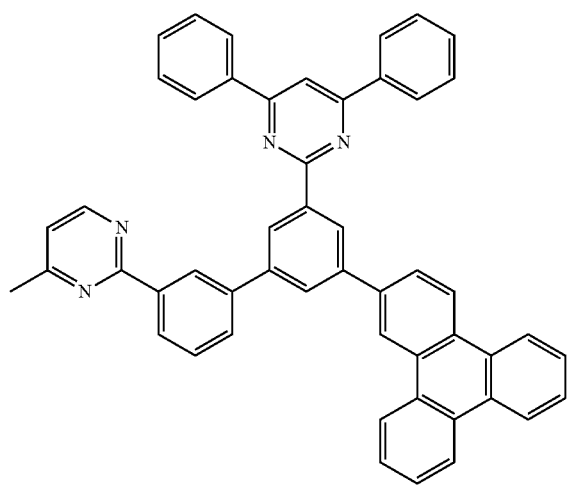

-continued
E-351
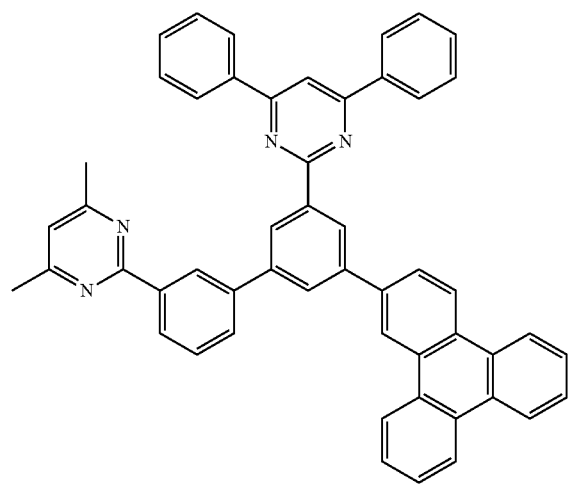
E-352
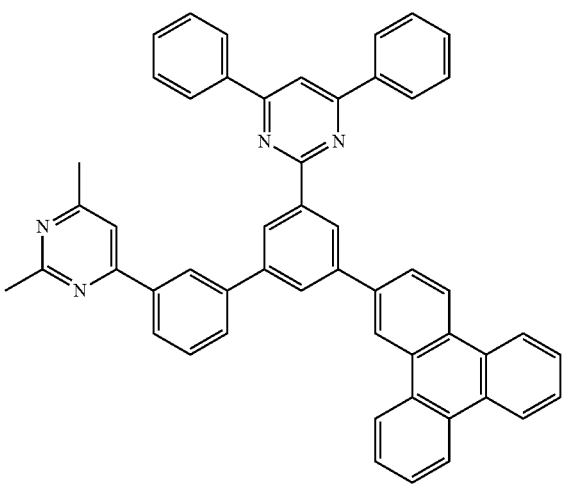
E-353
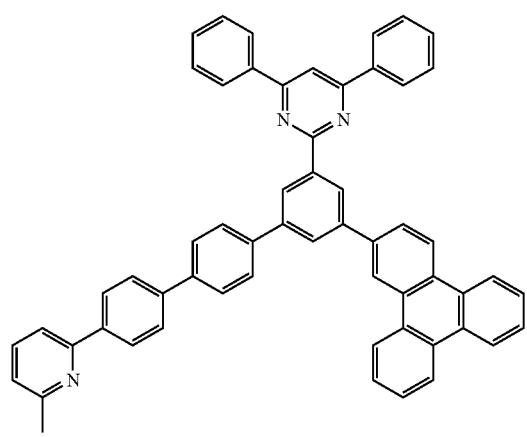
E-354
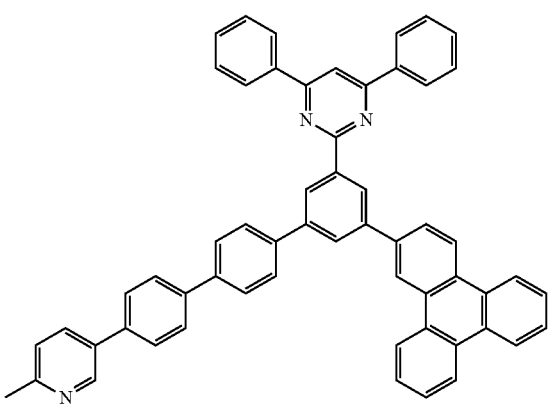
E-355
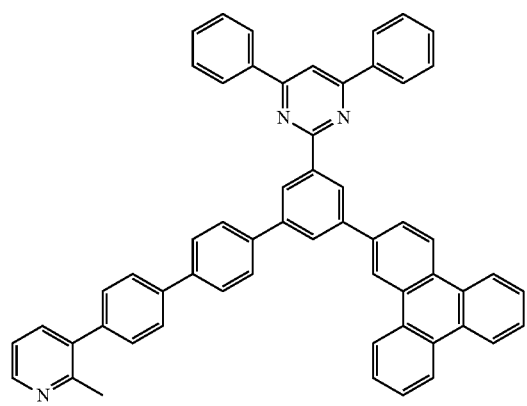
E-356
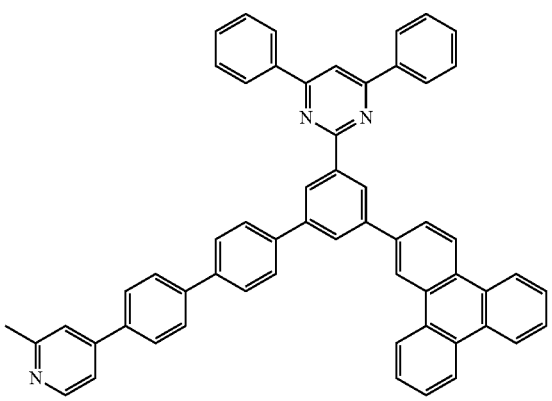

-continued
E-357
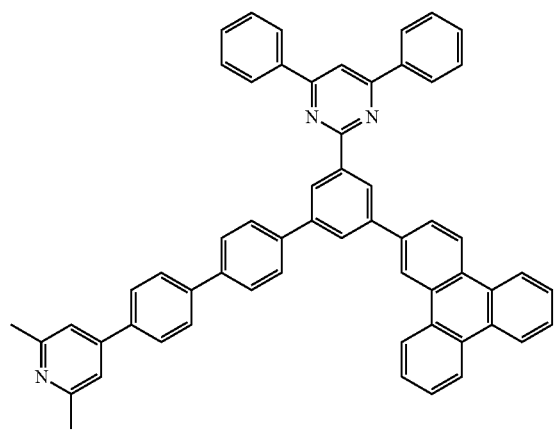
E-358
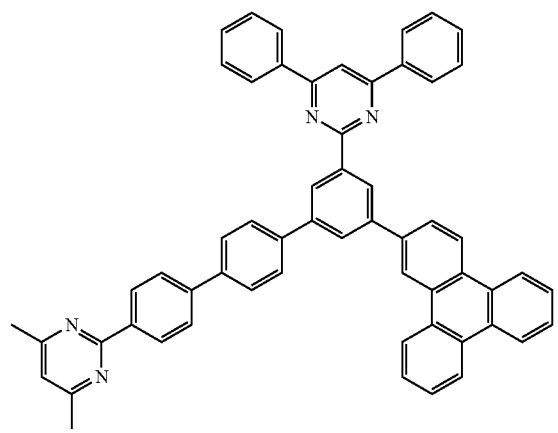
E-359
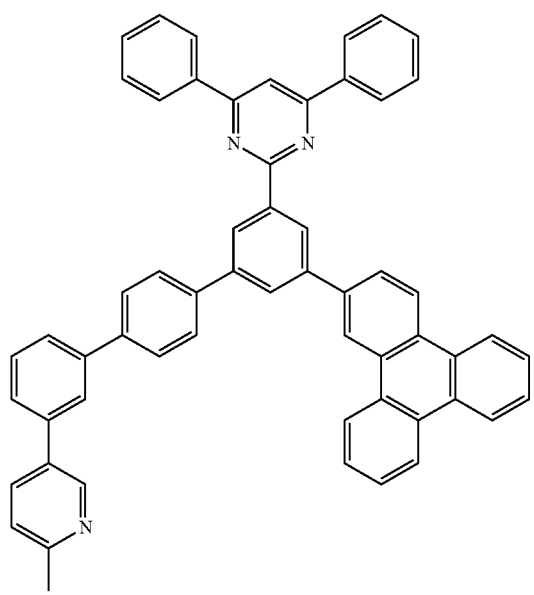
E-360
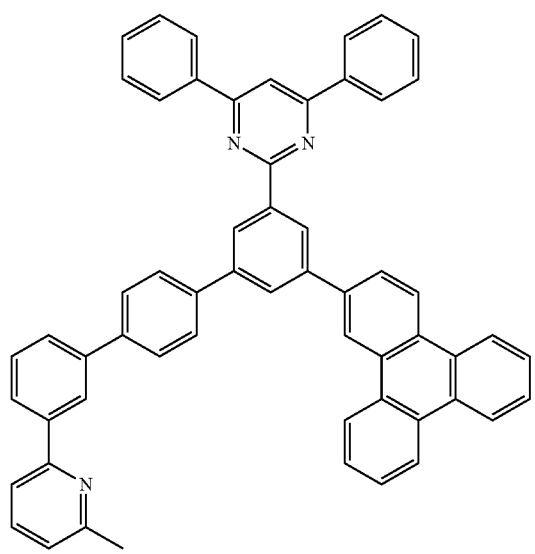
E-361
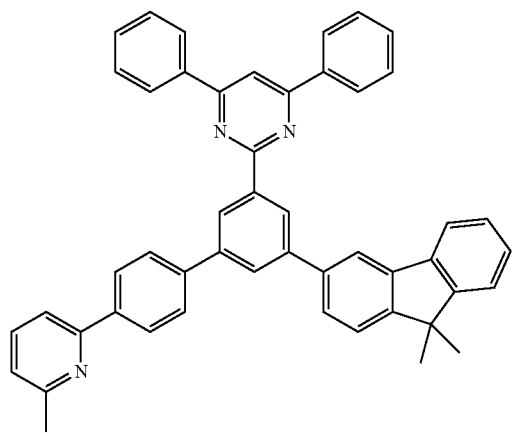
E-362
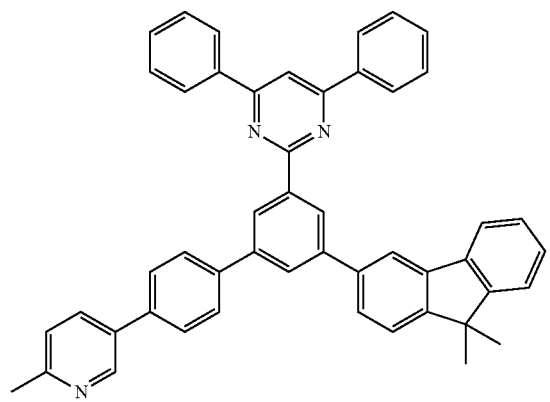

-continued
E-363
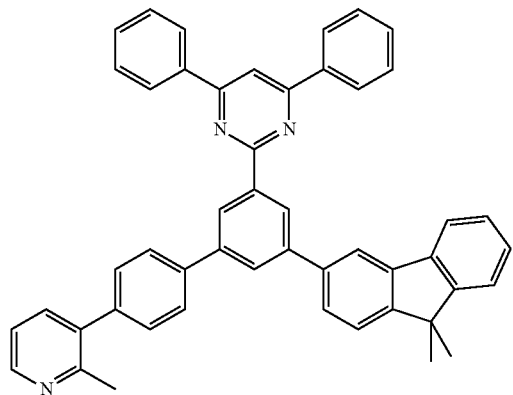
E-364
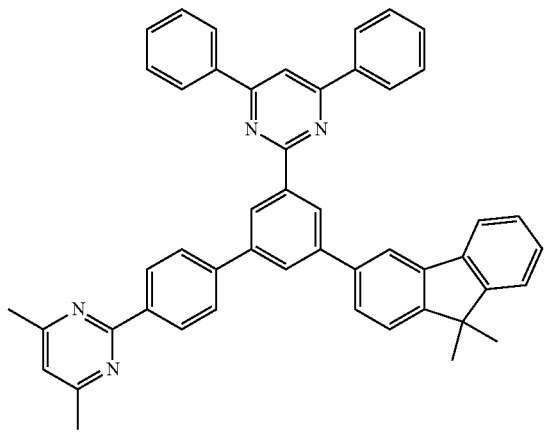
E-365
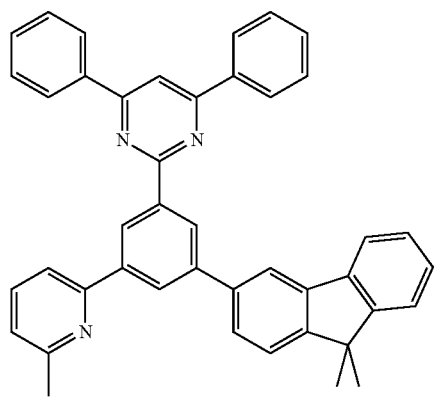
E-366
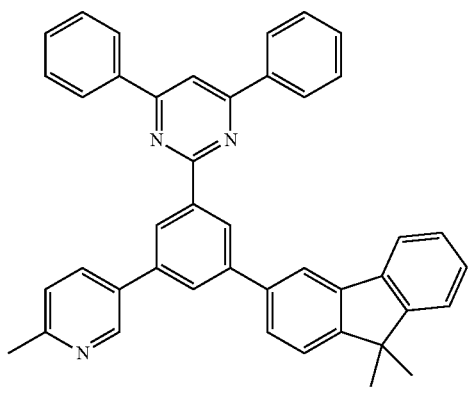
E-367
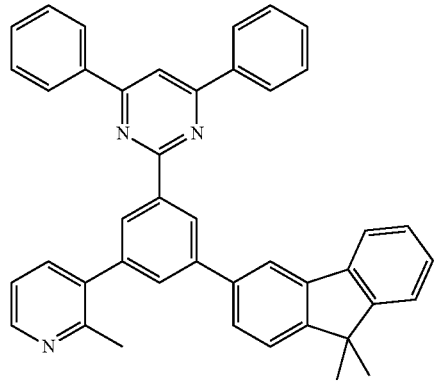
E-368
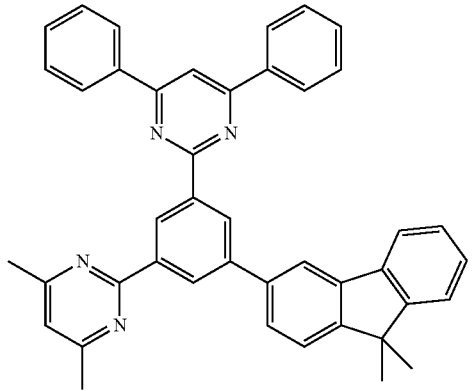
E-369
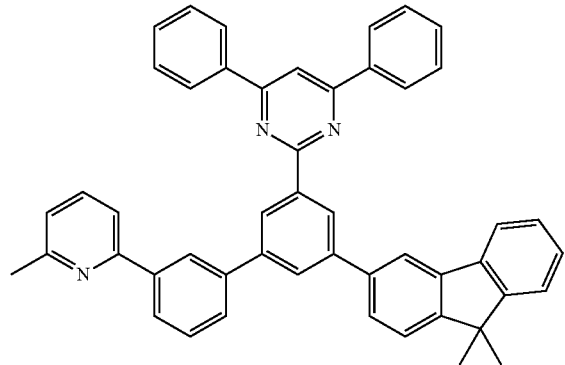
E-370
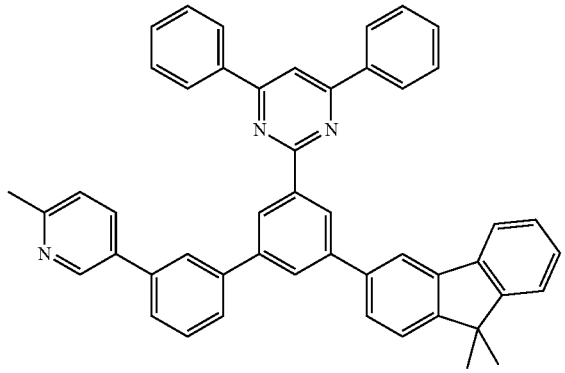

-continued
E-371
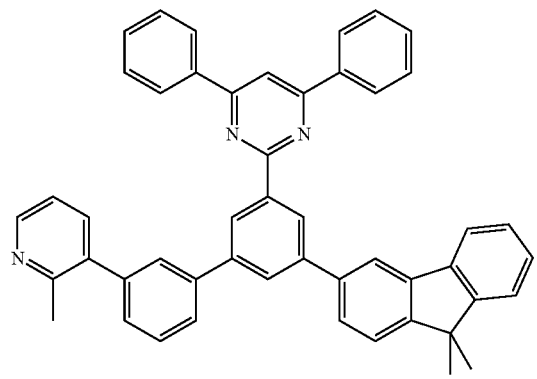
E-372
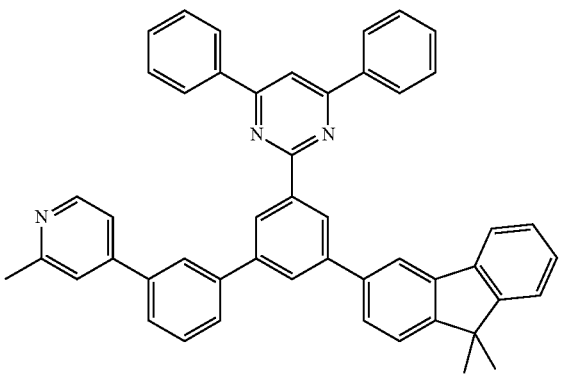
E-373
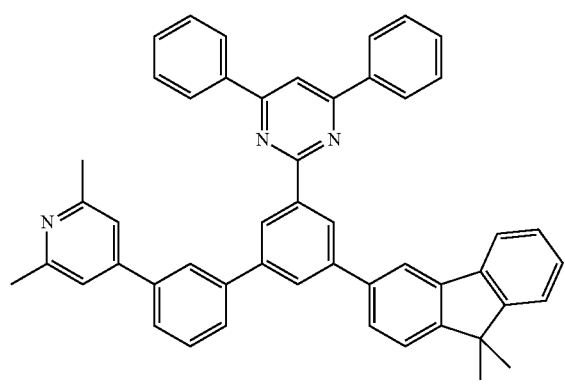
E-374
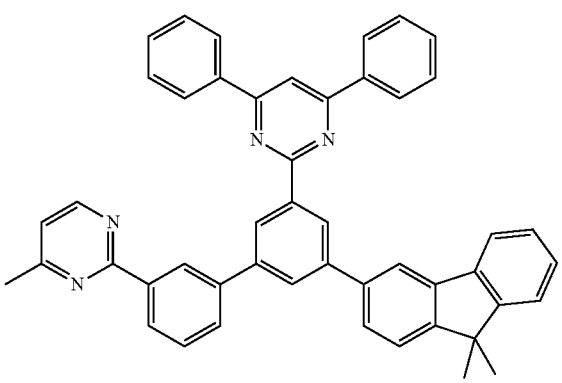
E-375
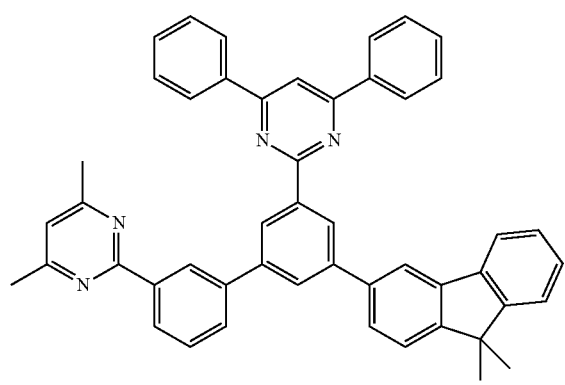
E-376
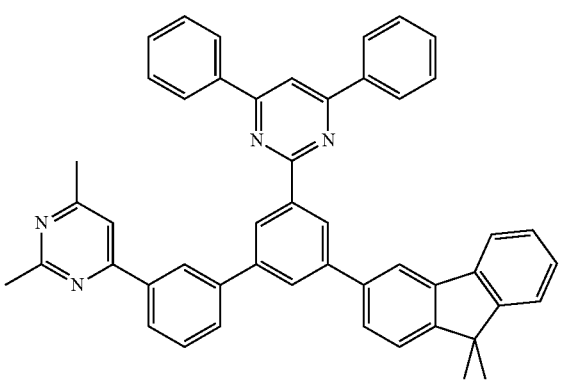
E-377
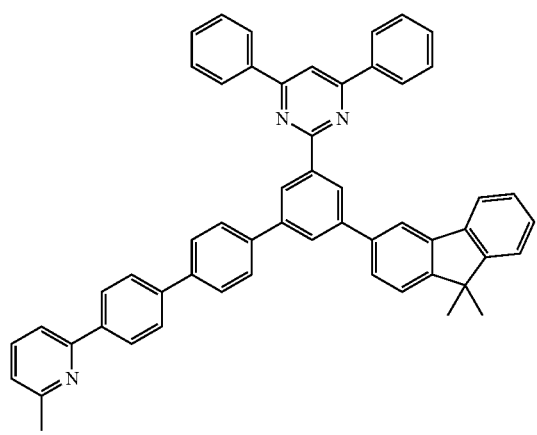
E-378
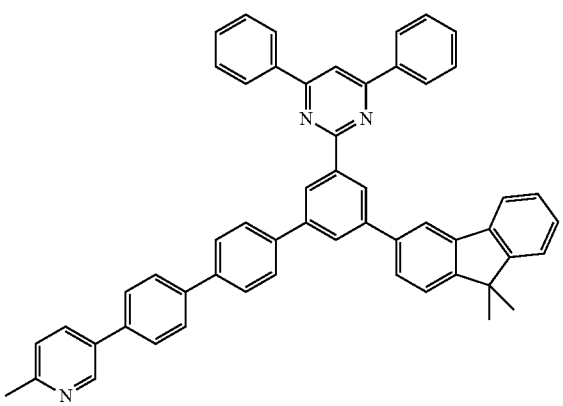

-continued
E-379
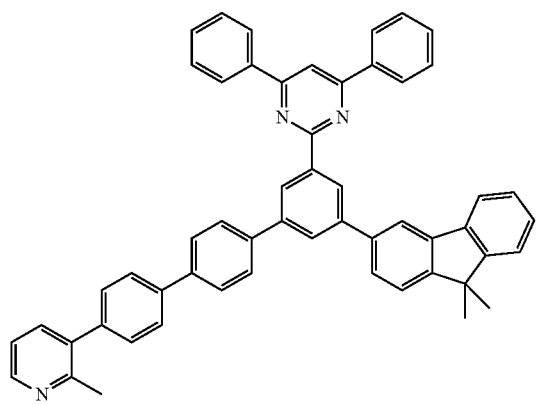
E-380
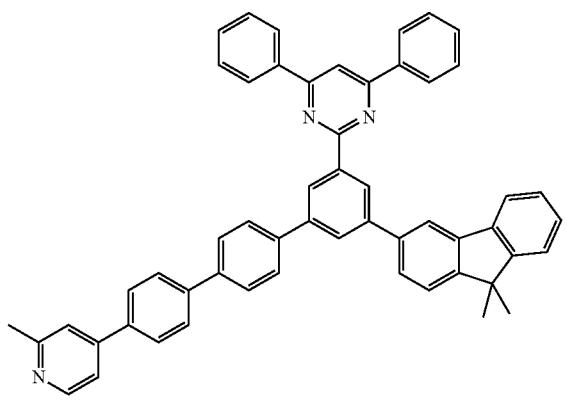
E-381
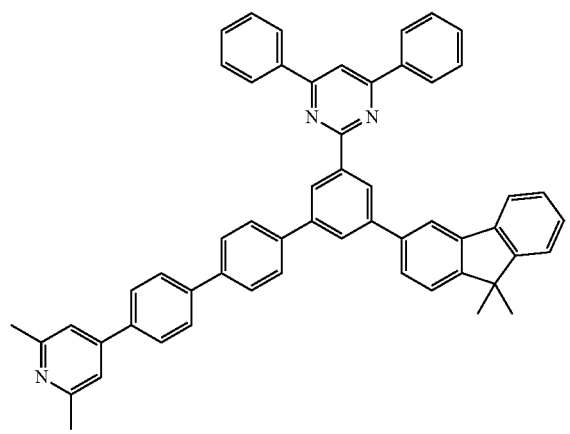
E-382
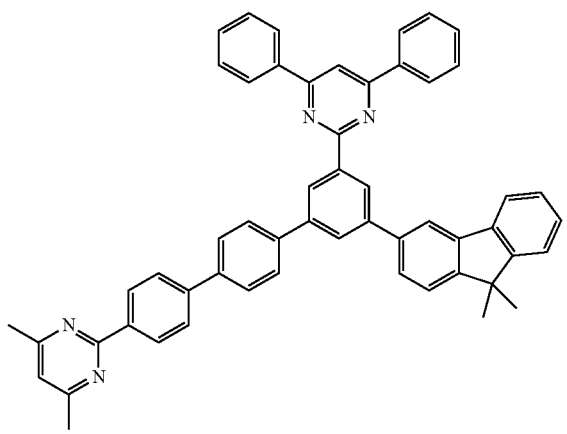
E-383
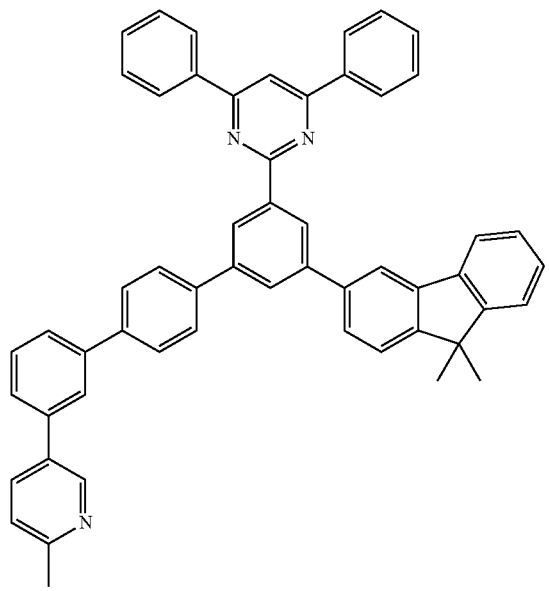
E-384
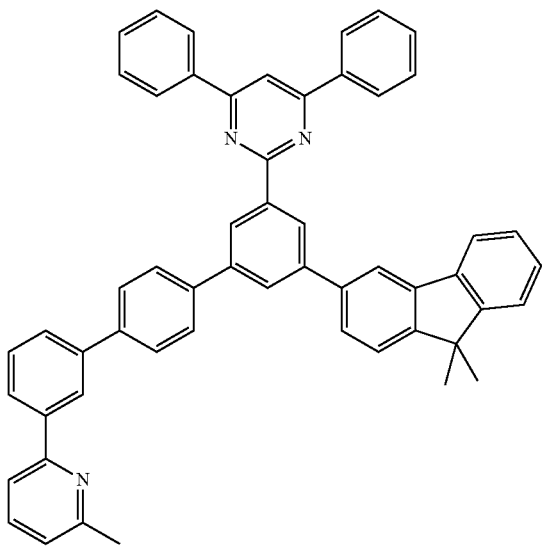

-continued
E-385
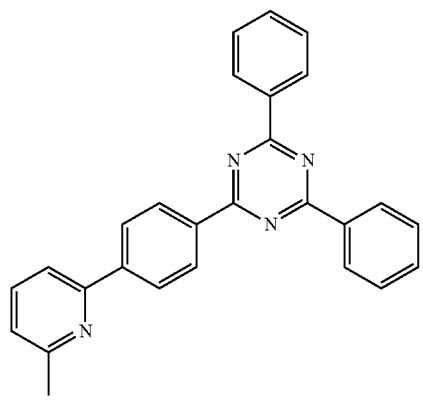
E-386
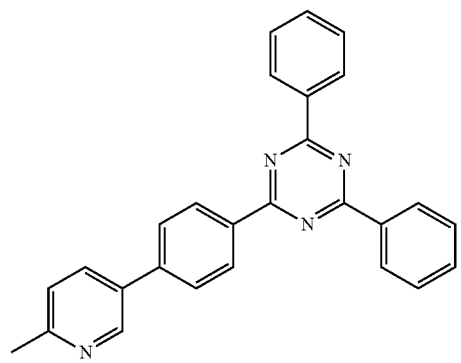
E-387
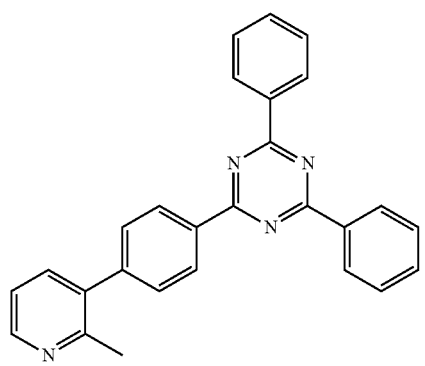
E-388
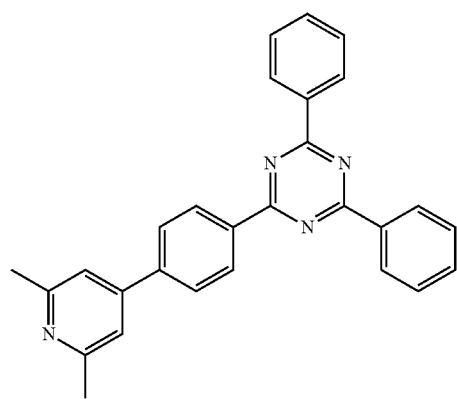
E-389
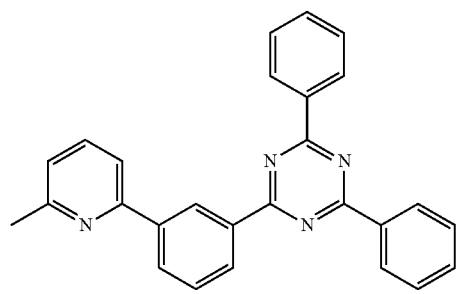
E-390
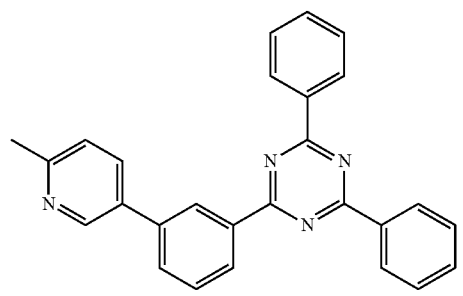
E-391
E-392
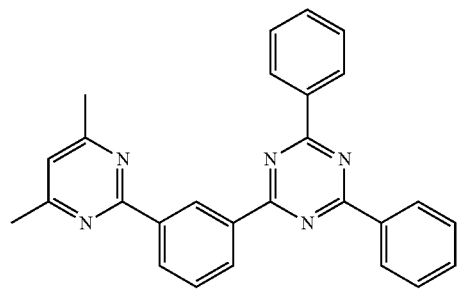

-continued
E-393
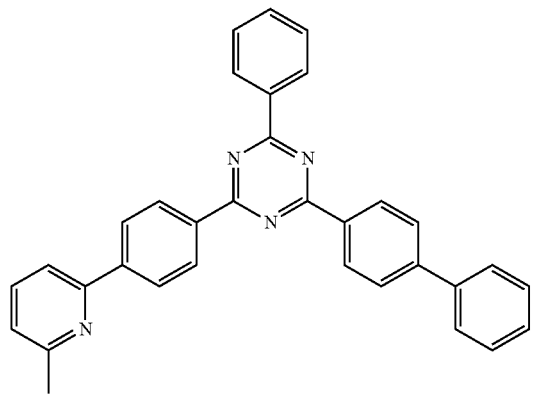
E-394
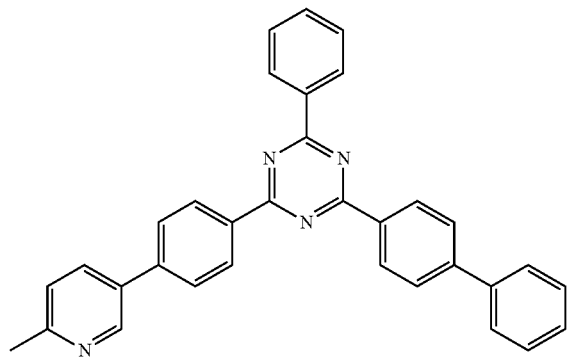
E-395
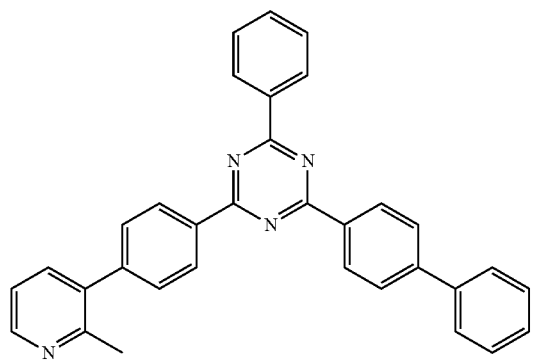
E-396
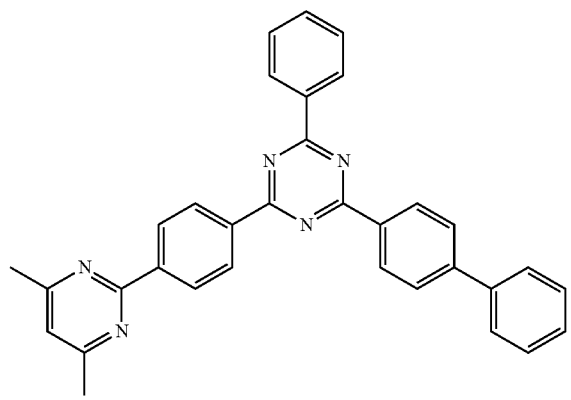
E-397
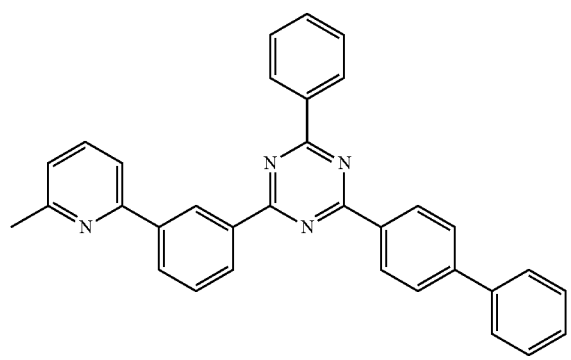
E-398
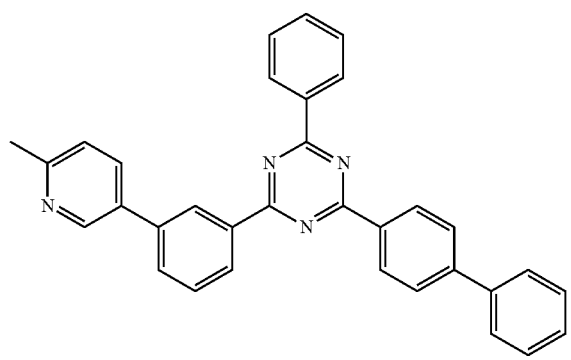
E-399
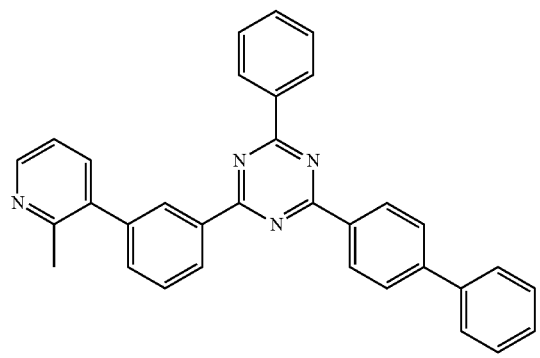
E-400
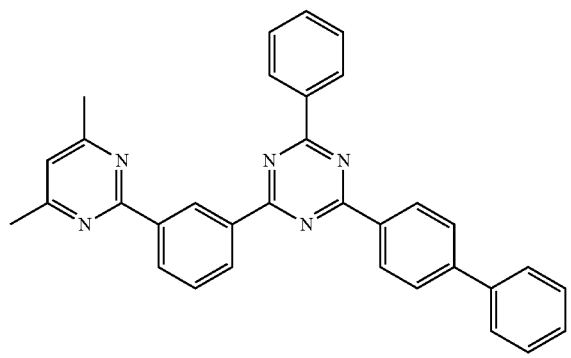

-continued
E-401
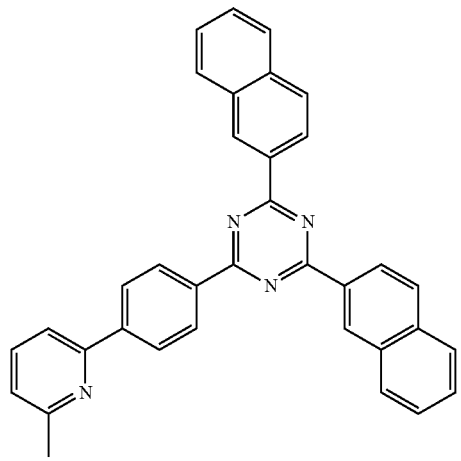
E-402
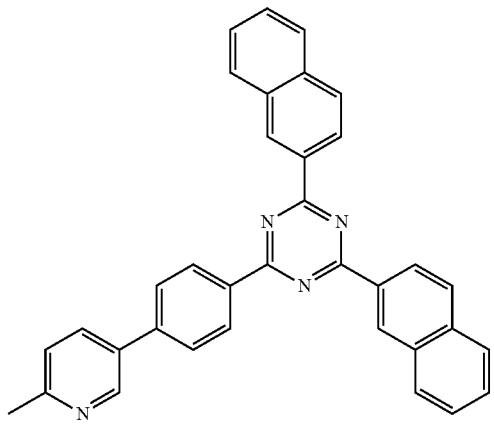
E-403
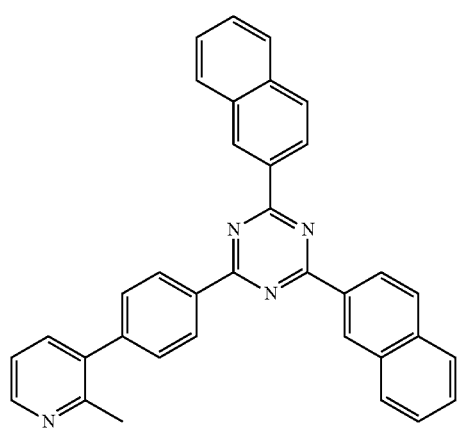
E-404
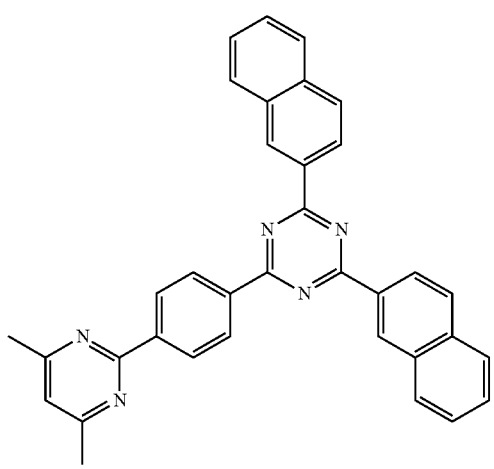
E-405
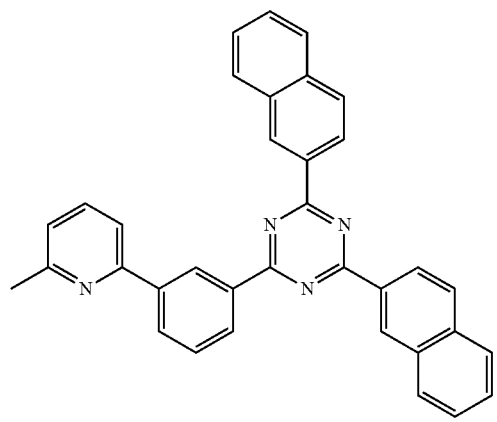
E-406
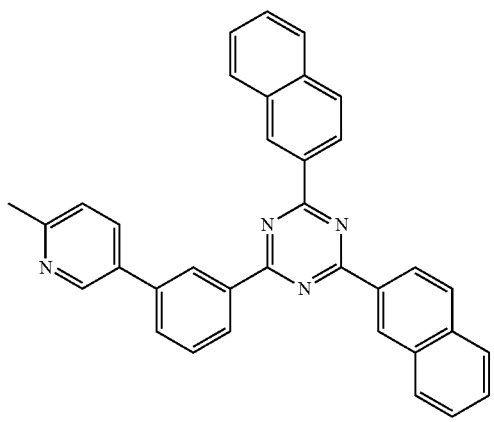

-continued
E-407
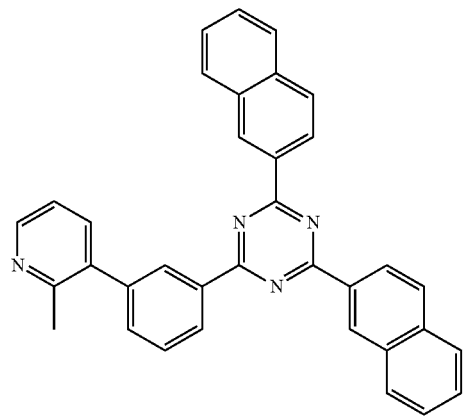
E-408
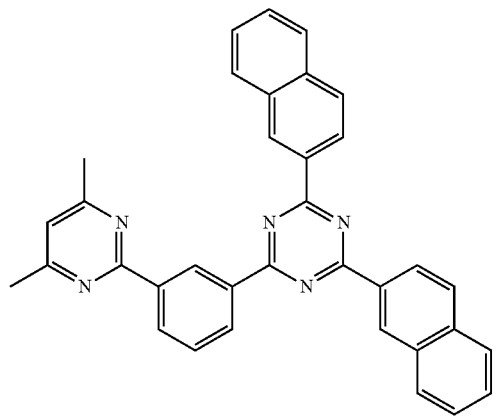
E-409
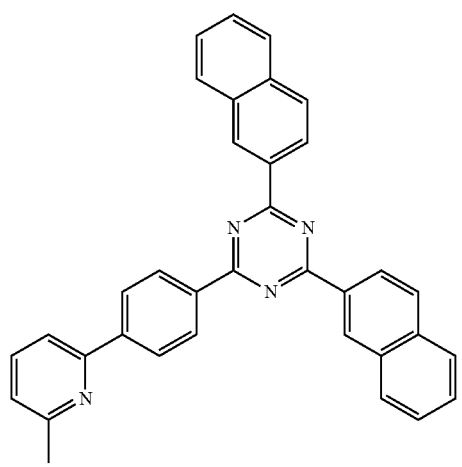
E-410
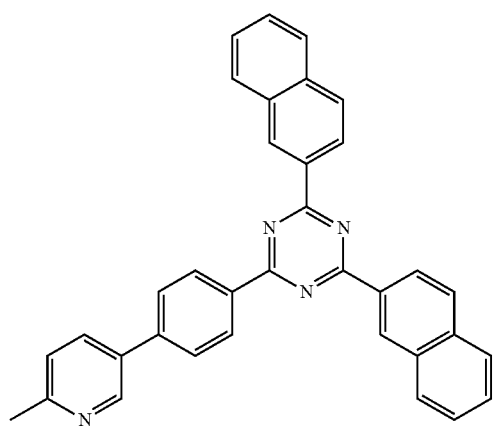
E-411
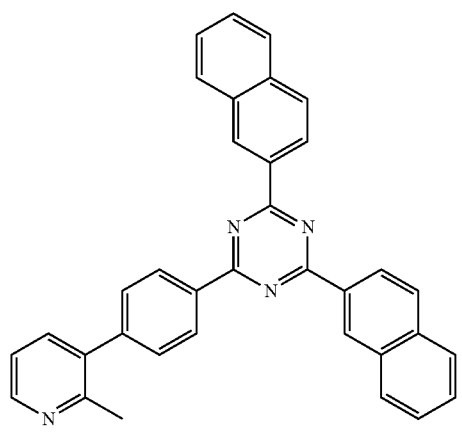
E-412
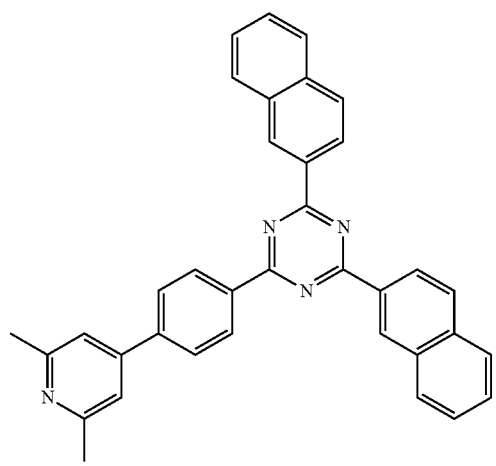

-continued
E-413
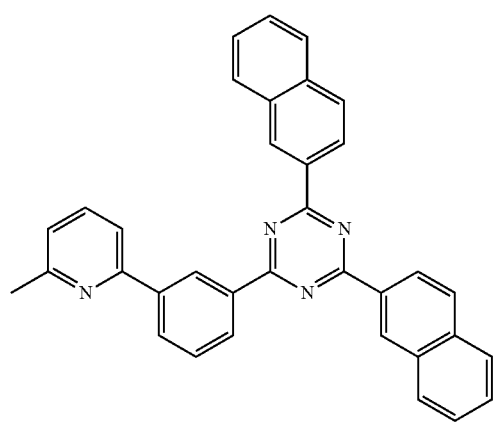
E-414
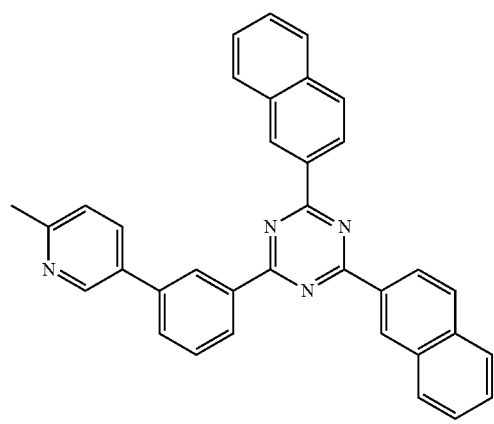
E-415
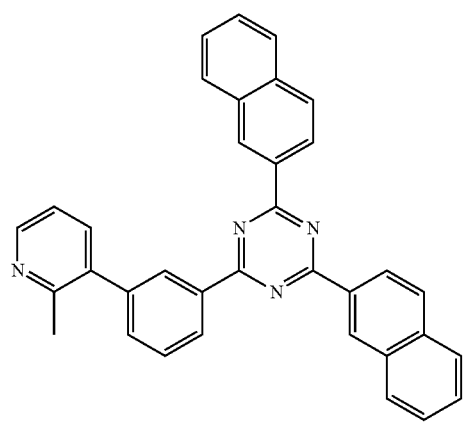
E-416
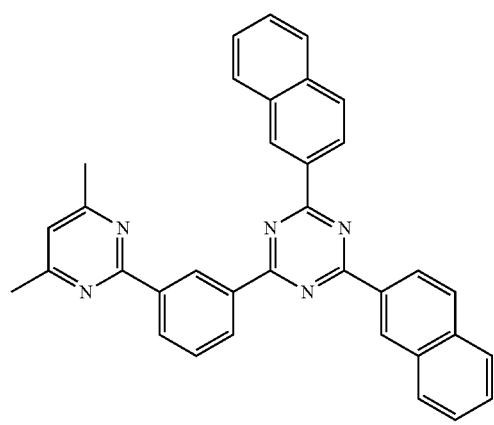
E-417
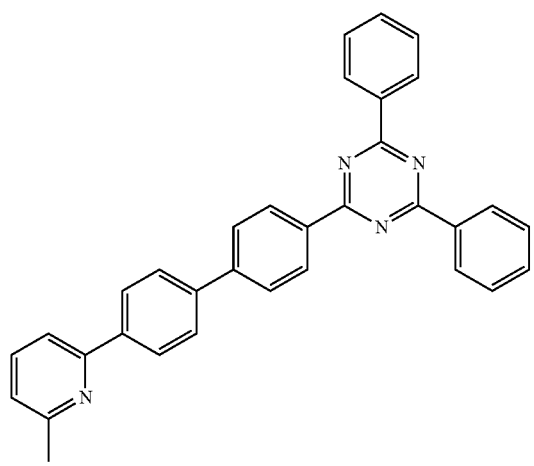
E-418
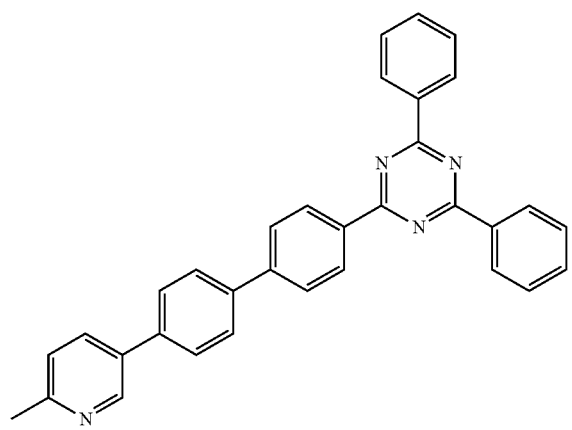

-continued
E-419
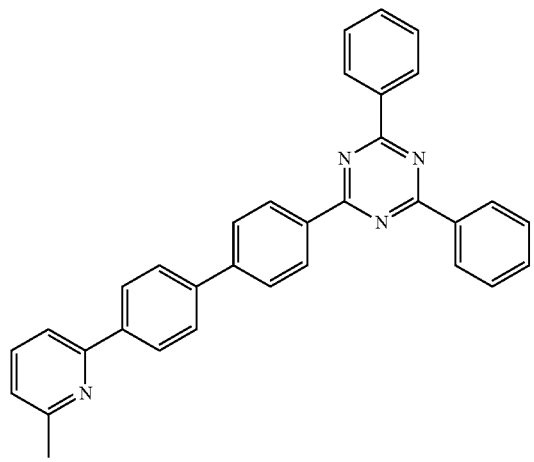
E-420
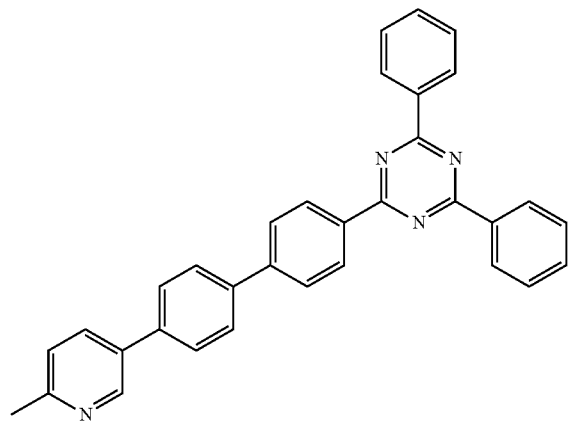
E-421
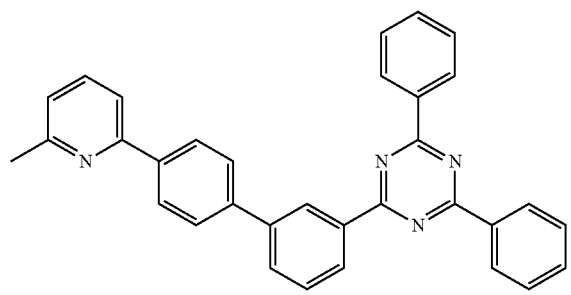
E-422
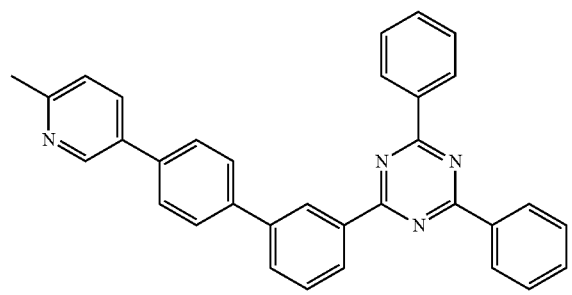
E-423
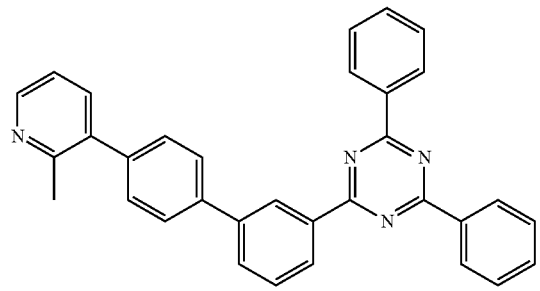
E-424
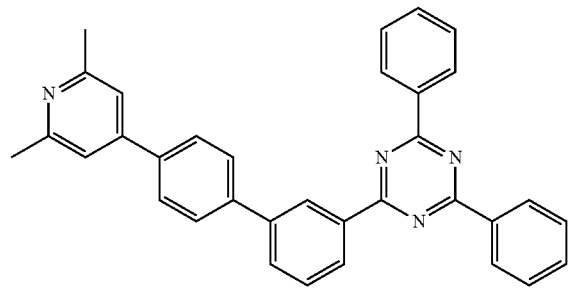
E-425
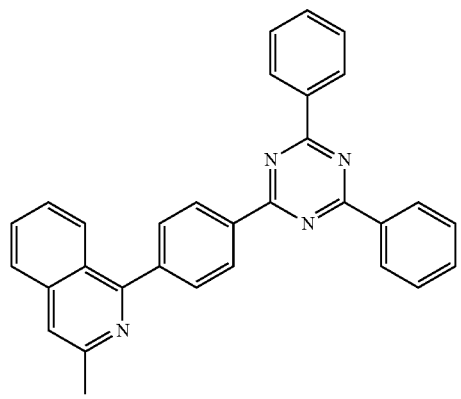
E-426
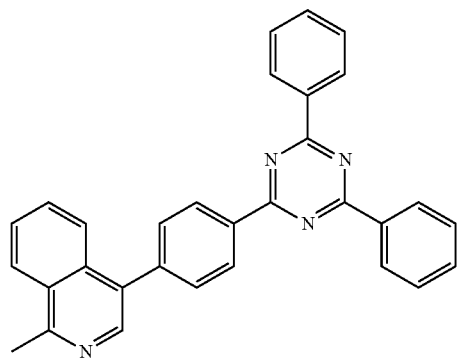

-continued
E-427
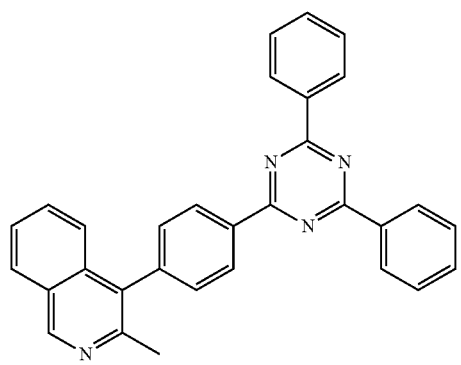
E-428
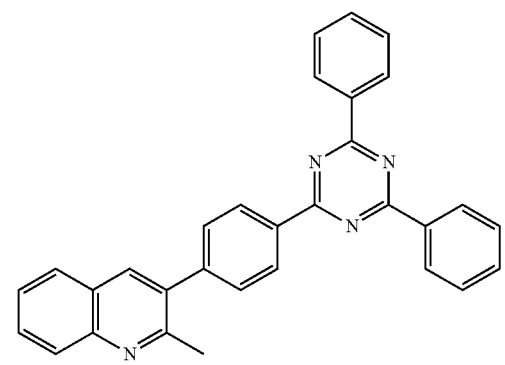
E-429
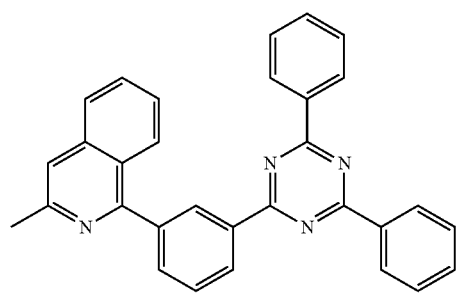
E-430
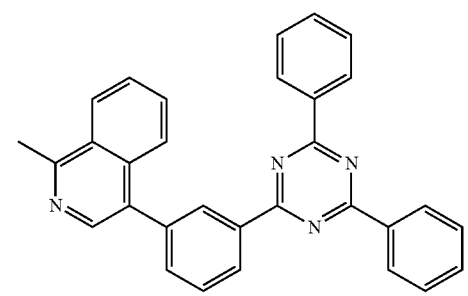
E-431
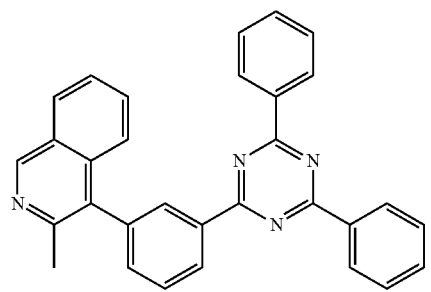
E-432
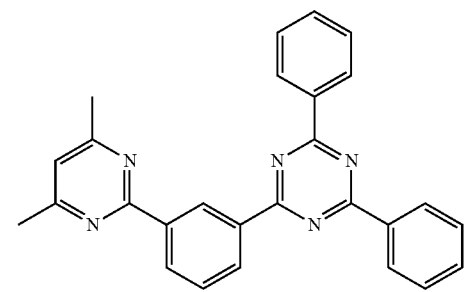
E-433
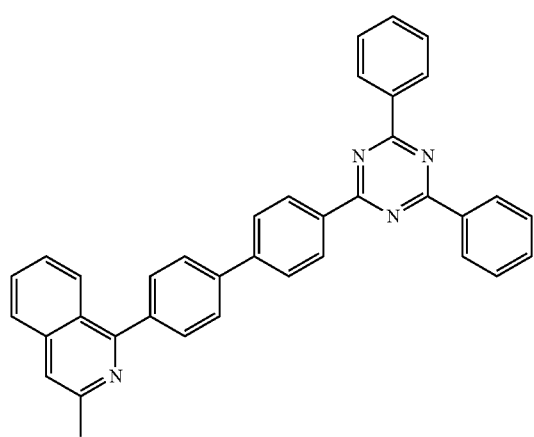
E-434
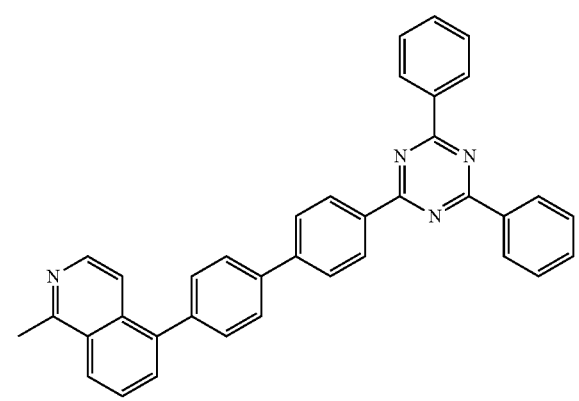

-continued
E-435
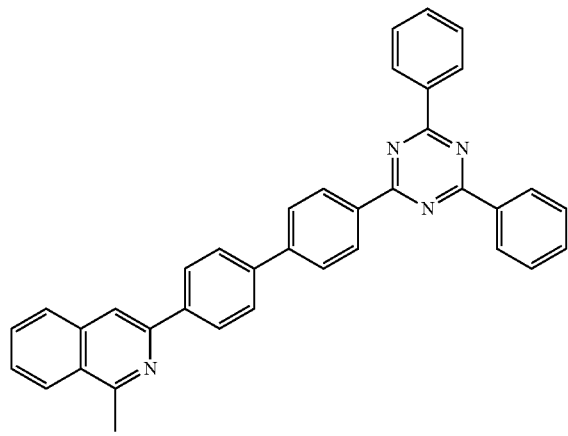
E-436
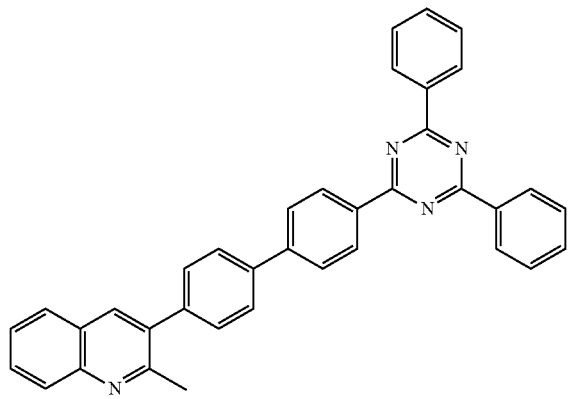
E-437
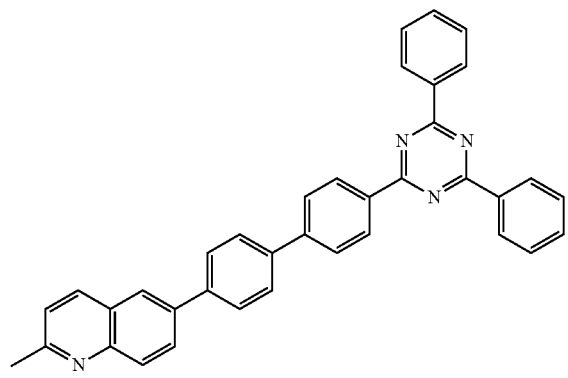
E-438
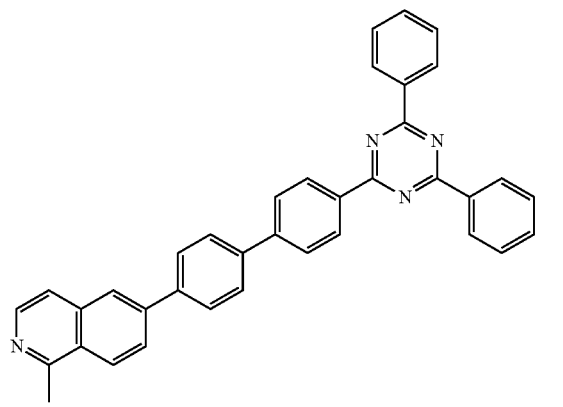
E-439
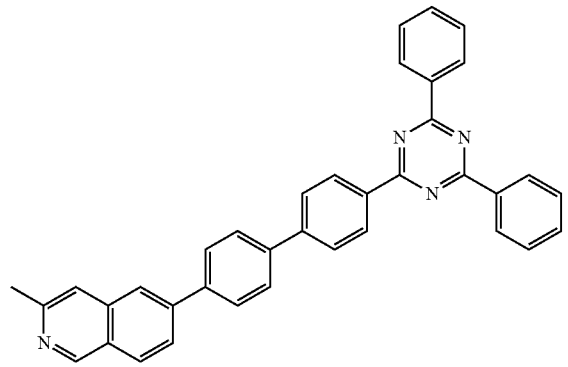
E-440
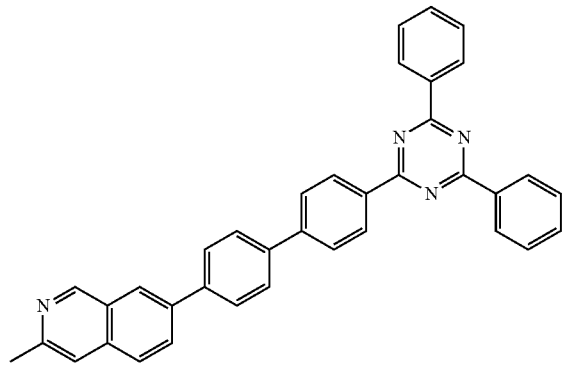
E-441
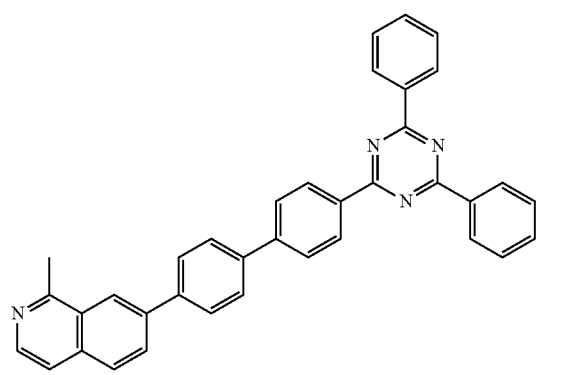
E-442
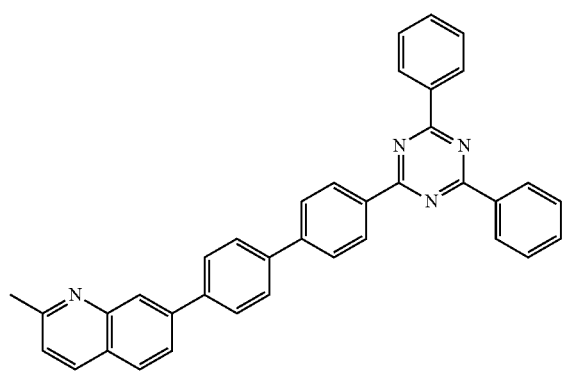

-continued
E-443
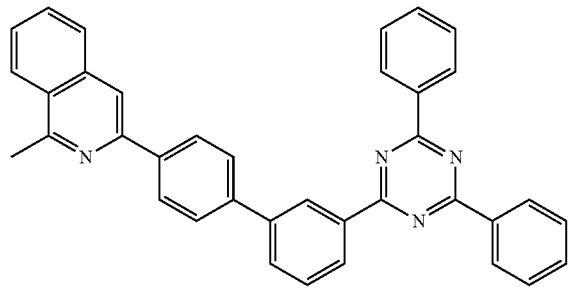
E-444
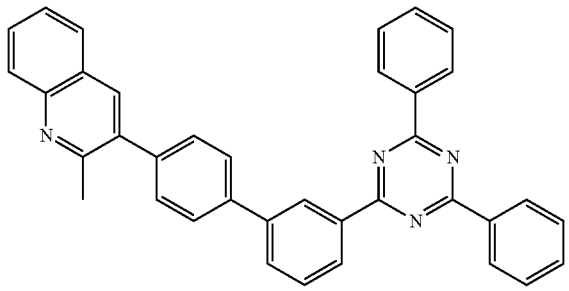
E-445
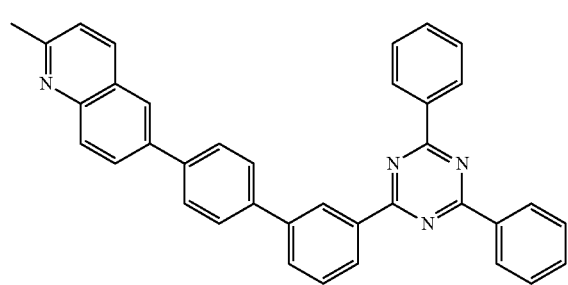
E-446
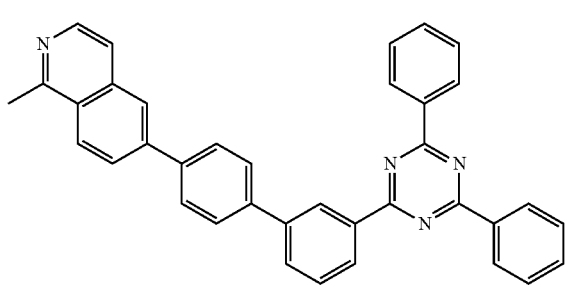
E-447
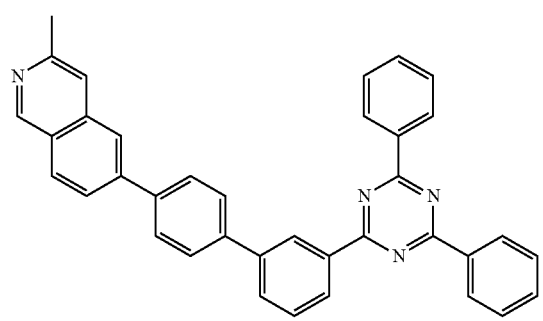
E-448
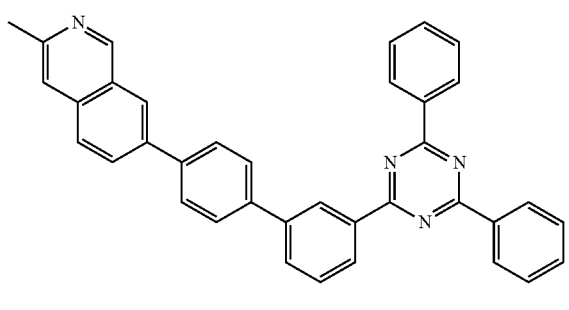
E-449
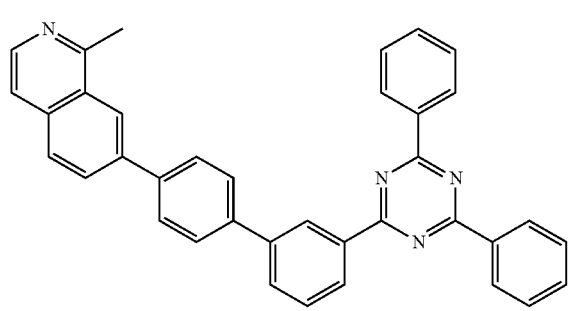
E-450
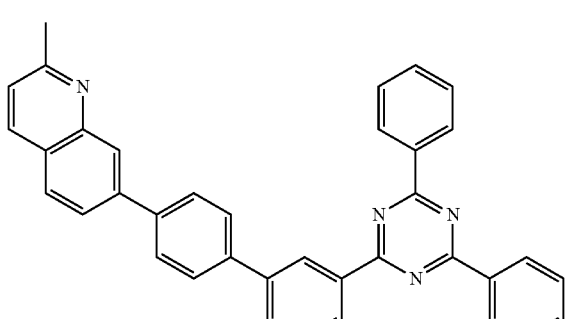
E-451
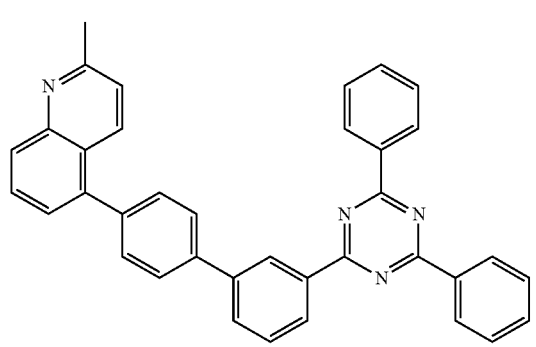
E-452
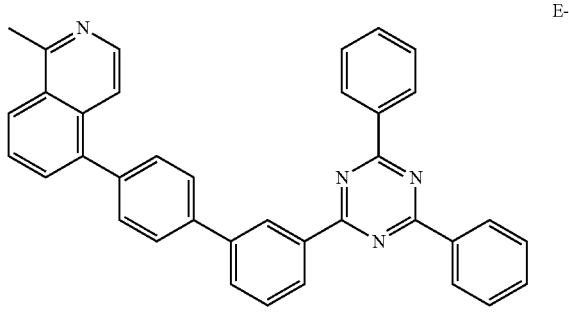

-continued
E-453
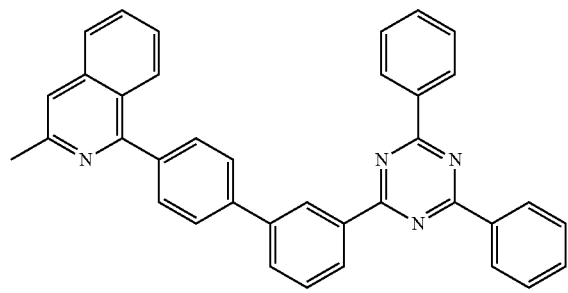
E-454
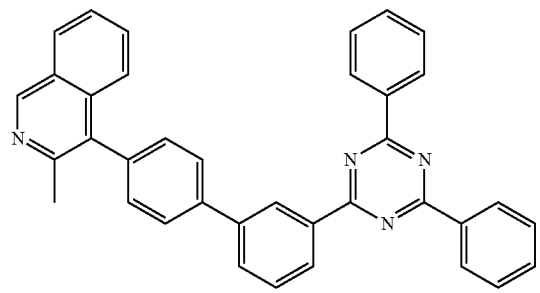
E-455
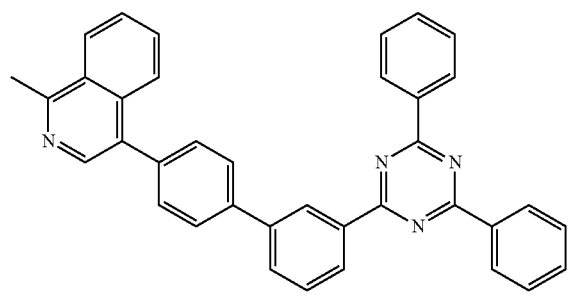
E-456
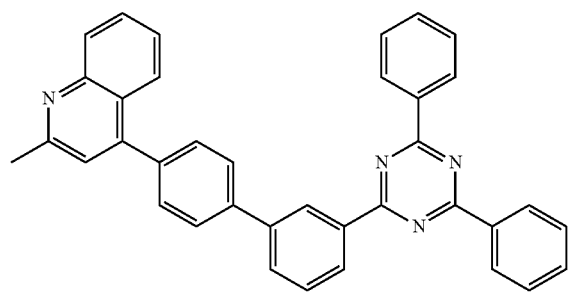
E-457
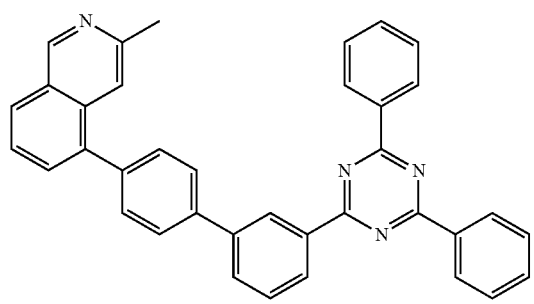
E-458
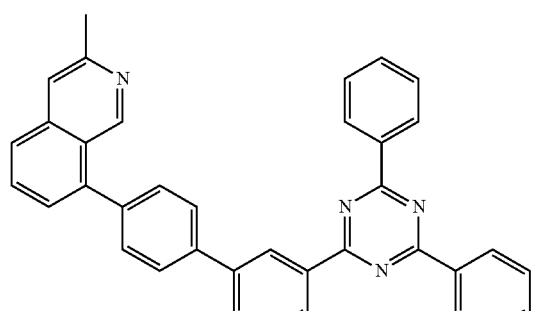
E-459
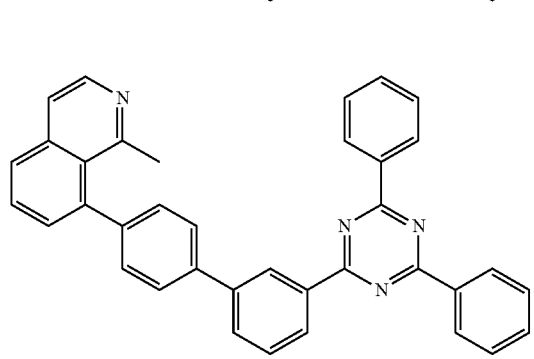
E-460
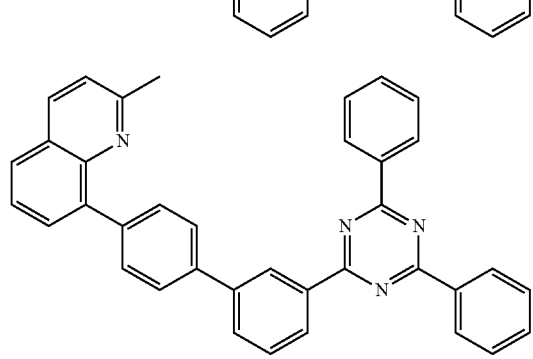
E-461
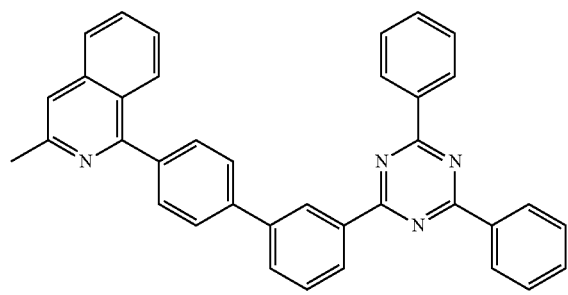
E-462
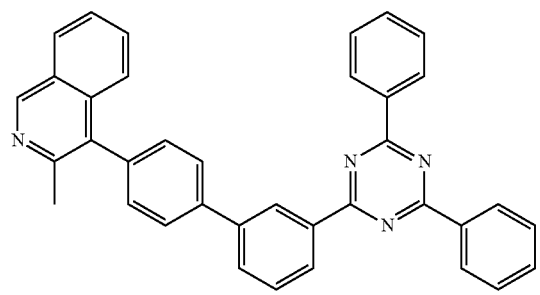

-continued
E-463
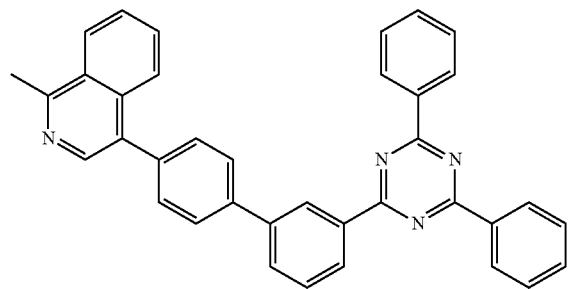
E-464
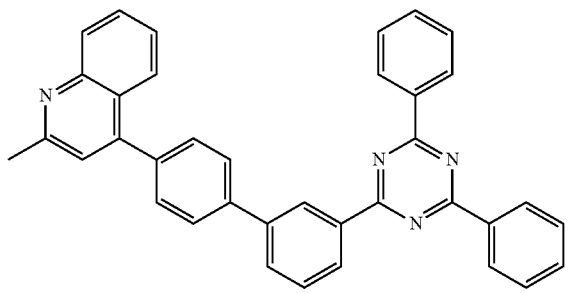
E-465
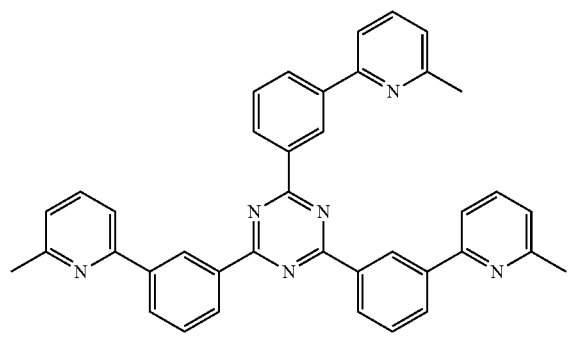
E-466
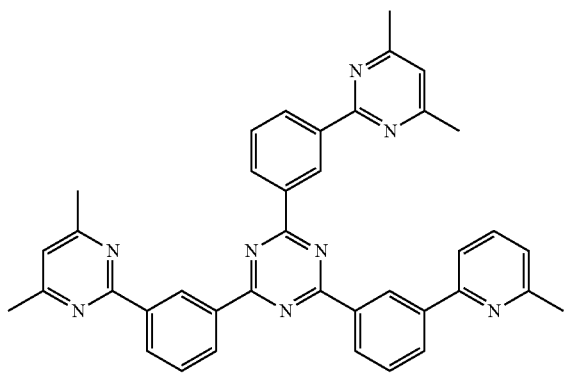
E-467
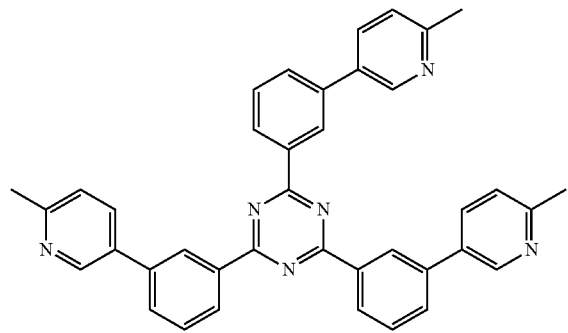
E-468
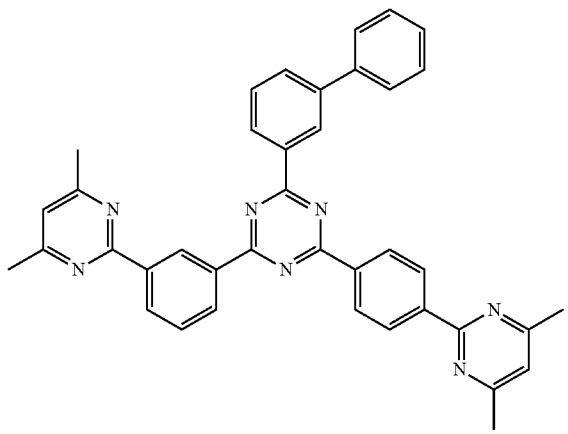
E-469
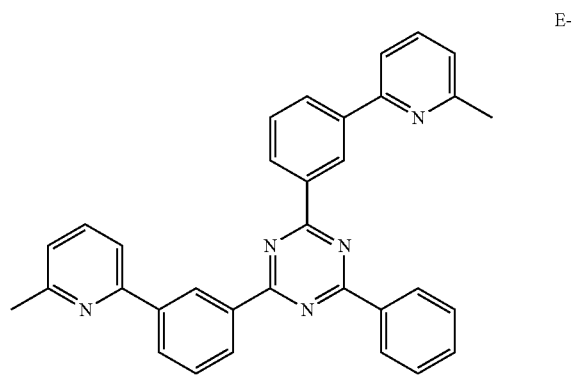
E-470
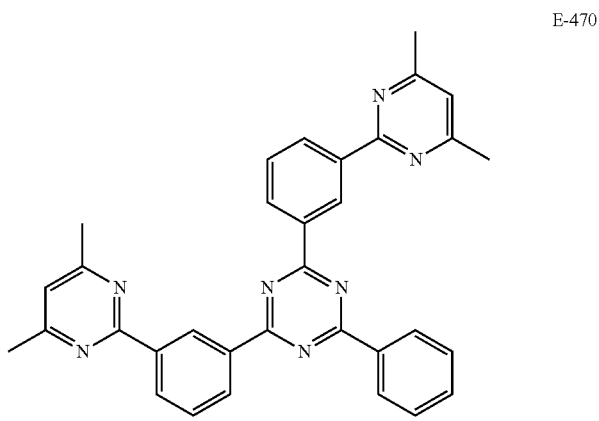

-continued
E-471
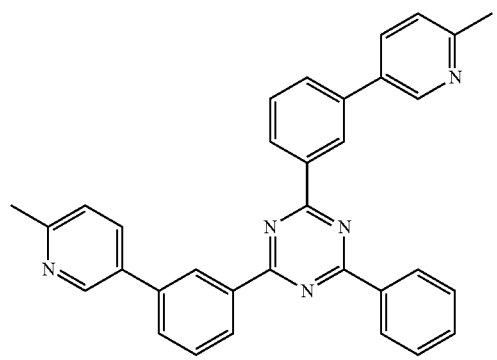
E-472
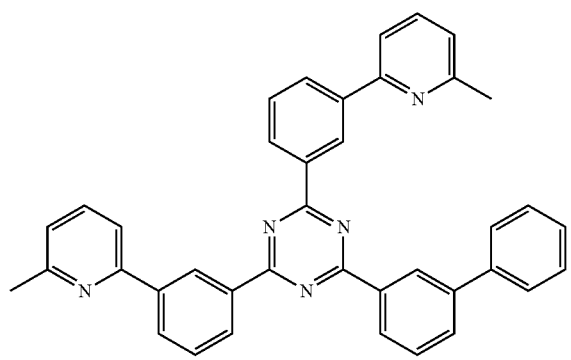
E-473
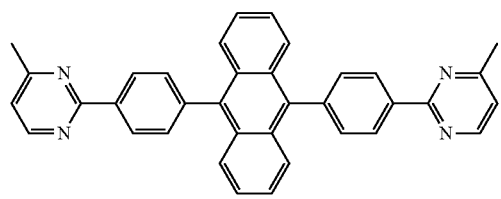
E-474
E-475
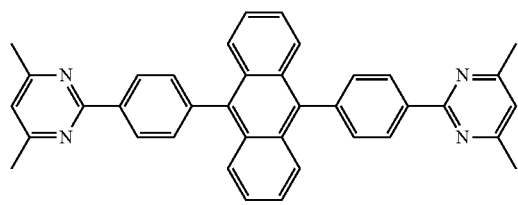
E-476
E-477
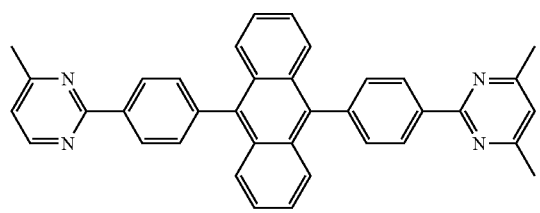
E-478
E-479
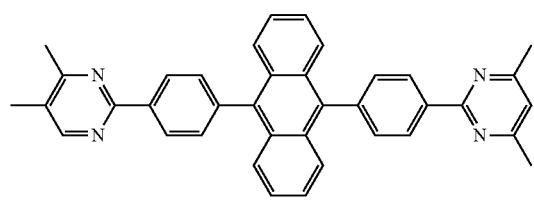
E-480
E-481
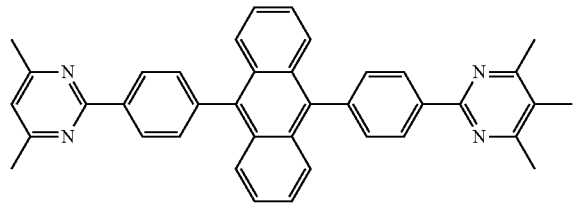
E-482
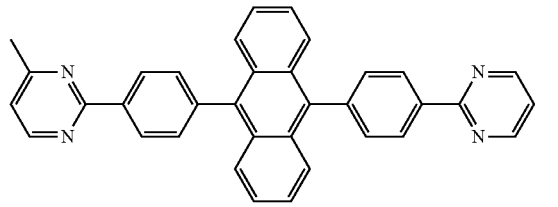

-continued
E-483
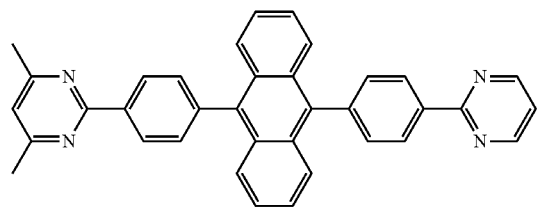
E-484
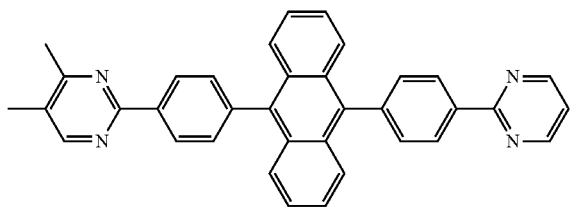
E-485
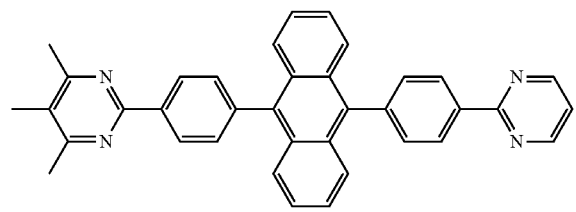
E-486
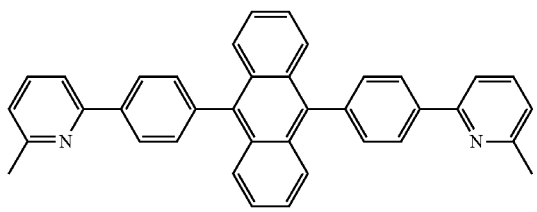
E-487
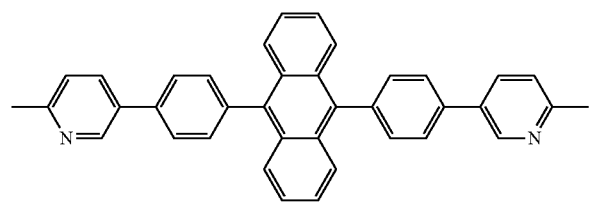
E-488
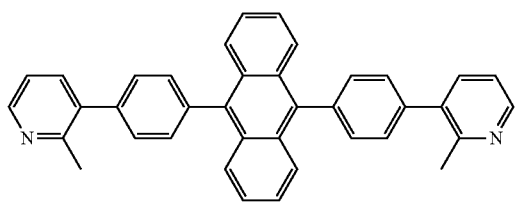
E-489
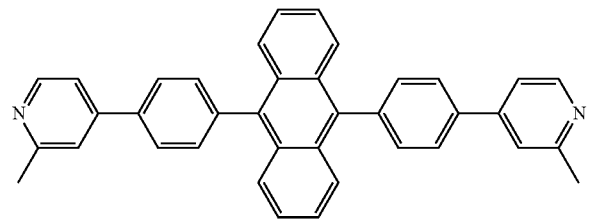
E-490
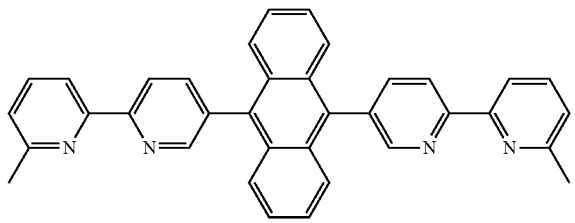
E-491
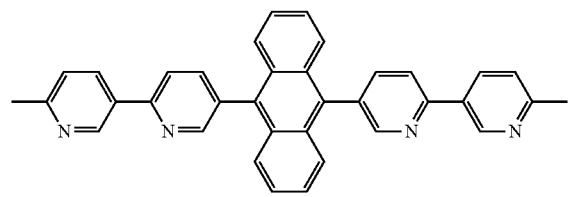
E-492
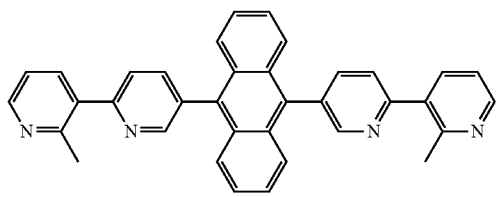
E-493
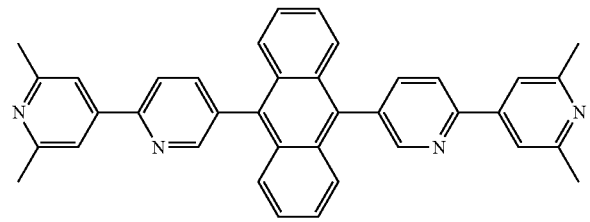
E-494
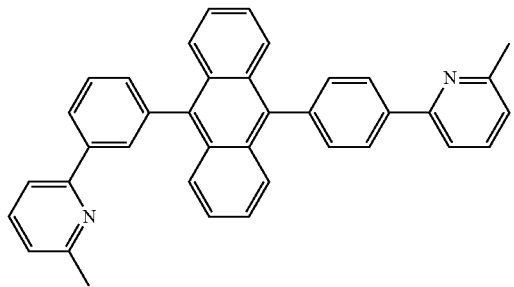

-continued
E-495
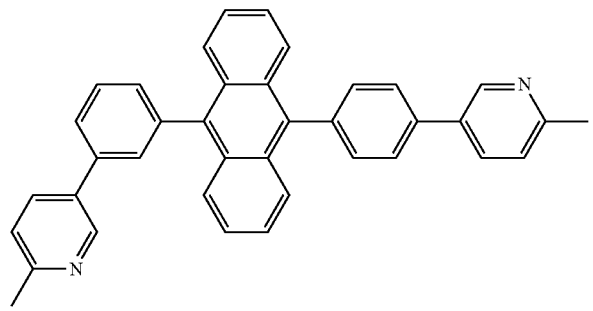
E-495
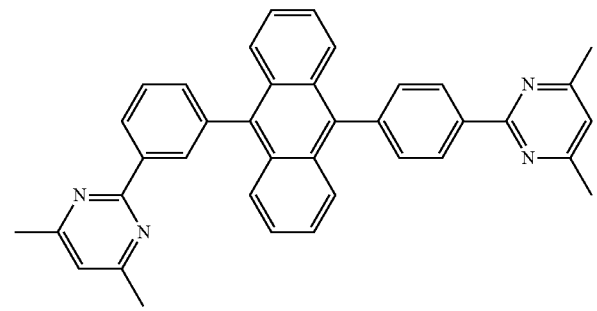
E-497
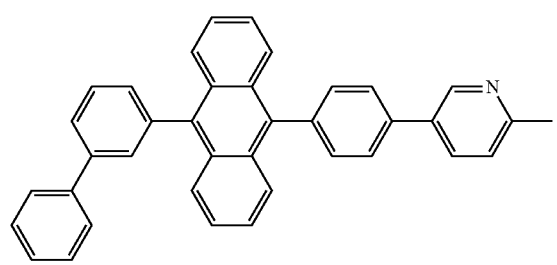
E-498
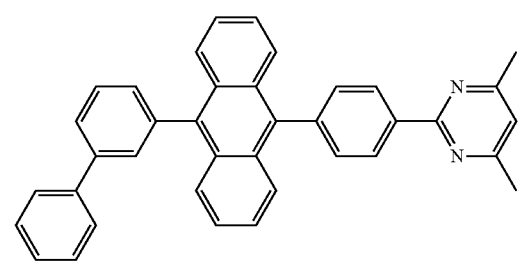
E-499
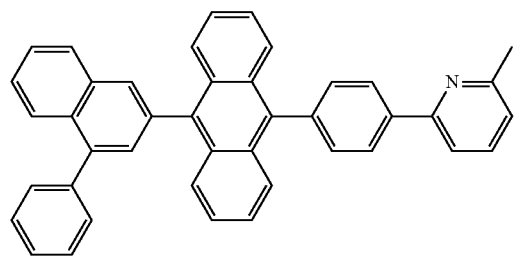
E-500
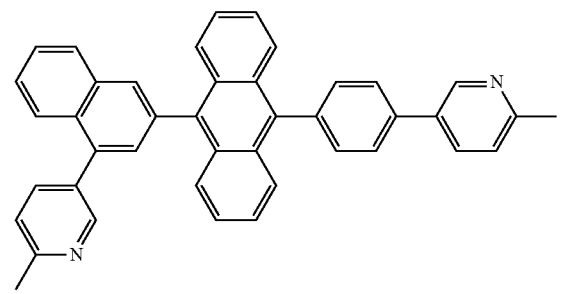
E-501
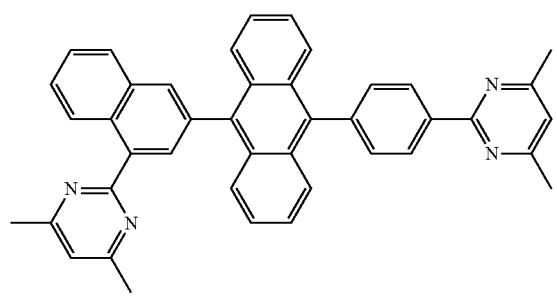
E-502
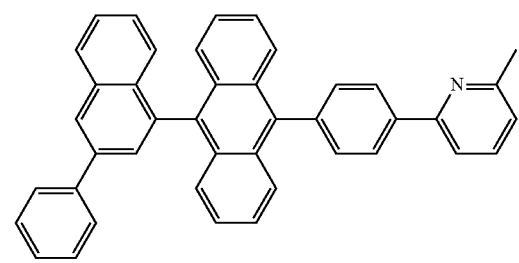
E-503
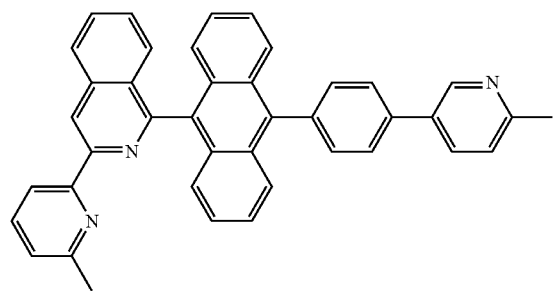
E-504
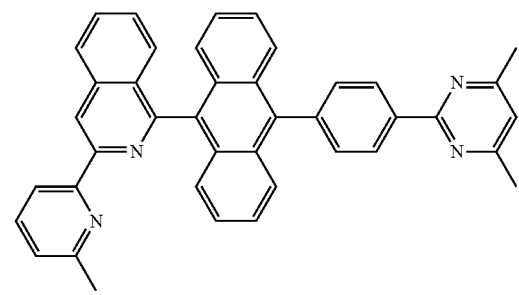

-continued
E-505
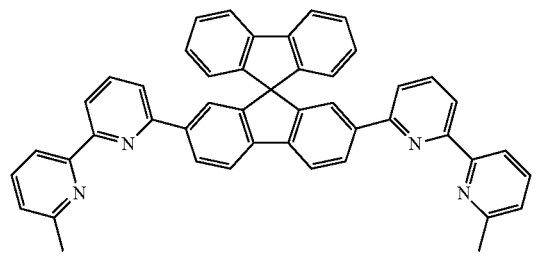
E-506
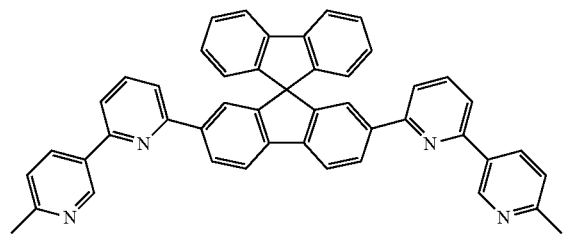
E-507
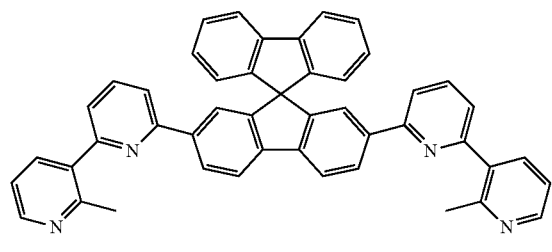
E-508
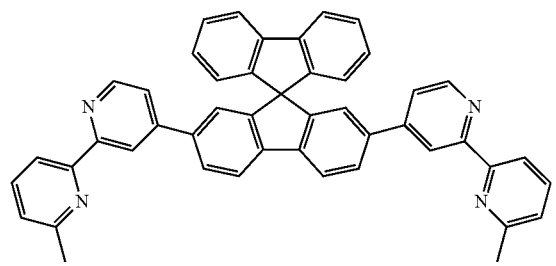
E-509
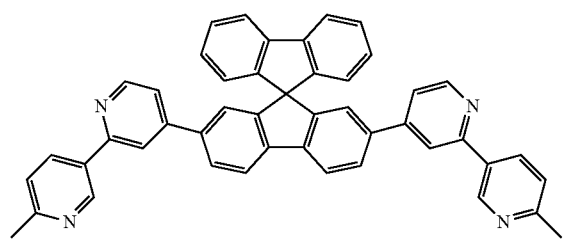
E-510
E-511
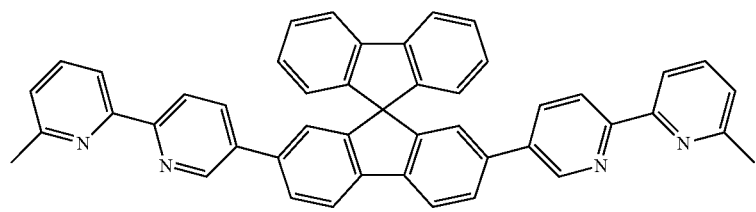
E-512
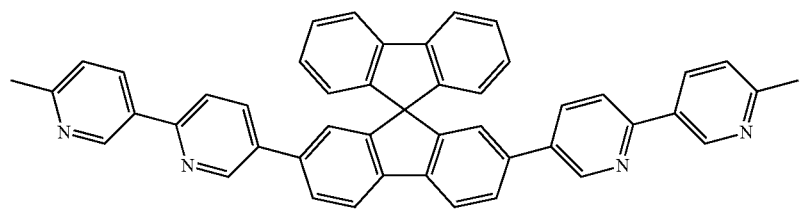
E-513
E-514
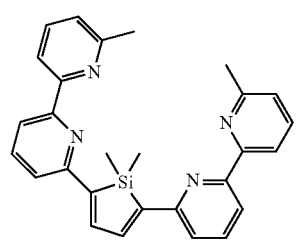

-continued
| E-515 | E-516 |
|---|---|
| 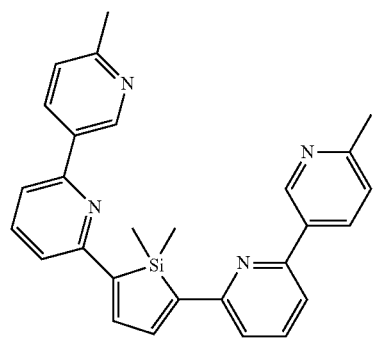 | 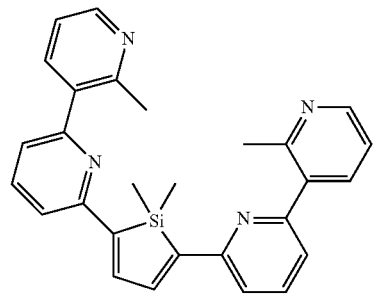 |
| E-517 | E-518 |
| 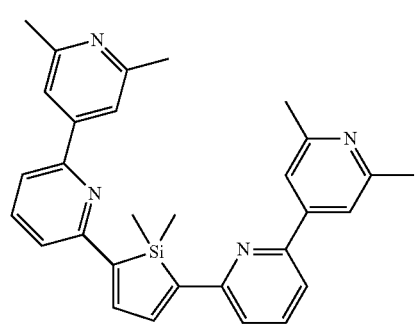 | 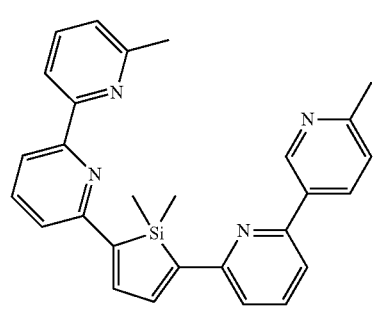 |
| E-519 | E-520 |
| 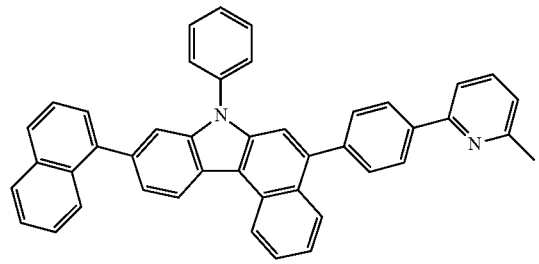 | 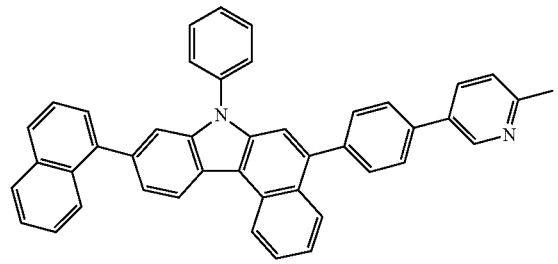 |
| E-521 | E-522 |
| 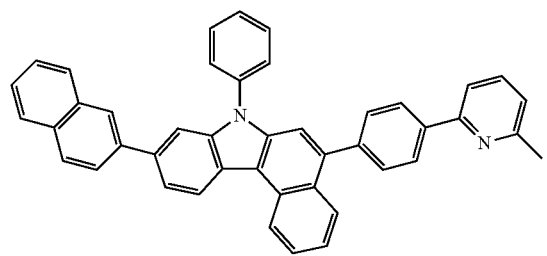 | 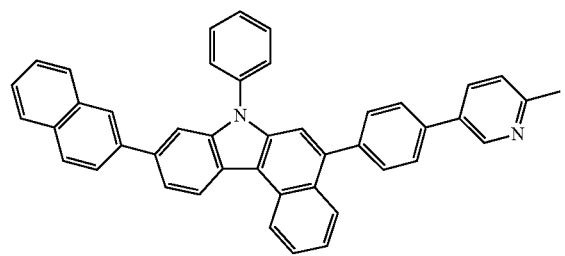 |
| E-523 | E-524 |
| 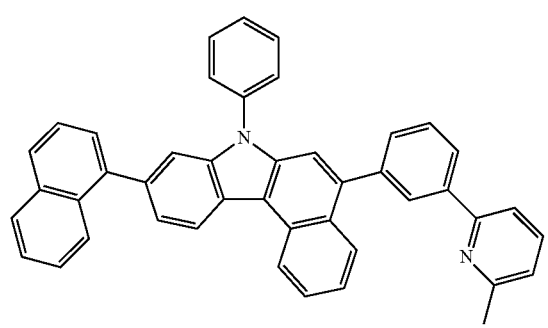 | 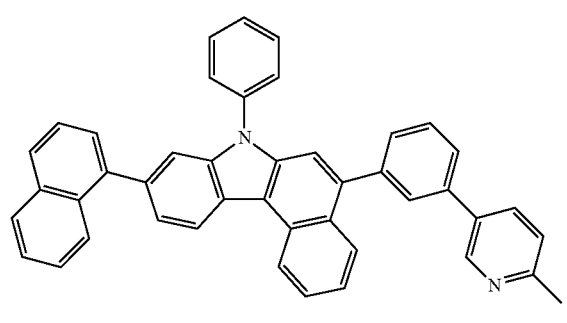 |

-continued
E-525
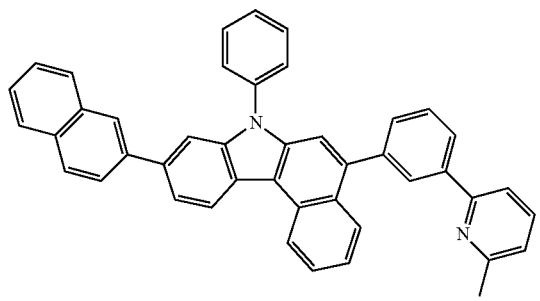
E-526
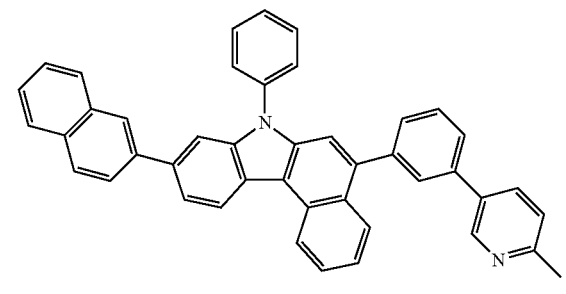
E-527
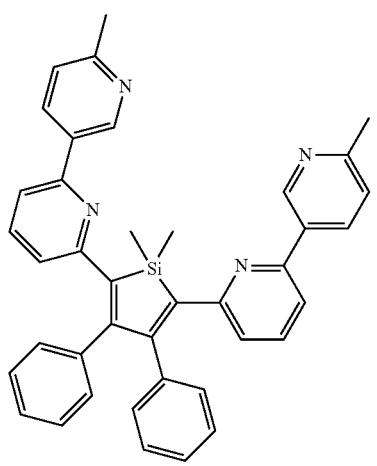
E-528
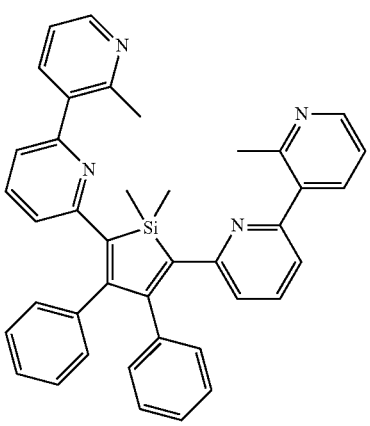
E-529
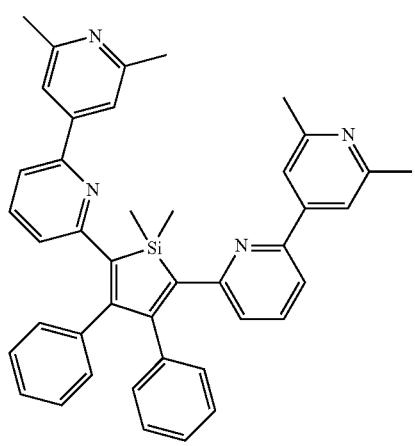
E-530
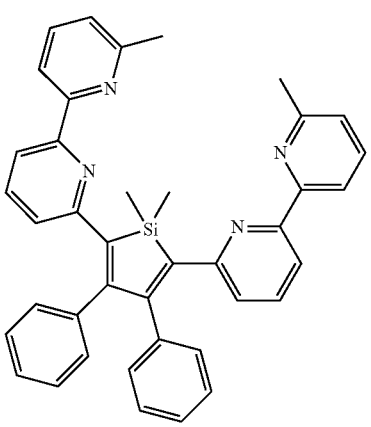
E-531
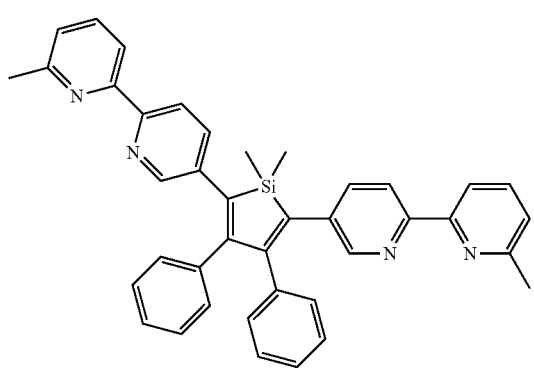
E-532
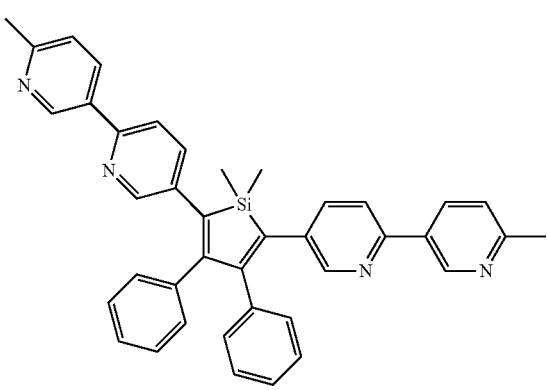

-continued
E-533
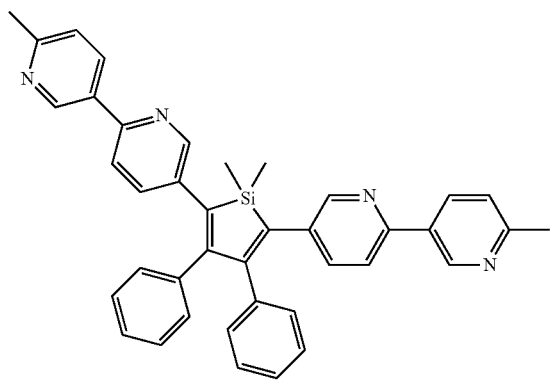
E-534
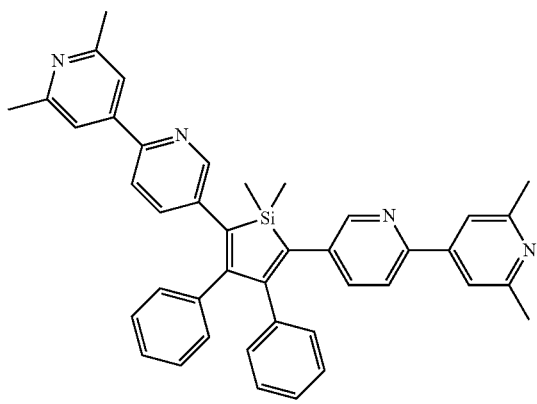
E-535
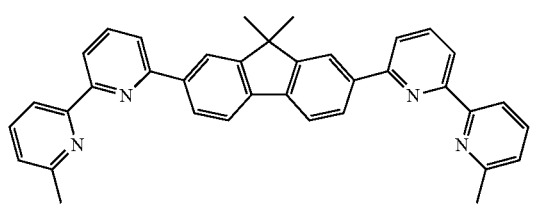
E-536
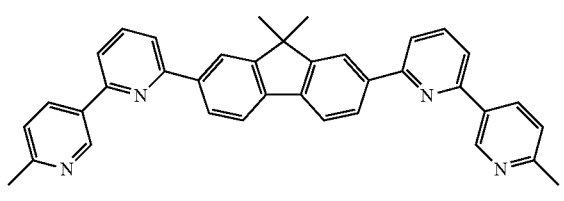
E-537
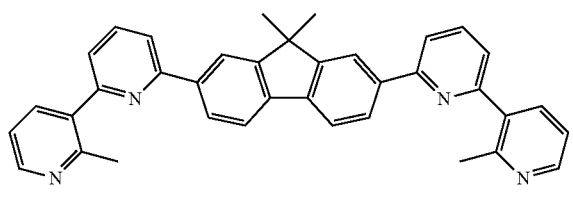
E-538
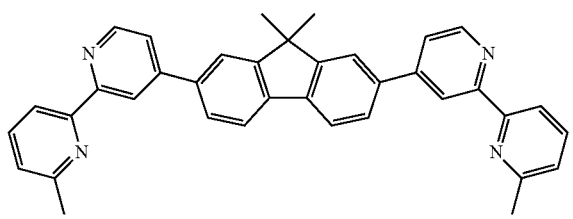
E-539
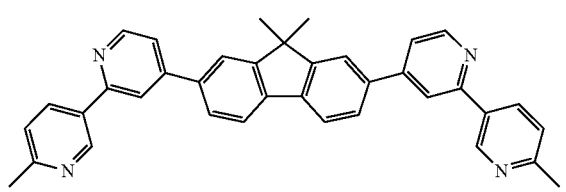
E-540
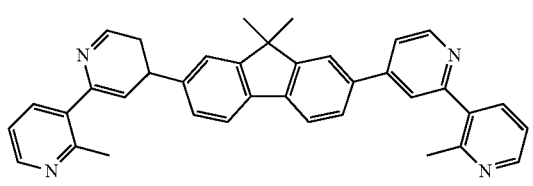
E-541
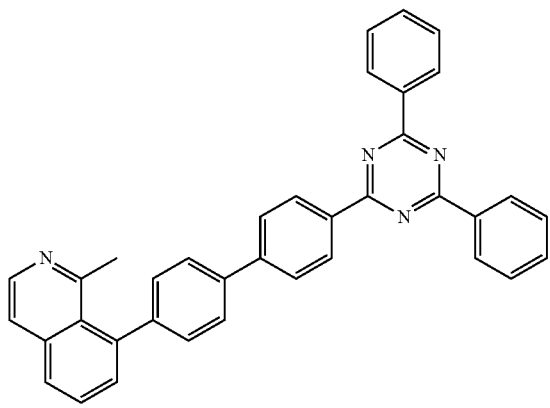
E-542
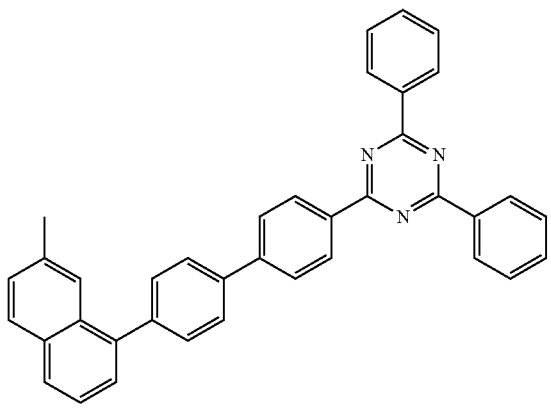

-continued
E-543
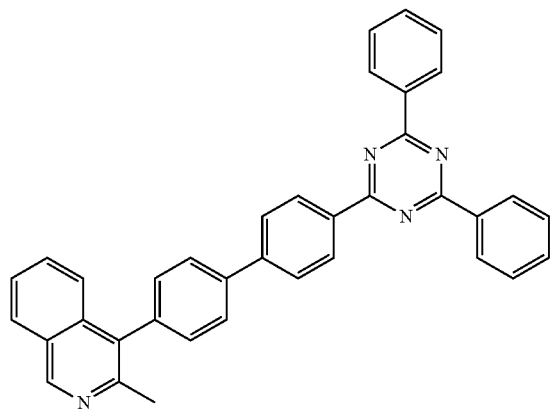
E-544
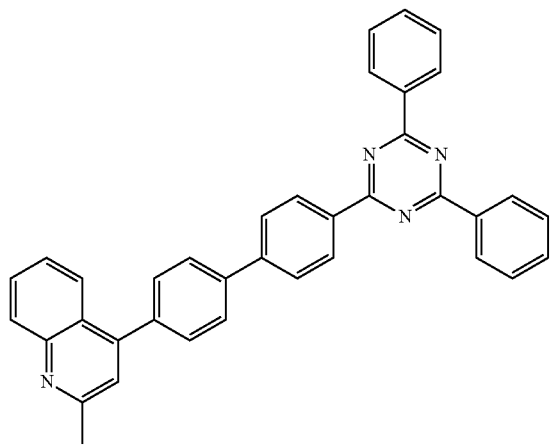
E-545
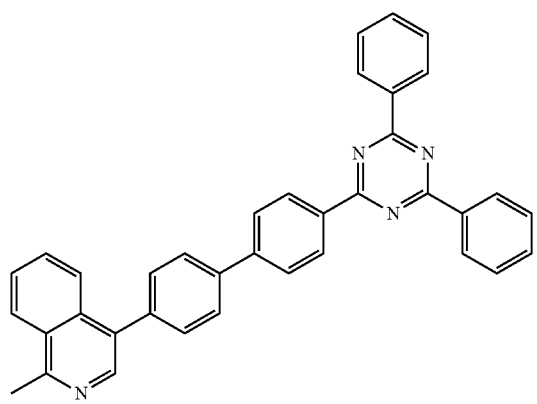
E-546
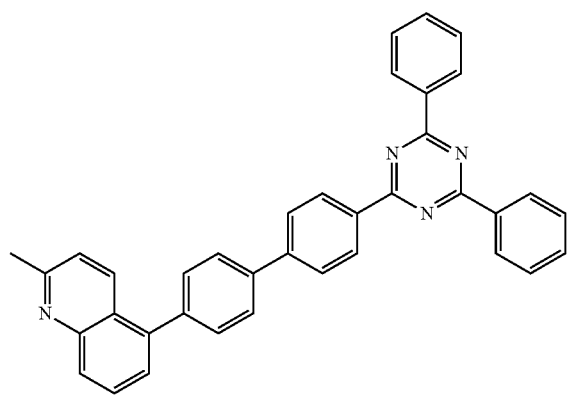
E-547
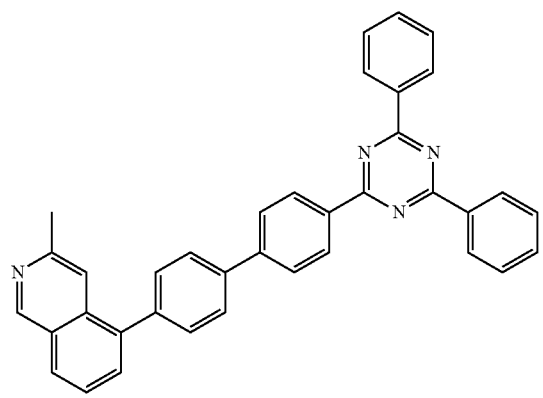
E-548
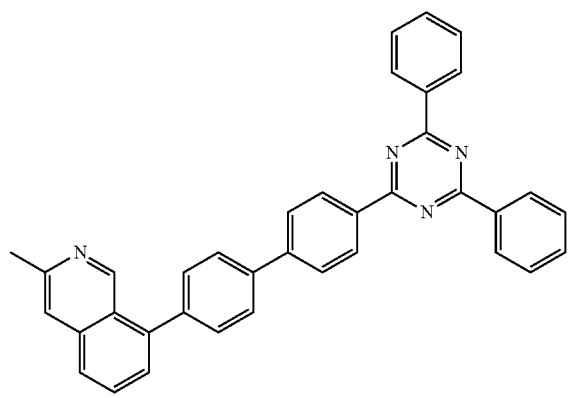
As compound A represented by the general formula (1), general formula (2) or general formula (2'), the following cyclic azine compounds represented by the formulae (A-1) to (A-23), (A-27) to (A-34), (A-37) to (A-39) and (A-41) to (A-44) are preferred, from the viewpoint of good performance of the organic electroluminescent device.

355 356
A-1
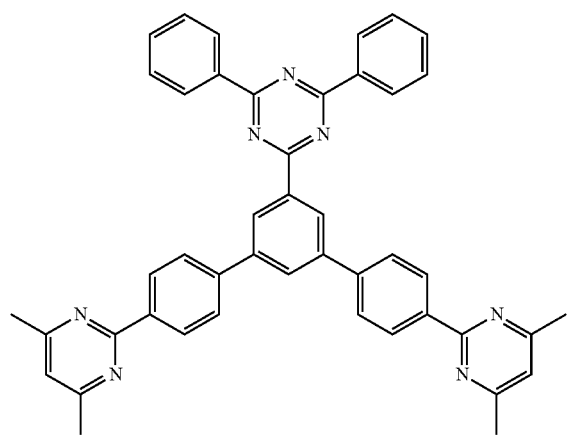
A-2
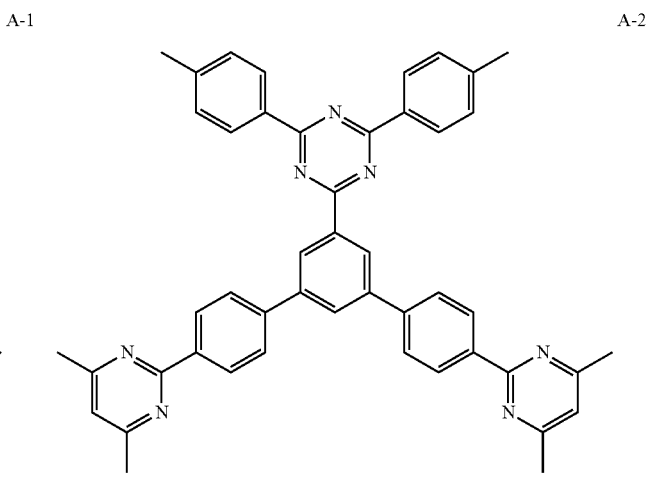
A-3
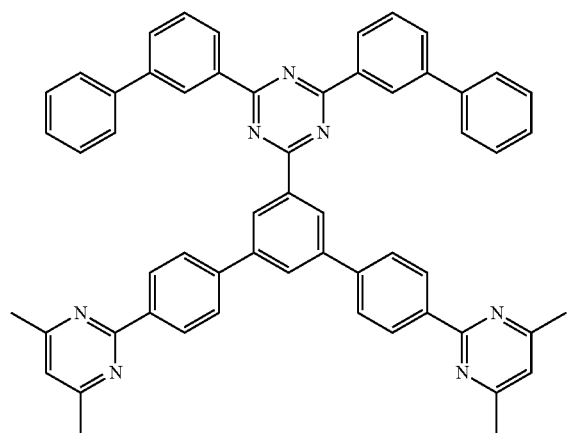
A-4
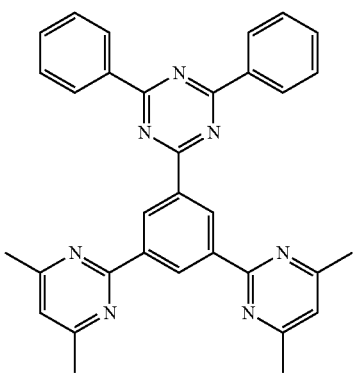
A-5
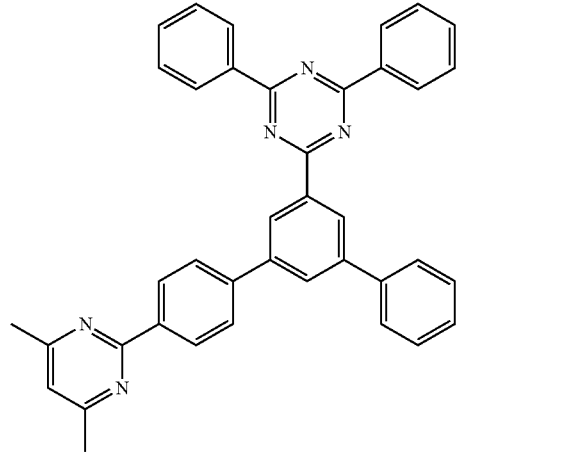
A-6
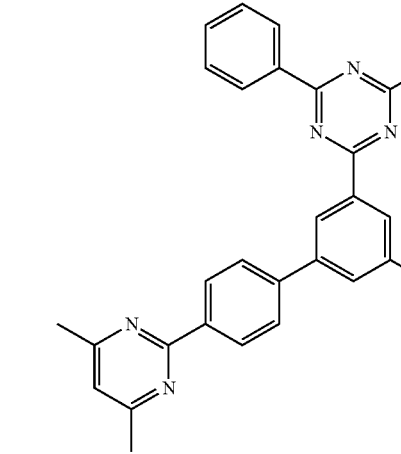

-continued
A-7
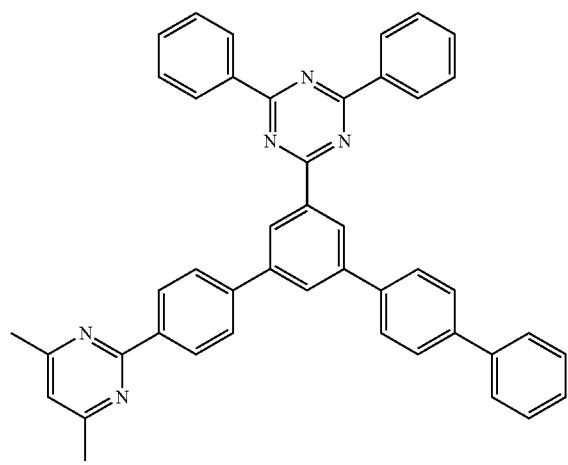
A-8
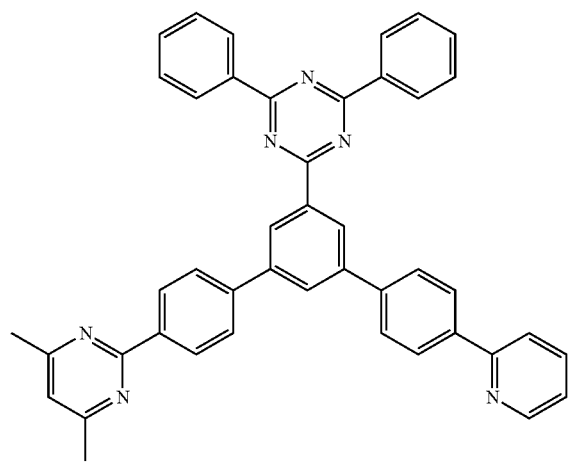
A-9
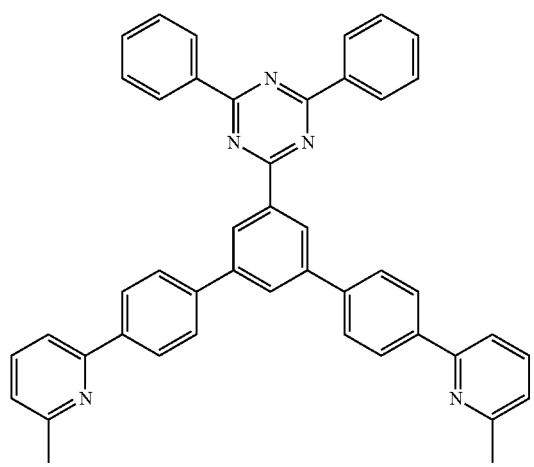
A-10
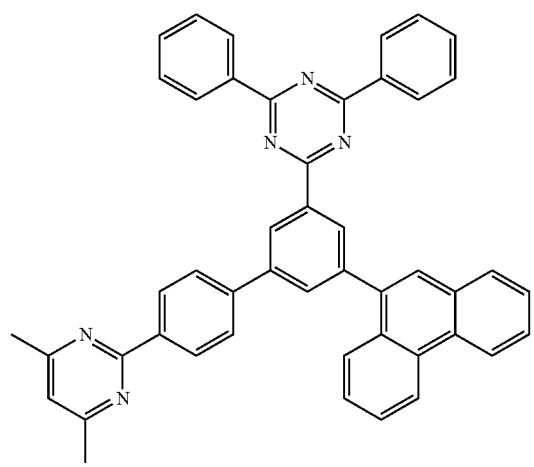
A-11
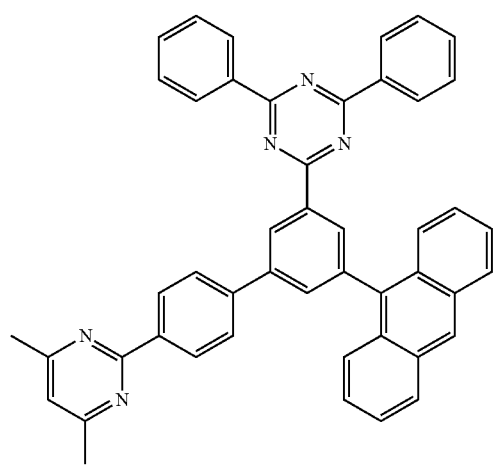
A-12
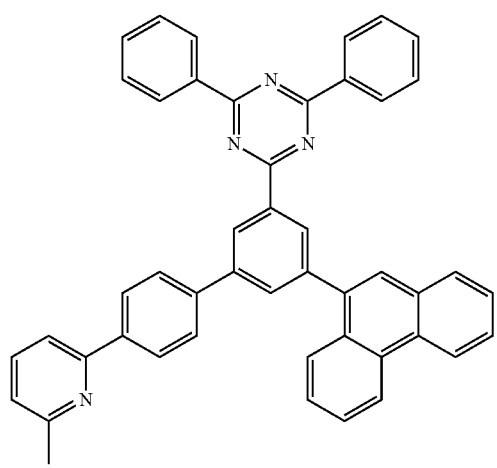

-continued
A-13
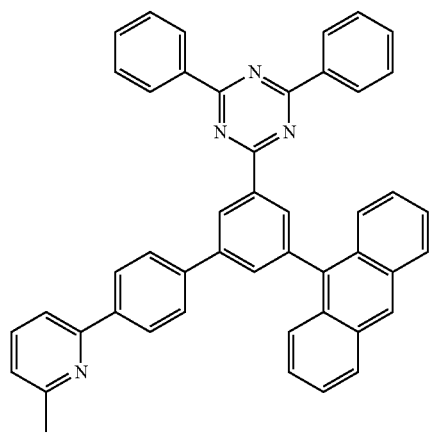
A-14
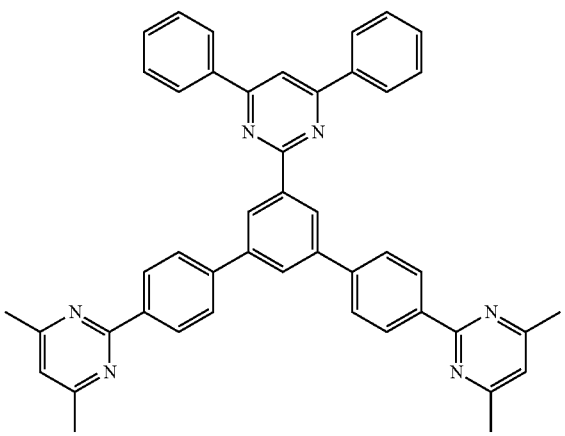
A-15
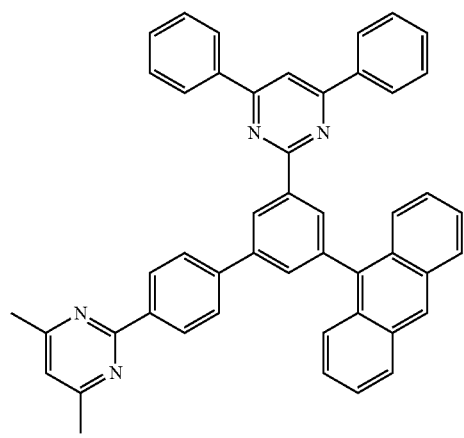
A-16
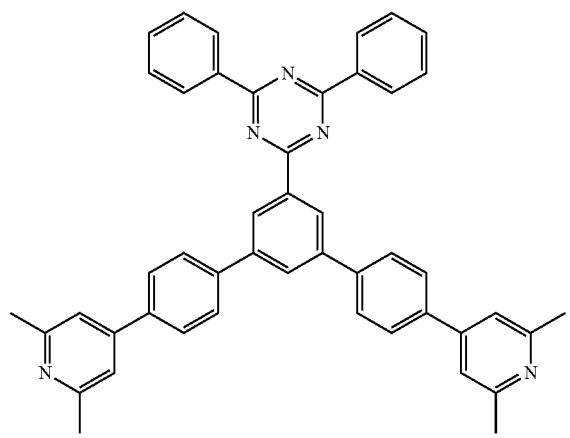
A-17
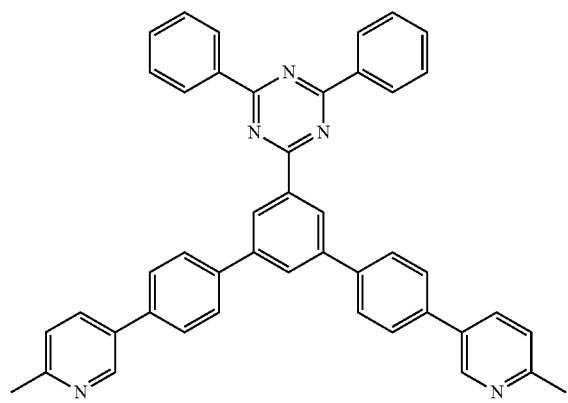
A-18
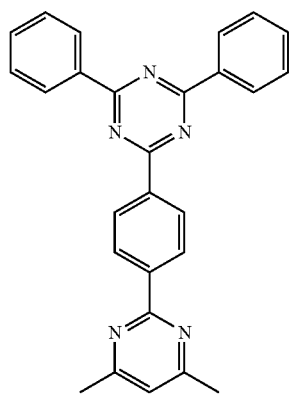

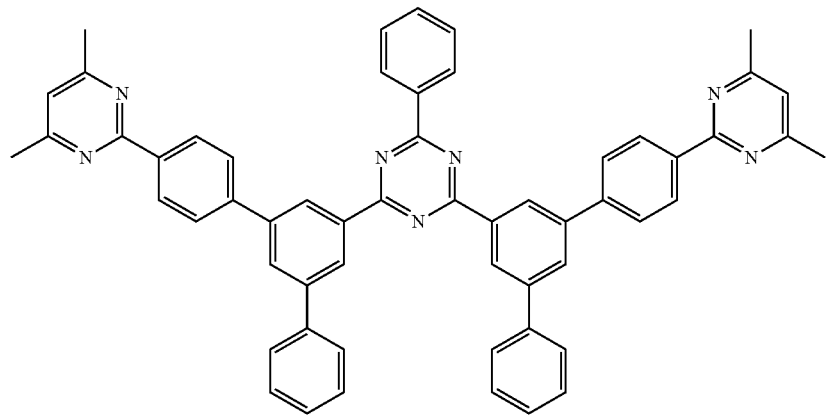
A-19
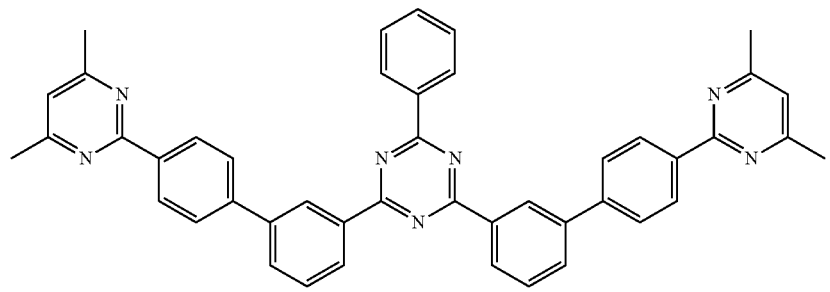
A-20
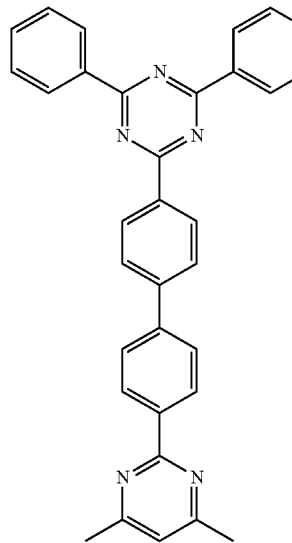
A-21
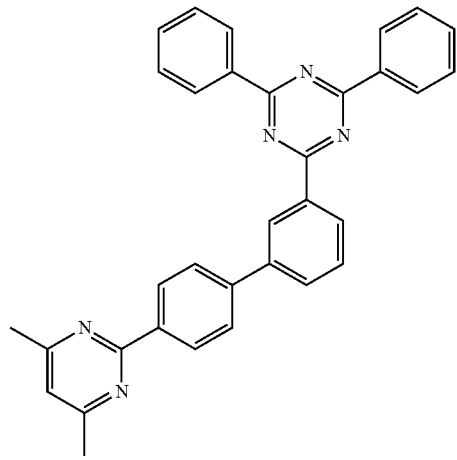
A-22

-continued
A-23
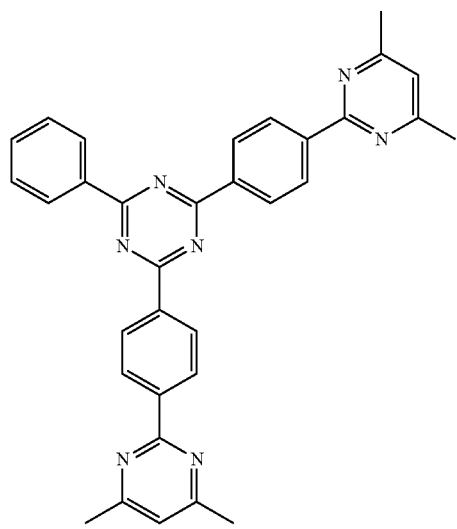
A-27
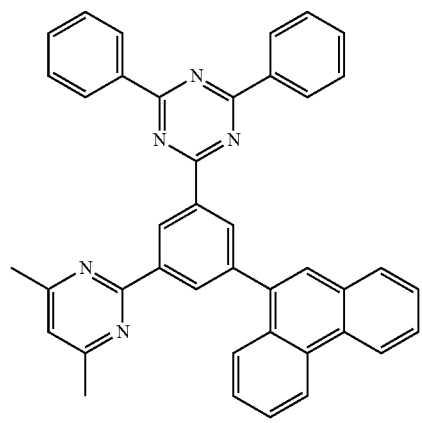
A-28
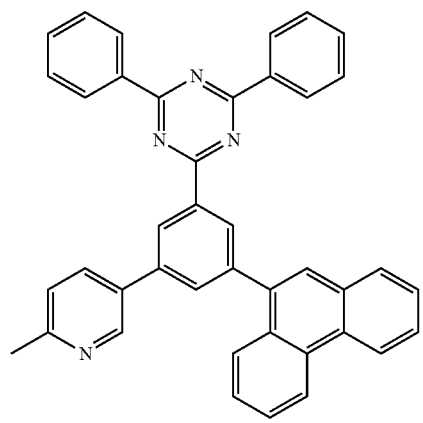
A-29
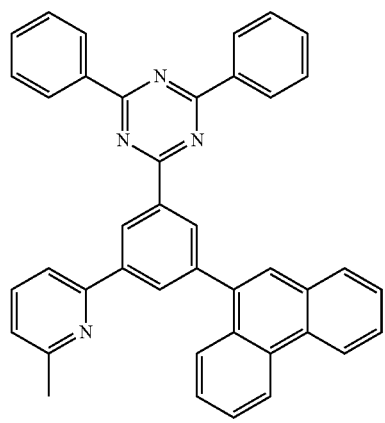
A-30
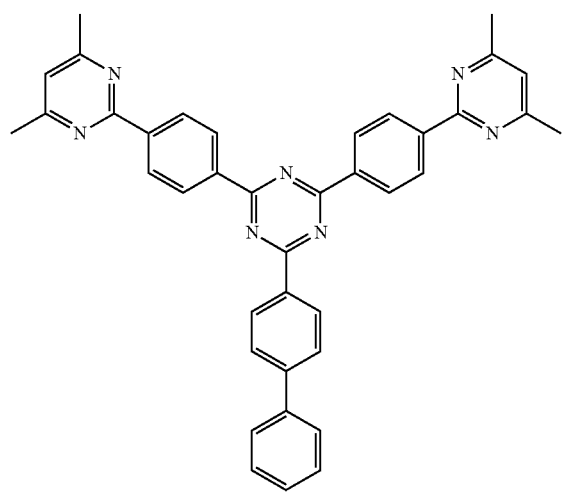
A-31
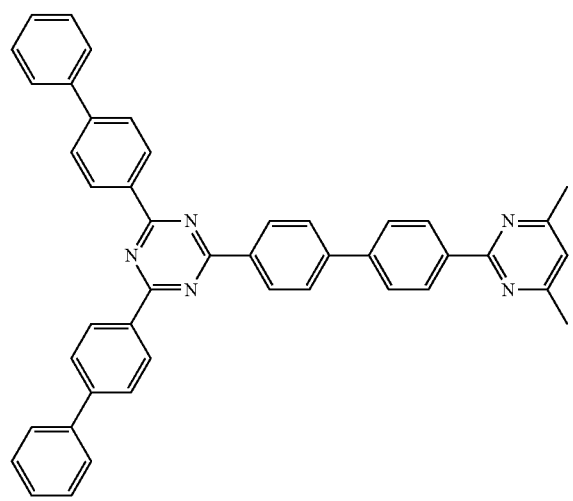

-continued
A-32
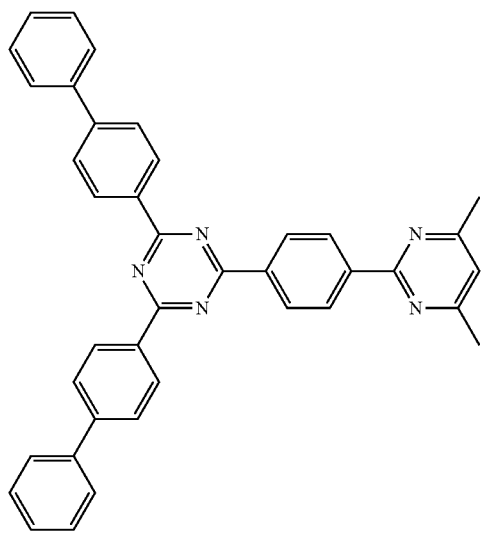
A-33
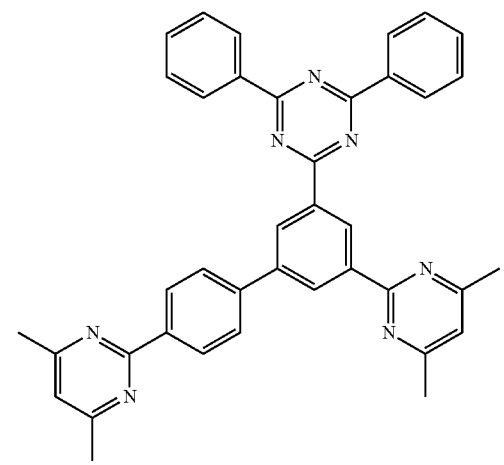
A-34
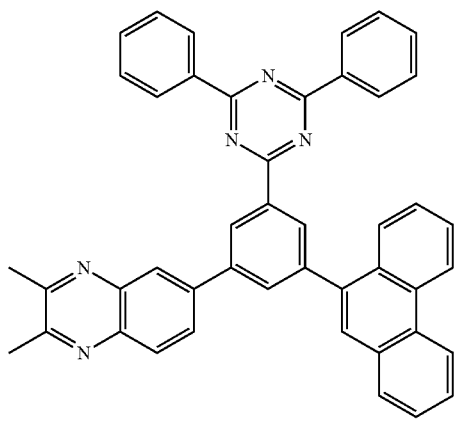
A-37
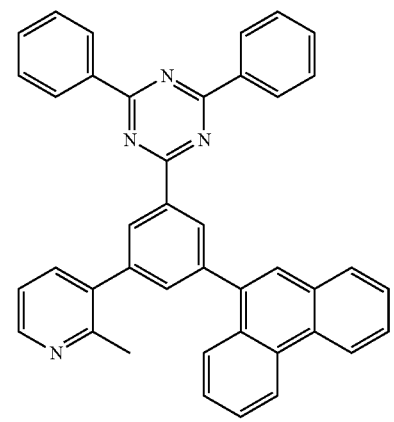
A-38
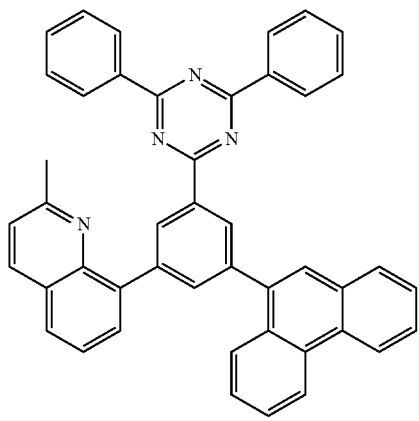
A-39
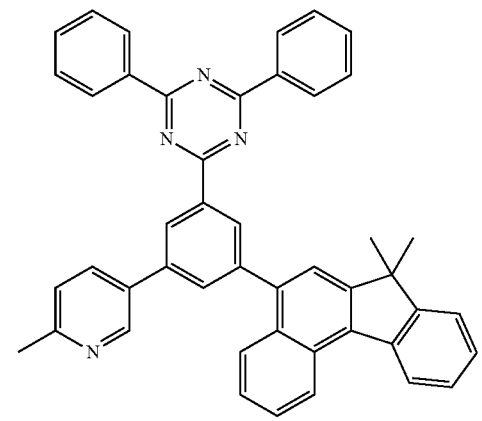

A-41
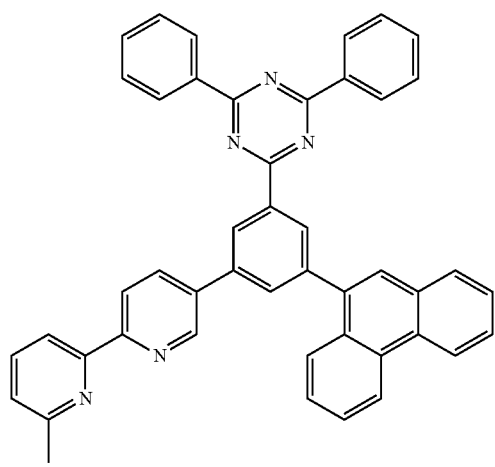
A-42
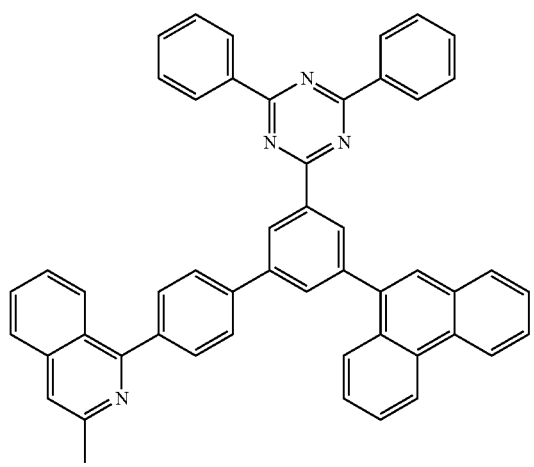
A-43
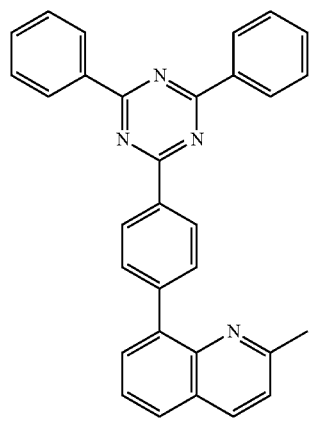
A-44
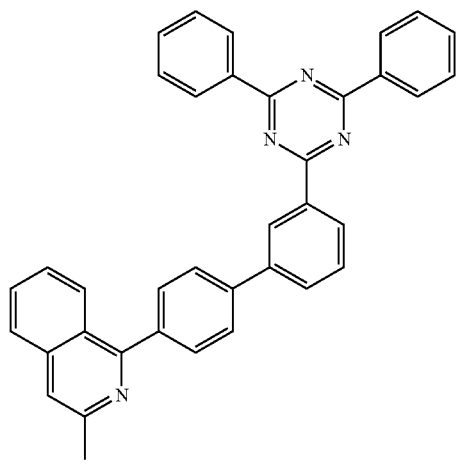
As compound A, the following formulae (A-1) to (A-34) may be mentioned as preferred examples, although it is not particularly limited thereto.
A-1
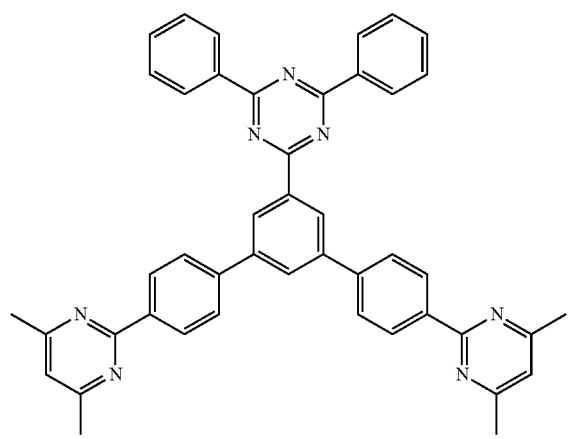
A-2
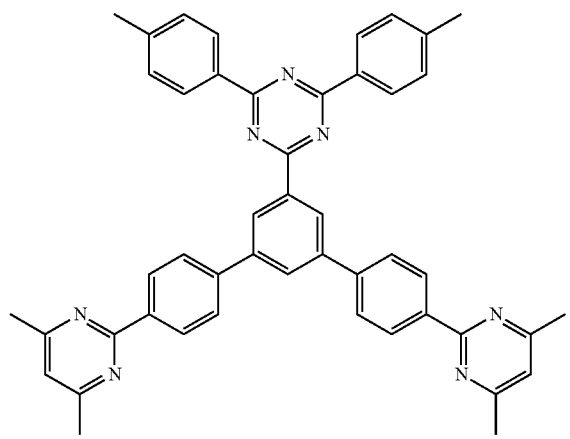

-continued
A-3
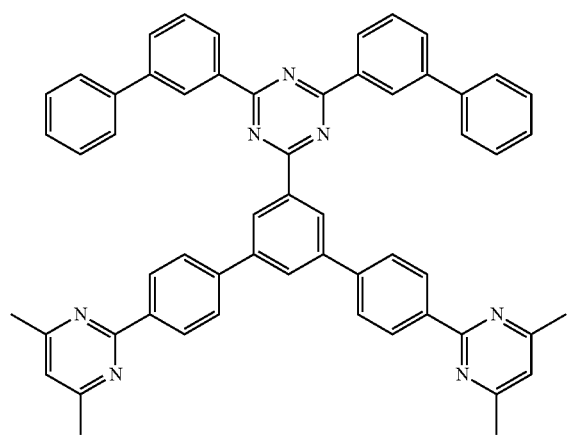
A-4
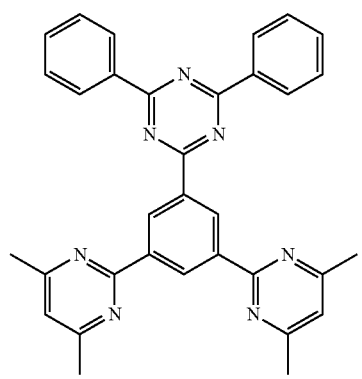
A-5
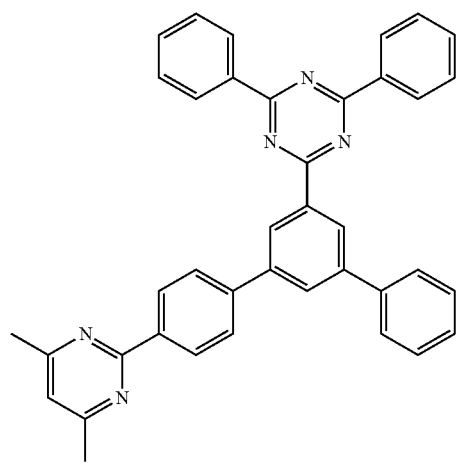
A-6
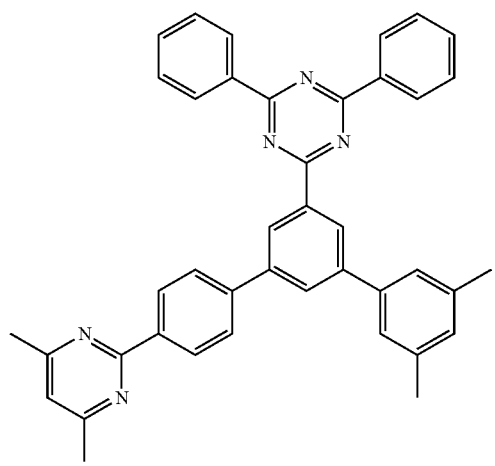
A-7
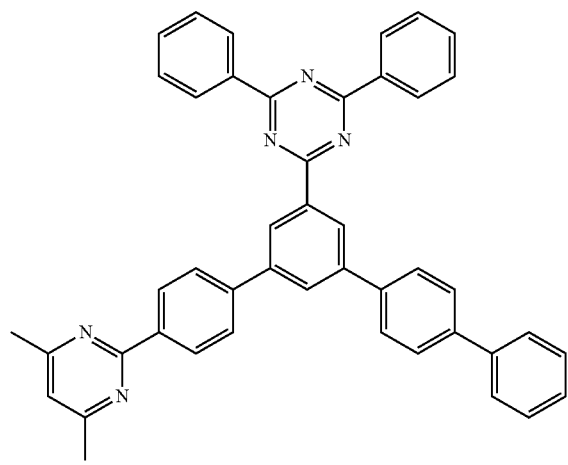
A-8
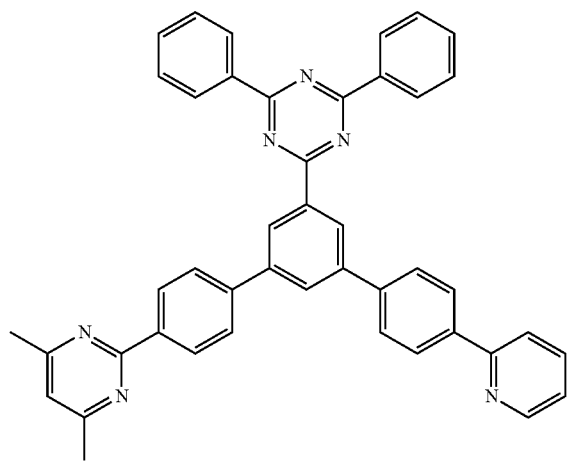

-continued
A-9
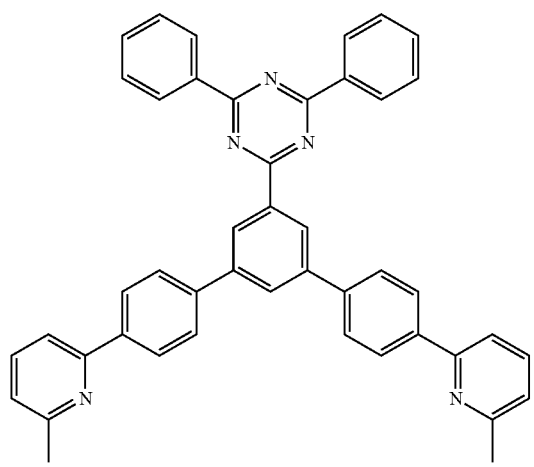
A-10
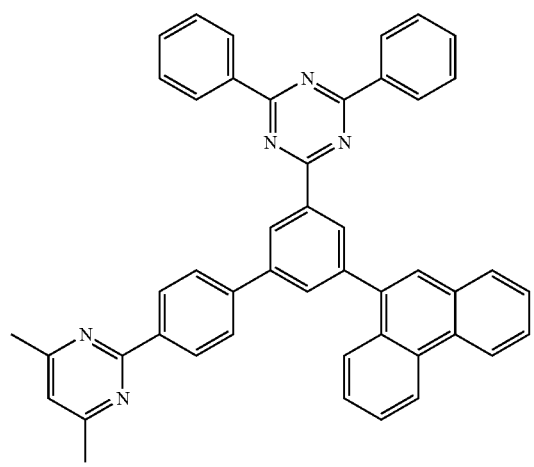
A-11
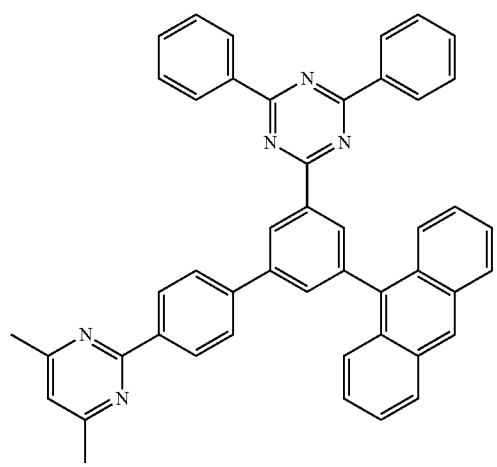
A-12
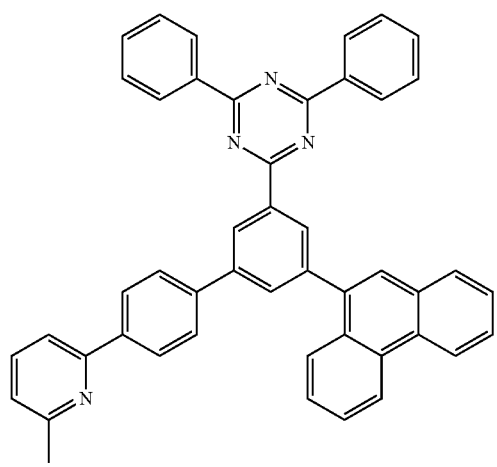
A-13
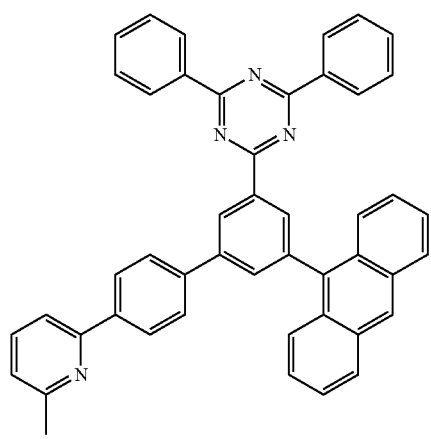
A-14
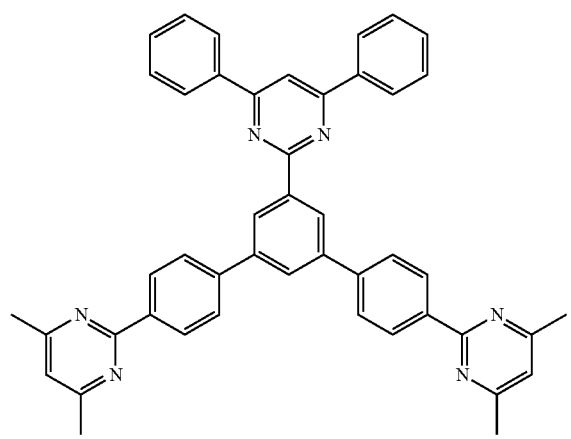

-continued
A-15
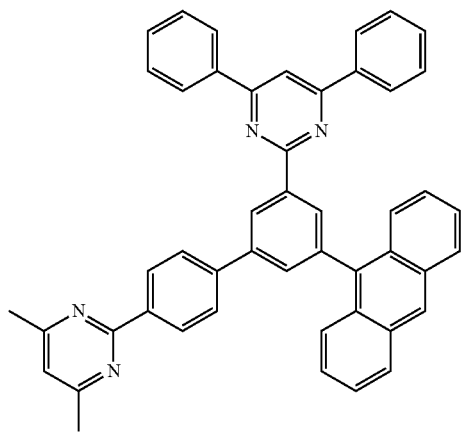
A-16
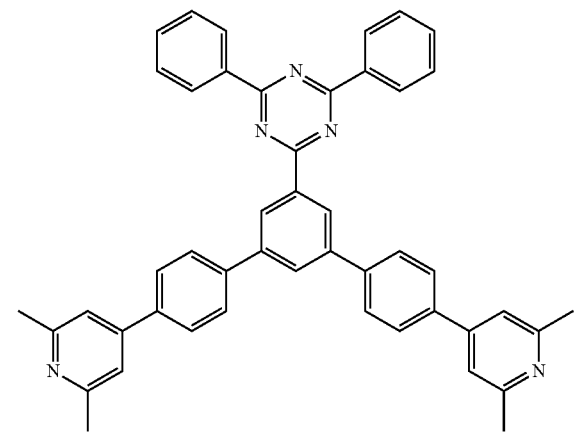
A-17
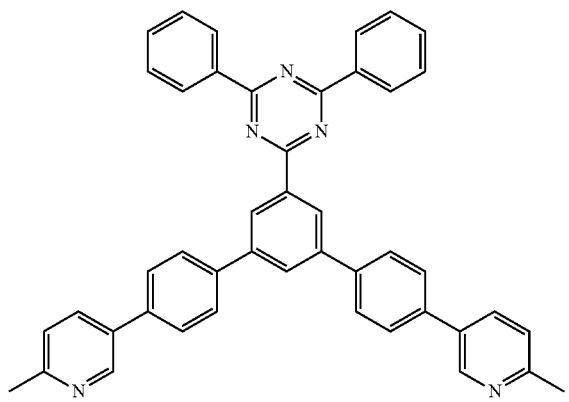
A-18
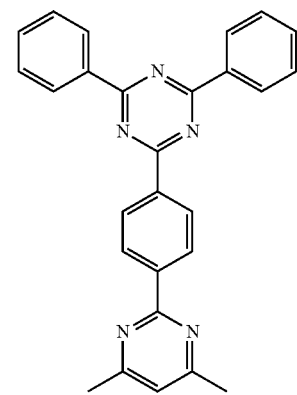
A-19
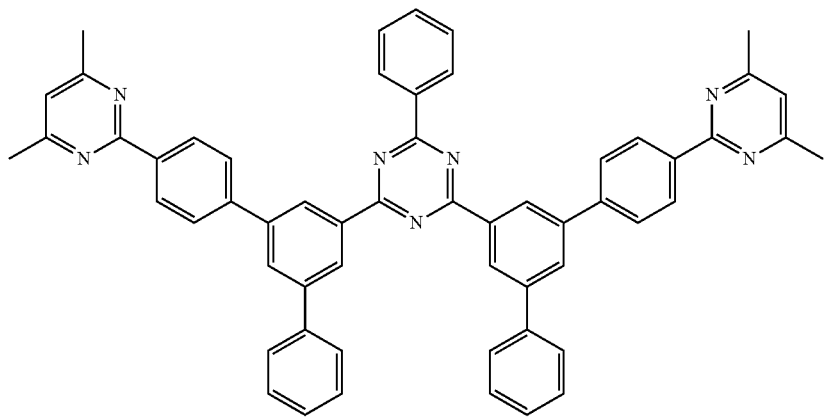
A-20
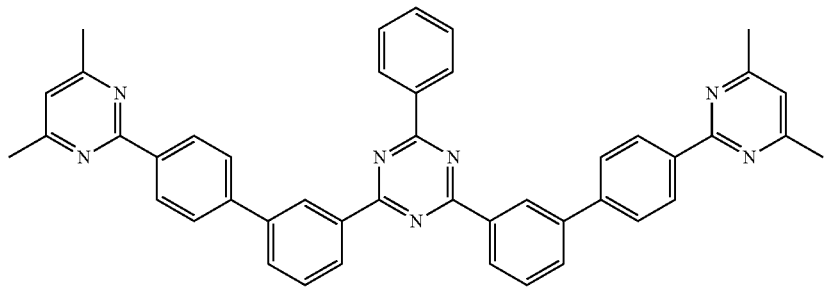

A-21
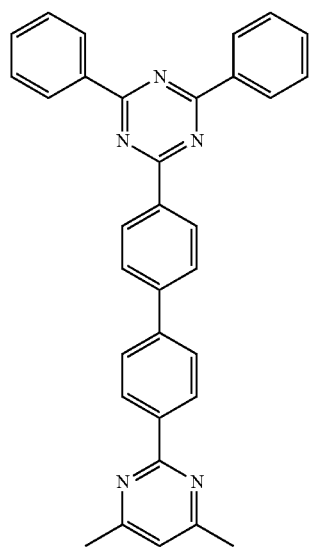
A-22
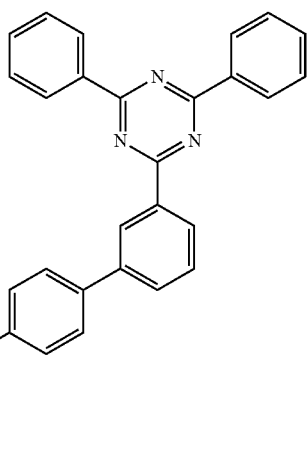
A-23
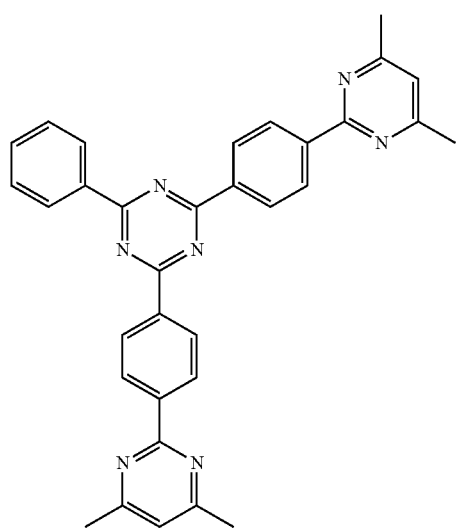
A-24
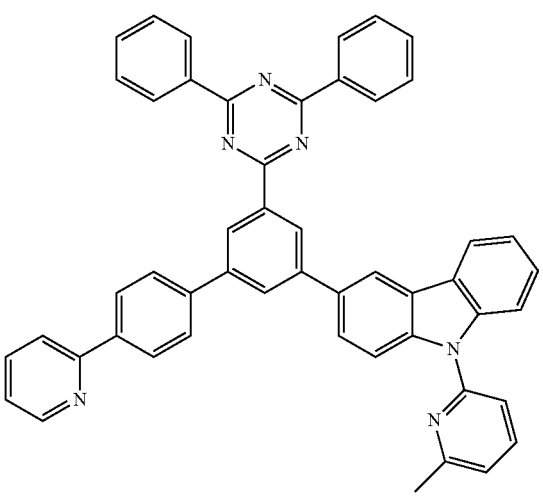
A-25
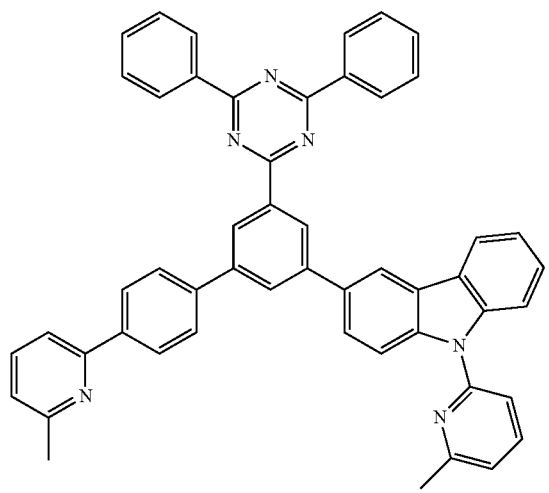
A-26
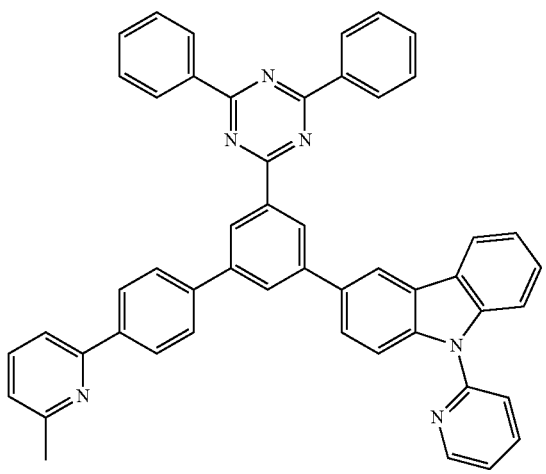

-continued
A-27
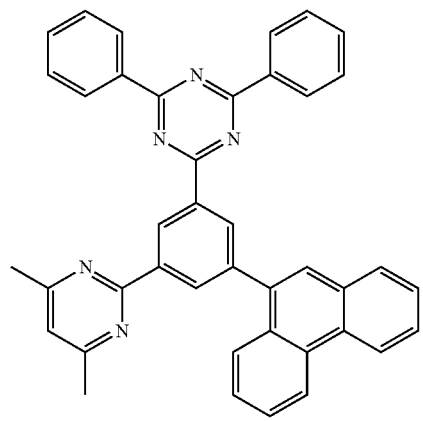
A-28
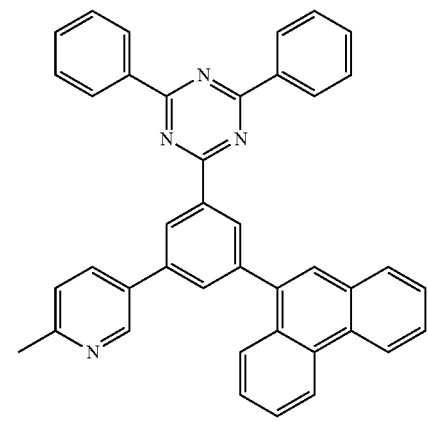
A-29
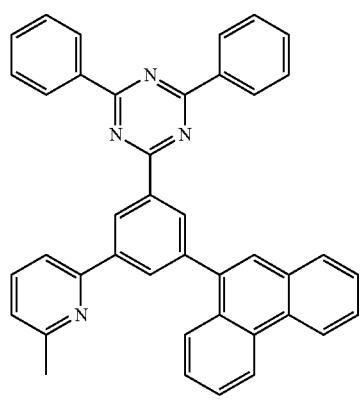
A-30
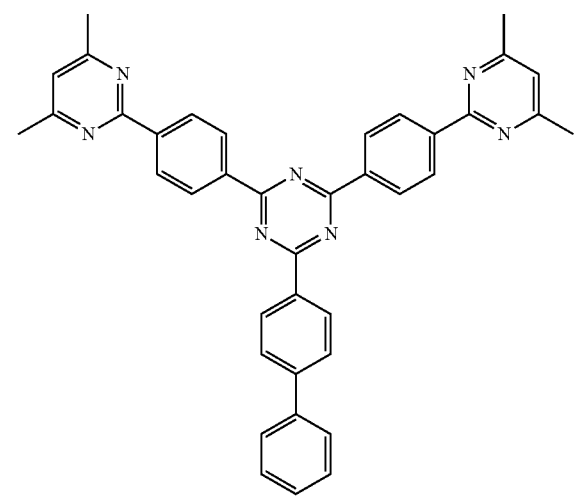
A-31
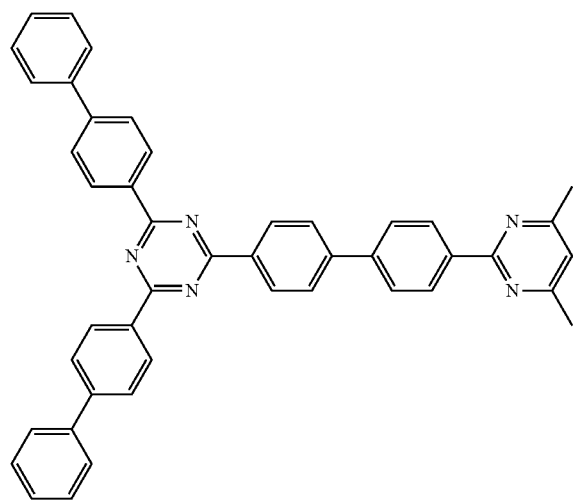
A-32
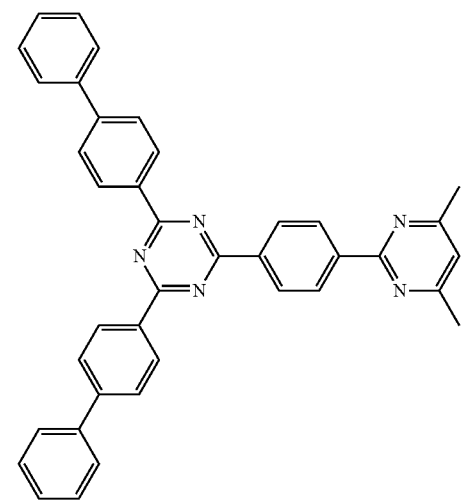

A-33
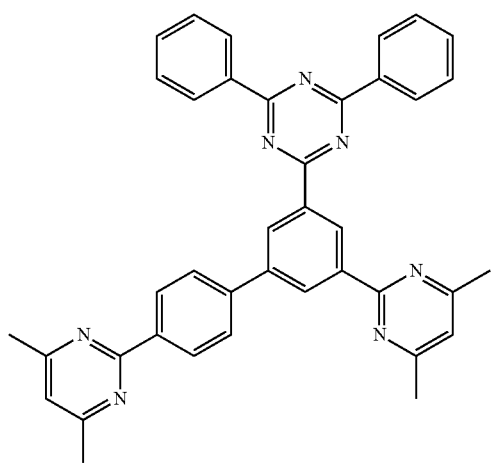
A-34
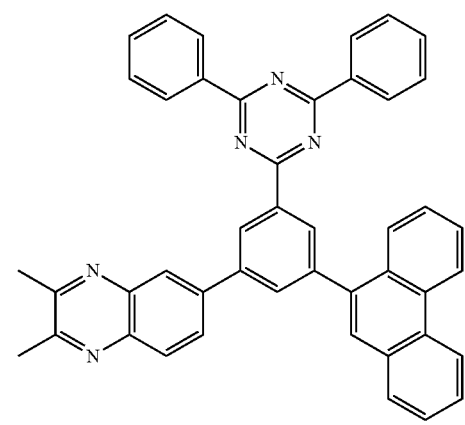
Among these, the following formulae (A-1) to (A-26) may be mentioned as more preferred examples.
A-1
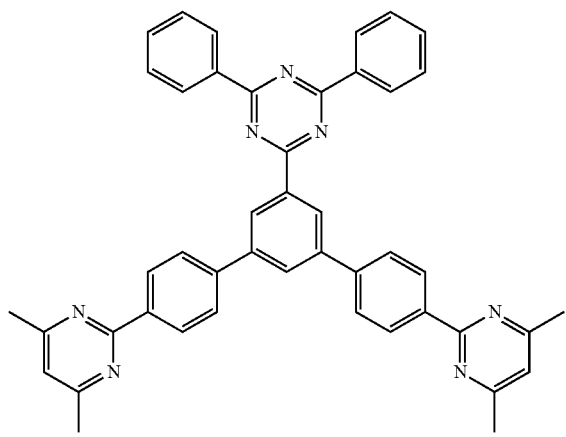
A-2
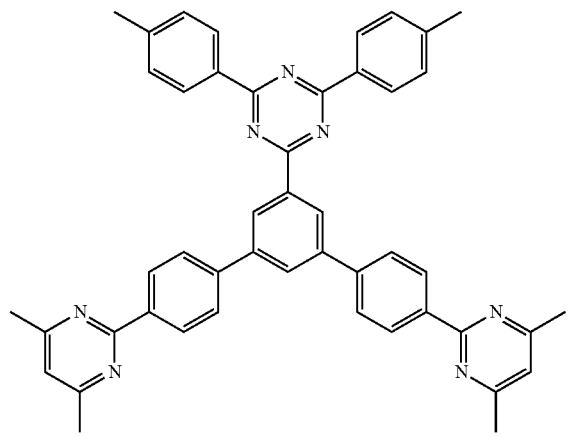
A-3
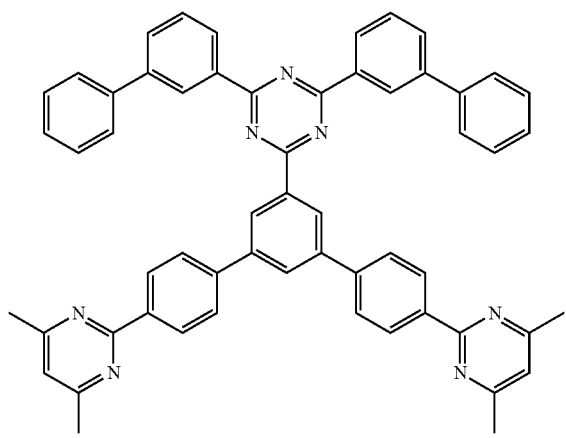
A-4
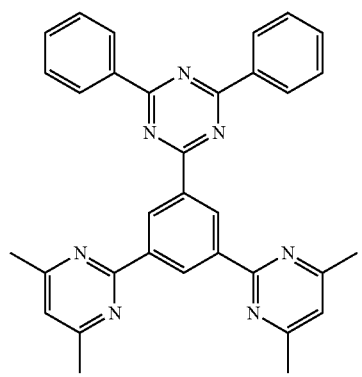

-continued
A-5
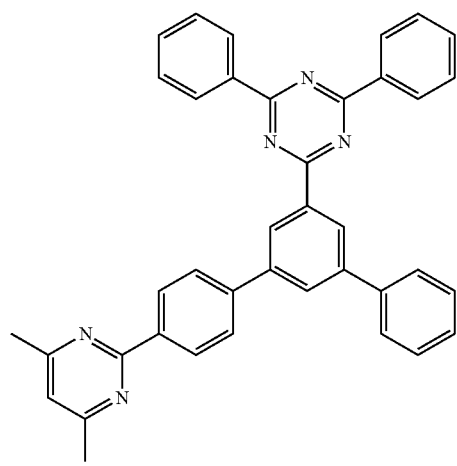
A-6
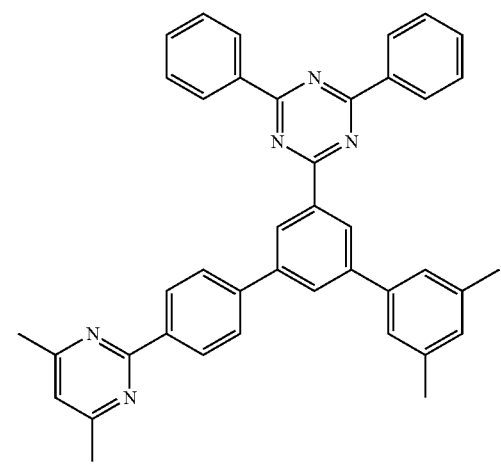
A-7
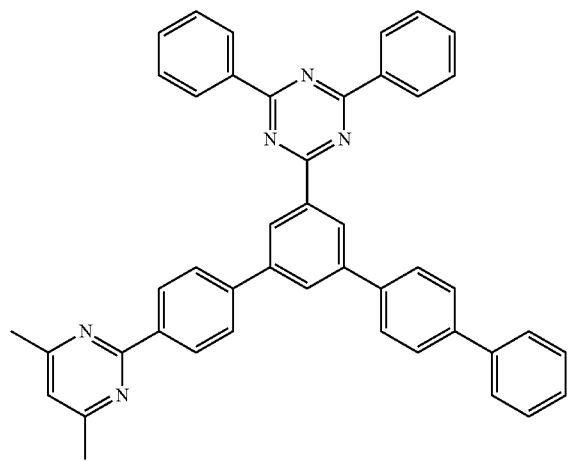
A-8
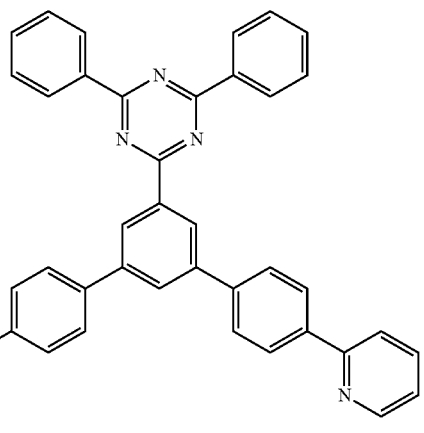
A-9
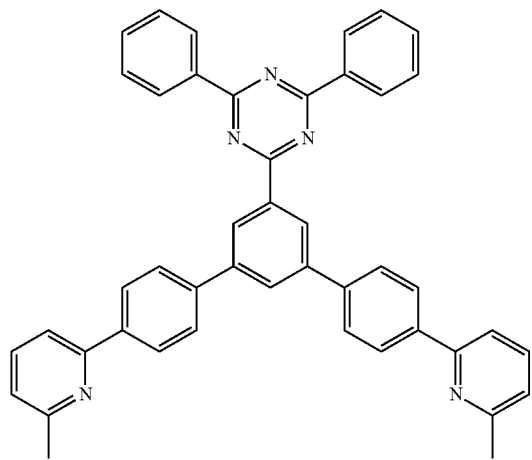
A-10
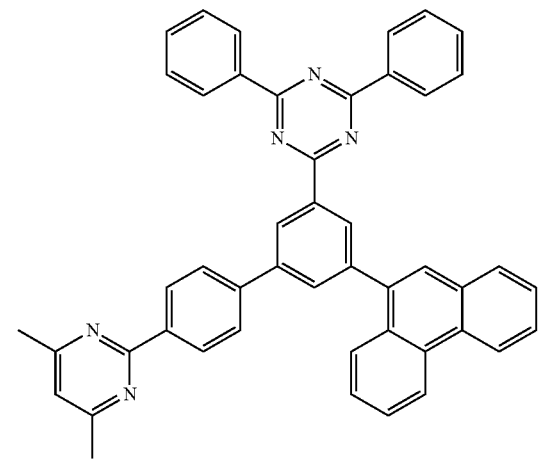

-continued
A-11
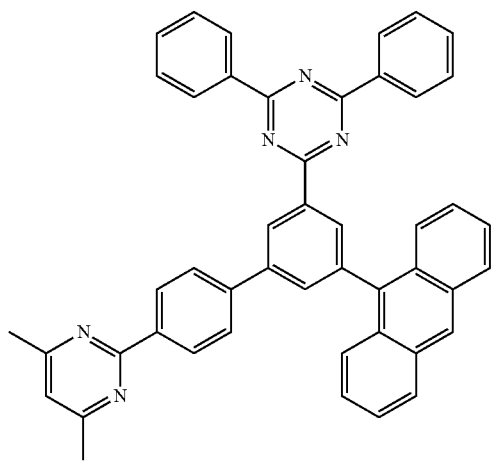
A-12
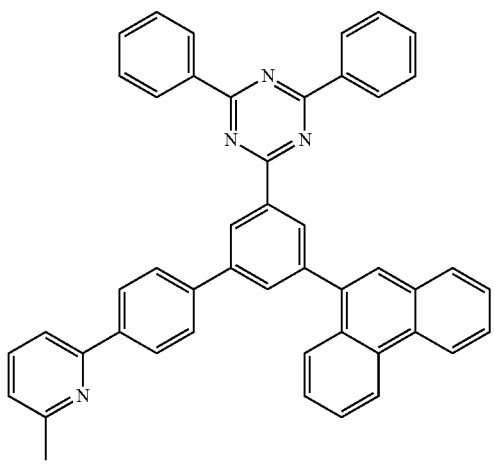
A-13
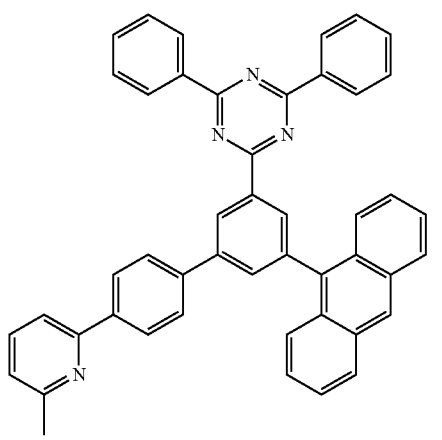
A-14
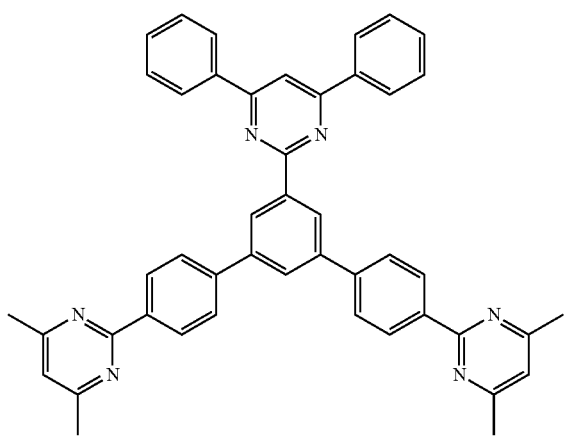
A-15
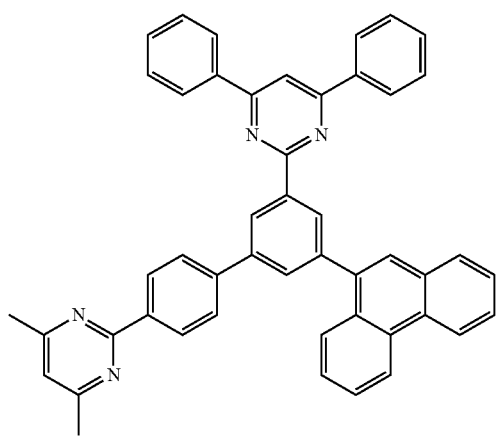
A-16
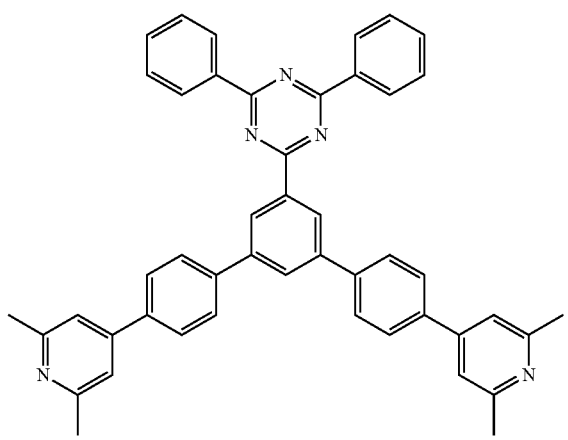

-continued
A-17
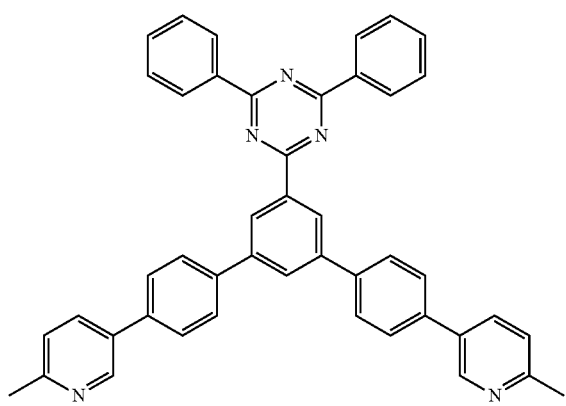
A-18
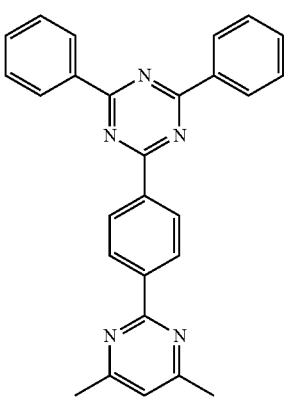
A-19
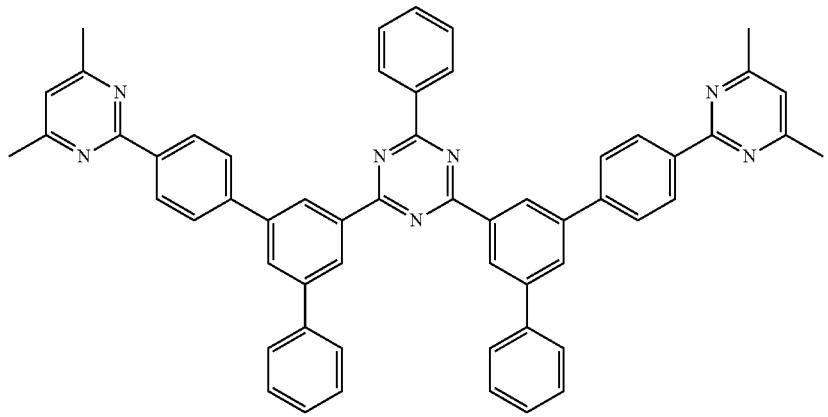
A-20
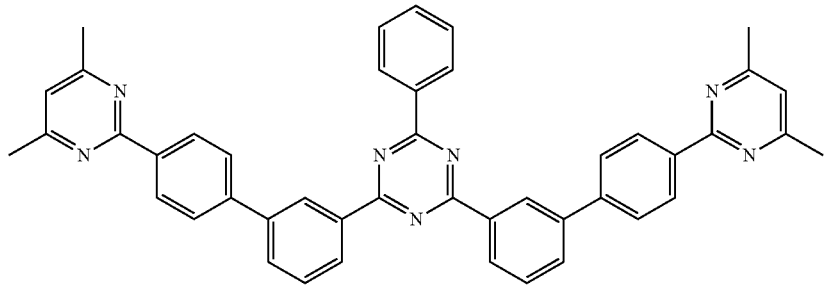

-continued
A-21
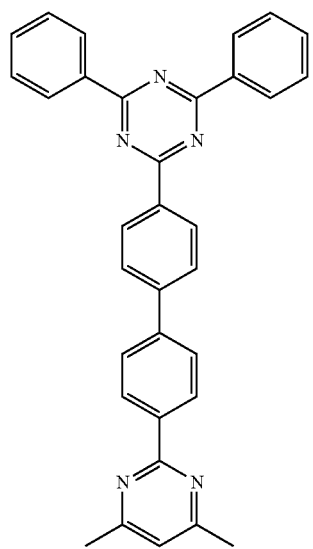
A-22
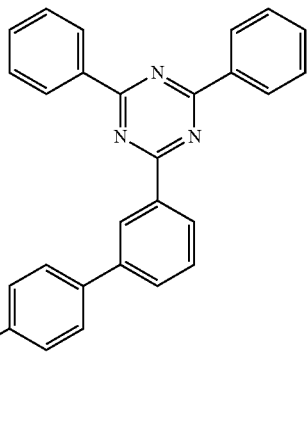
A-23
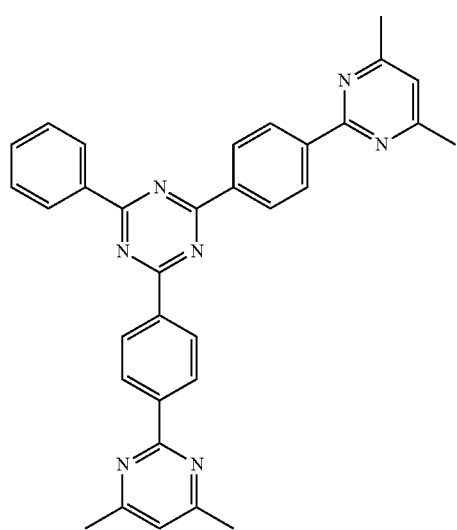
A-24
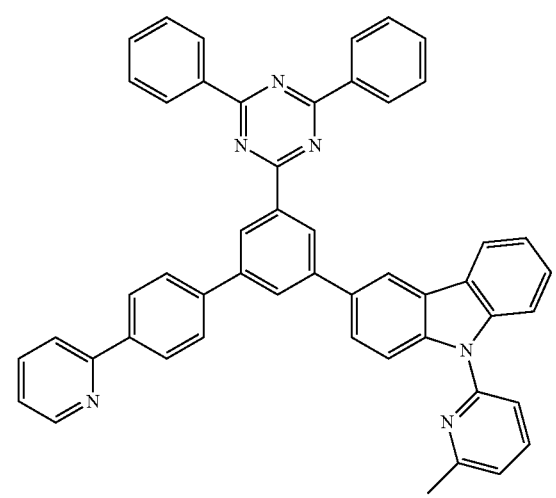
A-25
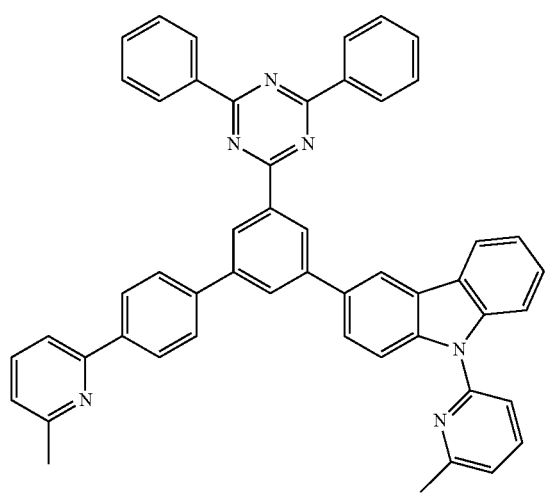
A-26
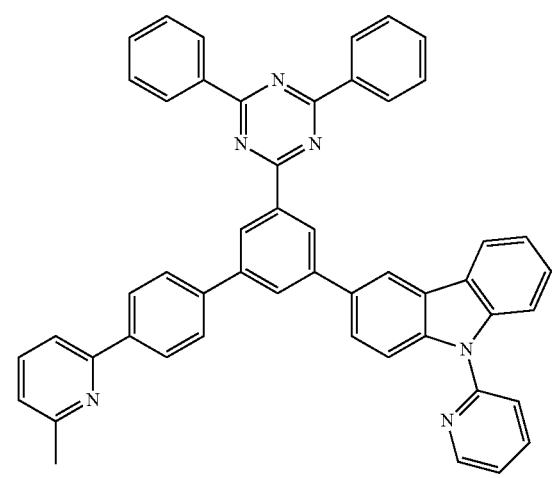

Now, the method for producing compound A (specifically, a compound represented by the general formula (1), general formula (2), general formula (2'), general formula (3) or general formula (3')) will be described.

A compound represented by the general formula (1), general formula (2) or general formula (2') can be produced by any of the following methods represented by the reaction formulae (1) to (10).

Reaction formula (1)

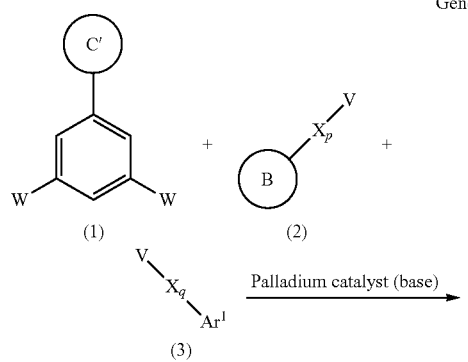

Reaction formula (2)

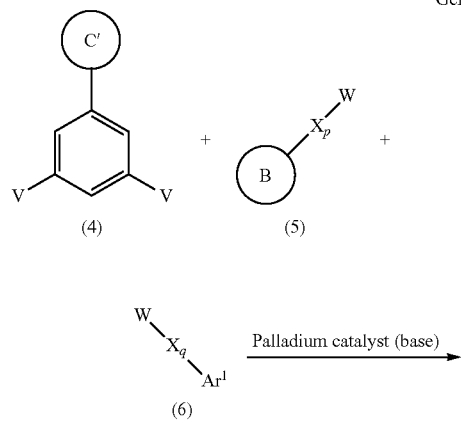

Reaction formula (3)

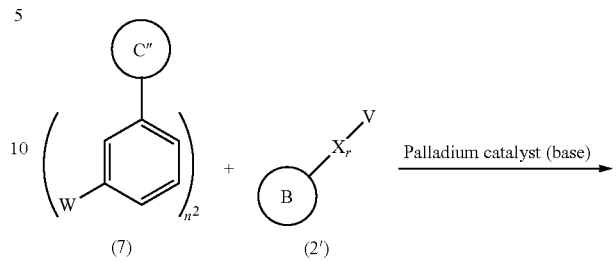

Reaction formula (4)

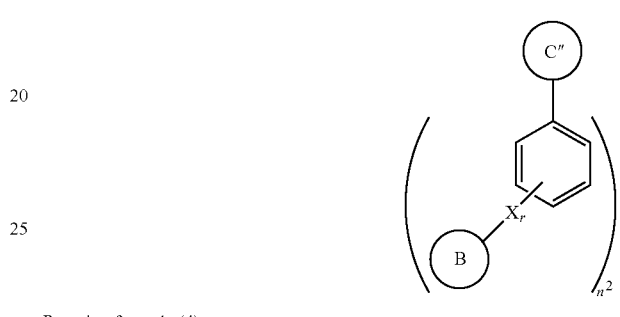

Reaction formula (5)

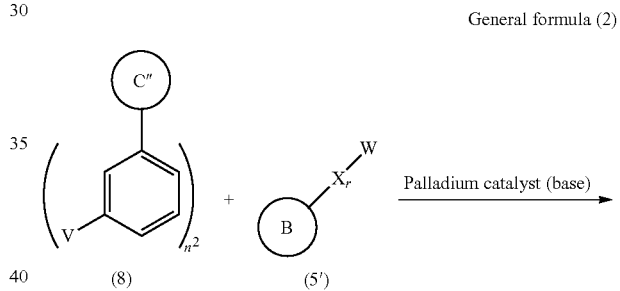

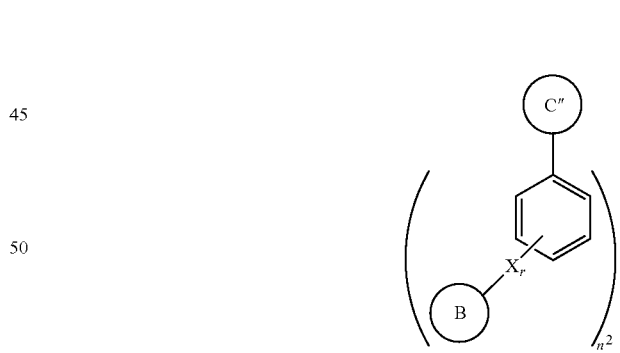

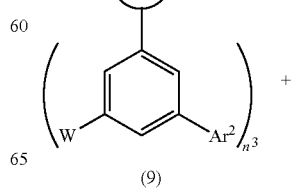

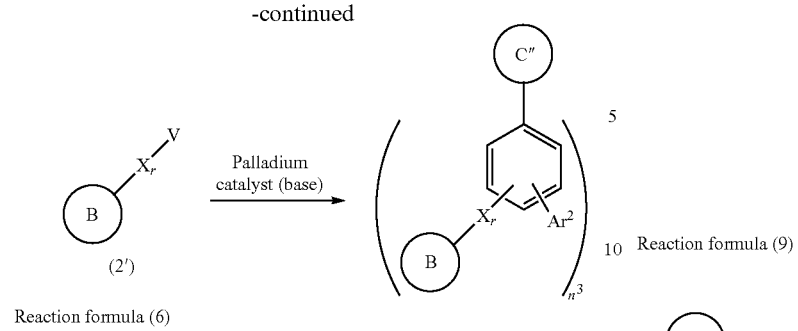
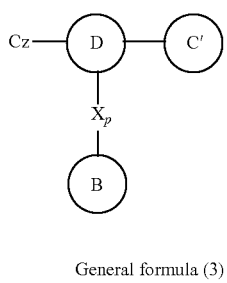
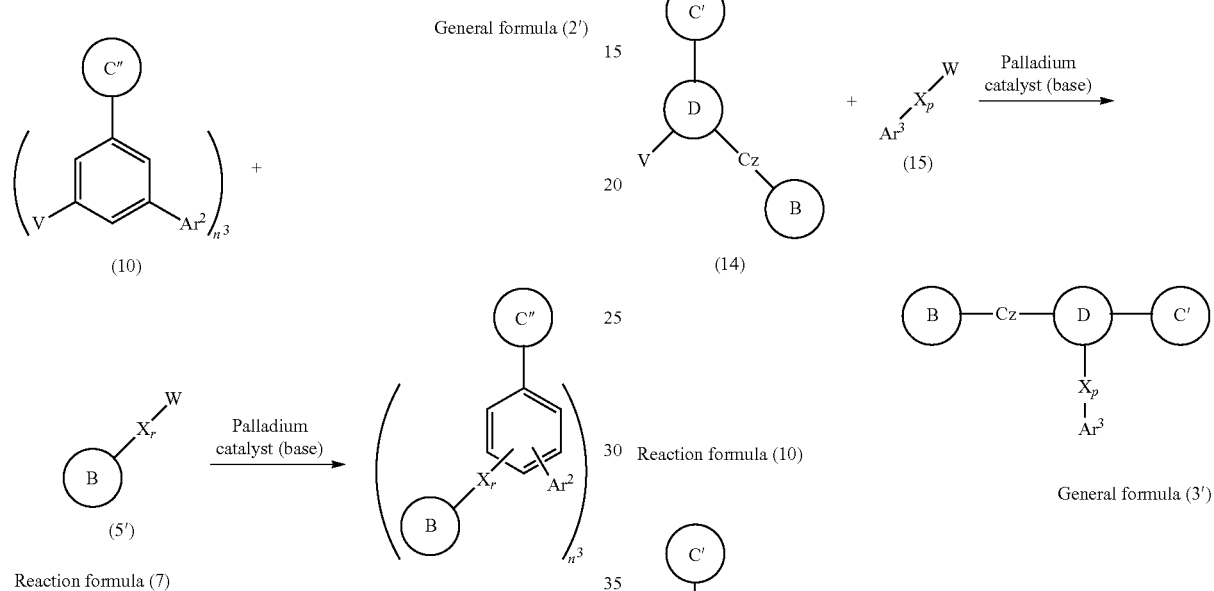
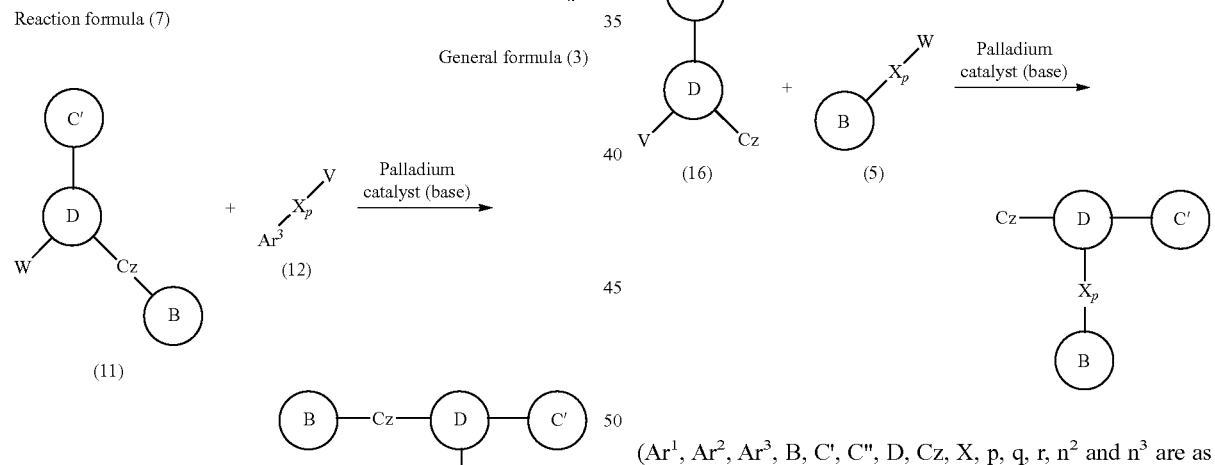
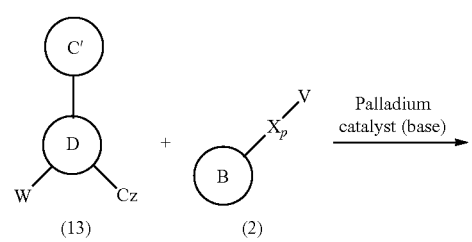

($Ar^1$, $Ar^2$, $Ar^3$, B, C', C'', D, Cz, X, p, q, r, $n^2$ and $n^3$ are as defined above.)

In the reaction formulae (1) to (10), W represents a leaving group and may, for example, be a chlorine atom, a bromine atom, a triflate group or an iodine atom. Among them, a bromine atom or a chlorine atom is preferred, as the reaction yield will thereby be good.

In the reaction formulae (1) to (10), V represents a boronic acid compound or a metal-containing group and may, for example, be Li, Na, MgCl, MgBr, MgI, CuCl, CuBr, CuI, $AlCl_2$, $AlBr_2$, $Al(Me)_2$, $Al(Et)_2$, $Al(^tBu)_2$, $Sn(Me)_3$, $Sn(Bu)_3$, $SnF_3$, ZnCl, ZnBr, $BF_3K$, $B(OR^5)_2$, $B(OR^6)_3$ or $Si(R^7)_3$, although it is not particularly limited thereto.

$B(OR^5)_2$ may, for example, be $B(OH)_2$, $B(OMe)_2$, $B(O^iPr)_2$, $B(OBu)_2$ or $B(OPh)_2$, although it is not particularly limited thereto. Further, the following substituents may be mentioned as examples of B(OR⁵)₂ wherein two R⁵ together forms a ring containing oxygen atoms and a boron atom.

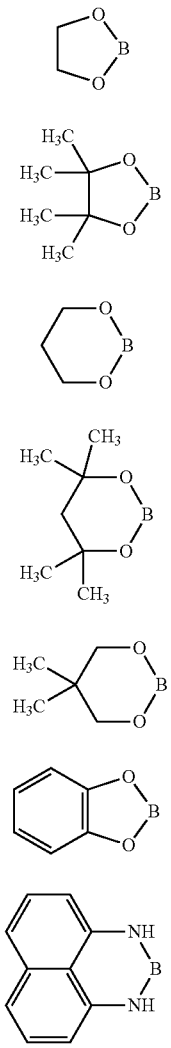

Among these substituents, (II) or (VI) is preferred from the viewpoint of good selectivity for the reaction, and (II) is more preferred from the viewpoint of good reaction yield.

As B(OR⁶)₃, the following substituents may be mentioned.

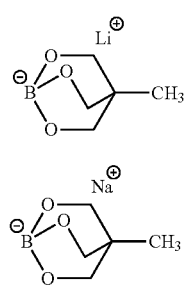

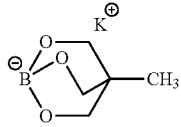

Si(R⁷)₃ may, for example, be SiMe₃, SiPh₃, SiMePh₂, SiCl₃, SiF₃, Si(OMe)₃, Si(OEt)₃ or Si(OMe)₂OH, although it is not particularly limited thereto.

As shown in the reaction formulae (1) to (10), compound (A) of the present invention can be synthesized by conducting a coupling reaction as disclosed in each reaction formula, in the presence of a palladium catalyst and a base.

The palladium catalyst which may be used in the reactions of the reaction formulae (1) to (10), is not particularly limited and may, for example, be a salt such as palladium chloride, palladium acetate, palladium trifluoroacetate or palladium nitrate. Further, π-allyl palladium chloride dimer, palladium acetylacetonate, bis(dibenzylidene acetone) palladium, tris(dibenzylidene acetone) palladium, dichlorobis(triphenyl phosphine) palladium, tetrakis(triphenyl phosphine) palladium, tri(tert-butyl) phosphine palladium, dichloro(1,1'-bis(diphenyl phosphine) ferrocene) palladium, etc. may be mentioned. Among them, a palladium complex having, as a ligand, a tertiary phosphine such as dichlorobis(triphenyl phosphine) palladium, tetrakis(triphenyl phosphine) palladium or tri(tert-butyl) phosphine palladium, is preferred from the viewpoint of good yield, and tetrakis(triphenyl phosphine) palladium or tri(tert-butyl) phosphine palladium, is more preferred from the viewpoint of availability. Further, such a palladium complex having a tertiary phosphine as a ligand, may also be prepared in the reaction system by adding a tertiary phosphine to a palladium salt or complex compound.

The tertiary phosphine is not particularly limited, and may, for example, be triphenylphosphine, trimethylphosphine, tributylphosphine, tri(tert-butyl) phosphine, tricyclohexylphosphine, tert-butyl diphenylphosphine, 9,9-dimethyl-4,5-bis(diphenylphosphino) xanthene, 2-(diphenylphosphino)-2'-(N,N-dimethylamino) biphenyl, 2-(di-tert-butylphosphino) biphenyl, 2-(dicyclohexylphosphino) biphenyl, bis(diphenylphosphino) methane, 1,2-bis(diphenylphosphino) ethane, 1,3-bis(diphenylphosphino) propane, 1,4-bis(diphenylphosphino) butane, 1,1'-bis(diphenylphosphino) ferrocene, tri(2-furyl) phosphine, tri(o-tolyl) phosphine, tris(2,5-xylyl) phosphine, (±)-2,2'-bis(diphenylphosphino)-1,1'-binaphthyl, 2-dicyclohexylphosphino-2',4',6'-triisopropyl biphenyl. Among these, (tert-butyl) phosphine or 2-dicyclohexylphosphino-2',4',6'-triisopropylbiphenyl is preferred in view of availability and good yield.

When the tertiary phosphine is added to the palladium salt or complex compound, the amount of the tertiary phosphine to be added, is preferably from 0.1 to 10 times by mol per mol (in terms of palladium atoms) of the palladium salt or complex compound. It is more preferably from 0.3 to 5 times by mol from the viewpoint of good yield.

In the reaction formulae (1) to (10), the base which may be used, is not particularly limited and may, for example, be sodium hydroxide, potassium hydroxide, sodium carbonate, potassium carbonate, lithium carbonate, cesium carbonate, potassium acetate, sodium acetate, potassium phosphate, sodium phosphate, sodium fluoride, potassium fluoride or cesium fluoride. Among these, from the viewpoint of good yield, potassium carbonate, potassium phosphate or sodium hydroxide is preferred.

The reactions of the reaction formulae (1) to (10) are preferably carried out in a solvent. The solvent is not particularly limited and may, for example, be water, dimethyl sulfoxide, dimethylformamide, tetrahydrofuran, toluene, benzene, diethyl ether, 1,4-dioxane, ethanol, butanol or xylene, and these may be suitably combined for use. Among these, from the viewpoint of good yield, tetrahydrofuran, 1,4-dioxane or a toluene-butanol mixed solvent is preferred.

Now, the reaction formula (1) will be explained.

Compound (1) may be produced by using the methods disclosed in e.g.

Yamanaka Hiroshi, "New edition, Heterocyclic compounds. Fundamentals", Kodansha, 2004, Yamanaka Hiroshi, "New edition, Heterocyclic compound, Application Guide", Kodansha, 2004, The Journal of Organic Chemistry, 1951, Volume 16, 461-465, Macromolecules, 2001, Vol. 6, 477-480, Report by Science and Technology Research Institute, Vol. 81, 441, 1986.

Substituent C' in compound (1) is as defined above with respect to the above-mentioned substituent C'.

Compound (1) is not particularly limited and may, for example, be the following (1-1) to (1-12).

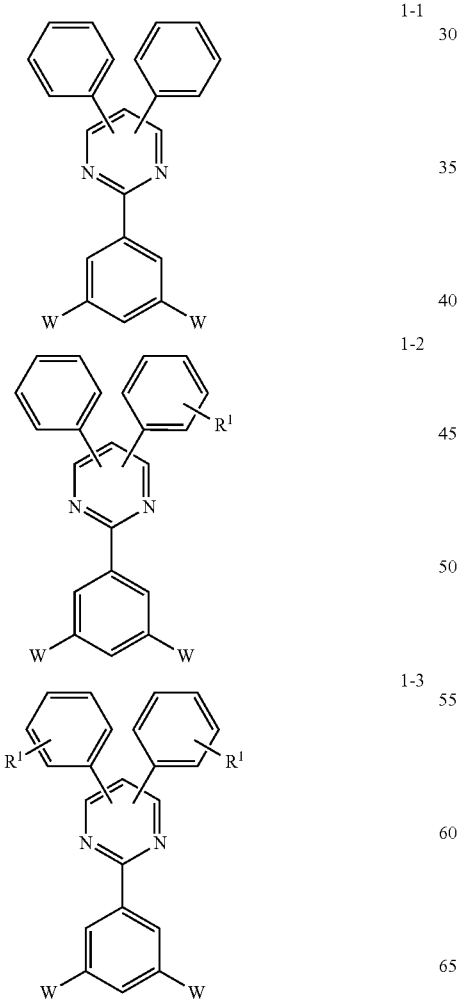

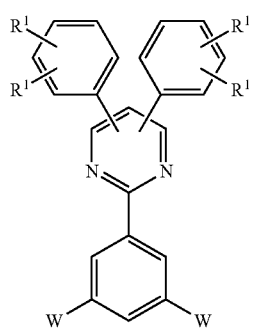

1-4

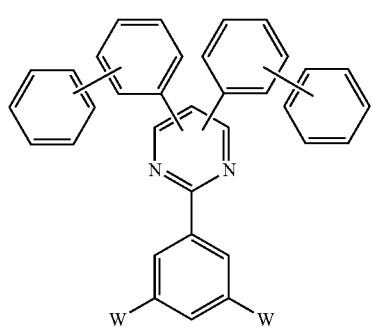

1-5

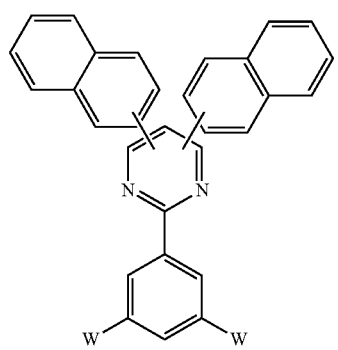

1-6

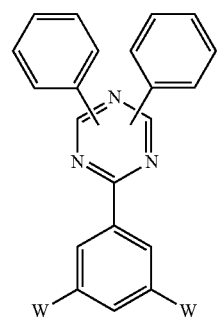

1-7

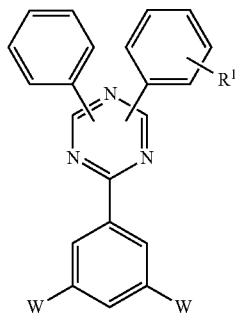

1-8

-continued

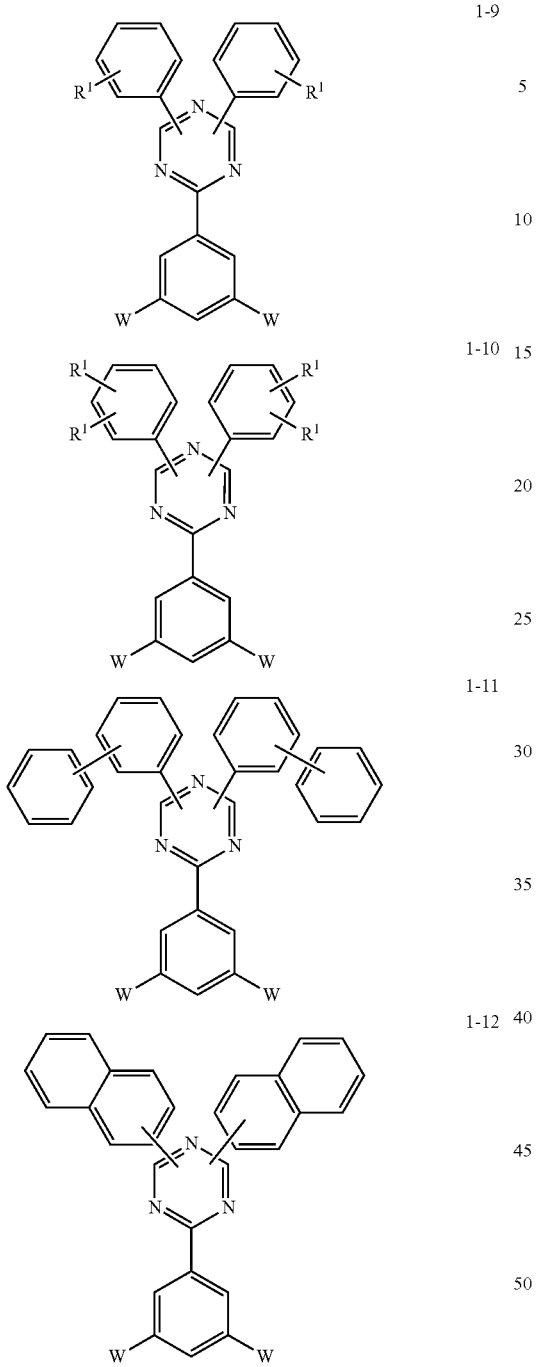

1-9

1-10

1-11

1-12

(Each R¹ independently represents a $C_{1-4}$ alkyl group, and V and W are as defined above.)

Compound (2) or compound (3) may be produced by using the method disclosed in, for example, The Journal of Organic Chemistry, 2001, 66, 4333-4339, or Chem. Rev., Vol. 95, 2457-2483, 1995.

Substituent B, X and p in compound (2), are as defined above with respect to the above-mentioned substituent B, X and p.

Compound (2) is not particularly limited and may, for example, be the following (2-1) to (2-69).

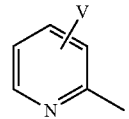

2-1

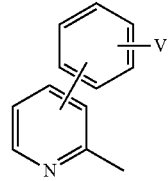

2-2

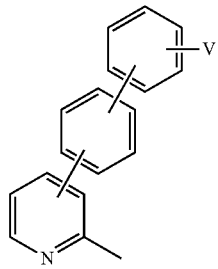

2-3

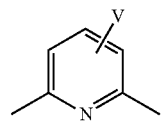

2-4

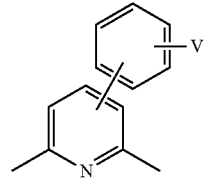

2-5

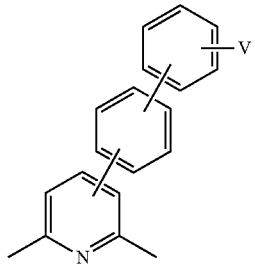

2-6

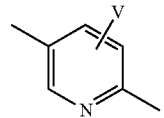

2-7

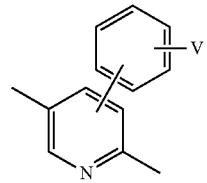

2-8

399
-continued
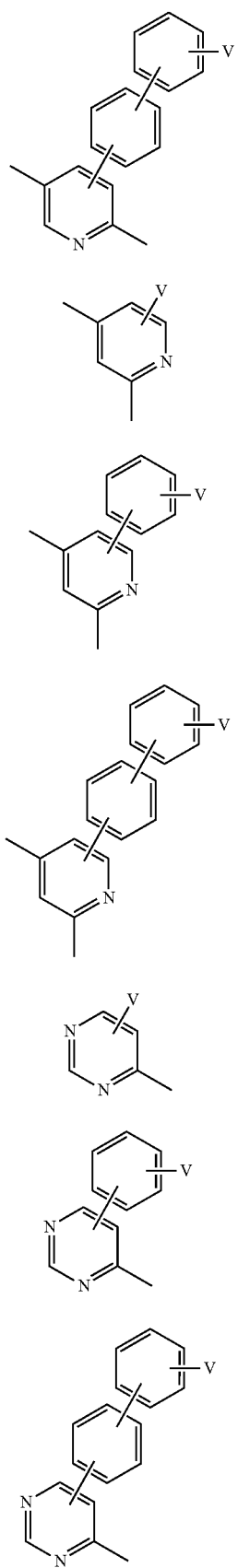
2-9
2-10
2-11
2-12
2-13
2-14
2-15
400
-continued
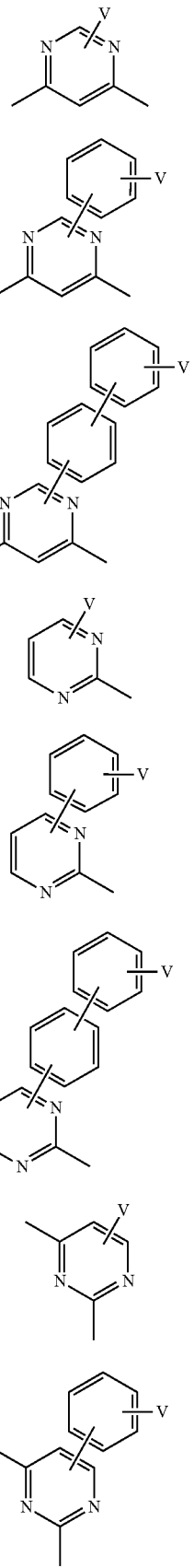
2-16
2-17
2-18
2-19
2-20
2-21
2-22
2-23

| 401 -continued | | 402 -continued | |
|---|---|---|---|
| | 2-24 | 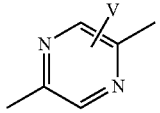 | 2-31 |
| 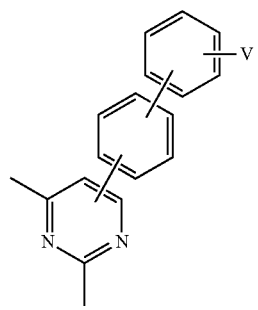 | | 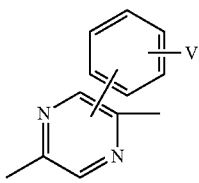 | 2-32 |
| | 2-25 | | |
| 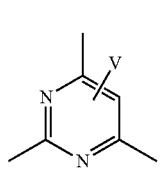 | | 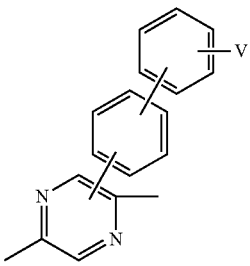 | 2-33 |
| | 2-26 | | |
| 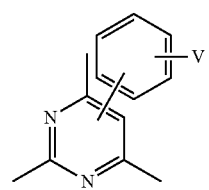 | | 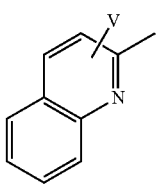 | 2-34 |
| | 2-27 | | |
| 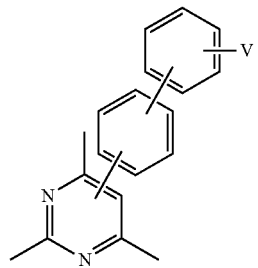 | | 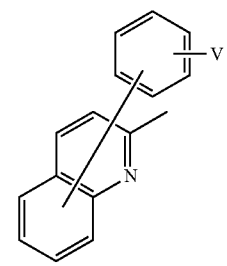 | 2-35 |
| | 2-28 | | |
| 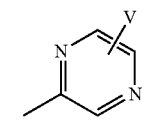 | | 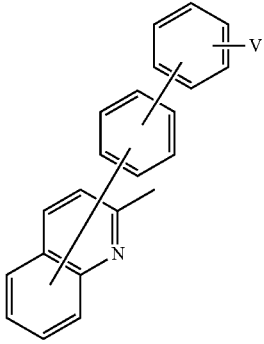 | 2-36 |
| | 2-29 | | |
| 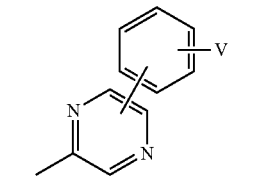 | | | |
| | 2-30 | | |
| 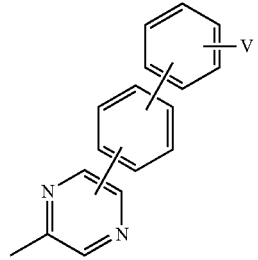 | | 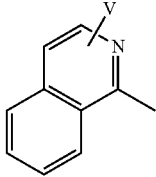 | 2-37 |

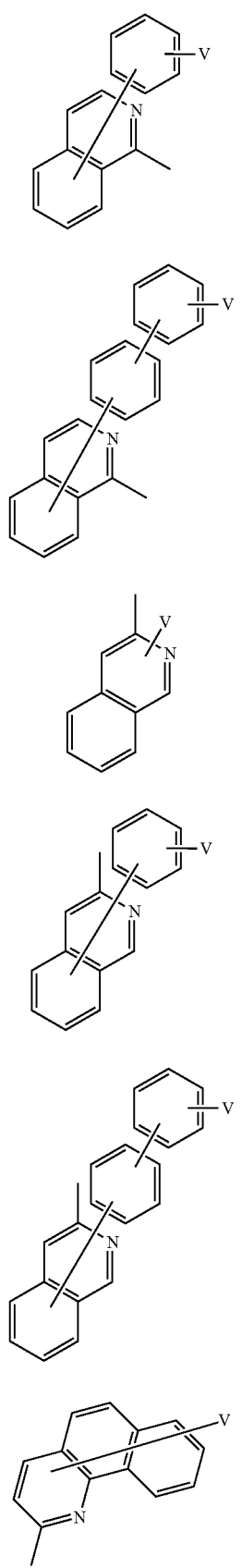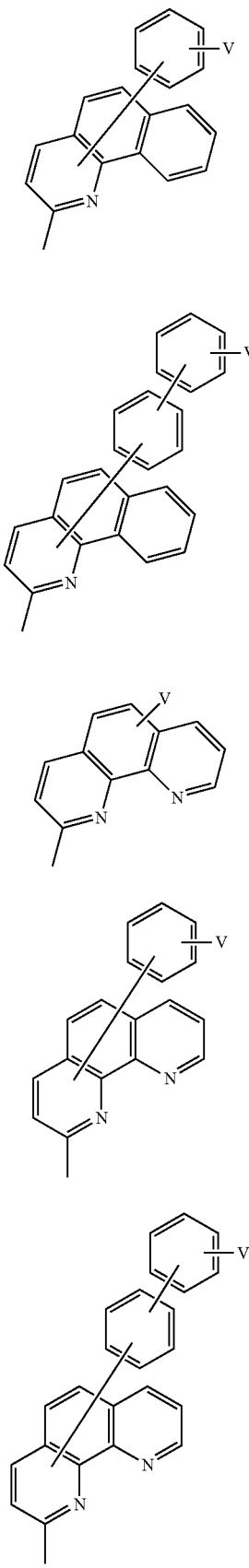

405
-continued
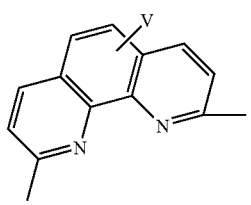
2-49
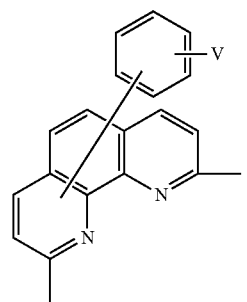
2-50
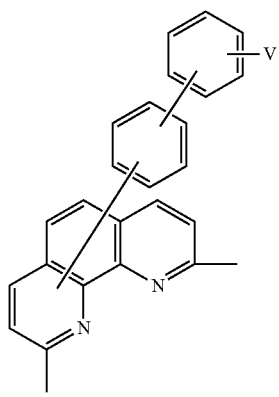
2-51
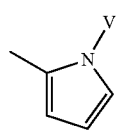
2-52
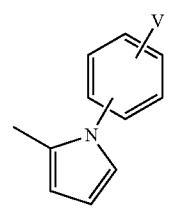
2-53
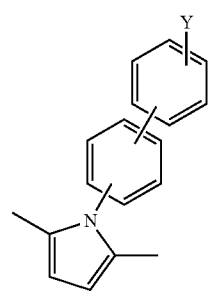
2-54
406
-continued
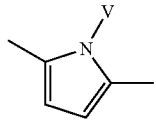
2-55
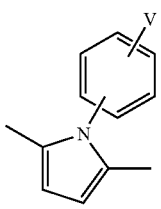
2-56
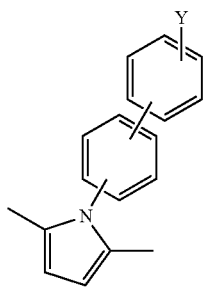
2-57
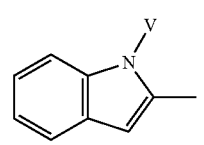
2-58
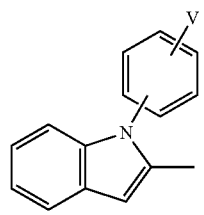
2-59
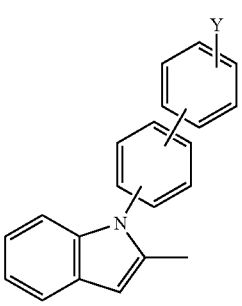
2-60
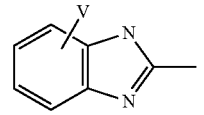
2-61
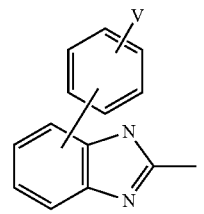
2-62

2-63
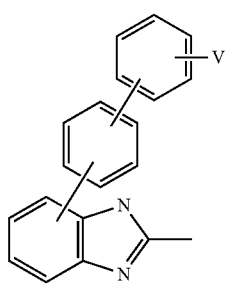
2-64
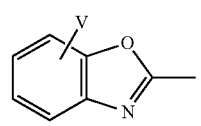
2-65
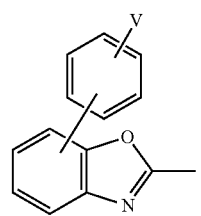
2-66
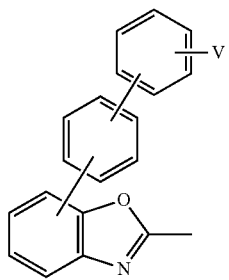
2-67
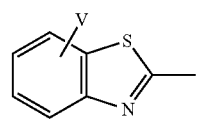
2-68
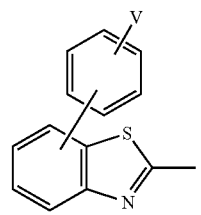
2-69
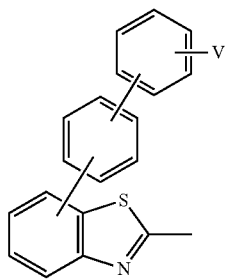
(V and W are as defined above.)
$Ar^1$, X and q in compound (3), are as defined above with respect to the above-mentioned $Ar^1$, X and q.
Compound (3) is not particularly limited and may, for example, be the following (3-1) to (3-84).
3-1
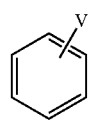
3-2
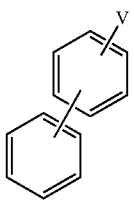
3-3
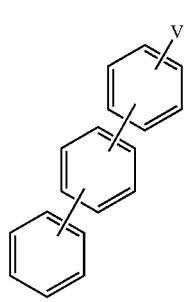
3-4
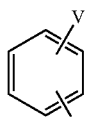
3-5
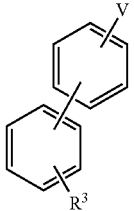
3-6
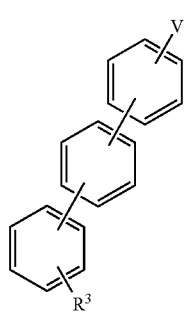
3-7
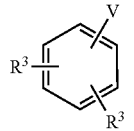

-continued
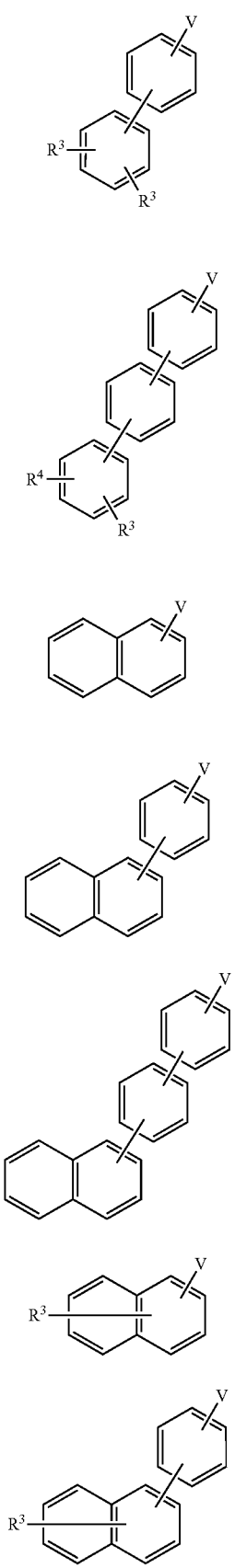
3-8
3-9
3-10
3-11
3-12
3-13
3-14
-continued
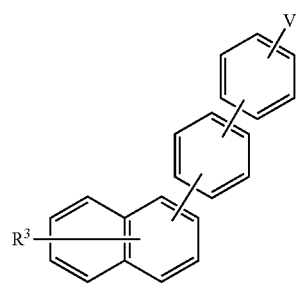
3-15
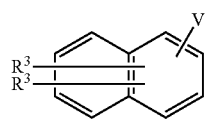
3-16
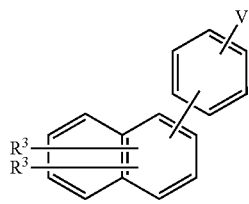
3-17
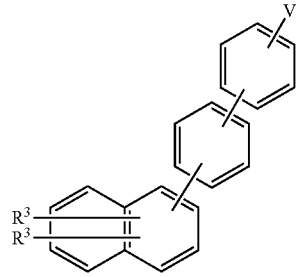
3-18
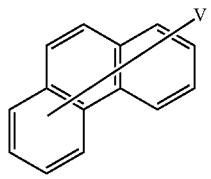
3-19
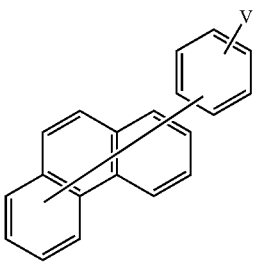
3-20

411
-continued
3-21
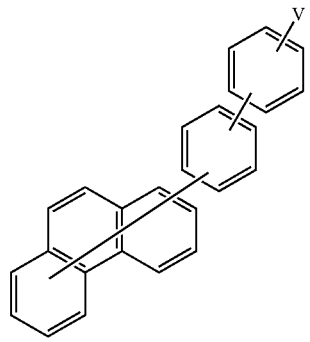
3-22
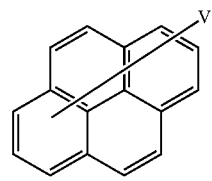
3-23
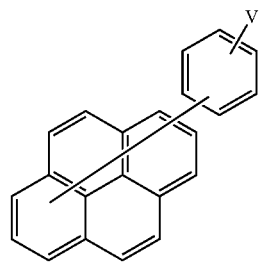
3-24
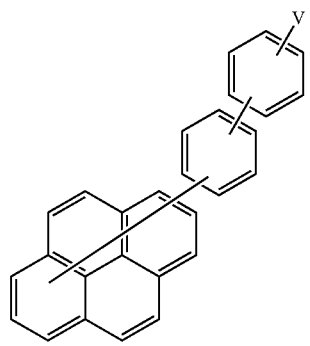
3-25
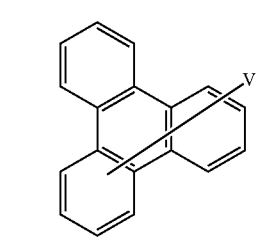
3-26
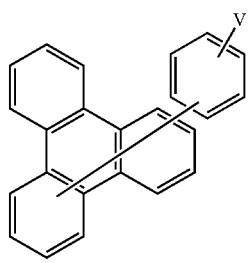
412
-continued
3-27
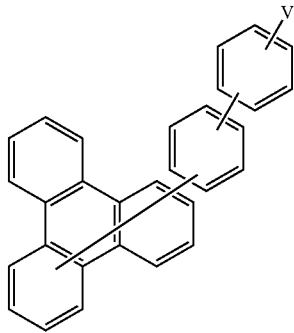
3-28
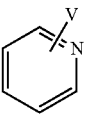
3-29
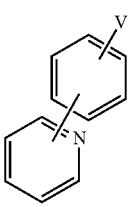
3-30
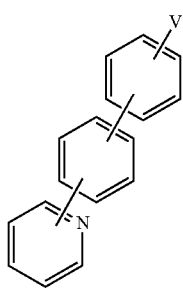
3-31
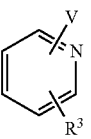
3-32
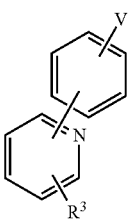
3-33
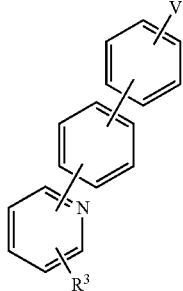

413
-continued
3-34
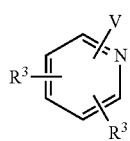
3-35
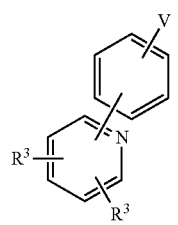
3-36
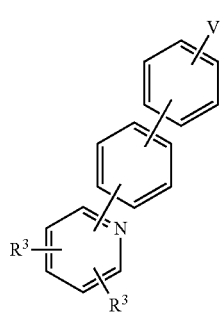
3-37
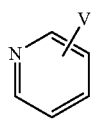
3-38
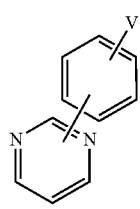
3-39
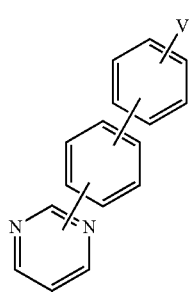
3-40
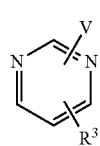
414
-continued
3-41
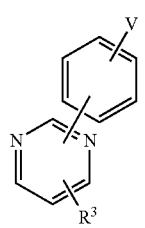
3-42
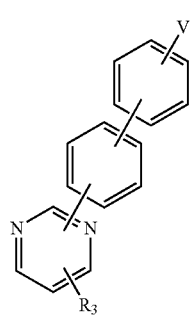
3-43
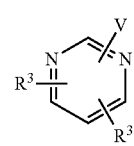
3-44
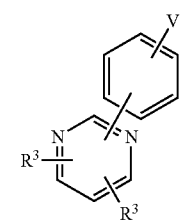
3-45
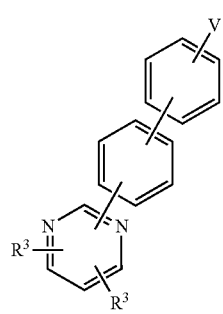
3-46
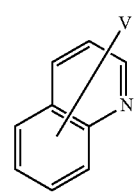

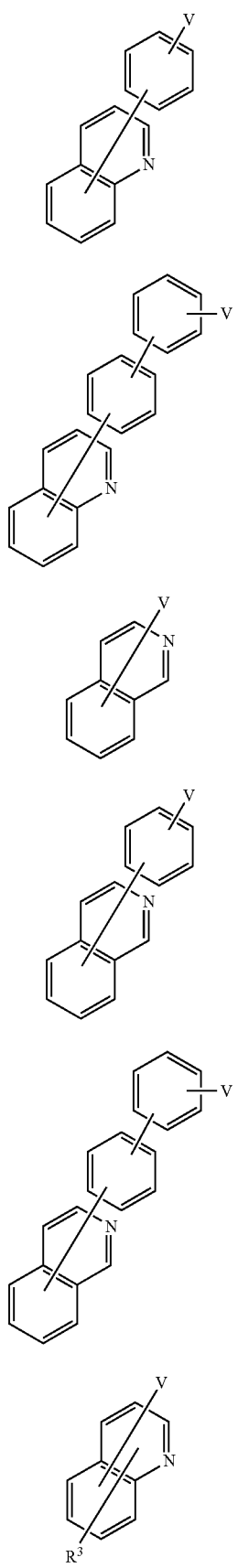
3-47
3-48
3-49
3-50
3-51
3-52
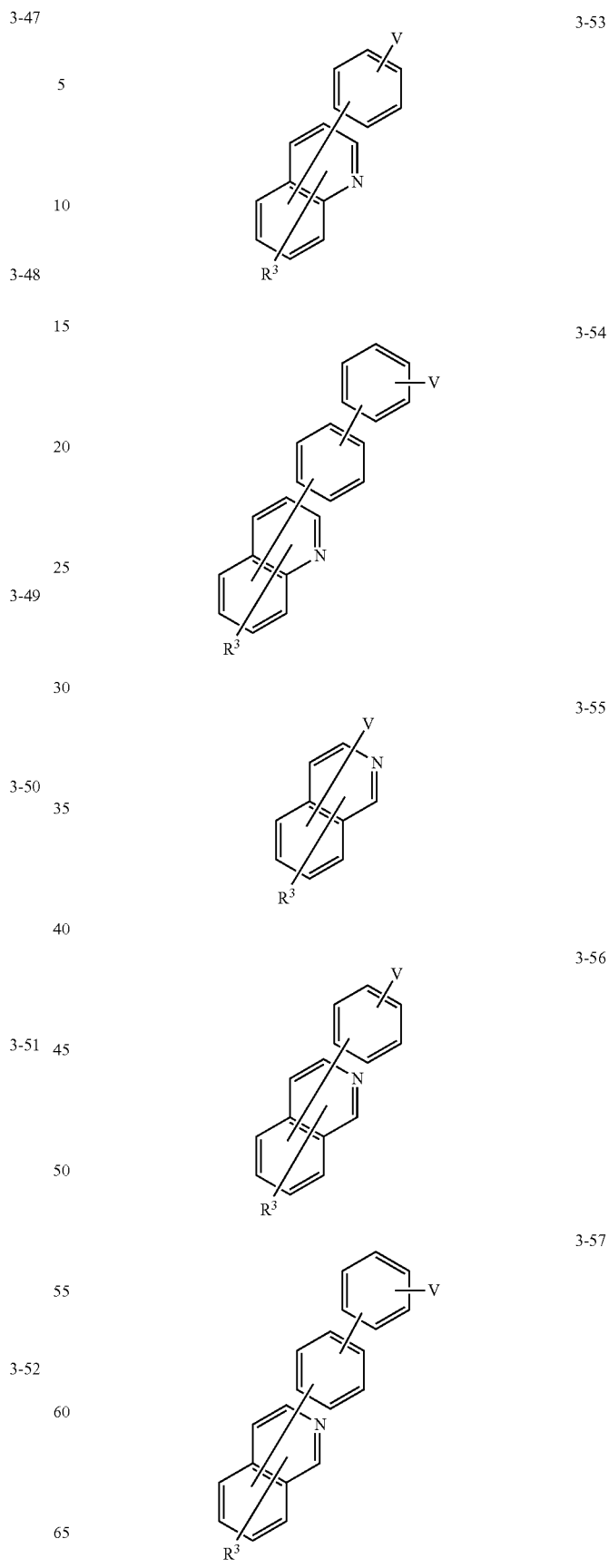
3-53
3-54
3-55
3-56
3-57

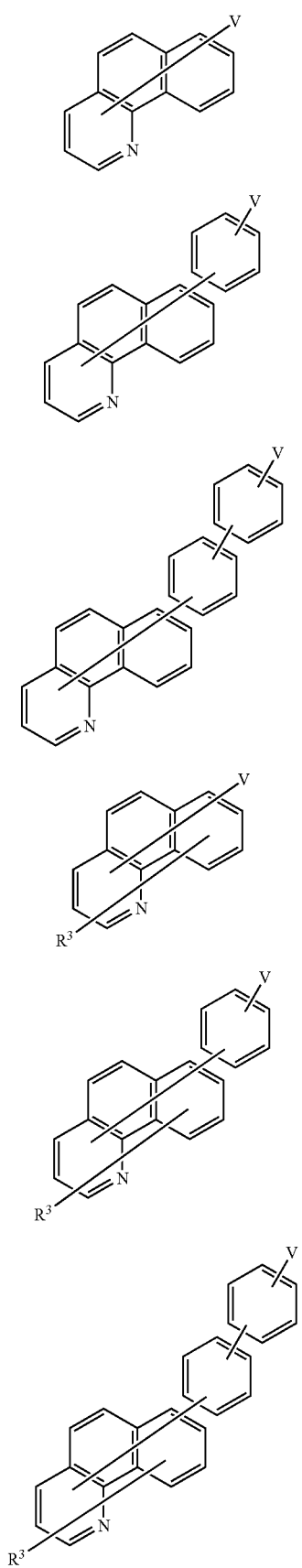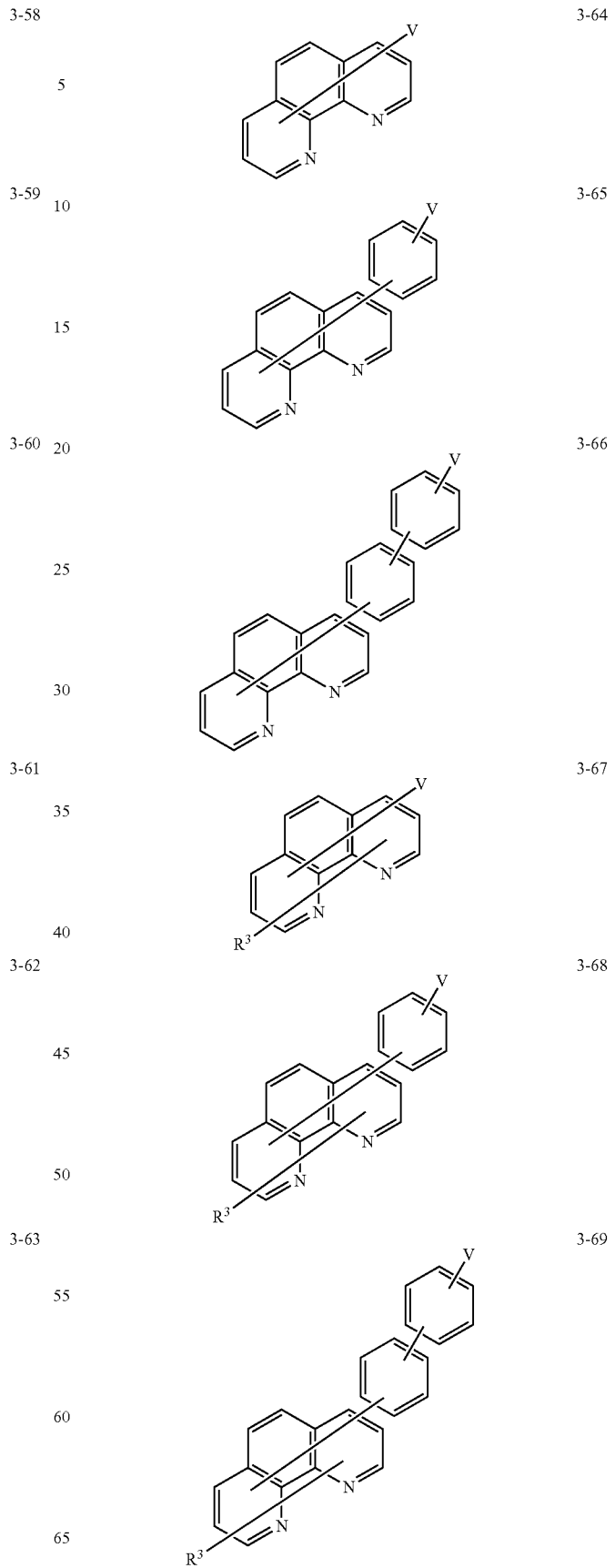

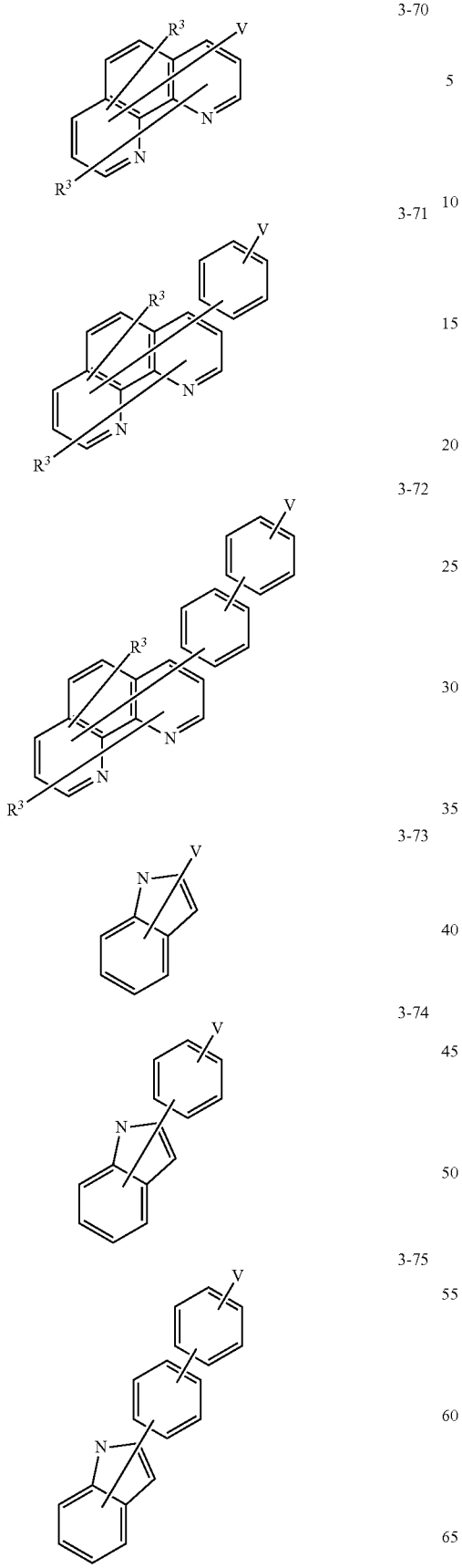

3-82

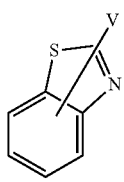

3-83

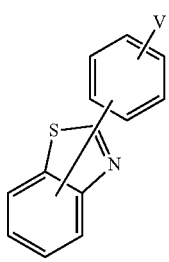

3-84

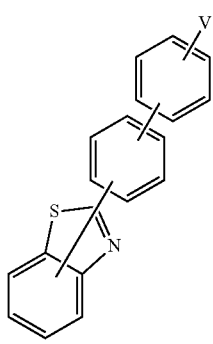

(Each R³ independently represents a $C_{1-4}$ alkyl group, and V and W are as defined above.)

In the reaction formula (1), compound (1) and compound (2) may firstly be reacted to form a reaction intermediate, which may then be reacted with compound (3) to synthesize a compound represented by the general formula (1). At that time, the reaction intermediate formed, may be isolated. Otherwise, compound (6) may be reacted to a product obtainable by reacting the reaction intermediate with the above-mentioned boronic acid compound or metal-containing group, to synthesize a compound represented by the general formula (1).

In the reaction formula (1), compound (1) and compound (3) may firstly be reacted to form a reaction intermediate, which may then be reacted with compound (2) to synthesize a compound represented by the general formula (1). At that time, the reaction intermediate formed, may be isolated. Otherwise, compound (5) may be reacted to a product obtainable by reacting the reaction intermediate with the above-mentioned boronic acid compound or metal-containing group, to synthesize a compound represented by the general formula (1). The amount of the palladium catalyst to be used in the reaction formula (1) is not particularly limited, so long as it is a so-called catalytic amount, but from the viewpoint of good yield, it is preferably from 0.1 to 0.01 time by mol (in terms of palladium atoms) per mol of compound (1).

The molar ratio of compound (1), compound (2) and compound (3) to be used in the reaction formula (1) is not particularly limited, but it is preferred that per mol of compound (1), compound (2) is preferably from 0.2 to 5 times by mol, and compound (3) is preferably from 0.2 to 5 times by mol.

The amount of the base to be used, is not particularly limited, but is preferably from 0.5 to 10 times by mol and in view of good yield, more preferably from 1 to 5 times by mol, per mol of compound (1).

Now, the reaction formula (2) will be explained.

Compound (4) may be produced by using the methods disclosed in e.g. Yamanaka Hiroshi, "New edition, Heterocyclic compounds. Fundamentals", Kodansha, 2004, Yamanaka Hiroshi, "New edition, Heterocyclic compound, Application Guide", Kodansha, 2004, or Chem. Rev., Vol. 95, 2457-2483, 1995.

Substituent C' in compound (4) is as defined above with respect to the above-mentioned substituent C'.

Compound (4) is not particularly limited and may, for example, be the following (4-1) to (4-12).

4-1

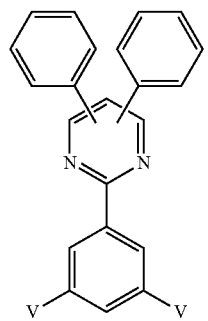

4-2

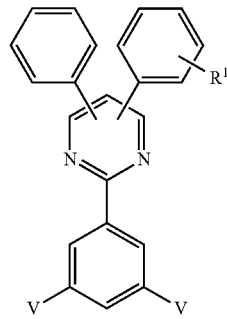

4-3

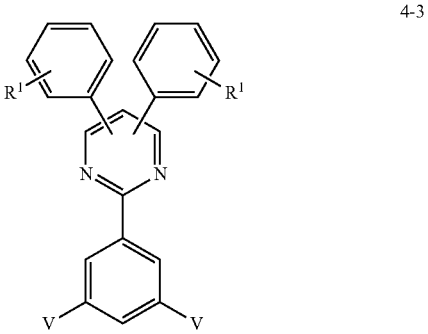

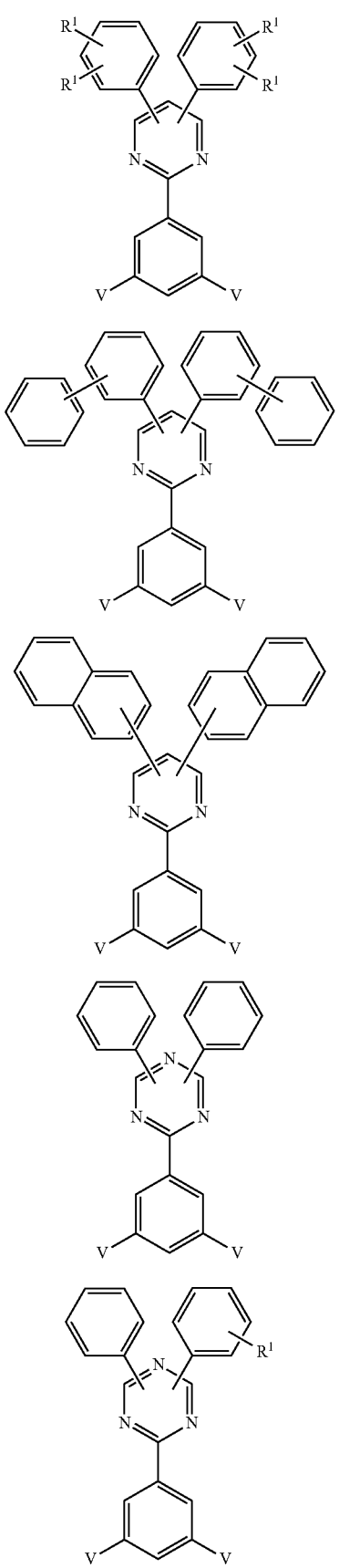
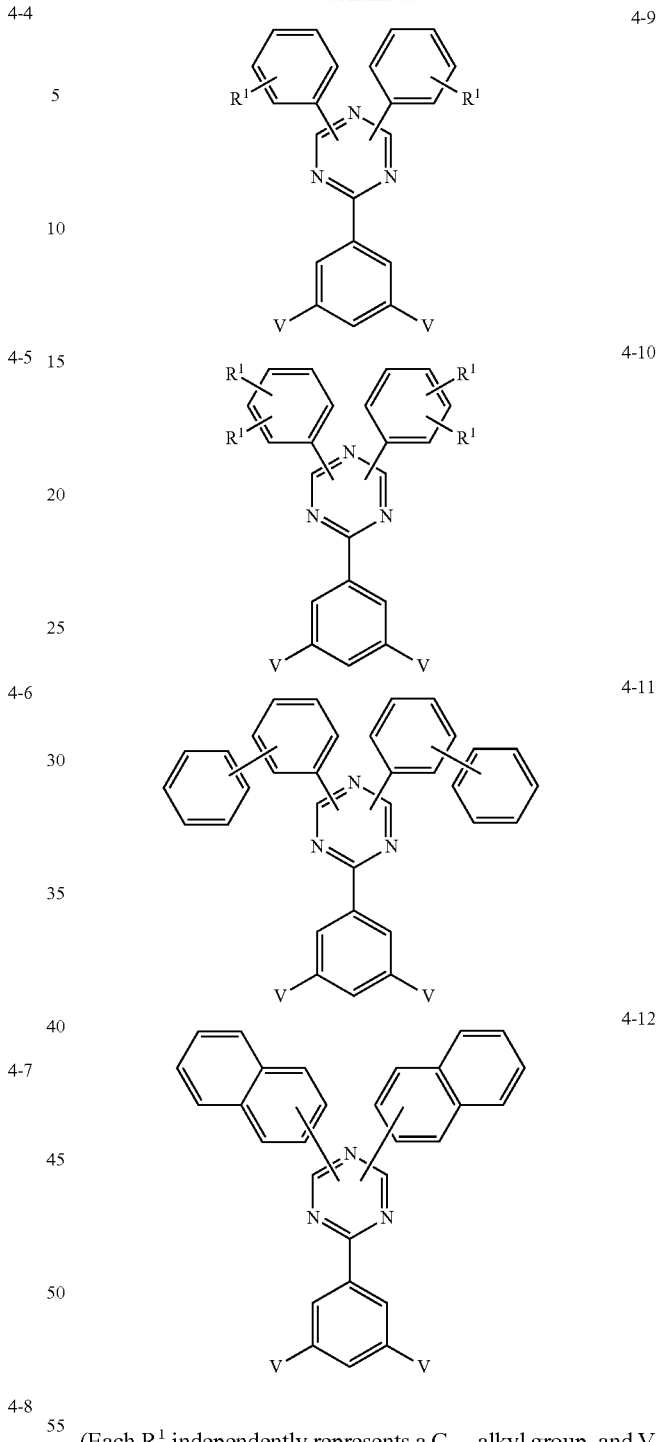

(Each R¹ independently represents a $C_{1-4}$ alkyl group, and V and W are as defined above.)

Compound (5) or compound (6) may be produced by using the method disclosed in, for example, The Journal of Organic Chemistry, 2001, 66, 4333-4339, or Chem. Rev., Vol. 95, 2457-2483, 1995.

Substituent B, X and p in compound (5), are as defined above with respect to the above-mentioned substituent B, X and p.

Compound (5) is not particularly limited and may, for example, be the following (5-1) to (5-69).

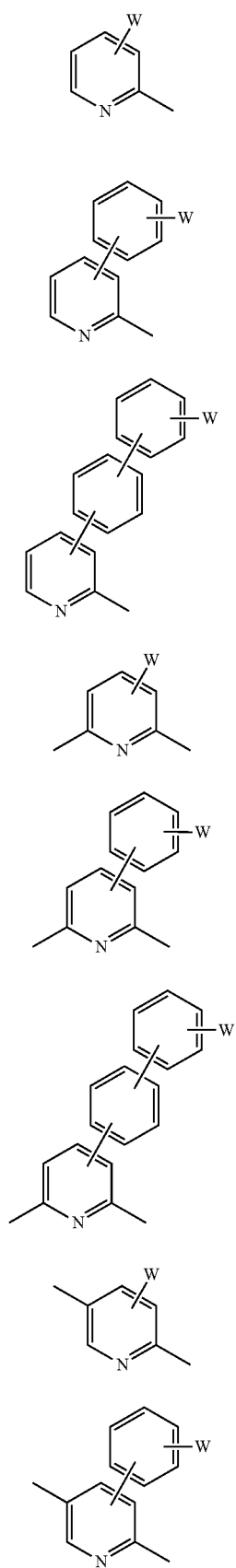
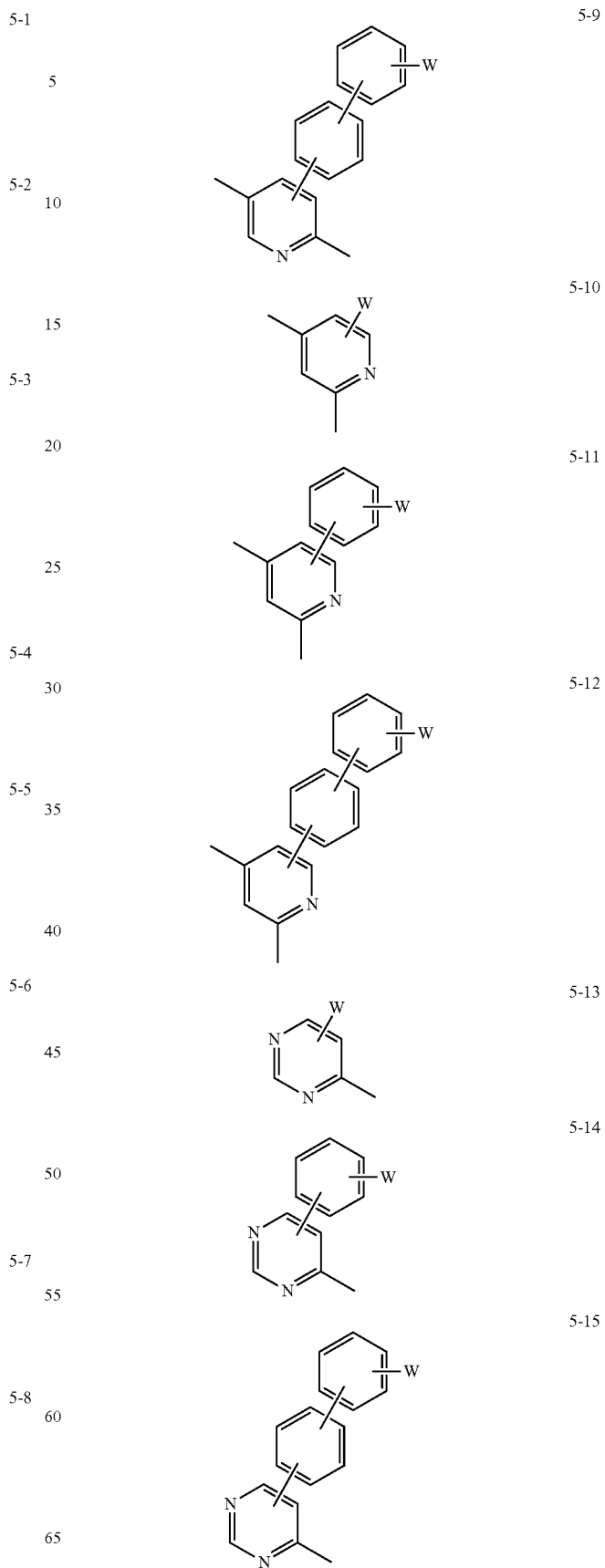

-continued
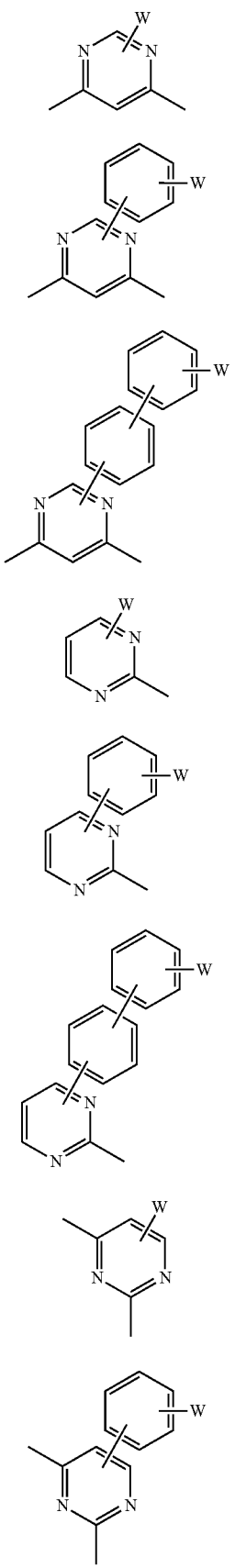
5-16
5-17
5-18
5-19
5-20
5-21
5-22
5-23
-continued
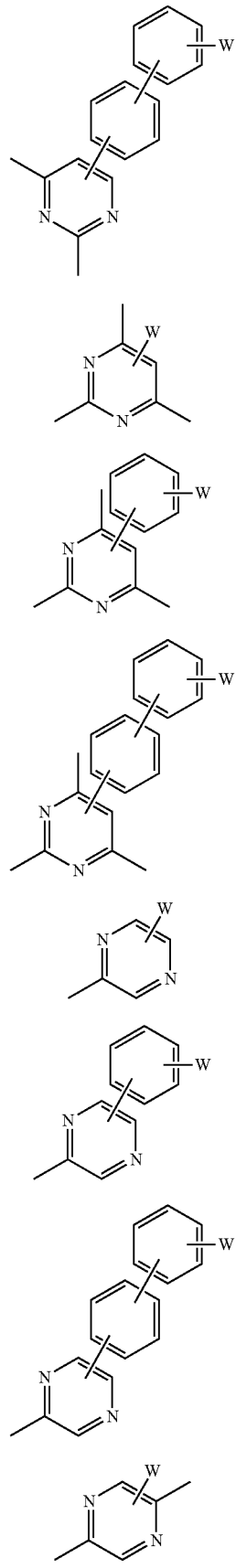
5-24
5-25
5-26
5-27
5-28
5-29
5-30
5-31

429
-continued
5-32
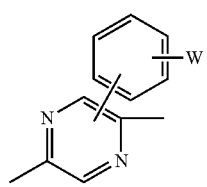
5-33
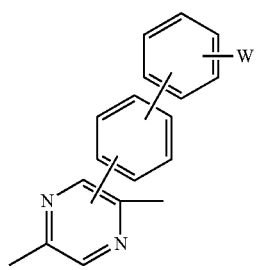
5-34
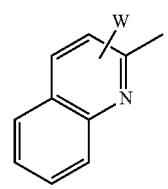
5-35
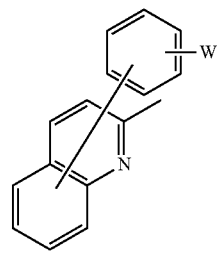
5-36
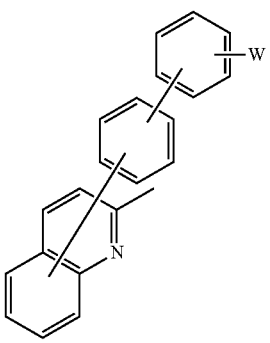
5-37
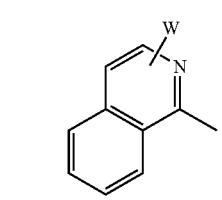
430
-continued
5-38
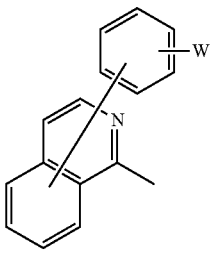
5-39
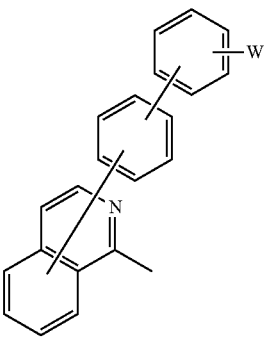
5-40
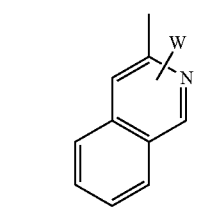
5-41
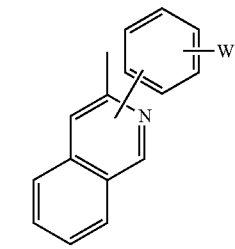
5-42
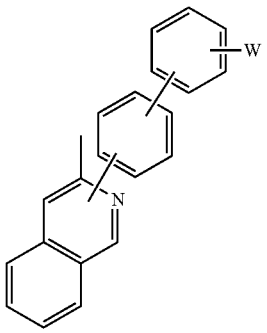
5-43
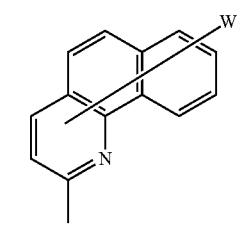

431
-continued
5-44
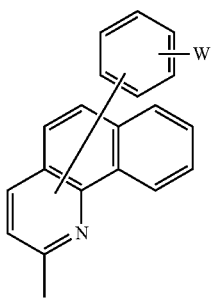
5-45
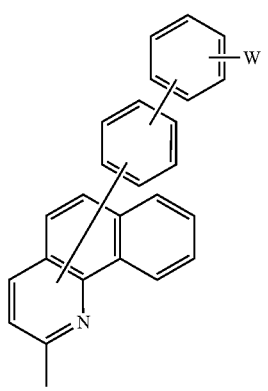
5-46
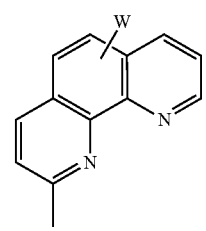
5-47
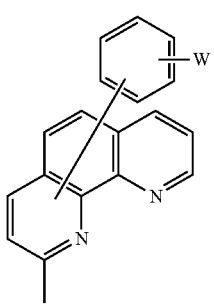
5-48
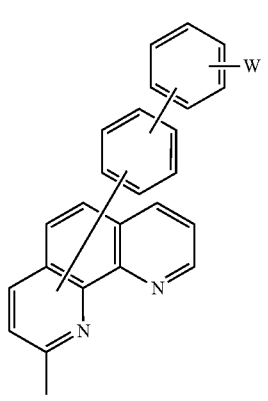
432
-continued
5-49
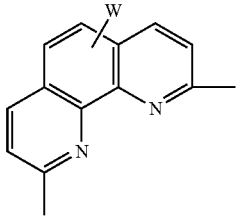
5-50
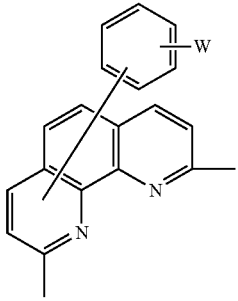
5-51
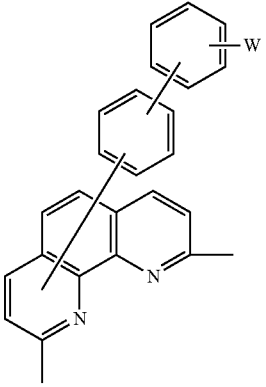
5-52
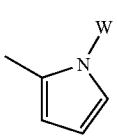
5-53
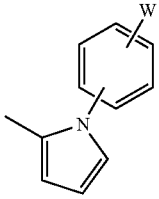
5-54
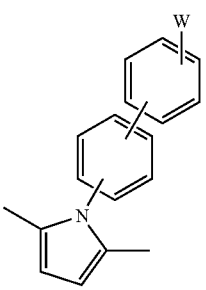

433
-continued
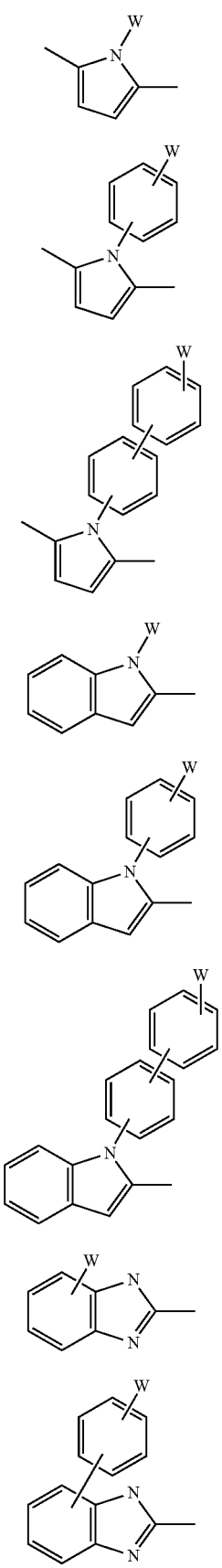
434
-continued
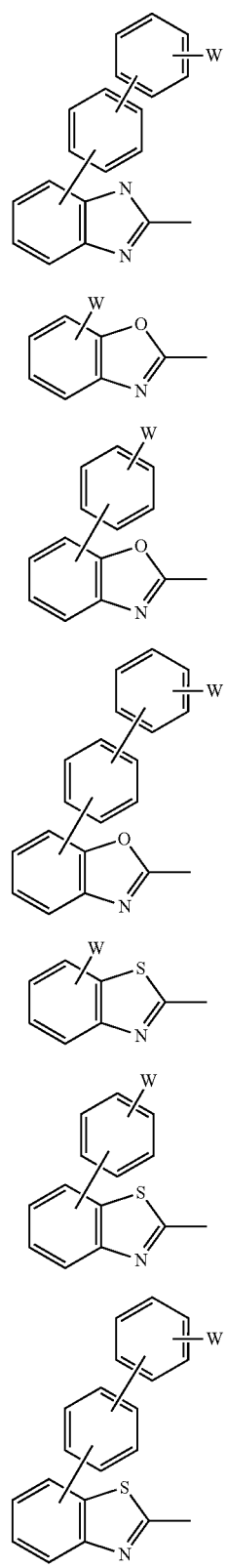
(V and W are as defined above.)
Ar¹, X and q in compound (6), are as defined above with respect to the above-mentioned Ar¹, X and q.

Compound (6) is not particularly limited and may, for example, be the following (6-1) to (6-84).
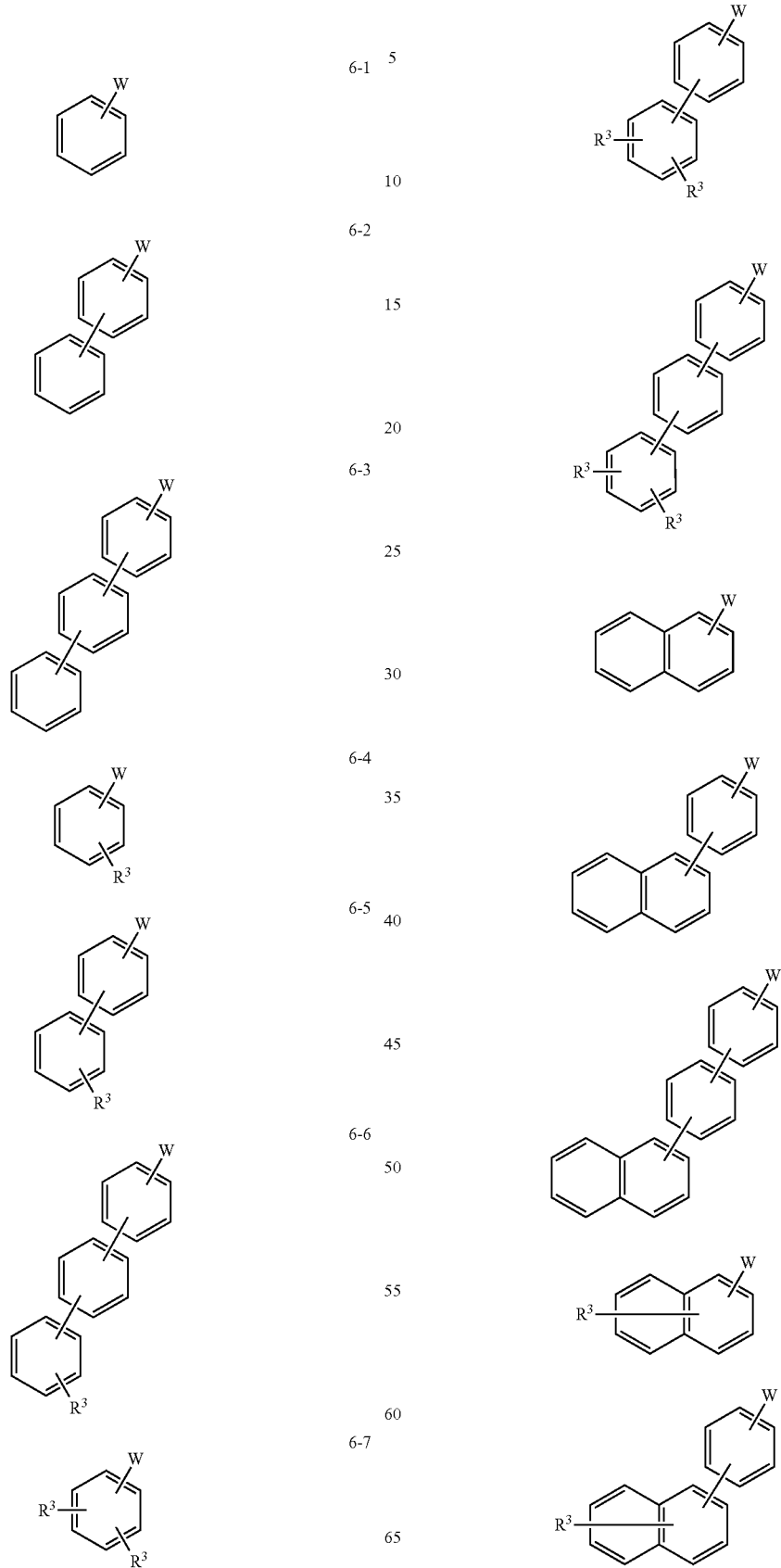

-continued 6-15

6-16

6-17

6-18

6-19

6-20

-continued 6-21

6-22

6-23

6-24

6-25

6-26

6-27
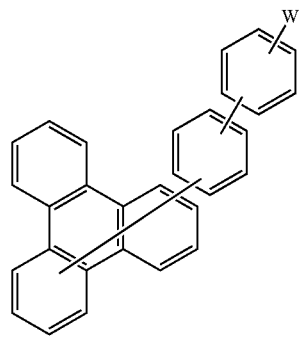
6-28
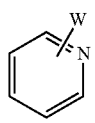
6-29
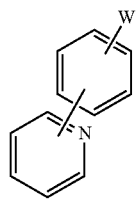
6-30
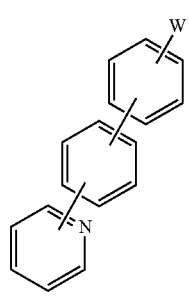
6-31
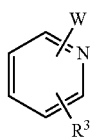
6-32
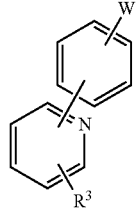
6-33
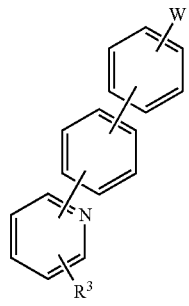
6-34
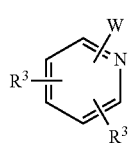
6-35
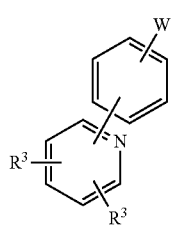
6-36
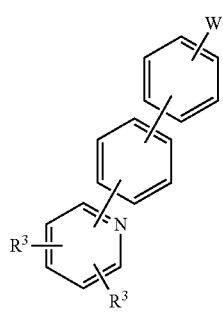
6-37
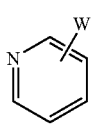
6-38
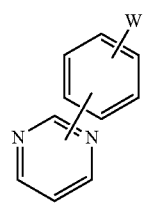
6-39
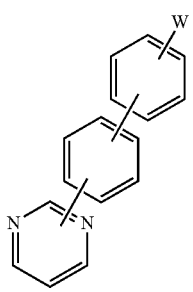
6-40
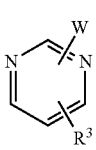

-continued
6-41 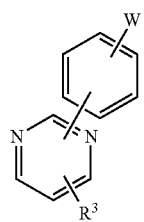
6-42 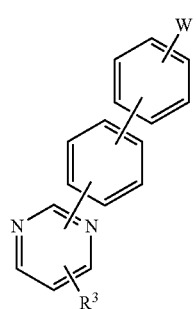
6-43 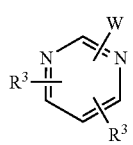
6-44 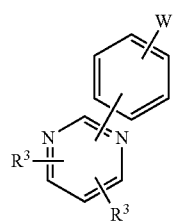
6-45 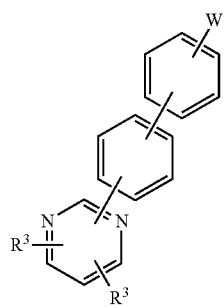
6-46 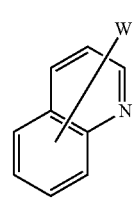
-continued
6-47 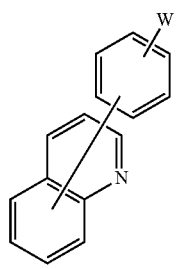
6-48 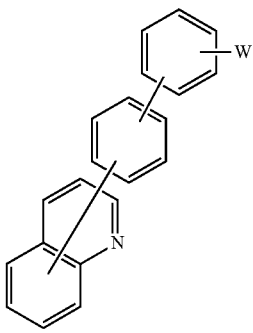
6-49 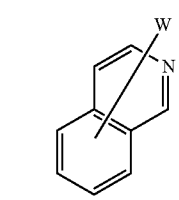
6-50 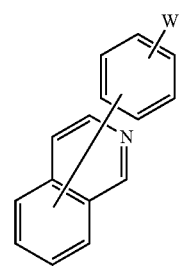
6-51 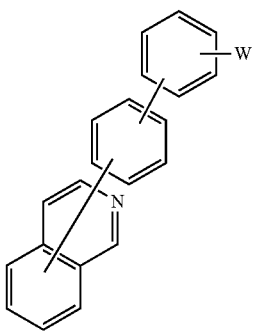
6-52 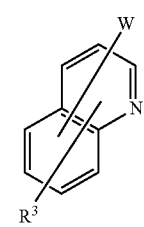

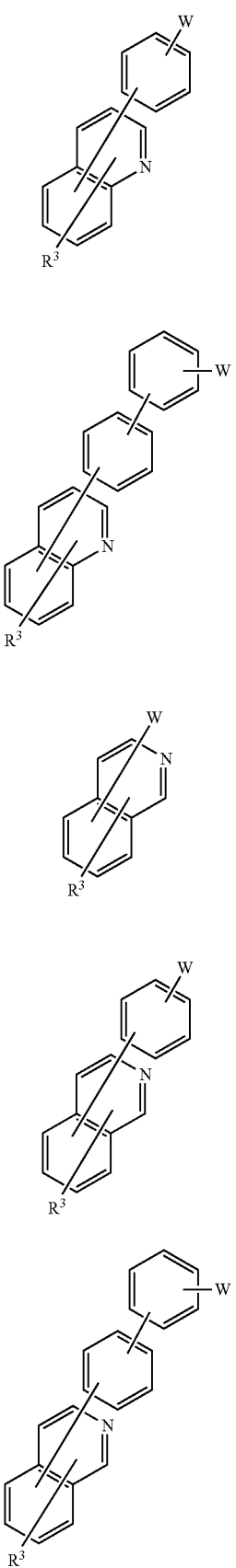
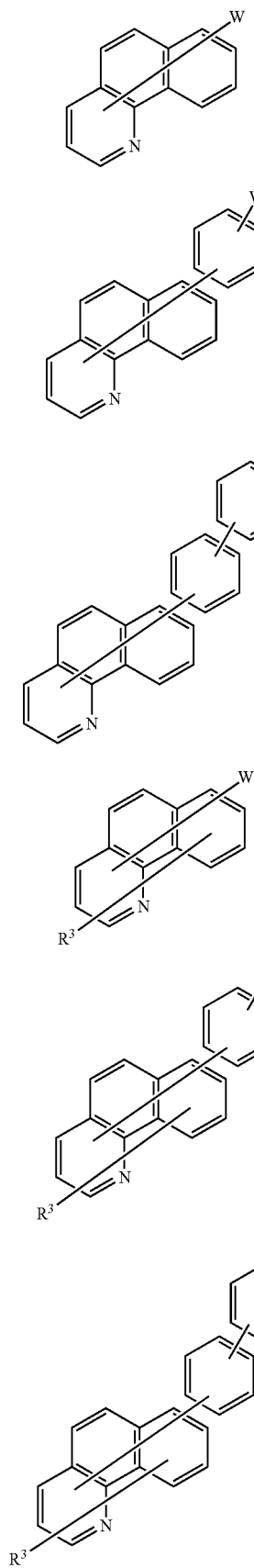

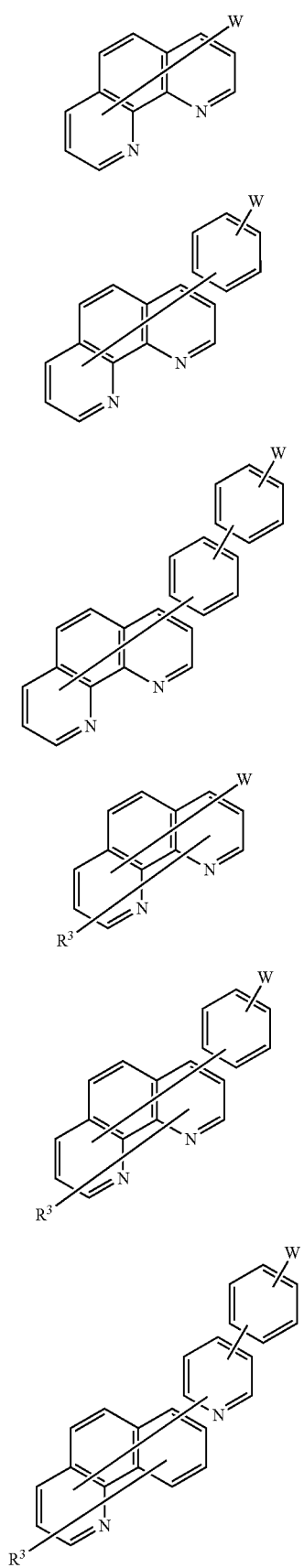
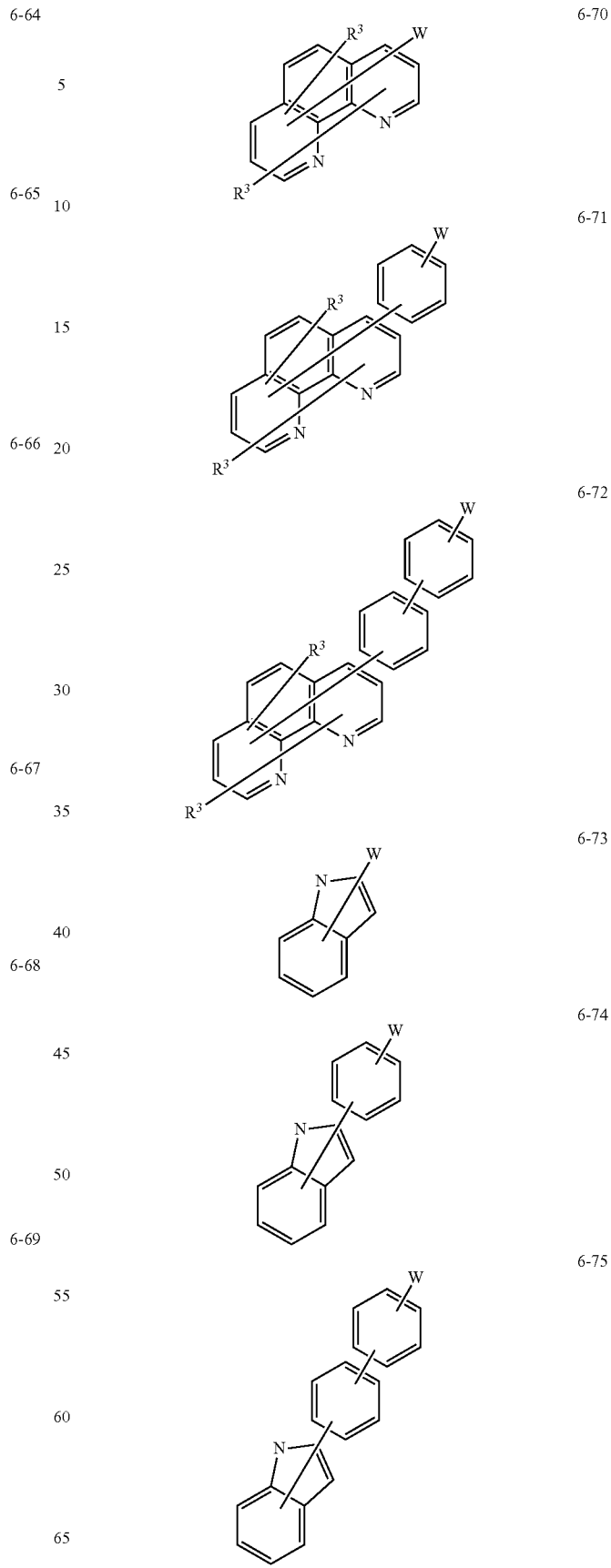

6-76 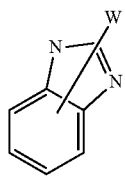

6-77 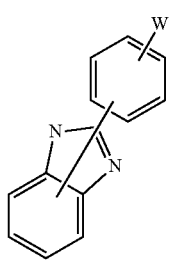

6-78 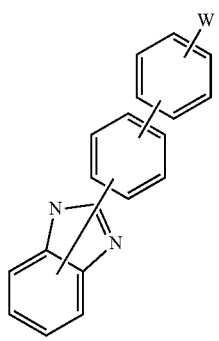

6-79 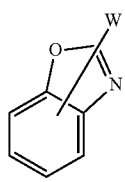

6-80 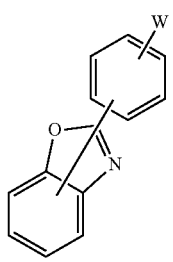

6-81 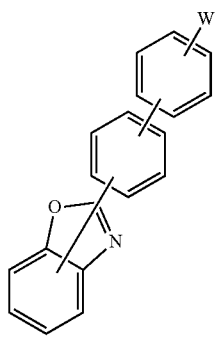

6-82 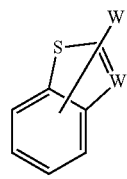

6-83 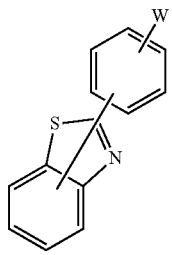

6-84 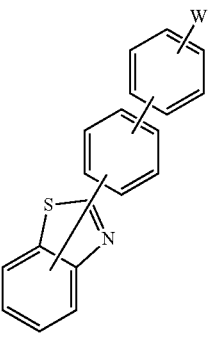

(Each $R^3$ independently represents a $C_{1-4}$ alkyl group, and V and W are as defined above.)

In the reaction formula (2), compound (4) and compound (5) may firstly be reacted to form a reaction intermediate, which may then be reacted with compound (6) to synthesize a compound represented by the general formula (1). At that time, the reaction intermediate formed, may be isolated.

In the reaction formula (2), compound (4) and compound (6) may firstly be reacted to form a reaction intermediate, which may then be reacted with compound (5) to synthesize a compound represented by the general formula (1). At that time, the reaction intermediate formed, may be isolated.

The amount of the palladium catalyst to be used in the reaction formula (2) is not particularly limited, so long as it is a so-called catalytic amount, but from the viewpoint of good yield, it is preferably from 0.1 to 0.01 time by mol (in terms of palladium atoms) per mol of compound (4).

The molar ratio of compound (4), compound (5) and compound (6) to be used in the reaction formula (2) is not particularly limited, but it is preferred that per mol of compound (4), compound (5) is preferably from 0.2 to 5 times by mol, and compound (6) is preferably from 0.2 to 5 times by mol.

The amount of the base to be used, is not particularly limited, but is preferably from 0.5 to 10 times by mol and, from the viewpoint of good yield, more preferably from 1 to 5 times by mol, per mol of compound (4).

Now, the reaction formula (3) will be explained.

Compound (7) may be produced by the same methods as for the above-mentioned compound (1).

Substituent C" in compound (7) is as defined above with respect to the above-mentioned substituent C".

Compound (7) is not particularly limited and may, for example, be the following (7-1) to (7-26).

-continued
7-1 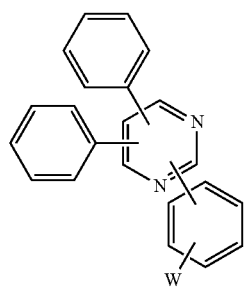
7-2 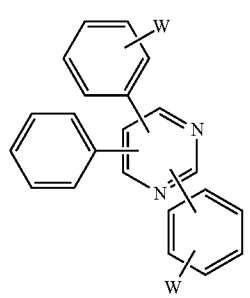
7-3 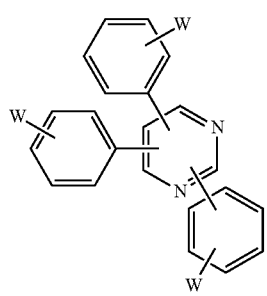
7-4 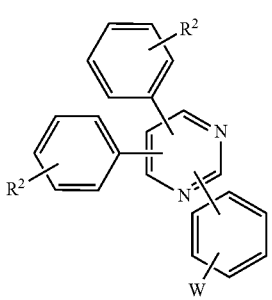
7-5 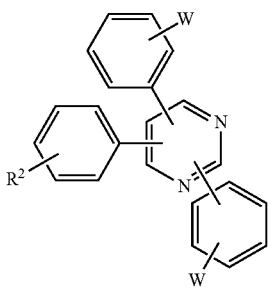
7-6 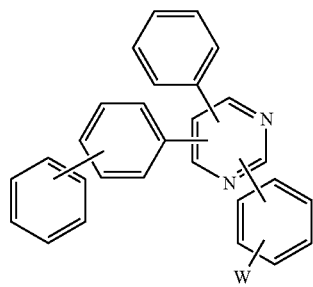
7-7 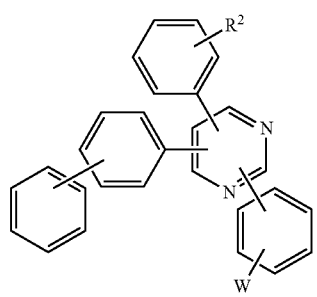
7-8 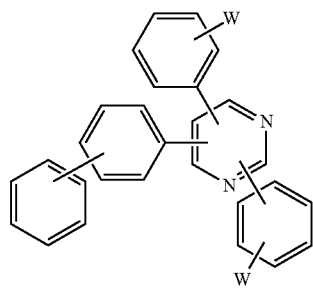
7-9 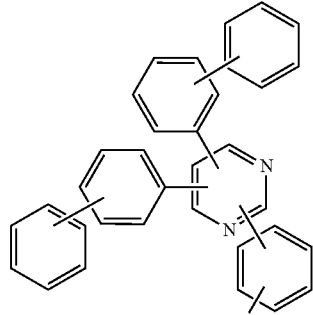
7-10 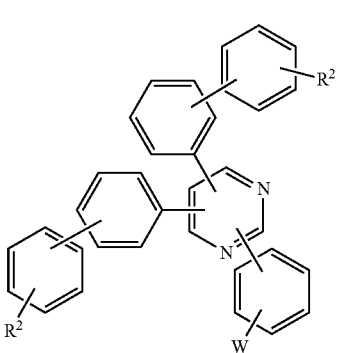

-continued
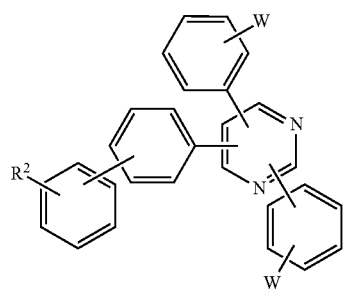
7-11
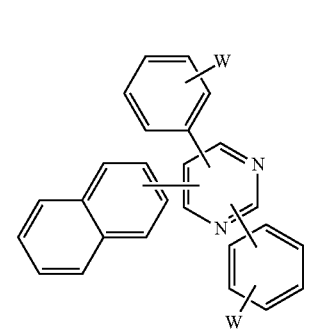
7-12
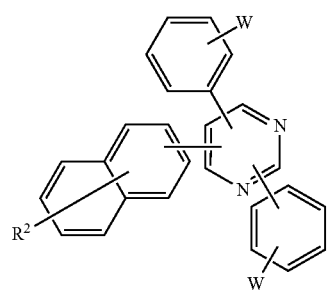
7-13
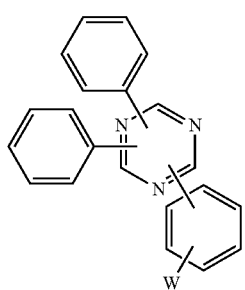
7-14
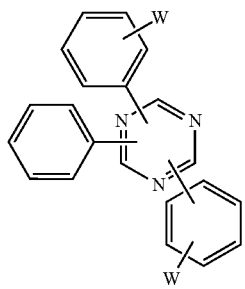
7-15
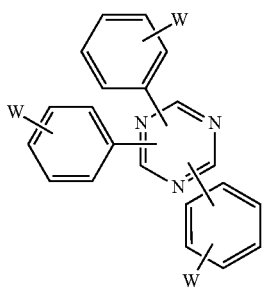
7-16
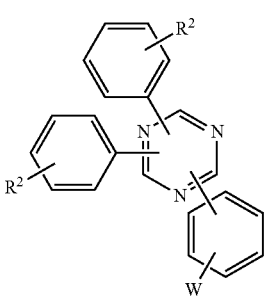
7-17
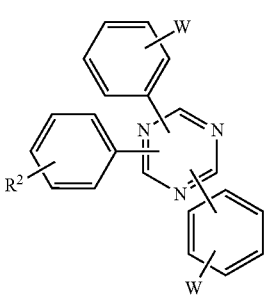
7-18
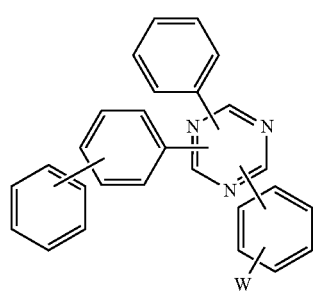
7-19
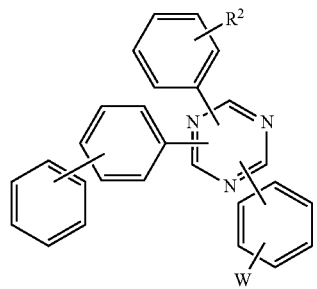
7-20

7-21 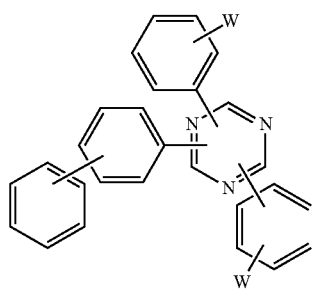

7-22 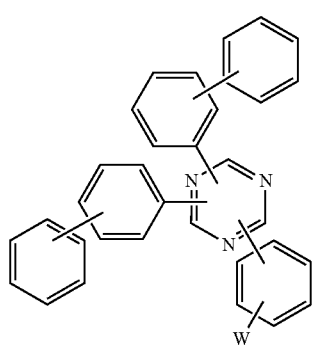

7-23 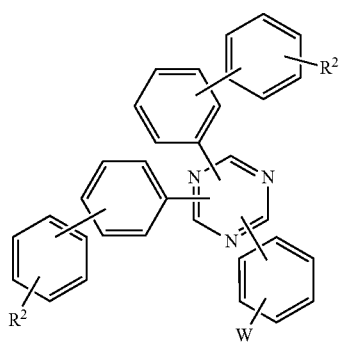

7-24 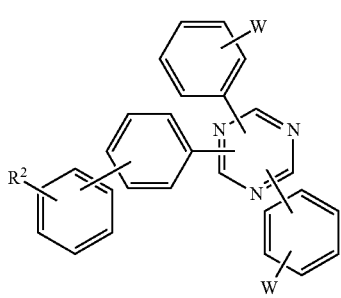

7-25 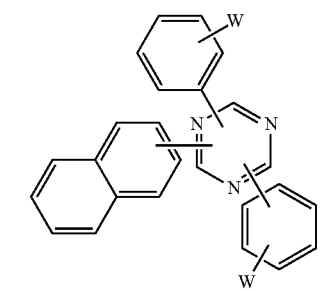

7-26 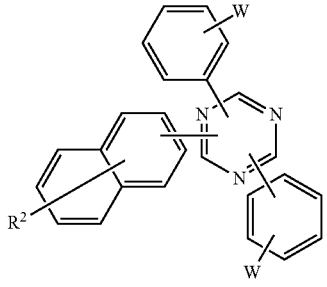

(Each $R^2$ independently represents a $C_{1-4}$ alkyl group, and V and W are as defined above.)

Compound (2') may be produced by the same method as for the above compound (2).

Substituent B, X and r in compound (2') are as defined above with respect to the above-mentioned substituent B, X and r.

Compound (2') is not particularly limited and may, for example, be the same compounds as for the above-mentioned compound (2).

The amount of the palladium catalyst to be used in the reaction formula (3) is not particularly limited, so long as it is a so-called catalytic amount, but from the viewpoint of good yield, it is preferably from 0.1 to 0.01 time by mol (in terms of palladium atoms) per mol of compound (7).

The molar ratio of compound (7) and compound (2') to be used in the reaction formula (3) is not particularly limited, but it is preferred that per mol of compound (7), compound (2') is preferably from 0.2 to 5 times by mol.

The amount of the base to be used, is not particularly limited, but is preferably from 0.5 to 10 times by mol and, from the viewpoint of good yield, more preferably from 1 to 5 times by mol, per mol of compound (7).

Now, the reaction formula (4) will be explained.

Compound (8) may be produced by the same methods as for the above-mentioned compound (4).

Substituent C" in compound (8) is as defined above with respect to the above-mentioned substituent C".

Compound (8) is not particularly limited and may, for example, be the following (8-1) to (8-26).

8-1 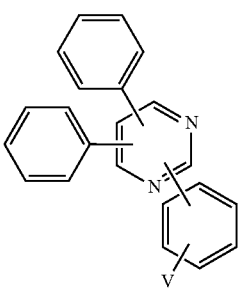

-continued 8-2

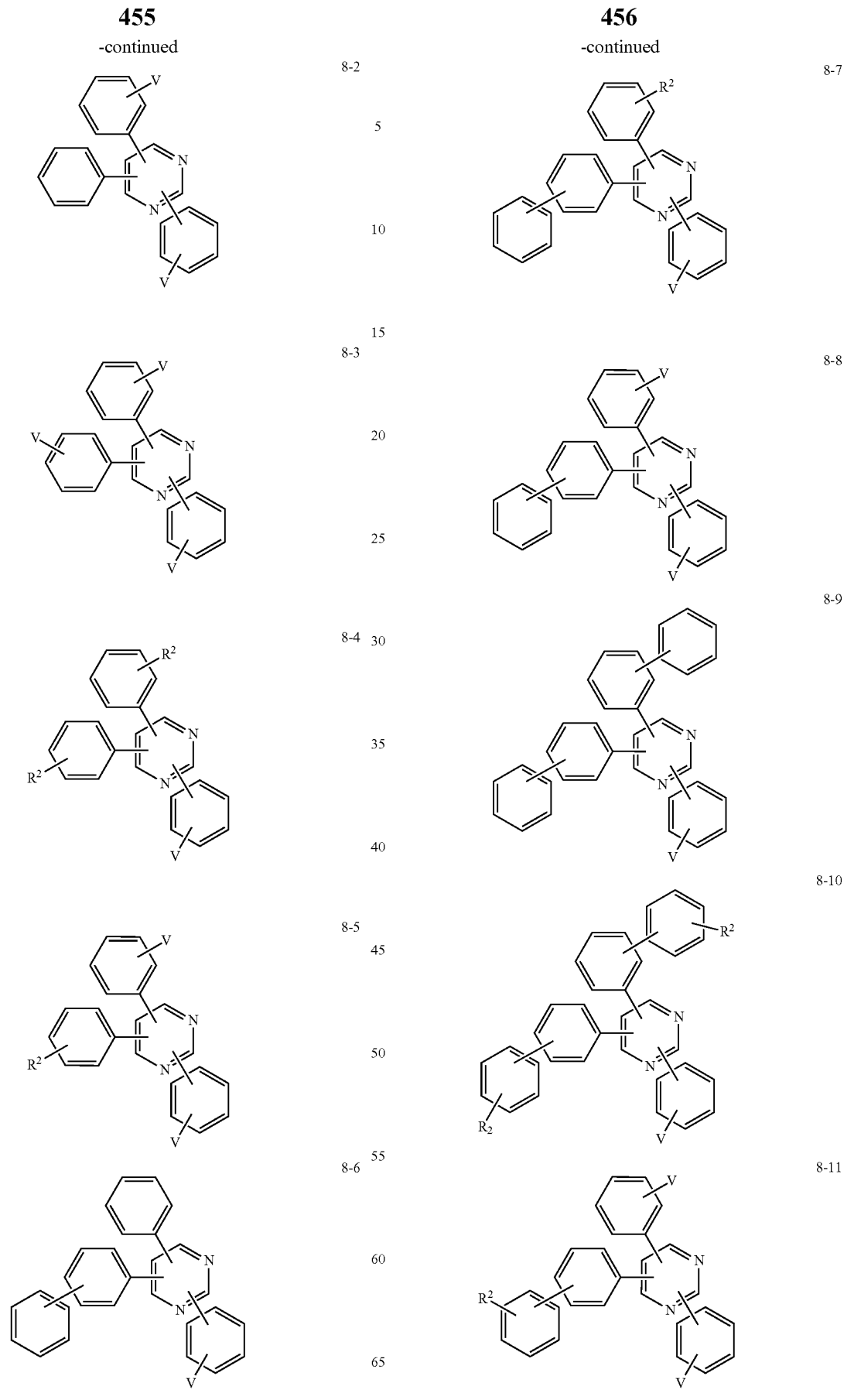

8-3

8-4

8-5

8-6

8-7

8-8

8-9

8-10

8-11

-continued
8-12
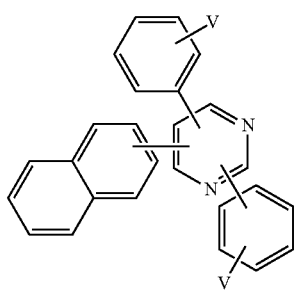
8-13
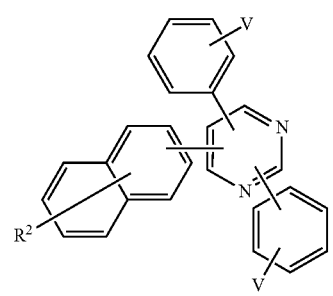
8-14
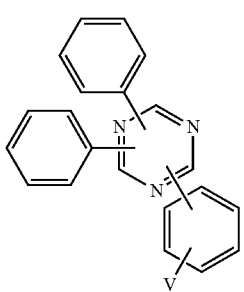
8-15
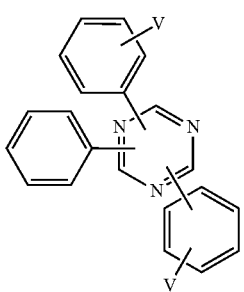
8-16
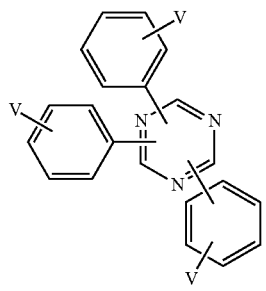
-continued
8-17
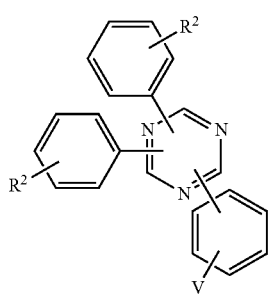
8-18
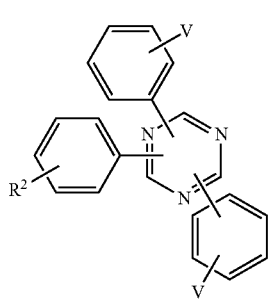
8-19
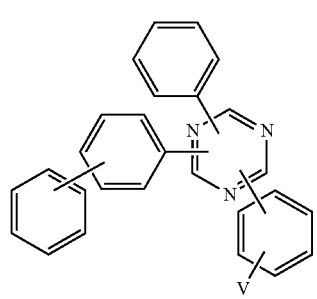
8-20
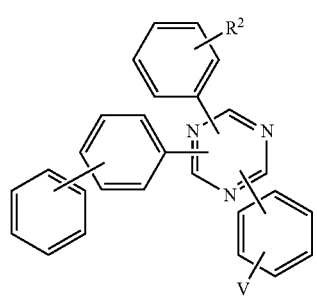
8-21
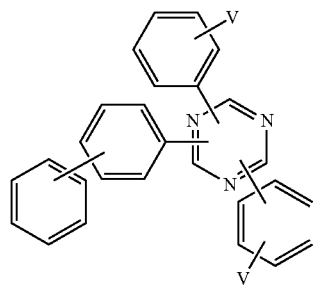

-continued

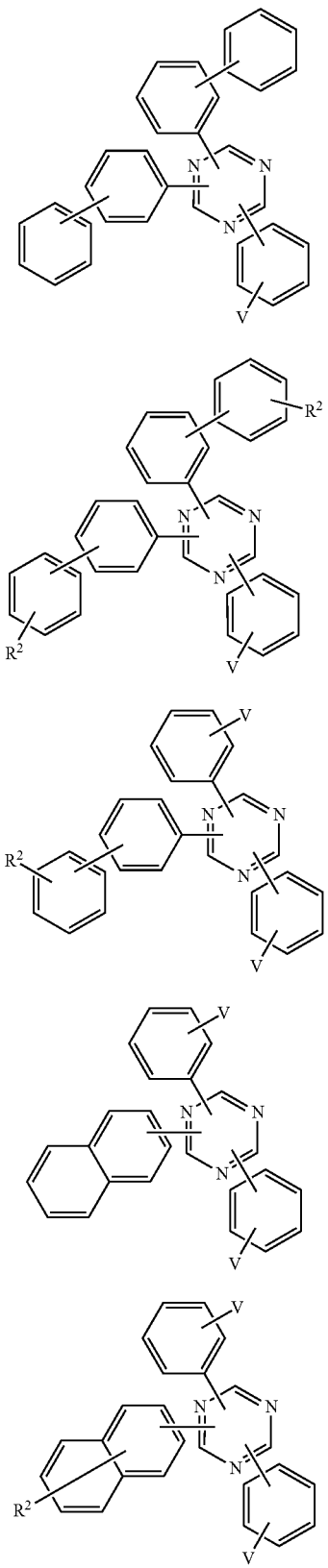

8-22

8-23

8-24

8-25

8-26

(Each $R^2$ independently represents a $C_{1-4}$ alkyl group, and V and W are as defined above.)

Compound (5') may be produced by the same method as for the above compound (5).

Substituent B, X and r in compound (5') are as defined above with respect to the above-mentioned substituent B, X and r.

Compound (5') is not particularly limited and may, for example, be the same compounds as for the above-mentioned compound (5).

The amount of the palladium catalyst to be used in the reaction formula (4) is not particularly limited, so long as it is a so-called catalytic amount, but from the viewpoint of good yield, it is preferably from 0.1 to 0.01 time by mol (in terms of palladium atoms) per mol of compound (8).

The molar ratio of compound (8) and compound (5') to be used in the reaction formula (4) is not particularly limited, but it is preferred that per mol of compound (8), compound (5') is preferably from 0.2 to 5 times by mol.

The amount of the base to be used, is not particularly limited, but is preferably from 0.5 to 10 times by mol and, from the viewpoint of good yield, more preferably from 1 to 5 times by mol, per mol of compound (8).

Now, the reaction formula (5) will be explained.

Compound (9) may be produced by the same methods as for the above-mentioned compound (1).

Substituent C" and $Ar^2$ in compound (9) are as defined above with respect to the above-mentioned substituent C" and $Ar^2$.

Compound (9) is not particularly limited and may, for example, be the following (9-1) to (9-12).

9-1

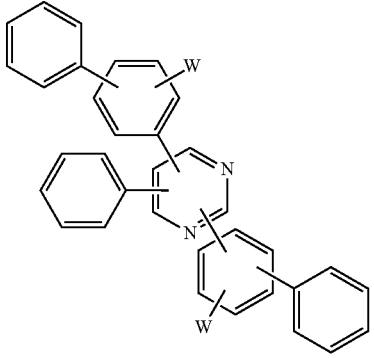

9-2

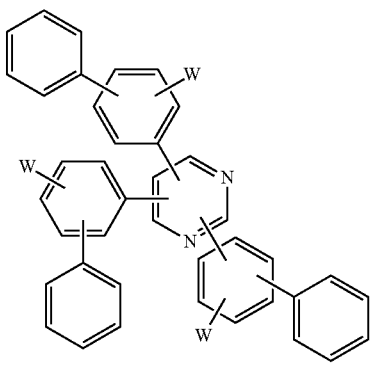

| | |
|---|---|
| 9-3 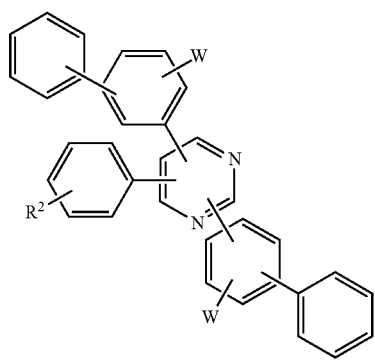 | 9-7 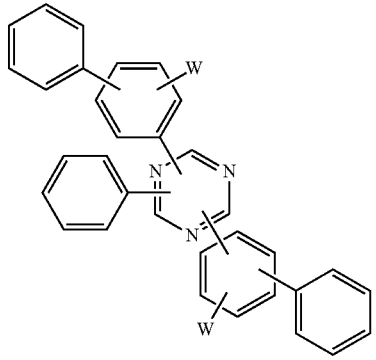 |
| 9-4 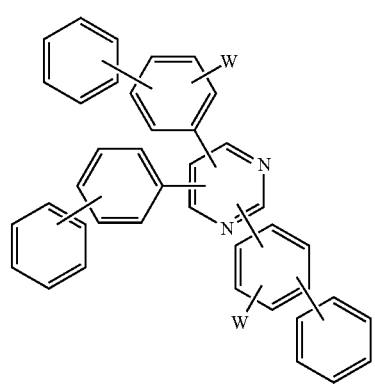 | 9-8 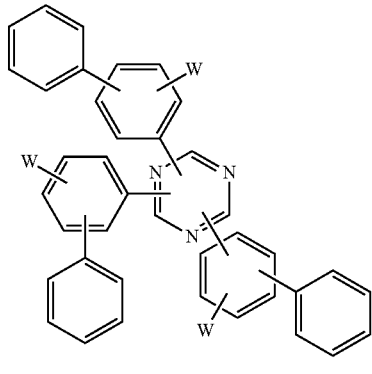 |
| 9-5 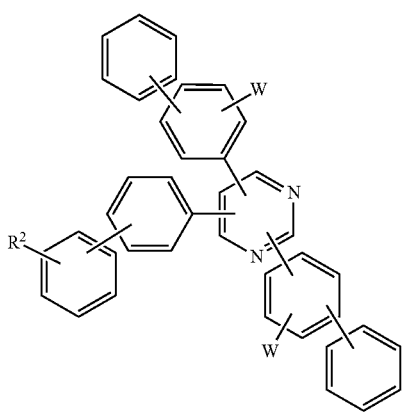 | 9-9 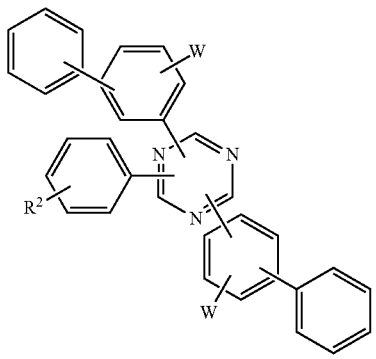 |
| 9-6 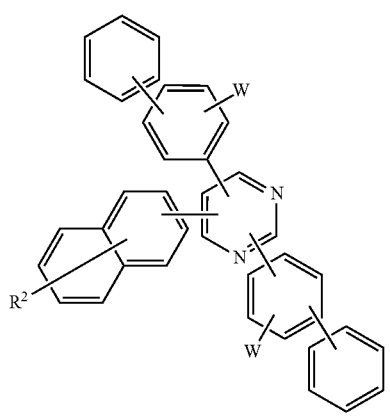 | 9-10 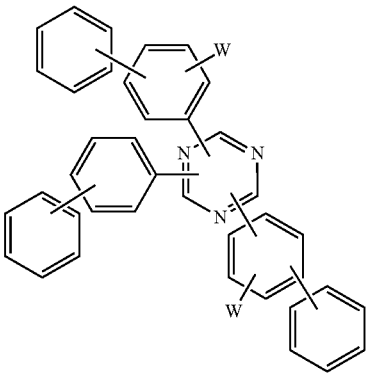 |

9-11

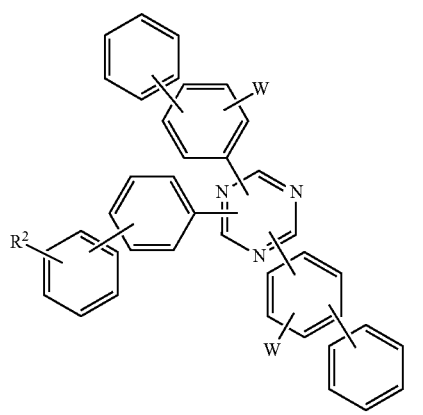

9-12

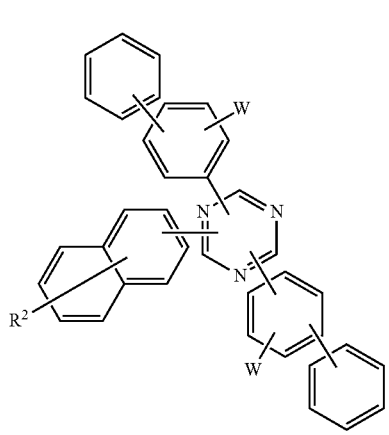

(Each R² independently represents a C₁₋₄ alkyl group, and V and W are as defined above.)

The amount of the palladium catalyst to be used in the reaction formula (5) is not particularly limited, so long as it is a so-called catalytic amount, but from the viewpoint of good yield, it is preferably from 0.1 to 0.01 time by mol (in terms of palladium atoms) per mol of compound (9).

The molar ratio of compound (9) and compound (2') to be used in the reaction formula (5) is not particularly limited, but it is preferred that per mol of compound (9), compound (2') is preferably from 0.2 to 5 times by mol.

The amount of the base to be used, is not particularly limited, but is preferably from 0.5 to 10 times by mol and, from the viewpoint of good yield, more preferably from 1 to 5 times by mol, per mol of compound (9).

Now, the reaction formula (6) will be explained.

Compound (10) may be produced by the same methods as for the above-mentioned compound (4).

Substituent C" and Ar² in compound (10) are as defined above with respect to the above-mentioned substituent C" and Ar².

Compound (10) is not particularly limited and may, for example, be the following (10-1) to (10-12).

10-1

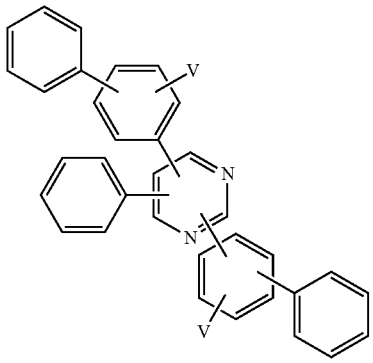

10-2

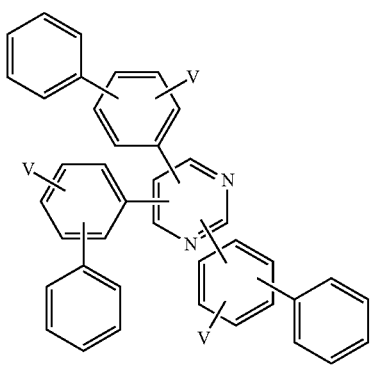

10-3

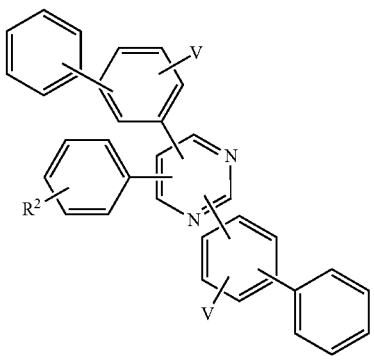

10-4

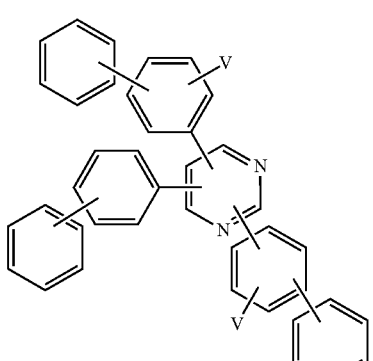

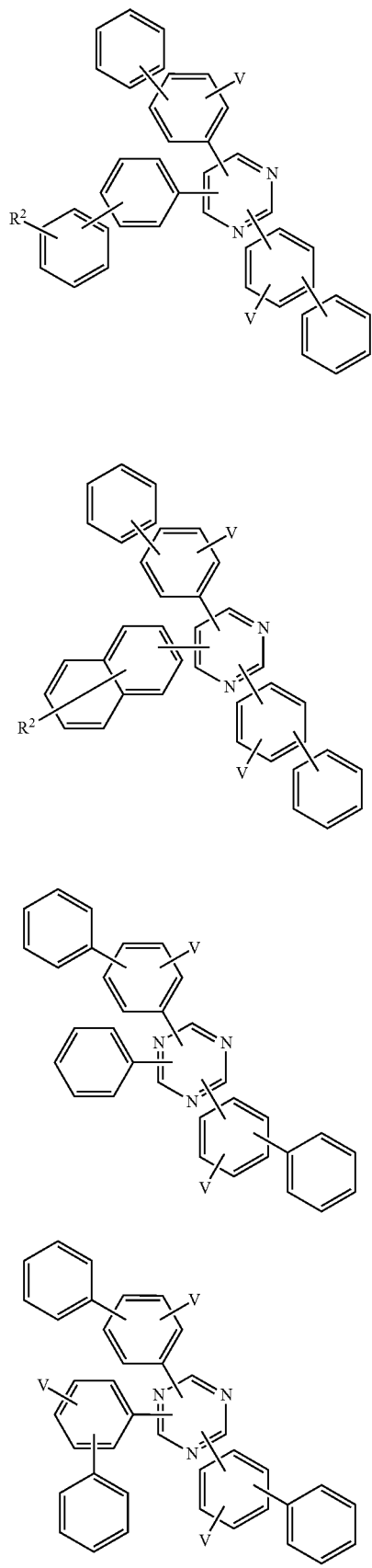
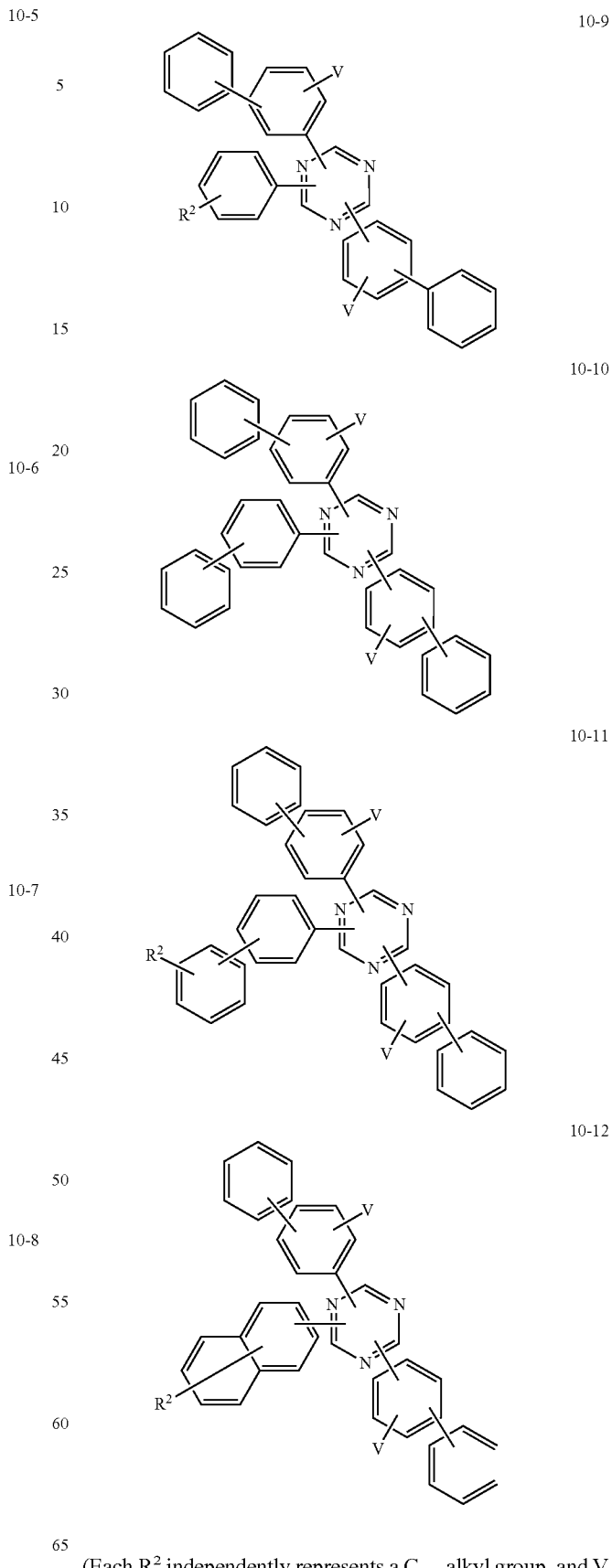
(Each R² independently represents a $C_{1-4}$ alkyl group, and V and W are as defined above.)

The amount of the palladium catalyst to be used in the reaction formula (6) is not particularly limited, so long as it is a so-called catalytic amount, but from the viewpoint of good yield, it is preferably from 0.1 to 0.01 time by mol (in terms of palladium atoms) per mol of compound (10).

The molar ratio of compound (10) and compound (5') to be used in the reaction formula (6) is not particularly limited, but it is preferred that per mol of compound (10), compound (5') is preferably from 0.2 to 5 times by mol.

The amount of the base to be used, is not particularly limited, but is preferably from 0.5 to 10 times by mol and, from the viewpoint of good yield, more preferably from 1 to 5 times by mol, per mol of compound (10).

Now, the reaction formula (7) will be explained.

Substituent B, C', D and Cz in compound (11) are as defined above with respect to the above-mentioned substituent B, C', D and Cz.

Compound (11) may be produced by the following reaction formula (11). Reaction formula (11)

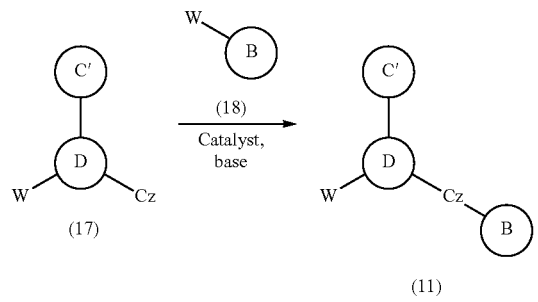

Substituent B, C', D and Cz in compound (17) are as defined above with respect to the above-mentioned substituent B, C', D and Cz.

W represents a leaving group and may, for example, be a chlorine atom, a bromine atom, a triflate group or an iodine atom. Among them, from the viewpoint of good reaction yield, a bromine atom or a chlorine atom is preferred.

Compound (17) may be produced by the same methods as for the above-mentioned compound (1).

As the catalyst which may be used for the reaction of the reaction formula (11), a palladium catalyst, a nickel catalyst, an iron catalyst, a copper catalyst, a ruthenium catalyst, a platinum catalyst, a rhodium catalyst, an iridium catalyst, an osmium catalyst, a cobalt catalyst, etc. may be exemplified. Among these, a copper catalyst is preferred from the viewpoint of good yield. As such a metal catalyst, it is possible to use a metal, a supported metal, a metal salt such as a chloride, a bromide, an iodide, a nitrate, a sulfate, a carbonate, an oxalate, an acetate or an oxide salt, or a complex compound such as an olefin complex, a phosphine complex, an amine complex, an ammine complex or an acetylacetonato complex. Moreover, such a metal, metal salt or complex compound may also be used in combination with a tertiary phosphine ligand.

The copper catalyst which may be used in the reaction of the reaction formula (11), is not particularly limited and may, for example, be copper(I) oxide, copper(II) oxide, copper(I) iodide, copper(II) iodide, copper(I) bromide, copper(II) bromide, copper(I) chloride, copper(II) chloride, copper(I) acetate, copper(II) acetate (II), copper(II) sulfate, copper(I) cyanide (I) or copper(II) cyanide (II), and among them, copper(I) oxide is preferred from the viewpoint of good yield.

In the reaction of the reaction formula (11), a diamine ligand may be added.

The diamine ligand which may be used for the reaction of the reaction formula (11) is not particularly limited and may, for example, be 1,10-phenanthroline or trans-1,2-cyclohexanediamine. Among these, 1,10-phenanthroline is preferred from the viewpoint of a good yield.

In the reaction of the reaction formula (11), a phase transfer catalyst represented by 18-crown-6-ether may be added.

In the reaction formula (11), the base which may be used, is not particularly limited and may, for example, be sodium hydroxide, potassium hydroxide, sodium carbonate, potassium carbonate, lithium carbonate, cesium carbonate, potassium acetate, sodium acetate, potassium phosphate, sodium phosphate, sodium fluoride, potassium fluoride or cesium fluoride. Among these, from the viewpoint of good yield, potassium carbonate is preferred.

The reaction of the reaction equation (11) is preferably carried out in a solvent. The solvent is not particularly limited and may, for example, be water, dimethyl sulfoxide, dimethylformamide, tetrahydrofuran, toluene, benzene, diethyl ether, 1,4-dioxane, ethanol, butanol or xylene, and these may suitably be used in combination. Among these, from the viewpoint of good yield, xylene is preferred.

The amount of the catalyst to be used in the reaction formula (11) is not particularly limited as long as it is a so-called catalytic amount, and from the viewpoint of good yield, it is preferably from 0.1 to 0.01 times by mol (in terms of metal atom) per mol of compound (17).

The amount of the diamine ligand to be used, is preferably 0.01 to 10 times by mol and from the viewpoint of good yield, more preferably from 0.02 to 2 times mol, per mol of compound (17), The amount of the phase transfer catalyst to be used, is preferably from 0.1 to 10 times by mol and from the viewpoint of good yield, more preferably from 0.2 to 2 times by mol, per mol of compound (17).

The molar ratio of compound (17) and compound (18) to be used in the reaction formula (11) is not particularly limited, but it is preferred that per mol of compound (17), compound (18) is from 0.2 to 5 times by mol.

The amount of the base to be used, is not particularly limited and is preferably from 0.5 to 10 times by mol and from the viewpoint of good yield, more preferably from 1 to 5 times by mol, per mole of the compound (17).

Compound (11) is not particularly limited and may, for example, be the following (11-1) to (11-24).

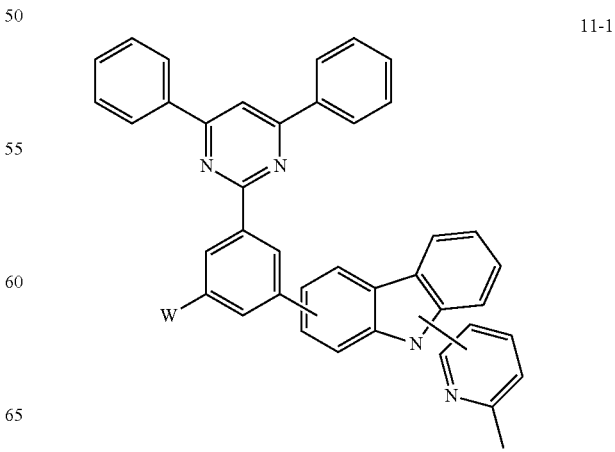

11-1

469
-continued
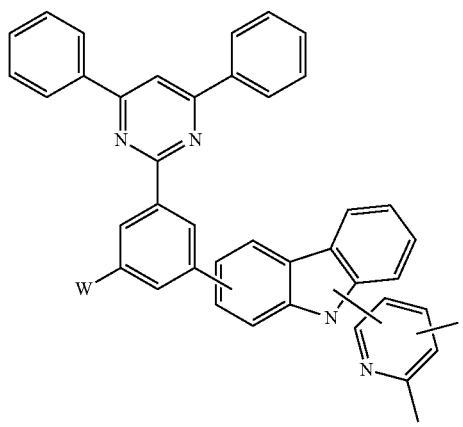
11-2
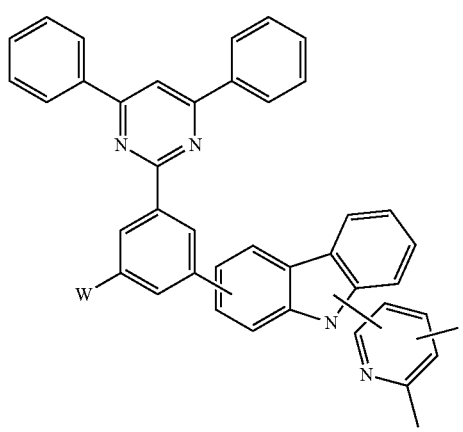
11-3
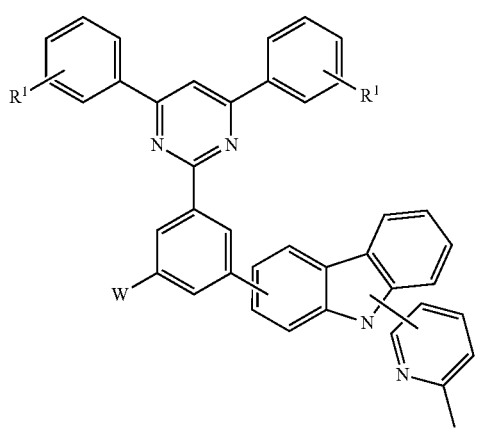
11-4
470
-continued
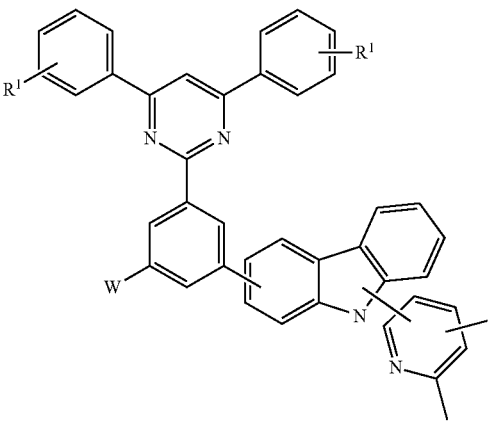
11-5
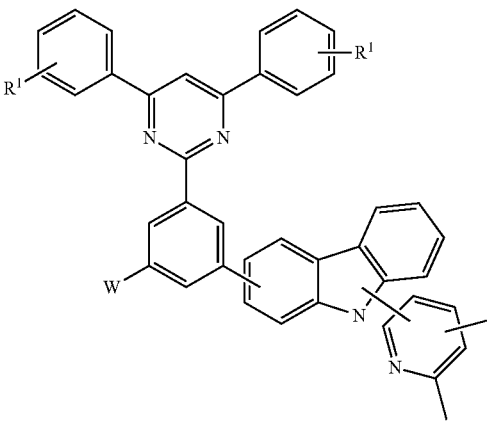
11-6
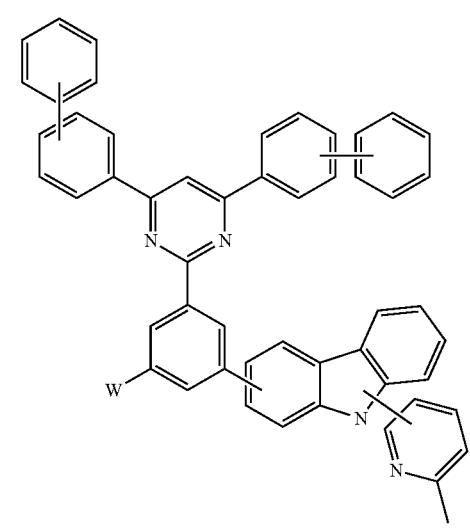
11-7

-continued
11-8
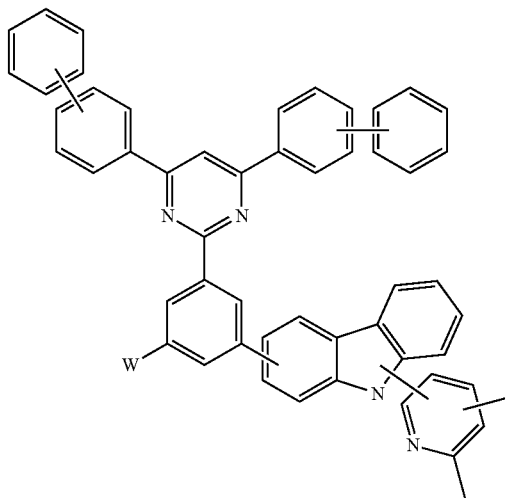
11-9
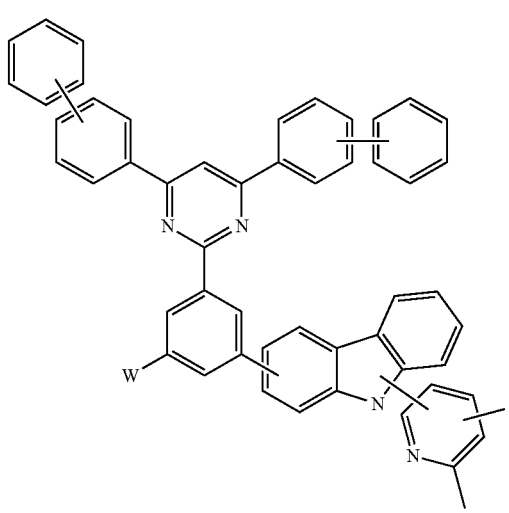
11-10
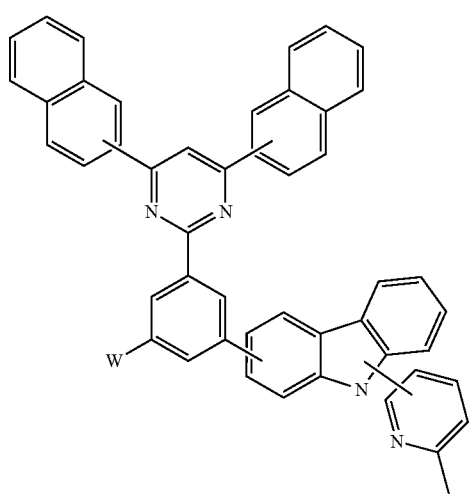
-continued
11-11
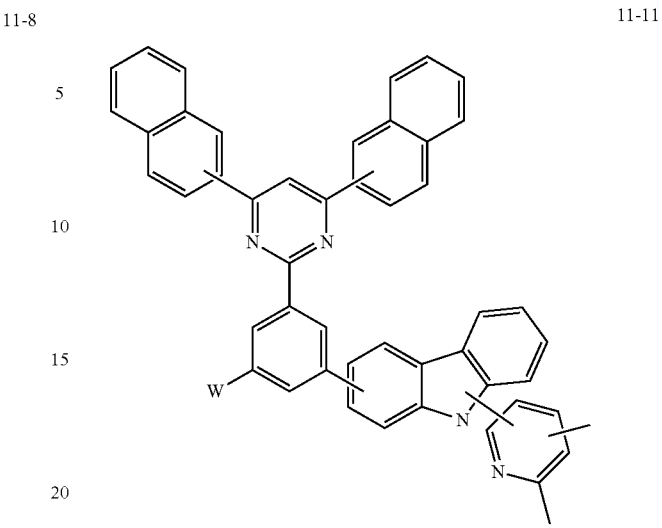
11-12
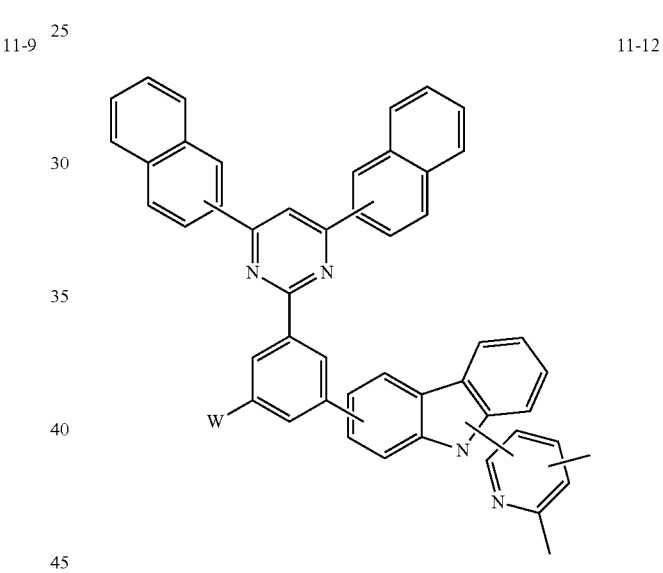
11-13
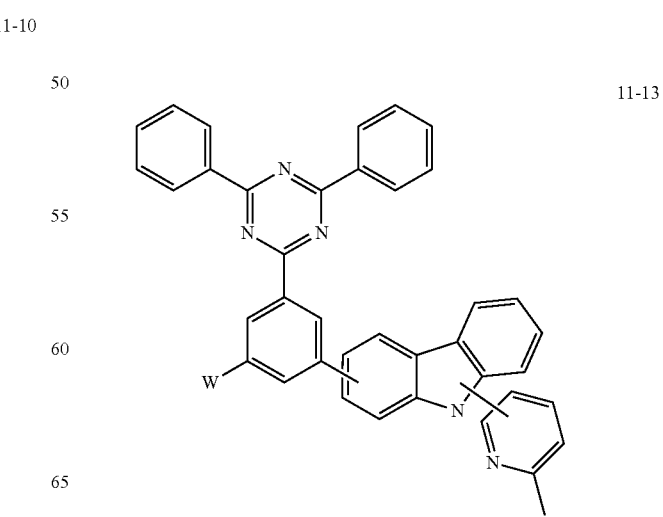

473
-continued
474
-continued
11-14
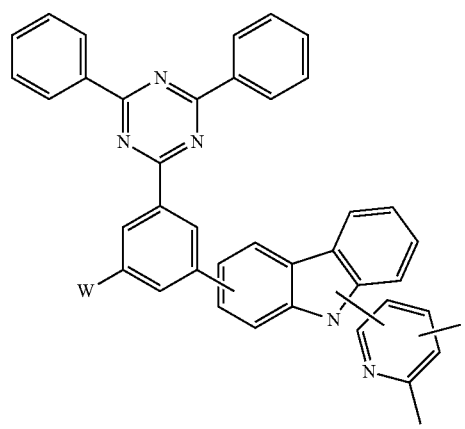
11-15
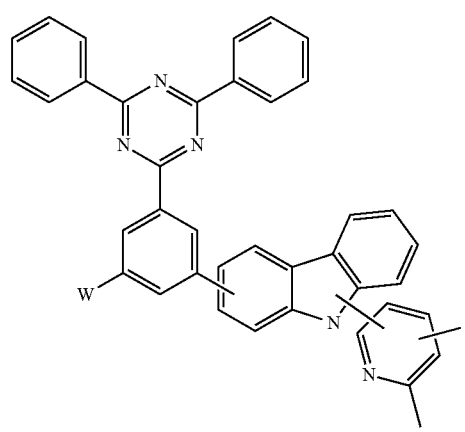
11-16
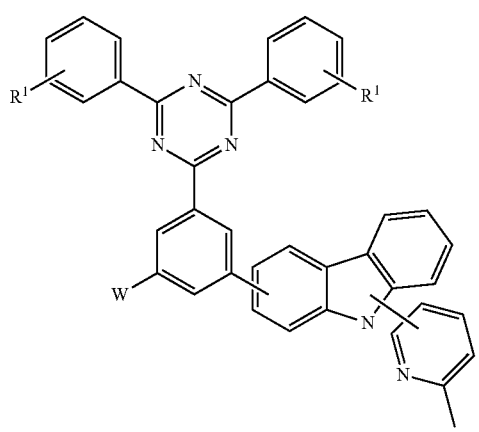
11-17
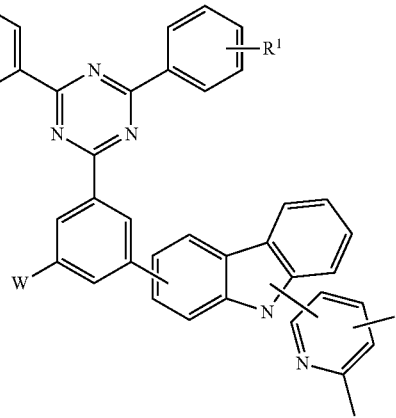
11-18
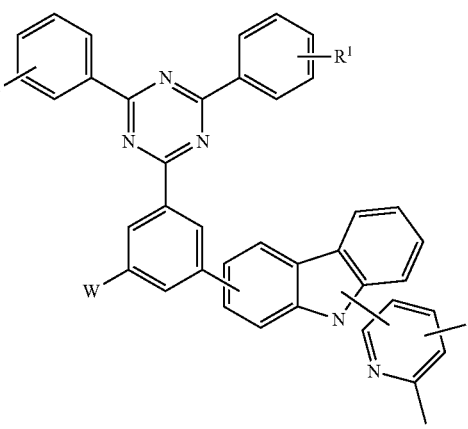
11-19
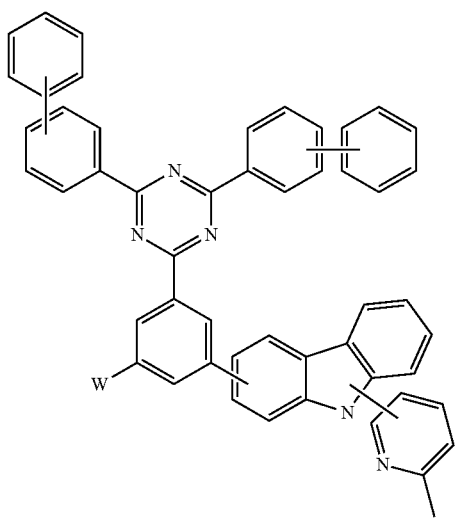

-continued
11-20
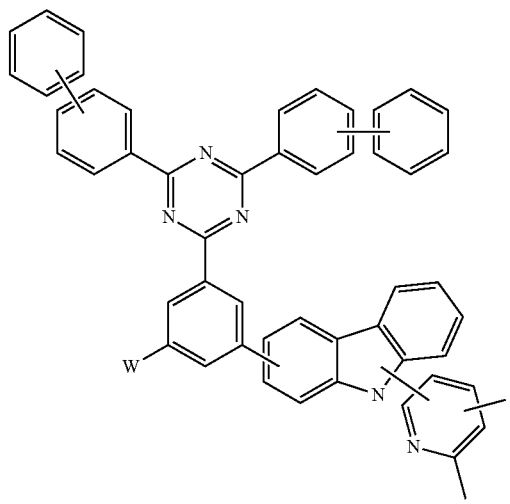
11-21
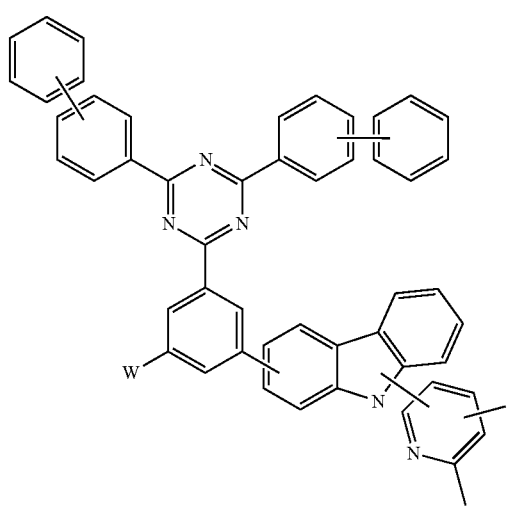
11-22
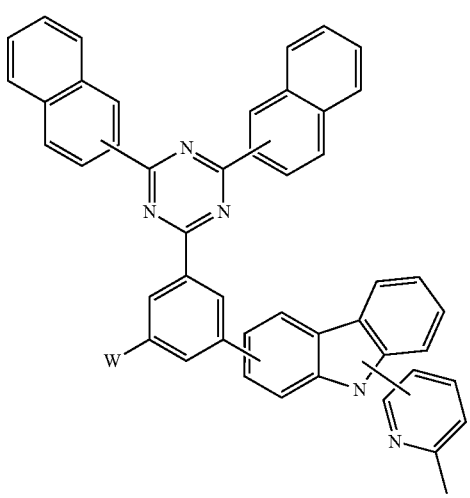
-continued
11-23
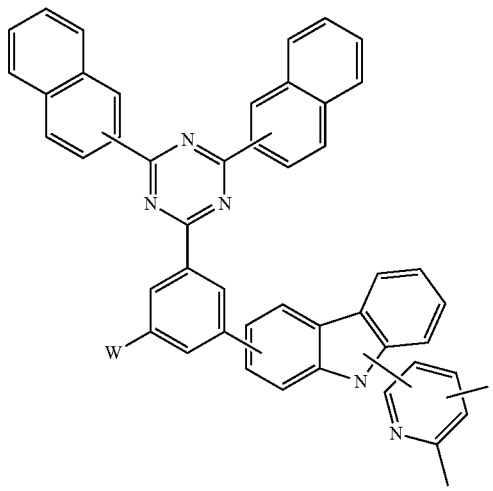
11-24
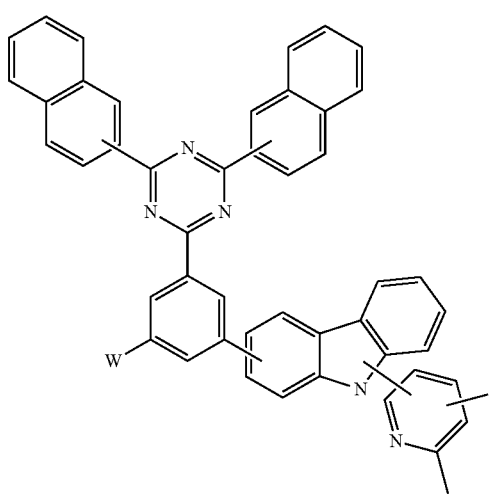
(Each $R^1$ independently represents a $C_{1-4}$ alkyl group, and V and W are as defined above.)
Compound (12) may be produced by the same method as for the above-mentioned compound (3).
$Ar^2$, X and p in compound (12) are as defined above with respect to the above-mentioned $Ar^2$, X and p.
Compound (12) is not particularly limited and may, for example, be the following (12-1) to (12-57).
12-1
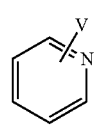
12-2
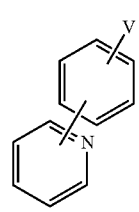

-continued
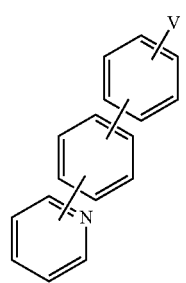
12-3
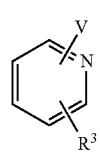
12-4
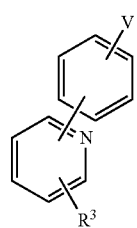
12-5
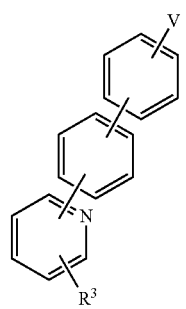
12-6
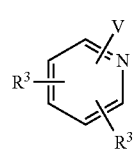
12-7
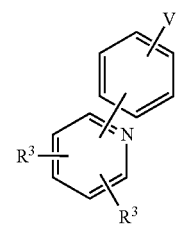
12-8
-continued
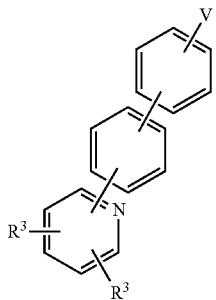
12-9
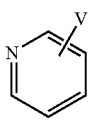
12-10
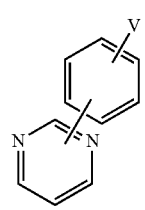
12-11
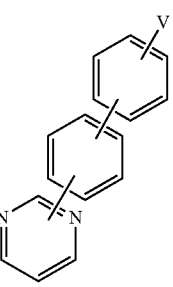
12-12
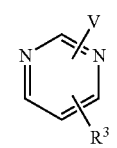
12-13
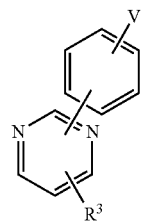
12-14
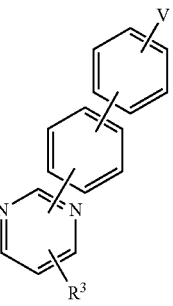
12-15

-continued
12-16
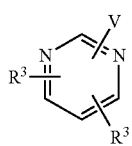
12-17
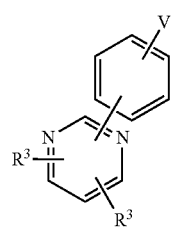
12-18
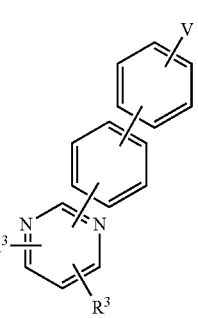
12-19
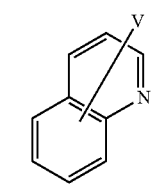
12-20
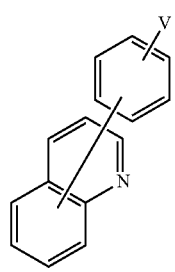
12-21
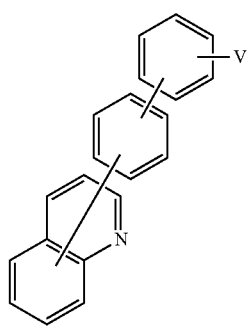
-continued
12-22
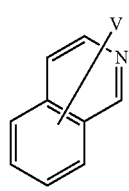
12-23
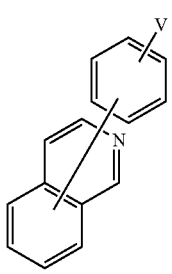
12-24
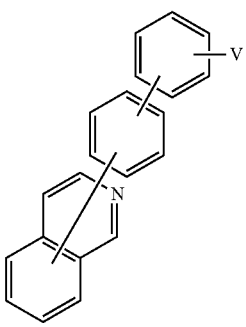
12-25
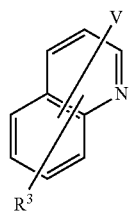
12-26
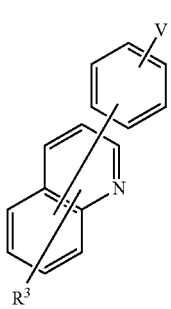

12-27 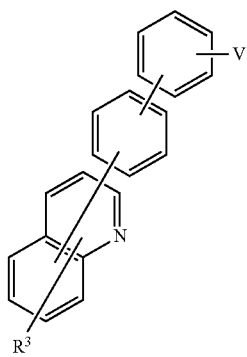
12-28 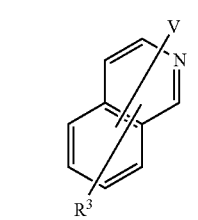
12-29 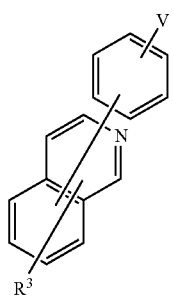
12-30 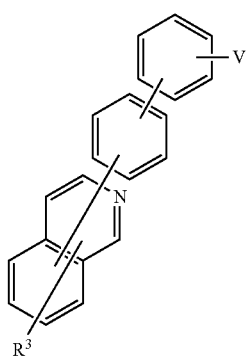
12-31 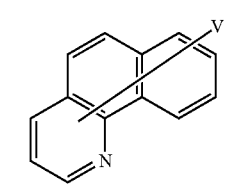
12-32 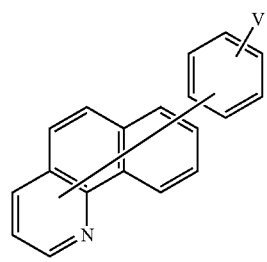
12-33 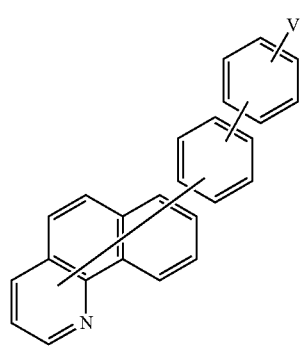
12-34 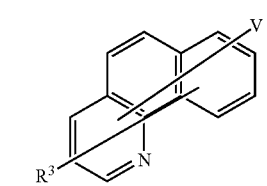
12-35 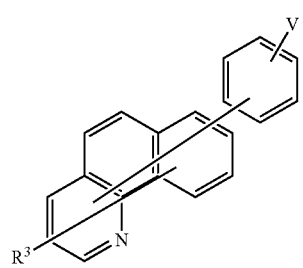
12-36 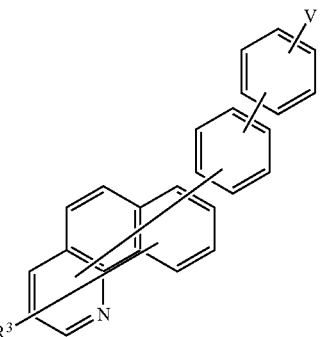
12-37 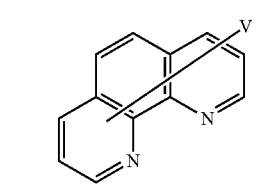

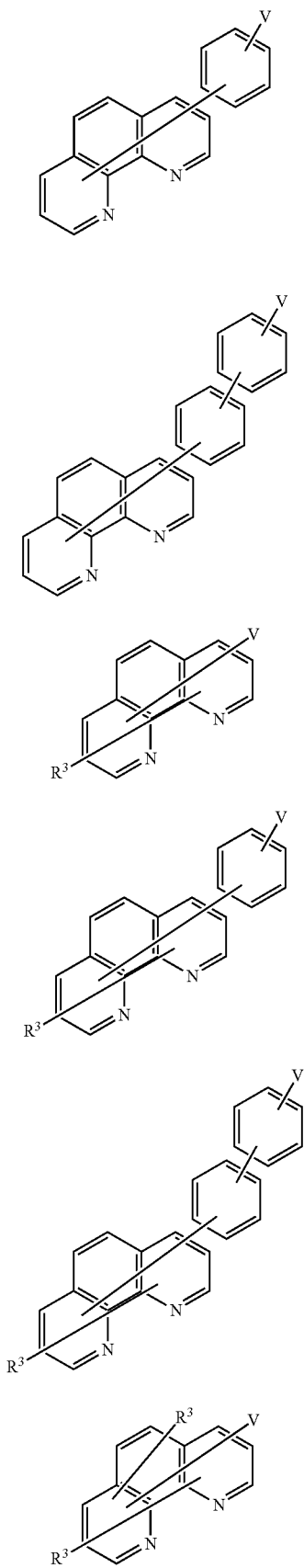
12-38
12-39
12-40
12-41
12-42
12-43
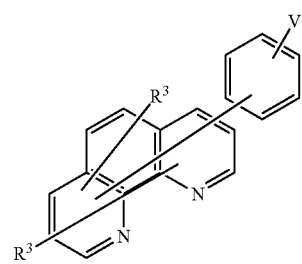
12-44
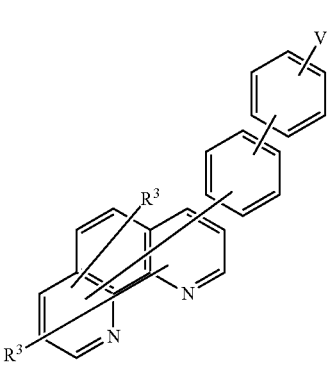
12-45
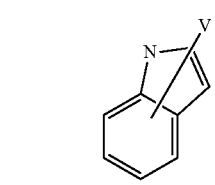
12-46
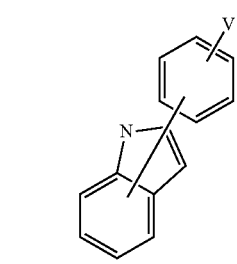
12-47
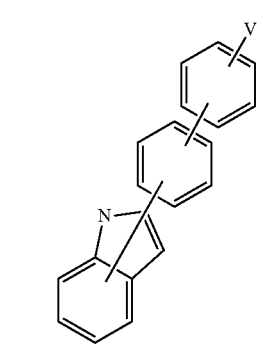
12-48
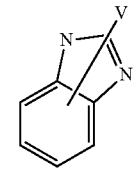
12-49

12-50 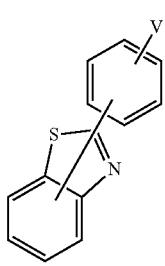

12-51 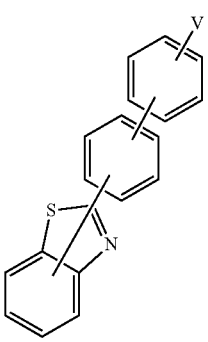

12-52 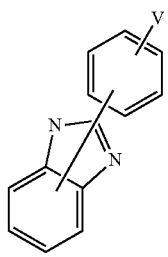

12-53 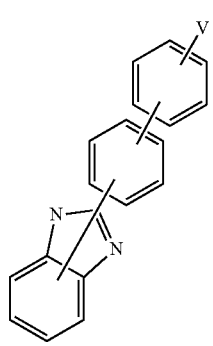

12-54 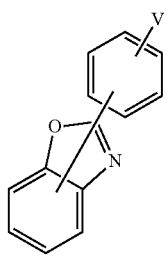

12-55 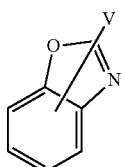

12-56 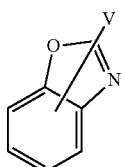

12-57 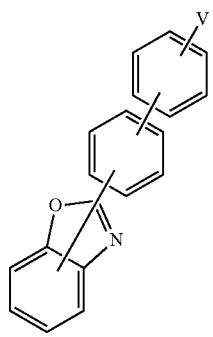

(Each $R^3$ independently represents a $C_{1-4}$ alkyl group, and V and W are as defined above.)

The amount of the palladium catalyst to be used in the reaction formula (7) is not particularly limited, so long as it is a so-called catalytic amount, but from the viewpoint of good yield, it is preferably from 0.1 to 0.01 time by mol (in terms of palladium atoms) per mol of compound (11).

The molar ratio of compound (11) and compound (12) to be used in the reaction formula (7) is not particularly limited, but it is preferred that per mol of compound (11), compound (12) is preferably from 0.2 to 5 times by mol.

The amount of the base to be used, is not particularly limited, but is preferably from 0.5 to 10 times by mol and, from the viewpoint of good yield, more preferably from 1 to 5 times by mol, per mol of compound (11).

Now, the reaction formula (8) will be explained.

Compound (13) may be produced by the same methods as for the above-mentioned compound (11).

Substituent C", D and Cz in compound (13) are as defined above with respect to the above-mentioned substituent C", D and Cz.

Compound (13) is not particularly limited and may, for example, be the following (13-1) to (13-16).

13-1 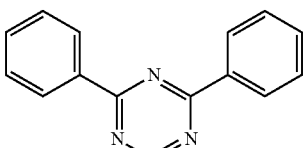
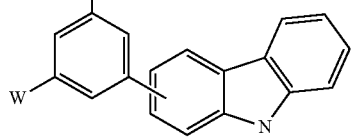

13-2 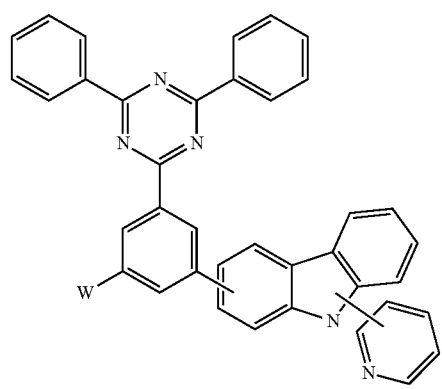
13-3 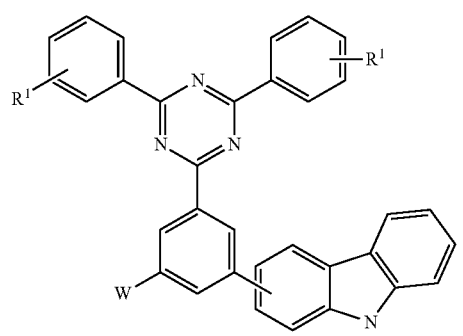
13-4 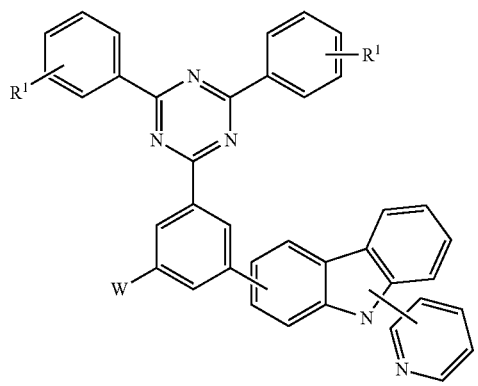
13-5 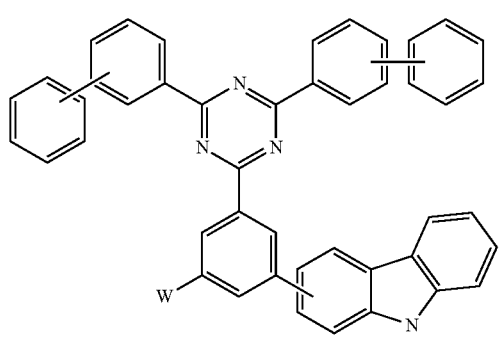
13-6 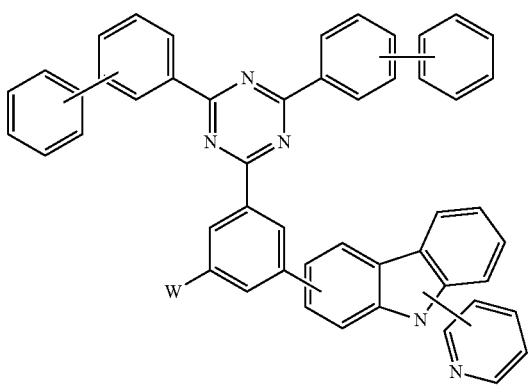
13-7 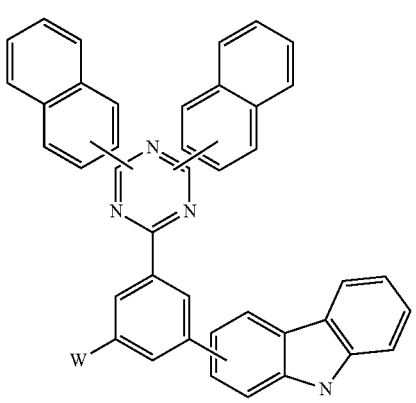
13-8 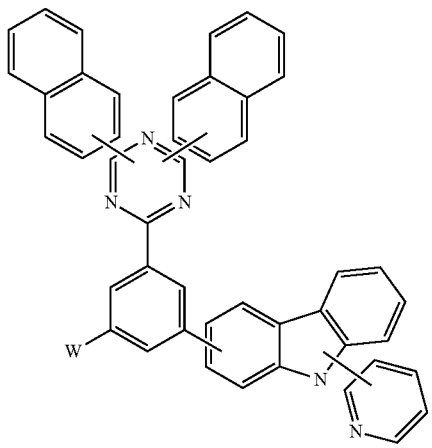
13-9 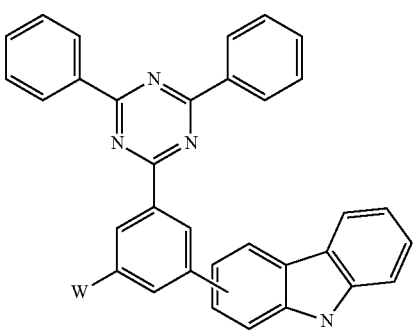

13-10
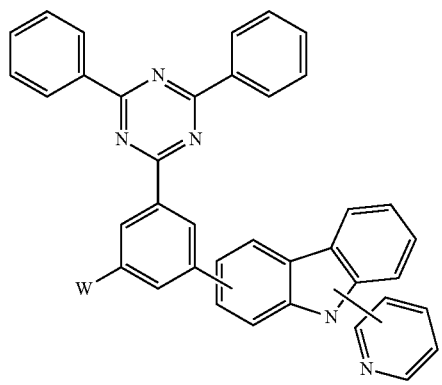

13-11
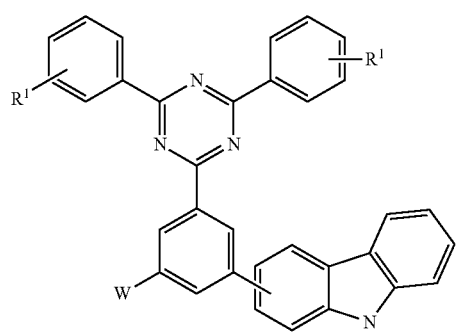

13-12
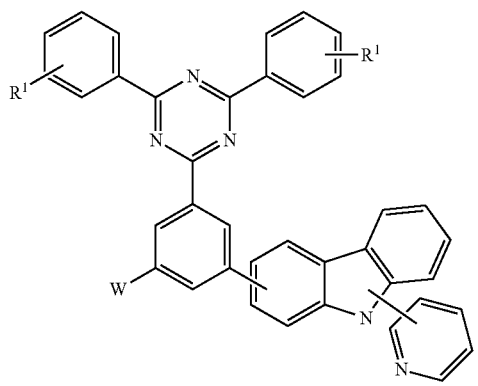

13-13
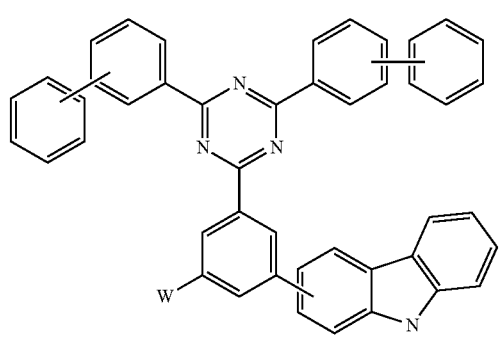

13-14
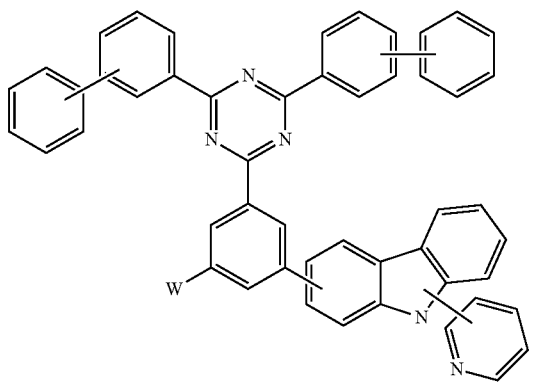

13-15
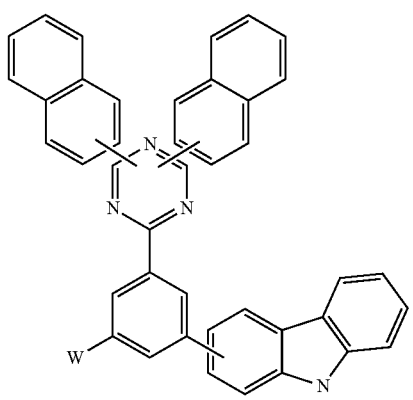

13-16
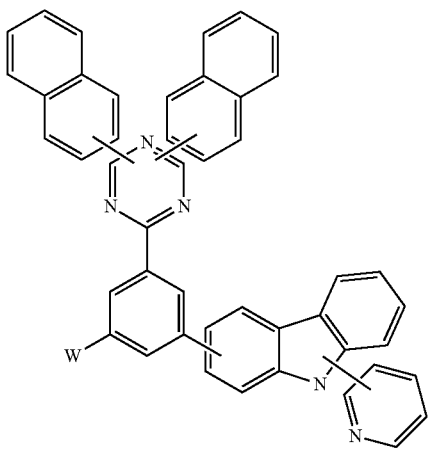

(Each $R^1$ independently represents a $C_{1-4}$ alkyl group, and V and W are as defined above.)

The amount of the palladium catalyst to be used in the reaction formula (8) is not particularly limited, so long as it is a so-called catalytic amount, but from the viewpoint of good yield, it is preferably from 0.1 to 0.01 time by mol (in terms of palladium atoms) per mol of compound (13).

The molar ratio of compound (13) and compound (2) to be used in the reaction formula (8) is not particularly limited, but it is preferred that per mol of compound (13), compound (2) is preferably from 0.2 to 5 times by mol.

The amount of the base to be used, is not particularly limited, but is preferably from 0.5 to 10 times by mol and, from the viewpoint of good yield, more preferably from 1 to 5 times by mol, per mol of compound (13).

Now, the reaction formula (9) will be explained.

Compound (14) may be produced by the same methods as for the above-mentioned compound (4) and compound (11).

Substituent B, C', D and Cz in compound (14) are as defined above with respect to the above-mentioned substituent B, C', D and Cz.

Compound (14) is not particularly limited and may, for example, be the following (14-1) to (14-24).

14-1
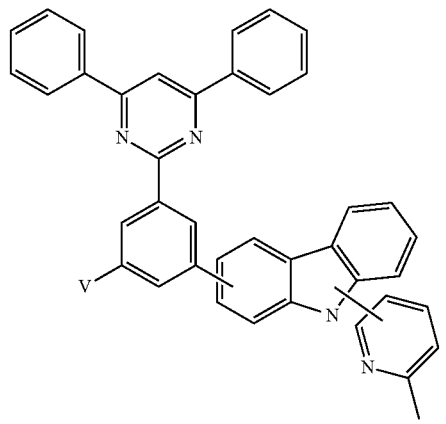

14-2
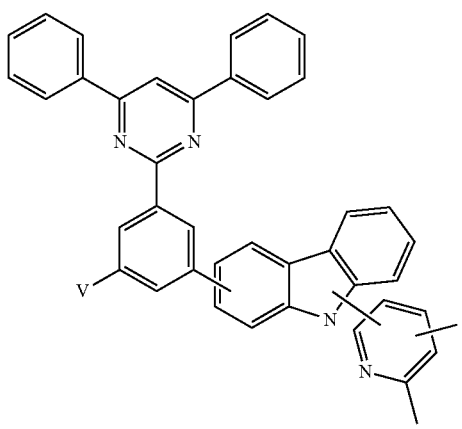

14-3
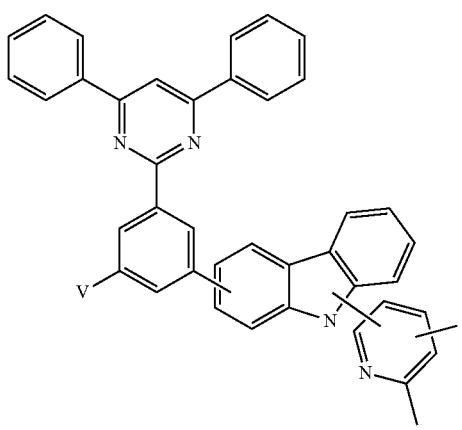

-continued 14-4
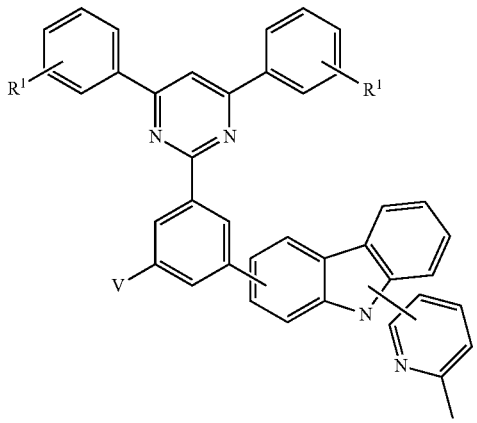

14-5
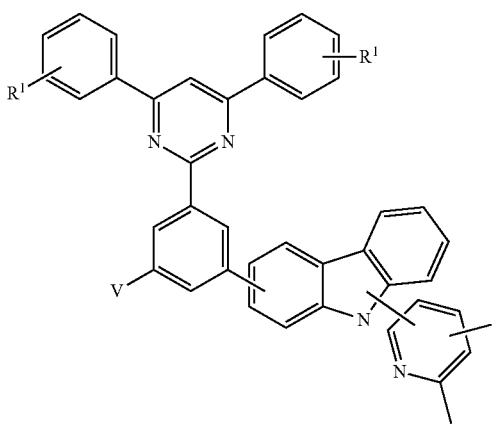

14-6
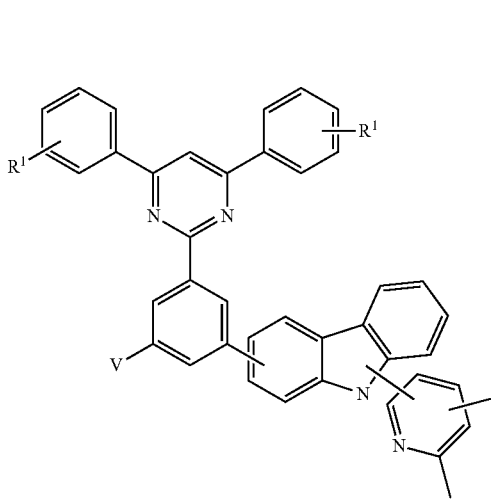

493
-continued
494
-continued
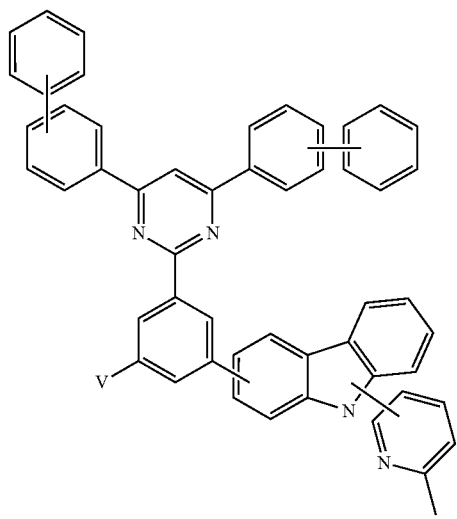
14-7
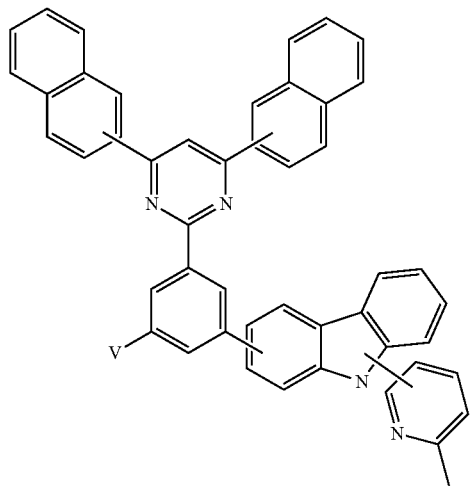
14-10
14-8
14-11
14-9
14-12

495
-continued
| | |
|---|---|
| 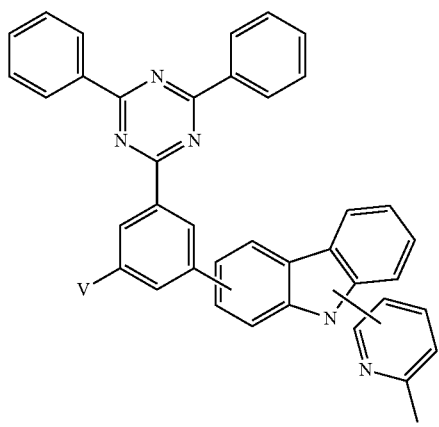 14-13 | 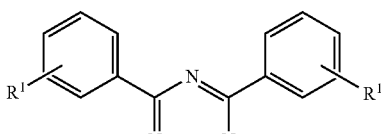 14-16 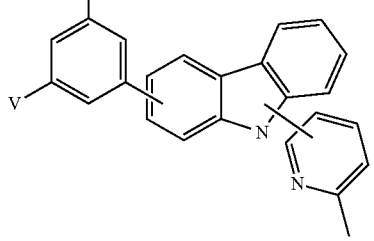 |
| 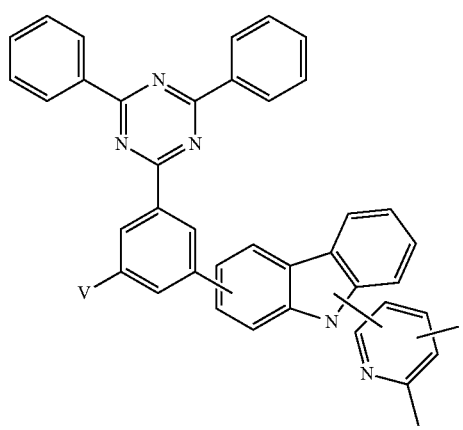 14-14 | 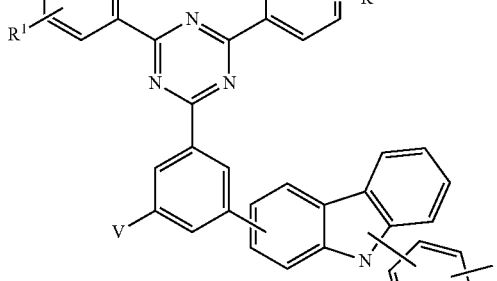 14-17 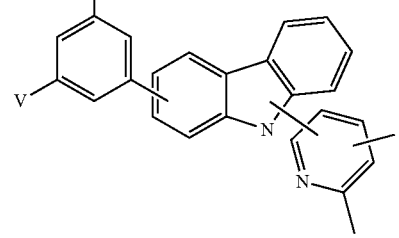 |
| 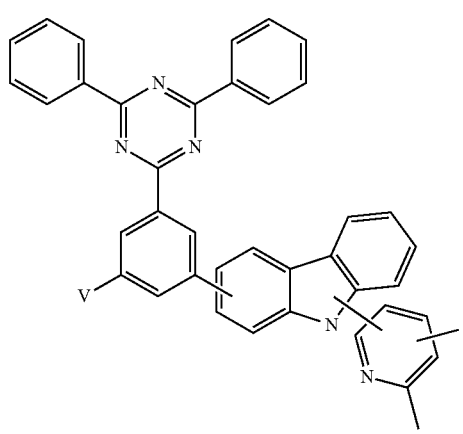 14-15 | 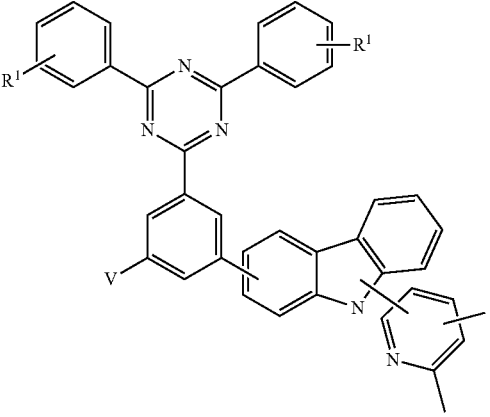 14-18 |
496
-continued

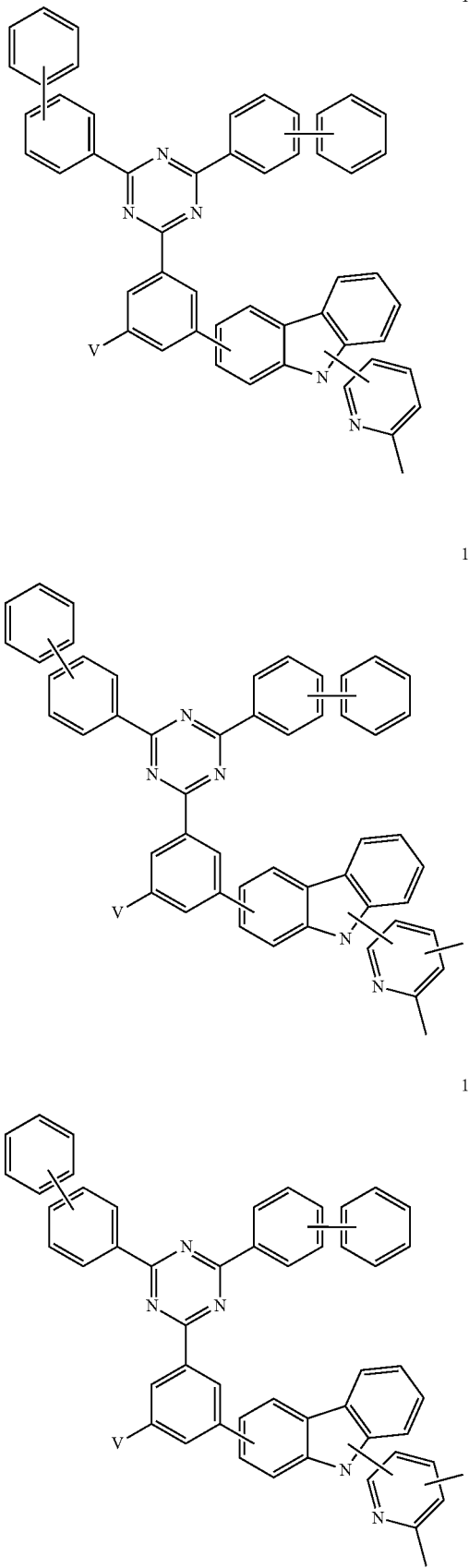
14-19
14-20
14-21
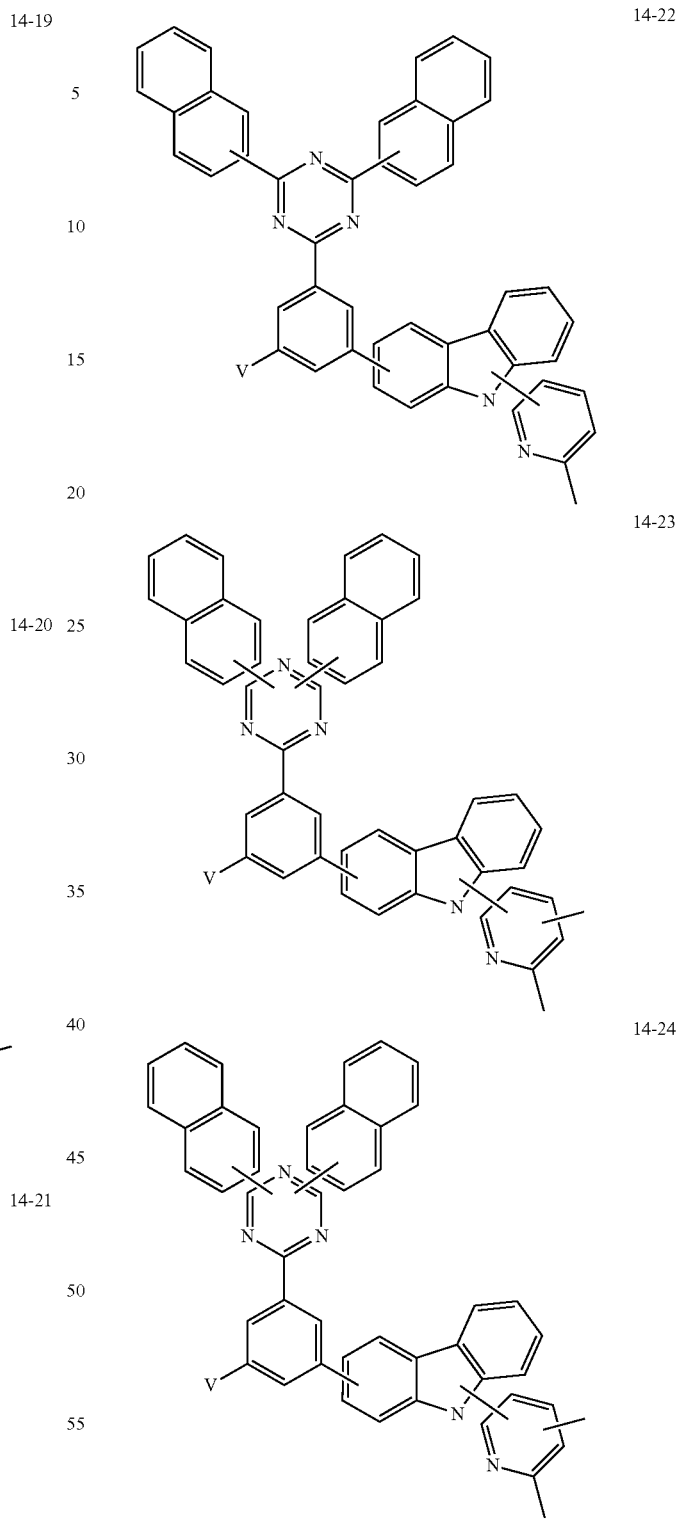
14-22
14-23
14-24
(Each $R^1$ independently represents a $C_{1-4}$ alkyl group, and V and W are as defined above.)
Compound (15) may be produced by the same method as for the above-mentioned compound (6).
Substituent $Ar^3$, X and p in compound (15) are as defined above with respect to the above-mentioned substituent $Ar^3$, X and p.

Compound (15) is not particularly limited and may, for example, be the following (15-1) to (15-24).
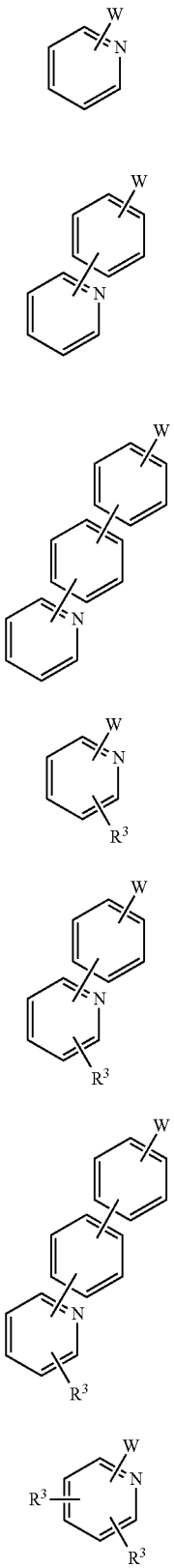
-continued
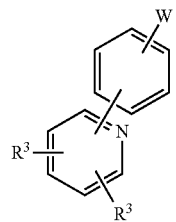 15-8
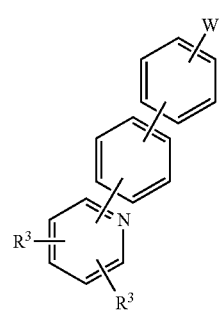 15-9
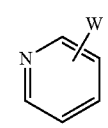 15-10
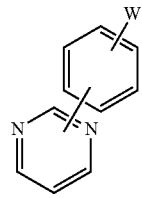 15-11
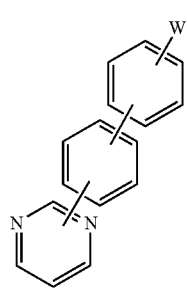 15-12
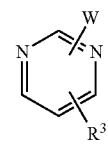 15-13
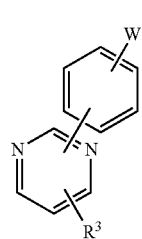 15-14

15-15
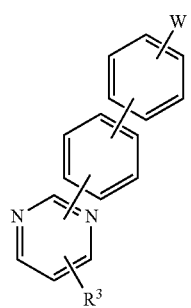
15-16
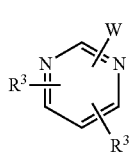
15-17
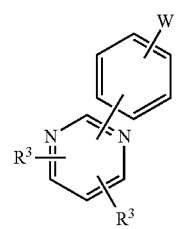
15-18
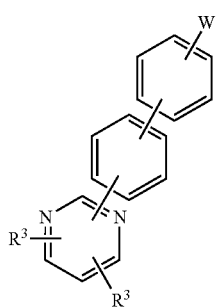
15-19
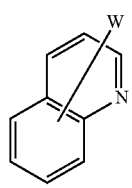
15-20
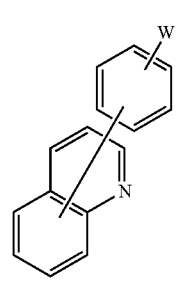
15-21
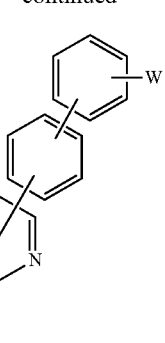
15-22
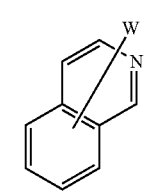
15-23
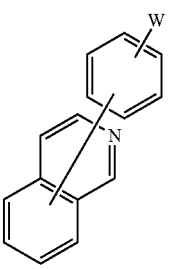
15-24
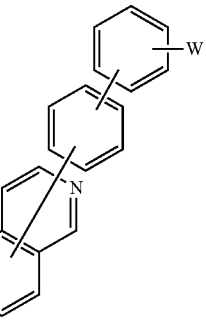
15-25
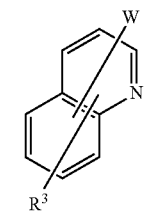
15-26
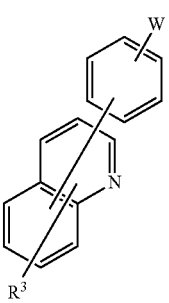

503
-continued
| | |
|---|---|
| 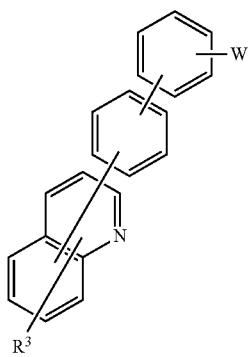 | 15-27 |
| 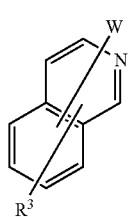 | 15-28 |
| 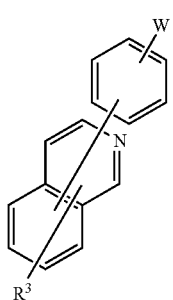 | 15-29 |
| 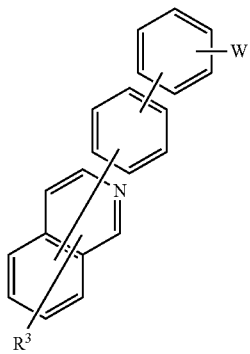 | 15-30 |
| 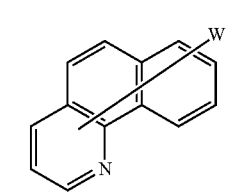 | 15-31 |
504
-continued
| | |
|---|---|
| 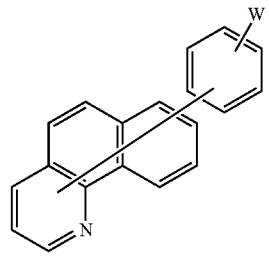 | 15-32 |
| 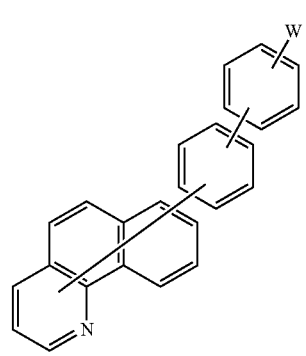 | 15-33 |
| 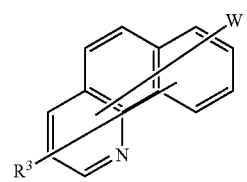 | 15-34 |
| 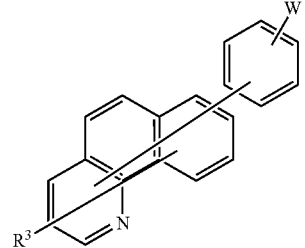 | 15-35 |
| 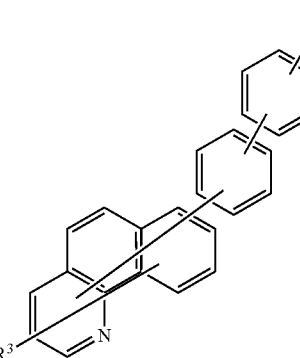 | 15-36 |
| 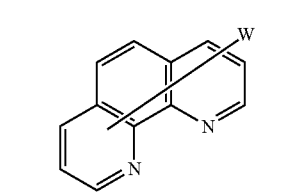 | 15-37 |

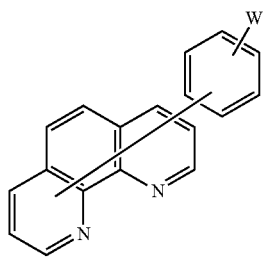 15-38
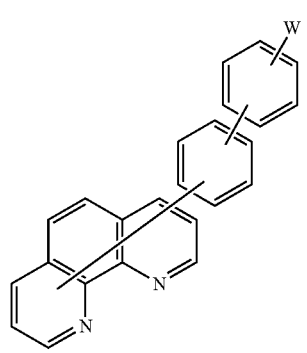 15-39
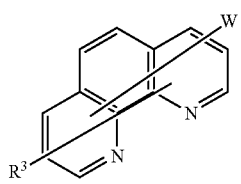 15-40
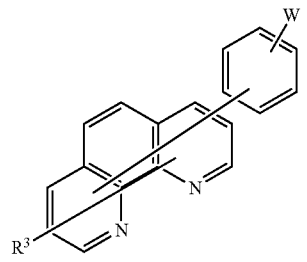 15-41
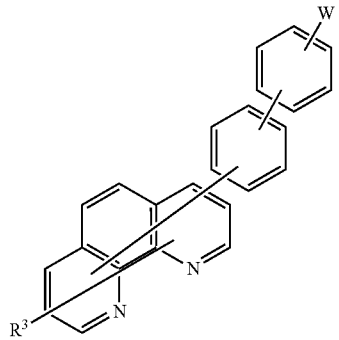 15-42
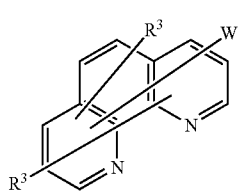 15-43
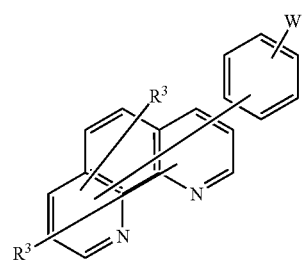 15-44
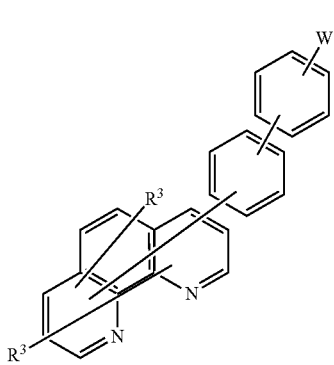 15-45
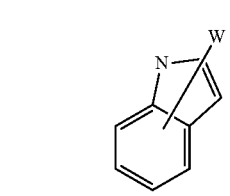 15-46
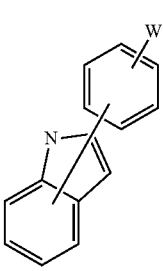 15-47
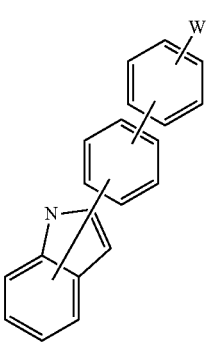 15-48
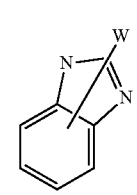 15-49

15-50 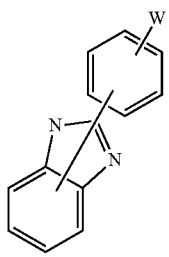

15-51 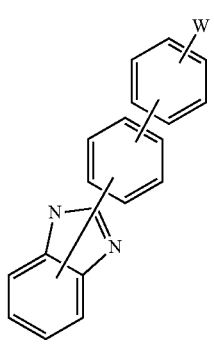

15-52 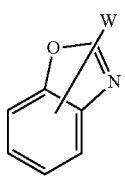

15-53 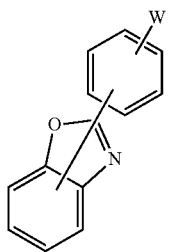

15-54 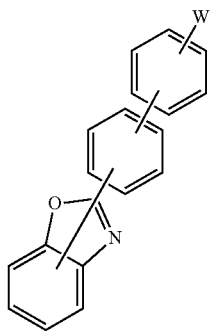

15-55 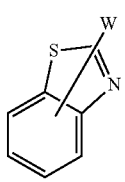

15-56 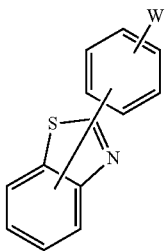

15-57 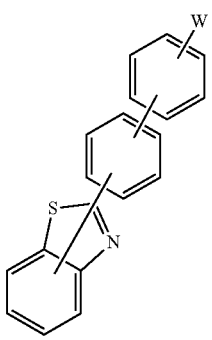

(Each $R^3$ independently represents a $C_{1-4}$ alkyl group, and V and W are as defined above.)

The amount of the palladium catalyst to be used in the reaction formula (9) is not particularly limited, so long as it is a so-called catalytic amount, but from the viewpoint of good yield, it is preferably from 0.1 to 0.01 time by mol (in terms of palladium atoms) per mol of compound (14).

The molar ratio of compound (14) and compound (15) to be used in the reaction formula (9) is not particularly limited, but it is preferred that per mol of compound (14), compound (15) is preferably from 0.2 to 5 times by mol.

The amount of the base to be used, is not particularly limited, but is preferably from 0.5 to 10 times by mol and, from the viewpoint of good yield, more preferably from 1 to 5 times by mol, per mol of compound (14).

Now, the reaction formula (10) will be explained.

Compound (16) may be produced by the same methods as for the above-mentioned compound (14).

Substituent C', D and Cz in compound (16) are as defined above with respect to the above-mentioned substituent C', D and Cz.

Compound (16) is not particularly limited and may, for example, be the following (16-1) to (16-16).

16-1 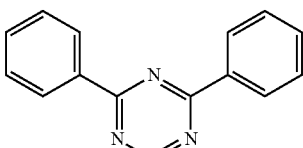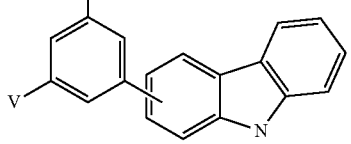

16-2
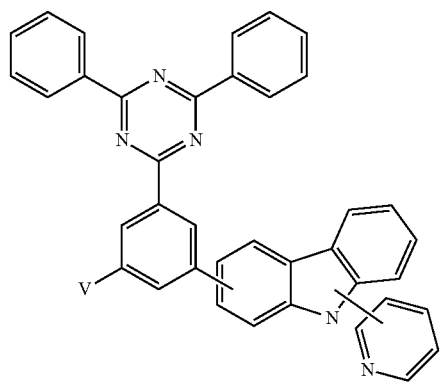
16-6
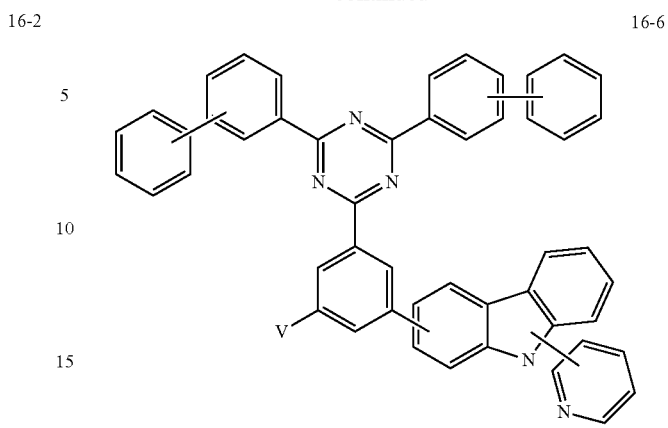
16-3
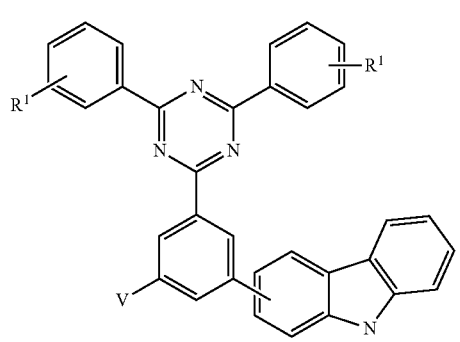
16-7
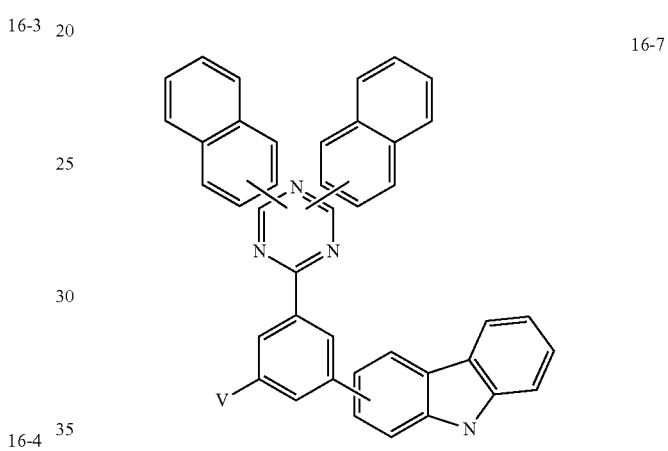
16-4
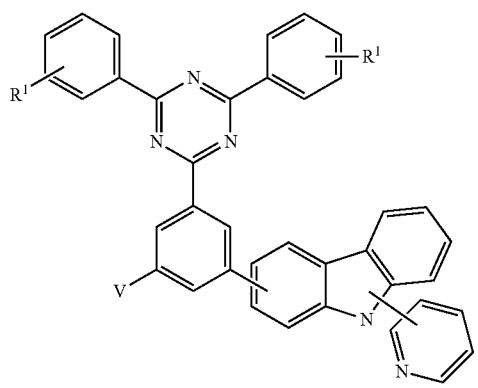
16-8
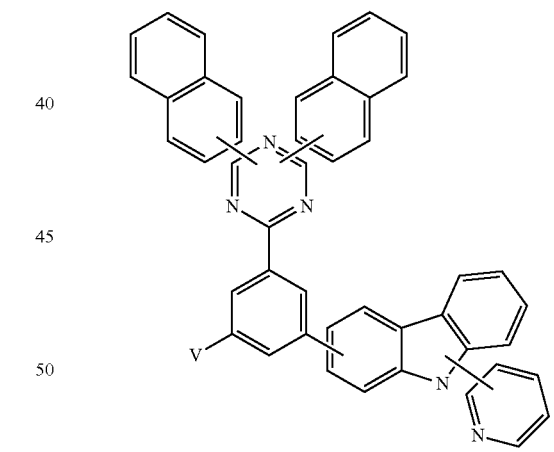
16-5
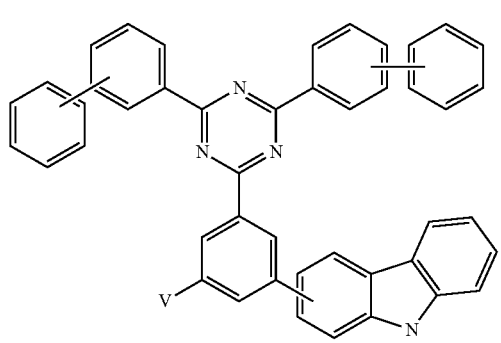
16-9
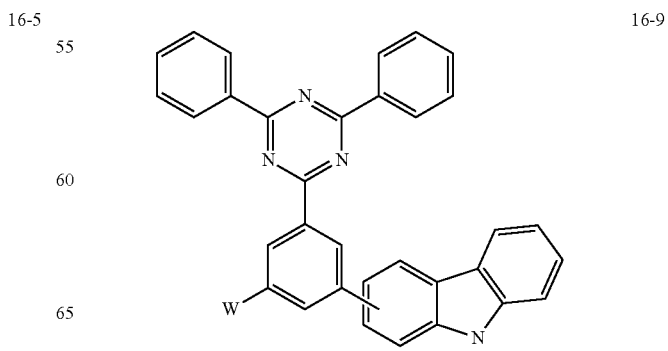

16-10
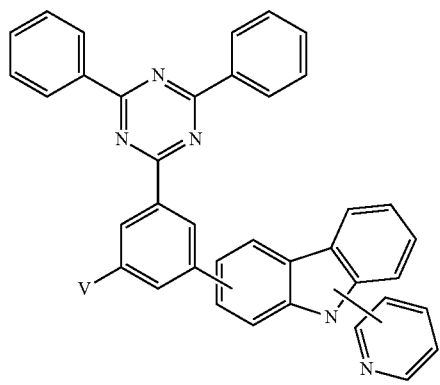

16-11
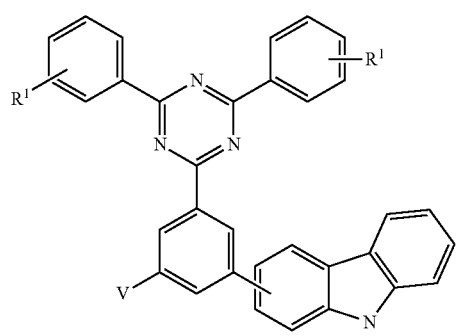

16-12
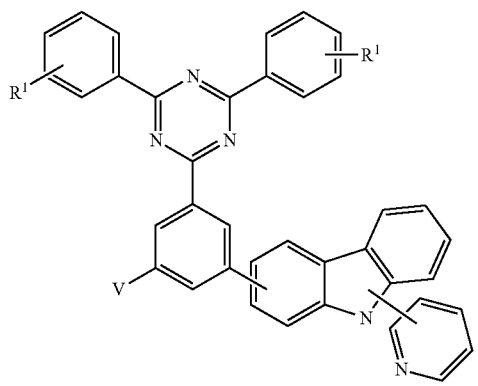

16-13
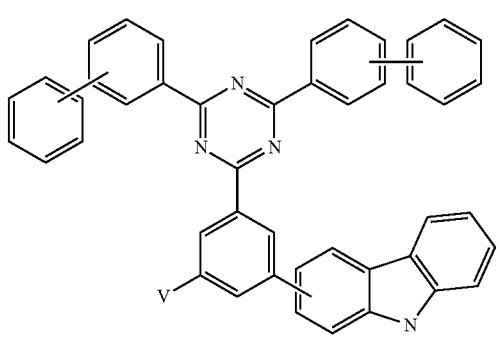

16-14
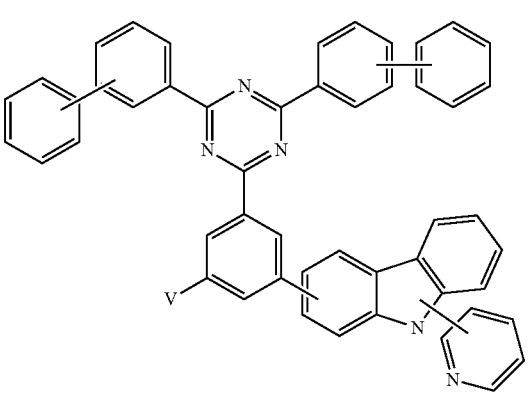

16-15
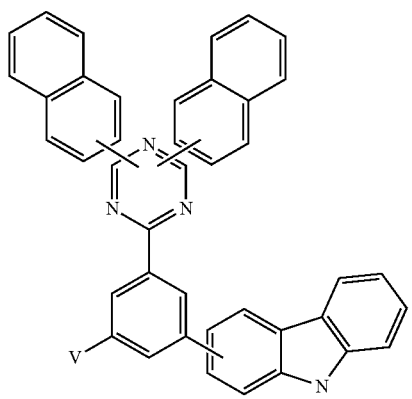

16-16
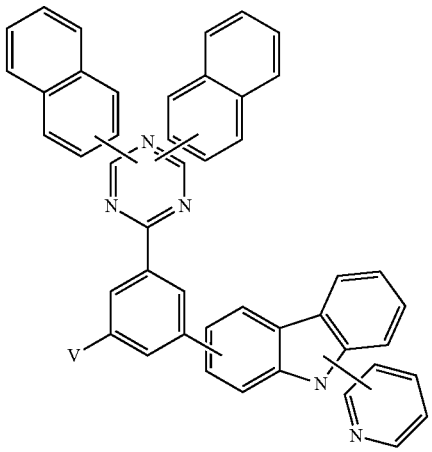

(Each $R^1$ independently represents a $C_{1-4}$ alkyl group, and V and W are as defined above.)

The amount of the palladium catalyst to be used in the reaction formula (10) is not particularly limited, so long as it is a so-called catalytic amount, but from the viewpoint of good yield, it is preferably from 0.1 to 0.01 time by mol (in terms of palladium atoms) per mol of compound (16).

The molar ratio of compound (16) and compound (5) to be used in the reaction formula (10) is not particularly limited, but it is preferred that per mol of compound (16), compound (5) is preferably from 0.2 to 5 times by mol.

The amount of the base to be used, is not particularly limited, but is preferably from 0.5 to 10 times by mol and, from the viewpoint of good yield, more preferably from 1 to 5 times by mol, per mol of compound (16).

A compound represented by the general formula (1), general formula (2) or general formula (2') is one which can be preferably used as a material for an organic electroluminescent device.

Further, a compound represented by the general formula (1), general formula (2), or general formula (2') is one which can be preferably used as an electron transport material or electron injecting material for an organic electroluminescent device.

The method for producing a thin film for an organic electroluminescent device containing a compound represented by the general formula (1), general formula (2) or general formula (2'), is not particularly limited, and film deposition by a vacuum vapor deposition method may be mentioned as a preferred example. Film deposition by vacuum vapor deposition method, may be carried out by using a common vacuum vapor deposition apparatus.

Vacuum in the vacuum chamber for forming a film by a vacuum vapor deposition method, is preferably at a level of from $1 \times 10^{-2}$ to $1 \times 10^{-6}$ which can be reached by e.g. a commonly used diffusion pump, turbo molecular pump or cryopump, more preferably from $1 \times 10^{-3}$ to $10^{-6}$ Pa, from such a viewpoint that the production tact time for preparing the organic electroluminescent device can be thereby shortened, such being advantageous for the production costs. Further, the deposition rate is preferably from 0.005 to 10 nm/sec., more preferably from 0.01 to 1 nm/sec., although it depends on the thickness of the film to be formed.

Also by a solution coating method, it is possible to produce a thin film for an organic electroluminescent device comprising compound A. For example, it is possible that compound A is dissolved in an organic solvent such as chloroform, dichloromethane, 1,2-dichloroethane, chlorobenzene, toluene, ethyl acetate or tetrahydrofuran, followed by film formation by e.g. a spin coating method, an inkjet method, a casting method or a dipping method, using a commonly employed apparatus.

As the basic construction to obtain the effects of the present invention, the organic electroluminescent device comprises a substrate, an anode, a hole injection layer, a hole transport layer, a light emitting layer, an electron transport layer, and a cathode.

The anode and cathode of the organic light emitting device are connected to a power source via an electrical conductor. By applying a potential between the anode and the cathode, the organic electroluminescent device is operated.

Holes are injected into the organic electroluminescent device from the anode, and electrons are injected into the organic electroluminescent device by the cathode.

The organic electroluminescent device is typically placed on a substrate, and the anode or cathode may be in contact with the substrate. The electrode in contact with the substrate is referred to as the lower electrode, for convenience sake. In general, the lower electrode is an anode, but the organic electroluminescent device of the present invention is not limited to such a form.

The substrate may be light transmissive or opaque, depending on the intended direction of light emission. Light transmission properties, can be confirmed by electroluminescence light emission through the substrate. In general, a transparent glass or plastic is employed as the substrate in such a case. The substrate may be of a composite structure comprising multiple material layers.

In a case where electroluminescence light emission is to be confirmed through an anode, the anode is formed of a material which permits the light emission to pass or substantially pass therethrough.

A common transparent anode material to be used in this invention is indium-tin oxide (ITO), indium-zinc oxide (IZO) or tin oxide. However, another metal oxide, such as aluminum or indium-doped tin oxide, magnesium-indium oxide, or nickel-tungsten oxide may also be used. In addition to these oxides, a metal nitride such as gallium nitride, a metal selenide such as zinc selenide, or a metal sulfide such as zinc sulfide, may be used as the anode.

The anode may be modified with plasma-deposited fluorocarbons. If electroluminescent light emission is confirmed only through the cathode, the transmission characteristics of the anode is not critical, and a transparent, opaque or reflective optional conductive material may be used. As an example of the conductor for this purpose, gold, iridium, molybdenum, palladium, platinum, etc. may be mentioned.

Between the anode and the hole transport layer, it is possible to provide a hole-injection layer. The hole injecting material improves the film forming properties of the subsequent organic layer and serves to facilitate injection of holes into the hole-transport layer.

Examples of the material suitable for use in the hole-injection layer, include a porphyrin compound, a plasma deposition type fluorocarbon polymer, an amine having an aromatic ring such as a biphenyl group or a carbazole group, for example, m-MTDATA (4,4',4"-tris[(3-methylphenyl) phenylamino]triphenylamine), 2T-NATA (4,4',4'-tris[(N-naphthalen-2-yl)-N-phenylamino]triphenylamine), triphenylamine, tritolylamine, tolyldiphenylamine, N,N'-diphenyl-N,N'-bis(3-methylphenyl)-1,1'-biphenyl-4,4'-diamine, N,N,N',N'-tetrakis(4-methylphenyl)-1,1'-biphenyl-4,4'-diamine, MeO-TPD (N,N,N',N'-tetrakis(4-methoxyphenyl)-1,1'-biphenyl-4,4'-diamine), N,N'-diphenyl-N,N'-dinaphthyl-1,1'-biphenyl-4,4'-diamine, N,N'-bis(methylphenyl)-N,N'-bis(4-n-butylphenyl) phenanthrene-9,10-diamine, or N,N'-diphenyl-N,N'-bis(9-phenyl-carbazol-3-yl)-1,1'-biphenyl-4,4'-diamine, etc.

The hole transport layer of the organic electroluminescent device, preferably contains at least one hole-transporting compound, for example, an aromatic tertiary amine. The aromatic tertiary amine is meant for a compound containing at least one trivalent nitrogen atom, wherein the trivalent nitrogen atom is attached only to carbon atoms, and at least one of these carbon atoms forms an aromatic ring. Specifically, the aromatic tertiary amine may be an arylamine, a monoarylamine, a diarylamine, a triarylamine or a polymeric arylamine.

As the hole transporting material, it is possible to use an aromatic tertiary amine having at least one amino group. Further, it is possible to use a polymer hole transporting material such as poly(N-vinyl carbazole) (PVK), polythiophene, polypyrrole, polyaniline or the like. For example, NPD (N,N'-bis(naphthalen-1-yl)-N,N'-diphenyl-1,1'-biphenyl-4,4'-diamine), α-NPD (N,N'-di(1-naphthyl)-N,N'-diphenyl-1,1'-biphenyl-4,4'-diamine), TPBi (1,3,5-tris(1-phenyl-1H-benzimidazol-2-yl) benzene), or TPD (N,N'-bis(3-methylphenyl)-N,N'-diphenyl-1,1'-biphenyl-4,4'-diamine) may be mentioned.

Between the hole injection layer and the hole transport layer, a layer containing dipyradino [2,3-f: 2',3'-h]quinoxaline-2,3,6,7,10,11-hexa-carbonitrile (HAT-CN) may be provided as a charge generation layer.

The light emitting layer of the organic electroluminescent device contains a phosphorescent or fluorescent material, and produces light emission as a result of recombination of electron-hole pairs in this region.

The light emitting layer may consist of a single material including both a low molecular compound and a polymer, but more commonly, it consists of a host material doped with a guest compound, and light emission is primarily from the dopant any may have an optional color.

The host material of the light-emitting layer may, for example, be a compound having a biphenyl group, a fluorenyl group, a triphenylsilyl group, a carbazole group, a pyrenyl group or an anthranyl group. For example, DPVBi (4,4'-bis(2,2-diphenyl-vinyl)-1,1'-biphenyl), BCzVBi (4,4'-bis(9-ethyl-3-carbazovinylene)1,1'-biphenyl), TBADN (2-tert-butyl-9,10-di(2-naphthyl) anthracene), ADN (9,10-di (2-naphthyl) anthracene), CBP (4,4'-bis(carbazol-9-yl) biphenyl), CDBP (4,4'-bis(carbazol-9-yl)-2,2'-dimethylbiphenyl) or 9,10-bis(biphenyl) anthracene, may be mentioned.

The host material in the luminescent layer may be an electron transporting material as defined below, a hole-transporting material as defined above, another material to assist (support) the hole-electron recombination, or a combination of these materials.

Examples of a fluorescent dopant include anthracene, tetracene, xanthene, perylene, rubrene, coumarin, rhodamine, quinacridone, dicyanomethylenepyran compounds, thiopyran compounds, polymethine compounds, pyrylium or thiapyrylium compounds, fluorene derivatives, periflanthene derivatives, indenoperylene derivatives, bis(azinyl) amine boron compounds, bis(azinyl)methane compounds, carbostyryl compounds, etc.

An example of a phosphorescent dopant is an organic metal complex of a transition metal such as iridium, platinum, palladium or osmium.

An example of a dopant is Alq$_3$ (tris(8-hydroxyquinoline) aluminum)), DPAVBi (4,4'-bis[4-(di-para-tolylamino) styryl]biphenyl), perylene, Ir(PPy)$_3$ (tris(2-phenylpyridine) iridium (III), or FIrPic (bis(3,5-difluoro-2-(2-pyridyl)phenyl-(2-carboxy-pyridyl) iridium (Ill).

Thin film-forming material for use in forming the electron-transport layer of the organic electroluminescent device of the present invention is a cyclic azine compound of the present invention. Here, the electron transport layer may also contain other electron-transporting materials. As such other electron-transporting materials, alkali metal complexes, alkaline earth metal complexes, earth metal complexes, etc., may be mentioned. Such alkali metal complexes, alkaline earth metal complexes or earth metal complexes, may, for example, be lithium 8-hydroxyquinolinate (Liq), zinc bis(8-hydroxyquinolinate), copper bis(8-hydroxyquinolinate), manganese bis(8-hydroxyquinolinate), aluminum tris(8-hydroxyquinolinate), aluminum tris (2-methyl-8-hydroxyquinolinate), gallium tris(8-hydroxyquinolinate), beryllium bis(10-hydroxybenzo[h] quinolinate), zinc bis(10-hydroxybenzo[h]quinolinate), chlorogallium bis(2-methyl-8-quinolinate), gallium bis(2-methyl-8-quinolinate) (o-cresolate), aluminum bis(2-methyl-8-quinolinate)-1-naphtholate, gallium bis(2-methyl-8-quinolinate)-2-naphtholate, etc.

Between the light emitting layer and the electron transport layer, a hole blocking layer may be provided for the purpose of improving the carrier balance. A compound desirable for such a hole blocking layer, may, for example, be BCP (2,9-dimethyl-4,7-diphenyl-1,10-phenanthroline), Bphen (4,7-diphenyl-1,10-phenanthroline), BAlq (aluminum bis(2-methyl-8-quinolinolato)-4-(phenyl-phenolate)), or beryllium bis(10-hydroxybenzo[h]quinolinate).

In the organic electroluminescent device of the present invention, an electron injection layer may be provided for the purpose of improving the electron injection property thereby to improve device characteristics (for example, luminous efficiency, constant voltage drive, or high durability).

A compound desirable for the electron injection layer may, for example, be fluorenone, anthraquinodimethane, diphenoquinone, thiopyran dioxide, oxazole, oxadiazole, triazole, imidazole, perylenetetracarboxylic acid, fluorenylidenemethane, anthraquinodimethane or anthrone. Further, the above-mentioned metal complexes and inorganic compounds such as alkali metal oxides, alkaline earth oxides, rare earth oxides, alkali metal halides, alkaline earth halides, rare earth halides, and various oxides, nitrides and oxynitrides, such as SiOx, AlOx, SiNx, SiON, AlON, GeOx, LiOx, LiON, TiOx, TiON, TaOx, TaON, TaNx, C, etc. may also be used.

When light emission is confirmed only through the anode, the cathode used in the present invention may be formed from any conductive material. The preferred cathode material includes sodium, a sodium-potassium alloy, magnesium, lithium, a magnesium/copper mixture, a magnesium/silver mixture, a magnesium/aluminum mixture, a magnesium/indium mixture, an aluminum/aluminum oxide (Al$_2$O$_3$) mixture, indium, a lithium/aluminum mixture, and rare earth metals.

EXAMPLES

Now, the present invention will be described in further detail with reference to Preparation Examples, Synthesis Examples, Test Examples and Comparative Examples, but it should be understood that the present invention is by no means limited thereto.

Preparation Example 1

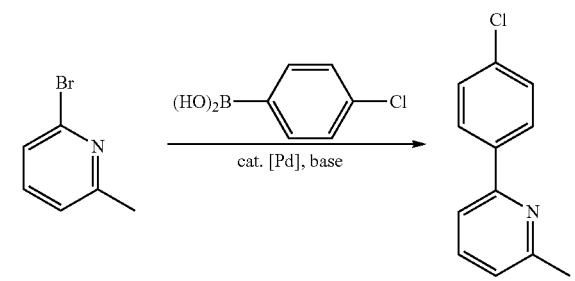

Under an argon stream, 2-bromo-6-methylpyridine (30.2 g, 0.18 mol), 4-chlorophenyl boronic acid (21.1 g, 0.13 mol) and tetrakis(triphenylphosphine) palladium (3.12 g, 2.7 mmol) were suspended in 1,4-dioxane (340 mL) and heated to 70° C. After slowly dropwise adding a 1.0M-potassium carbonate aqueous solution (405 mL) thereto, the mixture was heated to 90° C. and stirred for 18 hours. After cooling, it was subjected to liquid separation with chloroform, and the organic layer was concentrated, whereupon the crude product obtained, was purified by silica gel chromatography (developing solvent chloroform:hexane=1:1 (volume ratio, the same applies hereinafter)), to obtain yellow crystals of 2-(4-chlorophenyl)-6-methylpyridine as the desired product (amount: 27.0 g, yield: 99%).

¹H-NMR (CDCl₃): δ. 2.62 (s, 3H), 7.11 (d, J=7.5 Hz, 1H), 7.41-7.44 (m, 2H), 7.49 (d, J=7.7 Hz, 1H), 7.64 (t, J=7.7 Hz, 1H), 7.93 (d, J=8.7 Hz, 2H)

Preparation Example 2

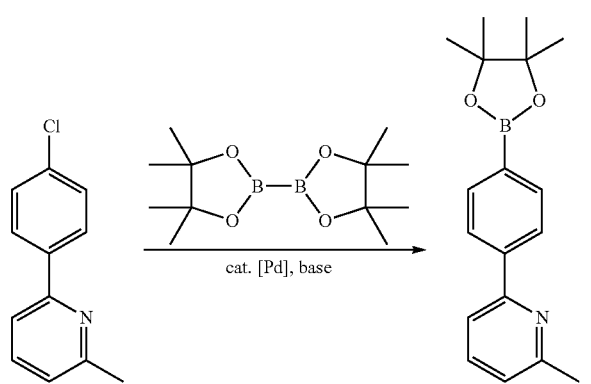

Under an argon stream, 2-(4-chlorophenyl)-6-methylpyridine (27.0 g, 0.13 mol), 4,4,4',4',5,5,5',5'-octamethyl-2,2'-bi-1,3,2-dioxaborolane (51.4 g, 0.20 mol), tris(dibenzylideneacetone) dipalladium (1.23 g, 1.3 mmol), 2-dicyclohexylphosphino-2',4',6'-triisopropyl biphenyl (1.29 g, 2.7 mmol) and potassium acetate (26.5 g, 0.27 mol) were suspended in 1,4-dioxane (520 mL) and heated to 100° C. After stirring for 18 hours, the mixture was left to cool. It was subjected to liquid separation with chloroform, and the organic layer was concentrated, whereupon the crude product obtained, was purified by silica gel chromatography (developing solvent: chloroform:hexane=1:1) to obtain yellowish white crystals of 6-methyl-2-[4-(4,4,5,5-tetramethyl-1,3,2-dioxaborolan-2-yl)phenyl]pyridine as the desired product (amount: 25.8 g, yield: 66%).

¹H-NMR (CDCl₃): δ. 1.37 (s, 12H), 2.64 (s, 3H), 7.11 (d, J=7.5 Hz, 1H), 7.55 (d, J=7.8 Hz, 1H), 7.64 (t, J=7.8 Hz, 1H), 7.89 (d, J=8.3 Hz, 2H), 7.99 (d, J=8.3 Hz, 2H)

Preparation Example 3

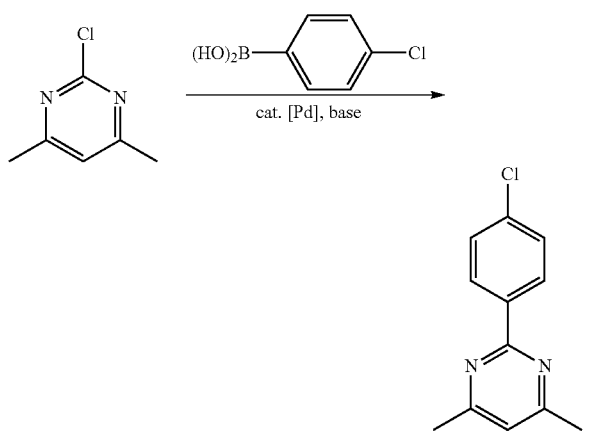

Under an argon stream, 2-chloro-4,6-dimethylpyrimidine (3.00 g, 21 mmol), 4-chlorophenyl boronic acid (2.74 g, 18 mmol) and tetrakis(triphenylphosphine) palladium (404 mg, 0.35 mmol) were suspended in 1,4-dioxane (31 mL) and heated to 70° C. After slowly dropwise adding a 3.0M potassium carbonate aqueous solution (12.8 mL) thereto, the mixture was heated to 100° C. and stirred for 18 hours. After cooling, it was subjected to liquid separation with chloroform, and the organic layer was concentrated, whereupon the crude product obtained, was purified by silica gel chromatography (developing solvent: chloroform:hexane=1:1) to obtain yellow crystals of 2-(4-chlorophenyl)-4,6-dimethylpyrimidine as the desired product (amount: 3.31 g, yield: 86%).

¹H-NMR (CDCl₃): δ. 2.53 (s, 6H), 6.93 (s, 1H), 7.42 (d, J=8.8 Hz, 2H), 8.39 (d, J=8.8 Hz, 2H).

Preparation Example 4

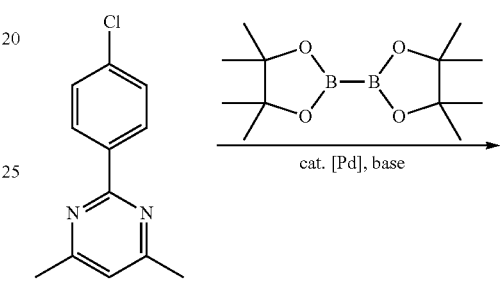

Under an argon stream, 2-(4-chlorophenyl)-4,6-dimethylpyrimidine (3.31 g, 15.1 mmol), 4,4,4',4',5,5,5',5'-octamethyl-2,2'-bi-1,3,2-dioxaborolane (4.23 g, 17 mmol), tris(dibenzylideneacetone) dipalladium (138 mg, 0.15 mmol), 2-dicyclohexylphosphino-2',4',6'-triisopropyl biphenyl (144 mg, 0.30 mmol) and potassium acetate (2.96 g, 30. mmol) were suspended in 1,4-dioxane (76 mL) and heated to 100° C. After stirring for 18 hours, the mixture was left to cool. It was subjected to liquid separation with chloroform, and the organic layer was concentrated, whereupon the crude product obtained, was purified by silica gel chromatography (developing solvent: chloroform:hexane=3:2) to obtain yellowish white crystals of 4,6-dimethyl-2-[4-(4,4,5,5-tetramethyl-1,3,2-dioxaborolan-2-yl)phenyl]pyrimidine as the desired product (amount: 4.23 g, yield: 90%).

¹H-NMR (CDCl₃): δ. 1.37 (s, 12H), 2.54 (s, 6H), 6.93 (s, 1H), 7.90 (d, J=8.3 Hz, 2H), 8.43 (d, J=8.35 Hz, 2H).

Preparation Example 5

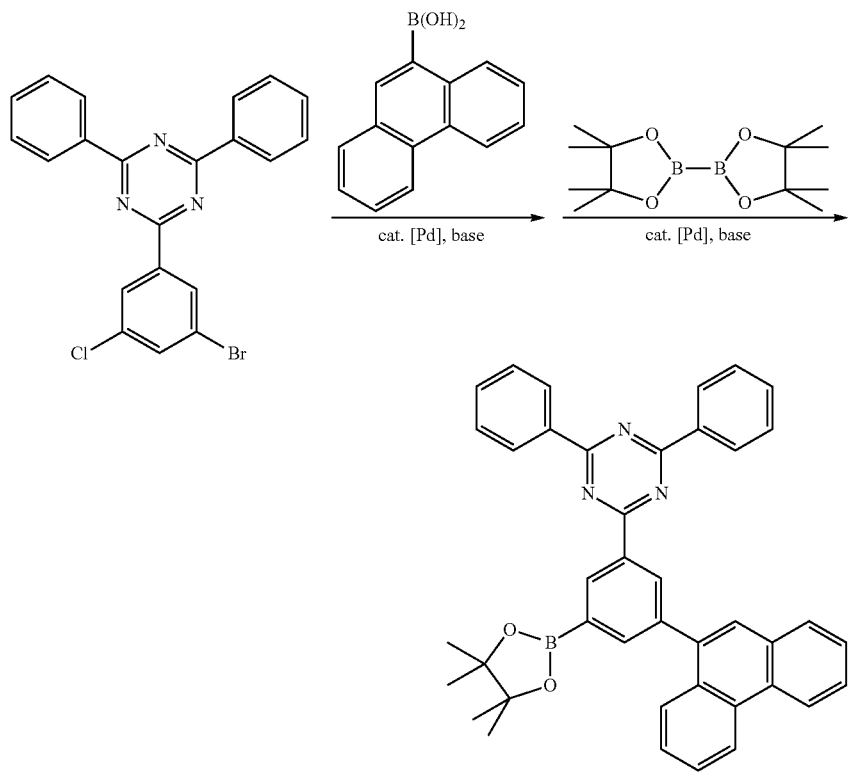

Under an argon stream, 2-(3-bromo-5-chlorophenyl)-4,6-diphenyl-1,3,5-triazine (70.0 g, 0.166 mol), 9-phenanthrene boronic acid (38.6 g, 0.174 mol) and tetrakis(triphenylphosphine) palladium (3.83 g, 3.31 mmol) were weighed and suspended in a 4.0M sodium hydroxide aqueous solution (124 mL, 0.497 mol) and tetrahydrofuran (1.0L). The mixture was heated and refluxed for 24 hours. After cooling, water (550mL) was added, and the precipitated solid was separated by filtration, followed by washing with water, methanol and hexane in this order. By recrystallization (toluene), a white solid of 2-[3-chloro-5-(9-phenanthryl)phenyl]-4,6-diphenyl-1,3,5-triazine was obtained as a reaction intermediate (amount: 78.9 g, yield: 92%).

Then, under an argon stream, 2-[3-chloro-5-(9-phenanthryl)phenyl]-4,6-diphenyl-1,3,5-triazine (5.20 g, 10.0 mmol), 4,4,4',4',5,5,5',5'-octamethyl-2,2'-bi-1,3,2-dioxaborolane (3.81 g, 15.0 mmol), palladium acetate (22.5 mg, 0.10 mmol), 2-dicyclohexylphosphino-2',4',6'-triisopropyl biphenyl (95.4 mg, 0.20 mmol) and potassium acetate (2.95 g, 30 mmol), were suspended in 1,4-dioxane (200 mL), and the mixture was stirred for 4 hours at 100° C. After cooling, the precipitate was removed by filtration using a filter paper. Further, liquid separation was conducted with chloroform, and the organic layer was concentrated to obtain a crude solid. Hexane was added to the crude solid, followed by cooling to ice temperature, and then, the solid was separated by filtration, followed by drying under vacuum to obtain a white solid of 4,6-diphenyl-2-[5-(9-phenanthryl)-3-(4,4,5,5-tetramethyl-1,3,2-dioxaborolan-2-yl)phenyl]-1,3,5-triazine as an intermediate (amount: 6.07 g, yield: 99%).

Synthesis Example 1

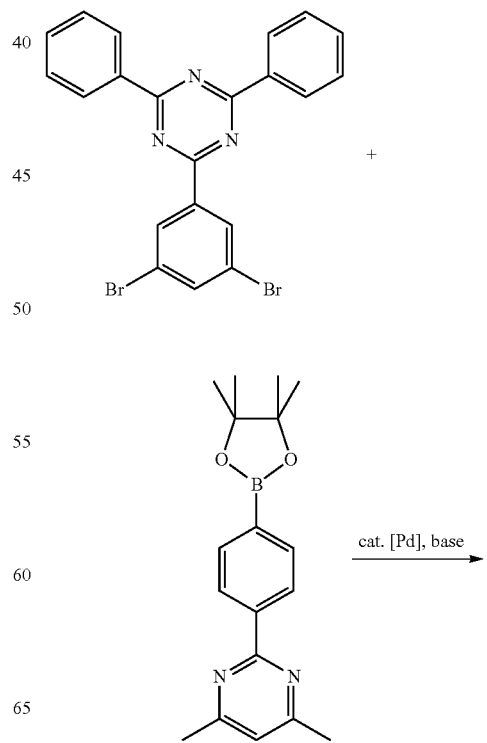

-continued

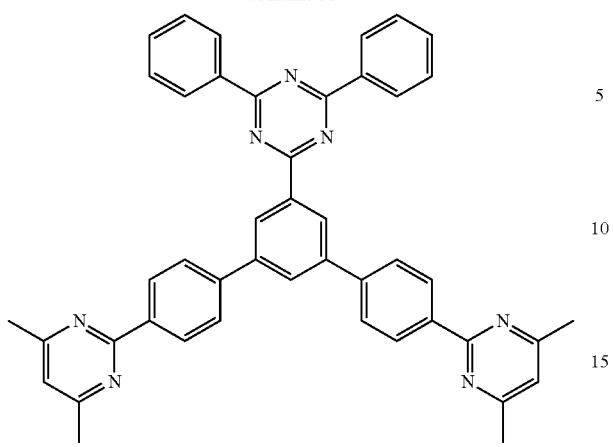

Under an argon stream, 2-(3,5-dibromophenyl)-4,6-diphenyl-1,3,5-triazine (935 mg, 2.0 mmol), 4,6-dimethyl-2-[4-(4,4,5,5-tetramethyl-1,3,2-dioxaborolan-2-yl)phenyl]pyrimidine (1.49 g, 4.8 mmol) and dichlorobis(triphenylphosphine) palladium (56.2 mg, 80.µmol) were weighed and suspended in a 1.0M tripotassium phosphate aqueous solution (9.6 mL, 9.6 mmol) and 1,4-dioxane (100 mL). The mixture was heated and refluxed for 23 hours. After cooling, a low-boiling point component was distilled off under reduced pressure. Hexane was added, and the precipitated solid was separated by filtration, followed by washing with water, methanol and hexane in this order. To the obtained crude product, alumina (1.5 g) and chloroform (50 mL) were added, followed by heating and stirring for 0.5 hour at 60° C. This suspension was filtered hot, and the filtrate was concentrated under reduced pressure, whereupon the obtained solid was recrystallized (toluene) to obtain a white solid of the desired 2-[4,4"-bis(4,6-dimethylpyrimidin-2-yl)-1,1':3', 1"-terphenyl-5'-yl]-4,6-diphenyl-1,3,5-triazine (Compound A-1) (amount: 1.07 g, yield: 66%).

$^1$H-NMR (CDCl$_3$) δ (ppm): 2.59 (s, 12H), 6.97 (s, 2H), 7.57-7.69 (m, 6H), 7.94 (brd, J=8.5 Hz, 4H), 8.18 (brs, 1H), 8.63 (brd, J=8.5 Hz, 4H), 8.57 (brd, J=7.7 Hz, 4H), 9.07 (brs, 2H).

Synthesis Example-2

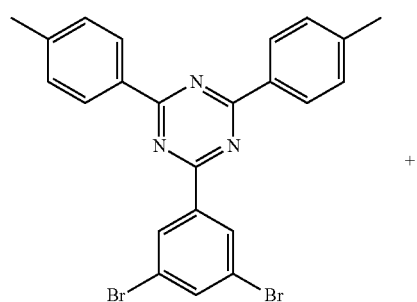

+

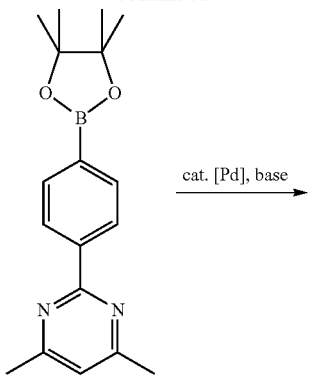

cat. [Pd], base →

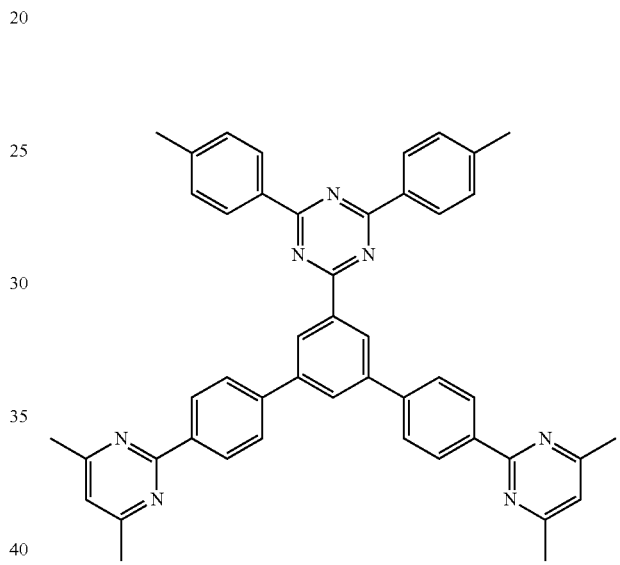

Under an argon stream, 2-(3,5-dibromophenyl)-4,6-di(4-tert-butyl)-1,3,5-triazine (1.50 g, 3.0 mmol), 4,6-dimethyl-2-[4-(4,4,5,5-tetramethyl-1,3,2-dioxaborolan-2-yl)phenyl]pyrimidine (2.26 g, 7.3 mmol), palladium acetate (20.4 mg, 91 µmol) and 1.0M of tert-butyl phosphine (0.270 mL, 0.27 mmol) were suspended in tetrahydrofuran (15 mL) and heated to 70° C. After slowly dropwise adding a 4.0M aqueous sodium hydroxide solution (5.7 mL) thereto, the mixture was heated to 75° C. and stirred for 4 hours. After cooling, a white solid was separated by filtration. The obtained crude product was purified by recrystallization (toluene) to obtain a white solid of 2-[4,4"-bis(4,6-dimethylpyrimidin-2-yl)-1,1';3',1"-terphenyl-5'-yl]-4,6-di(4-tert-butylphenyl)-1,3,5-triazine (Compound A-2) as the desired product (amount: 1.80 g, yield: 84%).

$^1$H-NMR (CDCl$_3$) δ (ppm): 2.50 (s, 6H), 2.59 (s, 12H), 6.97 (S, 2H), 7.39 (d, J=8.1 Hz, 4H), 7.93 (d, J=8.5 Hz, 4H), 8.16 (t, J=1.8 Hz, 1H), 8.63 (d, J=8.5 Hz, 4H), 8.69 (d, J=8.1 Hz, 4H), 9.06 (d, J=1.8 Hz, 2H).

Synthesis Example 3

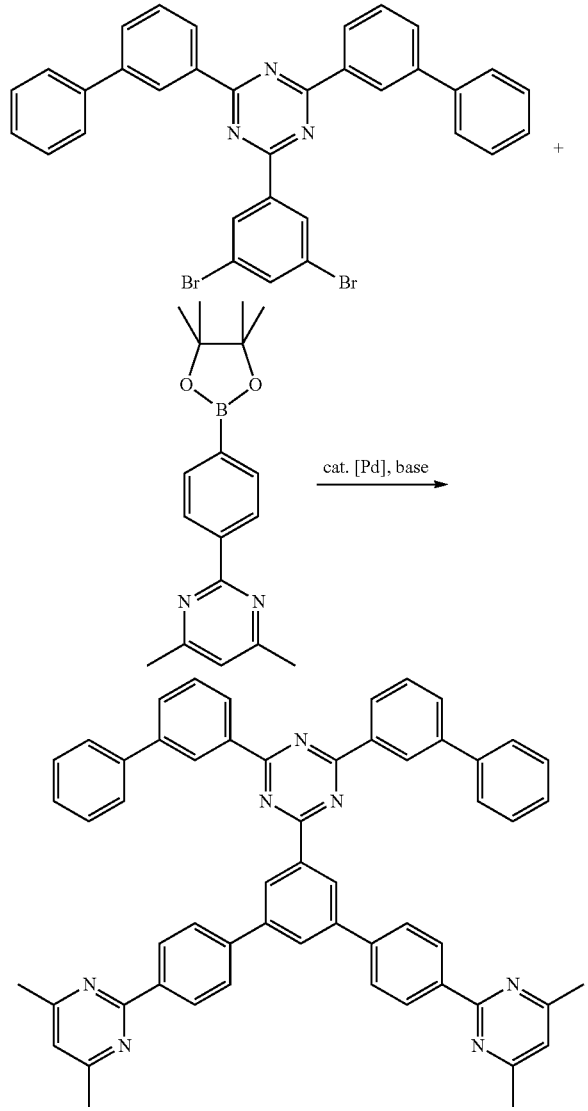

Under an argon stream, 4,6-bis(3-biphenylyl)-2-(3,5-dibromophenyl)-1,3,5-triazine (1.00 g, 1.6 mmol), 4,6-dimethyl-2-[4-(4,4,5,5-tetramethyl-1,3,2-dioxaborolan-2-yl)phenyl]pyrimidine (1.25 g, 4.0 mmol), palladium acetate (10.9 mg, 49 μmol) and 1.0M tert-butylphosphine (0.150 mL, 0.15 mmol) were suspended in tetrahydrofuran (8 mL) and heated to 70° C. After slowly dropwise adding a 4.0M aqueous sodium hydroxide solution (3.0 mL) thereto, the mixture was heated to 80° C. and stirred for 4 hours. After cooling, a white solid was separated by filtration. The obtained crude product was purified by recrystallization (toluene) to obtain a white solid of 4,6-bis(3-biphenylyl)-2-[4,4''-di(4,6-dimethylpyrimidin-2-yl)-1,1';3',1''-terphenyl-5'-yl]-1,3,5-triazine (compound A-3) as the desired product (amount: 1.23 g, yield: 93%).

$^1$H-NMR (CDCl$_3$) δ (ppm): 2.59 (s, 12H), 6.97 (s, 2H), 7.42 (t, J=7.3 Hz, 2H), 7.53 (t, J=7.3 Hz, 4H), 7.69 Hz (t, J=7.8 Hz, 2H), 7.77 (d, J=7.1 Hz, 4H), 7.87 (d, J=7.8 Hz, 2H), 7.94 (d, J=8.6 Hz, 4H), 8.19 (s, 1H), 8.62 (d, J=8.6 Hz, 4H), 8.80 (d, J=7.8 Hz, 2H), 9.05 (s, 2H), 9.08 (s, 1H), 9.08 (s, 1H)

Synthesis Example 4

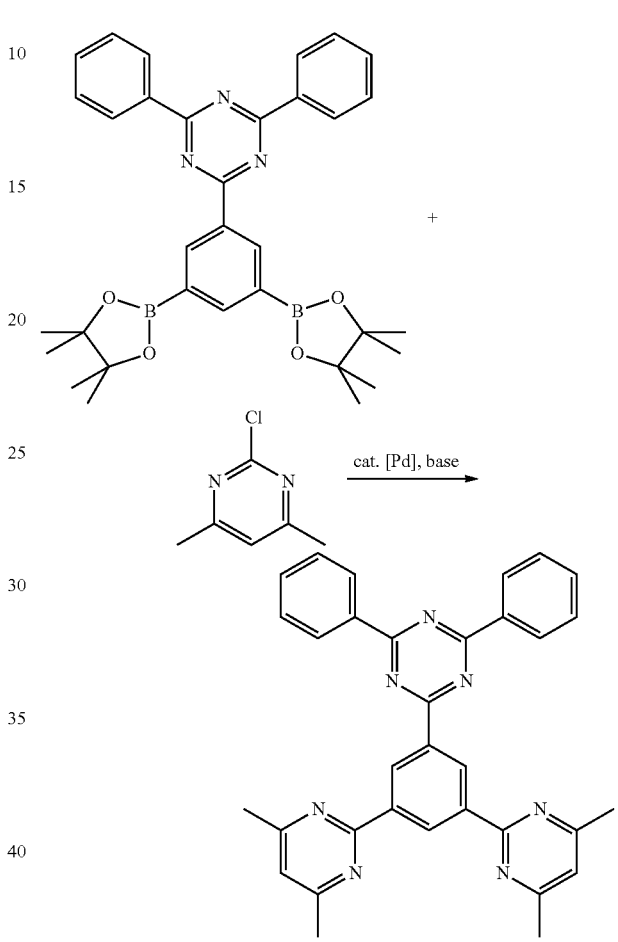

Under an argon stream, 2-[3,5-bis(4,4,5,5-tetramethyl-1,3,2-dioxaborolan-2-yl)phenyl]-4,6-diphenyl-1,3,5-triazine (1.68 g, 3.0 mmol), 4,6-dimethyl-2-chloropyrimidine (1.03 g, 7.2 mmol), tetrakis(triphenylphosphine) palladium (69.4 mg, 60.μmol) and tripotassium phosphate (3.06 g, 14.4 mmol) were weighed and suspended in 1,4-dioxane (40 mL) and water (14.4 mL). This mixture was heated and refluxed for 16 hours. After cooling, a low-boiling point component was distilled off under reduced pressure. Water was added, and the precipitated solid was separated by filtration and washed with water, methanol and hexane in this order. To the obtained crude product, 100 mL of toluene was added, followed by heating and stirring for 0.5 hour at 125° C. This suspension was filtered hot, and the obtained solid was recrystallized (toluene) to obtain a white solid of the desired 2-{3,5-bis[2-(4,6-dimethylpyrimidyl)phenyl]}-4,6-diphenyl-1,3,5-triazine (compound A-4) (amount: 1.28 g, yield: 81%).

$^1$H-NMR (CDCl$_3$) δ (ppm): 2.65 (s, 12H), 7.03 (s, 2H), 7.56-7.66 (m, 6H), 8.85-8.91 (m, 4H), 9.68 (brs, 1H), 9.87 (brs, 2H).

Synthesis Example 5

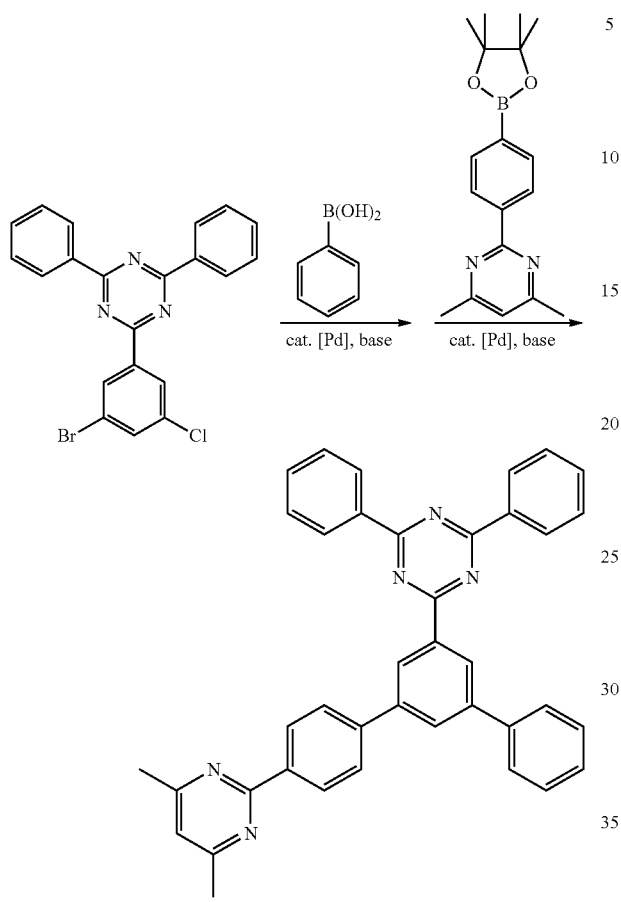

Under an argon stream, 2-(3-bromo-5-chlorophenyl)-4,6-diphenyl-1,3,5-triazine (3.17 g, 7.5 mmol), phenylboronic acid (1.01 g, 8.25 mmol) and tetrakis(triphenylphosphine) palladium (173.4 mg, 0.15 mmol) were weighed and suspended in a 4.0M aqueous sodium hydroxide solution (5.7 mL, 23 mmol) and tetrahydrofuran (47 mL). This mixture was heated and refluxed for 20 hours. After cooling, a low-boiling point component was distilled off under reduced pressure. Water (30 mL) was added, and the precipitated solid was separated by filtration and washed with water, methanol and hexane in this order, followed by vacuum drying, to obtain a yellowish white solid of 2-(5-chloro-biphenyl-3-yl)-4,6-diphenyl-1,3,5-triazine as a reaction intermediate (amount: 2.85 g, yield: 90%).

Then, under an argon stream, 2-(5-chloro-biphenyl-3-yl)-4,6-diphenyl-1,3,5-triazine (2.73 g, 6.5 mmol), 4,6-dimethyl-2-[4-(4,4,5,5-tetramethyl-1,3,2-dioxaborolan-2-yl)phenyl]pyrimidine (2.42 g, 7.8 mmol), palladium acetate (58.4 mg, 0.26 mmol) and 2-dicyclohexylphosphino-2',4',6'-triisopropyl biphenyl (247.9 mg) were weighed and suspended in a 1.0M potassium phosphate aqueous solution (13.0 mL, 13.0 mmol) and 1,4-dioxane (130 mL). This mixture was heated and refluxed for 17 hours. After cooling, a low-boiling point component was distilled off under reduced pressure. Water (100 mL) was added, and the precipitated solid was separated by filtration and washed with water, methanol and hexane in this order. Further, it was purified by column chromatography (developing solvent: chloroform:hexane) to obtain a milky white powder of 2-{4-[2-(4,6-dimethylpyrimidyl)]-1,1': 3',1"-terphenyl-5'-yl}-4,6-diphenyl-1,3,5-triazine (compound A-5) (amount: 3.59 g, yield: 97%).

$^1$H-NMR (CDCl$_3$) δ (ppm): 2.59 (s, 6H), 6.97 (s, 1H), 7.43-7.45 (m, 1H), 7.53-7.68 (m, 8H), 7.83 (brd, J=8.5 Hz, 2H), 7.92 (brd, J=8.5 Hz, 2H), 8.11 (brs, 1H), 8.62 (brd, J=8.5 Hz, 2H), 8.78-8.84 (m, 4H), 8.99 (brs, 1H), 9.05 (brs, 1H).

Synthesis Example 6

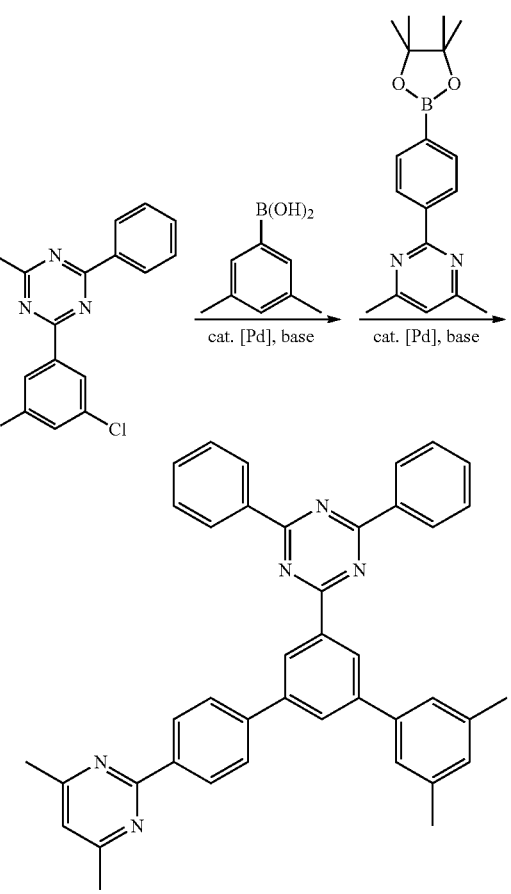

Under an argon stream, 2-(3-bromo-5-chlorophenyl)-4,6-diphenyl-1,3,5-triazine (5.07 g, 12 mmol), 3,5-dimethylphenyl boronic acid (1.98 g, 13 mmol), tetrakis(triphenylphosphine) palladium (277.4 mg, 0.24 mmol) and sodium hydroxide (1.44 g, 36 mmol) were weighed and suspended in tetrahydrofuran (72 mL) and water (9 mL). This mixture heated and refluxed for 23 hours. After cooling, a low-boiling point component was distilled off under reduced pressure. Water (100 mL) was added, and the precipitated solid was separated by filtration and washed with water, methanol and hexane in this order, followed by vacuum drying, to obtain a white solid of 2-(5-chloro-3', 5'-dimethyl-biphenyl-3-yl)-4,6-diphenyl-1,3,5-triazine (amount: 5.34 g, yield: 99%).

Then, under an argon stream, 2-(5-chloro-3',5'-dimethyl-biphenyl-3-yl)-4,6-diphenyl-1,3,5-triazine (1.35 g, 3.0 mmol), 4,6-dimethyl-2-[4-(4,4,5,5-tetramethyl-1,3,2-dioxaborolan-2-yl)phenyl]pyrimidine (1.12 g, 3.6 mmol), palladium acetate (27.0 mg, 0.12 mmol), 2-dicyclohexylphosphino-2',4',6'-triisopropylbiphenyl (115 mg, 0.24 mmol) and tripotassium phosphate (1.28 g, 6.0 mmol) were weighed and suspended in 1,4-dioxane (60 mL) or water (6 mL). This mixture was heated and refluxed for 16 hours. After cooling, the reaction mixture was heated as it was for 0.5 hour at 70° C. and filtered hot. From the obtained filtrate, a low-boiling component was removed under reduced pressure. Water (100 mL) was added, and the precipitated solid was separated by filtration and washed with water, methanol and hexane in this order. Further, it was purified by column chromatography (developing solvent: chloroform:hexane) and further purified by recrystallization (toluene), to obtain a white powder of 2,4-diphenyl-6-{3,5-dimethyl-4'-[2-(4,6-dimethylpyrimidyl)]-1,1':3',1"-terphenyl-5'-yl}-1,3,5-triazine (compound A-6) (amount: 0.96 g, yield: 54%).

$^1$H-NMR (CDCl$_3$) δ (ppm): 2.47 (s, 6H), 2.60 (s, 6H), 6.98 (s, 1H), 7.11 (brs, 1H), 7.41 (brs, 2H), 7.56-7.67 (m, 6H), 7.92 (brd, J=8.4 Hz, 2H), 8.07 (brs, 1H), 8.63 (brd, J=8.4 Hz, 2H), 8.78-8.85 (m, 4H), 8.94 (brs, 1H), 9.03 (brs, 1H).

Synthesis Example 7

Under an argon stream, 2-(3-bromo-5-chlorophenyl)-4,6-diphenyl-1,3,5-triazine (8.46 g, 20. mmol), 4-biphenyl boronic acid (4.36 g, 22 mmol), tetrakis(triphenylphosphine) palladium (462 mg, 0.40 mmol) and sodium hydroxide (2.40 g, 60. mmol) were weighed and suspended in tetrahydrofuran (100 mL) and water (15 mL). This mixture was heated and refluxed for 16 hours. After cooling, water (150 mL) was added, and the precipitated solid was separated by filtration and washed with water, methanol and hexane in this order. Further, it was purified by recrystallization (toluene) to obtain a white solid of 2-(5-chloro-1,1':4':1"-terphenyl-3-yl)-4,6-diphenyl-1,3,5-triazine (amount: 9.48 g, yield: 96%).

Then, under an argon stream, 2-(5-chloro-1,1:4':1"-terphenyl-3-yl)-4,6-diphenyl-1,3,5-triazine (1.49 g, 3.0 mmol), 4,6-dimethyl-2-[4-(4,4,5,5-tetramethyl-1,3,2-dioxaborolan-2-yl)phenyl]pyrimidine (1.17 g, 3.8 mmol), palladium acetate (27.0 mg, 0.12 mmol), 2-dicyclohexylphosphino-2',4',6'-triisopropyl-biphenyl (115 mg, 0.24 mmol) and tripotassium phosphate (1.28 g, 6.0 mmol) were weighed and suspended in 1,4-dioxane (60 mL) and water (6 mL). This mixture was heated and refluxed for 21 hours. After cooling, water (100 mL) was added, and the precipitated solid was separated by filtration and washed with water, methanol and hexane in this order. Further, it was purified by recrystallization (toluene) to obtain a white powder of 2-{4-[2-(4,6-dimethylpyrimidyl)]-1,1:3',1":4",1'"-quaterphenyl-5'-yl}-4,6-diphenyl-1,3,5-triazine (compound A-7) (amount: 1.25 g, yield: 65%).

$^1$H-NMR (CDCl$_3$) δ (ppm): 2.59 (s, 6H), 6.97 (s, 1H), 7.37-7.43 (m, 1H), 7.47-7.53 (m, 2H), 7.58-7.67 (m, 6H), 7.71 (brd, J=8.5 Hz, 2H), 7.80 (brd, J=8.5 Hz, 2H) 7.89-7.96 (m, 4H), 8.16 (brs, 1H), 8.63 (brd, J=8.5 Hz, 2H), 8.80-8.85 (m, 4H), 9.05 (brs, 1H), 9.07 (brs, 1H).

Synthesis Example 8

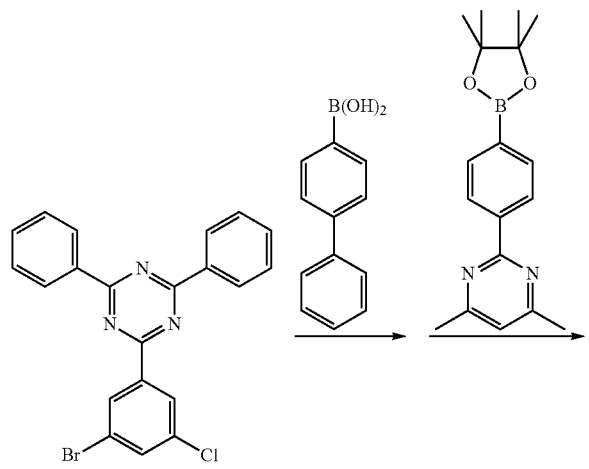

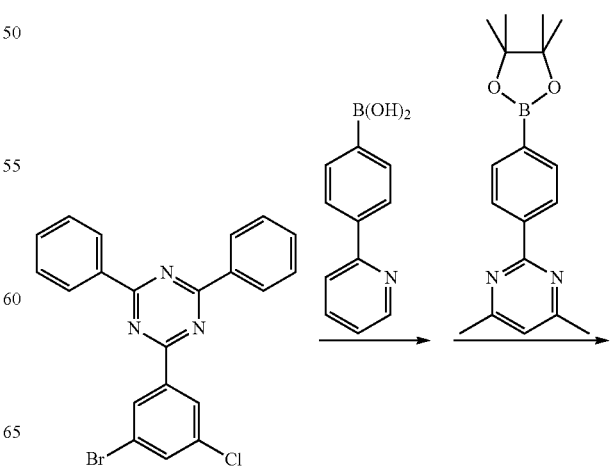

529
-continued

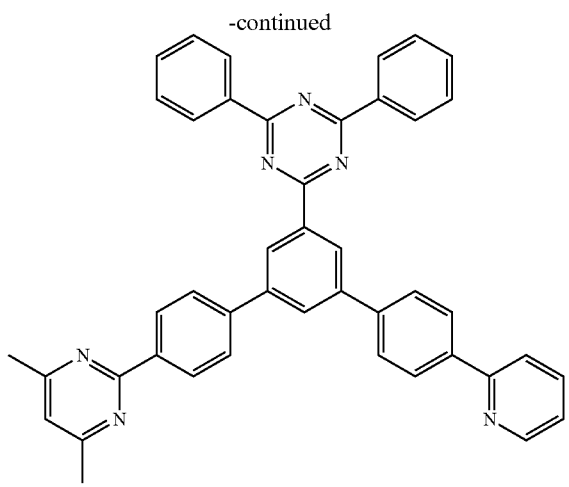

Under an argon stream, 2-(3-bromo-5-chlorophenyl)-4,6-diphenyl-1,3,5-triazine (8.46 g, 20. mmol), 4-(2-pyridyl)phenyl boronic acid (4.38 g, 22 mmol), tetrakis(triphenylphosphine) palladium (462.3 mg, 0.40 mmol) and sodium hydroxide (2.40 g, 60. mmol) were weighed and suspended in tetrahydrofuran (100 mL) and water (15 mL). This mixture was heated and refluxed for 16 hours. After cooling, water (150 mL) was added, and the precipitated solid was separated by filtration and washed with water, methanol and hexane in this order. Further, it was purified by recrystallization (toluene) to obtain a white solid of 2-[5-chloro-4'-(2-pyridyl)dimethylbiphenyl-3-yl]-4,6-diphenyl-1,3,5-triazine (amount: 9.30 g, yield: 94%).

Then, under an argon stream, 2-[5-chloro-4'-(2-pyridyl)dimethylbiphenyl-3-yl]-4,6-diphenyl-1,3,5-triazine (1.49 g, 3.0 mmol), 4,6-dimethyl-2-[4-(4,4,5,5-tetramethyl-1,3,2-dioxaborolan-2-yl)phenyl]pyrimidine (1.17 g, 3.8 mmol), palladium acetate (27.0 mg, 0.12 mmol), 2-dicyclohexylphosphino-2',4',6'-triisopropylbiphenyl (115 mg, 0.24 mmol) and tripotassium phosphate (1.28 g, 6.0 mmol) were weighed and suspended in 1,4-dioxane (60 mL) and water (6 mL). This mixture was heated and refluxed for 21 hours. After cooling, water (100 mL) was added, and the precipitated solid was separated by filtration and washed with water, methanol and hexane in this order. Further, it was purified by column chromatography (developing solvent: chloroform:methanol) to obtain a white powder of 4,6-diphenyl-2-{4-(2-pyridyl)-4'-[2-(4,6-dimethylpyrimidyl)]-1,1':3',1''-terphenyl-5'-yl}-1,3,5-triazine (compound A-8) (amount: 1.13 g, yield; 59%).

¹H-NMR (CDCl₃) δ (ppm): 2.59 (s, 6H), 6.97 (s, 1H), 7.24-7.32 (m, 1H), 7.57-7.68 (m, 6H), 7.77-7.89 (m, 2H), 7.90-7.98 (m, 4H), 8.17 (brs, 1H) 8.21 (brd, J=8.5 Hz, 2H), 8.63 (brd, J=8.5 Hz, 2H), 8.74-8.78 (m, 1H), 8.80-8.86 (m, 4H), 9.06 (brs, 1H), 9.08 (brs, 1H).

530
Synthesis Example 9

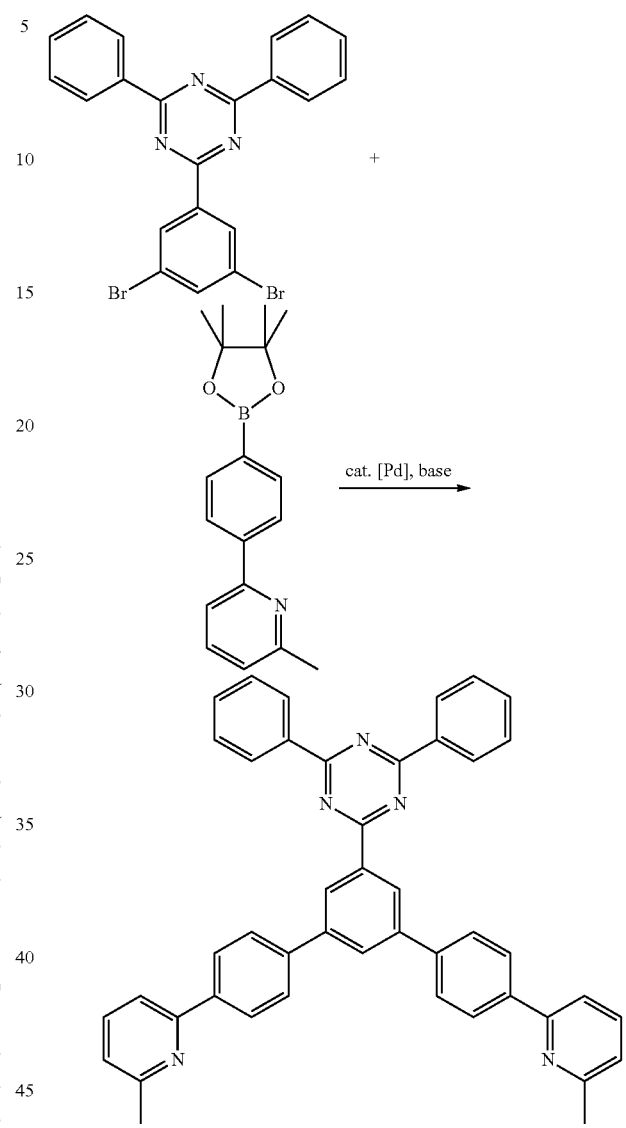

Under an argon stream, 2-(3,5-dibromo-phenyl)-4,6-diphenyl-1,3,5-triazine (1.00 g, 2.05 mmol), 2-methyl-6-[4-(4,4,5,5-tetramethyl-1,3,2-dioxaborolan-2-yl)phenyl]pyridine (1.45 g, 4.93 mmol), palladium acetate (23.0 mg, 0.10 mmol) and 2-dicyclohexyl phosphino-2',4',6'-triisopropylbiphenyl (97.7 mg, 0.205 mmol) were suspended in 1,4-dioxane (30 mL) and heated to 60° C. A 1.0M tripotassium phosphate aqueous solution (9.8 mL) was slowly dropwise added thereto, and the mixture was heated to 80° C. and stirred for 6 hours. After cooling, a white solid was separated by filtration. The obtained crude product was purified by recrystallization (toluene) to obtain a white solid of 2-[4,4''-bis(6-methylpyridin-2-yl)-1,1':3',1''-terphenyl-5'-yl]-4,6-diphenyl-1,3,5-triazine (compound A-9) as the desired product (amount: 861 mg, yield: 79%).

¹H-NMR (CDCl₃) δ (ppm): 2.68 (s, 6H), 7.12 (d, J=7.5 Hz, 2H), 7.59-7.71 (m, 10H), 7.92 (t, J=8.3 Hz, 4H), 8.15 (t, J=1.9 Hz, 1H), 8.19 (d, J=8.6 Hz, 4H), 8.82 (dd, J=1.9, 6.0 Hz, 4H), 9.05 (d, J=1.9 Hz, 2H).

Synthesis Example 10

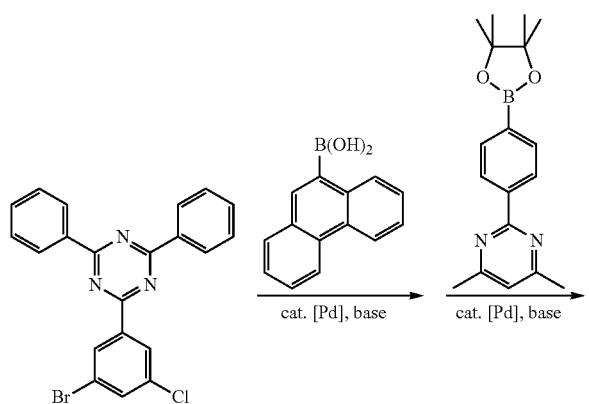

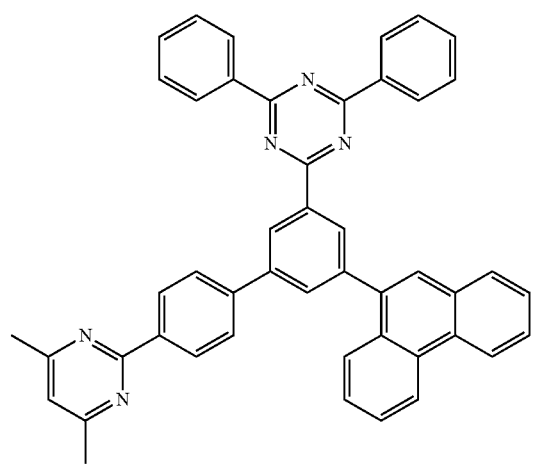

Under an argon stream, 2-(3-bromo-5-chlorophenyl)-4,6-diphenyl-1,3,5-triazine (70.0 g, 0.17 mol), 9-phenanthrene boronic acid (38.6 g, 0.17 mol) and tetrakis (triphenylphosphine) palladium (3.83 g, 3.3 mmol) were weighed and suspended in a 4.0M sodium hydroxide aqueous solution (124 mL, 0.50 mol) and tetrahydrofuran (1.03L). This mixture was heated and refluxed for 24 hours. After cooling, water (550mL) was added, and the precipitated solid was separated by filtration and washed with water, methanol and hexane in this order. By recrystallization (toluene), a white solid of 2-[3-chloro-5-(9-phenanthryl)phenyl]-4,6-diphenyl-1,3,5-triazine as a reaction intermediate was obtained (amount: 78.9 g, yield: 92%).

Then, under an argon stream, 2-[3-chloro-5-(9-phenanthryl)phenyl]-4,6-diphenyl-1,3,5-triazine (1.04 g, 2.0 mmol), 4,6-dimethyl-2-[4-(4,4,5,5-tetramethyl-1,3,2-dioxaborolan-2-yl)phenyl]pyrimidine (745 mg, 2.4 mmol), palladium acetate (18.0 mg, 80.μmol) and 2-dicyclohexylphosphino-2',4',6'-triisopropylbiphenyl (76.3 mg, 0.16 mmol) were weighed and suspended in a 1.0M tripotassium phosphate aqueous solution (4.00 mL, 4.0 mmol) and 1,4-dioxane (100 mL). This mixture was heated and refluxed for 17 hours. After cooling, a low-boiling point component was distilled off under reduced pressure. Methanol and water were added, and the precipitated solid was separated by filtration and washed with water, methanol and hexane in this order. Further, it was purified by recrystallization (toluene) to obtain a white solid of the desired 4,6-diphenyl-2-{5-(9-phenanthryl)-4'-[2-(4,6-dimethylpyrimidyl)]biphenyl-3-yl}-1,3,5-triazine (compound A-10) (amount: 949 mg, yield: 71%).

$^1$H-NMR (CDCl$_3$) δ (ppm): 2.57 (s, 6H), 6.96 (s, 1H), 7.50-7.78 (m, 10H), 7.90 (s, 1H), 7.95 (brd, J=8.5 Hz, 2H), 7.97-8.06 (m, 2H), 8.09 (brs, 1H), 8.61 (brd, J=8.5 Hz, 2H), 8.76-8.82 (m, 5H), 8.85 (brd, J=8.2 Hz, 1H), 8.94 (brs, 1H), 9.19 (brs, 1H).

Synthesis Example 11

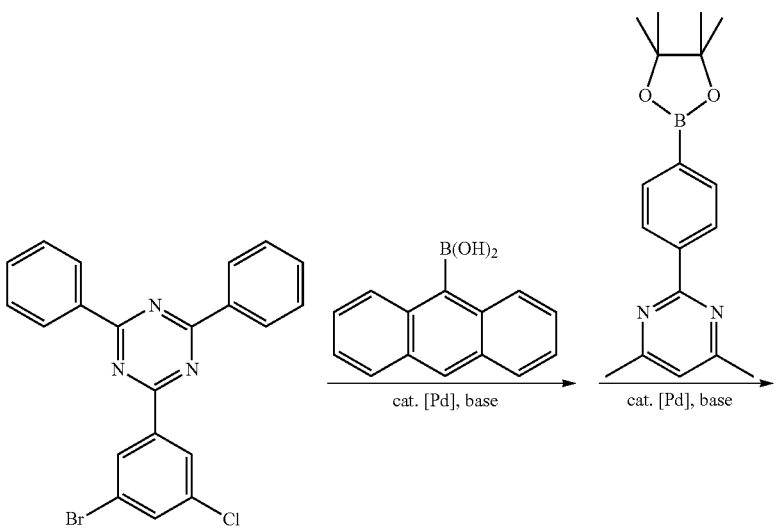

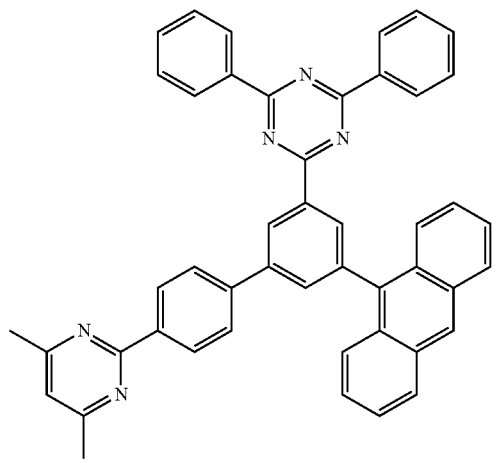

Under an argon stream, 2-(3-bromo-5-chlorobenzene-1-yl)-4,6-diphenyl-1,3,5-triazine (9.78 g, 23 mmol), 9-anthracene boronic acid (5.13 g, 23 mmol) and tetrakis(triphenylphosphine) palladium (267 mg, 0.23 mmol) were suspended in a mixed solution of toluene (780 mL) and ethanol (98 mL) and heated to 85° C. A 1.0M potassium carbonate aqueous solution (69.3 mL, 69.3 mmol) was slowly dropwise added thereto, followed by stirring for 20 hours. After cooling, it was extracted with dichloromethane, and the organic layer was concentrated. The obtained crude product was recrystallized (toluene) to obtain a white solid of 2-[3-chloro-5-(9-anthracenyl)phenyl]-4,6-diphenyl-1,3,5-triazine as a reaction intermediate (amount: 9.52 g, yield: 77%).

Then, under an argon stream, 2-[3-chloro-5-(9-anthracenyl)phenyl]-4,6-diphenyl-1,3,5-triazine (300. mg, 0.58 mmol), 4,6-dimethyl-2-[4-(4,4,5,5-tetramethyl-1,3,2-dioxaborolan-2-yl)phenyl]pyrimidine (232 mg, 0.749 mmol), palladium acetate (4.31 mg, 19.2 µmol), 2-dicyclohexylphosphino-2',4',6'-triisopropylbiphenyl (18.3 mg, 38.4 µmol) and potassium carbonate (0.207 g, 1.50 mmol) were suspended in a mixed solution of tetrahydrofuran (3.00 mL) and water (1.00 mL), followed by stirring for 24 hours at 65° C. After cooling, methanol and water were added, and the precipitated solid was separated by filtration and washed with water, methanol and hexane in this order. Further, it was purified by recrystallization (toluene) to obtain a while solid of the desired 2-[5-(9-anthracenyl)-4'-(4,6-dimethylpyrimidin-2-yl)biphenyl-3-yl]-4,6-diphenyl-1,3,5-triazine (compound A-11) (amount: 375 mg, yield: 98%).

$^1$H-NMR (CDCl$_3$) δ (ppm): 2.60 (s, 6H), 6.94 (s, 1H), 7.50-7.62 (m, 10H), 7.94 (d, J=8.5 Hz, 2H), 7.99 (s, 1H), 8.12 (d, J=8.5 Hz, 2H), 8.16 (d, J=8.5 Hz, 4H), 8.60 (s, 1H), 8.76 (d, J=8.0 Hz, 4H), 8.84 (s, 1H), 9.27 (s, 1H).

Synthesis Example 12

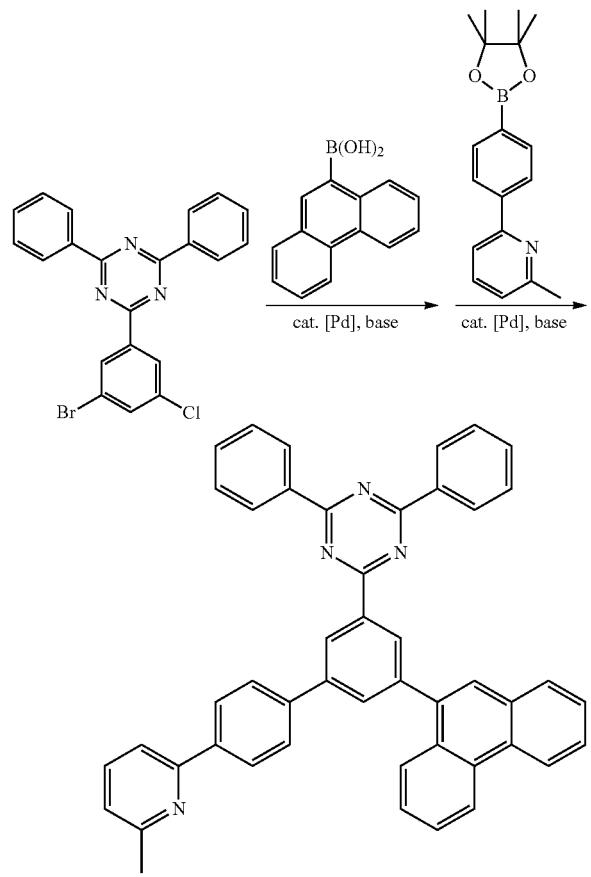

Under an argon stream, 2-(3-bromo-5-chlorophenyl)-4,6-diphenyl-1,3,5-triazine (70.0 g, 0.166 mol), 9-phenanthrene boronic acid (38.6 g, 0.174 mol) and tetrakis(triphenylphosphine) palladium (3.83 g, 3.31 mmol) were weighed and suspended in a 4.0M sodium hydroxide aqueous solution (124 mL, 0.497 mol) and tetrahydrofuran (1.0L). This mixture it was heated and refluxed for 24 hours. After cooling, water (550mL) was added, and the precipitated solid was separated by filtration and washed with water, methanol and hexane in this order. By recrystallization (toluene), a white solid of 2-[3-chloro-5-(9-phenanthryl)phenyl]-4,6-diphenyl-1,3,5-triazine as a reaction intermediate was obtained (amount: 78.9 g, yield: 92%).

Then, under an argon stream, 2-[3-chloro-5-(9-phenanthryl)phenyl]-4,6-diphenyl-1,3,5-triazine (300. mg, 0.58 mmol), 2-methyl-6-[4-(4,4,5,5-tetramethyl-1,3,2-dioxaborolan-2-yl)phenyl]pyridine (221 mg, 0.75 mmol), palladium acetate (3.89 mg, 17 μmol), 2-dicyclohexylphosphino-2',4',6'-triisopropyl biphenyl (16.5 mg, 35 μmol) and tripotassium phosphate (0.320 mg, 1.51 mmol) were weighed and suspended in 1,4-dioxane (29 mL) and water (8 mL), followed by stirring for 24 hours at 100° C. After cooling, methanol and water were added, and the precipitated solid was separated by filtration and washed with water, methanol and hexane in this order. Further, it was purified by recrystallization (toluene) to obtain a white solid of the desired 4,6-diphenyl-2-[4-(6-methylpyridin-2-yl)-3'-(9-phenanthryl)-1,1'-biphenyl-5-yl]-1,3,5-triazine (compound A-12) (amount: 290 mg, yield: 77%).

$^1$H-NMR (CDCl$_3$) δ (ppm): 2.62 (s, 3H), 7.20 (d, J=7.5 Hz, 1H), 7.50-7.78 (m, 12H), 7.95 (brd, J=8.5 Hz, 2H), 7.90-8.10 (m, 4H), 8.09 (brs, 1H), 8.61 (brd, J=8.5 Hz, 2H), 8.76-8.82 (m, 4H), 8.85 (brd, J=8.2 Hz, 1H), 8.88 (brs, 1H), 9.14 (brs, 1H).

Synthesis Example 13 enylphosphine) palladium (0.267 mg, 0.23 mmol) were suspended in a mixed solution of toluene (780 mL) and ethanol (98 mL) and heated to 85° C. A 1.0M potassium carbonate aqueous solution (69.3 mL, 69.3 mmol) was slowly dropwise added thereto, followed by stirring for 20 hours. After cooling, it was extracted with dichloromethane, and the organic layer was concentrated. The obtained crude product was recrystallized (toluene) to obtain a white solid of 2-[3-chloro-5-(9-anthracenyl)phenyl]-4,6-diphenyl-1,3,5-triazine as a reaction intermediate (amount: 9.52 g, yield; 77%).

Then, under an argon stream, 2-[3-chloro-5-(9-anthracenyl)phenyl]-4,6-diphenyl-1,3,5-triazine (300. mg, 0.576 mmol), 2-methyl-6-[4-(4,4,5,5-tetramethyl-1,3,2-dioxaborolan-2-yl)phenyl]pyridine (221 mg, 0.749 mmol), palladium acetate (4.31 mg, 19.2 μmol), 2-dicyclohexylphosphino-2',4',6'-triisopropylbiphenyl (18.3 mg, 38.4 μmol) and potassium carbonate (0.207 g, 1.50 mmol) were suspended in a mixed solution of tetrahydrofuran (3.0 mL) and water (1.0 mL) and stirred for 24 hours at 65° C. After cooling, methanol and water were added, and the precipitated solid was separated by filtration and washed with water, methanol and hexane in this order. Further, it was purified by recrystallization (toluene) to obtain a white solid of the desired 4,6-diphenyl-2-[5-(9-anthracenyl)-4'-(6-methylpyridin-2-yl)biphenyl-3-yl]-1,3,5-triazine (compound A-13) (amount: 371 mg, yield: 99%).

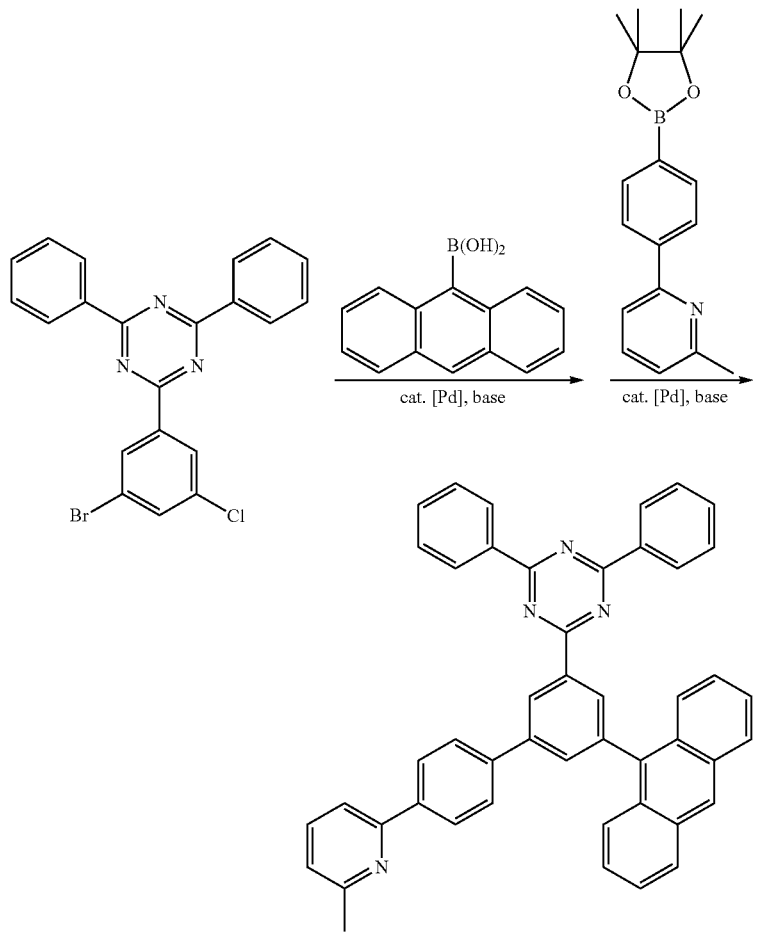

Under an argon stream, 2-(3-bromo-5-chlorobenzene-1-yl)-4,6-diphenyl-1,3,5-triazine (9.78 g, 23.1 mmol), 9-anthracene boronic acid (5.13 g, 23.1 mol) and tetrakis(triph- $^1$H-NMR (CDCl$_3$) δ (ppm): 2.66 (s, 3H), 7.12 (d, J=7.4 Hz, 1H), 7.40 (dd, J=6.5, 8.8 Hz, 2H), 7.50-7.62 (m, 10H), 7.83 (d, J=8.0 Hz, 2H), 7.94 (d, J=8.5 Hz, 2H), 7.99 (s, 1H), 8.12 (d, J=8.5 Hz, 2H), 8.16 (d, J=8.5 Hz, 2H), 8.60 (s, 1H), 8.76 (d, J=8.0 Hz, 4H), 8.84 (s, 1H), 9.27 (s, 1H).

Synthesis Example 14

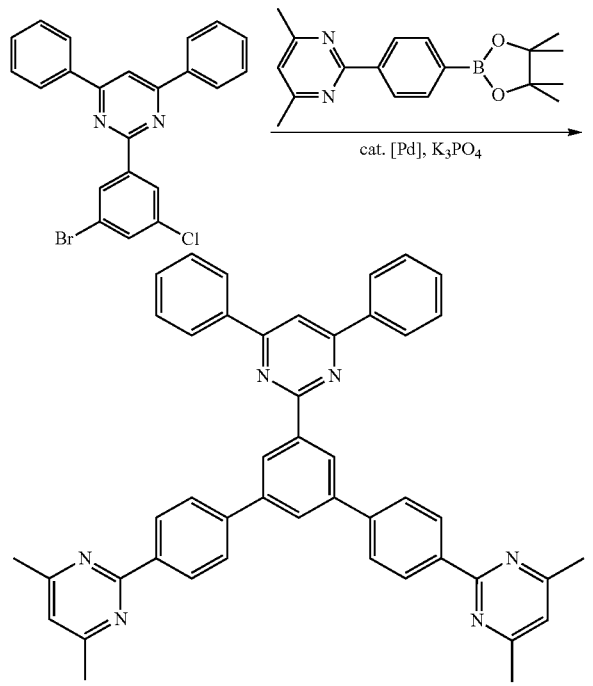

Under an argon stream, 2-(3-bromo-5-chlorophenyl)-4,6-diphenylpyrimidine (1.69 g, 4.0 mmol), 4,6-dimethyl-2-[4-(4,4,5,5-tetramethyl-1,3,2-dioxaborolan-2-yl)phenyl]-pyrimidine (2.98 g, 9.6 mmol), palladium acetate (18.0 mg, 80 μmol) and 2-dicyclohexylphosphino-2',4',6'-triisopropylbiphenyl (76.3 mg, 0.16 mmol) were weighed and suspended in a 1.0M tripotassium phosphate aqueous solution (16 mL, 16 mmol) and 1,4-dioxane (40 mL). This mixture was heated and refluxed for 24 hours. After cooling, water (80 mL) was added, and the precipitated solid was separated by filtration and washed with water, methanol and hexane in this order. To the obtained solid, chloroform was added, followed by heating and stirring for 0.5 hour at 70° C. After hot filtration, from the obtained filtrate, a low boiling point component was distilled off under reduced pressure, followed further by purification by recrystallization (toluene) to obtain a white solid of the desired 2-{4,4"-bis[2-(4,6-dimethylpyrimidyl)]-1,':3',1"-terphenyl-5'-yl}-4,6-diphenylpyrimidine (compound A-14) (amount: 2.26 g, yield: 84%).

$^1$H-NMR (CDCl$_3$) δ (ppm): 2.58 (s, 12H), 6.96 (s, 2H), 7.53-7.65 (m, 6H), 7.93 (brd, J=8.5 Hz, 4H), 8.09 (brs, 1H), 8.10 (s, 1H), 8.31-8.37 (m, 4H), 8.61 (brd, J=8.5 Hz, 4H), 9.04 (brs, 2H).

Synthesis Example 15

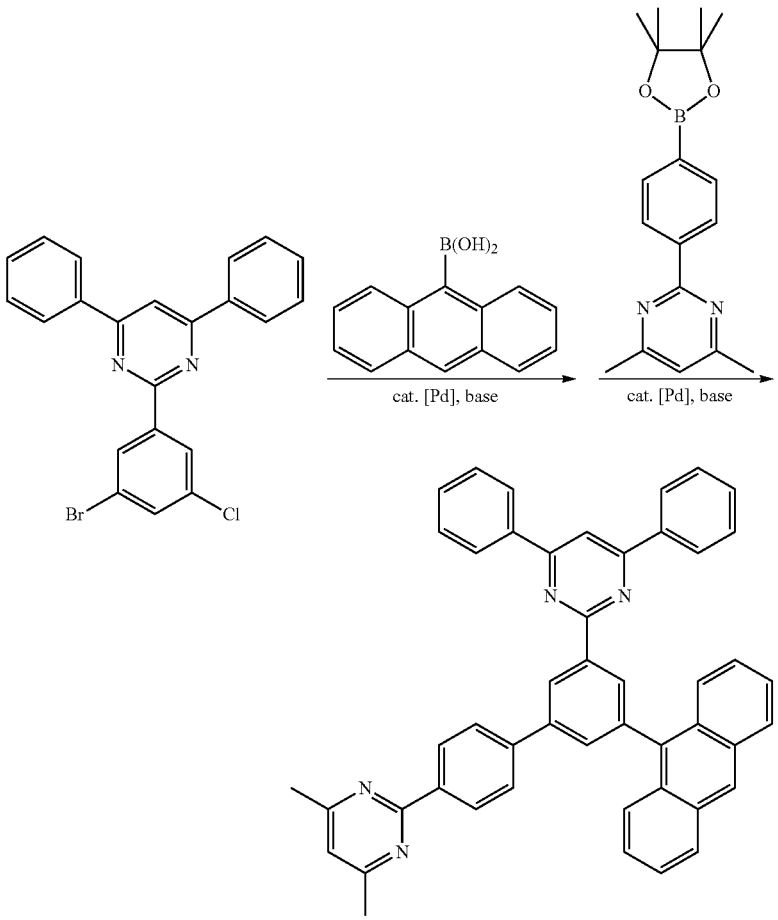

Under an argon stream, 2-(3-bromo-5-chlorophenyl)-4,6-diphenyl-pyrimidine (4.22 g, 10 mmol), 9-anthracene boronic acid (2.44 g, 11 mmol) and tetrakis(triphenylphosphine) palladium (231 mg, 0.2 mmol) were weighed and suspended in a 4.0M sodium hydroxide aqueous solution (7.5 mL, 30 mmol) and tetrahydrofuran (75 mL). This mixture was heated and refluxed for 21.5 hours. After cooling, a low-boiling point component was distilled off under reduced pressure. Water (40 mL) was added, and the precipitated solid was separated by filtration and washed with water, methanol, and hexane in this order. The obtained solid was added to toluene and heated with stirring for 0.5 hour at 120° C. After hot filtration, from the obtained filtrate, a low boiling point component was distilled off under reduced pressure, followed further by purification by recrystallization (toluene) to obtain a white solid of 2-[3-chloro-5-(9-anthracenyl)phenyl]-4,6-diphenylpyrimidine as a reaction intermediate (amount: 4.16 g, yield: 80%).

Then, under an argon stream, 2-[3-chloro-5-(9-anthracenyl)phenyl]-4,6-diphenylpyrimidine (1.56 g, 3.0 mmol), 4,6-dimethyl-2-[4-(4,4,5,5-tetramethyl-1,3,2-dioxaborolan-2-yl)phenyl]-pyrimidine (1.12 g, 3.6 mmol), palladium acetate (13.5 mg, 0.060 mmol), 2-dicyclohexylphosphino-2',4',6'-triisopropylbiphenyl (57.2 mg, 0.12 mmol) and tripotassium phosphate (1.28 g, 6.0 mmol) were weighed and suspended in 1,4-dioxane (40 mL) and water (6 mL). This mixture was heated and refluxed for 21 hours. After cooling, water (45 mL) was added, and the precipitated solid was separated by filtration and washed with water, methanol and hexane in this order. To the obtained solid, chloroform was added, followed by heating and stirring for 0.5 hour at 70° C. Thereafter, hot filtration was conducted, and from the obtained filtrate, a low boiling point component was distilled off under reduced pressure, followed further by purification by recrystallization (toluene) to obtain a yellow solid of the desired 2-{5-(9-anthracenyl)-4'-[2-(4,6-dimethylpyrimidyl)]biphenyl-3-yl}-4,6-diphenylpyrimidine (compound A-15) (amount: 1.27 g, yield: 64%).

$^1$H-NMR (CDCl$_3$) δ (ppm): 2.59 (s, 6H), 6.97 (s, 1H), 7.36-7.43 (m, 2H), 7.46-7.56 (m, 8H), 7.87 (brd, J=8.5 Hz, 2H), 7.91 (brs, 1H), 7.96 (brd, J=8.5 Hz, 2H), 8.08 (s, 1H), 8.11 (brd, J=8.5 Hz, 2H), 8.24-8.31 (m, 4H), 8.57-8.64 (m, 3H), 8.81 (brs, 1H), 9.24 (brs, 1H).

Synthesis Example 16

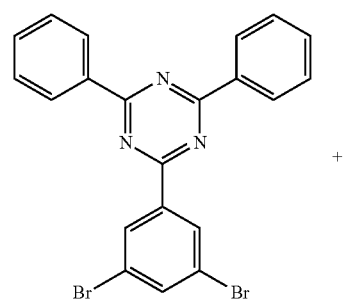

+

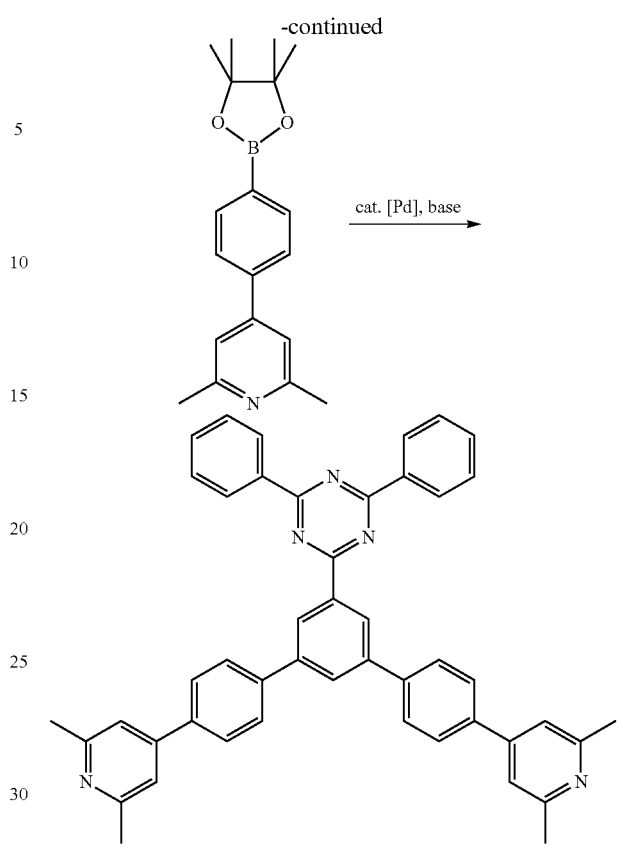

Under an argon stream, 2-(3,5-dibromo-phenyl)-4,6-diphenyl-1,3,5-triazine (1.56 g, 3.33 mmol), 2,6-dimethyl-4-[4-(4,4,5,5-tetramethyl-1,3,2-dioxaborolan-2-yl)phenyl]pyridine (3.09 g, 10.0 mmol) and dichlorobis(triphenylphosphine) palladium (93.5 mg, 0.133 mmol) were suspended in 1,4-dioxane (100 mL) and heated to 110° C. A 1.0M tripotassium phosphate aqueous solution (20 mL) was slowly dropwise added thereto, followed by stirring for 15 hours. After cooling, a white solid was separated by filtration. The obtained crude product was purified by recrystallization (toluene) to obtain a white solid of 2-[4,4"-bis(2,6-dimethyl-pyridin-4-yl)-1,1';3',1"-terphenyl-5'-yl]-4,6-diphenyl-1,3,5-triazine (compound A-16) as the desired product (amount: 1.78 g, yield; 80%).

$^1$H-NMR (CDCl$_3$) δ (ppm): 2.67 (s, 12H), 7.32 (brs, 4H), 7.57-7.69 (m, 6H), 7.83 (d, J=8.1 Hz, 4H), 7.93 (d, J=8.1 Hz, 4H), 8.12 (brs, 1H), 8.82 (brd, J=7.4 Hz, 4H), 9.05 (brs, 2H).

Synthesis Example 17

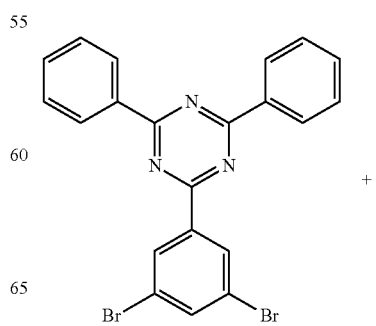

+

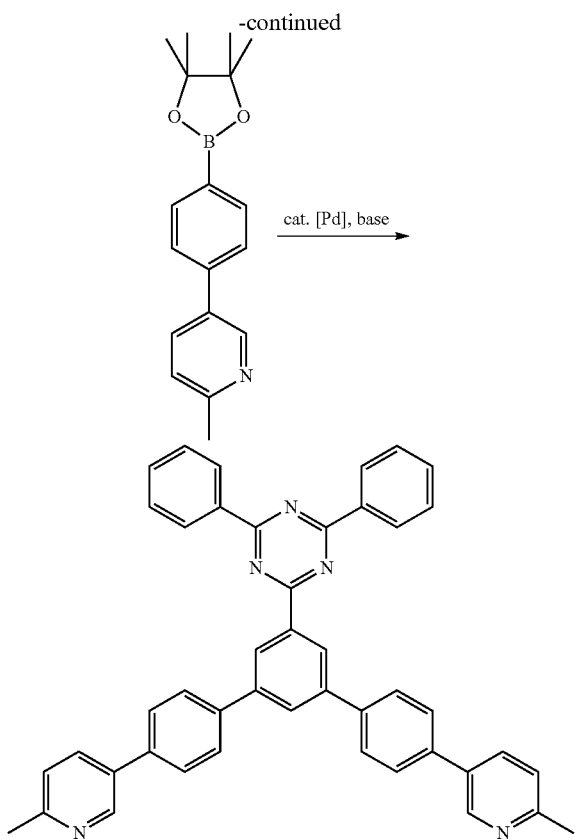

Under an argon stream, 2-(3,5-dibromo-phenyl)-4,6-diphenyl-1,3,5-triazine (800 mg, 1.64 mmol), 2-methyl-5-[4-(4,4,5,5-tetramethyl-1,3,2-dioxaborolan-2-yl)phenyl]pyridine (1.11 g, 3.78 mmol), palladium acetate (18.4 g, 0.0820 mmol) and 2-dicyclohexylphosphino-2',4',6'-triisopropylbiphenyl (78.0 mg, 0.164 mmol) were suspended in 1,4-dioxane (16 mL) and heated to 60° C. A 1.0M tripotassium phosphate aqueous solution (7.87 mL) was slowly dropwise added thereto, and then, the temperature was raised to 80° C., followed by stirring for 4 hours. After cooling, a white solid was separated by filtration. The obtained crude product was purified by recrystallization (chloroform), to obtain a white solid of 2-[4,4"-bis(6-methylpyridin-3-yl)-1,1';3',1"-terphenyl-5'-yl]-4,6-diphenyl-1,3,5-triazine (compound A-17) as the desired product (amount: 566 mg, yield: 54%).

$^1$H-NMR (CDCl$_3$) δ (ppm): 2.65 (s, 6H), 7.29 (d, J=8.28 Hz, 2H), 7.58-7.64 (m, 6H), 7.77 (d, J=8.53 Hz, 4H), 7.93-7.89 (m, 6H), 8.11 (t, J=1.9 Hz, 1H), 8.85-8.80 (m, 6H), 9.04 (d, J=1.9 Hz, 2H).

Synthesis Example 18

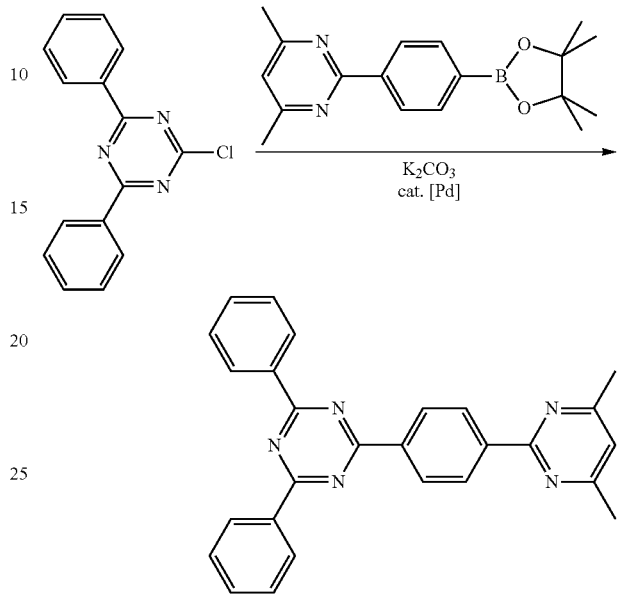

Under an argon stream, 2-chloro-4,6-diphenyl-1,3,5-triazine (268 mg, 1.0 mmol), 4,6-dimethyl-2-[4-(4,4,5,5-tetramethyl-1,3,2-dioxaborolan-2-yl)phenyl]pyrimidine (372 mg, 1.2 mmol), tetrakis(triphenylphosphine) palladium (23 mg, 0.02 mmol) and potassium carbonate (415 mg, 3.0 mmol) were suspended in 1,4-dioxane (10 mL) and water (1 mL). After the temperature was raised to 100° C., the mixture was stirred for 21 hours. After cooling to room temperature, water was added, and the precipitated solid was separated by filtration. The obtained crude product was recrystallized from toluene to obtain a gray solid of 2-[4-(4,6-dimethylpyrimidin-2-yl)phenyl]-4,6-diphenyl-1,3,5-triazine (compound A-18) as the desired product (amount: 324 mg, yield: 78%).

$^1$H-NMR (CDCl$_3$) δ (ppm): 2.60 (s, 6H), 7.00 (s, 1H), 7.59-7.65 (m, 6H), 8.65 (d, J=8.5 Hz, 2H), 8.81 (d, J=7.5 Hz, 4H), 8.88 (d, J=8.0 Hz, 2H).

Synthesis Example 19

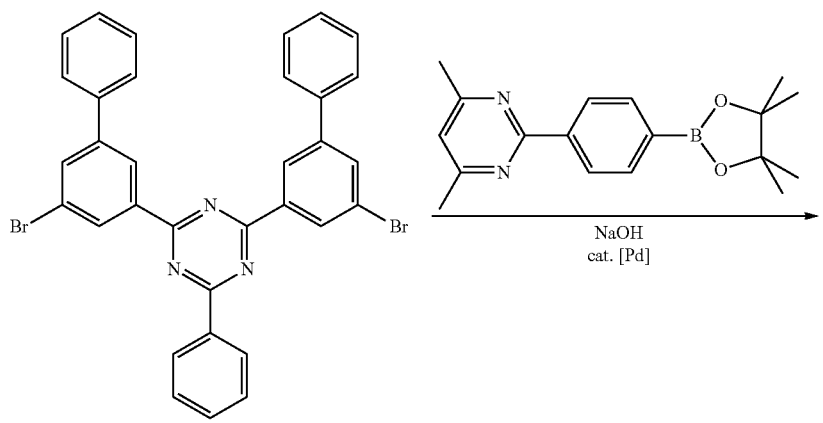

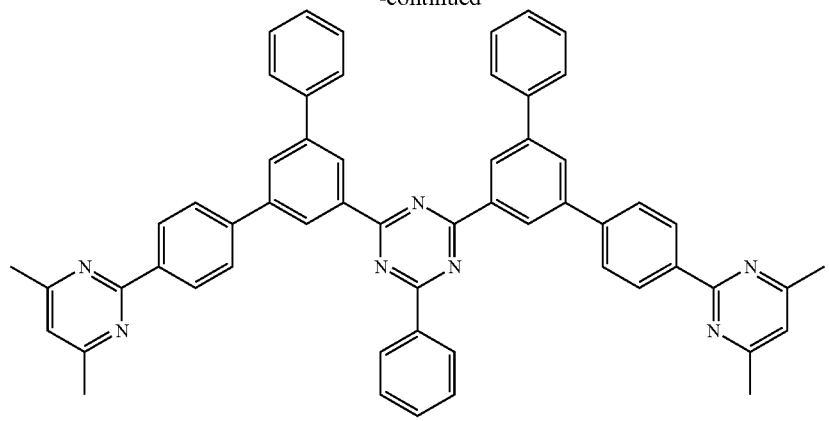

Under an argon atmosphere, 2,4-bis(5-bromo-biphenyl-3-yl)-6-phenyl-1,3,5-triazine (619 mg, 1.0 mmol), 4,6-dimethyl-2-[4-(4,4,5,5-tetramethyl-1,3,2-dioxaborolan-2-yl)phenyl]pyrimidine (677 mg, 2.4 mmol), and tetrakis(triphenylphosphine) palladium (23 mg, 20.μmol) were suspended in tetrahydrofuran (10 mL), and a 4.0N sodium hydroxide aqueous solution (1.5 mL, 6.0 mmol) was added. After the temperature was raised to 70° C., and the mixture was stirred for 22 hours. After cooling to room temperature, water was added, and the precipitated solid was separated by filtration. The obtained crude product was recrystallized from toluene to obtain a gray solid of 2,4-bis[4-(4,6-dimethylpyrimidin-2-yl)-1,1': 3',1''-terphenyl-5'-yl]-6-phenyl-1,3,5-triazine (compound A-19) as the desired product (amount: 763 mg, yield: 92%).

$^1$H-NMR (CDCl$_3$) δ (ppm): 2.59 (s, 12H), 6.98 (s, 2H), 7.46 (t, J=7.5 Hz, 2H) 7.57 (t, J=7.8 Hz, 4H), 7.60-7.68 (m, 3H), 8.84 (d, J=6.5 Hz, 4H), 7.93 (d, J=8.5 Hz, 4H), 8.13 (s, 2H), 8.62 (d, J=8.0 Hz, 4H), 8.85 (d, J=6.0 Hz, 2H), 9.03 (s, 2H), 9.06 (s, 2H).

Under an argon atmosphere, 2,4-bis(3-bromophenyl)-6-phenyl-1,3,5-triazine (1.40 g, 3.0 mmol), 4,6-dimethyl-2-[4-(4,4,5,5-tetramethyl-1,3,2-dioxaborolan-2-yl)phenyl]pyrimidine (2.23 g, 7.2 mmol) and tetrakis(triphenylphosphine) palladium (69 mg, 0.06 mmol) were suspended in tetrahydrofuran (30 mL), and a 4.0N sodium hydroxide aqueous solution (4.5 mL, 18 mmol) was added. After the temperature was raised to 70° C., the mixture was stirred for 22 hours. After cooling to room temperature, water was added, and the precipitated solid was separated by filtration. The obtained crude product was recrystallized from o-xylene to obtain a gray crystal of 2,4-bis[4'-(4,6-dimethylpyrimidin-2-yl) biphenyl-3-yl]-6-phenyl-1,3,5-triazine (compound A-20) as the desired product (amount: 1.54 g, yield: 76%).

$^1$H-NMR (CDCl$_3$) δ (ppm): 2.58 (s, 12H), 6.70 (s, 2H), 7.65-7.60 (m, 3H), 7.70 (t, J=7.8 Hz, 2H), 7.88 (d, J=9.0 Hz, 4H), 7.93 (d, J=8.5 Hz, 2H), 8.60 (d, J=8.5 Hz, 4H), 8.84-8.80 (m, 4H), 9.09 (s, 2H).

Synthesis Example 20

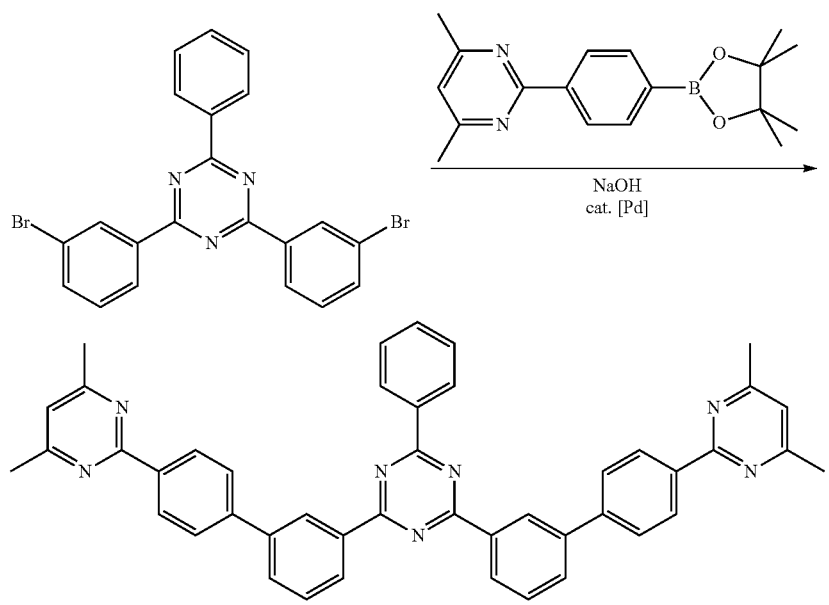

Synthesis Example 21

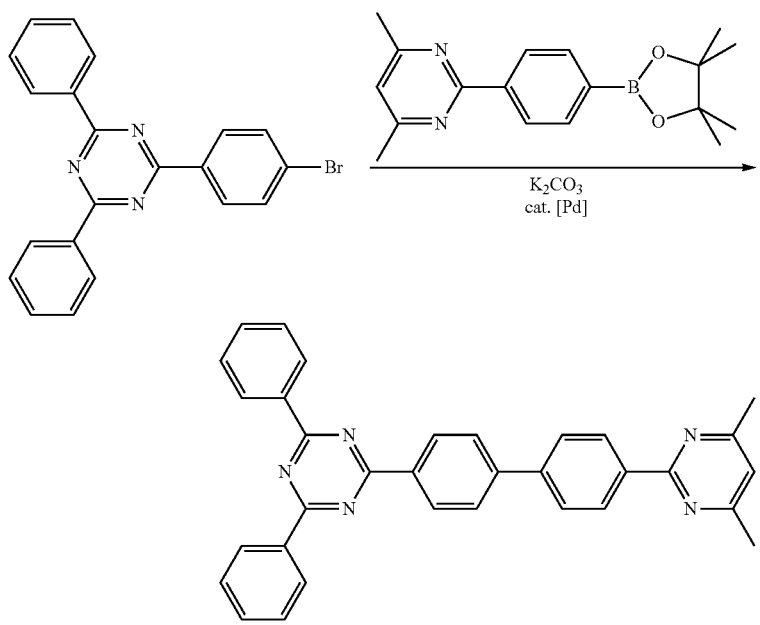

Under an argon stream, 2-(4-bromophenyl)-4,6-diphenyl-1,3,5-triazine (1.50 g, 3.86 mmol), 4,6-dimethyl-2-[4-(4,4,5,5-tetramethyl-1,3,2-dioxaborolan-2-yl)phenyl]pyrimidine (1.44 g, 4.64 mmol), palladium acetate (26.0 mg, 0.116 mmol) and 1.0M tert-butyl phosphine (0.350 mL, 0.350 mmol) were suspended in tetrahydrofuran (39 mL) and heated to 70° C. After slowly dropwise adding a 4.0M sodium hydroxide aqueous solution (7.20 mL) thereto, the temperature was raised to 75° C., followed by stirring for 5 hours. After cooling, a white solid was separated by filtration. The obtained crude product was purified by recrystallization (toluene) to obtain a white solid of 2-[4'-(4,6-dimethylpyrimidin-2-yl)biphenyl-4-yl]4,6-diphenyl-1,3,5-triazine (compound A-21) as the desired product (amount: 1.05 g, yield: 55%).

$^1$H-NMR (CDCl$_3$) δ (ppm): 2.57 (s, 6H), 6.96 (s, 1H), 7.58-7.64 (m, 6H), 7.83 (d, J=8.6 Hz, 2H), 7.89 (d, J=8.6 Hz, 2H), 8.60 (d, J=8.4 Hz, 2H) 8.81 (d, J=8.4 Hz, 4H), 8.91 (d, J=8.6 Hz, 2H).

Synthesis Example 22

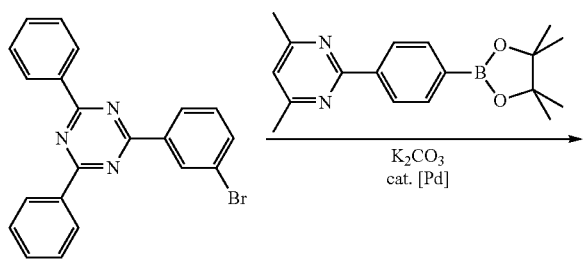

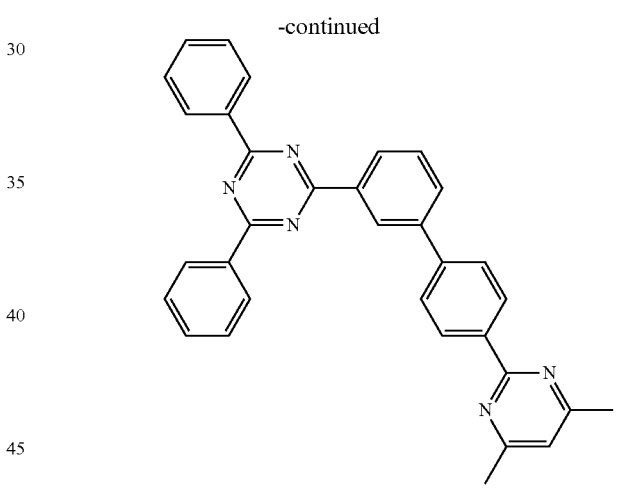
-continued

Under an argon stream, 2-(3-bromophenyl)-4,6-diphenyl-1,3,5-triazine (2.09 g, 5.4 mmol), 4,6-dimethyl-2-[4-(4,4,5,5-tetramethyl-1,3,2-dioxaborolan-2-yl)phenyl]pyrimidine (2.00 g, 6.5 mmol), palladium acetate (36.3 mg, 0.16 mmol) and 1.0M tert-butyl phosphine (0.480 mL, 0.48 mmol) were suspended in tetrahydrofuran (50 mL) and heated to 70° C. After slowly dropwise adding a 4.0M sodium hydroxide aqueous solution (10 mL) thereto, the temperature was raised to 75° C., followed by stirring for 2 hours. After cooling, a white solid was separated by filtration. The obtained crude product was purified by recrystallization (toluene) to obtain a white solid of 2-[4'-(4,6-dimethylpyrimidin-2-yl) biphenyl-3-yl]-4,6-diphenyl-1,3,5-triazine (compound A-22) as the desired product (amount: 1.22 g, yield: 46%).

$^1$H-NMR (CDCl$_3$) δ (ppm): 2.57 (s, 6H), 6.98 (s, 1H), 7.58-7.64 (m, 6H), 7.68 (t, J=7.8 Hz, 1H), 7.85 (d, J=9.0 Hz, 2H), 7.93 (d, J=8.5 Hz, 2H), 8.60 (d, J=8.5 Hz, 2H), 8.80-8.84 (m, 4H), 9.09 (s, 1H).

Synthesis Example 23

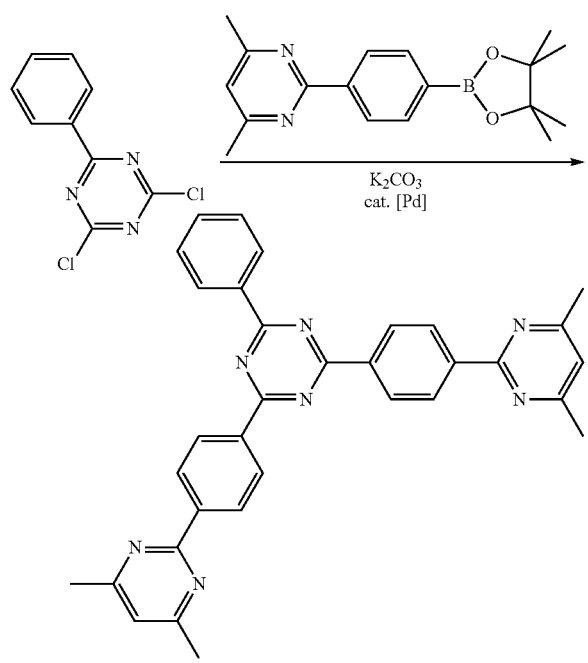

Under an argon stream, 2,4-dichloro-6-phenyl-1,3,5-triazine (0.800 g, 3.5 mmol), 4,6-dimethyl-2-[4-(4,4,5,5-tetramethyl-1,3,2-dioxaborolan-2-yl)phenyl]pyrimidine (2.60 g, 8.4 mmol), tetrakis(triphenylphosphine) palladium (0.122 g, 0.11 mmol) and tripotassium phosphate (3.46 g, 16 mmol), were suspended in N-dimethylformamide (18 mL). After the temperature was raised to 100° C., the mixture was stirred for 14 hours. After cooling to room temperature, water was added, and the precipitated solid was separated by filtration. The obtained crude product was recrystallized from toluene to obtain a gray solid of 2,4-bis[4-(4,6-dimethylpyrimidin-2-yl)phenyl]-6-phenyl-1,3,5-triazine (compound A-23) as the desired product (amount: 800 mg, yield: 43%).

$^1$H-NMR (CDCl$_3$) δ (ppm): 2.59 (s, 12H), 6.97 (s, 2H), 7.60-7.78 (m, 3H), 8.67 (d, J=8.0 Hz, 4H), 8.81 (d, J=7.5 Hz, 2H), 8.90 (d, J=8.0 Hz, 4H).

Synthesis Reference Example 1

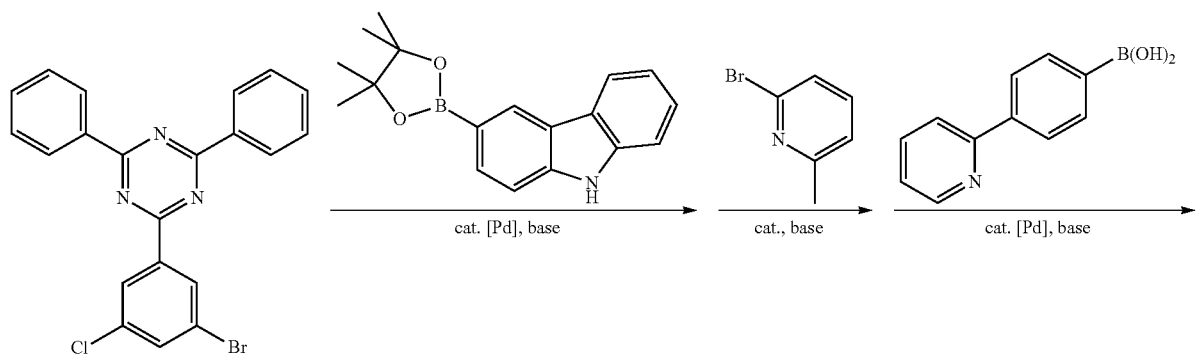

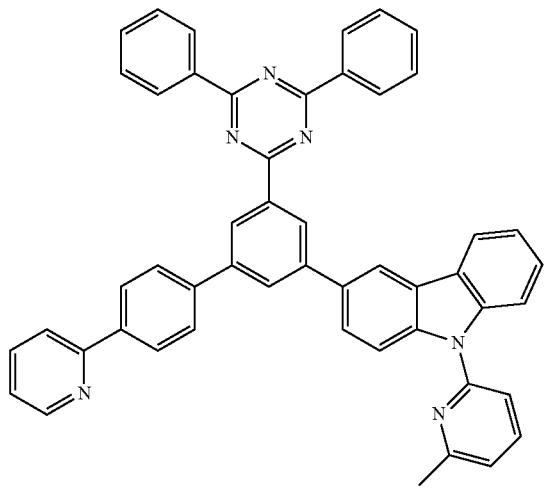

Under an argon stream, 2-(3-bromo-5-chlorobenzene-1-yl)-4,6-diphenyl-1,3,5-triazine (30.0 g, 71 mmol), 3-[4-(4,4,5,5-tetramethyl-1,3,2-dioxaborolan-2-yl)]carbazole (18.3 g, 75 mmol) and dichlorobis(triphenylphosphine) palladium (0.996 g, 1.4 mmol) were suspended in 1,4-dioxane (710 mL) and heated to 100° C. A 3.0M potassium carbonate aqueous solution (49.7 mL, 0.15 mol) was dropwise slowly added thereto, followed by stirring for 24 hours. After cooling, the precipitated solid was washed with water, methanol and hexane in this order, to obtain 3-[3-chloro-5-(4,6-diphenyl-1,3,5-triazin-2-yl)phenyl]carbazole (amount: 36.1 g, yield: 99%).

Then, under an argon stream, 3-[3-chloro-5-(4,6-diphenyl-1,3,5-triazin-2-yl)phenyl]carbazole (4.07 g), 2-bromo-6-methylpyridine (2.06 g), copper(I) oxide (57 mg), 1,10-phenanthroline (144 mg), 18-crown-6-ether (423 mg) and potassium carbonate (2.21 g) were suspended in xylene (80 mL) and heated and refluxed for 20 hours. After cooling the reaction mixture, water and methanol were added. The precipitated solid was washed with water, methanol and hexane in this order, to obtain a yellow powder of 3-[1-chloro-5-(4,6-diphenyl-1,3,5-triazin-2-yl)-phenyl-3-yl]-9-(6-methylpyridin-2-yl) carbazole (amount: 4.24 g, yield: 88%).

$^1$H-NMR (CDCl$_3$) δ (ppm): 2.75 (s, 3H), 7.24 (d, J=7.1 Hz, 1H), 7.39 (t, J=7.2 Hz, 1H), 7.50-7.54 (m, 2H), 7.60-7.68 (m, 6H), 7.83 (d, J=8.6 Hz, 1H), 7.87-7.91 (m, 2H), 7.97 (s, 1H), 8.01 (d, J=8.6 Hz, 1H), 8.25 (d, J=7.6 Hz, 1H), 8.45 (s, 1H), 8.75 (s, 1H), 8.82-8.84 (m, 4H), 9.00 (s, 1H).

Then, under an argon stream, 3-[1-chloro-5-(4,6-diphenyl-1,3,5-triazine-2-yl)-phenyl-3-yl]-9-(6-methylpyridin-2-yl) carbazole (1.80 g), 4-(2-pyridyl)phenyl boronic acid (717 mg), palladium acetate (13.5 mg) and 2-dicyclohexylphosphino-2',4',6'-triisopropylbiphenyl (86 mg), were suspended in a mixed solvent of toluene (40 mL) and 1-butanol (3.0 mL), and a 3M potassium carbonate aqueous solution (2.4 mL) was added, followed by heating and refluxing for 6.5 hours. After cooling the reaction mixture, water and methanol were added. The precipitated solid was washed with water, methanol and hexane in this order, to obtain a gray powder of the desired 9-(6-methylpyridin-2-yl)-3-[5-(4,6-diphenyl-1,3,5-triazin-2-yl)-4'-(2-pyridyl)biphenyl-3-yl] carbazole (compound A-24) (amount: 2.00 g, yield: 93%).

$^1$H-NMR (CDCl$_3$) δ (ppm): 2.75 (s, 3H), 7.23 (d, J=7.5 Hz, 1H), 7.31-7.34 (m, 1H), 7.39 (t, J=7.4 Hz, 1H), 7.51 (dd, J=8.3, 7.2 Hz, 1H), 7.84 (d, J=7.8 Hz, 1H), 7.60-7.68 (m, 6H), 7.84-7.94 (m, 5H), 8.01 (d, J=8.4 Hz, 2H), 8.04 (d, J=8.6 Hz, 1H), 8.24 (d, J=8.5 Hz, 2H), 8.27 (d, J=8.4 Hz, 2H), 8.53 (s, 1H), 8.79 (d, J=4.7 Hz, 1H), 8.85 (d, J=7.9 Hz, 4H), 9.07 (s, 1H), 9.12 (s, 1H).

Synthesis Reference Example 2

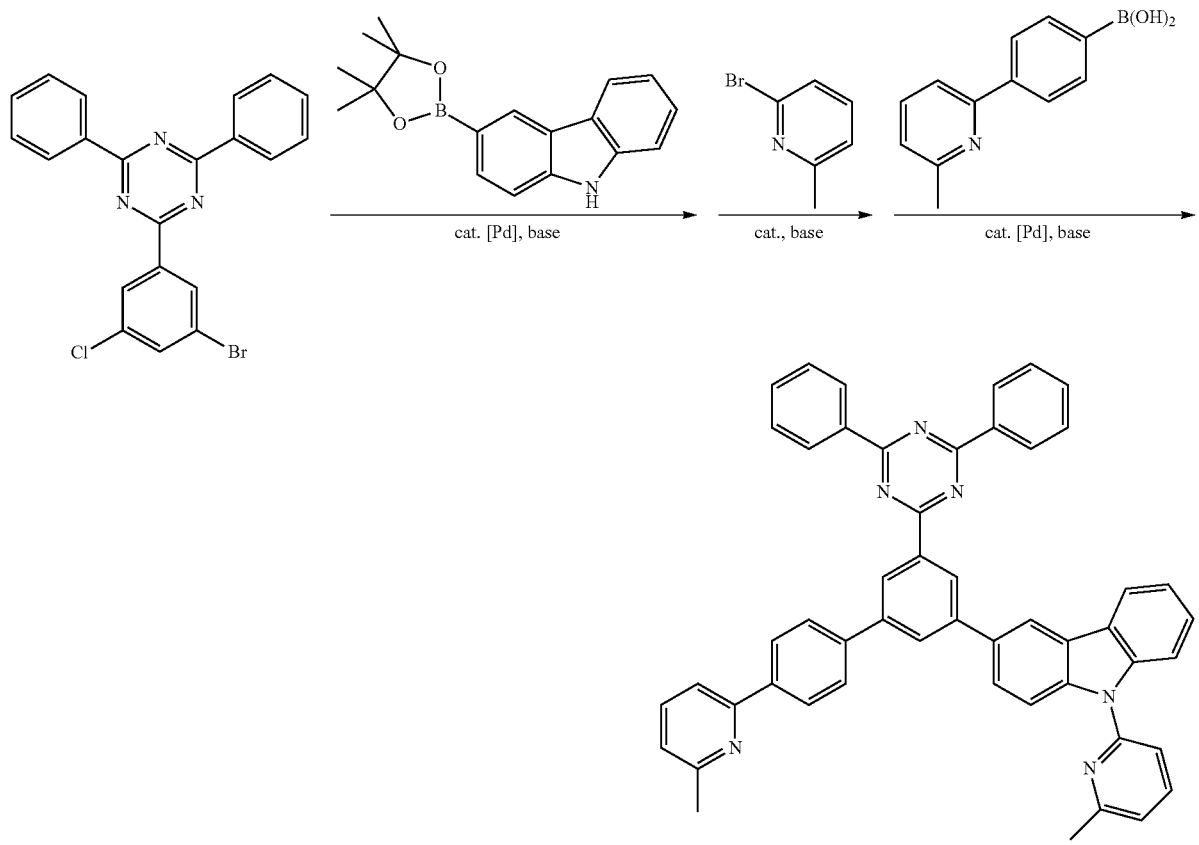

Under an argon stream, 2-(3-bromo-5-chlorobenzene-1-yl)-4,6-diphenyl-1,3,5-triazine (30.0 g, 71 mmol), 3-[4-(4,4,5,5-tetramethyl-1,3,2-dioxaborolan-2-yl)]carbazole (18.3 g, 75 mmol) and dichlorobis(triphenylphosphine) palladium (0.996 g, 1.4 mmol) were suspended in 1,4-dioxane (710 mL) and heated to 100° C. A 3.0M potassium carbonate aqueous solution (49.7 mL, 0.15 mol) was dropwise slowly added thereto, followed by stirring for 24 hours. After cooling, the precipitated solid was washed with water, methanol and hexane in this order, to obtain 3-[3-chloro-5-(4,6-diphenyl-1,3,5-triazin-2-yl)-phenyl]carbazole (amount: 36.1 g, yield: 99%).

Then, under an argon stream, 3-[3-chloro-5-(4,6-diphenyl-1,3,5-triazin-2-yl)phenyl]carbazole (4.07 g), 2-bromo-6-methylpyridine (2.06 g), copper(I) oxide (57 mg), 1,10-phenanthroline (144 mg), 18-crown-6-ether (423 mg) and potassium carbonate (2.21 g) were suspended in xylene (80 mL) and heated and refluxed for 20 hours. After cooling the reaction mixture, water and methanol were added. The precipitated solid was washed with water, methanol and hexane in this order, to obtain a yellow powder of 3-[1-chloro-5-(4,6-diphenyl-1,3,5-triazin-2-yl)-phenyl-3-yl]-9-(6-methylpyridin-2-yl) carbazole (amount: 4.24 g, yield: 88%).

Then, under an argon stream, 3-[1-chloro-5-(4,6-diphenyl-1,3,5-triazin-2-yl)-phenyl-3-yl]-9-(6-methylpyridin-2-yl) carbazole (1.80 g), 2-methyl-6-[4-(4,4,5,5-tetramethyl-1,3,2-dioxaborolan-2-yl)phenyl]pyridine (1.15 g), palladium acetate (13.5 mg) and 2-dicyclohexylphosphino-2',4',6'-triisopropylbiphenyl (86 mg) were suspended in a mixed solvent of toluene (60 mL) and 1-butanol (3.0 mL), and a 3M potassium carbonate aqueous solution (2.6 mL) was added, followed by heating and refluxing for 23 hours. After cooling the reaction mixture, water and methanol were added. The precipitated solid was washed with water, methanol and hexane in this order, to obtain a gray powder of the desired 9-(6-methylpyridin-2-yl)-3-[5-(4,6-diphenyl-1,3,5-triazin-2-yl)-4'-(6-methylpyridin-2-yl)biphenyl-3-yl]carbazole (compound A-25) (amount: 1.63 g, yield: 74%).

$^1$H-NMR (CDCl$_3$) δ (ppm): 2.74 (s, 3H), 2.76 (s, 3H), 7.19 (d, J=7.4 Hz, 1H), 7.24 (d, J=7.6 Hz, 1H), 7.39 (t, J=7.4 Hz, 1H), 7.51 (t, J=7.7 Hz, 1H), 7.53 (D, J=8.0 Hz, 1H), 7.61-7.68 (m, 7H), 7.75 (t, J=7.6 Hz, 1H), 7.88 (d, J=7.7 Hz, 1H), 7.91-7.94 (m, 2H), 8.00 (d, J=8.4 Hz, 2H), 8.04 (d, J=8.5 Hz, 1H), 8.23-8.25 (m, 3H), 8.27 (d, J=7.4 Hz, 1H), 8.54 (s, 1H), 8.85-8.88 (m, 4H), 9.06 (s, 1H), 9.12 (s, 1H).

Synthesis Reference Example 3

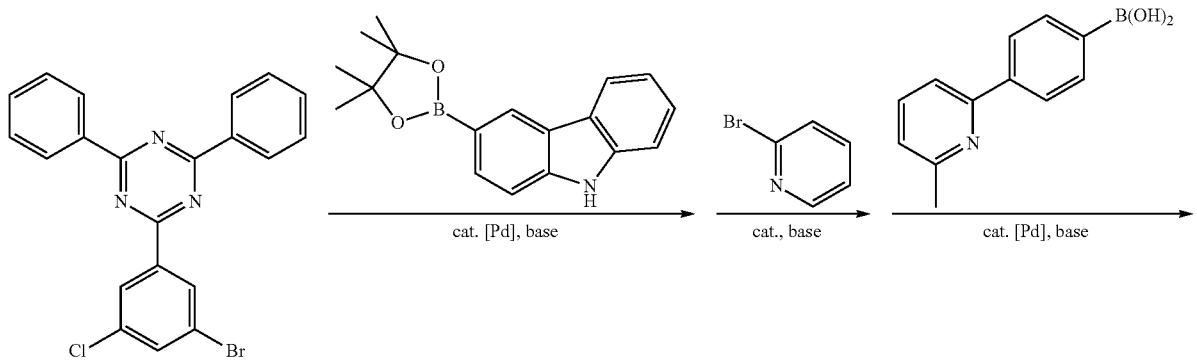

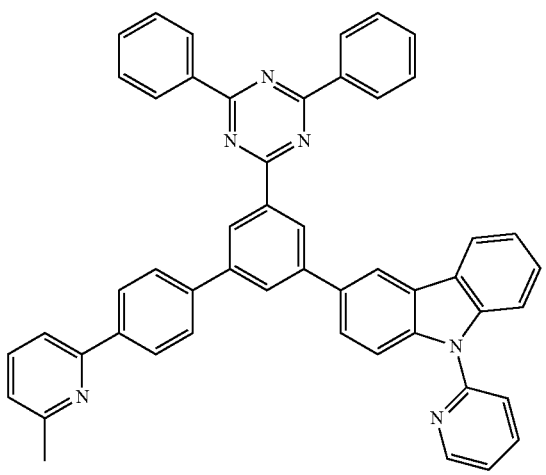

Under an argon stream, 2-(3-bromo-5-chlorobenzene-1-yl)-4,6-diphenyl-1,3,5-triazine (30.0 g, 71 mmol), 3-[4-(4,4,5,5-tetramethyl-1,3,2-dioxaborolan-2-yl)]carbazole (18.3 g, 75 mmol) and dichlorobis(triphenylphosphine) palladium (0.996 g, 1.4 mmol) were suspended in 1,4-dioxane (710 mL) and heated to 100° C. A. 3.0M potassium carbonate aqueous solution (49.7 mL, 0.15 mol) was dropwise slowly added thereto, followed by stirring for 24 hours. The precipitated solid was washed with water, methanol and hexane in this order, to obtain 3-[3-chloro-5-(4,6-diphenyl-1,3,5-triazin-2-yl)-phenyl]carbazole (amount: 36.1 g, yield: 99%).

Then, under an argon stream, 3-[3-chloro-5-(4,6-diphenyl-1,3,5-triazin-2-yl)phenyl]carbazole (2.00 g), 2-bromopyridine (745 mg), copper oxide (56.23 mg), 1,10-phenanthroline (70.82 mg), 18-crown-6-ether (207.76 mg) and potassium carbonate (1358 mg) were suspended in xylene (20 mL) and heated and refluxed for 16 hours. After cooling the reaction mixture, water was added. The precipitated solid was washed with water, methanol and hexane in this order, to obtain a yellow powder of 3-[1-chloro-5-(4,6-diphenyl-1,3,5-triazin-2-yl)-phenyl-3-yl]-9-(2-pyridyl) carbazole (amount: 2110 mg, yield: 92%).

$^1$H-NMR (CDCl$_3$): δ7.33-7.39 (m, 2H), 7.48 (t, J=7.2 Hz, 1H), 7.56-7.64 (m, 6H), 7.69 (d, J=8.0 Hz, 1H), 7.80 (d, J=8.0 Hz, 1H), 7.86 (d, J=7.6 Hz, 1H), 7.92 (s, 1H), 7.95-8.00 (m, 2H), 8.22 (d, J=7.6 Hz, 1H), 8.41 (s, 1H), 8.71 (s, 1H), 8.78-8.80 (m, 5H), 8.97 (s, 1H).

Then, under an argon stream, 3-[3-chloro-5-(4,6-diphenyl-1,3,5-triazin-2-yl)-phenyl-3-yl]-9-(2-pyridyl) carbazole (1.76 g), 2-methyl-6-[4-(4,4,5,5-tetramethyl-1,3,2-dioxaborolan-2-yl)phenyl]pyridine (1.15 g), palladium acetate (13.5 mg) and 2-dicyclohexylphosphino-2',4',6'-triisopropylbiphenyl (86 mg) were suspended in a mixed solvent of toluene (60 mL) and 1-butanol (3.0 mL), and a 3M potassium carbonate aqueous solution (2.6 mL) was added, followed by heating and refluxing for 16 hours. After cooling the reaction mixture, water and methanol were added. The precipitated solid was washed with water, methanol and hexane in this order, to obtain a gray powder of the desired 9-(2-pyridyl)-3-[5-(4,6-diphenyl-1,3,5-triazin-2-yl)-4'-(6-methylpyridin-2-yl)biphenyl-3-yl]carbazole (compound A-26) (amount: 1.84 g, yield: 85%).

$^1$H-NMR (CDCl$_3$) δ (ppm): 2.72 (s, 3H), 7.17 (d, J=7.4 Hz, 1H), 7.38 (t, J=5.0 Hz, 1H), 7.40 (t, J=7.4 Hz, 1H), 7.52 (t, J=7.2 Hz, 1H), 7.61-7.68 (m, 7H), 7.72 (d, J=7.6 Hz, 1H), 7.75 (d, J=7.6 Hz, 1H), 7.92-7.94 (m, 2H), 7.99 (d, J=8.3 Hz, 2H), 8.01 (t, J=8.1 Hz, 1H), 8.05 (d, J=8.5 Hz, 1H), 8.22 (d, J=8.3 Hz, 2H), 8.24 (s, 1H), 8.28 (d, J=7.6 Hz, 1H), 8.54 (s, 1H), 8.81 (d, J=5.0 Hz, 1H), 8.85 (d, J=7.8 Hz, 4H), 9.07 (s, 1H), 9.11 (s, 1H).

Synthesis Example 27

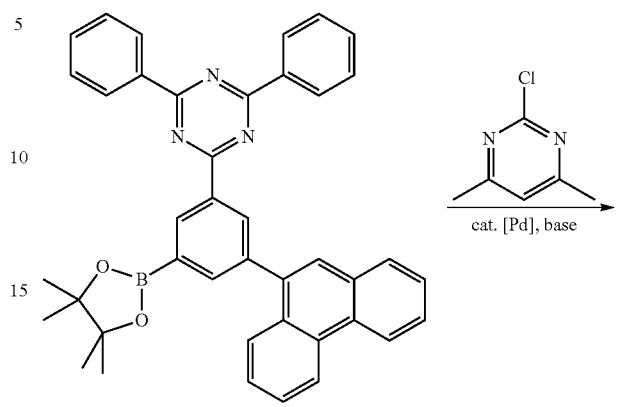

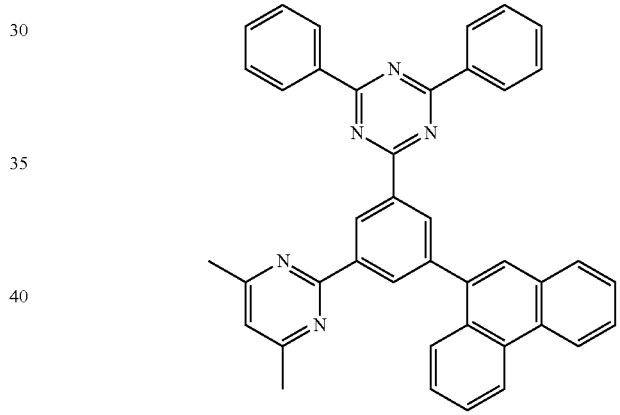

4,6-Diphenyl-2-[5-(9-phenanthryl)-3-(4,4,5,5-tetramethyl-1,3,2-dioxaborolan-2-yl)phenyl]-1,3,5-triazine (1.84 g, 3.0 mmol), 2-chloro-4,6-dimethylpyrimidine (513 mg, 3.6 mmol), tetrakis(triphenylphosphine) palladium (34.7 mg, 0.030 mmol) and tripotassium phosphate (1.53 g, 7.2 mmol) were weighed and suspended in 1,4-dioxane (20 mL) and water (7.2 mL). This mixture was heated and refluxed for 23 hours. After cooling, water (50 mL) was added and the precipitated solid was separated by filtration and washed with water, methanol and hexane in this order. Further, it was purified by recrystallization (toluene) to obtain a white solid of 2-[3-{2-(4,6-dimethyl-pyrimidyl)}-5-(9-phenanthryl)phenyl}]-4,6-diphenyl-1,3,5-triazine (compound A-27) (amount: 1.40 g, yield: 79%).

$^1$H-NMR (CDCl$_3$) δ (ppm): 2.60 (s, 6H), 7.02 (s, 1H), 7.51-7.76 (m, 10H), 7.90 (s, 1H), 7.95-8.01 (m, 2H), 8.76-8.86 (m, 6H), 8.87 (brs, 1H), 9.02 (brs, 1H), 9.89 (brs, 1H).

Synthesis Example 28

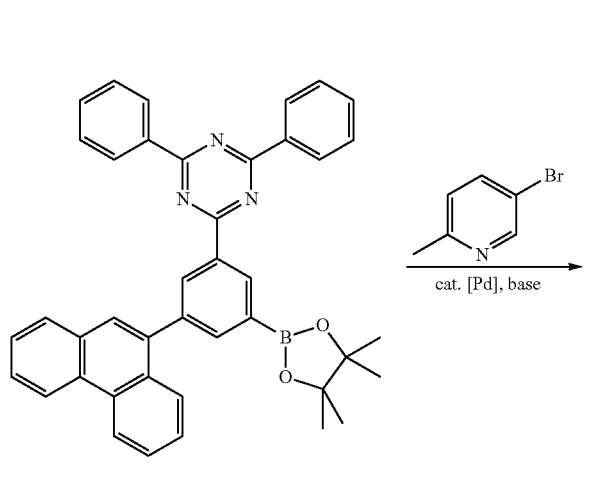

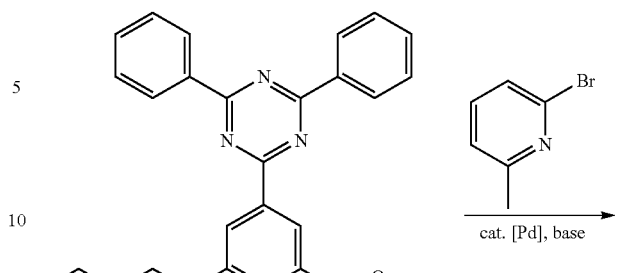

Under an argon stream, 4,6-diphenyl-2-[5-(9-phenanthryl)-3-(4,4,5,5-tetramethyl-1,3,2-dioxaborolan-2-yl)phenyl]-1,3,5-triazine (2.00 g, 3.3 mmol), 5-bromo-2-methylpyridine (0.675 g, 3.9 mmol), palladium acetate (22.0 mg, 98 µmol) and 2-dicyclohexylphosphino-2',4',6'-triisopropylbiphenyl (93.5 mg, 0.20 mmol) were suspended in 1,4-dioxane (33 mL), and a 2.0M potassium carbonate aqueous solution (3.3 mL) was dropwise added, followed by stirring at 80° C. for 24 hours. After cooling, methanol and water were added, and the precipitated solid was separated by filtration and washed with water, methanol and hexane in this order. Further, it was purified by recrystallization (toluene), to obtain a white solid of the desired 4,6-diphenyl-2-[3-(6-methylpyridin-3-yl)-5-(9-phenanthryl)phenyl]-1,3,5-triazine (compound A-28) (amount: 1.78 g, yield: 94%).

$^1$H-NMR (CDCl$_3$) δ (ppm): 2.67 (s, 3H), 7.52-7.61 (m, 8H), 7.69-7.75 (m, 3H), 7.88 (s, 1H), 7.97-8.00 (m, 3H), 8.76-8.81 (m, 6H), 8.85 (d, J=8.3 Hz, 1H), 8.96 (t, J=1.7 Hz, 1H), 9.00 (d, J=2.2 Hz, 1H), 9.11 (t, J=1.7 Hz, 1H).

Synthesis Example 29

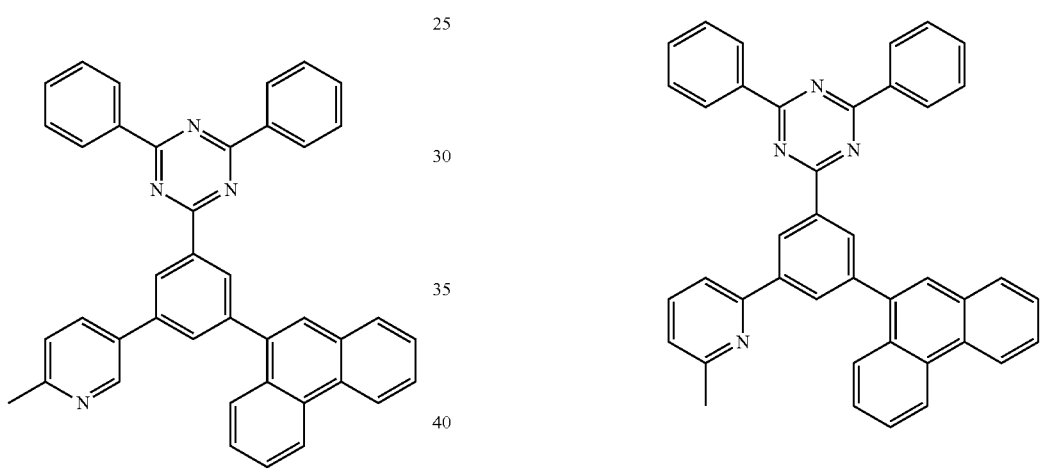

Under an argon stream, 4,6-diphenyl-2-[5-(9-phenanthryl)-3-(4,4,5,5-tetramethyl-1,3,2-dioxaborolan-2-yl)phenyl]-1,3,5-triazine (2.00 g, 3.3 mmol), 2-bromo-6-methylpyridine (0.450 mL, 3.9 mmol), palladium acetate (22.0 mg, 98 µmol) and 2-dicyclohexylphosphino-2',4',6'-triisopropylbiphenyl (93.5 mg, 0.20 mmol) were suspended in 1,4-dioxane (33 mL), and a 2.0M potassium carbonate aqueous solution (3.3 mL) was dropwise added, followed by stirring for 4 hours at 90° C. After cooling, methanol and water were added, and the precipitated solid was separated by filtration and washed with water, methanol and hexane in this order. It was purified by column chromatography (developing solvent: chloroform:hexane), to obtain a white solid of the desired 4,6-diphenyl-2-[3-(6-methylpyridin-2-yl)-5-(9-phenanthryl)phenyl]-1,3,5-triazine (compound A-29) (amount: 1.13 g, yield: 60%).

$^1$H-NMR (CDCl$_3$) δ (ppm): 2.68 (s, 3H), 7.19 (d, J=7.5 Hz, 1H), 7.52-7.79 (m, 12H), 7.90 (s, 1H), 7.98 (d, J=8.2 Hz, 1H), 8.00 (d, J=8.2 Hz, 1H), 8.47 (t, J=1.8 Hz, 1H), 8.78-8.81 (m, 5H), 8.84 (d, J=8.0 Hz, 1H), 8.98 (d, J=1.6 Hz, 1H), 9.43 (t, J=1.8 Hz, 1H).

Synthesis Example 30

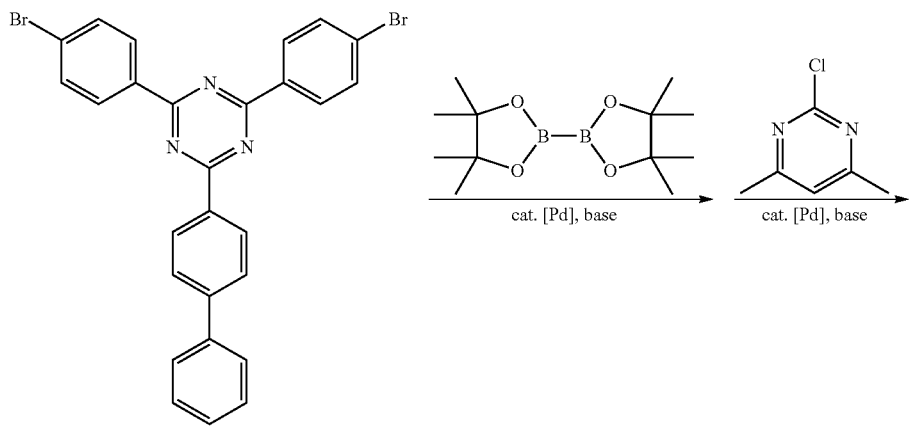

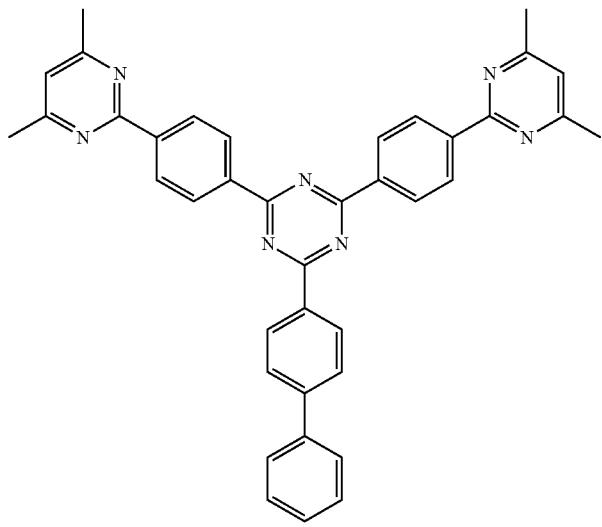

Under an argon stream, 6-(biphenyl-4-yl)-2,4-di(4-bromo-phenyl)-1,3,5-triazine (5.43 g, 10.0 mmol), 4,4,4',4',5,5,5',5'-octamethyl-2,2'-bi-1,3,2-dioxaborolane (6.10 g, 24.0 mmol), dichlorobistriphenylphosphine palladium (211 mg, 0.30 mmol) and potassium acetate (4.72 g, 48 mmol) were suspended in tetrahydrofuran (150 mL), and heated and refluxed for 5 hours at 75° C. After cooling, the precipitate was removed by filtration using a filter paper. Further, liquid separation was conducted with chloroform, and the organic layer was concentrated. Further, it was purified by column chromatography (developing solvent chloroform). To the obtained solid, hexane was added and cooled to ice temperature, whereupon the solid was separated by filtration and dried under reduced pressure, to obtain a milky white powder of 6-(biphenyl-4-yl)-2,4-di{4-(4,4,5,5-tetramethyl-1,3,2-dioxaborolan-2-yl)phenyl}-1,3,5-triazine as an intermediate (amount: 3.82 g, yield: 60%).

Then, under an argon stream, 6-(biphenyl-4-yl)-2,4-di{4-(4,4,5,5-tetramethyl-1,3,2-dioxaborolan-2-yl)phenyl}-1,3,5-triazine (1.91 g, 3.0 mmol), 2-chloro-4,6-dimethylpyrimidine (1.03 g, 7.2 mmol), tetrakis(triphenylphosphine)palladium (69.4 mg, 0.060 mmol) and tripotassium phosphate (3.06 g, 14.4 mmol) were weighed and suspended in 1,4-dioxane (20 mL) and water (14.4 mL). This mixture was heated and refluxed for 23 hours. After cooling, water (50 mL) was added, and the precipitated solid was separated by filtration and washed with water, methanol and hexane in this order. Further, purification by recrystallization (toluene) was conducted twice, and then purification by column chromatography (developing solvent: chloroform) was further conducted, to obtain a white solid of 6-(biphenyl-4-yl)-2,4-bis{4-(4,6-dimethylpyrimidyl)phenyl}-1,3,5-triazine (compound A-30) (amount: 0.98 g, yield: 55%).

$^1$H-NMR (CDCl$_3$) δ (ppm): 2.60 (s, 12H), 7.02 (s, 2H), 7.42 (brdd, J=7.3, 7.3 Hz, 1H), 7.52 (brdd, J=7.3, 7.3 Hz, 2H), 7.74 (brd, J=8.5 Hz, 2H), 7.85 (brd, J=8.5 Hz, 2H), 8.68 (brd, J=8.5 Hz, 4H), 8.86-8.93 (m, 6H).

Synthesis Example 31

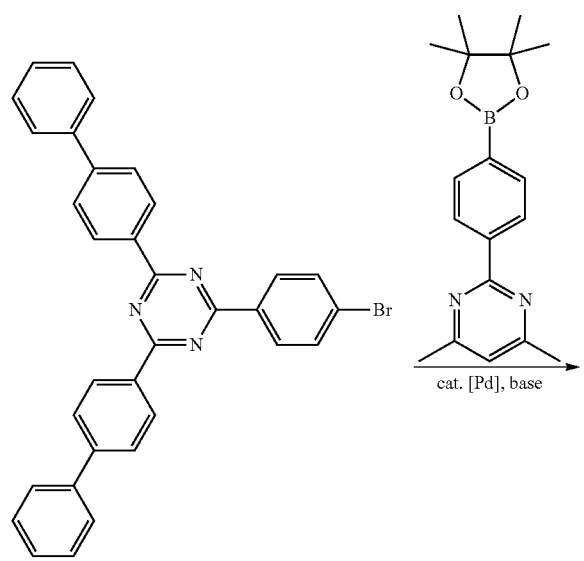

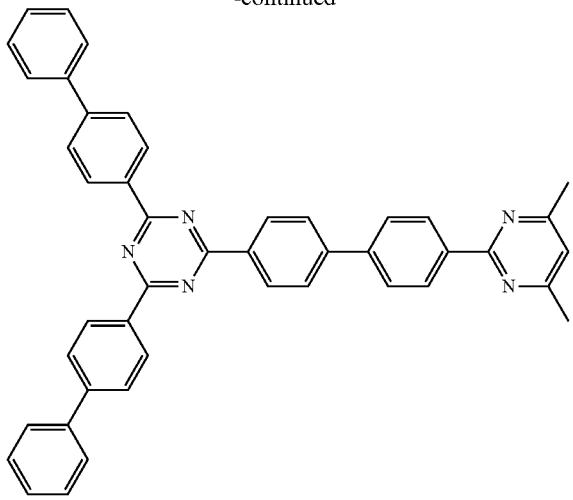

Under an argon atmosphere, 4,6-bis(biphenyl-4-yl)-2-(4-bromo-phenyl)-1,3,5-triazine (1.08 g, 2.0 mmol), 4,6-dimethyl-2-[4-(4,4,5,5-tetramethyl-1,3,2-dioxaborolan-2-yl)phenyl]pyrimidine (745 mg, 2.4 mmol), dichlorobis(triphenylphosphine) palladium (28.1 mg, 0.040 mmol) and tripotassium phosphate (1.02 g, 4.8 mmol a) were suspended in 1,4-dioxane (20 mL) and water (4.8 mL). This mixture was heated and refluxed for 23 hours. After cooling, water (20 mL) was added, and the precipitated solid was separated by filtration and washed with water, methanol and hexane in this order. Further, purification by the recrystallization (toluene) was conducted, and then, purification by column chromatography (developing solvent: chloroform) was further conducted, to obtain a white solid of 4,6-bis(biphenyl-4-yl)-2-{4'-(4,6-dimethylpyrimidyl)biphenyl-4-yl}-1,3,5-triazine (compound A-31) (amount: 620 mg, yield: 48%).

$^1$H-NMR (CDCl$_3$) δ (ppm): 2.58 (s, 6H), 6.96 (s, 1H), 7.42 (brdd, J=7.4, 7.4 Hz, 2H), 7.48-7.55 (m, 4H), 7.69-7.76 (m, 4H), 7.80-7.86 (m, 6H), 7.89 (brd, J=8.6 Hz, 2H), 8.58 (brd, J=8.6 Hz, 2H), 8.85-8.91 (m, 6H).

Synthesis Example 32

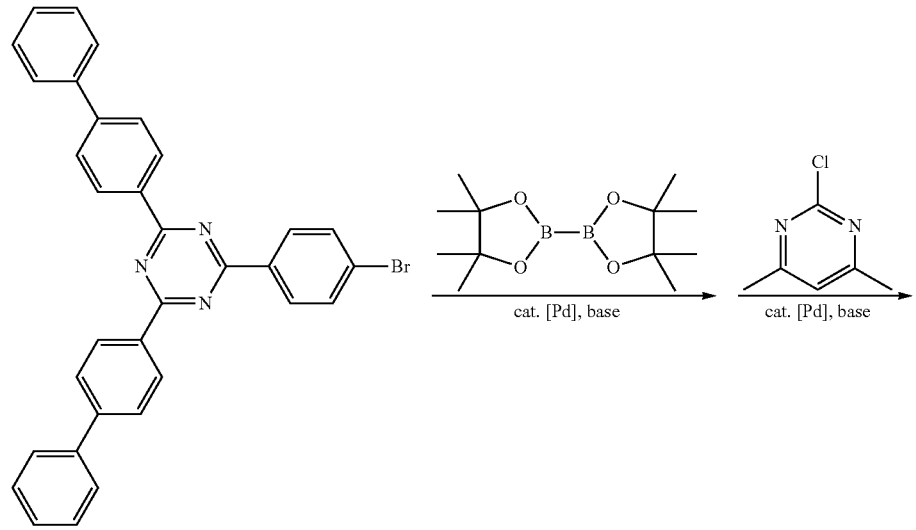

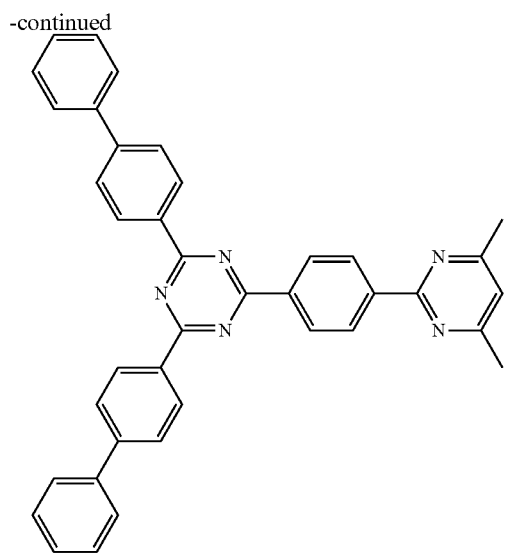

Under an argon atmosphere, 4,6-bis(biphenyl-4-yl)-2-(4-bromo-phenyl)-1,3,5-triazine (2.70 g, 5.0 mmol), 4,4,4',4',5,5,5',5'-octamethyl-2,2'-bi-1,3,2-dioxaborolane (1.91 g, 7.5 mmol), palladium acetate (11.3 mg, 0.050 mmol), 2-dicyclohexylphosphino-2',4',6'-triisopropylbiphenyl (47.8 mg, 0.10 mmol) and potassium acetate (1.48 g, 15 mmol) were suspended in 1,4-dioxane (100 mL), then, heated and stirred for 14 hours at 60° C., and further heated and refluxed for 5 hours at 100° C. After cooling, the precipitate was removed by filtration using filter paper, and the organic layer was concentrated. Further, it was purified by column chromatography (developing solvent chloroform). To the obtained solid, hexane was added and cooled to ice temperature, whereupon the solid was separated by filtration and dried under reduced pressure, to obtain a milky white powder of 2,4-di(biphenyl-4-yl)-6-{4-(4,4,5,5-tetramethyl-1,3,2-dioxaborolan-2-yl)phenyl}-1,3,5-triazine as an intermediate (amount: 2.60 g, yield: 89%).

Then, under an argon stream, 2,4-di(biphenyl-4-yl)-6-{4-(4,4,5,5-tetramethyl-1,3,2-dioxaborolan-2-yl)phenyl}1,3,5-triazine (1.47 g, 2.5 mmol), 2-chloro-4,6-dimethyl-pyrimidine (428 mg, 3.0 mmol), tetrakis(triphenylphosphine)palladium (28.9 mg, 0.025 mmol) and tripotassium phosphate (1.28 g, 6.0 mmol) were weighed and suspended in 1,4-dioxane (25 mL) and water (6.0 mL). This mixture was heated and refluxed for 25.5 hours. After cooling, the precipitated solid was separated by filtration and washed with water, methanol and hexane in this order. Further, purification by recrystallization (toluene) was carried out three times, to obtain a white solid of 2,4-di(biphenyl-4-yl)-6-{4-(4,6-dimethylpyrimidyl)phenyl}-1,3,5-triazine (compound A-32) (amount: 1.04 g, yield: 74%).

$^1$H-NMR (CDCl$_3$) δ (ppm): 2.60 (s, 6H), 7.00 (s, 1H), 7.42 (brdd, J=7.4, 7.4 Hz, 2H), 7.52 (brdd, J=7.4, 7.4 Hz, 4H), 7.70-7.76 (m, 4H), 7.83 (brd, J=8.6 Hz, 4H), 8.67 (brd, J=8.6 Hz, 2H), 8.85-8.94 (m, 6H).

Synthesis Example 33

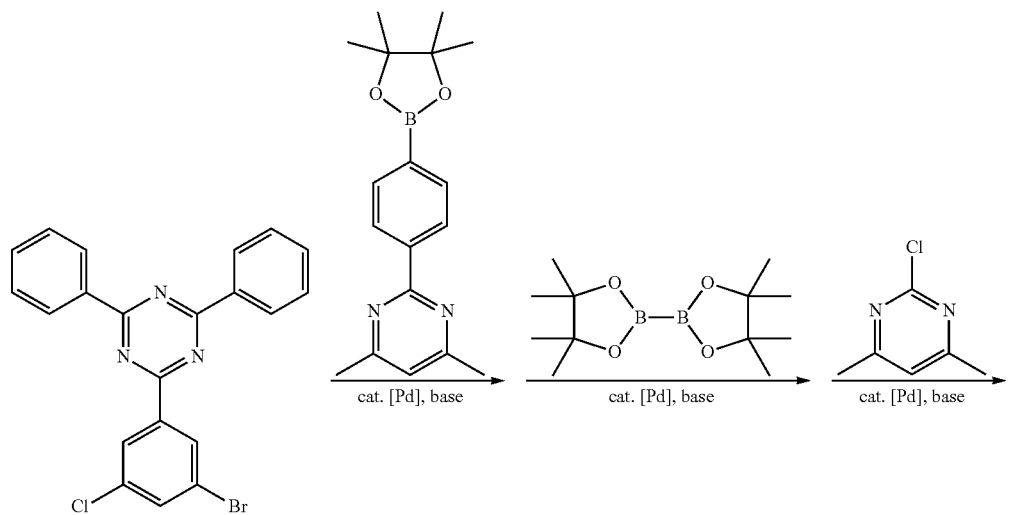

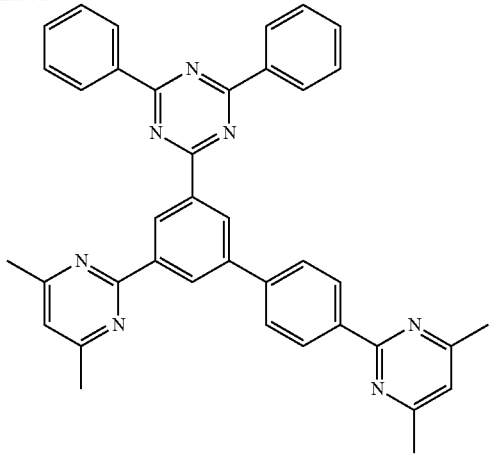

Under an argon stream, 2-(3-bromo-5-chlorophenyl)-4,6-diphenyl-1,3,5-triazine (4.23 g, 10 mmol), 4,6-dimethyl-2-[4-(4,4,5,5-tetramethyl-1,3,2-dioxaborolan-2-yl)phenyl]pyrimidine (3.41 g, 11 mmol), tetrakis(triphenylphosphine) palladium (231 mg, 0.20 mmol) and sodium hydroxide (1.21 g, 30 mmol) were weighed and suspended in tetrahydrofuran (60 mL) and water (7.5 mL). This mixture was heated and refluxed for 21.5 hours. After cooling, the solvent was distilled off under reduced pressure, then, water (100 mL) was added, and the precipitated solid was separated by filtration and washed with water, methanol and hexane in this order. Recrystallization (toluene) was carried out, to obtain a white solid of 2-{5-chloro-4'-[2-(4,6-dimethylpyrimidyl)]biphenyl-3-yl}-4,6-diphenyl-1,3,5-triazine as a synthetic intermediate (amount: 4.49 g, yield: 85%).

$^1$H-NMR (CDCl$_3$) δ (ppm): 2.58 (s, 6H), 6.98 (s, 1H), 7.57-7.67 (m, 6H), 7.84 (brd, J=8.6 Hz, 2H), 7.88 (brs, 1H), 8.61 (brd, J=8.6 Hz, 2H), 8.74 (brs, 1H), 8.77-8.82 (m, 4H), 8.95 (brs, 1H).

Then, under an argon stream, 2-{5-chloro-4'-[2-(4,6-dimethylpyrimidyl)]biphenyl-3-yl}-4,6-diphenyl-1,3,5-triazine (2.63 g, 5.0 mmol), 4,4,4',4',5,5,5',5'-octamethyl-2,2'-bi-1,3,2-dioxaborolane (1.91 g, 7.5 mmol), palladium acetate (11.3 mg, 0.050 mmol), 2-dicyclohexylphosphino-2',4',6'-triisopropylbiphenyl (47.7 mg, 0.10 mmol) and potassium acetate (1.48 g, and 15 mmol) were suspended in 1,4-dioxane (100 mL) and stirred for 4 hours at 100° C. After cooling, the precipitate was removed by filtration using a filter paper. Further liquid separation was conducted with chloroform, and the organic layer was concentrated to obtain a crude solid. To this crude solid, hexane was added and cooled to ice temperature, whereupon the solid was separated by filtration and dried under reduced pressure, to obtain a white solid of 2-{5-(4,4,5,5-tetramethyl-1,3,2 dioxaborolan-2-yl)-4'-[2-(4,6-dimethylpyrimidyl)]biphenyl-3-yl}-4,6-diphenyl-1,3,5 triazine as an intermediate (amount: 2.99 g, yield: 97%).

$^1$H-NMR (CDCl$_3$) δ (ppm): 1.45 (s, 12H), 2.58 (s, 6H), 6.96 (s, 1H), 7.56-7.67 (m, 6H), 7.90 (brd, J=8.5 Hz, 2H), 8.34-8.37 (m, 1H), 8.59 (brd, J=8.5 Hz, 2H), 8.79-8.85 (m, 4H), 9.13-9.18 (m, 2H).

Then, 2-{5-(4,4,5,5-tetramethyl-1,3,2-dioxaborolan-2-yl)-4'-[2-(4,6-dimethyl-pyrimidyl)]biphenyl-3-yl}-4,6-diphenyl-1,3,5-triazine (1.85 g, 3.0 mmol), 2-chloro-4,6-dimethylpyrimidine (513 mg, 3.6 mmol), tetrakis(triphenyl phosphine) palladium (34.7 mg, 0.030 mmol) and tripotassium phosphate (1.53 g, weighed 7.2 mmol) were suspended in 1,4-dioxane (20 mL) and water (7.2 mL). This mixture was heated and refluxed for 23 hours. After cooling, water (50 mL) was added, and the precipitated solid was separated by filtration and washed with water, methanol and hexane in this order. Further, it was purified three times by recrystallization (toluene) to obtain a white solid of 2-{5,4'-di[2-(4,6-dimethylpyrimidyl)]biphenyl-3-yl}-4,6-diphenyl-1,3,5-triazine (compound A-33) (amount: 1.39 g, yield: 78%).

$^1$H-NMR (CDCl$_3$) δ (ppm): 2.59 (s, 6H), 2.65 (s, 6H), 6.97 (s, 1H) 7.03 (s, 1H), 7.56-7.68 (m, 6H), 7.98 (brd, J=8.6 Hz, 2H), 8.63 (brd, J=8.6 Hz, 2H), 8.82-8.88 (m, 4H), 9.00 (brs, 1H), 9.17 (brs, 1H), 9.78 (brs, 1H).

Synthesis Example 34

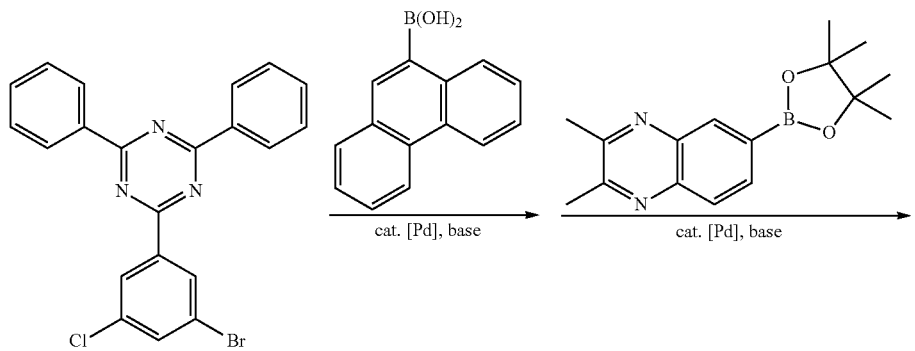

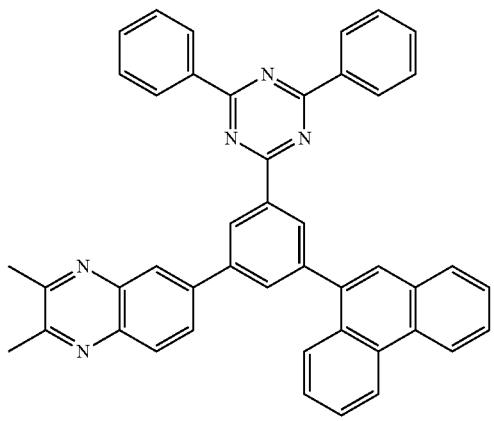

Under an argon stream, 2-(3-bromo-5-chlorophenyl)-4,6-diphenyl-1,3,5-triazine (70.0 g, 0.166 mol), 9-phenanthrene boronic acid (38.6 g, 0.174 mol) and tetrakis(triphenylphosphine) palladium (3.83 g, 3.31 mmol) were weighed and suspended in a 4.0M sodium hydroxide aqueous solution (124 mL, 0.497 mol) and tetrahydrofuran (1.0L). This mixture was heated and refluxed for 24 hours. After cooling, water (550 mL) was added, and the precipitated solid was separated by filtration and washed with water, methanol and hexane in this order. By recrystallization (toluene), a white solid of 2-[3-chloro-5-(9-phenanthryl)phenyl]-4,6-diphenyl-1,3,5-triazine was obtained as a reaction intermediate (amount: 78.9 g, yield: 92%).

Then, under an argon stream, 2-[3-chloro-5-(9-phenanthryl)phenyl]-4,6-diphenyl-1,3,5-triazine (3.64 g, 7.0 mmol), 6-(4,4,5,5-tetramethyl-1,3,2-dioxaborolan-2-yl)-2,3-dimethylquinoxaline (2.39 g, 8.4 mmol), palladium acetate (31.5 mg, 0.14 mmol), 2-dicyclohexylphosphino-2',4',6'-triisopropylbiphenyl (133.5 mg, 0.28 mmol) and tripotassium phosphate (3.57 g, 16.8 mmol) were weighed and suspended in water (16.8 mL) and 1,4-dioxane (100 mL). This mixture was heated and refluxed for 16.5 hours. After cooling, water (70 mL) was added, and the precipitated solid was separated by filtration and washed with water, methanol and hexane in this order. Further, it was purified by recrystallization (toluene) to obtain a white solid of the desired 4,6-diphenyl-2-{3-[2-(2,3-dimethylquinoxalin-6-yl)-5-(9-phenanthryl)]phenyl}-1,3,5-triazine (amount: 3.96 g, yield: 88%).

$^1$H-NMR (CDCl$_3$) δ (ppm): 2.77-2.81 (m, 6H), 7.53-7.77 (m, 10H), 7.90 (s, 1H), 7.99 (brd, J=8.0 Hz, 1H), 8.05 (brd, J=8.0 Hz, 1H), 8.11-8.21 (m, 3H), 8.47 (brs, 1H), 8.76-8.83 (m, 5H), 8.86 (brd, J=8.0 Hz, 1H), 9.00 (brs, 1H), 9.25 (brs, 1H).

Synthesis Reference Example 4

(A-35)

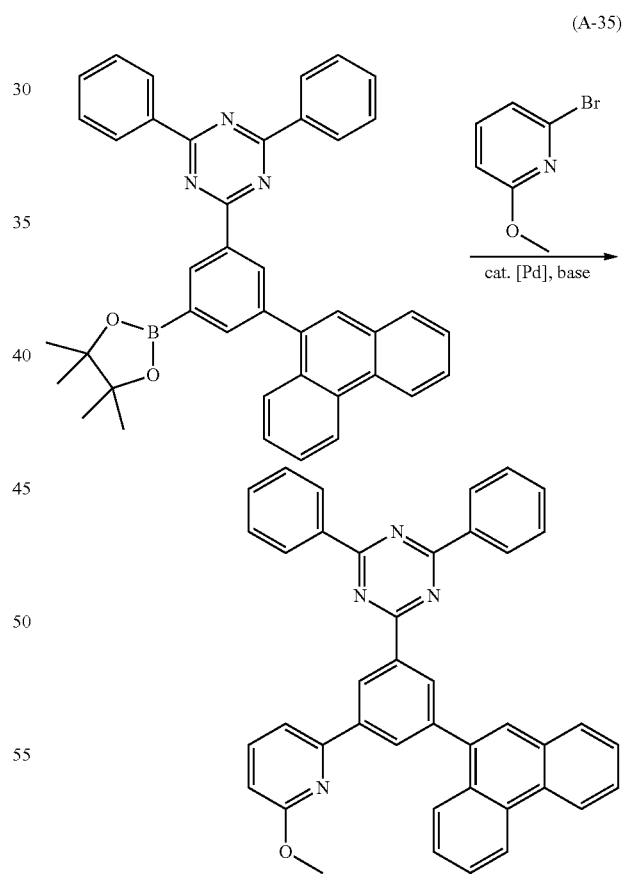

Under an argon stream, 4,6-diphenyl-2-[5-(9-phenanthryl)-3-(dioxaborolan-2-yl)phenyl]-1,3,5-triazine (0.300 g, 0.49 mmol), 2-bromo-6-methoxypyrimidine (0.111 g, 0.59 mmol), tetrakis(triphenylphosphine) palladium (17.3 mg, 0.015 mmol) and potassium carbonate (0.207 g, 1.5 mmol) were weighed and suspended in tetrahydrofuran (7.5 mL)

and water (1.5 mL). This mixture was heated and refluxed for 2 hours. After cooling, water was added, and the precipitated solid was separated by filtration and washed with water, methanol and hexane in this order. Further, it was purified by recrystallization (toluene), to obtain a white solid of 4,6-diphenyl-2-[3-(6-methoxy-2-yl)-5-(9-phenanthryl)phenyl]-1,3,5-triazine (compound A-35) (amount: 0.261 g, yield: 90%).

¹H-NMR (CDCl₃) δ (ppm): δ 4.13 (s, 3H), 6.79 (d, J=8.7 Hz, 1H), 7.54-7.83 (m, 12H), 7.87 (s, 1H), 7.94 (d, J=8.7 Hz, 1H), 8.06-8.13 (m, 1H), 8.25 (dd, J=1.8, 4.9 Hz, 1H), 8.79-8.82 (m, 4H), 8.79 (d, J=8.7 Hz, 1H), 8.82 (d, J=8.7 Hz, 1H), 9.38 (t, J=1.8 Hz, 1H), 9.56 (t, J=1.8 Hz, 1H).

Synthesis Reference Example 5

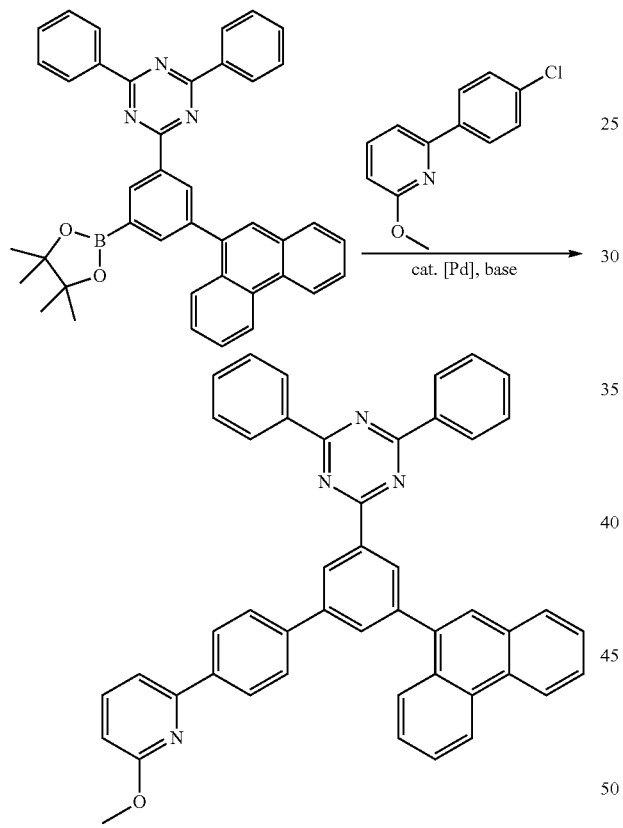

(A-36)

Under an argon stream, 4,6-diphenyl-2-[5-(9-phenanthryl)-3-(dioxaborolan-2-yl)phenyl]-1,3,5-triazine (1.50 g, 2.5 mmol), 6-(4-chlorophenyl)-2-methoxy pyridine (0.659 g, 3.0 mmol), palladium acetate (1.12 mg, 5.0 μmol), 2-dicyclohexylphosphino-2',4',6'-triisopropylbiphenyl (4.76 mg, 10.μmol) and potassium carbonate (1.04 g, 7.5 mmol) were weighed, and tetrahydrofuran (35 mL) and water (7 mL) were dropwise added, to obtain a suspension. The suspension was heated for 4 hours at 70° C. After cooling, water was added, and the precipitated solid was separated by filtration using a filter paper, and washed with water, methanol and hexane in this order. The obtained crude product was purified by column chromatography (developing solvent chloroform:hexane), to obtain a white solid of 4,6-diphenyl-2-[4'-(6-methoxy-2-yl)-5-(9-phenanthryl)biphenyl-3-yl]-1,3,5-triazine as the desired product (amount: 1.05 g, yield: 64%).

¹H-NMR (CDCl₃) δ (ppm): δ. 4.03 (s, 3H), 6.74 (d, J=8.6 Hz, 1H), 7.57-7.65 (m, 7H), 7.68-7.78 (m, 4H), 7.92 (s, 1H), 7.96 (d, J=8.1 Hz, 2H), 8.00-8.07 (m, 4H), 8.11 (t, J=1.7 Hz, 1H), 8.81-8.89 (m, 7H), 8.97 (t, J=1.7 Hz, 1H), 9.20 (t, J=1.7 Hz, 1H).

Synthesis Example 37

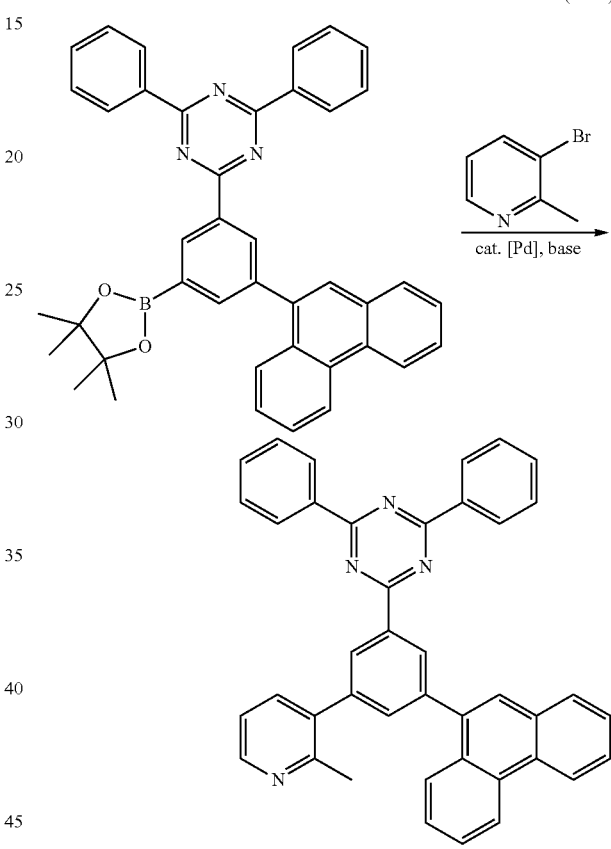

(A-37)

Under an argon stream, 4,6-diphenyl-2-[5-(9-phenanthryl)-3-(dioxaborolan-2-yl)phenyl]-1,3,5-triazine (1.35 g, 2.2 mmol), 3-bromo-2-methylpyridine (0.30 mL, 2.7 mmol) and tetrakis(triphenylphosphine) palladium (76.7 mg, 0.066 mmol) were weighed and suspended in tetrahydrofuran (22 mL). To this mixture, a 2.0M potassium carbonate aqueous solution (3.3 mL, 6.6 mmol) was dropwise added, followed by heating at 70° C. for 13 hours. After cooling, water was added, and the precipitated solid was separated by filtration and washed with water, methanol and hexane in this order. Further, it was purified by recrystallization (toluene), to obtain a white solid of 2-[3-{3-(2-methylpyridyl)-5-(9-phenanthryl)phenyl}]-4,6-diphenyl-1,3,5-triazine (compound A-37) (amount: 1.24 g, yield: 97%).

¹H-NMR (CDCl₃) δ (ppm): δ. 2.72 (s, 3H), 7.30 (dd, J=4.6, 7.4 Hz, 1H), 7.52-7.63 (m, 7H), 7.65-7.79 (m, 5H), 7.87 (s, 1H), 7.98 (d, J=8.0 Hz, 1H), 8.00 (d, J=8.3 Hz, 1H), 8.60 (dd, J=1.8, 4.9 Hz, 1H), 8.76 (m, 4H), 8.79 (d, J=7.3 Hz, 1H), 8.85 (d, J=8.2 Hz, 1H), 8.85 (t, J=1.6 Hz, 1H), 8.97 (t, J=1.6 Hz, 1H)

Synthesis Example 38

(A-38)

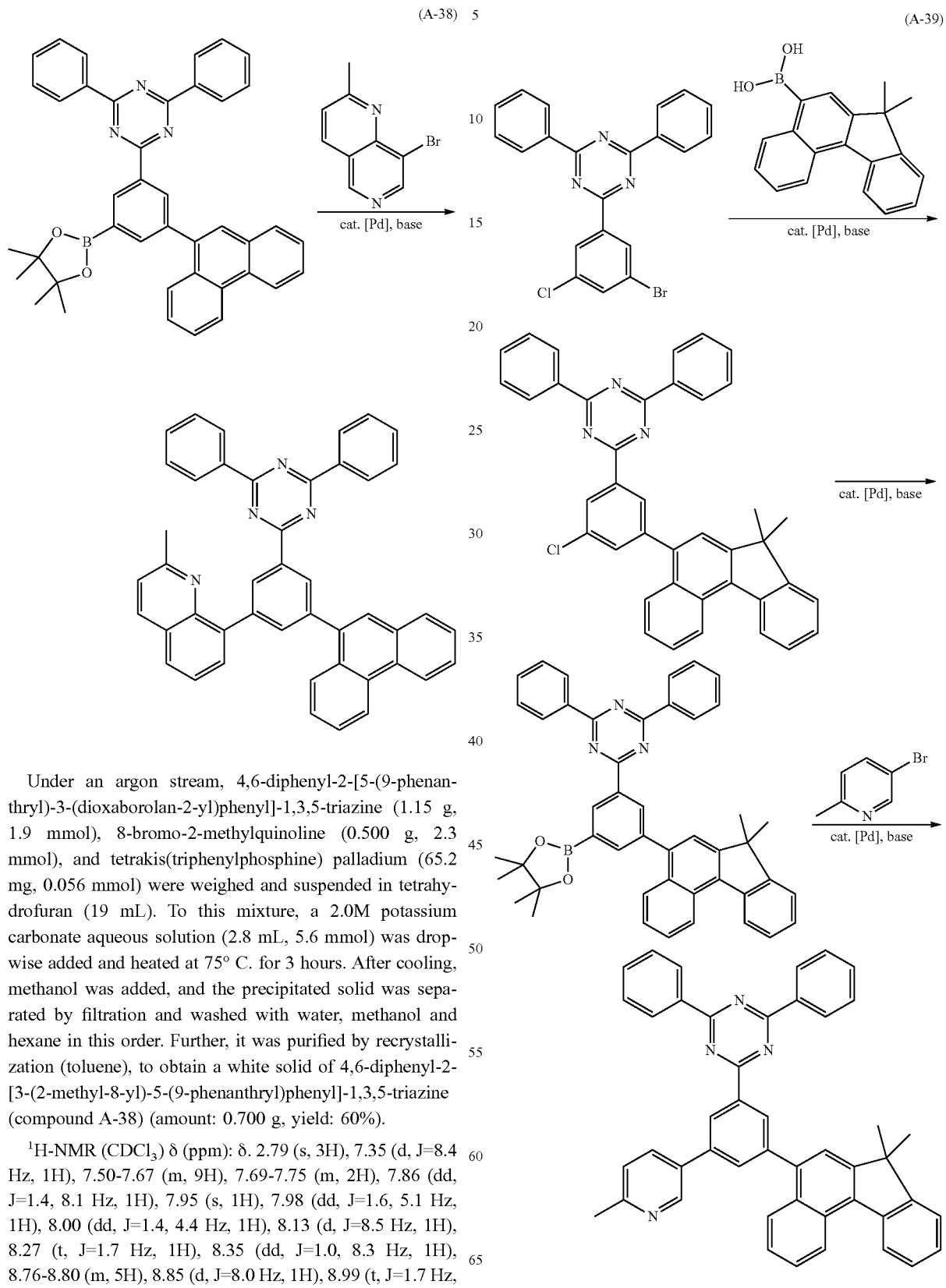

Under an argon stream, 4,6-diphenyl-2-[5-(9-phenanthryl)-3-(dioxaborolan-2-yl)phenyl]-1,3,5-triazine (1.15 g, 1.9 mmol), 8-bromo-2-methylquinoline (0.500 g, 2.3 mmol), and tetrakis(triphenylphosphine) palladium (65.2 mg, 0.056 mmol) were weighed and suspended in tetrahydrofuran (19 mL). To this mixture, a 2.0M potassium carbonate aqueous solution (2.8 mL, 5.6 mmol) was dropwise added and heated at 75° C. for 3 hours. After cooling, methanol was added, and the precipitated solid was separated by filtration and washed with water, methanol and hexane in this order. Further, it was purified by recrystallization (toluene), to obtain a white solid of 4,6-diphenyl-2-[3-(2-methyl-8-yl)-5-(9-phenanthryl)phenyl]-1,3,5-triazine (compound A-38) (amount: 0.700 g, yield: 60%).

$^1$H-NMR (CDCl$_3$) δ (ppm): δ. 2.79 (s, 3H), 7.35 (d, J=8.4 Hz, 1H), 7.50-7.67 (m, 9H), 7.69-7.75 (m, 2H), 7.86 (dd, J=1.4, 8.1 Hz, 1H), 7.95 (s, 1H), 7.98 (dd, J=1.6, 5.1 Hz, 1H), 8.00 (dd, J=1.4, 4.4 Hz, 1H), 8.13 (d, J=8.5 Hz, 1H), 8.27 (t, J=1.7 Hz, 1H), 8.35 (dd, J=1.0, 8.3 Hz, 1H), 8.76-8.80 (m, 5H), 8.85 (d, J=8.0 Hz, 1H), 8.99 (t, J=1.7 Hz, 1H), 9.28 (t, J=1.7 Hz, 1H).

Synthesis Example 39

(A-39)

Under an argon stream, 2-(3-bromo-5-chlorophenyl)-4,6-diphenyl-1,3,5-triazine (2.00 g, 4.6 mmol), (7,7-dimethyl-7H-benzo[c]fluoren-5-yl) boronic acid (1.59 g, 5.5 mmol) and tetrakis(triphenylphosphine) palladium (0.159 g, 0.14 mmol) were weighed and suspended in tetrahydrofuran (23 mL). To this mixture, a 2.0M potassium carbonate aqueous solution (6.9 mL, 14 mmol) was dropwise added and heated at 70° C. for 4 hours. After cooling, methanol was added, and the precipitated solid was separated by filtration and washed with water, methanol and hexane in this order. Further, it was purified by recrystallization (toluene), to obtain a white solid of 2-[3-chloro-5-(7,7-dimethyl-7H-benzo[c]fluoren-5-yl)phenyl]-4,6-diphenyl-1,3,5-triazine (amount: 2.12 g, yield: 79%).

Then, under an argon stream, 2-[3-chloro-5-(7,7-dimethyl-7H-benzo[c]fluoren-5-yl)phenyl]-4,6-diphenyl-1,3,5-triazine (2.00 g, 3.5 mmol), 4,4,4',4',5,5,5',5'-octamethyl-2,2'-bi-1,3,2-dioxaborolane (1.13 g, 4.4 mmol), palladium acetate (23.0 mg, 0.10 mmol), 2-dicyclohexylphosphino-2',4',6'-triisopropylbiphenyl (97.6 mg, 0.21 mmol) and potassium acetate (1.00 g, 10. mmol) were suspended in 1,4-dioxane (17 mL), and heated and stirred for 10 hours at 85° C. After cooling, the precipitate was removed by filtration using filter paper, and the organic layer was concentrated. Further, it was purified by column chromatography (developing solvent: chloroform), to obtain a white powder of 2-[3-(7,7-dimethyl-7H-benzo[c]fluoren-5-yl)-5-(4,4,5,5-tetramethyl-1,3,2-dioxaborolan-2-yl)phenyl]-4,6-diphenyl-1,3,5-triazine as an intermediate (amount: 2.60 g, yield: 85%).

Then, under an argon stream, 2-[3-(7,7-dimethyl-7H-benzo[c]fluoren-5-yl)-5-(4,4,5,5-tetramethyl-1,3,2-dioxaborolan-2-yl)phenyl]-4,6-diphenyl-1,3,5-triazine (1.50 g, 2.2 mmol), 5-bromo-2-methylpyridine (0.457 g, 2.7 mmol) and tetrakis(triphenylphosphine) palladium (76.7 mg, 66 μmol) were weighed and suspended in tetrahydrofuran (22 mL). To this mixture, a 2.0M potassium carbonate aqueous solution (3.3 mL, 6.6 mmol) was dropwise added, followed by heating at 70° C. for 13 hours. After cooling, water was added, and the precipitated solid was separated by filtration and washed with water, methanol and hexane in this order. Further, it was purified by recrystallization (toluene), to obtain a yellowish white solid of 2-[3-(7,7-dimethyl-7H-benzo[c]fluoren-5-yl)-5-(6-methylpyridin-3-yl)phenyl]-4,6-diphenyl-1,3,5-triazine (compound A-39) (amount: 0.893 g, yield: 63%).

$^1$H-NMR (CDCl$_3$) δ (ppm): δ. 1.62 (s, 6H), 2.67 (s, 3H), 7.33 (d, J=8.0 Hz, 1H), 7.42 (t, J=7.5 Hz, 1H), 7.48-7.63 (m, 9H), 7.71 (t, J=7.7 Hz, 1H), 7.72 (s, 1H), 7.98 (t, J=1.8 Hz, 1H), 8.01 (dd, J=2.5, 8.0 Hz, 1H), 8.07 (d, J=7.6 Hz, 1H), 8.42 (d, J=7.8 Hz, 1H), 8.78 (brd, J=6.8 Hz, 4H), 8.91 (d, J=8.8 Hz, 1H), 8.95 (t, J=1.8 Hz, 1H), 9.02 (d, J=2.0 Hz, 1H), 9.10 (t, J=1.8 Hz, 1H).

Synthesis Reference Example 6

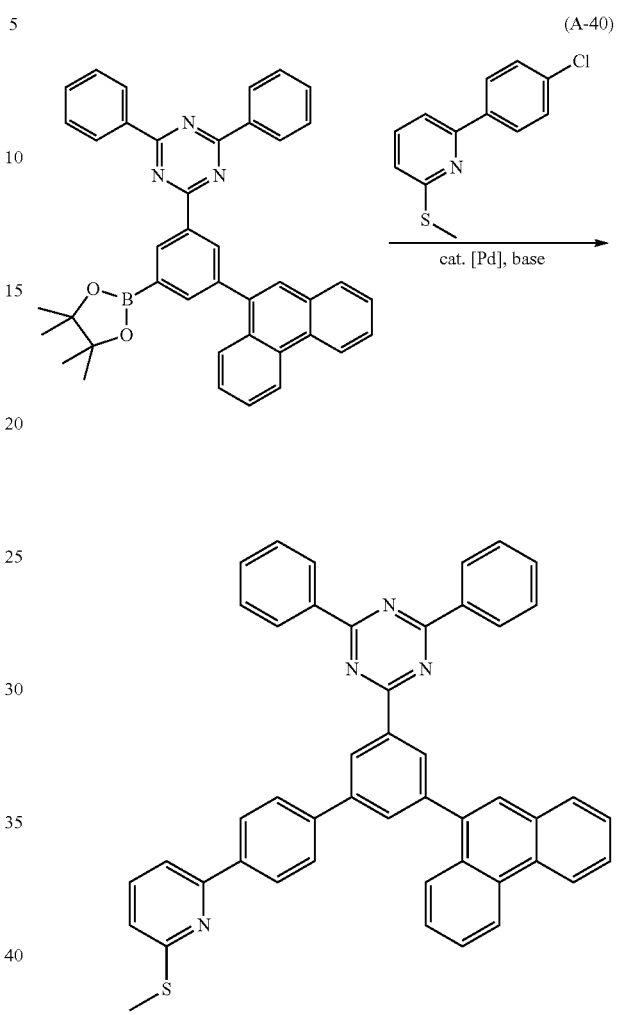

(A-40)

Under an argon stream, 4,6-diphenyl-2-[5-(9-phenanthryl)-3-(4,4,5,5-tetramethyl-1,3,2-dioxaborolan-2-yl)phenyl]-1,3,5-triazine (3.24 g, 5.3 mmol), 6-(4-chlorophenyl)-2-(methylthio)pyridine (1.50 g, 6.4 mmol), palladium acetate (23.8 mg, 0.106 mmol) and 2-dicyclohexylphosphino-2',4',6'-triisopropylbiphenyl (0.101 g, 0.21 mmol) were weighed, and 1,4-dioxane (53 mL) and a 2.0M potassium carbonate aqueous solution (8 mL) were dropwise added to obtain a suspension. The suspension was heated for 4 hours at 100° C. After cooling, water was added, followed by liquid separation, and the organic layer was concentrated. The obtained crude product was purified by column chromatography (developing solvent: chloroform:hexane) to obtain a white solid of 4,6-diphenyl-2-{4'-[(6-methylthio)pyridin-2-yl]-5-(9-phenanthryl)biphenyl-3-yl}-1,3,5-triazine as the desired product (amount: 1.50 g, yield: 41%).

$^1$H-NMR (CDCl$_3$) δ (ppm): δ. 2.13 (s, 3H), 7.54-7.78 (m, 8H), 7.92-8.12 (m, 10H), 8.23 (d, J=8.5 Hz, 2H), 8.80-8.83 (m, 7H), 8.99 (t, J=1.7 Hz, 1H), 9.20 (t, J=1.7 Hz, 1H).

Synthesis Example 41

Synthesis Example 42

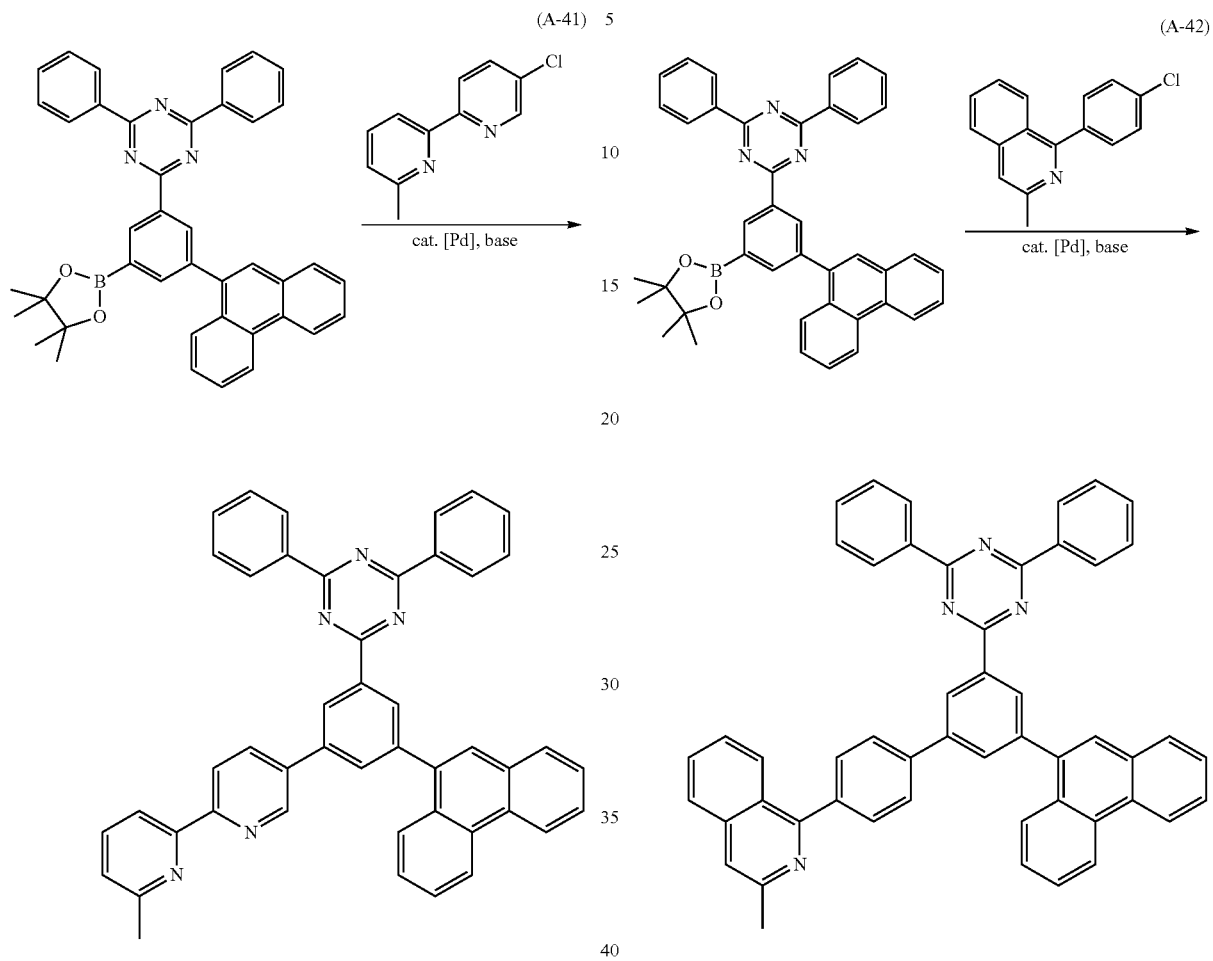

Under an argon stream, 4,6-diphenyl-2-[5-(9-phenanthryl)-3-(4,4,5,5-tetramethyl-1,3,2-dioxaborolan-2-yl)phenyl]-1,3,5-triazine (1.17 g, 1.9 mmol), 2-(5-chloropyridin-2-yl)-6-methylpyridine (0.471 g, 2.3 mmol), palladium acetate (8.53 mg, 38 μmol), 2-dicyclohexylphosphino-2',4',6'-triisopropylbiphenyl (36.2 mg, 76 μmol) and potassium carbonate (0.788 g, 5.7 mmol) were weighed, and tetrahydrofuran (25 mL) and water (5 mL) were dropwise added, to obtain a suspension. The suspension was heated for 4 hours at 70° C. After cooling, water was added, and the precipitated solid was separated by filtration and washed with water, methanol and hexane in this order. Further, it was purified by recrystallization (toluene), to obtain a white solid of 4,6-diphenyl-2-[4-{6'-methyl(1,1'-bipyridin-5-yl)}-5-(9-phenanthryl)phenyl-3-yl]-1,3,5-triazine as the desired product (amount: 0.740 g, yield: 59%).

$^1$H-NMR (CDCl$_3$) δ (ppm): δ. 2.79 (s, 3H), 7.54-7.66 (m, 8H), 7.69-7.79 (m, 6H), 7.92 (s, 1H), 8.01 (d, J=7.6 Hz, 2H), 8.11 (t, J=1.8 Hz, 1H), 8.80-8.84 (m, 6H), 8.89 (d, J=8.3 Hz, 1H), 9.06 (brs, 1H), 9.22 (t, J=1.8 Hz, 1H), 9.26 (t, J=1.8 Hz, 1H).

Under an argon stream, 4,6-diphenyl-2-[5-(9-phenanthryl)-3-(4,4,5,5-tetramethyl-1,3,2-dioxaborolan-2-yl)phenyl]-1,3,5-triazine (3.24 g, 5.3 mmol), 1-(4-chlorophenyl)-3-methylisoquinoline (1.50 g, 6.4 mmol), palladium acetate (23.8 mg, 0.106 mmol) and 2-dicyclohexylphosphino-2',4',6'-triisopropylbiphenyl (0.101 g, 0.21 mmol) were weighed, and 1,4-dioxane (53 mL) and a 2.0M potassium carbonate aqueous solution (8 mL) were dropwise added to obtain a suspension. The suspension was heated for 4 hours at 100° C. After cooling, water was added, followed by liquid separation, and the organic layer was concentrated. The obtained crude product was purified by column chromatography (developing solvent: chloroform:hexane), to obtain a white solid of 4,6-diphenyl-2-{4'-[3-methyl-pyridin-2-yl]-5-(9-phenanthryl)biphenyl-3-yl}-1,3,5-triazine as the desired product (amount: 1.50 g, yield: 41%).

$^1$H-NMR (CDCl$_3$) δ (ppm): δ. 2.83 (s, 3H), δ. 7.53-7.62 (m, 7H), 7.64-7.75 (m, 5H), 7.86-7.92 (m, 4H), 7.96-8.02 (m, 3H), 8.05 (d, J=8.5 Hz, 1H), 8.10 (t, J=1.8 Hz, 1H), 8.23 (d, J=8.5 Hz, 1H), 8.65 (d, J=5.7 Hz, 1H), 8.76-8.80 (m, 5H), 8.84 (d, J=8.3 Hz, 1H), 8.95 (s, 1H), 9.20 (s, 1H).

Synthesis Example 43

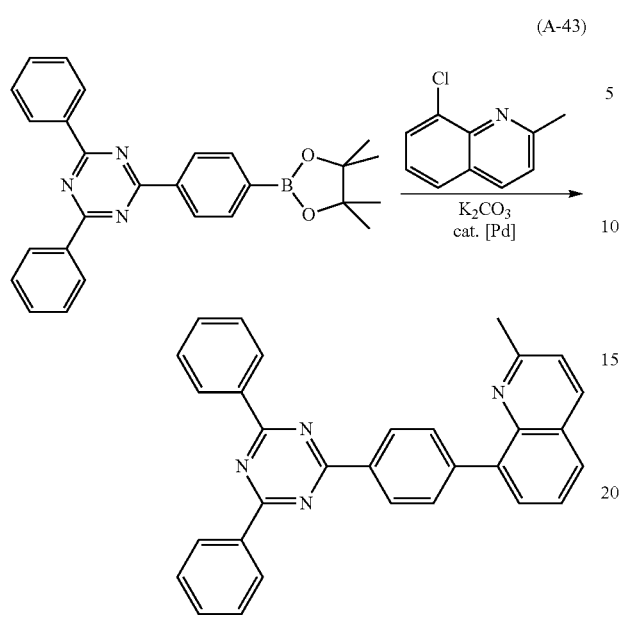

(A-43)

Under an argon stream, 2,4-diphenyl-6-[4-(4,4,5,5-tetramethyl-1,3,2-dioxaborolan-2-yl)phenyl]-1,3,5-triazine (0.500 g, 1.1 mmol), 8-chloro-2-methylquinoline (0.245 g, 1.4 mmol), palladium acetate (7.74 mg, 35 μmol) and 2-dicyclohexylphosphino-2',4',6'-triisopropylbiphenyl (32.8 mg, 69 μmol) were suspended 1,4-dioxane (11 mL) and heated to 70° C. A 2.0M tripotassium phosphate aqueous solution (1.7 mL) was dropwise added thereto, the temperature was raised to 70° C., and the mixture was stirred for 1.5 hours. After cooling, a white solid was separated by filtration. The obtained crude product was purified by recrystallization (toluene), to obtain a white solid of 2-[4'-(4,6-dimethylpyrimidin-2-yl)biphenyl-4-yl]-4,6-diphenyl-1,3,5-triazine (compound A-43) as the desired product (amount: 0.450 g, yield: 87%).

$^1$H-NMR (CDCl$_3$) δ (ppm): δ. 2.72 (s, 3H), 7.33 (d, J=8.4 Hz, 1H), 7.56-7.65 (m, 7H), 7.82 (d, J=7.6 Hz, 2H), 8.01 (d, J=8.2 Hz, 2H), 8.11 (d, J=8.4 Hz, 1H), 8.83 (dd, J=1.5, 7.7 Hz, 4H), 8.90 (d, J=8.6 Hz, 2H)

Synthesis Example 44

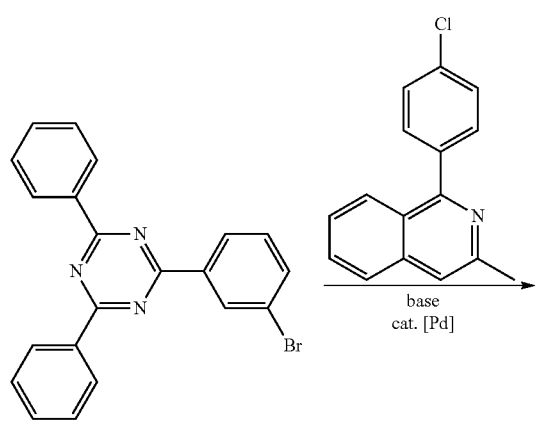

(A-44)

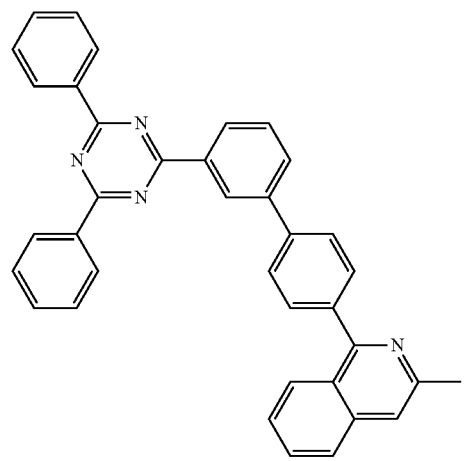

Under an argon stream, 2-bromophenyl-4,6-diphenyl-1,3,5-triazine (1.50 g, 3.9 mmol), 1-(4-chlorophenyl)-3-methylisoquinoline (1.53 g, 4.6 mmol) and tetrakis(triphenylphosphine) palladium (0.134 g, 0.12 mmol) were suspended in tetrahydrofuran (39 mL). A 2.0M potassium carbonate aqueous solution (5.8 mL) was slowly dropwise added thereto, and the mixture was heated 70° C. and stirred for 2 hours. After cooling, water was added, followed by liquid separation, and the organic layer was concentrated. The obtained crude product was purified by column chromatography (developing solvent: chloroform:hexane), to obtain a white solid of 4,6-diphenyl-2-[4'-(3-methylisoquinolin-1-yl)biphenyl-3-yl]-1,3,5-triazine (compound A-44) as the desired product (amount: 1.18 g, yield: 58%).

$^1$H-NMR (CDCl$_3$) δ (ppm): 2.58 (s, 3H), 7.68-7.82 (m, 9H), 7.68 (t, J=7.8 Hz, 1H), 7.85 (d, J=9.0 Hz, 2H), 7.87 (d, J=8.3 Hz, 2H), 8.50 (d, J=8.3 Hz, 2H), 8.80-8.84 (m, 6H), 9.19 (s, 1H).

Now, Device Preparation Examples will be shown below, but the present invention is by no means limited thereto. The structural formulae and abbreviations of the compounds used are as follows.

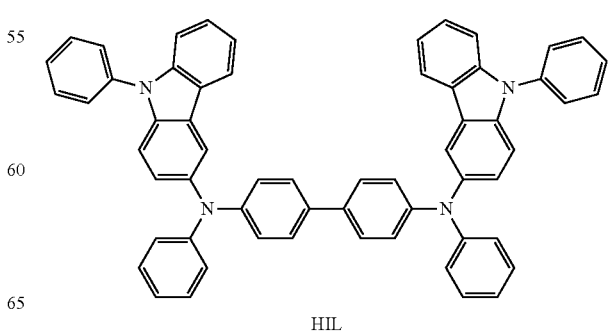

HIL

577
-continued
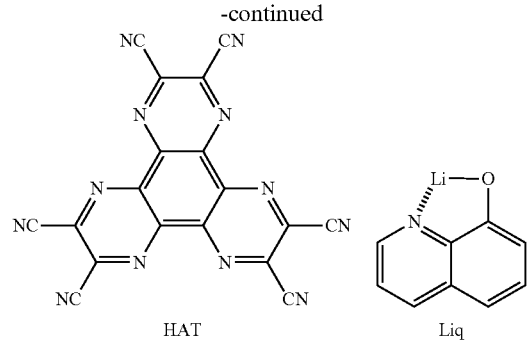
HAT
Liq
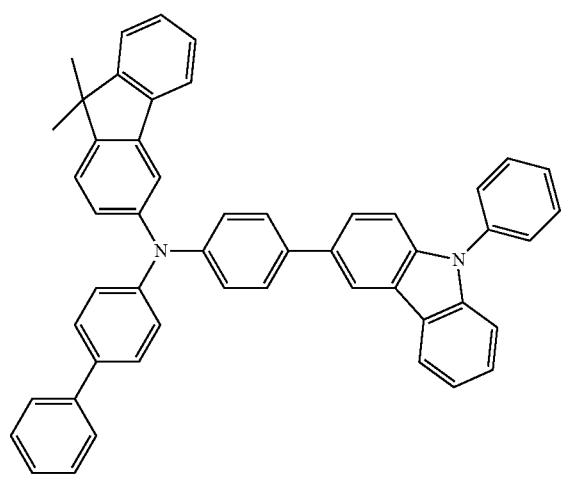
HTL
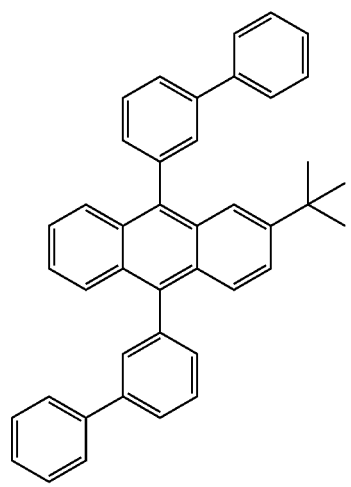
EML-1
578
-continued
EML-2
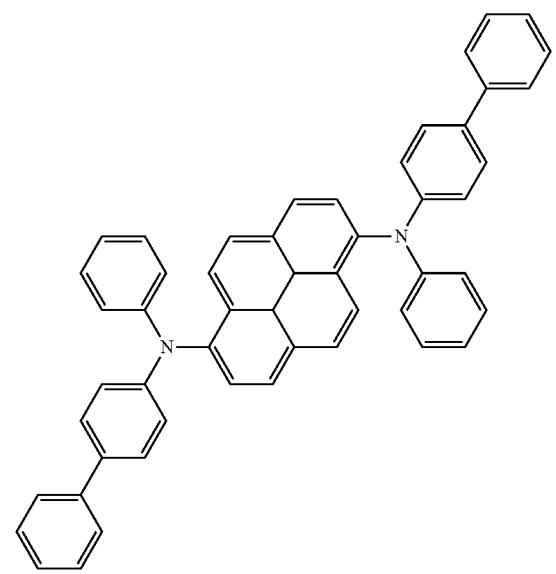
EML-3
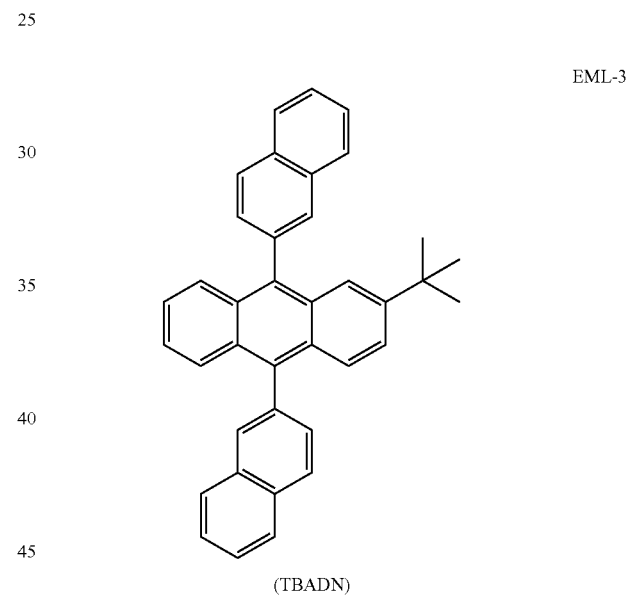
(TBADN)
ETL-1
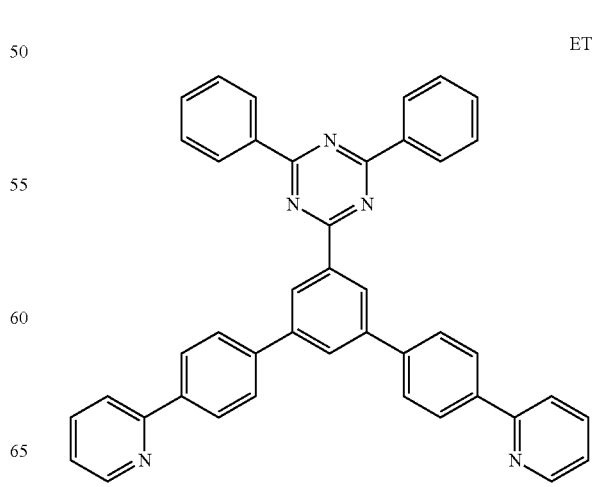

579
-continued
ETL-2
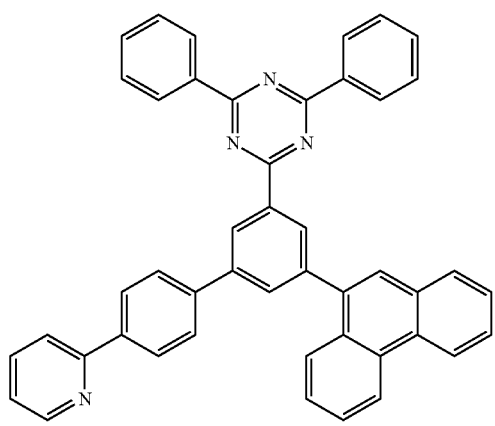
ETL-3
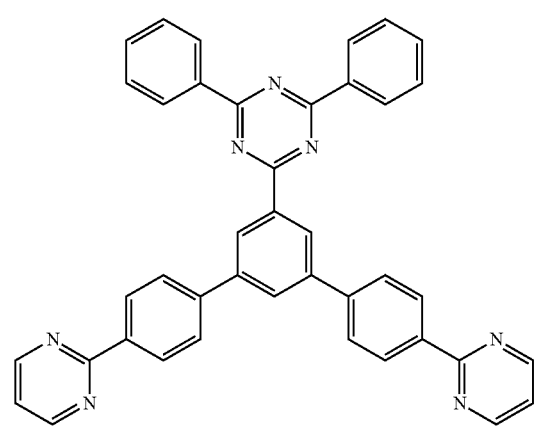
ETL-4
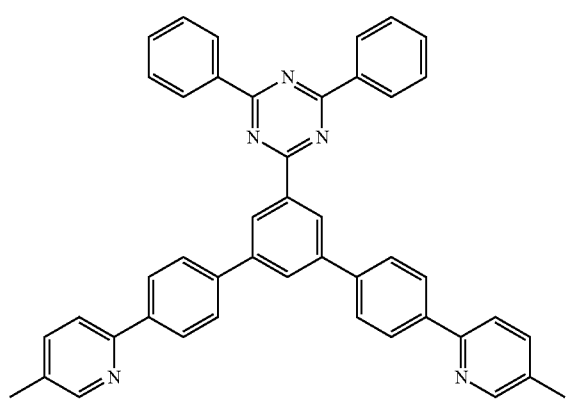
580
-continued
ETL-5
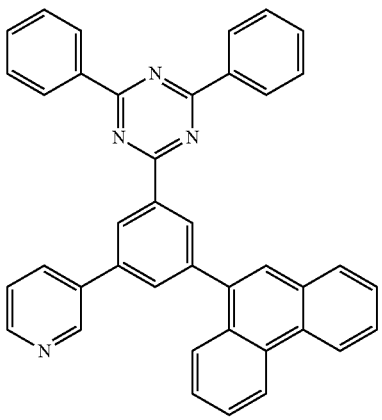
ETL-6
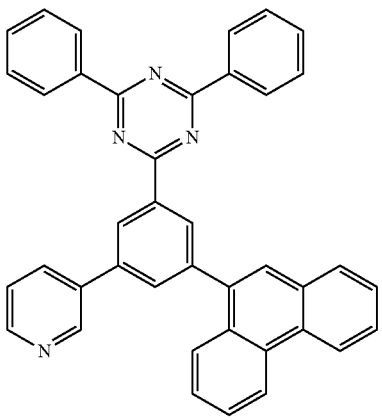
ETL-7
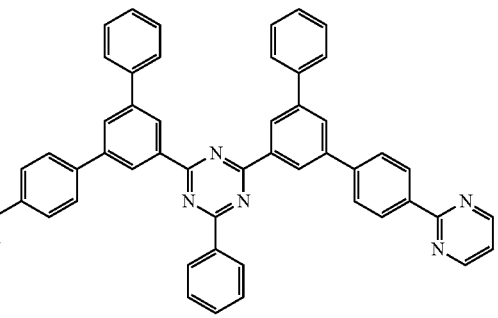

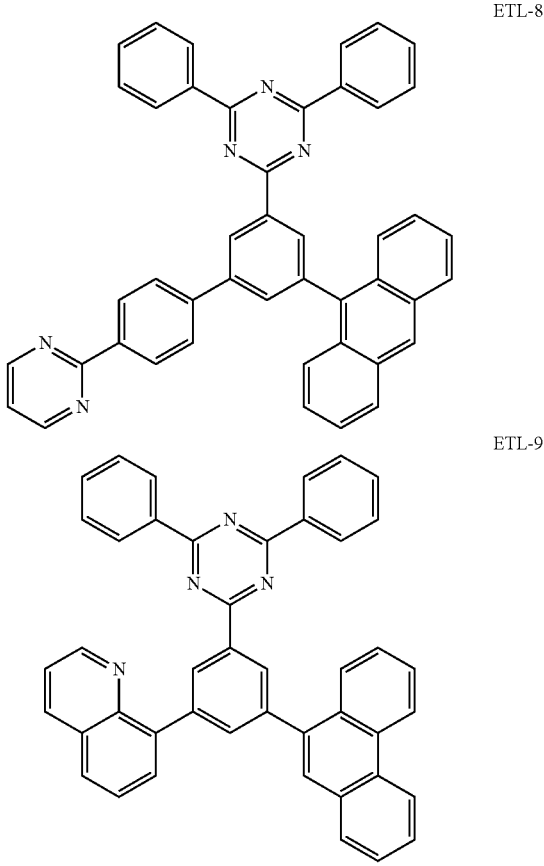

Device Example 1

As a substrate, a glass substrate provided with an ITO transparent electrode, was used, which had an indium tin oxide (ITO) film (thickness 110 nm) of 2 mm in width patterned in a stripe shape. This substrate was washed with isopropyl alcohol, and then, subjected to surface treatment with ozone UV cleaning. The substrate after washing, was subjected to vacuum deposition of each layer by a vacuum vapor deposition method to prepare an organic electroluminescent device (light-emitting area of 4 mm$^2$) as shown in FIG. 1 (schematic view of the layered construction in the cross-sectional direction).

Firstly, the glass substrate was introduced into a vacuum vapor deposition chamber, and the pressure was reduced to 1.0×10$^{-4}$ Pa.

Then, as organic compound layers on the glass substrate, an ITO transparent electrode-attached glass substrate (anode layer) 1, a hole injection layer 2, a charge generation layer 3, a hole transport layer 4, a light-emitting layer 5, an electron transport layer 6 and an electron injection layer 7 were sequentially formed each by a resistance heating system, and thereafter, a cathode layer 8 was formed.

As the hole injection layer 2, sublimation-purified HIL was vacuum-deposited in a film thickness of 45 nm (deposition rate: 0.15 nm/sec).

As the charge generation layer 3, sublimation-purified HAT was vacuum-deposited in a thickness of 5 nm (deposition rate: 0.025 nm/sec).

As the hole transport layer 4, HTL was vacuum-deposited in a film thickness of 30 nm (deposition rate: 0.15 nm/sec).

As the light emitting layer 5, EML-1 and EML-2 were vacuum-deposited in a ratio of 95:5 (weight ratio) in a film thickness of 20 nm (deposition rate: 0.18 nm/sec).

As the electron transport layer 6, 2-[4,4''-bis(4,6-dimethylpyrimidin-2-yl)-1,1:3',1''-terphenyl-5'-yl]-4,6-diphenyl-1,3,5-triazine (A–1) synthesized in Synthesis Example 1, was vacuum-deposited in a thickness of 30 nm (deposition rate: 0.15 nm/sec).

As the electron injection layer 7, sublimation-purified Liq was vacuum-deposited in a thickness of 0.45 nm (deposition rate: 0.005 nm/sec).

Finally, a metal mask was placed to be orthogonal to the ITO stripe, to form the cathode layer 8.

For the cathode layer 8, a silver magnesium (weight ratio: silver/magnesium=1/10) was vacuum-deposited in a film thickness of 80 nm (deposition rate: 0.5 nm/sec), and further silver was then vacuum-deposited in a thickness of 20 nm (deposition rate: 0.2 nm/sec.), to obtain a two-layer structure.

Each of the film thicknesses was measured by a contact-type thickness meter (DEKTAK). Further, this device was sealed in a glove box of nitrogen atmosphere with oxygen and moisture concentrations being at most 1 ppm. For the sealing, a sealing cap made of glass and the film forming substrate epoxy type ultraviolet curable resin (manufactured by Nagase Chemtex Corporation) were used.

Reference Example 1

An organic electroluminescent device was prepared in the same manner as in Device Example 1 except that in the electron transport layer 6 in Device Example 1, ETL-1 was used instead of 2-[4,4''-bis(4,6-dimethylpyrimidin-2-yl)-1,1:3',1''-terphenyl-5'-yl]-4,6-diphenyl-1,3,5-triazine (A–1).

Reference Example 2

An organic electroluminescent device was prepared in the same manner as in Device Example 1 except that in the electron transport layer 6 in Device Example 1, ETL-3 was used instead of 2-[4,4''-bis(4,6-dimethylpyrimidin-2-yl)-1,1:3',1''-terphenyl-5'-yl]-4,6-diphenyl-1,3,5-triazine (A–1).

A direct current was applied to the organic light emitting element prepared, and the light emission characteristics were evaluated by using a luminance meter i.e. LUMINANCE METER (BM-9) manufactured by TOPCON Corp. As the light emission characteristics, the voltage (V) and the current efficiency (cd/A) when a current density of 10 mA/cm$^2$ was applied, were measured, and the luminance half-life during continuous lighting was measured. Further, the luminance decay time during continuous lighting under driving at an initial luminance of 800 cd/m$^2$, was measured. The time when the luminance (cd/m$^2$) was reduced 30%, is shown below as the device lifetime (h).

TABLE 1

| | Voltage (V) | Current efficiency (cd/A) | Device lifetime (h) |
|---|---|---|---|
| Device Example 1 (A-1) | 3.85 | 4.38 | 403 |
| Reference Example 1 (ETL-1) | 3.92 | 4.00 | 233 |
| Reference Example 2 (ETL-3) | 4.03 | 4.56 | 213 |

From Table 1, the organic electroluminescent device of the present invention was found to be equivalent in the initial characteristics and excellent in life characteristics, as compared to the Reference Examples.

Device Example 2

In Device Example 1, the film thicknesses of the hole injection layer 2, the hole transport layer 4, the light-emitting layer 5 and the electron injection layer 7, were changed to 40 nm, and 25 nm, 25 nm, and 0.5 nm, respectively. Further, in the electron transport layer 6, instead of 2-[4,4"-bis(4,6-dimethylpyrimidin-2-yl)-1,1':3',1"-terphenyl-5'-yl]-4,6-diphenyl-1,3,5-triazine (A–1), 2-[4,4"-bis(6-methyl-2-yl)-1,1';3',1"-terphenyl-5'-yl]-4,6-diphenyl-1,3,5-triazine (A-9) synthesized in Synthesis Example 9, was used. Otherwise, in the same manner as in Device Example 1, an organic electroluminescent device was prepared.

Reference Example 3

An organic electroluminescent device was prepared in the same manner as in Device Example 2 except that in the electron transport layer 6 in Device Example 2, ETL-1 was used, instead of 2-[4,4"-bis(6-methylpyridin-2-yl)-1,1';3',1"-terphenyl-5'-yl]-4,6-diphenyl-1,3,5-triazine (A-9).

Reference Example 4

An organic electroluminescent device was prepared in the same manner as in Device Example 2 except that in the electron transport layer 6 in Device Example 2, ETL-4 was used, instead of 2-[4,4"-bis(6-methylpyridin-2-yl)-1,1';3',1"-terphenyl-5'-yl]-4,6-diphenyl-1,3,5-triazine (A-9).

A direct current was applied to the organic light emitting element prepared, and the light emission characteristics were evaluated by using a luminance meter i.e. LUMINANCE METER (BM-9) manufactured by TOPCON Corp. As the light emission characteristics, the voltage (V) and the current efficiency (cd/A) when a current density of 10 mA/cm$^2$ was applied, were measured, and the luminance half-life during continuous lighting was measured. Further, the luminance decay time during continuous lighting under driving at an initial luminance of 1200 cd/m$^2$, was measured. The time when the luminance (cd/m$^2$) was reduced 50%, is shown below as the device lifetime (h).

TABLE 2

| | Voltage (V) | Current efficiency (cd/A) | Device lifetime (h) |
|---|---|---|---|
| Device Example 2 (A-9) | 4.25 | 5.47 | 1172 |
| Reference Example 3 (ETL-1) | 4.18 | 4.85 | 925 |
| Reference Example 4 (ETL-4) | 4.23 | 5.61 | 90 |

From Table 2, the organic electroluminescent device of the present invention was found to be equivalent in the initial characteristics and excellent in life characteristics, as compared to the Reference Examples.

Device Example 3

An organic electroluminescent device was prepared in the same manner as in Device Example 2 except that in the electron transport layer 6 in Device Example 2, instead of 2-[4,4"-bis(6-methylpyridin-2-yl)-1,1';3',1"-terphenyl-5'-yl]-4,6-diphenyl-1,3,5-triazine (A-9), 4,6-diphenyl-2-{5-(9-phenanthryl)-4'-[2-(4,6-dimethylpyrimidyl)]biphenyl-3-yl}-1,3,5-triazine (A-10) synthesized in Example 10, was used.

Reference Example 5

An organic electroluminescent device was prepared in the same manner as in Device Example 3 except that in the electron transport layer 6 in Device Example 3, ETL-2 was used instead of 4,6-diphenyl-2-{5-(9-phenanthryl)-4'-[2-(4,6-dimethylpyrimidyl)]biphenyl-3-yl}-1,3,5-triazine (A-10).

A direct current was applied to the organic light emitting element prepared, and the light emission characteristics were evaluated by using a luminance meter i.e. LUMINANCE METER (BM-9) manufactured by TOPCON Corp. As the light emission characteristics, the voltage (V) and the current efficiency (cd/A) when a current density of 10 mA/cm$^2$ was applied, were measured, and the luminance half-life during continuous lighting was measured. Further, the luminance decay time during continuous lighting under driving at an initial luminance of 800 cd/m$^2$, was measured. The time when the luminance (cd/m$^2$) was reduced 30%, is shown below as the device lifetime (h).

TABLE 3

| | Voltage (V) | Current efficiency (cd/A) | Device lifetime (h) |
|---|---|---|---|
| Device Example 3 (A-10) | 4.45 | 4.96 | 1176 |
| Reference Example 5 (ETL-2) | 4.46 | 4.69 | 865 |

From Table 3, the organic electroluminescent device of the present invention was found to be equivalent in the initial characteristics and excellent in life characteristics, as compared to the Reference Example.

Device Example 4

In Device Example 1, the film thicknesses of the hole injection layer 2, the hole transport layer 4, the electron transport layer 6 and the electron injection layer 7, were changed to 20 nm, 25 nm, 45 nm, and 1.0 nm, respectively.

Further, in the light emitting layer 5, EML-3 and EML-2 were vacuum-deposited in a ratio of 97:3 (weight ratio) in a film thickness of 35 nm (deposition rate: 0.18 nm/sec).

Further, in the electron transport layer 6, 4,6-diphenyl-2-[4-(6-methylpyridin-2-yl)-3'-(9-phenanthryl)-1,1'-biphenyl-5'-yl]-1,3,5-triazine (A-12) synthesized in Synthesis Example 12, was vacuum-deposited in a film thickness of 45 nm (deposition rate: 0.25 nm/sec).

Reference Example 6

An organic electroluminescent device was prepared in the same manner as in Device Example 4 except that in the electron transport layer 6 in Device Example 4, ETL-2 was used instead of 4,6-diphenyl-2-[4-(6-methylpyridin-2-yl)-3'-(9-phenanthryl)-1,1'-biphenyl-5'-yl]-1,3,5-triazine (A-12).

A direct current was applied to the organic light emitting element prepared, and the light emission characteristics were evaluated by using a luminance meter i.e. LUMINANCE METER (BM-9) manufactured by TOPCON Corp. As the light emission characteristics, the voltage (V) and the current efficiency (cd/A) when a current density of 10 mA/cm$^2$ was applied, were measured, and the luminance half-life during continuous lighting was measured. Further, the luminance decay time during continuous lighting under driving at an initial luminance of 1200 cd/m$^2$, was measured. The time when the luminance (cd/m$^2$) was reduced 50%, is shown below as the device lifetime (h).

TABLE 4

|  | Voltage (V) | Current efficiency (cd/A) | Device lifetime (h) |
| --- | --- | --- | --- |
| Device Example 4 (A-12) | 5.56 | 4.06 | 2380 |
| Reference Example 6 (ETL-2) | 6.15 | 3.07 | 888 |

From Table 4, the organic electroluminescent device of the present invention was found to be excellent in life characteristics, as compared to the Reference Examples.

Device Example 5

In Device Example 1, the film thicknesses of the hole injection layer 2, the hole transport layer 4, the light emission layer 5 and the electron injection layer 7, were changed to 65 nm, 10 nm, 25 nm, and 0.5 nm, respectively.

Further, an organic electroluminescent device was prepared in the same manner as in Device Example 1 except that in the electron transport layer 6, 4,6-diphenyl-2-[3-(6-methylpyridin-3-yl)-5-(9-phenanthryl)phenyl]-1,3,5-triazine (A-28) synthesized in Synthesis Example 28, was used.

Device Example 6

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), 4,6-diphenyl-2-[3-(6-methyl-pyridin-2-yl)-5-(9-phenanthryl)phenyl]-1,3,5-triazine (A-29) synthesized in Synthesis Example 29, was used.

Device Example 7

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), 2-{3-[2-(4,6-dimethylpyrimidyl)]-5-(9-phenanthryl)phenyl]-4,6-diphenyl-1,3,5-triazine (A-27) synthesized in Synthesis Example 27, was used.

Device Example 8

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), 4,6-bis(biphenyl-4-yl)-2-[4'-(4,6-dimethylpyrimidyl)biphenyl-4-yl]-1,3,5-triazine (A-31) synthesized in Synthesis Example 31, was used.

Device Example 9

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), 2,4-di(biphenyl-4-yl)-6-[4-(4,6-dimethylpyrimidyl)phenyl]-1,3,5-triazine (A-32) synthesized in Synthesis Example 32, was used.

Device Example 10

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), 2-{4-[2-(4,6-dimethylpyrimidyl)]-1,1':3',1''-terphenyl-5'-yl}-4,6-diphenyl-1,3,5-triazine (A-5) synthesized in Synthesis Example 5, was used.

Device Example 11

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), 2-[4'-(4,6-dimethylpyrimidin-2-yl)biphenyl-3-yl]-4,6-diphenyl-1,3,5-triazine (A-22) synthesized in Synthesis Example 22, was used.

Device Example 12

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), 2-[4-(4,6-dimethylpyrimidin-2-yl)phenyl]-4,6-diphenyl-1,3,5-triazine (A-18) synthesized in Synthesis Example 18, was used.

Device Example 13

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), 2-{4-[2-(4,6-dimethylpyrimidyl)]-1,1':3',1''-terphenyl-5'-yl}-4,6-diphenyl-1,3,5-triazine (A-5) synthesized in Synthesis Example 5, was used.

Device Example 14

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), 4,6-diphenyl-2-{5-(9-phenanthryl)-4'-[2-(4,6-dimethylpyrimidyl)]biphenyl-3-yl}-1,3,5-triazine (A-10) synthesized in Synthesis Example 10, was used.

Reference Example 7

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), ETL-5 was used.

Reference Example 8

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), ETL-6 was used.

Reference Example 9

An organic electroluminescent device was prepared in the same manner as in Device Example 5 except that in the electron transport layer 6 in Device Example 5, instead of 4,6-diphenyl-2-[3-(6-methylpyridin-3-yl)-5-(9-phenanthryl)phenyl]-1,3,5-triazine (A-28), ETL-2 was used.

A direct current was applied to the organic light emitting element prepared, and the light emission characteristics were evaluated by using a luminance meter i.e. LUMINANCE METER (BM-9) manufactured by TOPCON Corp. As the light emission characteristics, the voltage (V) and the current efficiency (cd/A) when a current density of 10 mA/cm$^2$ was applied, were measured, and the luminance half-life during continuous lighting was measured. Further, the luminance decay time during continuous lighting under driving at an initial luminance of 800 cd/m$^2$, was measured. The time when the luminance (cd/m$^2$) was reduced 30%, is shown below as the device lifetime (h).

TABLE 5

|  | Voltage (V) | Current efficiency (cd/A) | Device lifetime (h) |
| --- | --- | --- | --- |
| Device Example 5 (A-28) | 4.31 | 4.99 | 828 |
| Device Example 6 (A-29) | 4.36 | 5.03 | 877 |
| Device Example 7(A-27) | 4.55 | 4.64 | 796 |
| Reference Example 7(ETL-5) | 4.37 | 4.51 | 484 |
| Device Example 8(A-31) | 4.57 | 4.13 | 443 |
| Device Example 9(A-32) | 5.02 | 4.13 | 372 |
| Device Example 10(A-5) | 4.52 | 4.40 | 761 |
| Device Example 11 (A-2) | 4.96 | 4.00 | 941 |
| Device Example 12 (A-18) | 3.66 | 3.19 | 91 |
| Reference Example 8(ETL-6) | 4.45 | 3.27 | 2 |
| Device Example 13 (A-5) | 4.51 | 4.32 | 891 |
| Device Example 14 (A-10) | 4.39 | 4.98 | 961 |
| Reference Example 9(ETL-2) | 4.28 | 4.94 | 805 |

From Table 5, the organic electroluminescent device of the present invention was found to be equivalent in the initial characteristics and excellent in life characteristics, as compared to the Reference Example.

Device Example 15

An organic electroluminescent device was prepared in the same manner as in Device Example 1 except that EML-1 and EML-2 in Device Example 1 were adjusted to be in a ratio of 93:7 (by weight), and in the electron transport layer 6, instead of 2-[4,4''-bis(4,6-dimethylpyrimidin-2-yl)-1,1':3',1''-terphenyl-5'-yl]-4,6-diphenyl-1,3,5-triazine (A-1), 2,4-bis-[4-(4,6-dimethylpyrimidin-2-yl)-1,1':3',1''-terphenyl-5'-yl]-6-phenyl-1,3,5-triazine (A-19) synthesized in Synthesis Example 19 was used.

Device Example 16

An organic electroluminescent device was prepared in the same manner as in Device Example 15 except that in the electron transport layer 6, instead of 2,4-bis-[4-(4,6-dimethylpyrimidin-2-yl)-1,1':3',1''-terphenyl-5'-yl]-6-phenyl-1,3,5-triazine (A-19), 2-[5-(9-anthracenyl)-4'-(4,6-dimethylpyrimidin-2-yl)biphenyl-3-yl]-4,6-diphenyl-1,3,5-triazine (A-11) synthesized in Synthesis Example 11 was used.

Reference Example 10

An organic electroluminescent device was prepared in the same manner as in Device Example 15 except that in the electron transport layer 6, instead of 2,4-bis-[4-(4,6-dimethylpyrimidin-2-yl)-1,1':3',1''-terphenyl-5'-yl]-6-phenyl-1,3,5-triazine (A-19), ETL-7 was used.

Reference Example 11

An organic electroluminescent device was prepared in the same manner as in Device Example 15 except that in the electron transport layer 6, instead of 2,4-bis-[4-(4,6-dimethylpyrimidin-2-yl)-1,1':3',1''-terphenyl-5'-yl]-6-phenyl-1,3,5-triazine (A-19), ETL-8 was used.

A direct current was applied to the organic light emitting element prepared, and the light emission characteristics were evaluated by using a luminance meter i.e. LUMINANCE METER (BM-9) manufactured by TOPCON Corp. As the light emission characteristics, the voltage (V) and the current efficiency (cd/A) when a current density of 10 mA/cm$^2$ was applied, were measured, and the luminance half-life during continuous lighting was measured. Further, the luminance decay time during continuous lighting under driving at an initial luminance of 800 cd/m$^2$, was measured. The time when the luminance (cd/m$^2$) was reduced 30%, is shown below as the device lifetime (h).

TABLE 6

|  | Voltage (V) | Current efficiency (cd/A) | Device lifetime (h) |
| --- | --- | --- | --- |
| Device Example 15 (A-19) | 4.39 | 5.14 | 574 |
| Reference Example 10(ETL-7) | 4.25 | 5.05 | 353 |
| Device Example 16 (A-11) | 4.35 | 4.66 | 494 |
| Reference Example 11 (ETL-8) | 4.53 | 4.61 | 343 |

From Table 6, the organic electroluminescent device of the present invention was found to be equivalent in the initial characteristics and excellent in life characteristics, as compared to the Reference Example.

Device Example 17

An organic electroluminescent device was prepared in the same manner as in Device Example 15 except that in the electron transport layer 6 in Device Example 15, instead of 2,4-bis-[4-(4,6-dimethylpyrimidin-2-yl)-1,1':3',1''-terphenyl-5'-yl]-6-phenyl-1,3,5-triazine (A-19), 2-{3-[3-(2-methylpyridyl)-5-(9-phenanthryl)phenyl]}-4,6-diphenyl-1,3,5-triazine (A-37) synthesized in Synthesis Example 37, was used.

Device Example 18

An organic electroluminescent device was prepared in the same manner as in Device Example 17 except that in the electron transport layer 6 in Device Example 17, instead of 2-{3-[3-(2-methylpyridyl)-5-(9-phenanthryl)phenyl]}-4,6-diphenyl-1,3,5-triazine (A-37), 4,6-diphenyl-2-[4-(6-methylpyridin-2-yl)-3'-(9-phenanthryl)-1,1'-biphenyl-5'-yl]-1,3,5-triazine (A-12) synthesized in Synthesis Example 12, was used.

Device Example 19

An organic electroluminescent device was prepared in the same manner as in Device Example 17 except that in the electron transport layer 6 in Device Example 17, instead of 2-{3-[3-(2-methylpyridyl)-5-(9-phenanthryl)phenyl]}-4,6-diphenyl-1,3,5-triazine (A-37), 4,6-diphenyl-2-[3-(2-methylquinolin-8-yl)-5-(9-phenanthryl)phenyl]-1,3,5-triazine (A-38) synthesized in Synthesis Example 38, was used.

Reference Example 12

An organic electroluminescent device was prepared in the same manner as in Device Example 17 except that in the electron transport layer 6 in Device Example 17, instead of 2-{3-[3-(2-methylpyridyl)-5-(9-phenanthryl)phenyl]}-4,6-diphenyl-1,3,5-triazine (A-37), ETL-5, was used.

Reference Example 13

An organic electroluminescent device was prepared in the same manner as in Device Example 17 except that in the electron transport layer 6 in Device Example 17, instead of 2-{3-[3-(2-methylpyridyl)-5-(9-phenanthryl)phenyl]}-4,6-diphenyl-1,3,5-triazine (A-37), ETL-2, was used.

Reference Example 14

An organic electroluminescent device was prepared in the same manner as in Device Example 17 except that in the electron transport layer 6 in Device Example 17, instead of 2-{3-[3-(2-methylpyridyl)-5-(9-phenanthryl)phenyl]}-4,6-diphenyl-1,3,5-triazine (A-37), ETL-9, was used.

Reference Example 16

An organic electroluminescent device was prepared in the same manner as in Device Example 17 except that in the electron transport layer 6 in Device Example 17, instead of 2-{3-[3-(2-methylpyridyl)-5-(9-phenanthryl)phenyl]}-4,6-diphenyl-1,3,5-triazine (A-37), 4,6-diphenyl-2-[4'-(6-methoxypyridin-2-yl)-5-(9-phenanthryl)biphenyl-3-yl]-1,3,5-triazine (A-36) synthesized in Synthesis Reference Example 5, was used.

Reference Example 17

An organic electroluminescent device was prepared in the same manner as in Device Example 17 except that in the electron transport layer 6 in Device Example 17, instead of 2-{3-[3-(2-methylpyridyl)-5-(9-phenanthryl)phenyl]}-4,6-diphenyl-1,3,5-triazine (A-37), 4,6-diphenyl-2-{4'-[(6-methylthio)pyridin-2-yl]-5-(9-phenanthryl)biphenyl-3-yl}-1,3,5-triazine (A-40) synthesized in Synthesis Reference Example 6, was used.

A direct current was applied to the organic light emitting element prepared, and the light emission characteristics were evaluated by using a luminance meter i.e. LUMINANCE METER (BM-9) manufactured by TOPCON Corp. As the light emission characteristics, the voltage (V) and the current efficiency (cd/A) when a current density of 10 mA/cm$^2$ was applied, were measured, and the luminance half-life during continuous lighting was measured. Further, the luminance decay time during continuous lighting under driving at an initial luminance of 800 cd/m$^2$, was measured. The time when the luminance (cd/m$^2$) was reduced 10%, is shown below as the device lifetime (h).

TABLE 7

|  | Voltage (V) | Current efficiency (cd/A) | Device lifetime (h) |
|---|---|---|---|
| Device Example 17(A-37) | 3.62 | 4.33 | 60 |
| Reference Example 12 (ETL-5) | 3.67 | 3.89 | 38 |
| Device Example 18(A-12) | 3.99 | 4.63 | 42 |
| Reference Example 13 (ETL-2) | 3.61 | 4.41 | 29 |
| Device Example 19(A-38) | 4.12 | 5.09 | 27 |
| Reference Example 14 (ETL-9) | 4.44 | 5.02 | 20 |
| Reference Example 16 (A-36) | 3.73 | 5.00 | 8 |
| Reference Example 17(A-40) | 5.35 | 4.60 | 1 |

From Table 7, the organic electroluminescent device of the present invention was found to be excellent in life characteristics, as compared to the Reference Example.

Device Example 20

An organic electroluminescent device was prepared in the same manner as in Device Example 15 except that in the electron transport layer 6 in Device Example 15, instead of 2,4-bis-[4-(4,6-dimethylpyrimidin-2-yl)-1,1':3',1"-terphenyl-5'-yl]-6-phenyl-1,3,5-triazine (A-19), 4,6-diphenyl-2-{4-[6'-methyl(1,1'-bipyridin-5-yl)]-5-(9-phenanthryl)phenyl-3-yl}-1,3,5-triazine (A-41) synthesized in Synthesis Example 41, was used.

Reference Example 15

An organic electroluminescent device was prepared in the same manner as in Device Example 20 except that in the electron transport layer 6 in Device Example 20, instead of 4,6-diphenyl-2-[4-(6-methylpyridin-2-yl)-3'-(9-phenanthryl)-1,1'-biphenyl-5'-yl]-1,3,5-triazine (A-41), ETL-2, was used.

A direct current was applied to the organic light emitting element prepared, and the light emission characteristics were evaluated by using a luminance meter i.e. LUMINANCE METER (BM-9) manufactured by TOPCON Corp. As the light emission characteristics, the voltage (V) and the current efficiency (cd/A) when a current density of 10 mA/cm$^2$ was applied, were measured, and the luminance half-life during continuous lighting was measured. Further, the luminance decay time during continuous lighting under driving at an initial luminance of 800 cd/m$^2$, was measured. The time when the luminance (cd/m$^2$) was reduced 25%, is shown below as the device lifetime (h).

TABLE 8

|  | Voltage (V) | Current efficiency (cd/A) | Device lifetime (h) |
|---|---|---|---|
| Device Example 20(A-41) | 3.60 | 4.94 | 264 |
| Reference Example 15 (ETL-2) | 3.61 | 4.41 | 223 |

From Table 8, the organic electroluminescent device of the present invention was found to be excellent in life characteristics, as compared to the Reference Example.

INDUSTRIAL APPLICABILITY

The organic electroluminescent device having an electron transport layer or an electron injection layer containing a cyclic azine compound of the present invention can be driven for a long period of time as compared to conventional materials and excellent in luminous efficiency, and it can be applied to various organic electroluminescent devices using phosphorescent materials. In particular, in addition to applications such as flat panel displays, it is also applicable to illumination, etc. where low power consumption is demanded.

The entire disclosures of Japanese Patent Application No. 2013-087142 filed on Apr. 18, 2013 and Japanese Patent Application No. 2013-133811 filed on Jun. 26, 2013 including specifications, claims, drawings and summaries are incorporated herein by reference in their entireties.

REFERENCE SYMBOLS

1: Glass substrate provided with ITO transparent electrode, 2: Hole injection layer, 3: Charge generating layer, 4: Hole transport layer, 5: Light emitting layer, 6: Electron transport layer, 7: Electron injection layer, 8: Cathode layer

The invention claimed is:

1. A cyclic azine compound represented by the following formula (1):

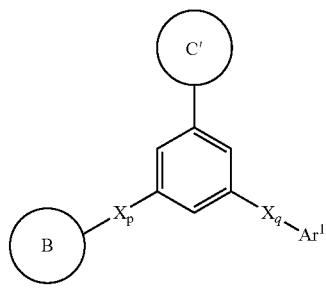

General formula (1)

wherein each substituent B represents an azabenzene group, or a diazabenzene group, which has a $C_{1-12}$ alkyl group on at least one carbon atom among carbon atoms adjacent to a nitrogen atom, which is represented by the following heteroaryl groups:

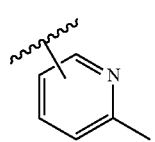
B-1

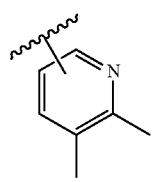
B-2

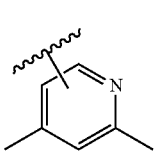
B-3

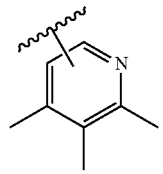
B-4

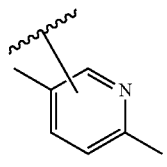
B-5

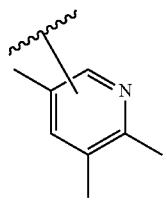
B-6

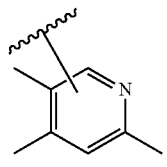
B-7

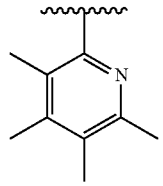
B-8

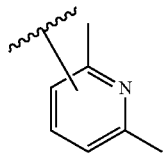
B-9

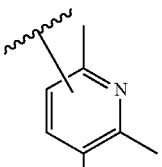
B-10

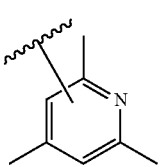
B-11

B-12 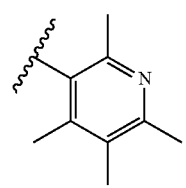
B-13 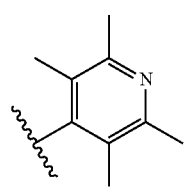
B-14 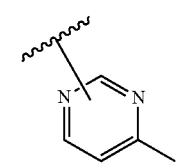
B-15 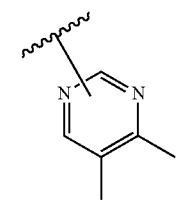
B-16 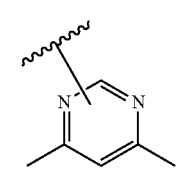
B-17 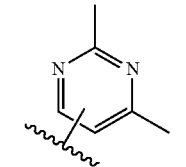
B-18 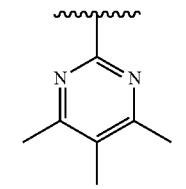
B-19 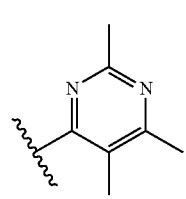
B-20 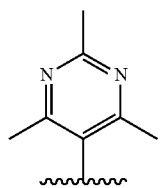
B-21 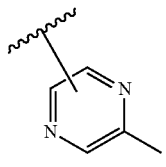
B-22 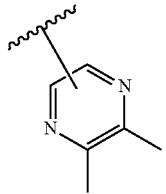
B-23 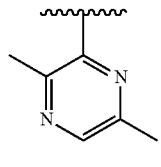
B-24 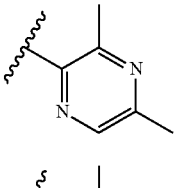
B-25 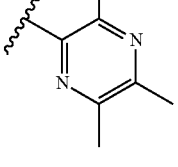
B-26 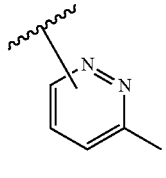
B-27 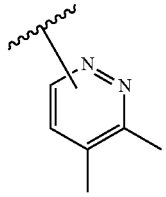
B-28 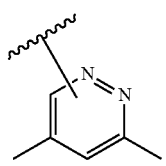

-continued
B-29
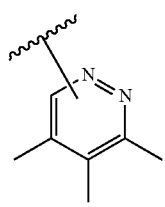
B-30
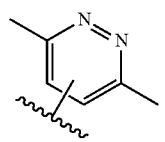
B-31
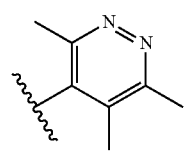
substituent C' represents (C'-46), (C'-48) or (C'-61):
C'-46
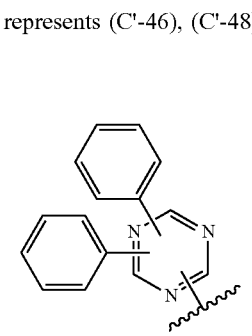
C'-48
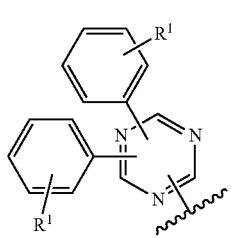
C'-61
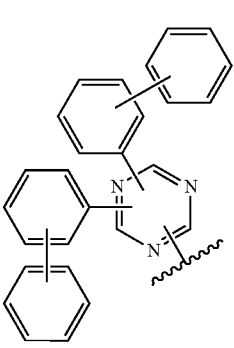
wherein R¹ represents a methyl group
Ar¹ represents the following substituents:
5
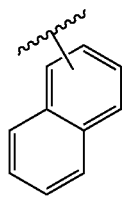
6
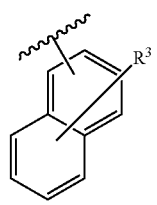
7
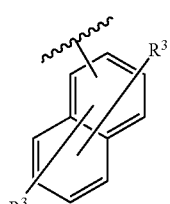
8
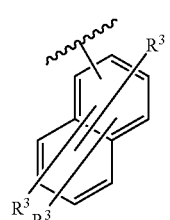
12
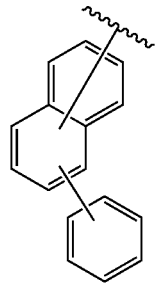
13
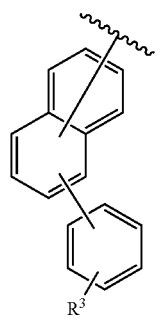

14 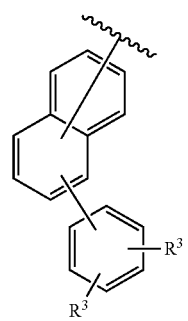
15 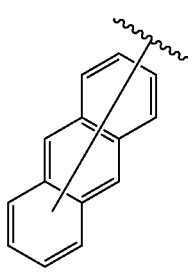
16 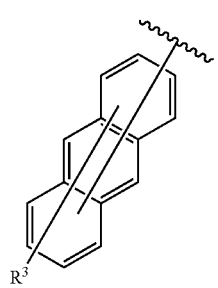
17 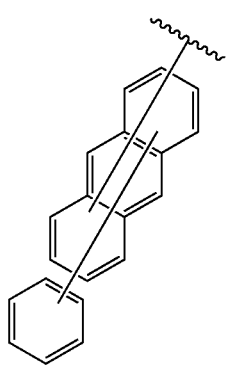
18 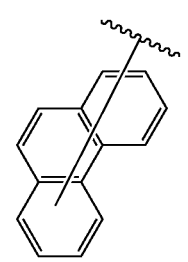
19 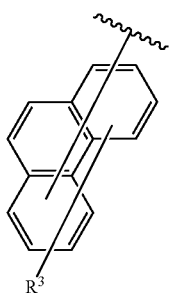
20 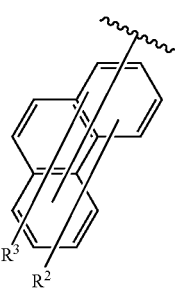
21 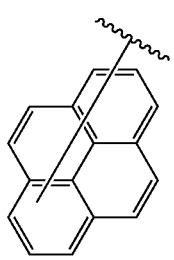
22 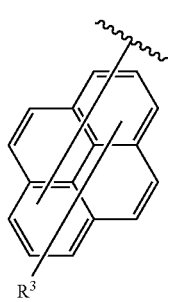
23 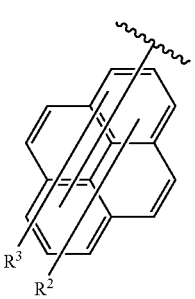

24 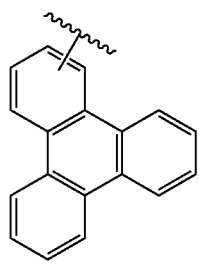

25 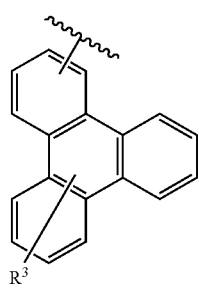

26 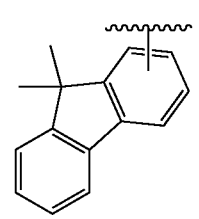

27 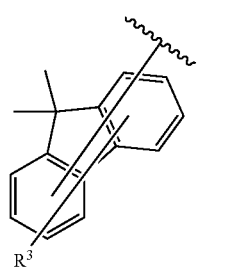

28 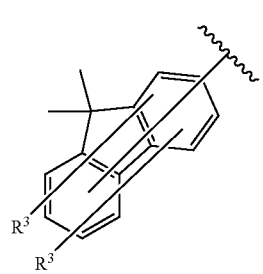

29 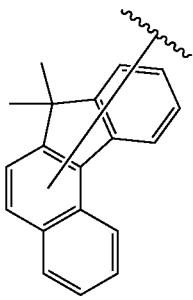

30 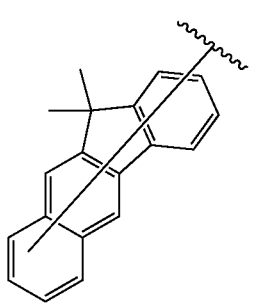

each X independently represents a phenylene group or an azabenzenediyl group, which may be substituted by a $C_{1-4}$ alkyl group, each of p and q independently represents 0, 1 or 2.

2. The cyclic azine compound according to claim 1, wherein substituent B is a 6-methylpyridin-2-yl group, a 6-methylpyridin-3-yl group, a 2-methylpyridin-3-yl group, a 4,6-dimethylpyrimidin-2-yl group, a 2-methylquinolin-8-yl group, a 3-methylisoquinolin-1-yl group or a 2,3-dimethylquinoxalin-6-yl group.

3. The cyclic azine compound according to claim 1, wherein each of p and q independently is 0 or 1.

4. The cyclic azine compound according to claim 1, wherein each X independently is a phenylene group or a pyridylene group.

5. The cyclic azine compound according to claim 1, which is any one of the following compounds of the formulae (A-10 to A-13), (A-27) to (A-29), (A-34) and (A-37 to A-42).

A-10

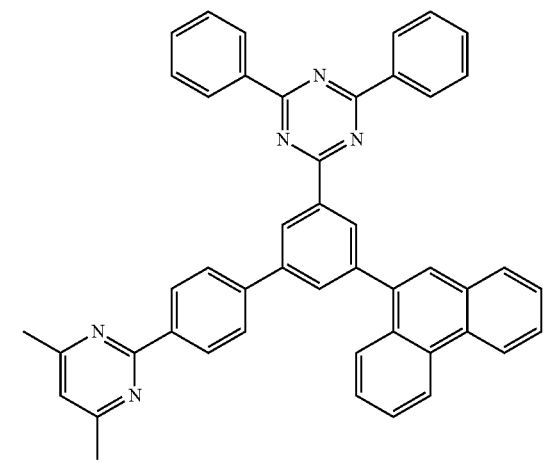

A-11
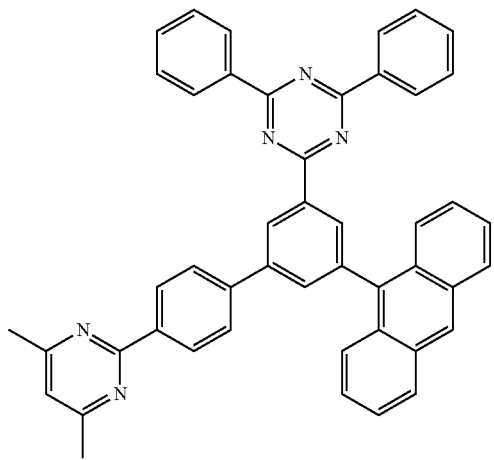
A-27
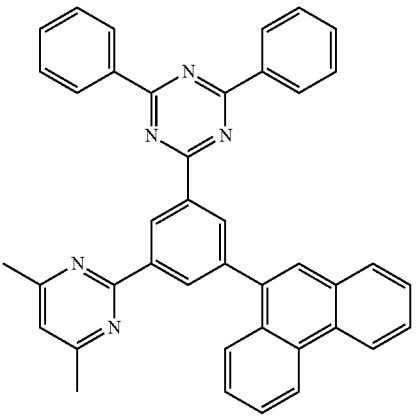
A-12
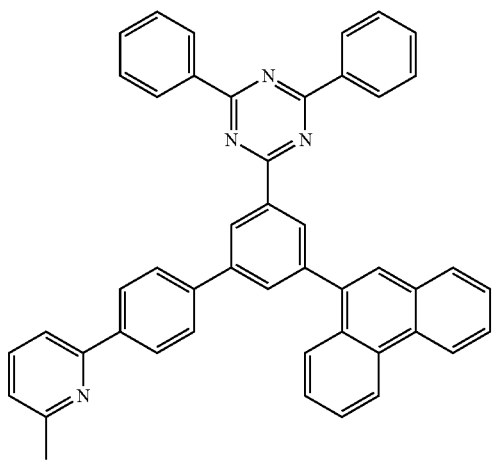
A-28
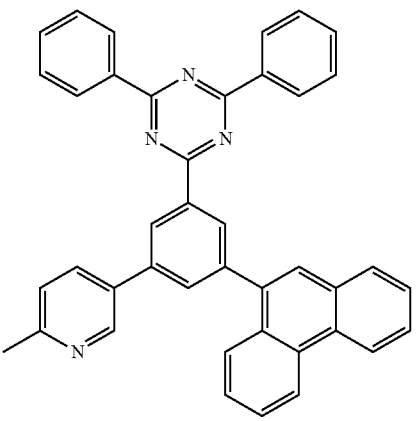
A-13
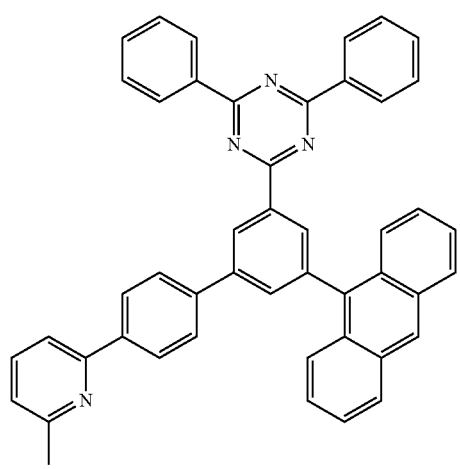
A-29

A-34
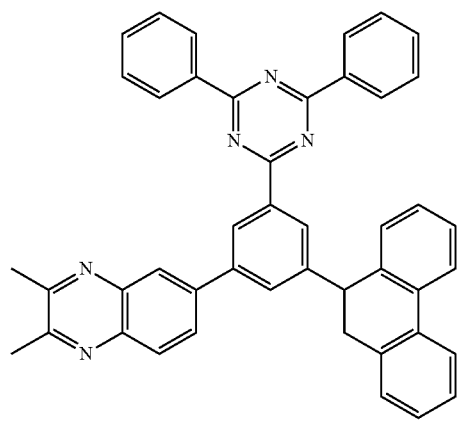
A-37
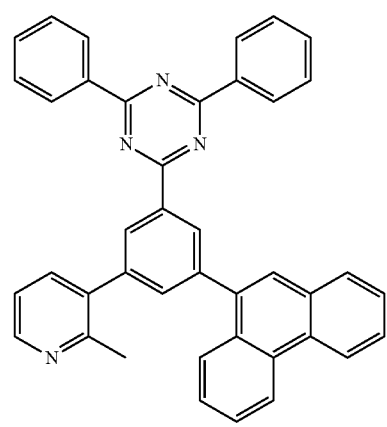
A-38
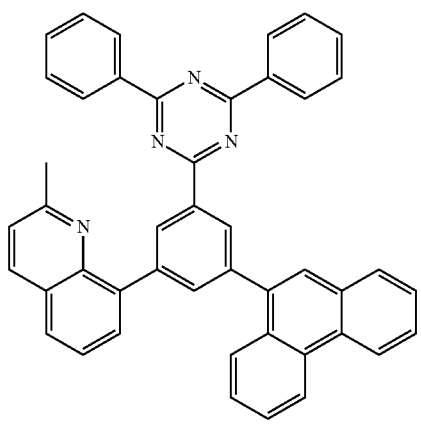
A-39
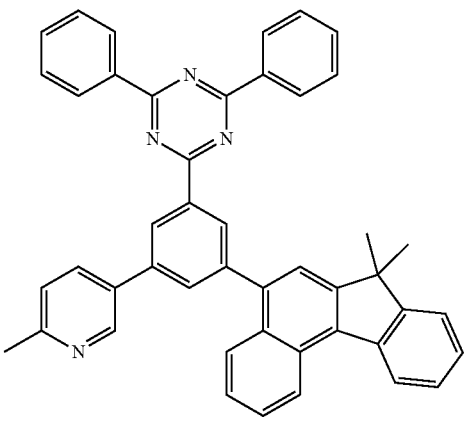
A-41
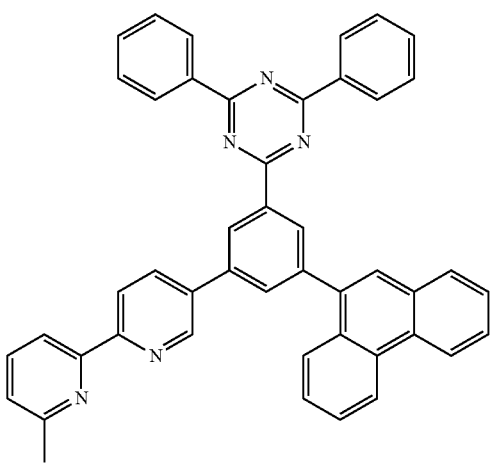
A-42
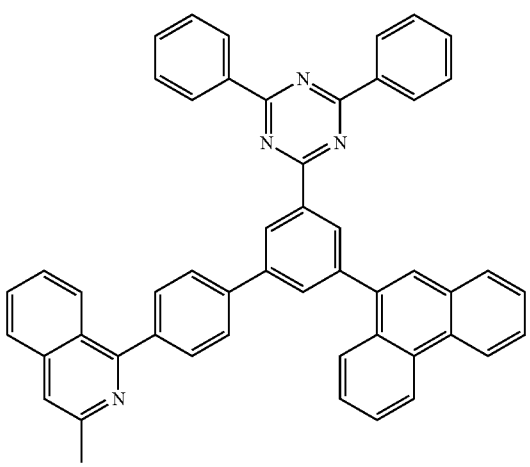
* * * * *